United States Patent
Oved et al.

(10) Patent No.: US 12,188,934 B2
(45) Date of Patent: Jan. 7, 2025

(54) SIGNATURES AND DETERMINANTS FOR DIAGNOSING INFECTIONS AND METHODS OF USE THEREOF

(71) Applicant: MeMed Diagnostics Ltd., Tirat HaCarmel (IL)

(72) Inventors: Kfir Oved, Hof HaCarmel (IL); Eran Eden, Haifa (IL); Ilan Ifergan, Haifa (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 0 days.

(21) Appl. No.: 17/507,994

(22) Filed: Oct. 22, 2021

(65) Prior Publication Data

US 2022/0042994 A1    Feb. 10, 2022

Related U.S. Application Data

(60) Continuation of application No. 16/687,726, filed on Nov. 19, 2019, now Pat. No. 11,175,291, which is a division of application No. 15/237,728, filed on Aug. 16, 2016, now Pat. No. 10,502,739, which is a division of application No. 14/377,887, filed as application No. PCT/EP2013/052619 on Feb. 8, 2013, now Pat. No. 9,726,668.

(60) Provisional application No. 61/652,631, filed on May 29, 2012, provisional application No. 61/596,950, filed on Feb. 9, 2012.

(51) Int. Cl.
| | |
|---|---|
| G01N 33/00 | (2006.01) |
| G01N 27/447 | (2006.01) |
| G01N 33/569 | (2006.01) |
| G01N 33/68 | (2006.01) |

(52) U.S. Cl.
CPC ..... *G01N 33/56983* (2013.01); *G01N 27/447* (2013.01); *G01N 27/44726* (2013.01); *G01N 27/44739* (2013.01); *G01N 33/56911* (2013.01); *G01N 33/6863* (2013.01); *G01N 33/6866* (2013.01); *G01N 2333/70575* (2013.01); *G01N 2800/52* (2013.01)

(58) Field of Classification Search
CPC ....... G01N 33/54387; G01N 33/54388; G01N 2800/52; G01N 33/6863
See application file for complete search history.

(56) References Cited

U.S. PATENT DOCUMENTS

| | | |
|---|---|---|
| 5,639,617 A | 6/1997 | Bohuon |
| 5,910,421 A | 6/1999 | Small, Jr. et al. |
| 6,077,665 A | 6/2000 | Welrich et al. |
| 6,136,526 A | 10/2000 | Venge |
| 6,210,661 B1 | 4/2001 | Enssle et al. |
| 6,709,855 B1 | 3/2004 | Stanton et al. |
| 6,756,483 B1 | 6/2004 | Bergmann et al. |
| 6,953,435 B2 | 10/2005 | Kondo et al. |
| 7,115,717 B2 | 10/2006 | Mori et al. |
| 7,132,246 B2 | 11/2006 | Bergmann et al. |
| 7,153,662 B2 | 12/2006 | Bergmann et al. |
| 7,157,081 B2 | 1/2007 | Bergmann et al. |
| 7,598,031 B2 | 10/2009 | Lew |
| 7,629,116 B2 | 12/2009 | Ott |
| 7,892,539 B2 | 2/2011 | Winoto et al. |
| 8,021,836 B2 | 9/2011 | Kolopp-Sarda et al. |
| 8,155,993 B2 | 4/2012 | de Nijs et al. |
| 8,465,951 B2 | 6/2013 | Rao et al. |
| 8,507,210 B2 | 8/2013 | Bergmann et al. |
| 8,563,476 B2 | 10/2013 | Lillard, Jr. |
| 8,697,370 B2 | 4/2014 | Kas et al. |
| 8,821,876 B2 | 9/2014 | Ginsburg et al. |
| 9,034,328 B2 | 5/2015 | Takahashi |
| 9,709,565 B2 | 7/2017 | Eden et al. |
| 9,726,668 B2 | 8/2017 | Oved et al. |
| 9,850,539 B2 | 12/2017 | Tsalik et al. |
| 10,010,252 B2 | 7/2018 | Ide et al. |
| 10,209,260 B2 | 2/2019 | Oved et al. |
| 10,303,846 B2 | 5/2019 | Eden et al. |
| 10,502,739 B2 | 12/2019 | Oved et al. |
| 10,859,574 B2 | 12/2020 | Oved et al. |
| 11,385,241 B2 | 7/2022 | Eden et al. |
| 11,466,331 B2 | 10/2022 | Oved et al. |
| 11,776,658 B2 | 10/2023 | Eden et al. |
| 2002/0001402 A1 | 1/2002 | Berliner |
| 2002/0055176 A1 | 5/2002 | Ray |
| 2002/0059030 A1 | 5/2002 | Otworth et al. |
| 2004/0038201 A1 | 2/2004 | Nau et al. |
| 2004/0043379 A1 | 3/2004 | Hashimoto et al. |
| 2004/0171013 A1 | 9/2004 | Lilius et al. |
| 2004/0197769 A1 | 10/2004 | Wong et al. |
| 2004/0209307 A1* | 10/2004 | Valkirs ................. C12Q 1/6883 435/7.1 |
| 2005/0164238 A1 | 7/2005 | Valkirs et al. |
| 2005/0227223 A1 | 10/2005 | Miyawaki |
| 2005/0233395 A1 | 10/2005 | Weiser et al. |

(Continued)

FOREIGN PATENT DOCUMENTS

| | | |
|---|---|---|
| AU | 2012244350 | 11/2012 |
| CN | 1656378 | 8/2005 |

(Continued)

OTHER PUBLICATIONS

Kramer et al. 2008 (Development and characterization of new rat monoclonal antibodies for procalcitonin; Anal Bioanal. Chem 392: 727-736). (Year: 2008).*
Vermot-Desroches et al. 2005 (Characterization of monoclonal antibodies directed against trail or trail receptors, Cellular Immunology 236: 86-91). (Year: 2005).* Communication of Notices of Opposition (R79(1) EPC) Dated May 4, 2022 From the European Patent Office Re. Application No. 17759388.6. (1 Page).

(Continued)

*Primary Examiner* — Mary Maille Lyons

(57) ABSTRACT

A kit is disclosed for distinguishing between bacterial and viral infections. One of the antibodies of the kit specifically binds to TNF-related apoptosis-inducing ligand (TRAIL) protein and another of the antibodies of the kit specifically binds to Procalcitonin (PCT) protein.

8 Claims, 91 Drawing Sheets

(56) References Cited

U.S. PATENT DOCUMENTS

Figure 1:
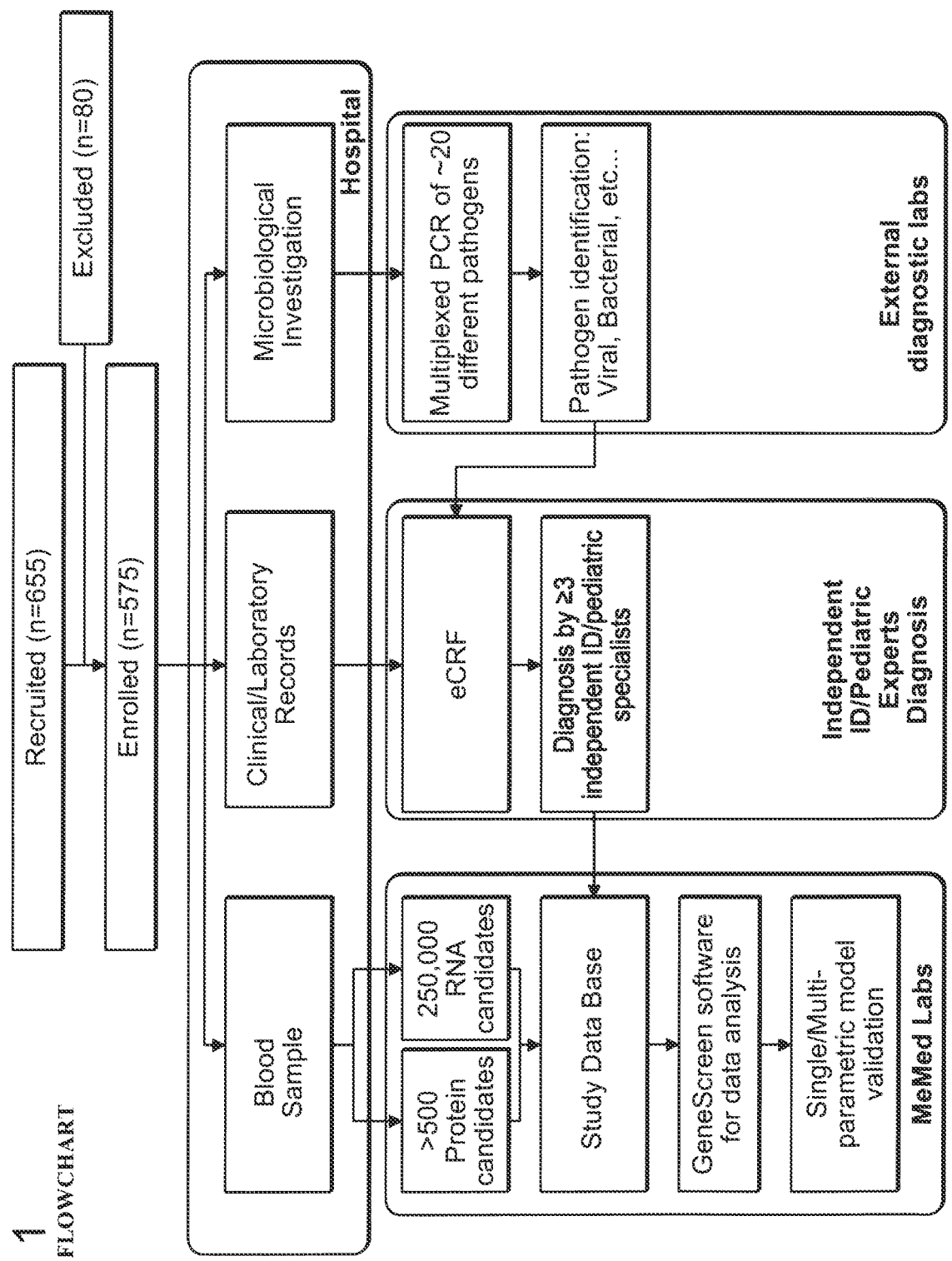

| | | |
|---|---|---|
| 2006/0040301 A1 | 2/2006 | Deirmengian |
| 2006/0052278 A1 | 3/2006 | Powell |
| 2006/0078998 A1 | 4/2006 | Puskas et al. |
| 2006/0099628 A1 | 5/2006 | Ching et al. |
| 2006/0246495 A1 | 11/2006 | Garrett et al. |
| 2007/0015172 A1 | 1/2007 | Zhang et al. |
| 2007/0184460 A1 | 8/2007 | Ching et al. |
| 2007/0231816 A1 | 10/2007 | Chaussabel et al. |
| 2007/0281319 A1 | 12/2007 | Kolopp-Sarda et al. |
| 2008/0020379 A1 | 1/2008 | Agan et al. |
| 2008/0064113 A1 | 3/2008 | Goix et al. |
| 2008/0171323 A1 | 7/2008 | Banchereau et al. |
| 2008/0261258 A1 | 10/2008 | Smith et al. |
| 2009/0155180 A1 | 6/2009 | Jump et al. |
| 2009/0203534 A1 | 8/2009 | Hossain et al. |
| 2009/0246790 A1 | 10/2009 | Cote et al. |
| 2010/0028874 A1 | 2/2010 | Ramachandran et al. |
| 2010/0068147 A1 | 3/2010 | Hibberd et al. |
| 2010/0143372 A1 | 6/2010 | Yao et al. |
| 2010/0267569 A1 | 10/2010 | Salmon et al. |
| 2010/0297611 A1 | 11/2010 | Sambursky et al. |
| 2011/0059858 A1 | 3/2011 | Kas et al. |
| 2011/0117563 A1 | 5/2011 | Filipowicz et al. |
| 2011/0144914 A1 | 6/2011 | Harrington |
| 2011/0166166 A1 | 7/2011 | Henkin |
| 2011/0183856 A1 | 7/2011 | Agan et al. |
| 2011/0225114 A1 | 9/2011 | Gotthardt |
| 2011/0275542 A1 | 11/2011 | Eden et al. |
| 2011/0312534 A1 | 12/2011 | Kayser et al. |
| 2012/0114661 A1 | 5/2012 | Ginsburg et al. |
| 2013/0166219 A1 | 6/2013 | Shaw |
| 2013/0309168 A1 | 11/2013 | Ho |
| 2014/0127827 A1 | 5/2014 | Kim et al. |
| 2014/0206016 A1 | 7/2014 | Lozano Sanchez et al. |
| 2014/0227324 A1 | 8/2014 | Robinson et al. |
| 2014/0277284 A1 | 9/2014 | Chen et al. |
| 2014/0349326 A1 | 11/2014 | Ingber |
| 2015/0017630 A1 | 1/2015 | Oved et al. |
| 2016/0041153 A1 | 2/2016 | Brown et al. |
| 2016/0153993 A1 | 6/2016 | Eden et al. |
| 2017/0030909 A1 | 2/2017 | Oved et al. |
| 2017/0234873 A1 | 8/2017 | Oved et al. |
| 2017/0235871 A1 | 8/2017 | Eden et al. |
| 2017/0269081 A1 | 9/2017 | Oved et al. |
| 2018/0074057 A1 | 3/2018 | Eden et al. |
| 2018/0310854 A1 | 11/2018 | Geva et al. |
| 2019/0011456 A1 | 1/2019 | Oved et al. |
| 2019/0041388 A1 | 2/2019 | Oved et al. |
| 2019/0085378 A1 | 3/2019 | Eden et al. |
| 2019/0120837 A1 | 4/2019 | Eden et al. |
| 2019/0161813 A1 | 5/2019 | Oved et al. |
| 2019/0237156 A1 | 8/2019 | Eden et al. |
| 2019/0242894 A1 | 8/2019 | Oved et al. |
| 2019/0242895 A1 | 8/2019 | Eden et al. |
| 2019/0271709 A1 | 9/2019 | Eden et al. |
| 2019/0339189 A1 | 11/2019 | Takeda et al. |
| 2020/0088728 A1 | 3/2020 | Oved et al. |
| 2020/0124593 A1 | 4/2020 | Oved et al. |
| 2020/0388347 A1 | 12/2020 | Eden et al. |
| 2020/0393463 A1 | 12/2020 | Oved et al. |
| 2020/0400668 A1 | 12/2020 | Eden et al. |
| 2022/0011320 A1 | 1/2022 | Eden et al. |
| 2022/0236269 A1 | 7/2022 | Eden et al. |
| 2022/0326256 A1 | 10/2022 | Eden et al. |
| 2022/0329345 A1 | 10/2022 | Kaplan |
| 2022/0399074 A1 | 12/2022 | Eden et al. |
| 2023/0045305 A1 | 2/2023 | Oved et al. |
| 2023/0184760 A1 | 6/2023 | Oved et al. |

FOREIGN PATENT DOCUMENTS

| | | |
|---|---|---|
| CN | 1751128 | 3/2006 |
| CN | 101208602 | 6/2008 |
| CN | 101479389 | 7/2009 |
| CN | 101523217 | 9/2009 |
| CN | 101541976 | 9/2009 |
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 101932940 | 12/2010 |
| CN | 102081101 | 6/2011 |
| CN | 102257386 | 11/2011 |
| CN | 102301002 | 12/2011 |
| CN | 102858991 | 1/2013 |
| CN | 103097891 | 5/2013 |
| CN | 103119444 | 5/2013 |
| CN | 104126125 | 10/2014 |
| CN | 104159616 | 11/2014 |
| CN | 104204803 | 12/2014 |
| CN | 104204808 | 12/2014 |
| CN | 104969071 | 10/2015 |
| CN | 105556308 | 5/2016 |
| EP | 1489416 | 12/2004 |
| JP | 2005-106694 | 4/2005 |
| JP | 2007-518062 | 7/2007 |
| JP | 2008-502908 | 1/2008 |
| JP | 2011-069696 | 4/2011 |
| KR | 10-2016-0072626 | 6/2016 |
| RU | 2007122617 | 12/2008 |
| RU | 2011111875 | 10/2012 |
| UA | 78641 | 3/2013 |
| UA | 92843 | 9/2014 |
| WO | WO 95/29404 | 11/1995 |
| WO | WO 99/33965 | 7/1999 |
| WO | WO 99/60171 | 11/1999 |
| WO | WO 01/14535 | 3/2001 |
| WO | WO 2004/108899 | 12/2004 |
| WO | WO2005/033327 | 4/2005 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2008/028489 | 3/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO 2009/100907 | 8/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/040062 | 3/2013 |
| WO | WO 2013/117746 | 8/2013 |
| WO | WO 2014/006408 | 1/2014 |
| WO | WO 2014/008545 | 1/2014 |
| WO | WO 2014/049255 | 4/2014 |
| WO | WO 2014/117873 | 8/2014 |
| WO | WO 2015/048098 | 4/2015 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

English Translation Dated May 10, 2022 of Examination Report Dated Apr. 14, 2022 From the Servico Publico Federal, Ministerio da Economia, Instituto Nacional da Propriedade Industrial do Brasil RE Application No. BR11 2017 002884 0. (3 Pages).

(56) References Cited

OTHER PUBLICATIONS

Notice of Allowance Dated May 17, 2022 From the US Patent and Trademark Office Re. U.S. Appl. No. 16/081,906. (14 Pages).
Notification of Office Action and Search Report Dated Apr. 20, 2022 From the State Intellectual Property Office of the People's Republic of China Re. Application No. 201780073531.5 and Its Translation Into English including Claims.. (31 Pages).
Opposition to European Patent No. 3423589 Memed Diagnostics Ltd. on Behalf of J.A. Kemp LLP Dated Apr. 21, 2022 From the European Patent Office Re. Application No. 17759388.6. (31 Pages).
Chaussabel et al. "Assessing the Human Immune System Through Blood Transcriptomics", BMC Biology, 8: 84-1-84-14, Jul. 1, 2010.
De la Grange et al. "A New Advance in Alternative Splicing Databases: From Catalogue to Detailed Analysis of Regulation of Expression and Function of Human Alternative Splicing Variants", BMC Bioinformatics, 8: 180-1-180-14, Jun. 4, 2007.
Hu et al. "Gene Expression Profiles in Febrile Children With Defined Viral and Bacterial Infection", Proc. Natl. Acad. Sci. USA, PNAS, 110(31): 12792-12797, Published Online Jul. 15, 2013.
Qian et al. "Identification of Genes Critical for Resistance to Infection by West Nile Virus Using RNA-Seq Analysis", Viruses, 5(7): 1664-1681, Jul. 8, 2013.
UCSC "Human Gene IFI27 (ENST00000621160.5) From GENCODE V39", UCSC Browser, Retrieved From the Internet, 3 Pages, Last Updated Jan. 17, 2022.
UCSC "Human Gene IFIT1 (ENST00000371804.4) From GENCODE V39", UCSC Browser, Retrieved From the Internet, 4 Pages, Last Updated Jan. 17, 2022.
UCSC "UCSC Genome Browser on Human (GRCh38/hg38)", UCSC Browser, Retrieved From the Internet, 1 Page, Apr. 14, 2022.
Notification of Office Action and Search Report Dated Dec. 23, 2021 From the State Intellectual Property Office of the People's Republic of China Re. Application No. 201780014541.1 and Its Translation of Office Action Into English. (14 Pages).
Final Official Action Dated Nov. 29 together with Interview Summary Dated Nov. 14, 2021 from US Patent and Trademark Office Re. U.S. Appl. No. 16/081,906. (45 pages).
Interview Summary Dated Dec. 3, 2021 from US Patent and Trademark Office Re. U.S. Appl. No. 16/081,069. (3 pages).
Ioannidis et al. "Plasticity and Virus Specifity of the Airway Epithelial Cell Immune Response During Respiratory Virus Infection", Journal of Virology, 86(10): 5422-36, Mar. 7, 2012.
Official Action Dated Jun. 9, 2022 from US Patent and Trademark Office Re. U.S. Appl. No. 17/007,095. (118 pages).
Requisition by the Examiner Dated Jun. 7, 2022 From the Innovation, Science and Economic Development Canada, Canadian Intellectual Property Office Re. Application No. 2,968,650. (3 Pages).
Requisition by the Examiner Dated Jul. 15, 2022 From the Innovation, Science and Economic Development Canada, Canadian Intellectual Property Office Re. Application No. 3,133,249. (4 Pages).
Notification of Office Action and Search Report Dated Sep. 30, 2021 From the State Intellectual Property Office of the People's Republic of China Re. Application No. 201780073531.5 and Its Translation of Office Action Into English. (14 Pages).
Vapnik "Statistical Learning Theory", Adaptive and Learning Systems for Signal Processing, Communications, and Control, p. 1-732, 1998. (Part 1).
Vapnik "Statistical Learning Theory", Adaptive and Learning Systems for Signal Processing, Communications, and Control, p. 1-732, 1998. (Part 2).
Vapnik "Statistical Learning Theory", Adaptive and Learning Systems for Signal Processing, Communications, and Control, p. 1-732, 1998. (Part 3).
Vapnik "Statistical Learning Theory", Adaptive and Learning Systems for Signal Processing, Communications, and Control, p. 1-732, 1998. (Part 4).
Zhang "Research Progress of Interferon-Inducible Protein 10 and Its Effect in Newborn Infection Diagnosis", Chinese Journal of Neonatology, 4: 60-62, Jul. 15, 2013.

Decision to Refuse a European Patent Application Dated Mar. 15, 2023 From the European Patent Office Re. Application No. 17759389.4. (4 Pages).
Summons to attend Oral Proceedings Pursuant to Rule 115(1) EPC Dated Jun. 10, 2022 From the European Patent Office Re. Application No. 17759389.4, (5 Pages).
Notice of Reason(s) for Rejection Dated Dec. 14, 2021 From the Japan Patent Office Re. Application No. 2020-109710 and Its Translation Into English. (7 Pages).
English Translation Dated Feb. 16, 2022 of Grounds of Reason of Rejection Dated Jan. 27, 2022 From the Korean Intellectual Property Office Re. Application No. 10-2017-7007002. (6 Pages).
Interview Summary Dated Feb. 22, 2022 from US Patent and Trademark Office Re. U.S. Appl. No. 16/081,706. (2 pages).
Notification of Office Action Dated Jan. 24, 2022 From the State Intellectual Property Office of the People's Republic of China Re. Application No. 201780014568.0 and its Translation into English. (9 Pages).
Advisory Action Dated Dec. 20, 2021 from US Patent and Trademark Office Re. U.S. Appl. No. 16/081,069. (7 pages).
Official Action Dated Nov. 22, 2021 from the US Patent and Trademark Office Re. U.S. Appl. No. 16/998,006. (116 pages).
Requisition by the Examiner Dated Nov. 5, 2021 From the Innovation, Science and Economic Development Canada, Canadian Intellectual Property Office Re. Application No. 2,968,650. (7 Pages).
Examination Report Dated Feb. 19, 2022 From the Servico Publico Federal, Ministerio da Economia, Instituto Nacional da Propriedade Industrial do Brasil RE Application No. BR112014 019733.4. (4 Pages).
Notice of Allowance Dated Mar. 16, 2022 from US Patent and Trademark Office Re. U.S. Appl. No. 16/998,006. (28 pages).
Notice of Allowance Dated Mar. 17, 2022 from US Patent and Trademark Office Re. U.S. Appl. No. 16/334,033. (29 pages).
Altmann et al. "Elevated Cardiac Troponin I in Sepsis and Septic Shock: No Evidence for Thrombus Associated Myocardial Necrosis", PLOSE One, 5(2): 1-5, 2010.
Ammann et al. "Elevation of Troponin I in Sepsis and Septic Shock", Intensive Care Medicine, 27: 965-969, May 16, 2001.
Arshed et al. "Elevated Troponin I in the Absence of Coronary Artery Disease: A Case Report with Review of Literature", Journal of Clinical Medicine Research, 7(10): 820-824, Aug. 23, 2015.
Bessiere et al. "Prognostic Value of Troponins in Sepsis: a Meta-Analysis", Intensive Care Medicine, 39: 1181-1189, Apr. 18, 2018.
Gaedtke et al. "Elevated Troponin is Associated with Mortality in Severe Sepsis and Septic Shock Patients", American Journal of Respiratory and Critical Care Medicine, 189: 1-2, 2014.
Sheyin et al. "The Prognostic Significance of Troponin Elevation in Patients with Sepsis: A Meta-Analysis", Heart & Lung, 44(1): 75-81, Jan.-Feb. 2015.
Wu "Increased Troponin in patients with Sepsis and Septic Shock: Myocardial Necrosis or Reversible Myocardial Depression", Intensive Care Medicine, 27: 959-961, 2001.
Notification of Office Action Dated May 11, 2022 From the State Intellectual Property Office of the People's Republic of China Re. Application No. 201780014541.1 and Its Translation Into English. (11 Pages).
Advisory Action Dated Mar. 9, 2022 from US Patent and Trademark Office Re. U.S. Appl. No. 16/081,906. (3 pages).
Decision on Rejection Dated Aug. 30, 2022 From the National Intellectual Property Administration of the People's Republic of China Re. Application No. 201780073531.5 and Its Translation Into English. (13 Pages).
Technical Examination Report Dated Aug. 11, 2022 from the National Institute of Industrial Property of Brazil Re. Application No. BR 11 2017 002884 0 with an English Translation. (8 pages).
Requisition by the Examiner Dated Mar. 21, 2023 From the Innovation, Science and Economic Development Canada, Canadian Intellectual Property Office Re. Application No. 3,015,046. (6 pages).

(56) References Cited

OTHER PUBLICATIONS

English Summary Dated Dec. 29, 2022 of Notification of Office Action Dated Dec. 2, 2022 From the State Intellectual Property Office of the People's Republic of China Re. Application No. 202010370187.X. (1 Page).
CNKI "Clinical Study on the Level of Plasma Tumor Necrosis Factor-Related Apoptosis-Inducing Ligand (TRAIL) in Evaluating the Prognosis of Patients With Sepsis", CNKI Master's E-Journals, 5: 4-26, Apr. 16, 2014.
Supplementary European Search Report and the European Search Opinion Dated Mar. 28, 2023 From the European Patent Office Re. Application No. 22204952.0. (12 Pages).
Abdel-Razik et al. "Diagnostic Utility of Interferon Gamma-induced Protein 10 kDa in Spontaneous Bacterial Peritonitis: Single-Center Study", European Journal of Gastroenterology & Hepatology, 27(9): 1087-1093, Sep. 2015.
Lighter et al. "Chemokine IP-10: an Adjunct Marker for Latent Tuberculosis Infection in Children", The International Journal of Tuberculosis and Lung Disease, 13(6): 731-736, Jun. 2009.
Punyadeera et al. "A Biomarker Panel to Discriminate Between Systemic Inflammatory Response Syndrome and Sepsis and Sepsis Severity", Journal of Emergencies, Trauma and Shock, 3(1): 26-35, Jan.-Mar. 2010.
Quint et al. "Serum IP-10 as a Biomarker of Human Rhinovirus Infection at Exacerbation of COPD", Science Direct, Chest, 137(4): 812-822, Apr. 2010.
Ruhwald et al. "IP-10 Can Be Measured in Dried Plasma Spots in Patients with Chronic Hepatitis C Infection", PLoS ONE 7(9): e45181, 1-4, Sep. 14, 2012.
"UCSC Genome Browser on Human (GRCh38/hg38)", UCSC Genome Browser, Version 440, Chr14: 94109241-94118186, Retrieved From the Internet, 7 Pages, Jan. 12, 2022.
"UCSC Genome Browser on Human (GRCh38/hg38)", UCSC Genome Browser, Version 440, Chr17: 41754609-41786711, Retrieved From the Internet, 4 Pages, Jan. 12, 2022.
Official Action Dated Dec. 6, 2022 from the US Patent and Trademark Office Re. U.S. Appl. No. 16/081,069. (20 pages).
Communication Pursuant to Article 94(3) EPC Dated Sep. 23, 2022 From the European Patent Office Re. Application No. 17855163.6. (7 Pages).
Interview Summary Dated Apr. 29, 2022 from US Patent and Trademark Office Re. U.S. Appl. No. 16/081,906. (2 pages).
Notification of Office Action and Search Report Dated Mar. 15, 2022 From the State Intellectual Property Office of the People's Republic of China Re. Application No. 201780055347.8 and Its Translation of Office Action Into English. (28 Pages).
Partial European Search Report and the European Search Opinion Dated Jan. 31, 2023 From the European Patent Office Re. Application No. 22169859.0. (13 Pages).
Advisory Action Before the Filing of An Appeal Brief Dated Dec. 23, 2019 From the US Patent and Trademark Office Re. U.S. Appl. No. 16/157,193. (3 pages).
Applicant-Initiated Interview Summary Dated Jul. 6, 2016 From the US Patent and Trademark Office Re. U.S. Appl. No. 14/377,887.
Applicant-Initiated Interview Summary Dated Feb. 10, 2020 From the US Patent and Trademark Office Re. U.S. Appl. No. 16/157,193. (3 pages).
Applicant-Initiated Interview Summary Dated Jul. 17, 2015 From the US Patent and Trademark Office Re. U.S. Appl. No. 13/090,893.
Applicant-Initiated Interview Summary Dated Feb. 22, 2017 From the US Patent and Trademark Office Re. U.S. Appl. No. 14/377,887. (3 Pages).
Applicant-Initiated Interview Summary Dated Oct. 26, 2017 From the US Patent and Trademark Office Re. U.S. Appl. No. 15/237,728. (3 pages).
Applicant-Initiated Interview Summary Dated Jul. 30, 2018 From the US Patent and Trademark Office Re. U.S. Appl. No. 15/641,400. (3 pages).

Communication Pursuant to Article 94(3) EPC Dated Jun. 2, 2021 From the European Patent Office Re. Application No. 17827121.9. (5 Pages).
Communication Pursuant to Article 94(3) EPC Dated Jun. 4, 2020 From the European Patent Office Re. Application No. 17759388.6. (3 Pages).
Communication Pursuant to Article 94(3) EPC Dated May 7, 2019 From the European Patent Office Re. Application No. 15831781.8. (3 Pages).
Communication Pursuant to Article 94(3) EPC Dated Dec. 9, 2016 From the European Patent Office Re. Application No. 13703112.6. (4 Pages).
Communication Pursuant to Article 94(3) EPC Dated Oct. 9, 2018 From the European Patent Office Re. Application No. 11748712.4. (8 Pages).
Communication Pursuant to Article 94(3) EPC Dated Nov. 12, 2020 From the European Patent Office Re. Application No. 17759389.4. (6 Page).
Communication Pursuant to Article 94(3) EPC Dated Jun. 17, 2016 From the European Patent Office Re. Application No. 11748712.4.
Communication Pursuant to Article 94(3) EPC Dated Mar. 17, 2021 From the European Patent Office Re. Application No. 15868614.7. (5 Pages).
Communication Pursuant to Article 94(3) EPC Dated Aug. 18, 2020 From the European Patent Office Re. Application No. 11748712.4. (3 Pages).
Communication Pursuant to Article 94(3) EPC Dated Mar. 25, 2020 From the European Patent Office Re. Application No. 18162713.4. (5 Pages).
Communication Pursuant to Article 94(3) EPC Dated May 25, 2020 From the European Patent Office Re. Application No. 11748712.4. (7 Pages).
Communication Pursuant to Article 94(3) EPC Dated Sep. 25, 2020 From the European Patent Office Re. Application No. 17827122.7. (5 Pages).
Communication Pursuant to Article 94(3) EPC Dated Mar. 27, 2020 From the European Patent Office Re. Application No. 15868614.7. (6 Pages).
Communication Pursuant to Article 94(3) EPC Dated Jul. 31, 2019 From the European Patent Office Re. Application No. 18162713.4. (4 Pages).
European Search Report and the European Search Opinion Dated Oct. 6, 2021 From the European Patent Office Re. Application No. 21178885.6. (10 Pages).
European Search Report and the European Search Opinion Dated Jul. 14, 2021 From the European Patent Office Re. Application No. 21170448.1. (6 Pages).
European Search Report and the European Search Opinion Dated May 16, 2018 From the European Patent Office Re. Application No. 18162713.4. (7 Pages).
European Search Report and the European Search Opinion Dated Sep. 28, 2020 From the European Patent Office Re. Application No. 20164056.2. (10 Pages).
Examination Report Dated Oct. 6, 2017 From the Australian Government, IP Australia Re. Application No. 2013217935. (2 Pages).
Examination Report Dated May 29, 2019 From the Australian Government, IP Australia Re. Application No. 2018202302. (5 Pages).
Examination Report Under Sections 12 & 13 of the Patents Act, 1970 and the Patents Rules, 2003 Dated Oct. 21, 2019 From the Government of India, Intellectual Property India, Patents, Designs, Trade Marks, Geographical Indications Re. Application No. 9122/DELNP/2012 (5 Pages).
Examination Report Under Sections 12 & 13 of the Patents Act, 1970 and the Patents Rules, 2003 Dated Mar. 26, 2018 From the Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 Dated Nov. 30, 2018 From the Government of India, Intellectual Property India, Patents, Designs, Trade Marks, Geographical Indications Re. Application No. 1780/MUMNP/2014. (7 Pages).

(56) References Cited

OTHER PUBLICATIONS

Examination Report Under Sections 12 & 13 of the Patents Act, 1970 and the Patents Rules, 2003 Dated Mar. 31, 2021 From the Government of India, Intellectual Property India, Patents, Designs, Trade Marks, Geographical Indications, The Patent Office Re. Application No. 201727005513. (7 Pages).
Examiner-Initiated Interview Summary Dated Nov. 27, 2017 From the US Patent and Trademark Office Re. U.S. Appl. No. 15/518,491. (2 pages).
Final Official Action Dated Sep. 3, 2021 From the US Patent and Trademark Office Re. U.S. Appl. No. 16/316,631. (37 Pages).
Final Official Action Dated Sep. 10, 2021 from the US Patent and Trademark Office Re. U.S. Appl. No. 16/081,069. (61 pages).
Final Official Action Dated Jun. 15, 2021 From the US Patent and Trademark Office Re. U.S. Appl. No. 16/334,033. (36 Pages).
Final Official Action Dated Sep. 8, 2020 from the US Patent and Trademark Office Re. U.S. Appl. No. 16/687,726. (28 pages).
Hearing Notice Dated Jul. 16, 2019 From the Government of India, Patent Office, Intellectual Property Building Re. Application No. 1780/MUMNP/2014. (3 Pages).
International Preliminary Report on Patentability Dated Apr. 11, 2019 From the International Bureau of WIPO Re. Application No. PCT/IL2017/051088. (6 Pages).
International Preliminary Report on Patentability Dated Apr. 11, 2019 From the International Bureau of WIPO Re. Application No. PCT/IL2017/051089. (7 Pages).
International Preliminary Report on Patentability Dated Sep. 13, 2018 From the International Bureau of WIPO Re. Application No. PCT/IL2017/050270. (7 Pages).
International Preliminary Report on Patentability Dated Sep. 13, 2018 From the International Bureau of WIPO Re. Application No. PCT/IL2017/050271. (9 Pages).
International Preliminary Report on Patentability Dated Jun. 22, 2017 From the International Bureau of WIPO Re. Application No. PCT/IL2015/051201. (7 Pages).
International Preliminary Report on Patentability Dated Feb. 23, 2017 From the International Bureau of WIPO Re. Application No. PCT/IL2015/050823. (7 Pages).
International Preliminary Report on Patentability Dated Jan. 24, 2019 From the International Bureau of WIPO Re. Application No. PCT/IL2017/050780. (9 Pages).
International Preliminary Report on Patentability Dated Jan. 24, 2019 From the International Bureau of WIPO Re. Application No. PCT/IL2017/050781. (7 Pages).
International Preliminary Report on Patentability Dated Apr. 27, 2017 From the International Bureau of WIPO Re. Application No. PCT/IL2015/051024. (7 Pages).
International Search Report and the Written Opinion Dated Mar. 12, 2012 From the International Searching Authority Re. Application No. PCT/IB2011/001299.
International Search Report and the Written Opinion Dated Sep. 14, 2017 From the International Searching Authority Re. Application No. PCT/IL2017/050781. (12 Pages).
International Search Report and the Written Opinion Dated Jun. 15, 2017 From the International Searching Authority Re. Application No. PCT/IL2017/050270. (13 Pages).
International Search Report and the Written Opinion Dated Jun. 15, 2017 From the International Searching Authority Re. Application No. PCT/IL2017/050271. (16 Pages).
International Search Report and the Written Opinion Dated Sep. 18, 2017 From the International Searching Authority Re. Application No. PCT/IL2017/050780. (15 Pages).
International Search Report and the Written Opinion Dated Jan. 20, 2016 From the International Searching Authority Re. Application No. PCT/IL2015/051024.
International Search Report and the Written Opinion Dated Feb. 22, 2016 From the International Searching Authority Re. Application No. PCT/IL2015/051201.
International Search Report and the Written Opinion Dated Dec. 25, 2017 From the International Searching Authority Re. Application No. PCT/IL2017/051088. (9 Pages).
International Search Report and the Written Opinion Dated Dec. 28, 2017 From the International Searching Authority Re. Application No. PCT/IL2017/051089. (10 Pages).
International Search Report and the Written Opinion Dated Nov. 29, 2015 From the International Searching Authority Re. Application No. PCT/IL2015/050823.
International Search Report Dated Apr. 5, 2013 From the International Searching Authority Re. Application No. PCT/EP2013/052619.
Interview Summary Dated Feb. 1, 2021 From the US Patent and Trademark Office Re. U.S. Appl. No. 16/687,726. (2 Pages).
Interview Summary Dated Oct. 14, 2020 from the US Patent and Trademark Office Re. U.S. Appl. No. 16/081,906. (3 pages).
Notice of Allowance Dated Feb. 4, 2019 From the US Patent and Trademark Office Re. U.S. Appl. No. 15/503,439. (6 pages).
Notice of Allowance Dated Sep. 10, 2020 from the US Patent and Trademark Office Re. U.S. Appl. No. 16/157,193. (13 pages).
Notice of Allowance Dated Apr. 19, 2021 from the US Patent and Trademark Office Re. U.S. Appl. No. 16/238,582. (22 pages).
Notice of Allowance Dated May 22, 2020 from the US Patent and Trademark Office Re. U.S. Appl. No. 16/355,984. (18 pages).
Notice of Allowance Dated Jul. 29, 2019 From the US Patent and Trademark Office Re. U.S. Appl. No. 15/237,728. (21 pages).
Notice of Allowance Dated and Interview Summary Jul. 19, 2021 from the US Patent and Trademark Office Re. U.S. Appl. No. 16/687,726. (24 pages).
Notice of Non-Compliant Amendment Dated Aug. 4, 2015 From the US Patent and Trademark Office Re. U.S. Appl. No. 13/090,893.
Notice of Reason for Rejection Dated Nov. 12, 2019 From the Japan Patent Office Re. Application No. 2017-126712 and an English Summary. (3 Pages).
Notice of Reason for Rejection Dated Aug. 20, 2019 From the Japan Patent Office Re. Application No. 2017-507867 and Its Translation Into English. (5 Pages).
Notice of Reason(s) for Rejection Dated Jun. 15, 2021 From the Japan Patent Office Re. Application No. 2020-109710 and Its Translation Into English. (12 Pages).
Notice of Reasons for Rejection Dated Nov. 1, 2016 From the Japan Patent Office Re. Application No. 2014-556086 and Its Translation Into English. (12 Pages).
Notice of Reasons for Rejection Dated Apr. 2, 2019 From the Japan Patent Office Re. Application No. 2017-126712 and Its Translation Into English. (8 Pages).
Notice of Reasons for Rejection Dated Jun. 19, 2018 From the Japan Patent Office Re. Application No. 2017-126712 and Its Translation Into English. (9 Pages).
Notice of Reasons for Rejection Dated Apr. 20, 2021 From the Japan Patent Office Re. Application No. 2020-021606 and Its Translation Into English. (9 Pages).
Notice on Office Action and the Search Report Dated Feb. 25, 2015 From the State Intellectual Property Office of the People's Republic of China Re. Application No. 201180030792.1 and Its Translation Into English.
Notification of Lack of Unity and Search Report Dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Notification of Office Action and Search Report Dated Jul. 2, 2021 From the State Intellectual Property Office of the People's Republic of China Re. Application No. 201780055014.5. (23 Pages).
Notification of Office Action and Search Report Dated Aug. 3, 2021 From the State Intellectual Property Office of the People's Republic of China Re. Application No. 201780055347.8 and Its Translation of Office Action Into English. (526Pages).
Notification of Office Action and Search Report Dated Jun. 3, 2021 From the State Intellectual Property Office of the People's Republic of China Re. Application No. 20180014541.1 and Its Translation Into English. (17 Pages).

(56) References Cited

OTHER PUBLICATIONS

Notification of Office Action and Search Report Dated Mar. 4, 2016 From the State Intellectual Property Office of the People's Republic of China Re. Application No. 201380019055.0.
Notification of Office Action and Search Report Dated Jan. 11, 2019 From the State Intellectual Property Office of the People's Republic of China Re. Application No. 201580055946.0. (5 Pages).
Notification of Office Action and Search Report Dated Feb. 13, 2017 From the State Intellectual Property Office of the People's Republic of China Re. Application No. 201380019055.0 and Its Translation of Office Action Into English. (10 Pages).
Notification of Office Action and Search Report Dated Jul. 13, 2021 From the State Intellectual Property Office of the People's Republic of China Re. Application No. 20180781584.9 and an English Summary. (4 Pages).
Notification of Office Action and Search Report Dated Feb. 19, 2019 From the State Intellectual Property Office of the People's Republic of China Re. Application No. 201580075265.0 and A Summary of the Notification of Office Action Into English.(7 Pages).
Notification of Office Action and Search Report Dated Jun. 19, 2018 From the State Intellectual Property Office of the People's Republic of China Re. Application No. 201580075265.0 and its English Summary. (14 Pages).
Notification of Office Action and Search Report Dated Feb. 20, 2021 From the State Intellectual Property Office of the People's Republic of China Re. Application No. 201780014568.0 and Its Translation Into English. (22 Pages).
Notification of Office Action and Search Report Dated Jul. 28, 2020 From the State Intellectual Property Office of the People's Republic of China Re. Application No. 201810781584.9 and Its Translation of Office Action Into English. (17 Pages).
Notification of Office Action and Search Report Dated Oct. 30, 2017 From the State Intellectual Property Office of the People's Republic of China Re. Application No. 201610817276.8. (10 Pages).
Notification of Office Action Dated Sep. 1, 2021 From the State Intellectual Property Office of the People's Republic of China Re. Application No. 201780014568.0 and Its Translation Into English. (7 Pages).
Notification of Office Action Dated Jul. 2, 2019 From the State Intellectual Property Office of the People's Republic of China Re. Application No. 201580075265.0. (3 Pages).
Notification of Office Action Dated Jul. 3, 2015 From the State Intellectual Property Office of the People's Republic of China Re. Application No. 201380019055.0.
Notification of Office Action Dated Jun. 3, 2019 From the China National Intellectual Property Administration Re. Application No. 201610817276.8 and Its Translation Into English. (10 Pages).
Notification of Office Action Dated Aug. 4, 2016 From the State Intellectual Property Office of the People's Republic of China Re. Application No. 201380019055.0 and Its Translation Into English.
Notification of Office Action Dated Mar. 5, 2021 From the State Intellectual Property Office of the People's Republic of China Re. Application No. 201810781584.9 and Its Translation of Office Action Into English. (13 Pages).
Notification of Office Action Dated May 6, 2014 From the State Intellectual Property Office of the People's Republic of China Re. Application No. 201180030792.1 and Its Translation Into English.
Notification of Office Action Dated Jun. 20, 2018 From the State Intellectual Property Office of the People's Republic of China Re. Application No. 201580055946.0 and Its Summary in English. (5 Pages).
Notification of Office Action Dated Jan. 21, 2016 From the State Intellectual Property Office of the People's Republic of China Re. Application No. 201180030792.1 and Its Translation Into English.
Notification of Office Action Dated Aug. 22, 2019 From the State Intellectual Property Office of the People's Republic of China Re. Application No. 201580055946.0. (3 Pages).
Notification of Office Action Dated Aug. 25, 2017 From the State Intellectual Property Office of the People's Republic of China Re. Application No. 201380019055.0. (6 Pages).
Notification of Office Action Dated Aug. 28, 2015 From the State Intellectual Property Office of the People's Republic of China Re. Application No. 201180030792.1 and Its Translation Into English.
Notification of Office Action Dated Aug. 30, 2018 From the State Intellectual Property Office of the People's Republic of China Re. Application No. 201610817276.8 and Its Translation Into English. (22 Pages).
Notification of Reexamination Dated Jan. 12, 2018 From the State Intellectual Property Office of the People's Republic of China Re. Application No. 2013800190 and Its Machine Translation into English.
Office Action Dated Feb. 18, 2019 From the Israel Patent Office Re. Application No. 250585 and Its Translation Into English. (6 Pages).
Office Action Dated Nov. 28, 2019 From the Israel Patent Office Re. Application No. 254095 and Its Translation Into English. (7 Pages).
Office Action Dated Feb. 29, 2016 From the Israel Patent Office Re. Application No. 233998 and Its Translation Into English.
Office Action Dated Jul. 30, 2020 From the Israel Patent Office Re. Application No. 261529 and Its Translation Into English. (5 Pages).
Office Action Dated Jul. 30, 2020 From the Israel Patent Office Re. Application No. 261530 and Its Translation Into English. (5 Pages).
Official Action Dated Sep. 1, 2015 From the US Patent and Trademark Office Re. U.S. Appl. No. 13/090,893.
Official Action Dated Feb. 3, 2020 From the US Patent and Trademark Office Re. U.S. Appl. No. 16/355,984. (24 pages).
Official Action Dated Apr. 4, 2016 From the US Patent and Trademark Office Re. U.S. Appl. No. 13/090,893.
Official Action Dated Jan. 4, 2019 From the US Patent and Trademark Office Re. U.S. Appl. No. 151713,722. (72 pages).
Official Action Dated Nov. 4, 2020 From the US Patent and Trademark Office Re. U.S. Appl. No. 16/238,582. (37 Pages).
Official Action Dated Mar. 5, 2020 From the US Patent and Trademark Office Re. U.S. Appl. No. 15/713,722. (24 pages).
Official Action Dated May 5, 2021 From the US Patent and Trademark Office Re. U.S. Appl. No. 16/336,528. (108 Pages).
Official Action Dated Feb. 6, 2018 From the US Patent and Trademark Office Re. U.S. Appl. No. 15/503,439. (63 pages).
Official Action Dated Nov. 7, 2016 From the US Patent and Trademark Office Re. U.S. Appl. No. 13/090,893. (26 pages).
Official Action Dated Mar. 9, 2021 From the US Patent and Trademark Office Re. U.S. Appl. No. 16/316,631. (121 Pages).
Official Action Dated Jun. 10, 2013 From the US Patent and Trademark Office Re. U.S. Appl. No. 13/090,893.
Official Action Dated Mar. 10, 2021 From the US Patent and Trademark Office Re. U.S. Appl. No. 16/081,906. (127 Pages).
Official Action Dated Apr. 12, 2018 From the US Patent and Trademark Office Re. U.S. Appl. No. 15/518,491. (59 pages).
Official Action Dated Aug. 12, 2015 From the US Patent and Trademark Office Re. U.S. Appl. No. 14/377,887.
Official Action Dated May 12, 2017 From the US Patent and Trademark Office Re. U.S. Appl. No. 15/237,728. (27 pages).
Official Action Dated Apr. 13, 2016 From the US Patent and Trademark Office Re. U.S. Appl. No. 14/377,887.
Official Action Dated Mar. 13, 2014 From the US Patent and Trademark Office Re. U.S. Appl. No. 13/090,893.
Official Action Dated Apr. 15, 2019 From the US Patent and Trademark Office Re. U.S. Appl. No. 15/237,728. (16 Pages).
Official Action Dated Dec. 15, 2016 From the US Patent and Trademark Office Re. U.S. Appl. No. 14/377,887. (22 pages).
Official Action Dated May 15, 2018 From the US Patent and Trademark Office Re. U.S. Appl. No. 15/237,728. (55 pages).
Official Action Dated May 15, 2020 From the US Patent and Trademark Office Re. U.S. Appl. No. 16/238,582. (92 Pages).
Official Action Dated Oct. 15, 2019 From the US Patent and Trademark Office Re. U.S. Appl. No. 151713,722. (57 Pages).
Official Action Dated Nov. 16, 2018 From the US Patent and Trademark Office Re. U.S. Appl. No. 15/503,439. (41 pages).
Official Action Dated Sep. 16, 2019 From the US Patent and Trademark Office Re. U.S. Appl. No. 16/355,984. (44 pages).
Official Action Dated Dec. 17, 2018 From the US Patent and Trademark Office Re. U.S. Appl. No. 15/237,728. (39 pages).
Official Action Dated Nov. 18, 2016 From the US Patent and Trademark Office Re. U.S. Appl. No. 15/237,728. (33 pages).

(56) References Cited

OTHER PUBLICATIONS

Official Action Dated Sep. 18, 2019 From the US Patent and Trademark Office Re. U.S. Appl. No. 16/157,193. (30 pages).
Official Action Dated Oct. 20, 2020 From the US Patent and Trademark Office Re. U.S. Appl. No. 16/081,069. (112 Pages).
Official Action Dated Apr. 23, 2019 From the US Patent and Trademark Office Re. U.S. Appl. No. 16/157,193. (47 pages).
Official Action Dated Nov. 23, 2020 From the US Patent and Trademark Office Re. U.S. Appl. No. 16/355,984. (9 pages).
Official Action Dated Oct. 24, 2019 From the US Patent and Trademark Office Re. U.S. Appl. No. 15/531,747. (37 Pages).
Official Action Dated Jan. 26, 2017 From the US Patent and Trademark Office Re. U.S. Appl. No. 15/015,309. (45 pages).
Official Action Dated Mar. 26, 2015 From the US Patent and Trademark Office Re. U.S. Appl. No. 13/090,893.
Official Action Dated Mar. 26, 2020 from the US Patent and Trademark Office Re. U.S. Appl. No. 16/687,726. (47 pages).
Official Action Dated Apr. 30, 2018 From the US Patent and Trademark Office Re. U.S. Appl. No. 15/641,400. (62 pages).
Official Action Dated Dec. 30, 2020 from the US Patent and Trademark Office Re. U.S. Appl. No. 16/334,033. (112 pages).
Official Action Dated Mar. 30, 2018 From the US Patent and Trademark Office Re. U.S. Appl. No. 15/531,747. (67 pages).
Official Action Dated Mar. 31, 2020 from the US Patent and Trademark Office Re. U.S. Appl. No. 15/531,747. (21 pages).
Official Action Dated May 7, 2020 from the US Patent and Trademark Office Re. U.S. Appl. No. 16/157,193. (23 pages).
Partial European Search Report and Provisional Opinion Dated Jun. 25, 2020 From the European Search Report Re. Application No. 20164056.2. (11 Pages).
Patent Examination Report Dated Feb. 8, 2021 From the Australian Government, IP Australia Re. Application No. 2015302870. (4 Pages).
Request for Examination Dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (11 Pages).
Requisition by the Examiner Dated Oct. 4, 2019 From the Innovation, Science and Economic Development Canada, Canadian Intellectual Property Office Re. Application No. 2,863,819. (3 Pages).
Requisition by the Examiner Dated Dec. 7, 2020 From the Innovation, Science and Economic Development Canada, Canadian Intellectual Property Office Re. Application No. 2,863,819. (4 Pages).
Requisition by the Examiner Dated Nov. 9, 2018 From the Innovation, Science and Economic Development Canada, Canadian Intellectual Property Office Re. Application No. 2,796,666. (3 Pages).
Requisition by the Examiner Dated Jan. 18, 2018 From the Innovation, Science and Economic Development Canada, Canadian Intellectual Property Office Re. Application No. 2,796,666. (5 Pages).
Requisition by the Examiner Dated Feb. 21, 2019 From the Innovation, Science and Economic Development Canada, Canadian Intellectual Property Office Re. Application No. 2,863,819. (8 Pages).
Requisition by the Examiner Dated Jul. 30, 2021 From the Innovation, Science and Economic Development Canada, Canadian Intellectual Property Office Re. Application No. 2,954,601. (4 Pages).
Restriction Official Action Dated Apr. 2, 2020 From the US Patent and Trademark Office Re. U.S. Appl. No. 16/081,069. (7 Pages).
Restriction Official Action Dated Nov. 2, 2017 From the US Patent and Trademark Office Re. U.S. Appl. No. 15/531,747. (9 pages).
Restriction Official Action Dated Dec. 5, 2019 From the US Patent and Trademark Office Re. U.S. Appl. No. 16/081,906. (9 pages).
Restriction Official Action Dated Nov. 8, 2018 From the US Patent and Trademark Office Re. U.S. Appl. No. 16/157,193. (5 pages).
Restriction Official Action Dated May 10, 2018 From the US Patent and Trademark Office Re. U.S. Appl. No. 15/713,722. (6 Pages).
Restriction Official Action Dated Sep. 10, 2020 from the US Patent and Trademark Office Re. U.S. Appl. No. 16/316,631. (6 pages).
Restriction Official Action Dated Feb. 13, 2013 From the US Patent and Trademark Office Re. U.S. Appl. No. 13/090,893.
Restriction Official Action Dated May 15, 2015 From the US Patent and Trademark Office Re. U.S. Appl. No. 14/377,887.
Restriction Official Action Dated Mar. 29, 2021 From the US Patent and Trademark Office Re. U.S. Appl. No. 16/081,069. (8 Pages).
Restriction Official Action Dated Nov. 29, 2019 From the US Patent and Trademark Office Re. U.S. Appl. No. 16/238,582. (7 pages).
Restriction Official Action Dated Jul. 30, 2020 from the US Patent and Trademark Office Re. U.S. Appl. No. 16/081,906. (7 pages).
Restriction Official Action Dated Aug. 31, 2017 From the US Patent and Trademark Office Re. U.S. Appl. No. 15/518,491. (6 pages).
Restriction Official Action Dated Dec. 9, 2020 from the US Patent and Trademark Office Re. U.S. Appl. No. 16/336,528. (7 pages).
Search Report and Opinion Dated Dec. 10, 2019 From the Servico Publico Federal, Ministerio da Economia, Instituto Nacional da Propriedade Industrial do Brasil Re. Application No. BR112017002884-0 and Its Translation Into English. (7 Pages).
Search Report and Opinion Dated Aug. 20, 2019 From the Servi?o Publico Federal, Ministerio da Economia, Instituto Nacional da Propriedade Industrial do Brasil Re. Application No. BR112014 019733-4 and Its Summary in English. (4 Pages).
Search Report Dated May 6, 2014 From the State Intellectual Property Office of the People's Republic of China Re. Application No. 201180030792.1 and Its Translation Into English.
Second Notice of Allowance Dated Dec. 12, 2018 From the US Patent and Trademark Office Re. U.S. Appl. No. 15/641,400. (7 pages).
Second Notice of Allowance Dated May 12, 2021 From the US Patent and Trademark Office Re. U.S. Appl. No. 16/355,984. (32 Pages).
Supplementary European Search Report and the European Search Opinion Dated May 4, 2020 From the European Patent Office Re. Application No. 17855163.6. (9 Pages.
Supplementary European Search Report and the European Search Opinion Dated Mar. 15, 2018 From the European Patent Office Re. Application No. 15831781.8. (11 Pages).
Supplementary European Search Report and the European Search Opinion Dated Sep. 17, 2018 From the European Patent Office Re. Application No. 15868614.7. (18 Pages).
Supplementary European Search Report and the European Search Opinion Dated Feb. 18, 2020 From the European Patent Office Re. Application No. 17827121.9. (5 Pages).
Supplementary European Search Report and the European Search Opinion Dated May 18, 2020 From the European Patent Office Re. Application No. 17855164.4. (13 Pages).
Supplementary European Search Report and the European Search Opinion Dated Jan. 21, 2020 From the European Patent Office Re. Application No. 17827122.7. (9 Pages).
Supplementary European Search Report and the European Search Opinion Dated Jan. 28, 2020 From the European Patent Office Re. Application No. 17759389.4. (11 Pages).
Supplementary European Search Report and the European Search Opinion Dated Sep. 30, 2019 From the European Patent Office Re. Application No. 17759388.6. (11 Pages).
Supplementary Partial European Search Report and the European Provisional Opinion Dated Jun. 1, 2018 From the European Patent Office Re. Application No. 15868614.7. (23 Pages).
Supplementary Partial European Search Report and the European Provisional Opinion Dated Oct. 24, 2019 From the European Patent Office Re. Application No. 17759389.4. (15 Pages).
Translation Dated Sep. 4, 2017 of Notification of Office Action Dated Aug. 25, 2017 From the State Intellectual Property Office of the People's Republic of China Re. Application No. 201380019055. 0.
Translation Dated Apr. 5, 2016 of Notification of Office Action Dated Mar. 4, 2016 From the State Intellectual Property Office of the People's Republic of China Re. Application No. 201380019055. 0.

(56) References Cited

OTHER PUBLICATIONS

Translation Dated Jul. 10, 2019 of Notification of Office Action Dated Jul. 2, 2019 From the State Intellectual Property Office of the People's Republic of China Re. Application No. 201580075265.0. (1 Page).
Translation Dated Sep. 11, 2019 of Notification of Office Action Dated Aug. 22, 2019 From the State Intellectual Property Office of the People's Republic of China Re. Application No. 201580055946.0. (1 Page).
Translation Dated Mar. 20, 2019 of Notification of Office Action Dated Feb. 19, 2019 From the State Intellectual Property Office of the People's Republic of China Re. Application No. 201580075265.0. (5 Pages).
Translation Dated Nov. 21, 2019 of Reason for Rejection From the Japanese Patent Office Re. Application No. 2017-126712. (2 Pages).
Translation Dated Sep. 21, 2015 of Office Action Dated Jul. 3, 2015 From the State Intellectual Property Office of the People's Republic of China Re. Application No. 201380019055.0.
Translation Dated Jul. 22, 2021 of Notification of Office Action Dated Jul. 13, 2021 From the State Intellectual Property Office of the People's Republic of China Re. Application No. 20180781584.9. (2 Pages).
Translation Dated Sep. 22, 2019 of Search Report and Opinion Dated Aug. 20, 2019 From the Serviço Publico Federal, Ministerio da Economia, Instituto Nacional da Propriedade Industrial do Brasil Re. Application No. BR112014 019733-4 and Its Summary in English. (4 Pages).
Translation Dated Jul. 27, 2021 of Notification of Office Action Dated Jul. 2, 2021 From the State Intellectual Property Office of the People's Republic of China Re. Application No. 201780055014.5. (12 Pages).
Translation Dated Jan. 30, 2019 of Notification of Office Action Dated Jan. 11, 2019 From the State Intellectual Property Office of the People's Republic of China Re. Application No. 201580055946.0.(1 Page).
Translation of Notification of Office Action and Search Report Dated Oct. 30, 2017 From the State Intellectual Property Office of the People's Republic of China Re. Application No. 201610817276.8. (16 Pages).
Affymetrix "Whole-Transcript Expression Analysis", Affymetrix, 8 pages, 2007.
Alexander et al. "*Staphylococcus aureus* and *Salmonella enterica* Serovar Dublin Induce Tumor Necrosis Factor-Related Apoptosis-Inducing Ligand Expression by Normal Mouse and Human Osteoblasts", Infection and Immunity, 69(3): 1581-1586, Mar. 2001.
Ali et al. "Reliability of Serum Procalcitonin Concentrations for the Diagnosis of Sepsis in Neonates", Egypt Journal of Immunology, 15(1): 75-84, 2008. Abstract only.
Bai et al. "A New Early Diagnostic Marker for Inflammatory Diseases—STREM-1", International Journal of Pathology and Clinical Medicine, 27(1): 73-76, Feb. 2007.
Barnhart et al. "Changes in Cellular mRNA Stability, Splicing, and Polyadenylation Through HuR Protein Sequestration by a Cytoplasmic RNA Virus", Cell Reports, XP055621573, 5(4): 909-917, Nov. 27, 2013.
Becker et al. "Procalcitonin in Sepsis and Systemic Inflammation: a Harmful Biomarker and a Therapeutic Target", British Journal of Pharmacology, 159: 253-264, 2010.
Biczcvcld ct al. "Sustainec Activation of Ncutrophils in the Coursc of Kawasaki Discasc: An Association with Matrix Mctalloprotcinascs", Clinical & Expcrimcntal Immunology 141(1): 183-188, Jul. 2005.
Bloos et al. "Rapid Diagnosis of Sepsis"; Virulence, 5(1): 154-160, 2014.
Boldrick et al. "Stereotyped and Specific Gene Expression Programs in Human Innate Immune Responses to Bacteria", Proc. Natl. Acad. Sci. USA, PNAS, 99(2): 972-977, Jan. 22, 2002.
Bone et al. "Definitions for Sepsis and Organ Failure and Guidelines for the Use of Innovative Therapies in Sepsis", Chest, 101(6): 1644-1655, 1992.

Borjesson et al. "Insights Into Pathogen Immune Evasion Mechanisms: Anaplasma Phagocytophilum Fails to Induce an Apoptosis Differentiation Program in Human Neutrophils", The Jurnal of Immunology, 174: 6364-6372, 2005.
Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.
Brost et al. "Differential Expression of the TRAIL/TRAIL-receptor System in Patients with Inflammatory Bowel Disease", Pathology—Research and Practice, 206(1):43-50, Jan. 15, 2010.
Cai et al. "The Study on the Relationship Between PCT and CRP in Infective Diseases", Journ al of Qiqihar University of Medicine, 32(5): 696-697, 2011.
Calvano et al. "A Network-Based Analysis of Systemic Inflammation in Humans", Nature, 437: 1032-1037, Oct. 13, 2005.
Carrol et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.
Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.
Chaussabel et al. "Analysis of Significance Patterns Identifies Ubiquitous and Disease-Specific Gene-Expression Signatures in Patient Peripheral Blood Leukocytes", Annals of the New York Academy of Sciences, 1062: 146-154, 2005.
Chen et al. "Discordant Protein and mRNA Expression in Lung Adenocarcinomas", Molecular & Cellular Proteomics: MCP, 1(4): 304-313, Apr. 2002.
Chieux et al. "MxA Protein in Capillary Blood of Children With Viral Infections", Journal of Medical Virology, 59: 547-551, 1999.
Chieux et al. "The MxA Protein Levels in Whole Blood Lysates of Patients With Various Viral Infections", Journal of Virological Methods, 70: 183-191, 1998.
Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.
Corada et al. "Monoclonal Antibodies Directed to Different Regions of Vascular Endothelial Cadherin Extracellular Dornain Affect Adhesion and Clustering of the Protein and Modulate Endothelial Permeability", Blood, 97(6): 1679-1684, Mar. 15, 2001.
Cowland et al. "Molerular Charaderization and Pattern of Tissue Expression of the Gene for Neutrophil Gelatinase-Associated Upocalin from Humans", Genomics, 45:17-23,1997.
Cristianini et al. "An Introduction to Support Vector Machines and Other Kernel-Based Learning Methods: Contents", Cambridge University Press, 4 P., 2000.
Crowe et al. "Quantitative lmmunocytofluorographic Analysis of CD4 Surface Antigen Expression and HIV Infection of Human Peripheral Blood Monocyte/Macrophages", Aids Research and Human Retroviruses, 3(2): 135-145, 1987.
Cummins et al. "The TRAIL to Viral Pathogenesis: The Good, the Bad and the Ugly", Current Molecular Medicine, XP055056835, 9(4): 495-505, May 1, 2009.
Dirke et al. "TRAIL and DcR1 Expressions Are Differentially Regulated in the Pancreatic Islets of STZ- Versus CY-AppHed NOD Mice", Experimental Diabetes Research, Article ID 625813, pp. 1-11, 2011.
Duda et al. "Contents", Pattern Classification, 2nd Ed., 11 P., 2001.
Eberl et al. "A Rapid Crosstalk of Human gamma delta T Cells and Monocytes Drives the Acute Inflammation in Bacterial Infections", PLOS Pathogens 5(2): 1-16, 2009.
Falschlehner et al. "Following TRAIL's Path in the Immune System", Immunology, XP055056763, 127(2): 145-154, Jun. 1, 2009. Chapter 'TRAIL in Viral and Bacterial Infections'.
Fcczor ct al. "Molccular Charactcrization of thc Acutc Inflammatory Rcsponsc to Infcctions With Gram-Ncgaitvc Vcrsus Gram-Positivc Bactcria", Infcction and Immunity, 71(10): 5803-5813, Oct. 2003.

(56) References Cited

OTHER PUBLICATIONS

Forde et al. "The Beneficial Pleiotropic Effects of Tumour Necrosis Factor-Related Apoptosis-Inducing Ligand (TRAIL) Within the Vasculature: A Review of the Evidence", Atherosclerosis, XP029468976, 247: 87-96, Available Online Feb. 9, 2016.

Furey et al. "Support Vector Machine Classification and Validation of Cancer Tissue Samples Using Microarray Expression Data", Bioinformatics, 16(10): 906-914, Oct. 2000.

Greenspan et al. "Defining Epitopes: It's Not as Easy as It Seems", Nature Biotechnology, 17: 936-937, Oct. 1999.

Halminen et al. "Expression of MxA Protein in Blood Lymphocytes Discriminates Between Viral and Bacterial Infections in Febrile Children", Pediatric Research, 41(5): 647-650, May 1997.

Hanley et al. "A Method of Comparing the Areas Under Receiver Operating Characteristics Curves Derived From the Same Cases", Radiology, 148(3): 839-843, Sep. 1983.

Hastie et al. "The Elements of Statistical Learning: Data Mining, Inference, and Prediction", Springcer Serics in Statistics, 2nd Ed., p. 1-745, 2001.

Henriquez-Camacho et al. "Biomarkers for Sepsis"; BioMed Research International, 547818: 6 pages, 2014.

Herzig et al. "The Role of CXCL10 in the Pathogenesis of Experimental Septic Shock", Critical Care, 18(3): R113-1-R113-18, Jun. 2, 2014.

Hinson et al. "Viperin Is Highly Induced in Neutrophils and Macrophages during Acute and Chronic Lymphocytic Choriomeningitis Virus Infection", The Journal of Immunology, 184:5723-5731, 2010.

Hoffmann et al. "TRAIL Limits Excessive Host Immune Responses in Bacterial Meningitis", JCI The Journal of Clinical Investigation, 117(7): 2004-2013, Jul. 2, 2007.

Holland et al. "STAT3 Mutations in the Hyper-IgE Syndrome", The New England Journal of Medicine, 357(16): 1608-1619, Oct. 18, 2007.

Janols et al. "Lymphocyte and Monocyte Flow Cytometry Immunophenotyping as a Diagnostic Tool in Uncharacteristic Inflammatory Disorders", BMC Infectious Diseases, XP002663504, 10(205): 1-9, 2010. Abstract.

Jenner et al. "Insights Into Host Responses Against Pathogens From Transcriptional Profiling", Nature Review Microbiology, 3: 281-294, Apr. 2005.

Ju et al. "Research Progress of Some Inflammatory Markers in Infectious Diseases", Chinese Journal of Practical Internal Medicine, 30(Suppl.1): 80-81, Jun. 2010.

Ju et al. "Research Progress of Some Inflammatory Markers in Infectious Diseases", Chinese Journal of Practical Internal Medicine, 30(Suppl.1): 80-81, Jun. 2010. With an English Translation.

Kaizer et al. "Gene Expression in Peripheral Blood Mononuclear Cells From Children With Diabetes", The Journal of Clinical Endocrinology & Metabolism, 92(9): 3705-3711, 2007.

Kang et al. "Low serum TNF-Related Apoptosis-Inducing Ligand (TRAIL) Levels Are Associated with Acute Ischemic Stroke Severity", Atherosclerosis, 240: 228-233, 2015.

Kawada et al. "Analysis of Gene-Expression Profiles by Oligonucleotide Microarray in Children With Influenza", Journal of General Virology, 87: 1677-1683, 2006.

Kichev et al. "Tumor Necrosis Factor-Related Apoptosis-Inducing Ligand (TRAiL) Signaling and Cell Death in the Immature Central Nervous System after Hypoxia-Ischemia and Inflammation", Journal of Biological Chemistry 289(13): 9430-9439, 2014.

Kohavi et al. "Wrappers for Feature Subset Selection", Artifical Intelligence, 97: 273-324, 1997.

Kotelkin et al. "Respiratory Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.

Lampe et al. "Expression of the Interferon-Induced MxA Protein in Viral Encephalitis", Neuropathology and Applied Neurobiology, 29(3): 273-279, May 27, 2003.

Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501, 5(Suppl.1): 28S-32S, 1998. Abstract.

Leibovici et al. "The Benefit of Appropriate Empirical Antibiotic Treatment in Patients with Bloodstream Infection", Journal of Internal Medicine, 244(5): 379-386, Nov. 1, 1998.

Liabeuf et al. "The Circulating Soluble TRAIL Is a Negative Marker for Inflammation Inversely Associated With the Mortality Risk in Chronic Kidney Disease Patients", Nephrology Dialysis Transplantation, XP055497900, 25(8): 2596-2602, Advance Access Publication Feb. 26, 2010. Abstract, p. 2597, Right Col., 2nd Para, Figs.2, 3.

Liu et al. "Early Days: Genomics and Human Responses to Infection", Current Opinion in Microbiology, 9: 312-319, Available Online May 6, 2006.

Lloyd et al. "Modelling The Human Immune Response: Performance of a 1011 Human Antibody Repertoire Against a Broad Panel of Therapeutically Relevant Antigens", Protein Engineering, Design & Selection 22(3): 159-168, Oct. 29, 2008.

Ludwig et al. "Tumor Necrosis Factor Related Apoptosis Inducing Ligand: A Novell Mechanism for Bacillus Calmette Guerin Induced Antitumor Activity" Cancer Research 64: 3386-3390, May 15, 2004.

Malcolm et al. "Microarrays Analysis of Lipopolysaccharide-Treated Human Neutrophils", American Journal of Physiology, Lung Cellular & Molecular Physiology, 284(4): L663-L670, First Published Dec. 20, 2002.

Michowitz et al. "The Involvement of Tumor Necrosis Factor-Related Apoptosis-Inducing Ligand(TRAIL) in Atherosclerosis.", Journal of the American College of Cardiology, 45(7): 1018-1024, 2005.

Mount "Bioinformatics: Sequence and Genome Analysis", Chaps. 1-10: 1-564, 2001.

Nakabayashi et al. "MxA-Based Recognition of Viral Illness in Febrile Children by a Whole Blood Assay", Pediatric Research, 60(6): 770-774, 2006.

Neu et al. "Expression of Tumor Necrosis Factor-Alpha-Related Apoptosis-Inducing Ligand and Its Proapoptotic Receptors Is Down-Regulated during Gastric Infection with Virulent cagA+/vacAsl+ Helicobacter pylori Strains", The Journal of Infectious Diseases 191(4): 571-578, Feb. 15, 2005.

New England Biolabs "New England Biolabs Catalog", New England Biolabs, 1-4 pages, 1996.

Ng et al. "IP-10 Is an Early Diagnostic Marker for Identification of Late-Onset Bacterial Infection in Preterm Infants", Pediatric Research, 61(1): 93-98, Jan. 2007.

Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.

Niessner et al. "Prognostic Value of Apoptosis Markers in Advanced Heart Failure Patients", European Heart Journal, XP055497907, 30(7): 789-796, Published Online Feb. 4, 2009. Abstract, Table 2, Fig.2.

Oda et al. "A Comprehensive Map of the Toll-Like Receptor Signaling Network", Molecular Systems Biology, 2(2006.0015): 1-20, Apr. 18, 2006.

Osmancik et al. "Prognostic Value of TNF-Related Apoptosis Inducing Ligand (TRAIL) in Acute Coronary Syndrome Patients", PLoS One, 8(2): e53860, 2013.

Oved et al. "A Novel Host-Proteome Signature for Distinguishing Between Acute Bacterial and Viral Infections", PLOS ONE, XP055456891, 10(3): e0120012-1-e120012-18, Mar. 18, 2015. Figs. 3C, 4.

Padlan "X-Ray Crystallography of Antibodies", Advances in Protein Chemistry, 49: 57-133; 1996.

Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.

Pepe et al. "Combining Diagnostic Test Results to Increase Accuracy", Biostatistics, XP055033234, 1(2): 123-140, Jun. 2000.

(56) References Cited

OTHER PUBLICATIONS

Povoa et al. "C-Reactive Protein, An Early Marker of Community-Acquired Sepsis Resolution: A Multi-Center Prospective Observational Study", Critical Care, 15(4): R169-1-R169-10, Published Online Jul. 15, 2011.
Radom-Aizik et al. "Effects of 30 Min. of Aerobic Exercise on Gene Expression in Human Neutrophils", Journal of Applied Physiology, 104: 236-243, 2008.
Ramilo et al. "Gene Expression Patterns in Blood Leukocytes Discriminate Patients With Acute Infections", Blood, 109(5): 2066-2077, Mar. 1, 2007.
RayBiotech "Mouse L308 Array, Membrane [AAM-BLM-1]1-Series-308-Label-Based-Mouse-Cytok", RayBiotech, XP055473187, Retrieved From the Internet, 7 P., May 7, 2018.
Rosseau et al. "Comparative Transcriptional Profiling of the Lung Reveals Shared and Distinct Features of *Streptococcus pneumoniae* and Influenza A Virus Infection", Immunology, 120: 380-391, 2006.
Rothstein et al. "Chronic Inhibition of Superoxide Dismutase Produces Apoptotic Death of Spinal Neurons", PNAS, (10): 4155-4159, May 1994.
Rudikoff et al. "Single Amino Acid Substitution Altering Antigen-Binding Specificity", PNAS, 79(6): 1979-1983, Mar. 1982.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80, Mar. 2002.
Secchiero et al. "Potential Prognostic Significance of Decreased Serum Levels of TRAIL After Acute Myocardial Infarction", PLoS ONE, XP055056988, 4(2): e4442-1-e4442-6, Feb. 16, 2009. Fig. 1.
Shair et al. "Epstein-Barr Virus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
Shimetani et al. "Levels of Three Inflammation Markers, C-Reactive Protein, Serum Amyloid A Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.
Shommu et al. "Metabolomic and Inflammatory Mediator Based Biomarker Profiling as a Potential Novel Method to Aid Pediatric Appendicitis Identification", PLOS ONE, XP055692841, 13(3): e0193563-1-e0193563-13, Mar. 12, 2018.
Singer et al. "The Third International Consensus Definitions for Sepsis and Septic Shock (Sepsis-3)", Journal of the American Medical Association, JAMA, 315(8): 801-810, Feb. 23, 2016. Box 3, Fig.
Smith et al. "Quantitative Assessment of Human Whole Blood RNA as a Potential Biomarker for Infectious Disease", Analyst, 132: 1200-1209, First Published Oct. 31, 2007.
Sukumaran et al. "Early Transcriptional Response of Human Neutrophils to Anaplasma Phagocytophilum Infection", Infection and Immunity, 73(12): 8089-8099, Dec. 1, 2005.
Sullivan Pepe et al. "Combining Diagnostic Test Results to Increase Accuracy", Biostatistics, XP055033234, 1(2): 123-140, Jun. 1, 2000. Abstract, Section 2.4.
Tang et al. "Gene-Expression Profiling of Gram-Positive and Gram-Negative Sepsis in Critically Ill Patients", Critical Care Medicine, 36(4): 1125-1128, 2008.
Tang et al. "Hypoxic Preconditioning Enhances the Benefit of Cardiac Progenitor Cell Therapy for Treatment of Myocardial Infarction by Inducing CXCR4 Expression", Circulation Research, XP055473182, 104(10): 1209-1216, May 22, 2009. Online Table 1.
Tang et al. "The Use of Gene-Expression Profiling to Identify Candidate Genes in Human Sepsis", American Journal of Respiratory and Critical Care Medicine, 176: 676-684, Originally Published Jun. 15, 2007.
ThermoFisher Scientific "Interferon Alpha Inducible Protein 27: IFI27", ThermoFisher Scientific, Product Details, 2 P., 2020.
ThermoFisher Scientific "Interferon Induced Protein 44 Like: IFI44L", ThermoFisher Scientific, Product Details, 2 P., 2020.
ThermoFisher Scientific "TaqMan Gene Expression Assay Solutions: Proven 5' Nuclease-Based Real-Time PCR Chemistry", Thermo Fisher Scientific, Applied Biosystems, 11 P., 2015.
Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, p. 220, r-h Col., Para 3-p. 222, r-h Col., Para 1.
Tian et al. "Soluble Tumor Necrosis Factor Related Apoptosis Inducing Ligand Level as a Predictor of Severity of Sepsis and the Risk of Mortality in Septic Patients", PLOS One, XP055497898, 8(12): e82204-1-e82204-5, Dec. 12, 2013.
Tisato et al. "Low Circulating TRAIL Levels Are Associated With Increase of Resistin and Lipocalin-2/ngal Adipokines in Postmenopausal Women", Mediators of Inflammation, Article ID 5356020, 8 Pages, 2017.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones, Carotenoids, Inflammatory Markers, and Proteomics as Examples", Cancer Epidemiol Biomarkers and Prevention, 15(9): 1578-1581, Sep. 2006.
UCSC "UCSC Browser on Human Feb. 2009 (GRCh37/hg19) Assembly: Showing Location of Probes on the Affymetrix ExonChip Binding to Exons of ANKRD22", UCSC Browser, XP055621243, Retrieved From the Internet, 7 P., Jan. 2009.
UCSC "UCSC Genome Browser on Human Feb. 2009 (GRCh37/hg19) Assembly: Showing Location of Probes on the Affymetrix ExonChip Binding to Exons of AIM2", UCSC Browser, XP055621240, Retrieved From the Interent, 8 P., Jan. 2009.
Vapnik "Statistical Learning Theory", Adaptive and Learning Systems for Signal Processing, Communications, and Control, p. 1-732, 1998.
Vogel et al. "Sequence Signatures and mRNA Concentration Can Explain Two-Thirds of Protein Abundance Variation in A Human Cell Line", Molecular Systems Biology, 6(Art.400): 1-9, Published Online Aug. 24, 2010.
Volpato et al. "Association of Tumor Necrosis Factor-Related Apoptosis-Inducing Ligand with Total and Cardiovascular Mortality in Older Adults", Atherosclerosis, 215: 452-458, 2011.
Wang et al. "Rotavirus Infection Alters Peripheral T-Cell Homeostasis in Children With Acute Diarrhea", Journal of Virology, 81(8): 3904-3912, Apr. 2007.
Whiteside et al. "Role of Human Natural Killer Cells in Health and Disease", Clinical and Diagnostic Laboratory Immunology, 1(2): 125-133, Mar. 31, 1994.
Xu et al. "Lipocalins as Biochemical Markers of Disease", Biochimica et Biophysica Acta, XP002376345, 1482(1): 298-307, Oct. 18, 2000.
Yamaji et al. "Significance of Eukaryotic Translation Elongation Factor 1A in Tobacco Mosaic Virus Infection", Archives of Virology, XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343, Published Online Jul. 18, 2013.
Zaas et al. "A Host-Based RT-PCR Gene Expression Signature to Identify Acute Respiratory Viral Infection", Science Translational Medicine, 5(203): 203ra126-1-203ra126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, p. 212, 1-h Col., p. 213, 1-h Col., Fig.4.
Zaas et al. "The Current Epidemiology and Clinical Decisions Surrounding Acute Respiratory Infections", Trends in Molecular Medicine, XP055522333, 20(10): 579-588, Published Online Sep. 5, 2014.

(56) References Cited

OTHER PUBLICATIONS

Zaas et al. Supplementary Materials for "A Host-Based RT-PCR Gene Expression Signature to Identify Acute Respiratory Viral Infection", Science Translational Medicine, 5(203): 203ra126-1-203ra126-21, Sep. 18, 2013.
Zhang et al. "Expression of Tumor Necrosis Factor-Related Apoptosis-Inducing Ligand in Serum of Severe Hepatitis Patients with Nosocomial Infections and its Clinical Significance", Chinese Journal of Nosocomiology, 24, Abstract, 2012.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zilliox et al. "Gene Expression Changes in Peripheral Blood Mononuclear Cells During Measles Virus Infection", Clinical and Vaccine Immunology, 14(7): 918-923, Jul. 2007.
Notice of Reason(s) for Rejection Dated Dec. 7, 2021 From the Japan Patent Office Re. Application No. 2020-021606 and Its Translation Into English. (11 Pages).
Notice of Allowance Dated Jan. 5, 2022 from US Patent and Trademark Office Re. U.S. Appl. No. 16/316,631. (9 pages).
Notification of Office Action Dated Dec. 3, 2021 From the State Intellectual Property Office of the People's Republic of China Re. Application No. 201780055014.5 and Its Translation Into English. (5 Pages).
Wang et al. "The significance of MMP-8, MMP-9 and FFN levels in pregnant women with bacterial vaginosis", Maternal and Child Health Care of China, vol. 28, No. 28, 2013, pp. 4615-4617.
Notification of Office Action and Search Report Dated Dec. 9, 2022 From the State Intellectual Property Office of the People's Republic of China Re. Application No. 202010215941.2. (11 Pages).
Summary Dated Dec. 22, 2022 of Notification of Office Action and Search Report Dated Dec. 9, 2022 From the State Intellectual Property Office of the People's Republic of China Re. Application No. 202010215941.2. (4 Pages).
Ip et al. "Value of serum procalcitonin, neopterin, and C-reactive protein in differentiating bacterial from viral etiologies in patients presenting with lower respiratory tract infections", Diagnostic Microbiology and Infectious Disease, 59(2): 131-136, Oct. 2007.
Pauksen et al. "Serum Mesurements of Human Neutrophil Lipocalin (HNL) Discriminate Between Acute Bacterial and Viral Infections", Scandinavian Journal of Clinical and Laboratory Investigation, 55(2):125-131, 1995.
Notice of Allowance Dated Mar. 2, 2022 from US Patent and Trademark Office Re. U.S. Appl. No. 16/081,069. (10 pages).
Grounds of Reason of Rejection Dated Jan. 27, 2022 From the Korean Intellectual Property Office Re. Application No. 10-2017-7007002. (6 Pages).
Notice of Allowance Dated Feb. 7, 2022 from US Patent and Trademark Office Re. U.S. Appl. No. 16/336,528. (46 pages).
Requisition by the Examiner Dated Feb. 9, 2022 From the Innovation, Science and Economic Development Canada, Canadian Intellectual Property Office Re. Application No. 2,954,601. (3 Pages).
Restriction Official Action Dated Feb. 4, 2022 from US Patent and Trademark Office Re. U.S. Appl. No. 17/007,095. (6 pages).
Examination Report Dated Apr. 14, 2022 From the Servico Publico Federal, Ministerio da Economia, Instituto Nacional da Propriedade Industrial do Brasil RE Application No. BR11 2017 002884 0 together with an English Summary and Pending Claims. ( Pages).
Requisition by the Examiner Dated Mar. 2, 2023 From the Innovation, Science and Economic Development Canada, Canadian Intellectual Property Office Re. Application No. 3,015,043. (5 Pages).
Notification of Office Action and Search Report Dated Dec. 2, 2022 From the State Intellectual Property Office of the People's Republic of China Re. Application No. 202010370187.X. (12 Pages).
Notification of Office Action Dated Aug. 29, 2023 From the State Intellectual Property Office of the People's Republic of China Re. Application No. 202010370187.X. (3 Pages).

Official Action Dated Aug. 29, 2023 from the US Patent and Trademark Office Re. U.S. Appl. No. 17/372,575. (144 pages).
Fosgerau et al. "Interleukin-6 Autoantibodies are Involved in the Pathogenesis of a Subset of Type 2 Diabetes", Journal of Endocrinology, 204: 265-273, 2010.
Gupta et al. "Dinstict Functions of Autoantibodies Against Interferon in Systemic Lupus Erythematosus", Arthritis & Rheumatology, 68(7): 1677-1687, Jul. 2016.
Meyer "Anti-CRP antibodies in Systemic Lupus Erythematosus", Joint Bone Spine, 77"384-389, Jun. 2, 2010.
Thermo Scientific "ELISA Technical Guide and Protocols", Thermo Scientific, TR0065.0, 2010 (14 Pages).
Examination Report Dated Nov. 1, 2023 From the Australian Government, IP Australia Re. Application No. 2022200802. (6 Pages).
Notice of Allowance Dated May 10, 2023 from the US Patent and Trademark Office Re. U.S. Appl. No. 17/875,467. (122 pages).
English Summary and Translation Dated Sep. 13, 2023 of Notification of Office Action Dated Aug. 29, 2023 From the State Intellectual Property Office of the People's Republic of China Re. Application No. 202010370187.X. (3 pages).
Hearing Notice Dated Sep. 9, 2023 From the Government of India, Intellectual Property India, The Patent Office Re. Application No. 201727005513. (3 Pages).
Communication Pursuant to Article 94(3) EPC Dated Jul. 21, 2023 From the European Patent Office Re. Application No. 21178885.6 (6 Pages).
CNKI English Translation of "Clinical Study on the Level of Plasma Tumor Necrosis Factor-Related Apoptosis-Inducing Ligand (TRAIL) in Evaluating the Prognosis of Patients With Sepsis", CNKI Master's E-Journals, 5: 4-26, Apr. 16, 2014.
English Summary Dated Jan. 25, 2024 of Decision on Rejection Dated Jan. 4, 2024 From the State Intellectual Property Office of the People's Republic of China Re. Application No. 202010370187.X (1 Page).
Communication Pursuant to Article 94(3) EPC Dated Oct. 30, 2023 From the European Patent Office Re. Application No. 17855164.4 (7 Pages).
Decision on Rejection Dated Jan. 4, 2024 From the State Intellectual Property Office of the People's Republic of China Re. Application No. 202010370187.X and Its Machine Translation Into English. (9 Pages).
Official Action Dated Oct. 26, 2023 from the US Patent and Trademark Office Re. U.S. Appl. No. 18/077,277. (252 pages).
Van Deursen et al. "Prognostic Value of Plasma Neutrophil Gelatinase-Associated Lipocalin for Mortality in Patients With Heart Failure", Circulation: Heart Failure, 7: 35-42, Jan. 2014.
Official Action Dated Jul. 17, 2023 from US Patent and Trademark Office Re. U.S. Appl. No. 17/717,200. (133 pages).
Liu et al. "CXCL10/IP-10 in Infectious Diseases Pathogenesis and Potential Therapeutic Implications", Cytokine & Growth Factor Reviews, 22(3): 121-130, Jun. 2011.
Requisition by the Examiner Dated Oct. 10, 2023 From the Innovation, Science and Economic Development Canada, Canadian Intellectual Property Office Re. Application No. 3,027,341. (5 Pages).
Notice of Allowance Dated Mar. 13, 2024 from the US Patent and Trademark Office Re. U.S. Appl. No. 17/372,575. (28 pages).
Official Action Dated Aug. 2, 2023 from the US Patent and Trademark Office Re. U.S. Appl. No. 16/081,069. (36 pages).
Restriction Official Action Dated Nov. 27, 2023 from the US Patent and Trademark Office Re. U.S. Appl. No. 17/010,912. (8 pages).
Communication Pursuant to Article 94(3) EPC Dated Jan. 31, 2024 From the European Patent Office Re. Application No. 17855163.6 (4 Pages).
Restriction Official Action Dated Feb. 1, 2024 from the US Patent and Trademark Office Re. U.S. Appl. No. 17/841,704. (6 pages).
Communication Pursuant to Article 94(3) EPC Dated Apr. 8, 2024 From the European Patent Office Re. Application No. 22169859.0. (6 Pages).
Notice of Allowance Dated Mar. 27, 2024 from the US Patent and Trademark Office Re. U.S. Appl. No. 17/717,200. (34 pages).

(56) References Cited

OTHER PUBLICATIONS

Official Action Dated Jun. 4, 2024 from the US Patent and Trademark Office Re. U.S. Appl. No. 16/081,069. (33 pages).
Official Action Dated Apr. 8, 2024 from the US Patent and Trademark Office Re. U.S. Appl. No. 17/010,912. (233 pages).
Official Action Dated May 8, 2024 from the US Patent and Trademark Office Re. U.S. Appl. No. 18/077,277. (63 pages).
Official Action Dated May 9, 2024 from the US Patent and Trademark Office Re. U.S. Appl. No. 17/841,704. (166 pages).
Official Action Dated Mar. 26, 2024 from the US Patent and Trademark Office Rc. U.S. Appl. No. 18/230,718. (67 pages).
Requisition by the Examiner Dated Apr. 5, 2024 From the Innovation, Science and Economic Development Canada, Canadian Intellectual Property Office Re. Application No. 3,190,715. (3 Pages).
Askarieh et al. "Systemic and Intrahepatic Interferon-Gamma-Inducible Protein 10 kDa Predicts the First-Phase Decline in Hepatitis C Virus RNA and Overall Viral Response to Therapy in Chronic Hepatitis C", Hepatology, 51: 1523-1530, 2010.
Bartolome et al. "Interleukin-28B Polymorphisms and Interferon Gamma Inducible Protein-10 Serum Levels in Seronegative Occult Hepatitis C Virus Infection", Journal of Medical Virology, 88(2):268-274, Feb. 2016.
Feld et al. "Plasma Interferon-Gamma-Inducible Protein-10 Levels Are Associated with Early, but Not Sustained Virological Response during Treatment of Acute or Early Chronic HCV Infection", PLoS One 8(11): e80003, 1-11, Nov. 20, 2013.
Grebely et al. "Plasma Interferon-gamma-Inducible Protein-10 (IP-10) Levels During Acute Hepatitis C Virus Infection", Hepatology 57(6): 2124-2134, Jun. 2013.
Haider et al. "C-Reactive Protein is Expressed and Secreted by Peripheral Blood Mononuclear Cells", Clinical and Experimental Immunology, 146: 533-539, 2006.
Lagging et al. "IP-10 Predicts Viral Response and Therapeutic Outcome in Difficult-to-treat Patients with HCV Genotype 1 Infection", Hepatolgy 44(6): 1617-1625, Dec. 2006.
Landro et al. "Decreased Serum Lipocalin-2 Levels in Human Immunodeficiency Virus-infected Patients: Increase During Highly Active Anti-retroviral Therapy", Clinical and Experimantal Immunology, 152: 57-63. 2008.
Nicholson et al. "Late-Breaking Abstract: Plasma Level of TRAIL is Associated with Severity of Sepsis and Predicts Survival After Critical Illness", European Respiratory Journal, 48:OA3021, pp. 1-5, Nov. 2016.
Reeeves "C-Reactive Protein", Australian Prescriber, 20(3): 74-76, Jun. 2007.
Sonneveld et al. "Pre-treatment Levels of IP-10 Predict Response to Peginterferon in HBeAg-positive Chronic Hepatitis B Patients 396", Hepatology 56(4): 386A-387A, Oct. 2012.
Stiver "The Treatment of Influenza With Antiviral Drugs", CMAJ, Canadian Medical Association, 168(1): 49-57, Jan. 7, 2003.
Suarez et al. "Superiority of Transcriptional Profiling Over Procalcitonin for Distinguishing Bacterial From Viral Lower respiratory Tract Infections in Hospitalized Adults", The Journal of Infectious Diseases, 212: 213-222, Jul. 15, 2015.

\* cited by examiner

STUDY FLOWCHART

Figures 2, 21A:
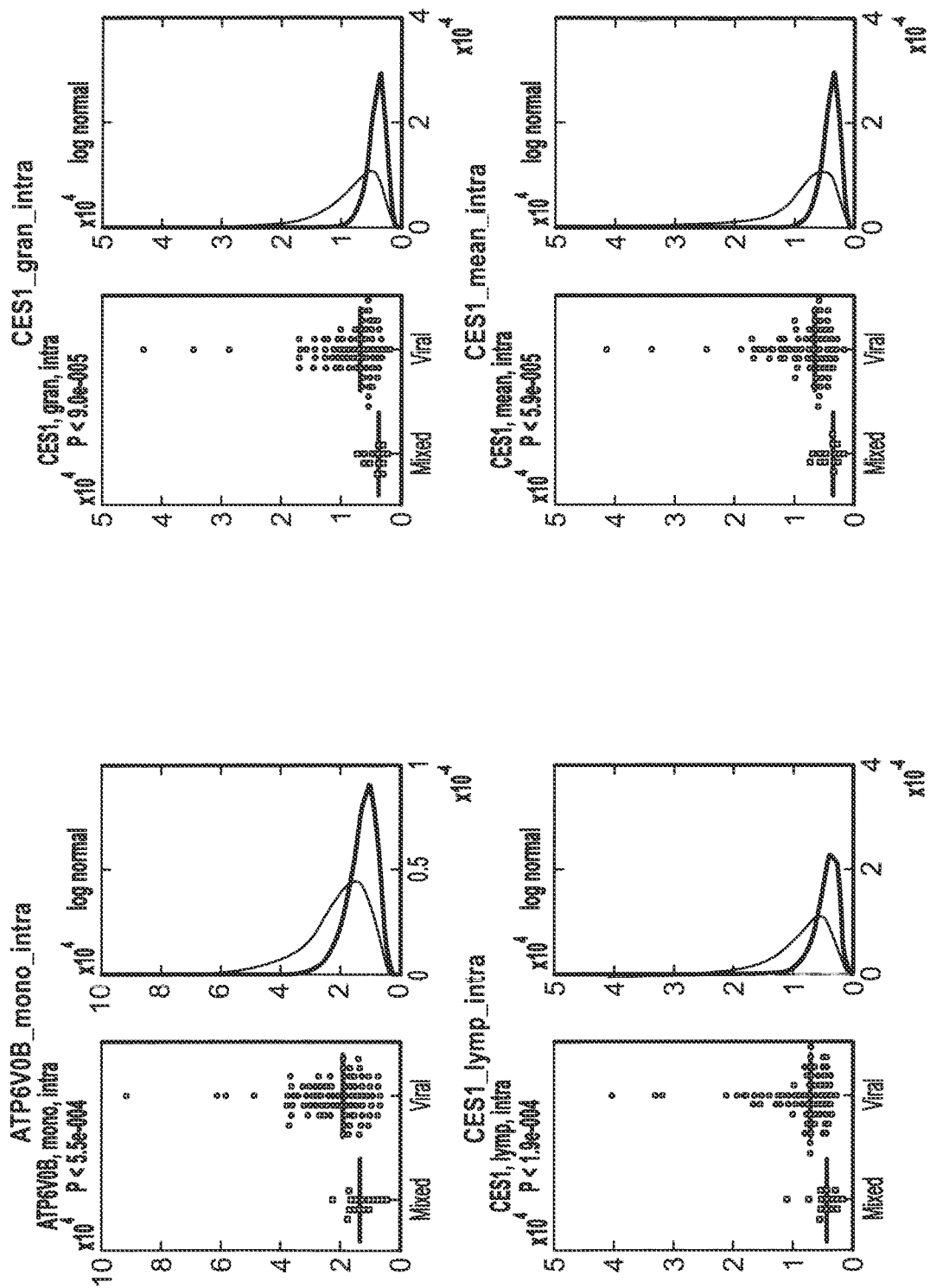

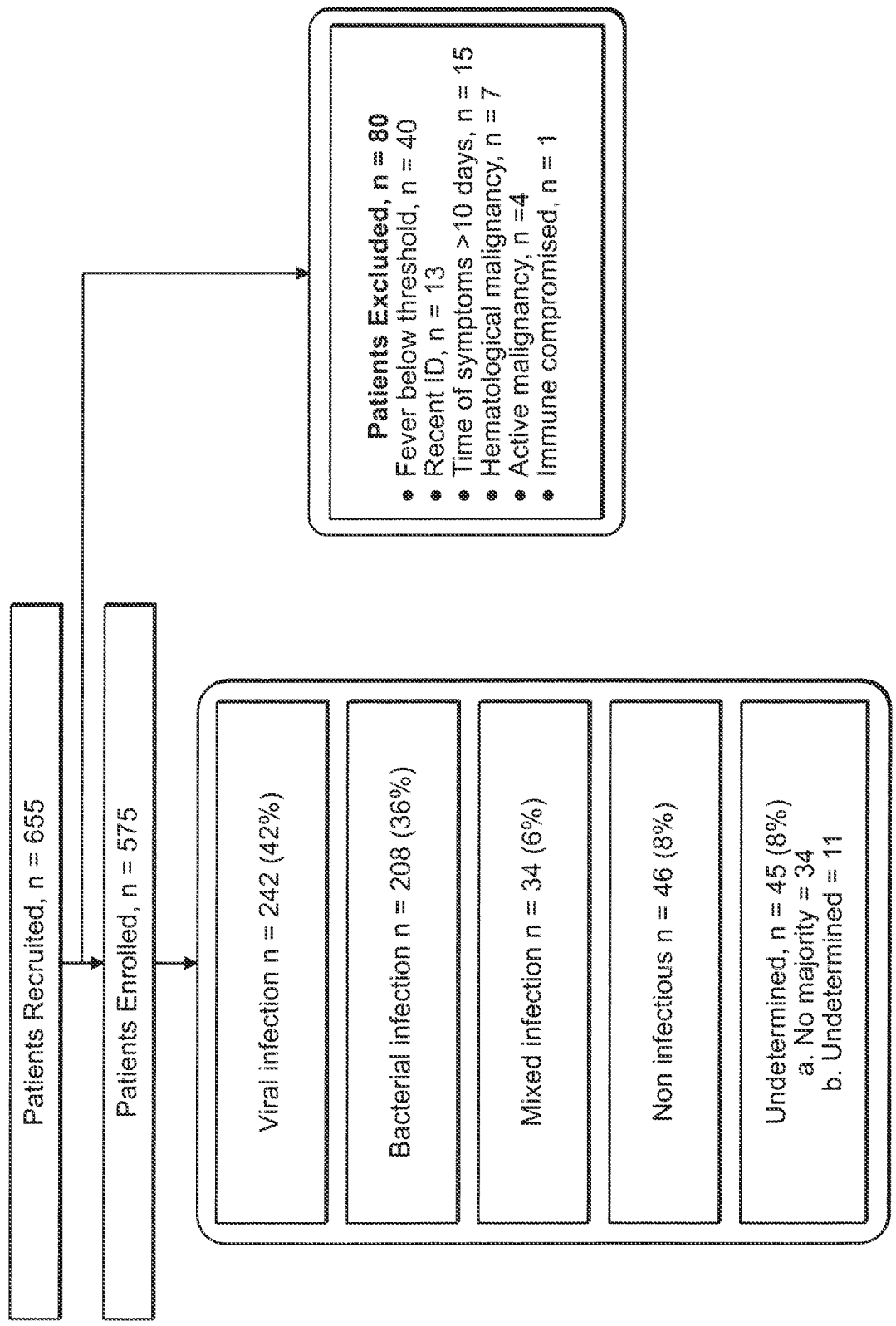
FIG. 2  PATIENT DISPOSITION: REFERENCE STANDARD-BASED DIAGNOSTIC LABELS.

Figures 3, 21A:
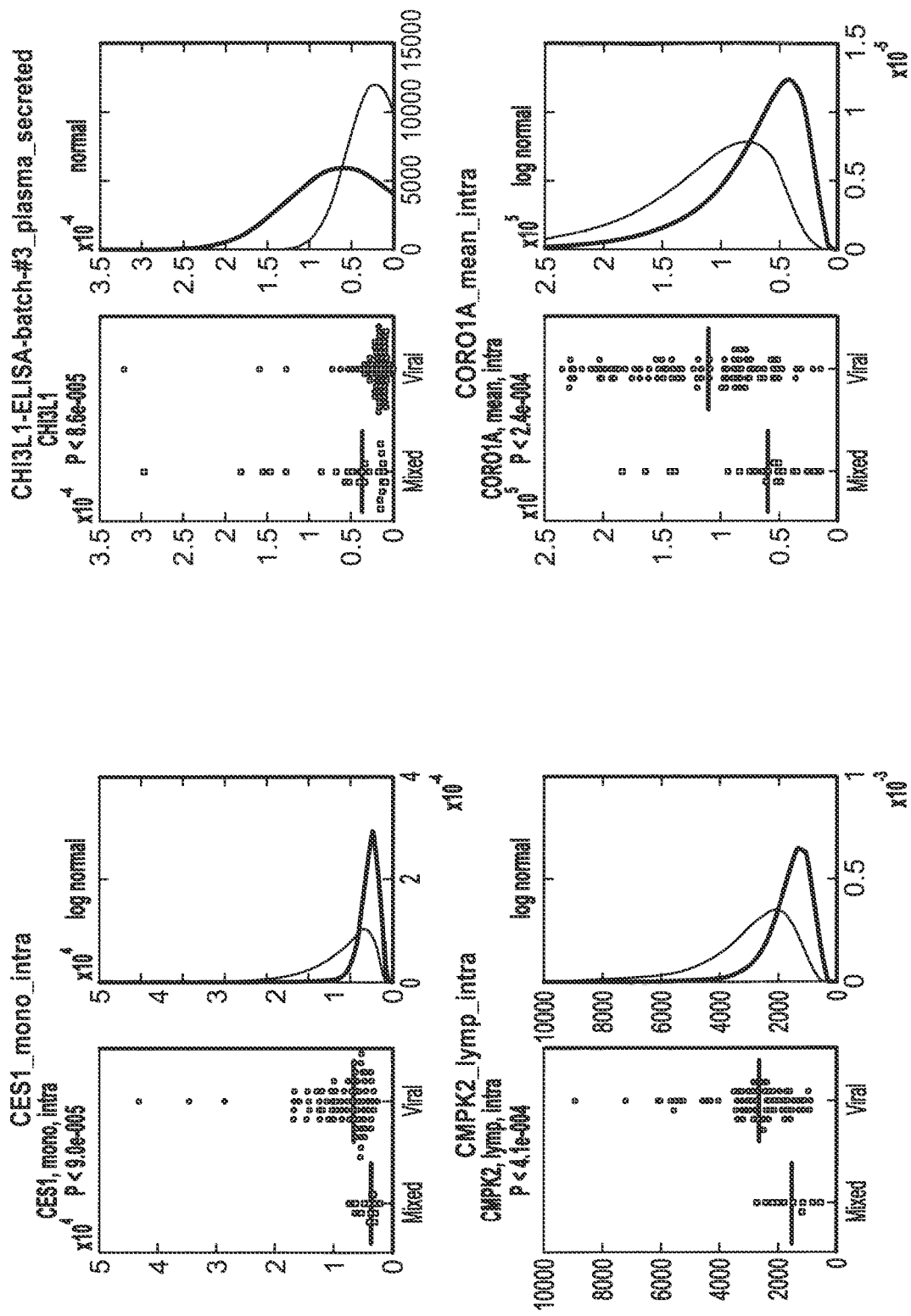
Figures 4, 21A:
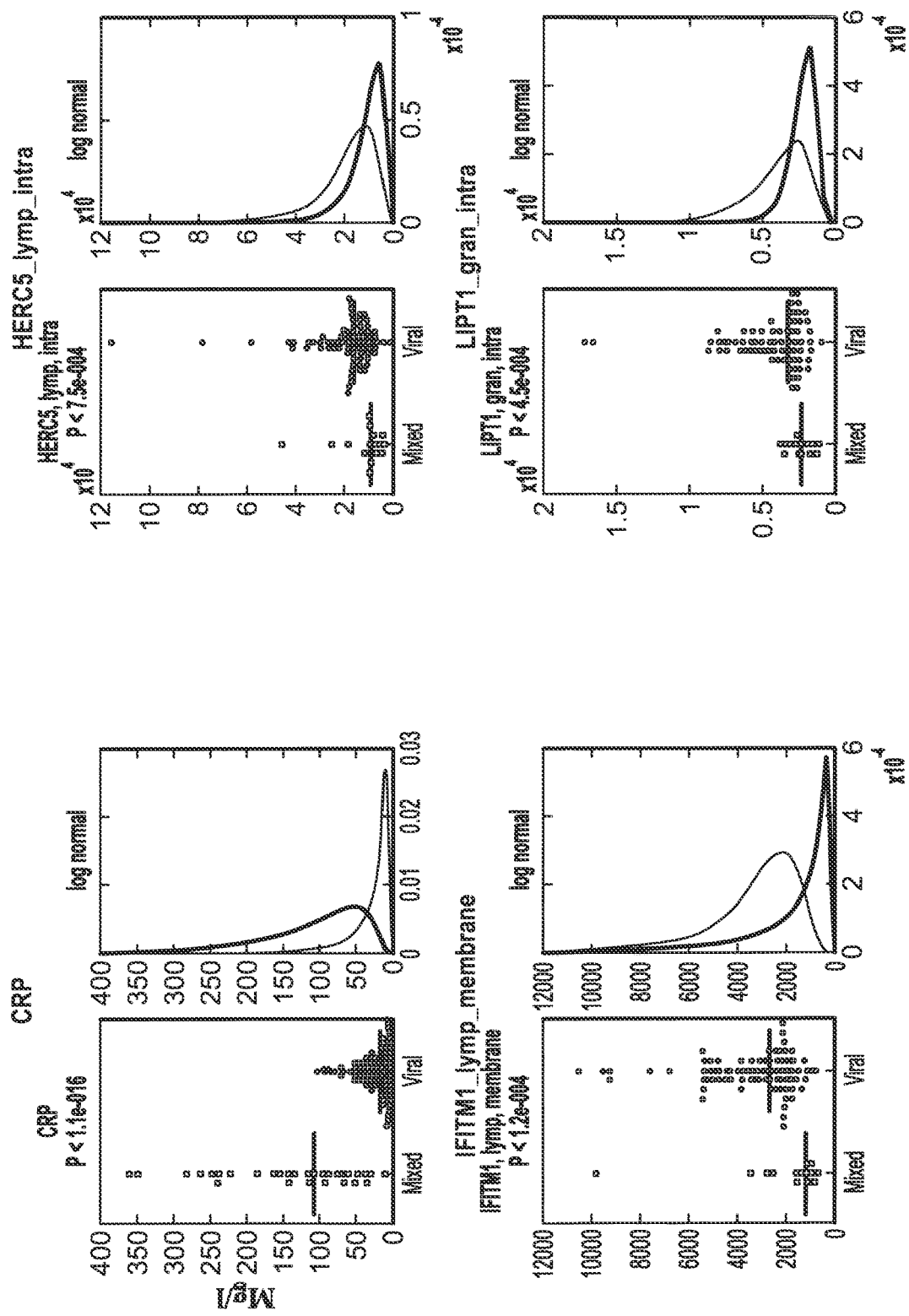
Figures 5, 21A:
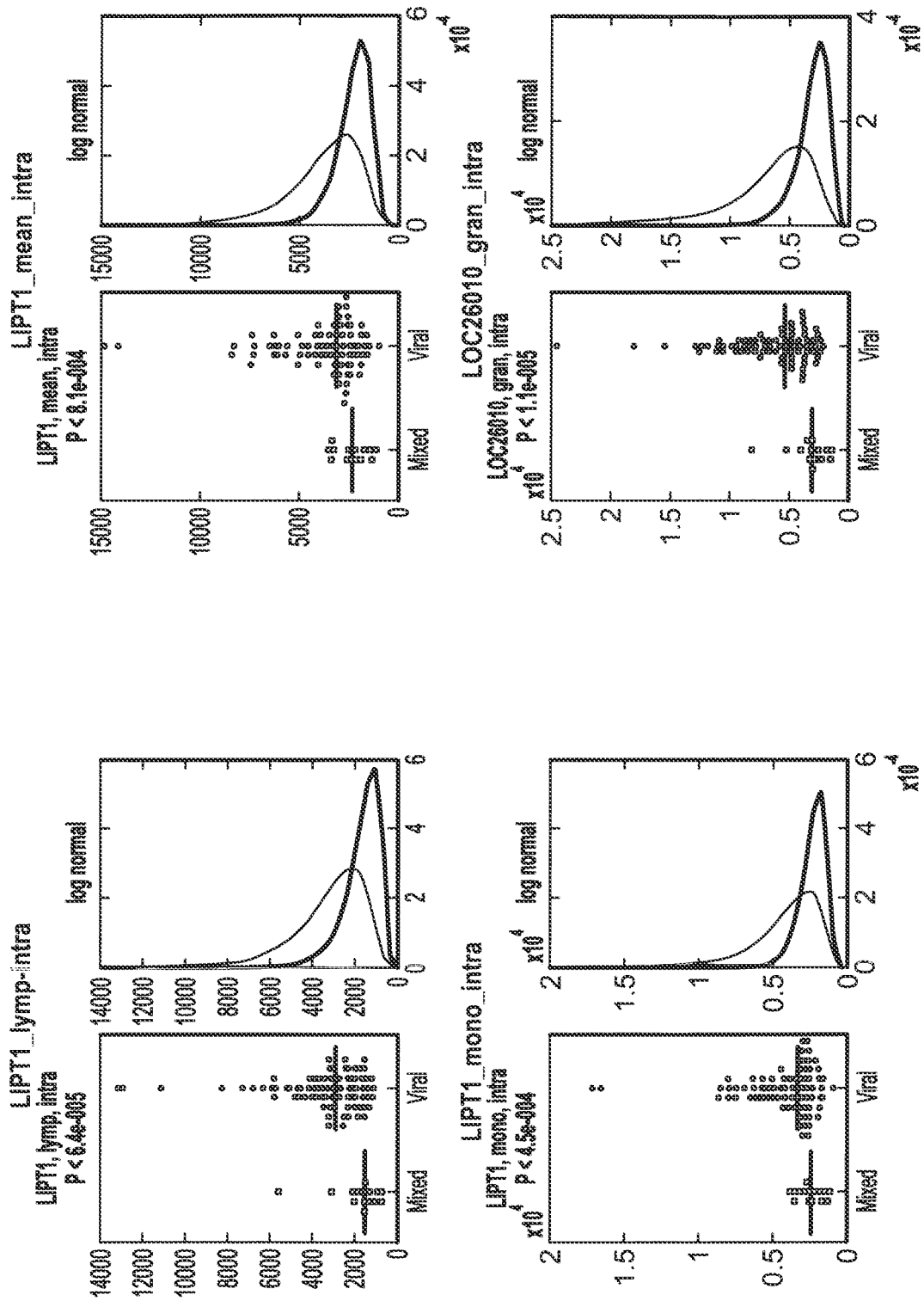

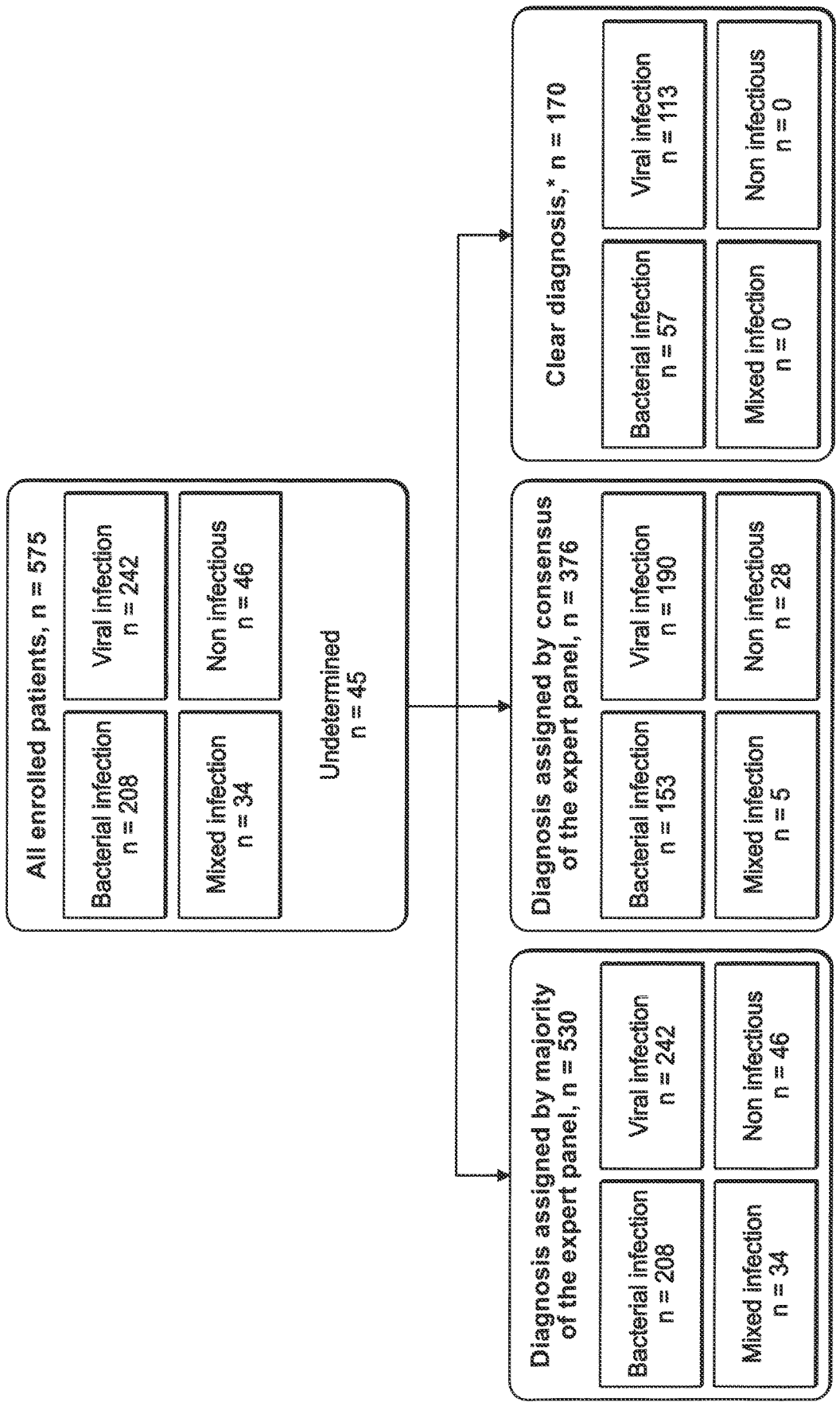
FIG. 3 SUMMARY OF PATIENT COHORTS

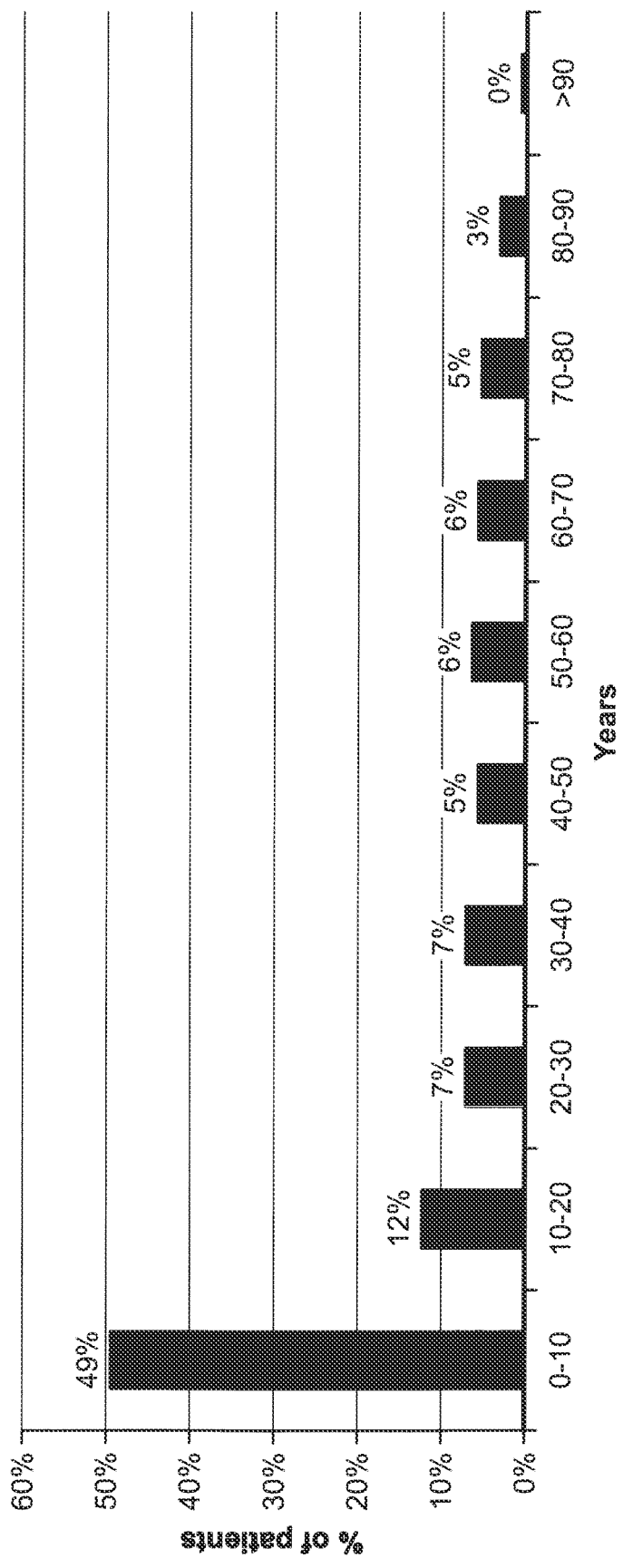
FIG. 4A AGE DISTRIBUTION OF THE STUDY POPULATION. THE ENTIRE STUDY POPULATION (N = 575)

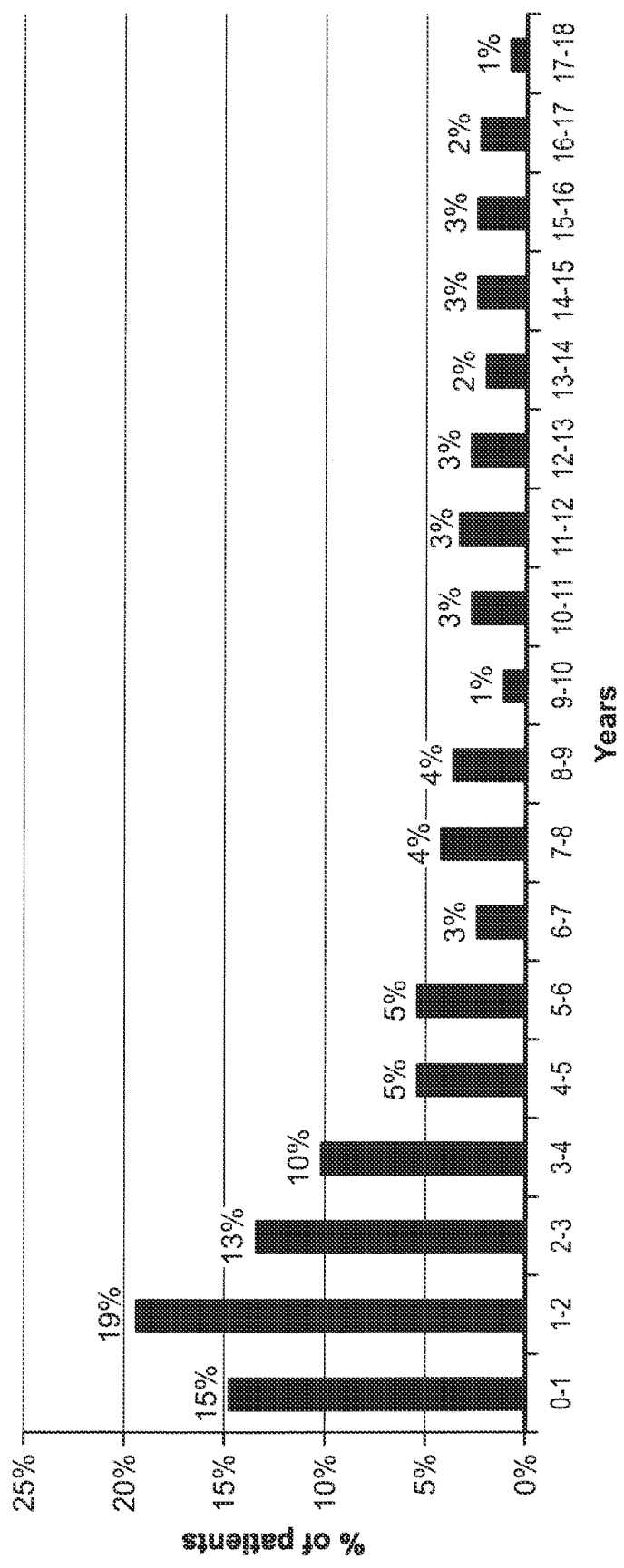
FIG. 4B AGE DISTRIBUTION OF THE STUDY POPULATION. PEDIATRIC PATIENTS ONLY (N = 350)

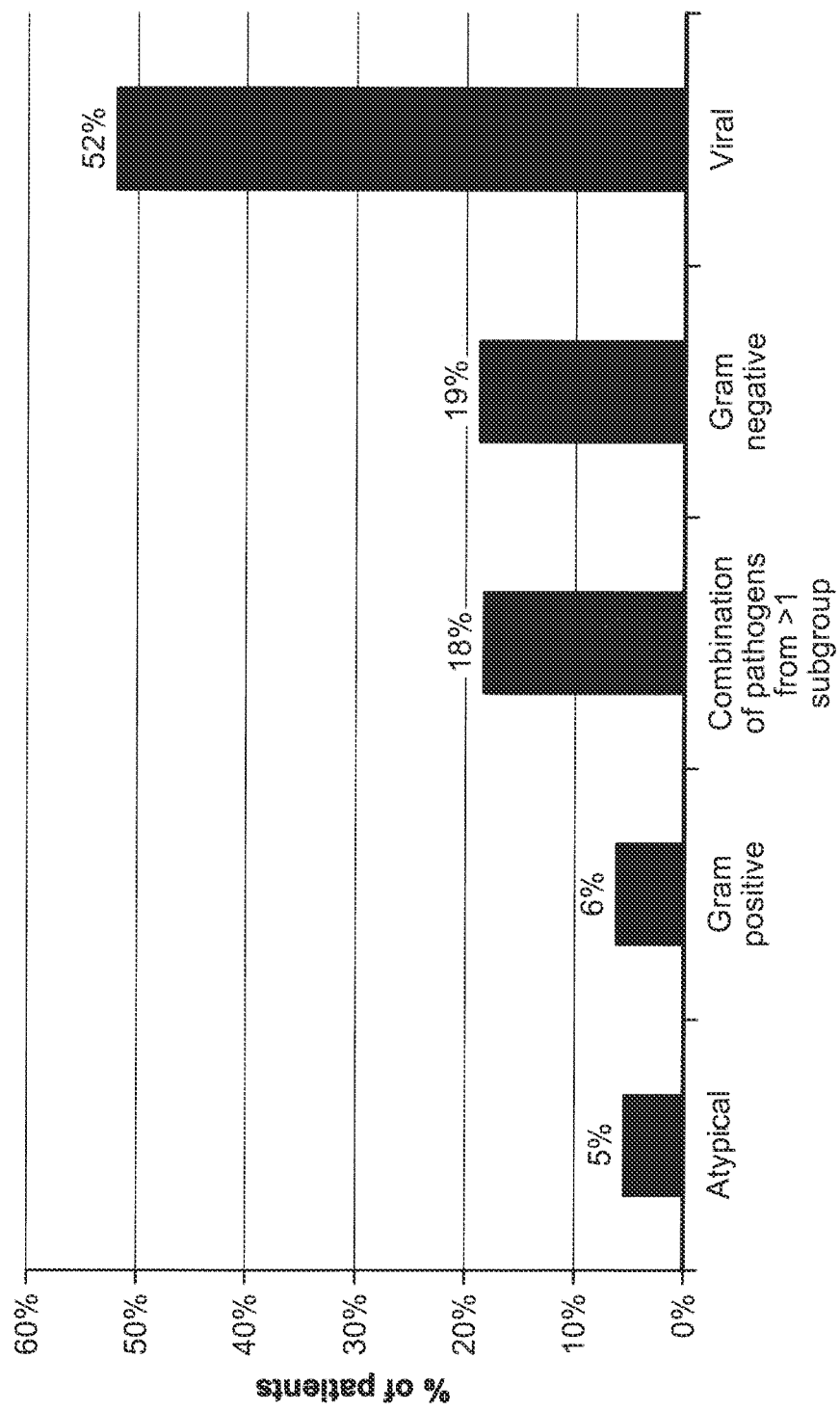
FIG. 5A PATHOGEN DISTRIBUTION.
DISTRIBUTION OF ISOLATED PATHOGENS BY PATHOGENIC SUBGROUPS

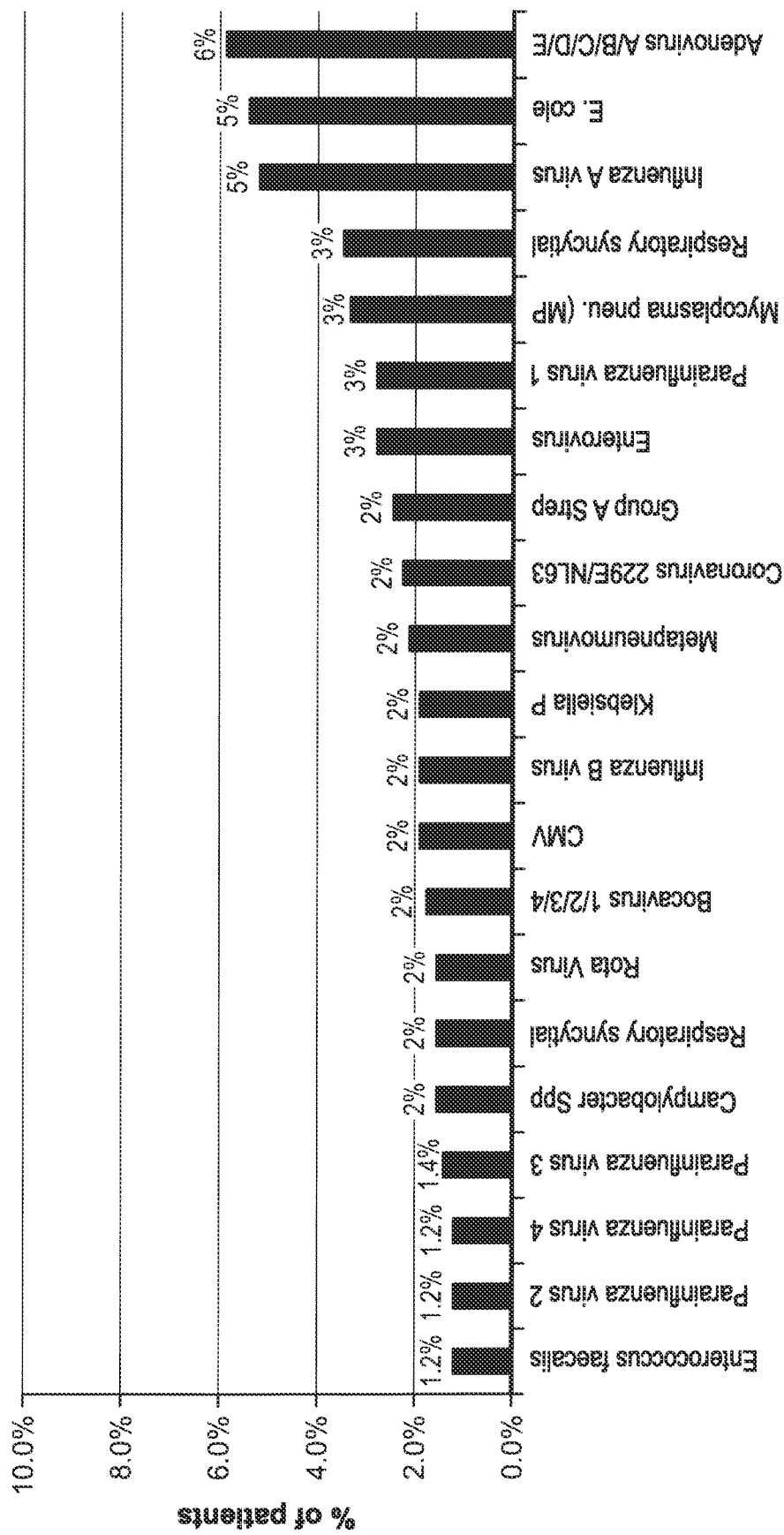
FIG. 5B PATHOGEN DISTRIBUTION.
DISTRIBUTION OF ISOLATED PATHOGENS BY STRAIN
(STRAINS ISOLATED FROM >1% OF PATIENTS ARE PRESENTED).

Figures 6, 21A:
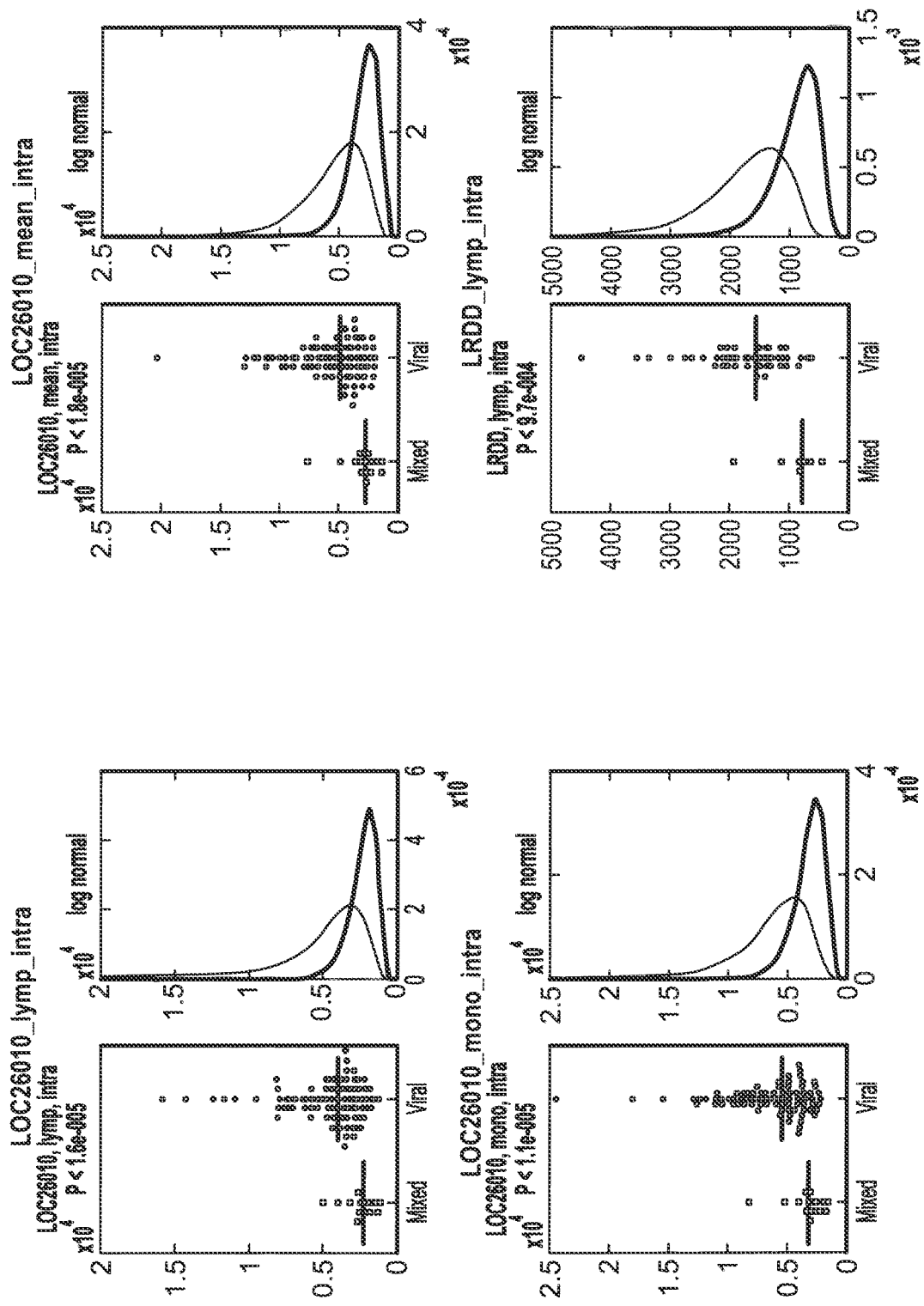

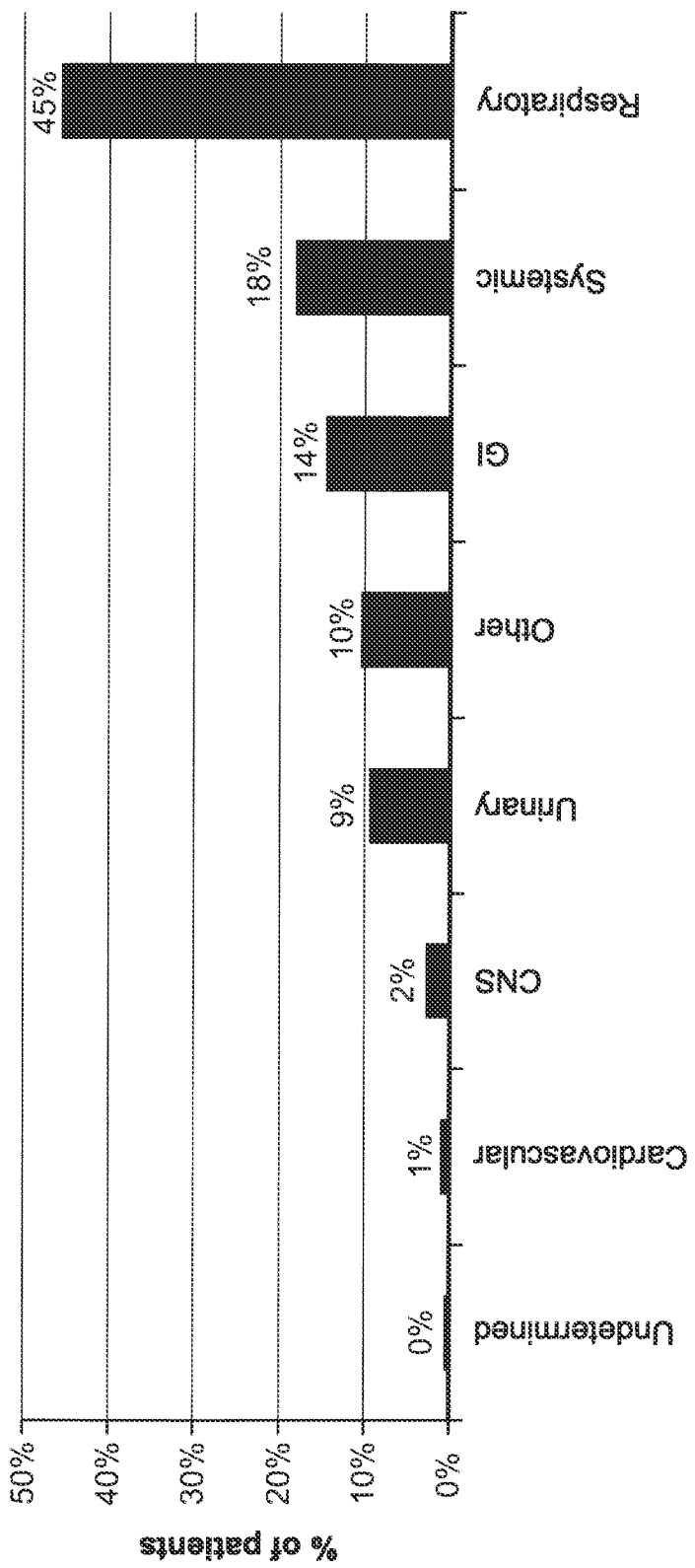
FIG. 6  DISTRIBUTION OF INVOLVED PHYSIOLOGIC SYSTEMS IN INFECTIOUS DISEASE PATIENTS (N = 484).

Figures 7, 21A:
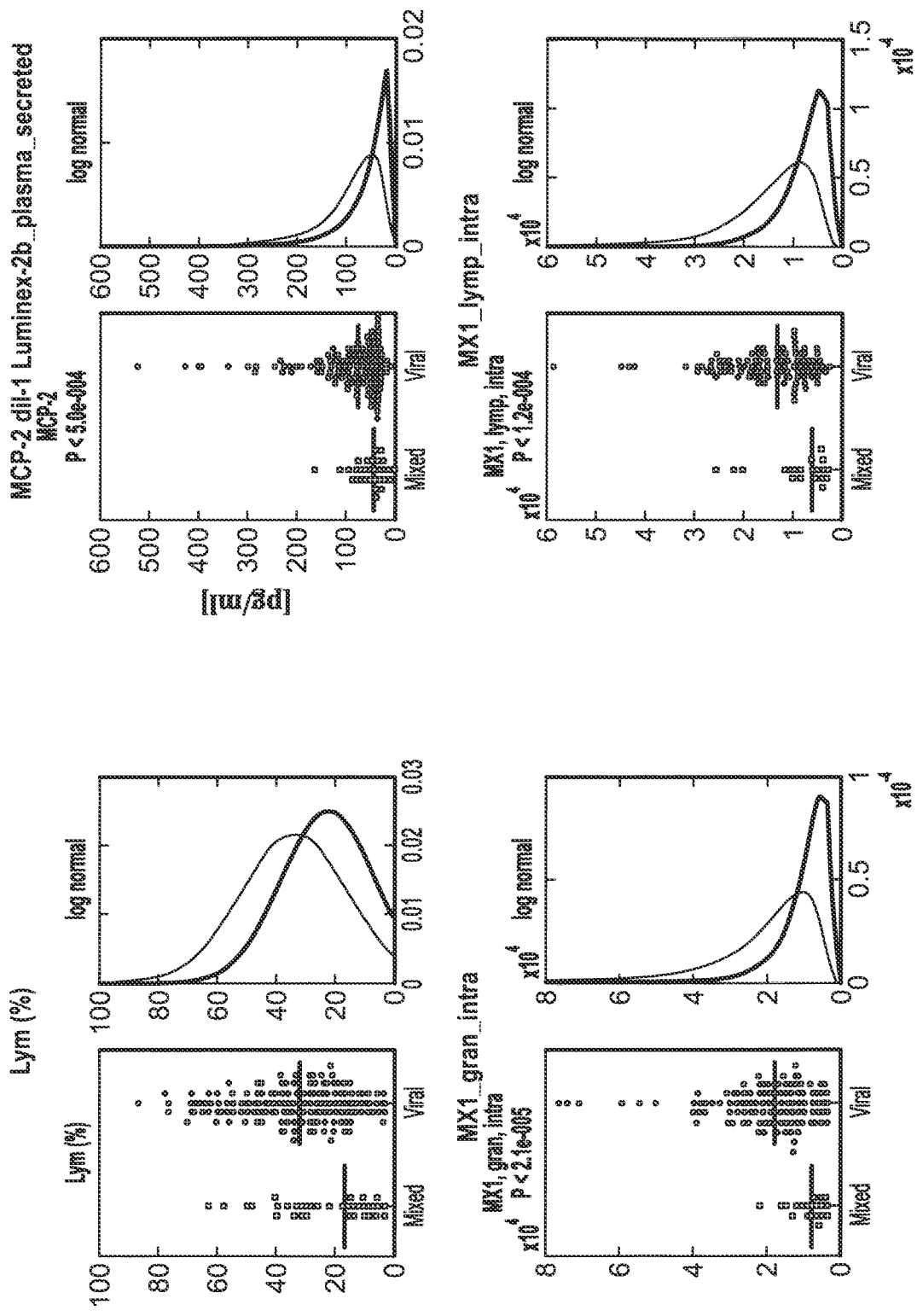

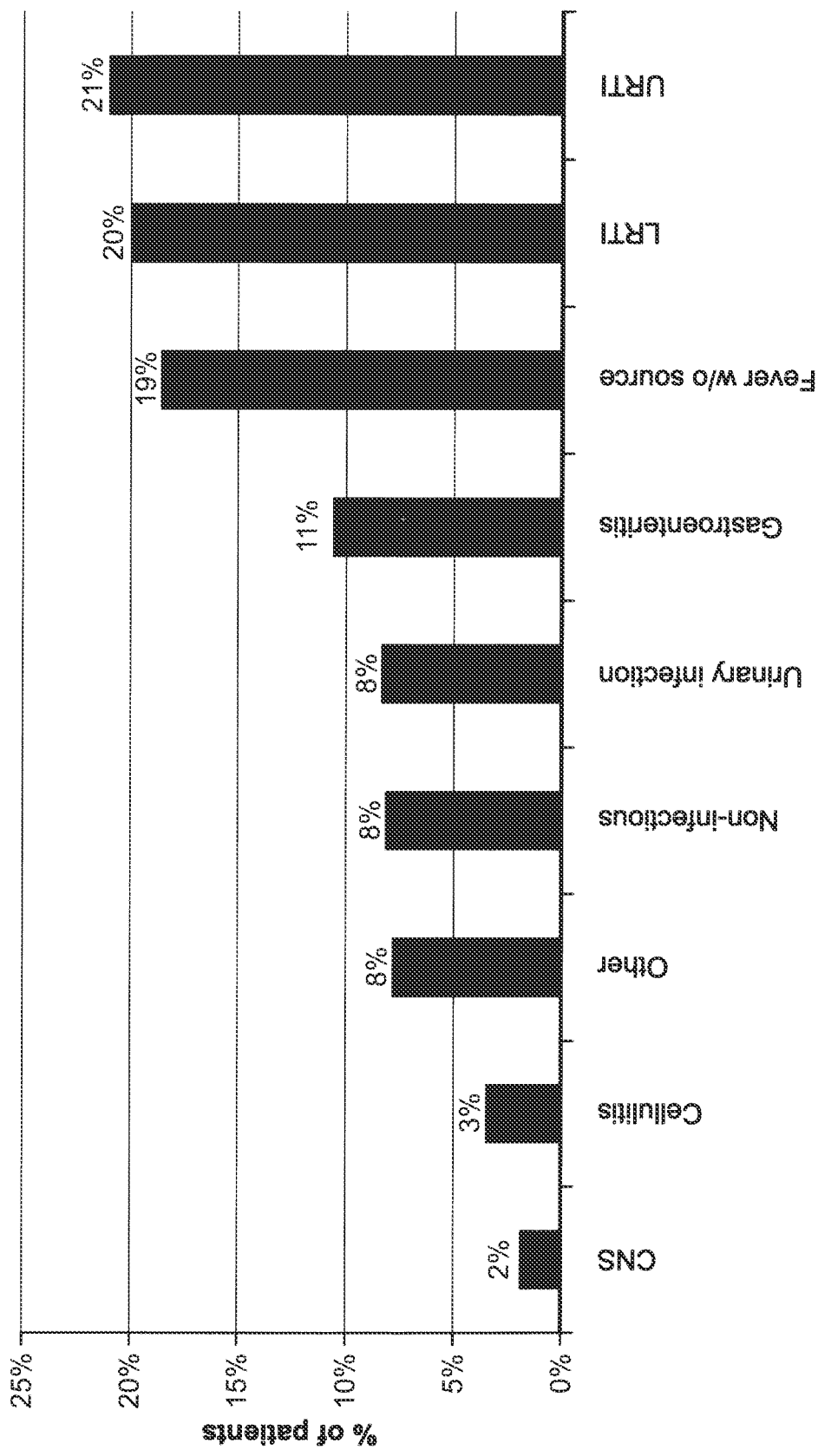
FIG. 7A  DISTRIBUTION OF CLINICAL SYNDROMES (ALL ENROLLED PATIENTS, N = 575). MAJOR CLINICAL SYNDROMES

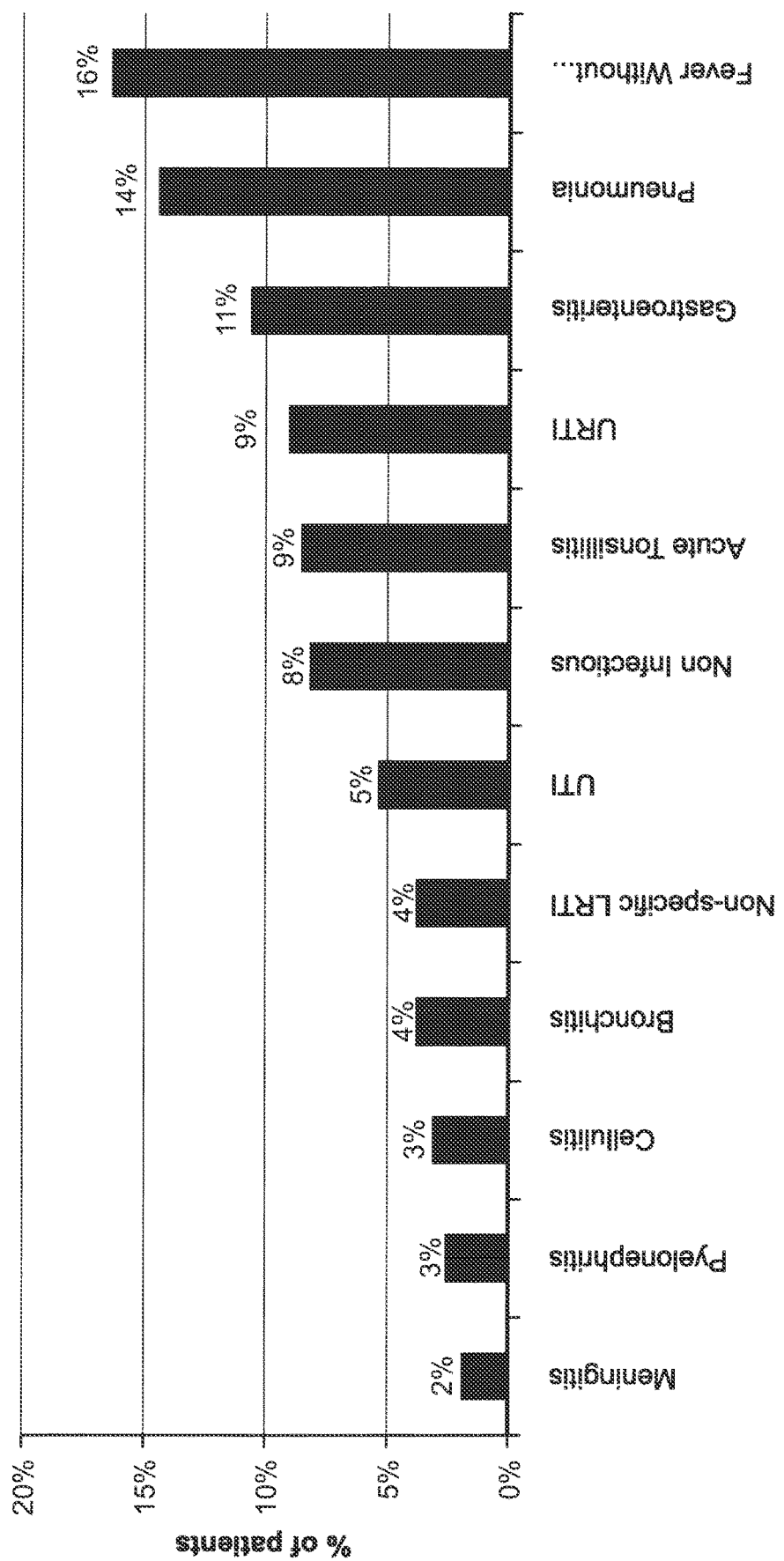
FIG. 7B  DISTRIBUTION OF CLINICAL SYNDROMES (ALL ENROLLED PATIENTS, N = 575). SPECIFIC CLINICAL SYNDROMES.

Figures 8, 21A:
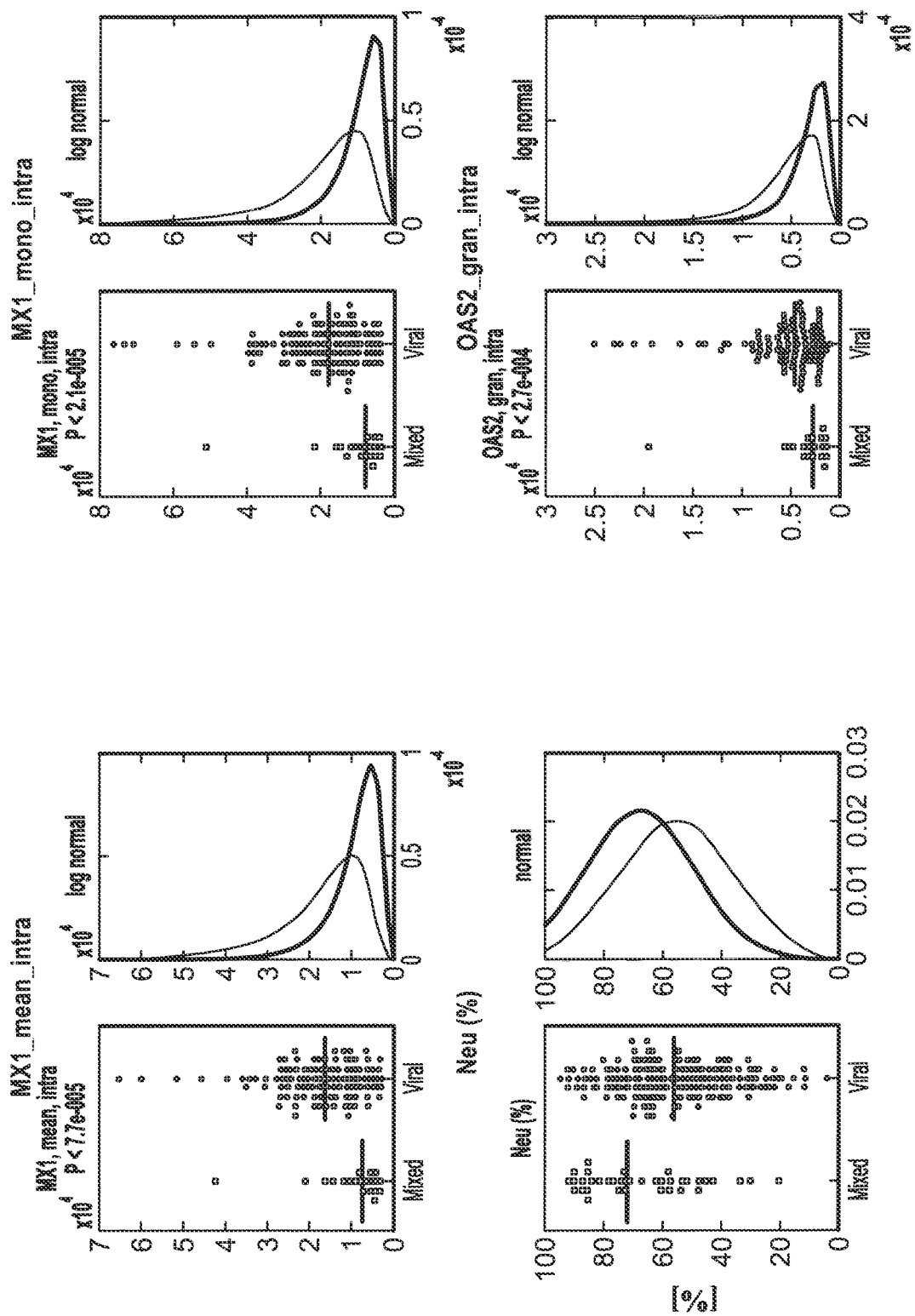

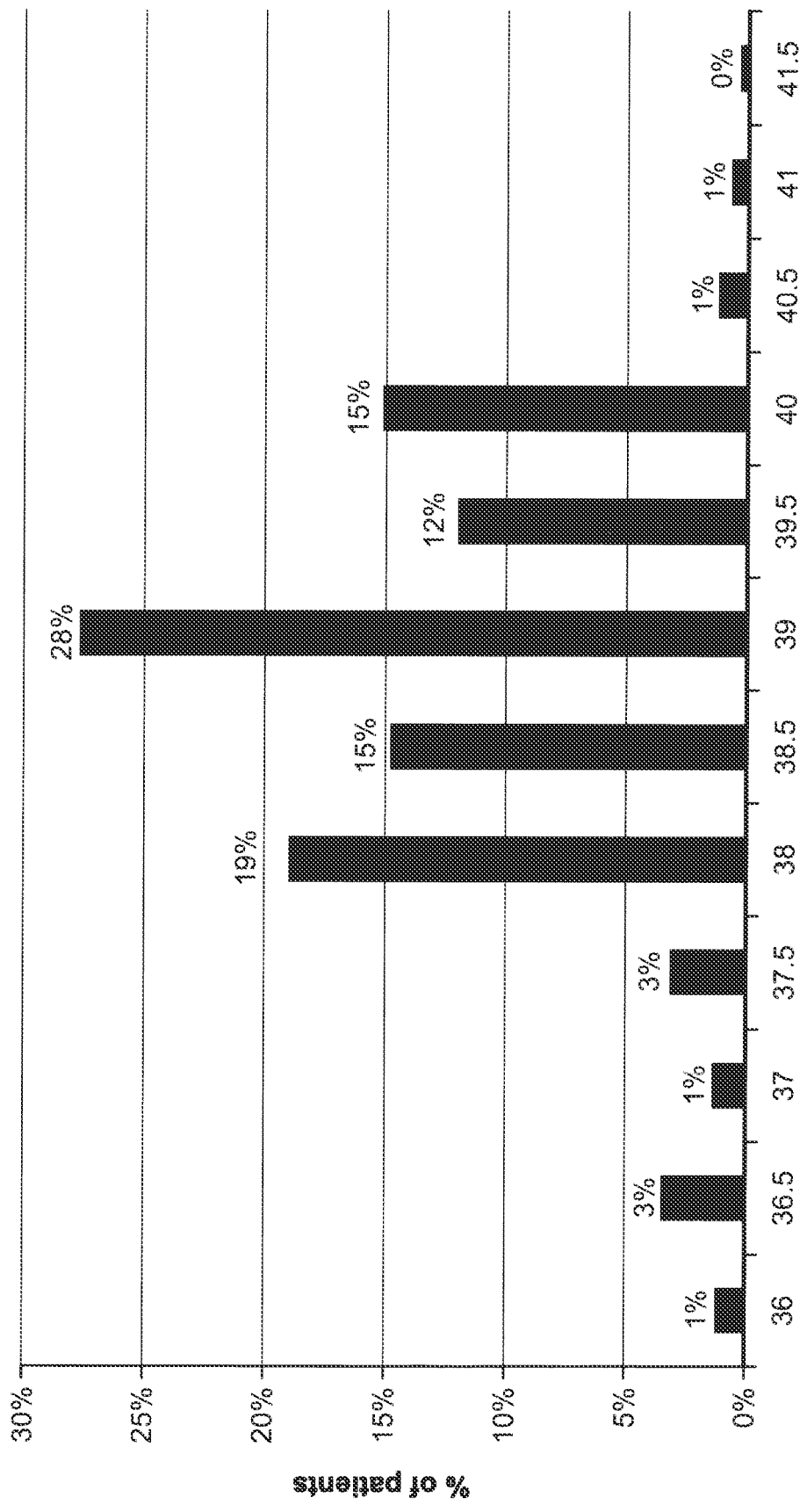
FIG. 8 DISTRIBUTION OF MAXIMAL BODY TEMPERATURES (ALL ENROLLED PATIENTS, N = 575).

Figures 9, 21A:
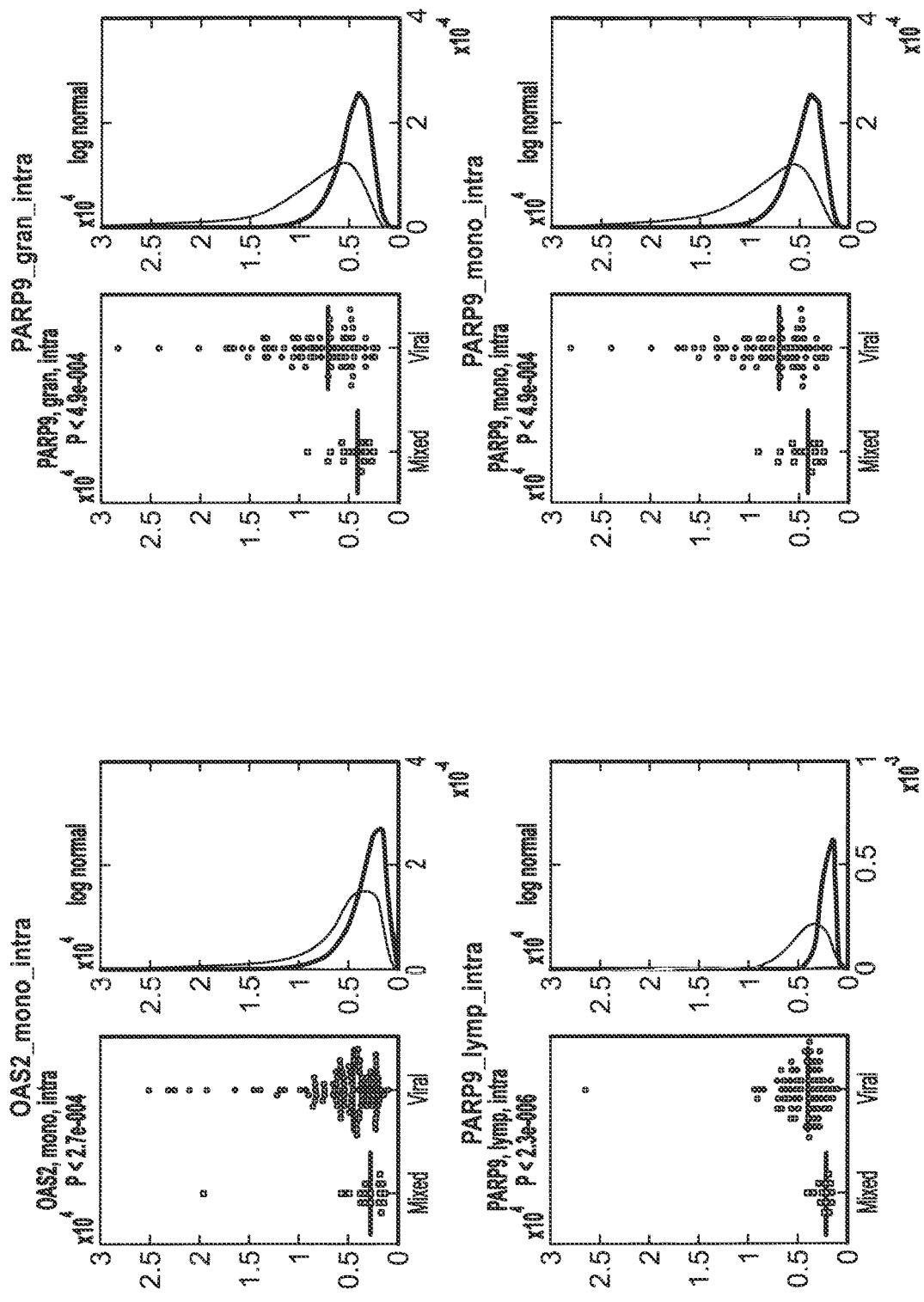

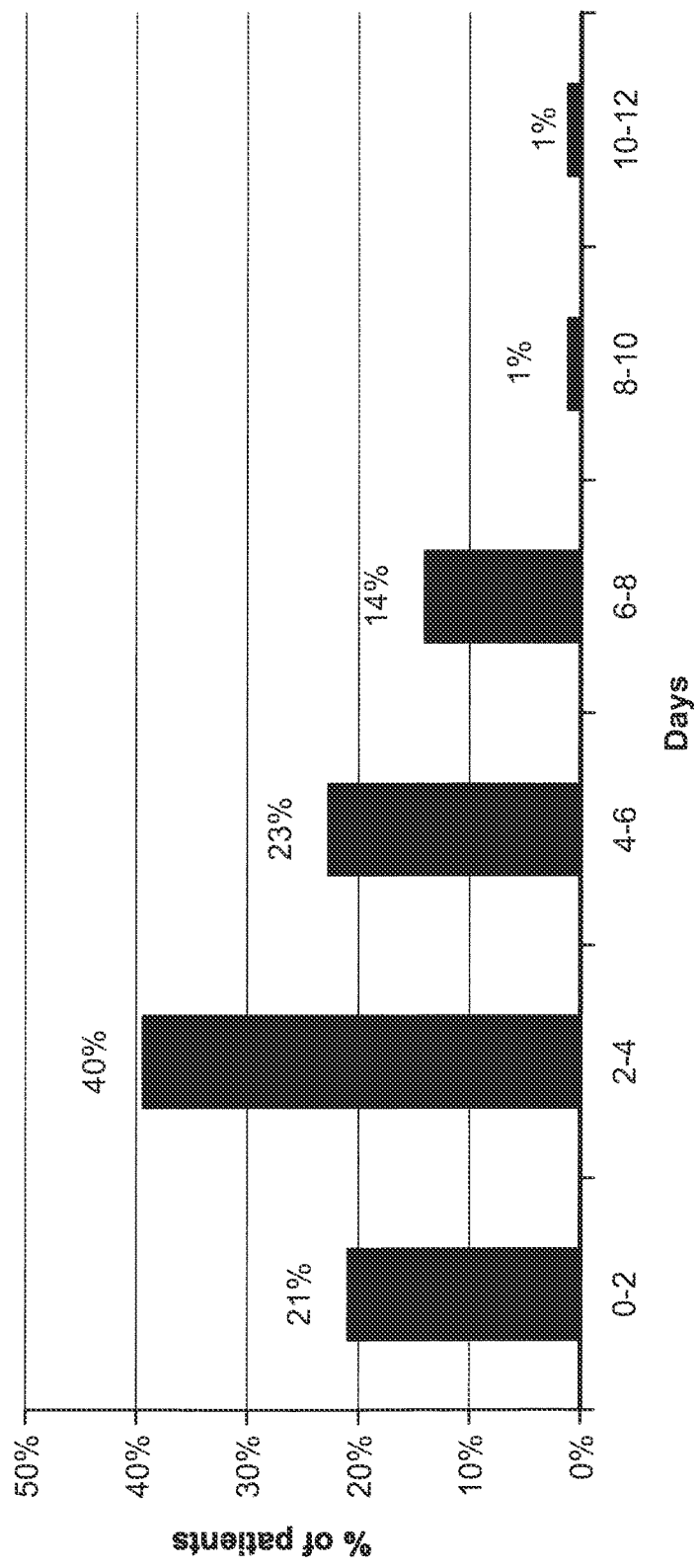
FIG. 9  DISTRIBUTION OF TIME FROM INITIATION OF SYMPTOMS (ALL ENROLLED PATIENTS, N = 575).

Figures 10, 21A:
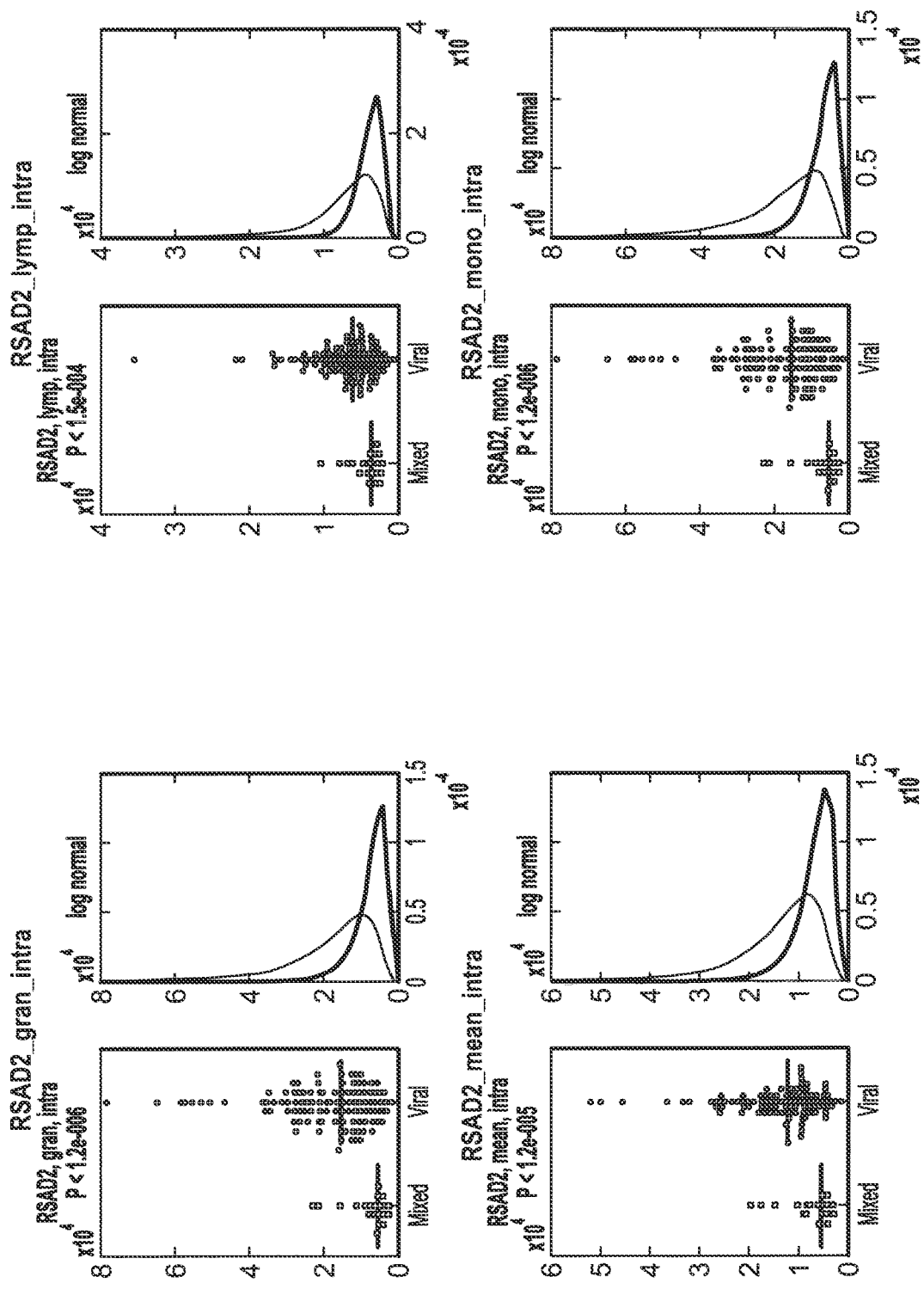

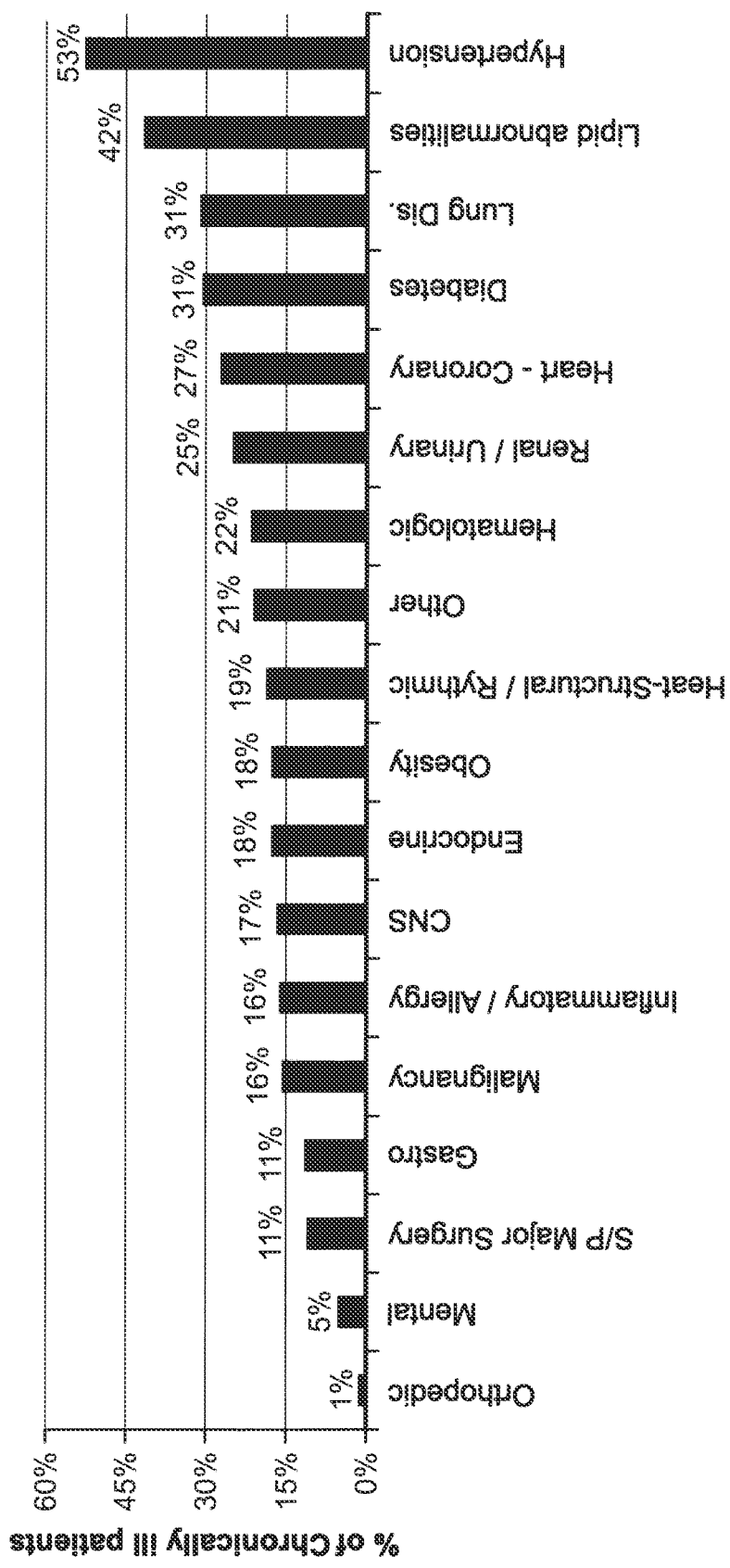
FIG. 10A COMORBIDITIES-RELATED CHARACTERIZATION OF THE PATIENT POPULATION. DISTRIBUTION OF COMORBIDITIES (ALL CHRONICALLY PATIENTS, N = 170)

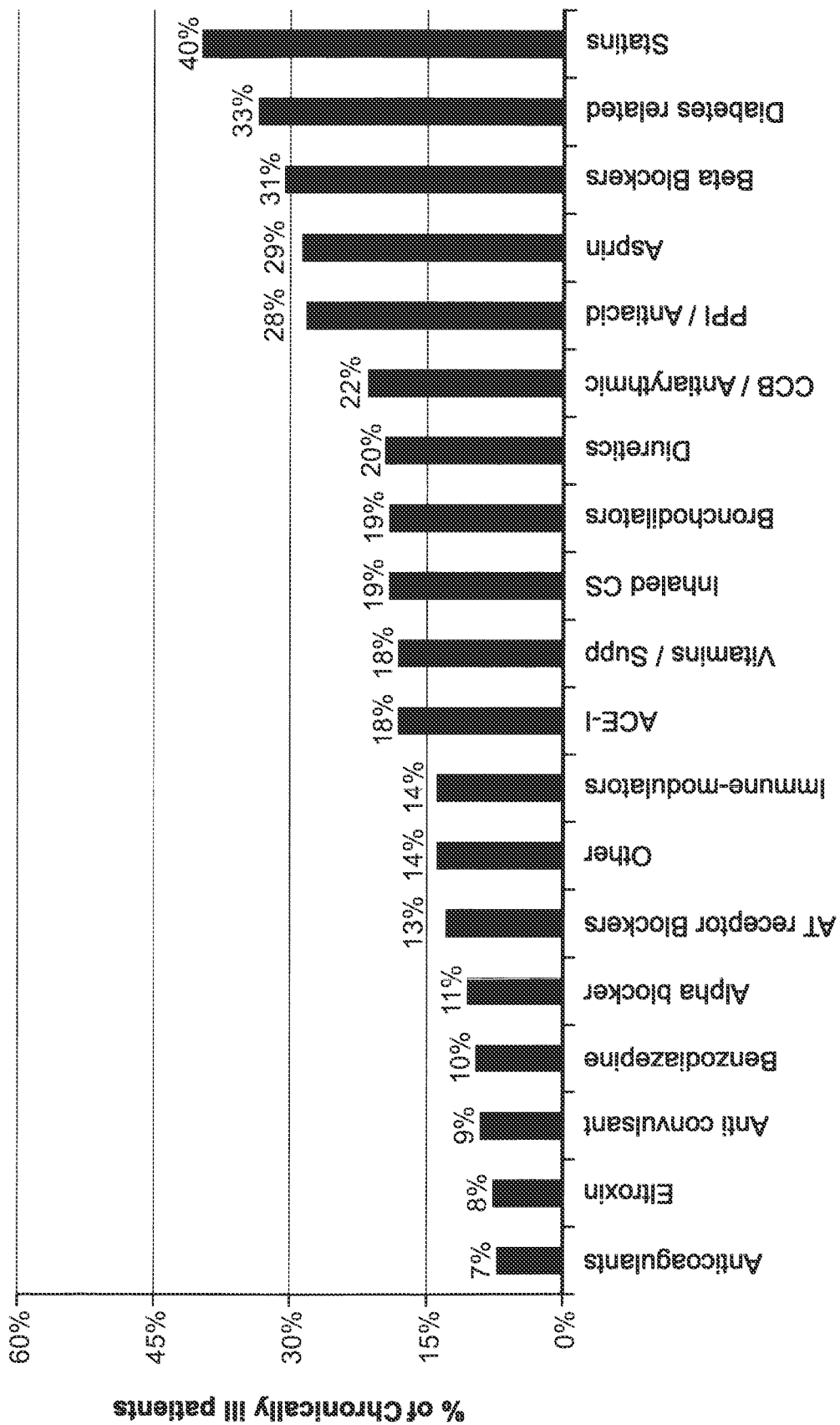
FIG. 10B COMORBIDITIES-RELATED CHARACTERIZATION OF THE PATIENT POPULATION. DISTRIBUTION OF CHRONIC MEDICATIONS (ALL CHRONICALLY ILL PATIENTS, N = 170).

Figures 11, 21A:
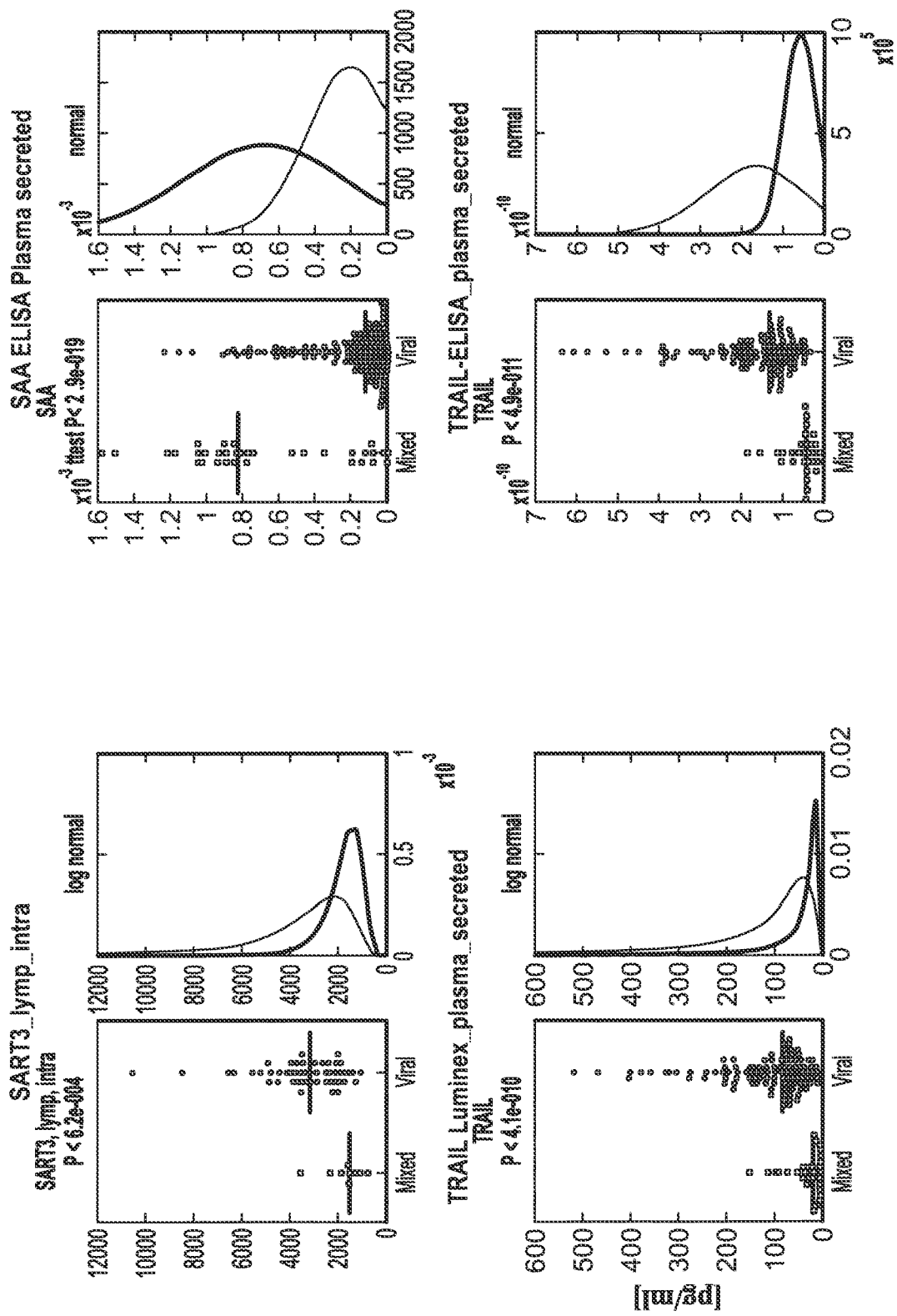
Figures 12, 21A:
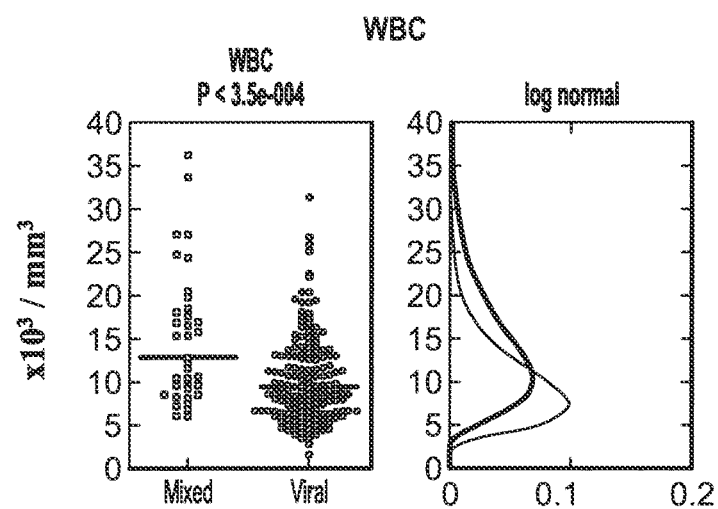

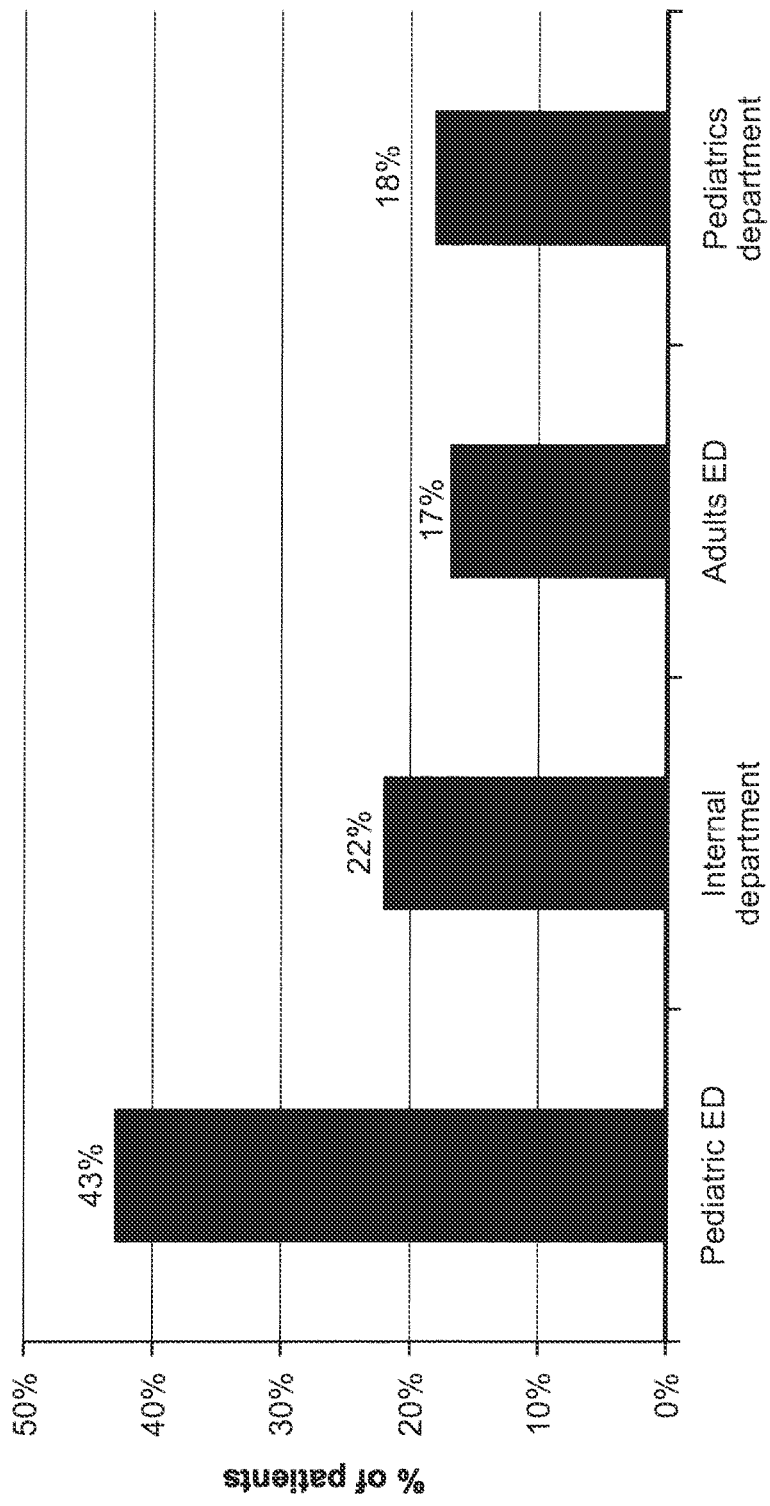
FIG. 11 DISTRIBUTION OF RECRUITMENT SITES (ALL ENROLLED PATIENTS, N = 575).

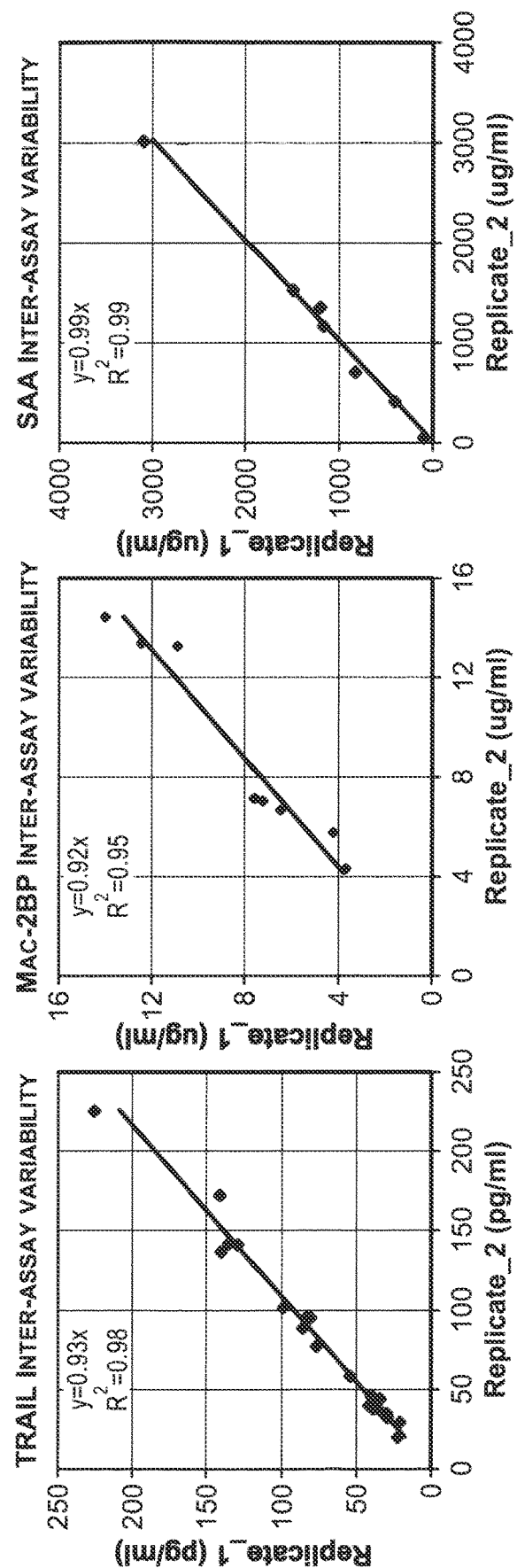

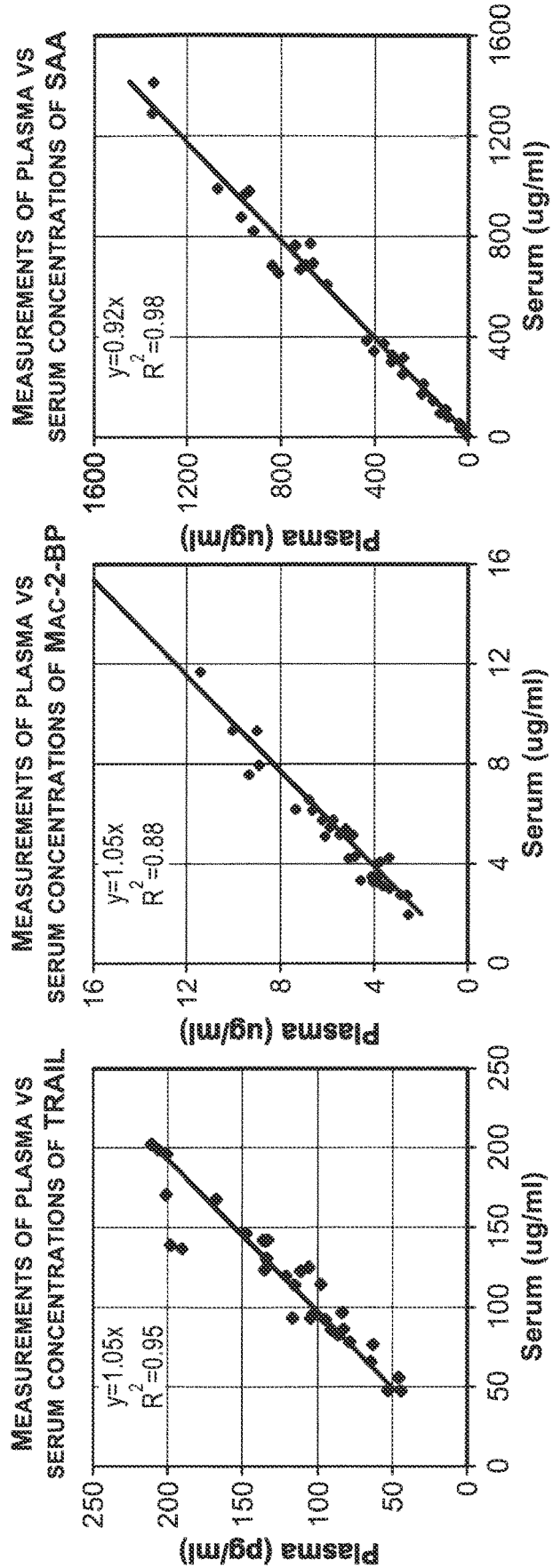

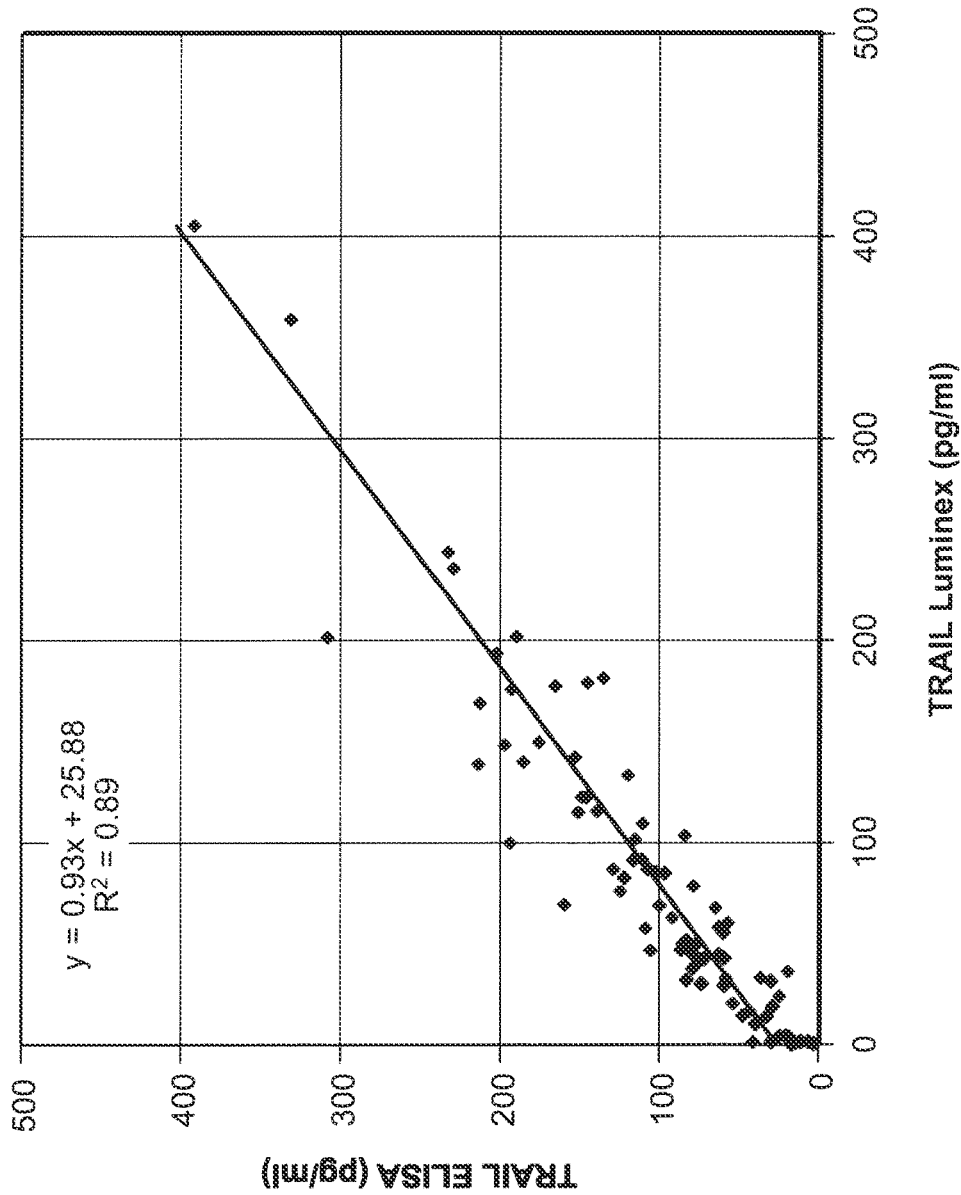
FIG. 17 CORRELATION OF TRAIL LEVELS MEASURED USING ELISA AND LUMINEX.

Figure 18B:
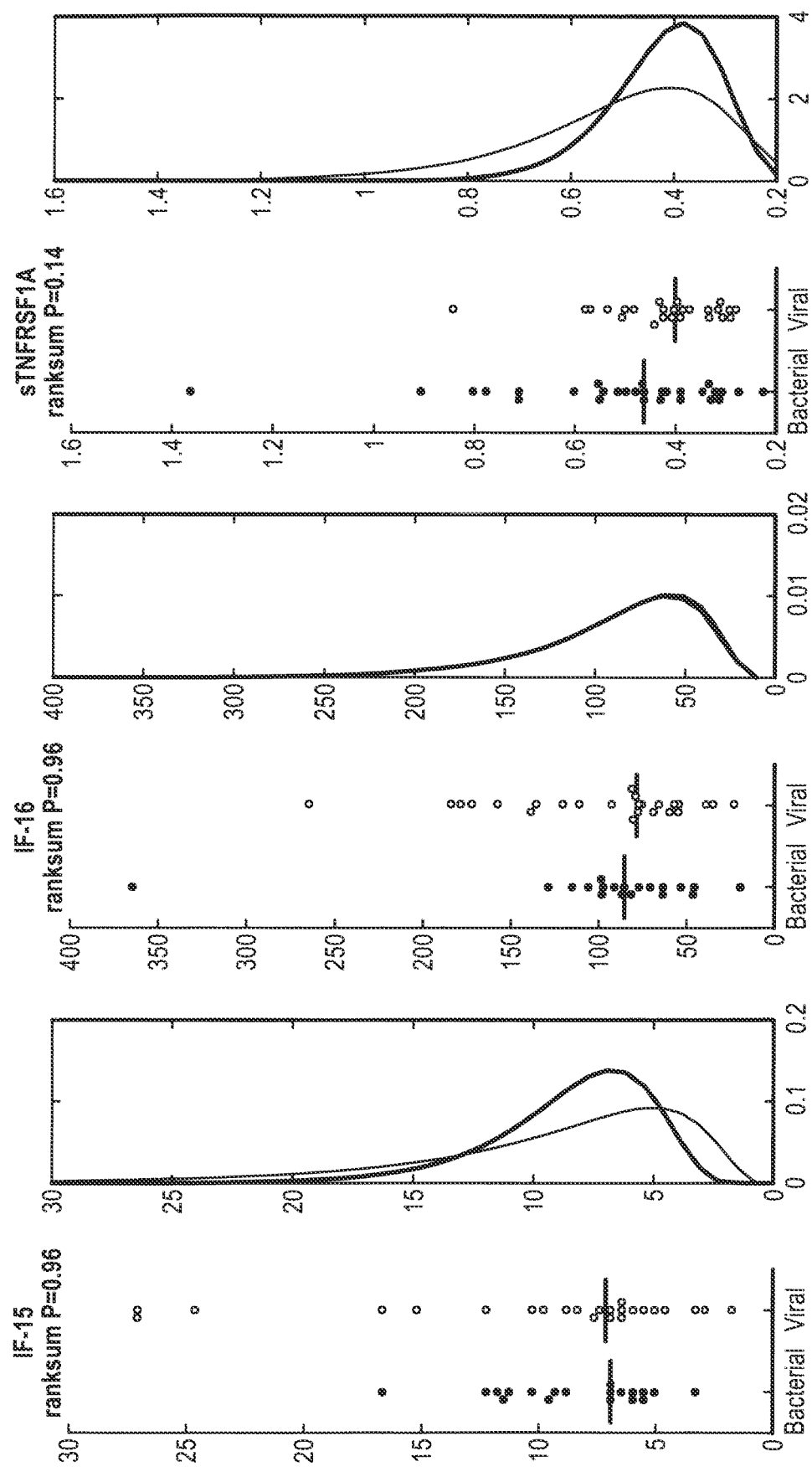
Figure 18C:
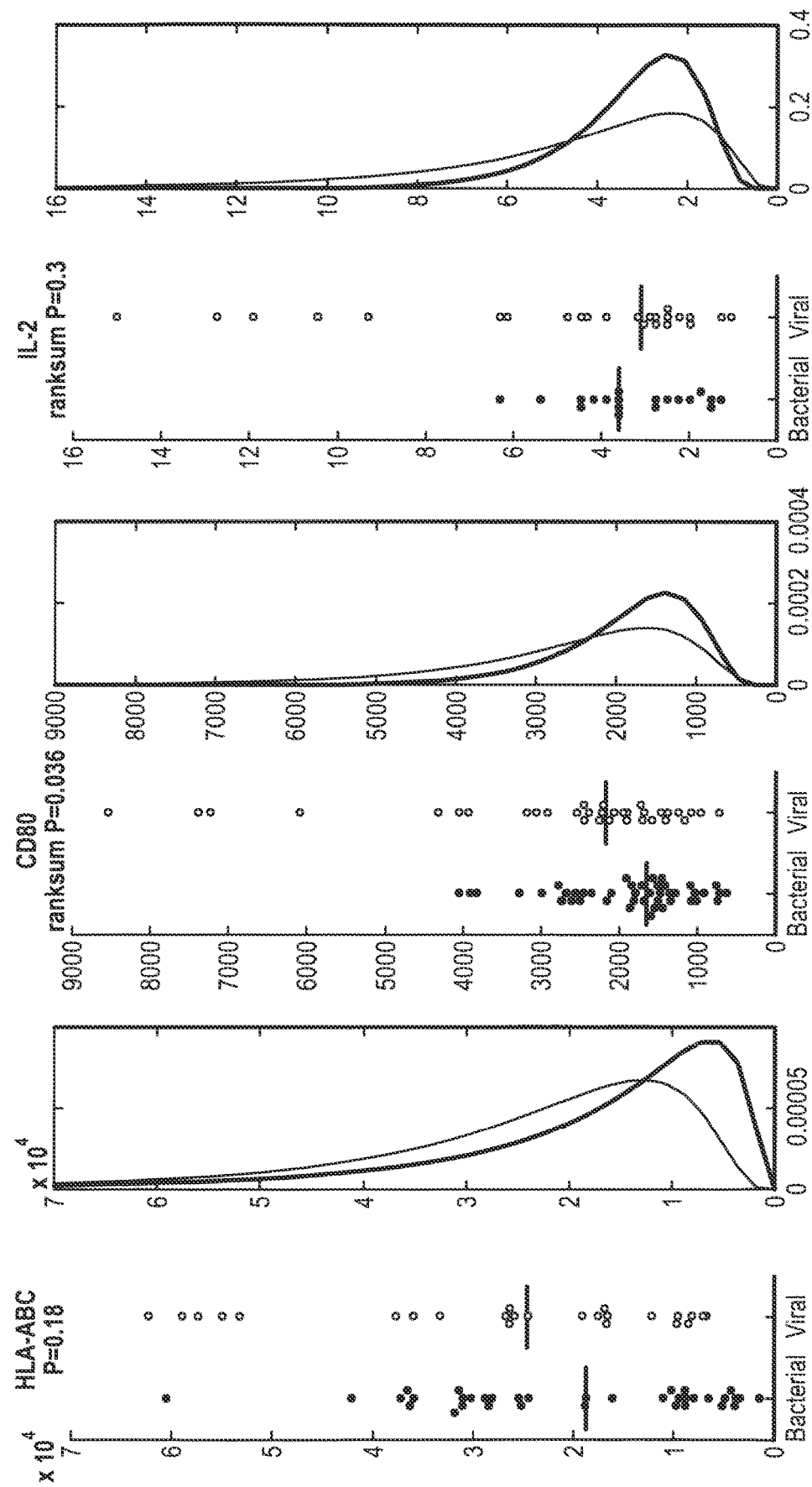
Figure 18D:
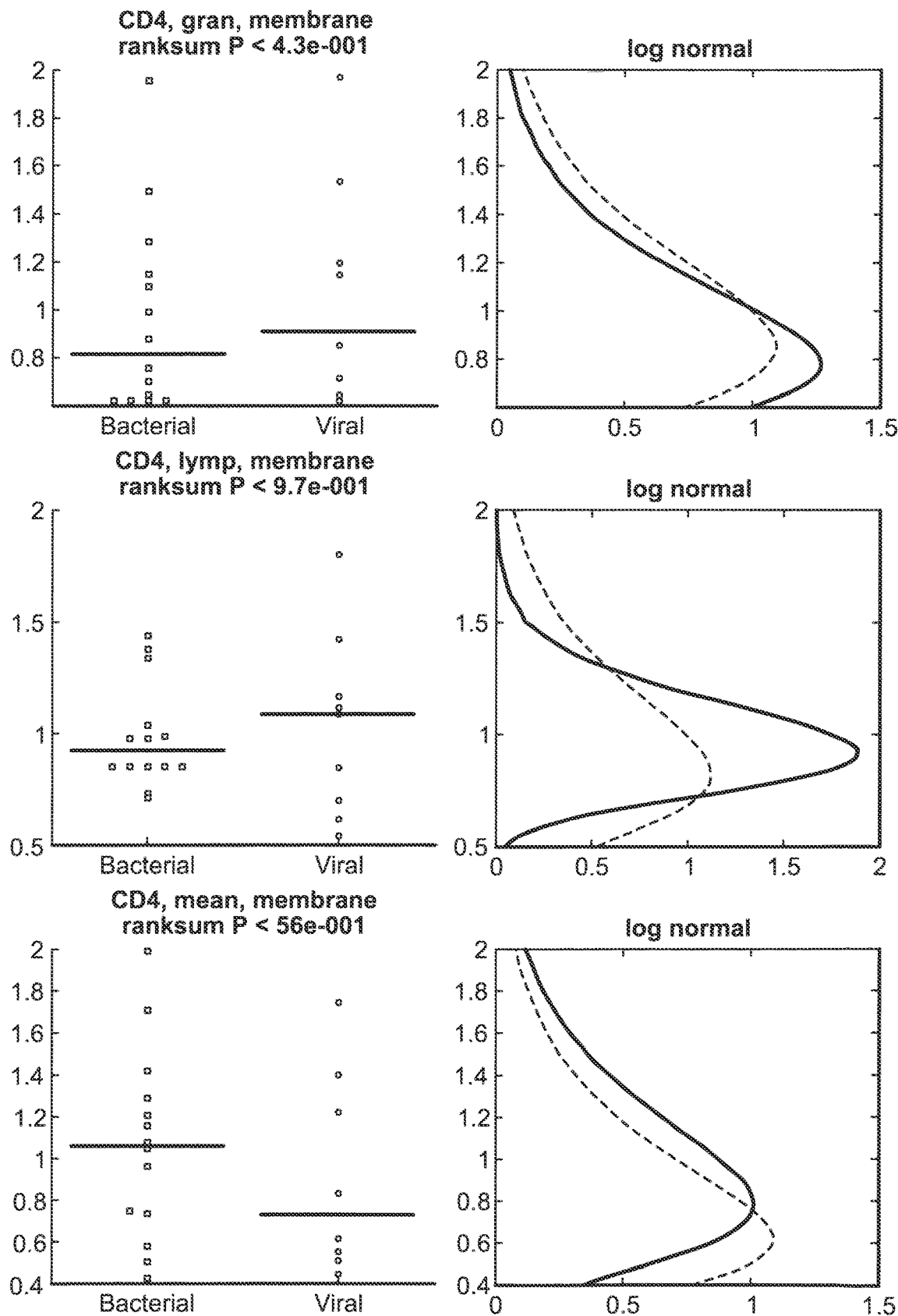
Figure 18E:
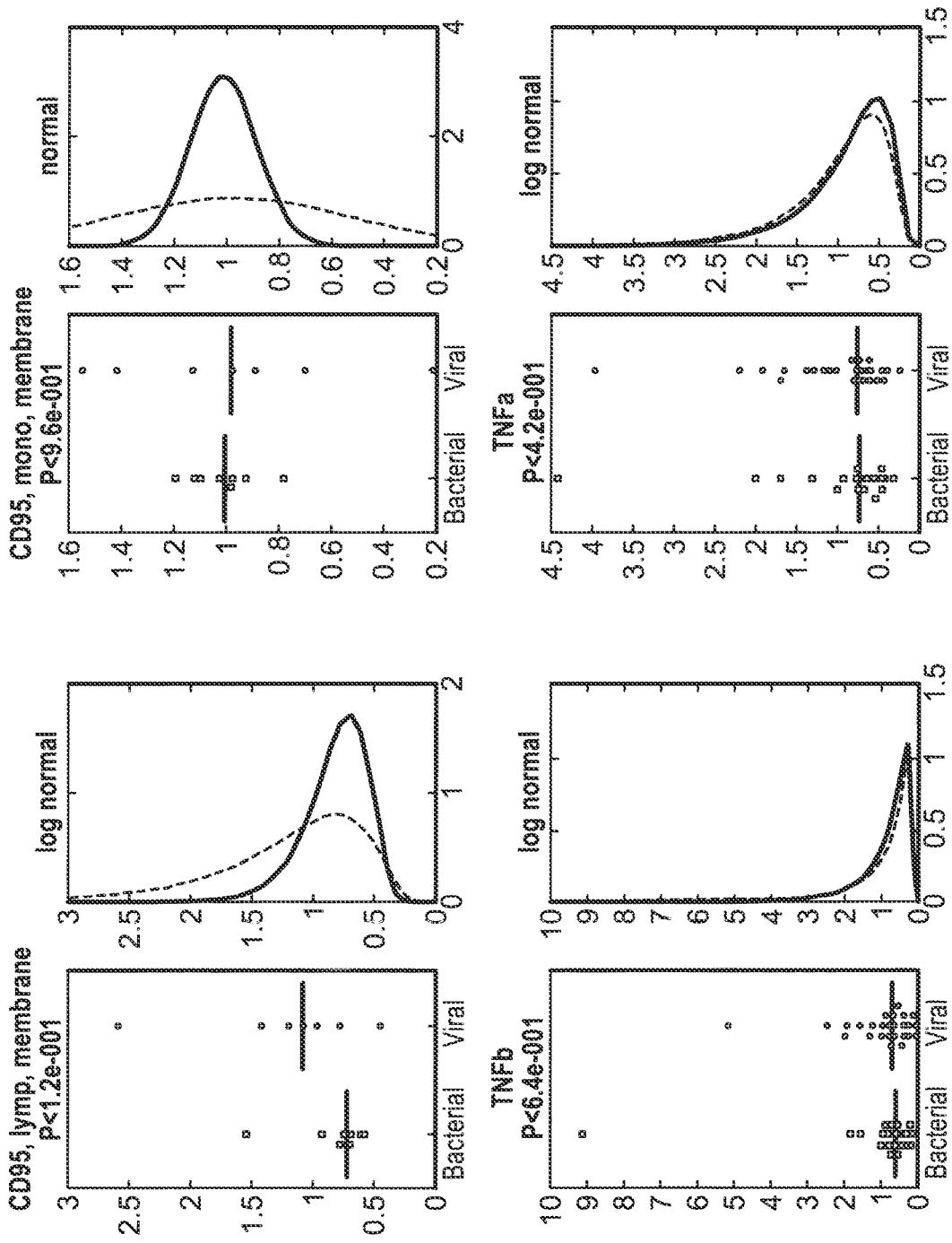
Figure 18F:
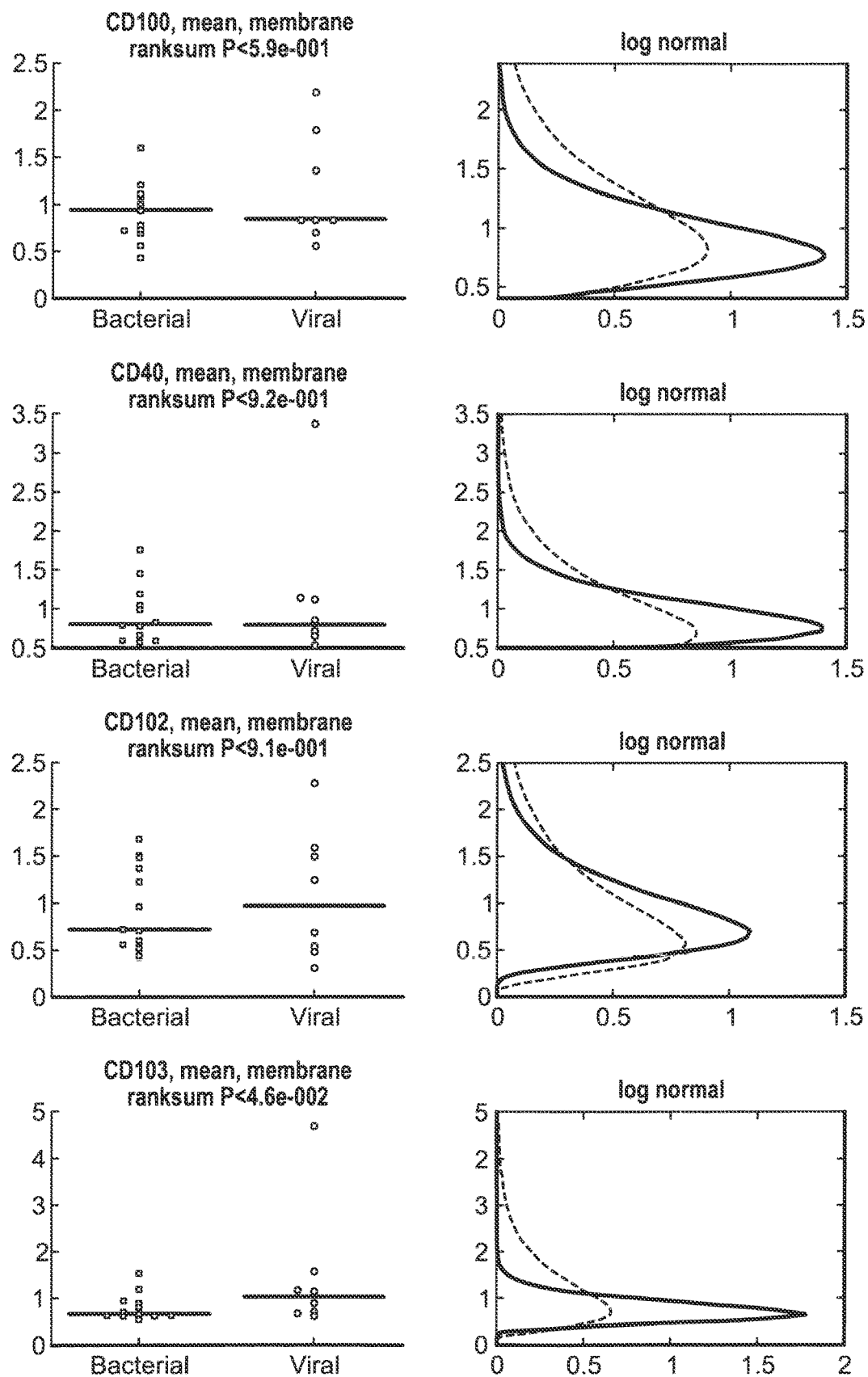
Figure 18G:
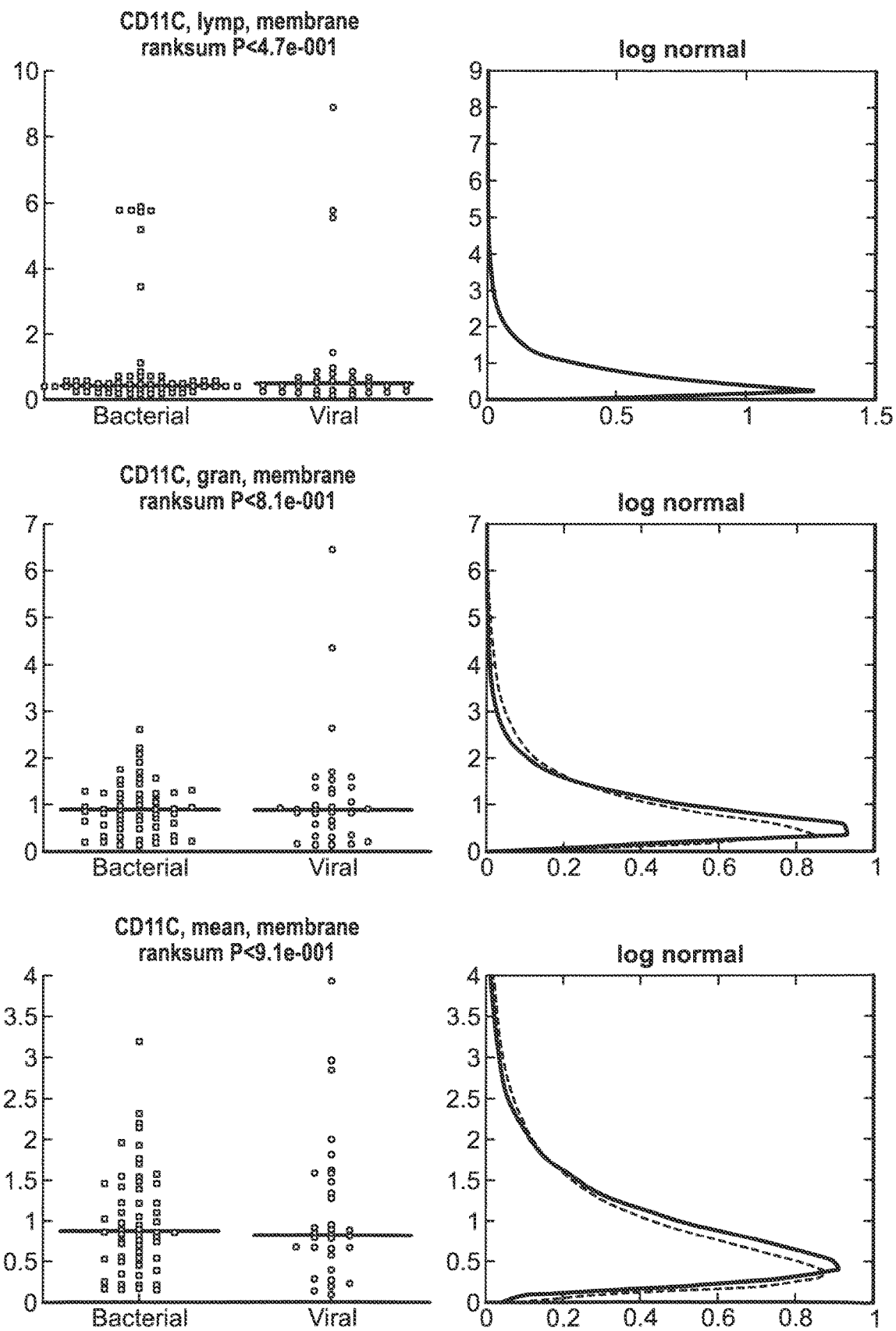
Figure 18H:
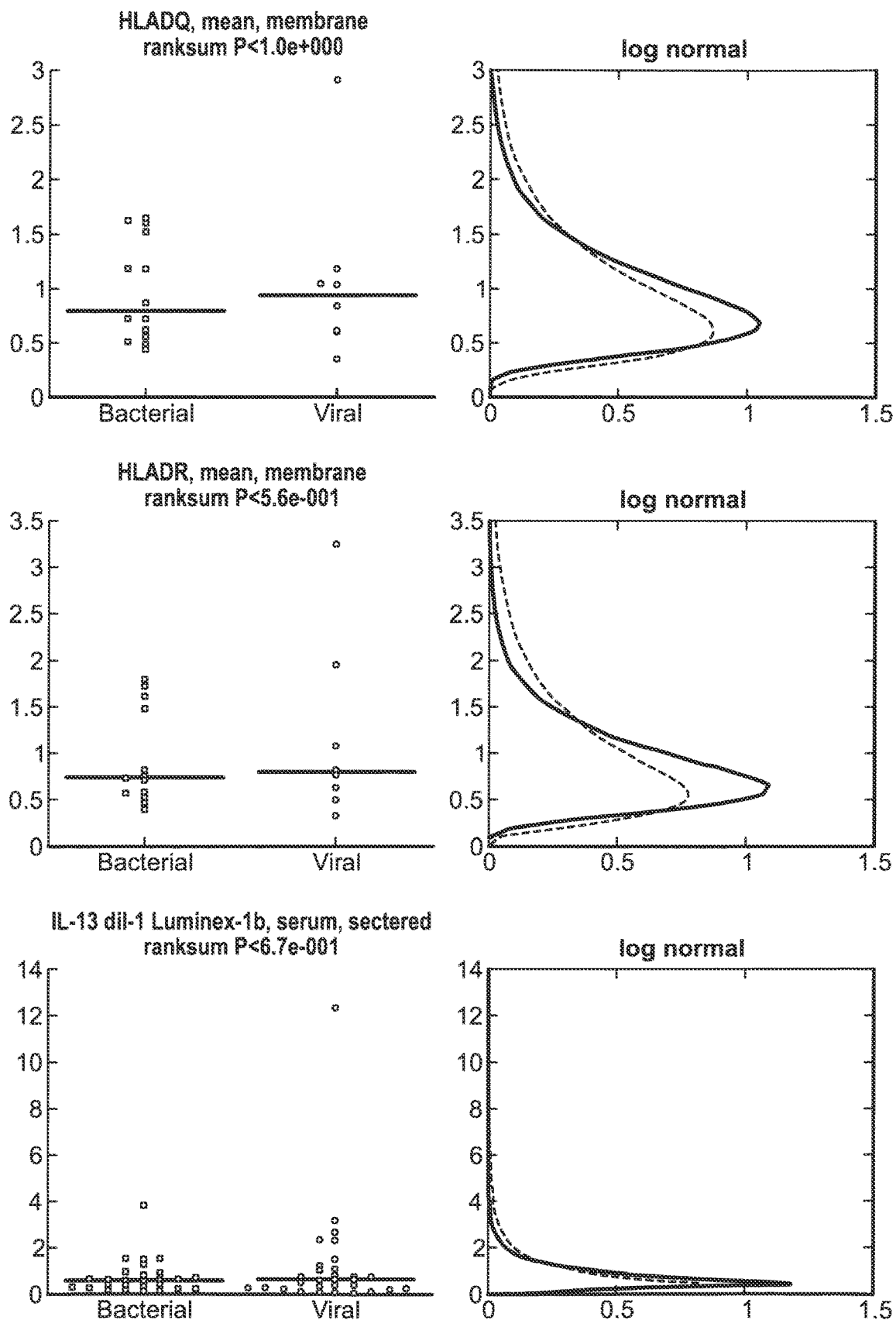

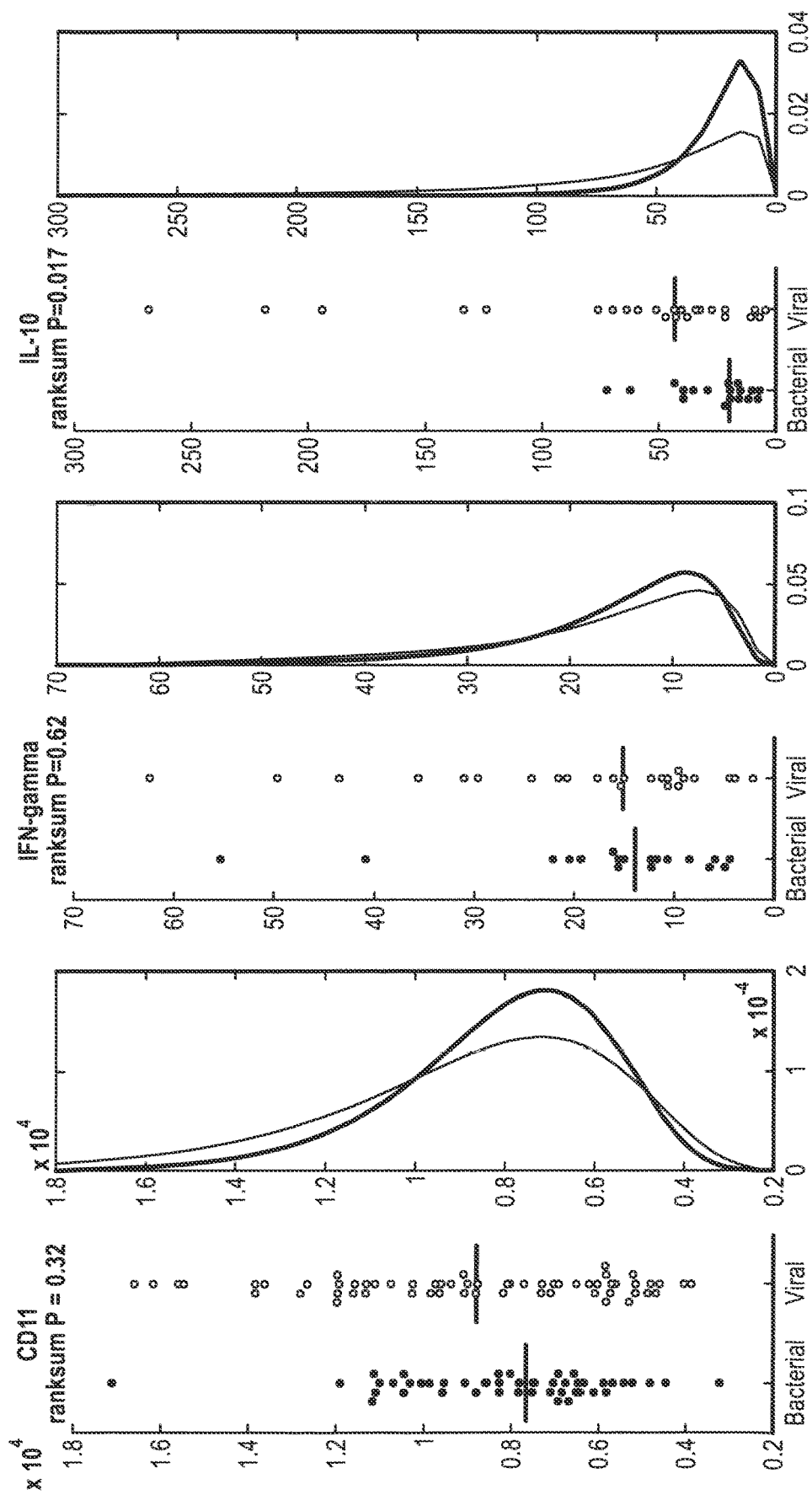
FIG. 18A POLYPEPTIDES WITH AN IMMUNOLOGICAL ROLE DO NOT NECESSARILY SHOW A DIFFERENTIAL RESPONSE

FIG. 19
IN-VITRO DIFFERENTIALLY EXPRESSED POLYPEPTIDES DO NOT NECESSARILY SHOW IN-VIVO DIFFERENTIAL EXPRESSION.
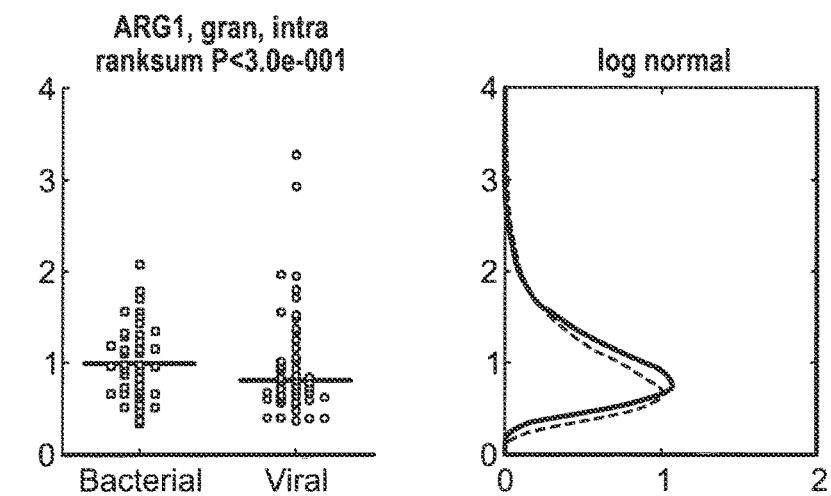
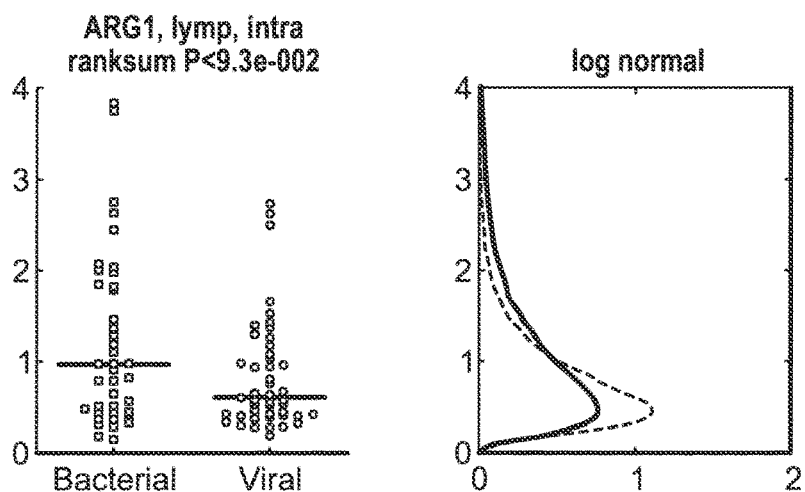
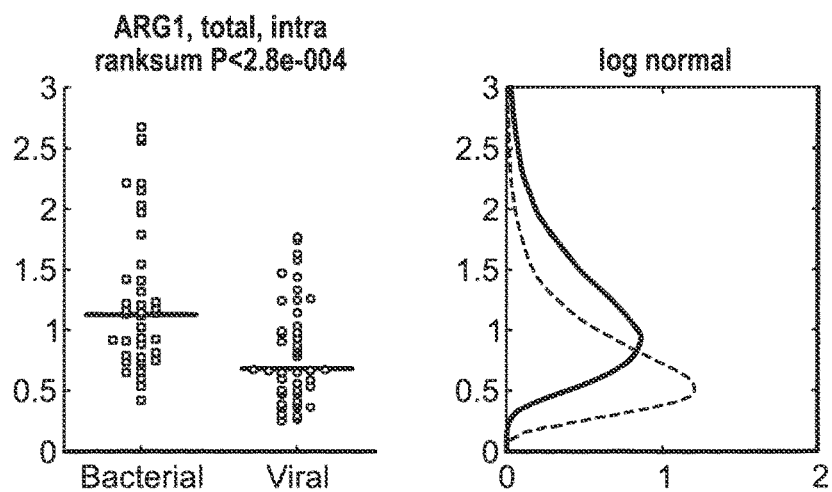

Figure 20B:
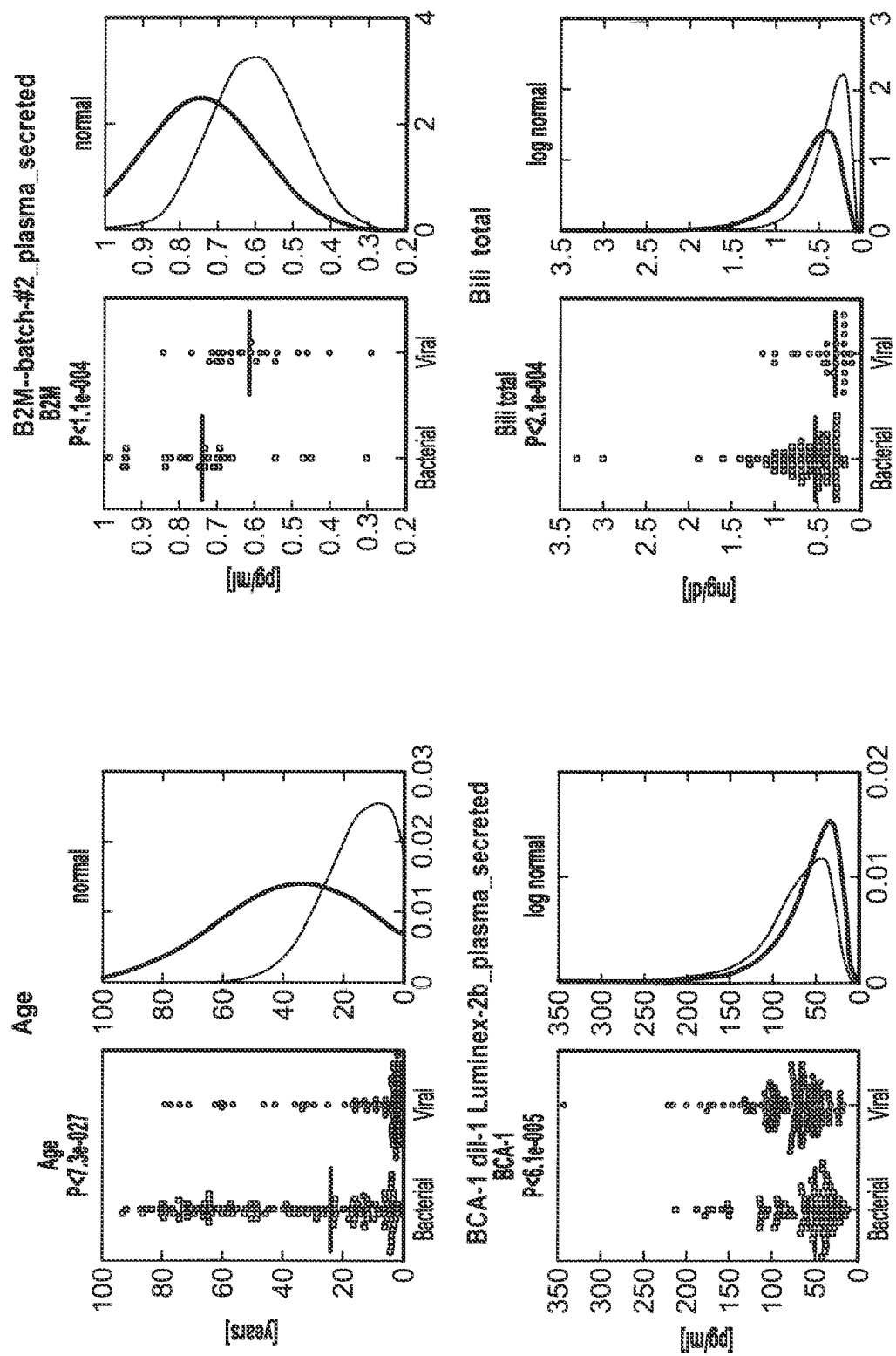
Figure 20C:
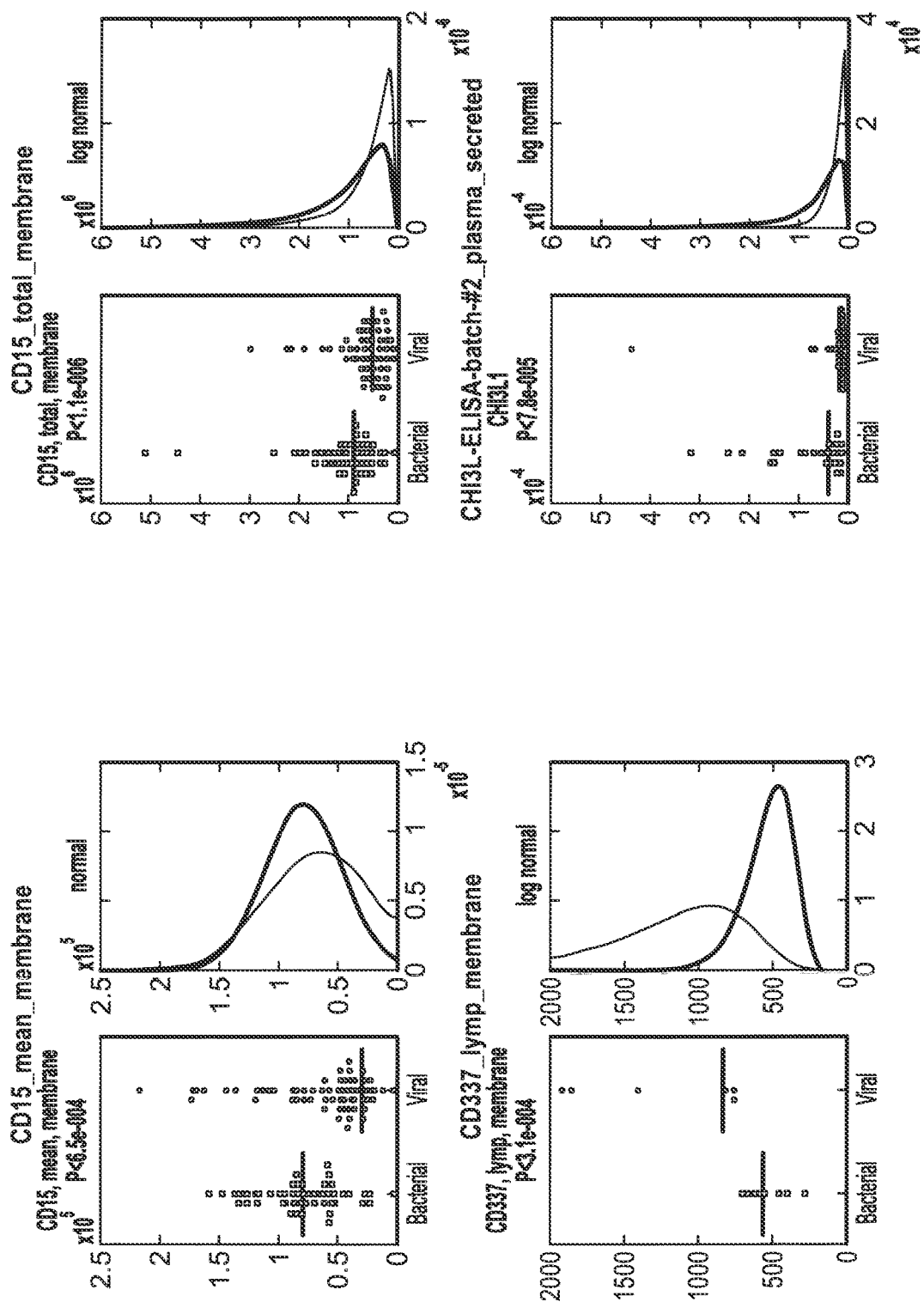
Figure 20D:
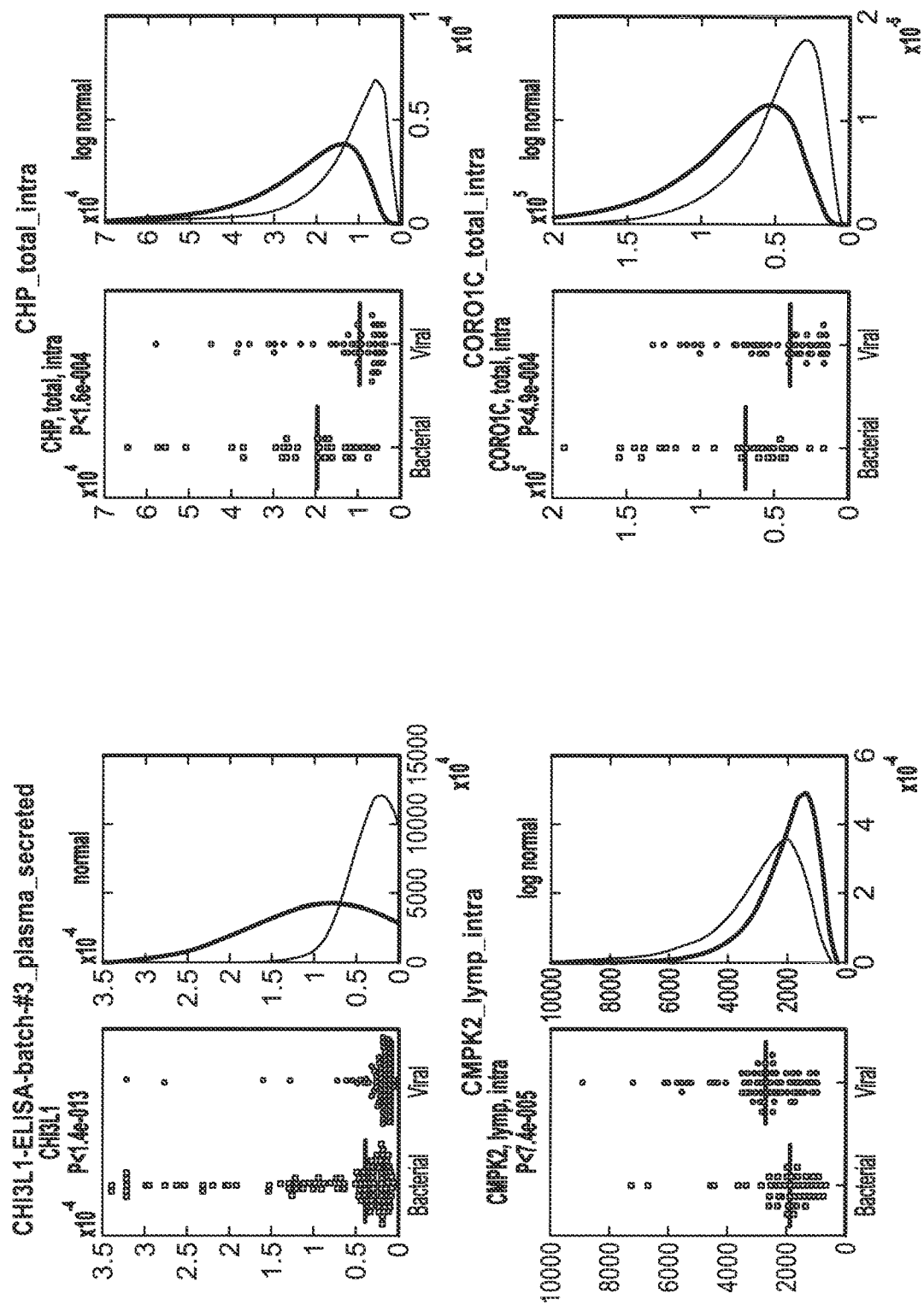
Figure 20E:
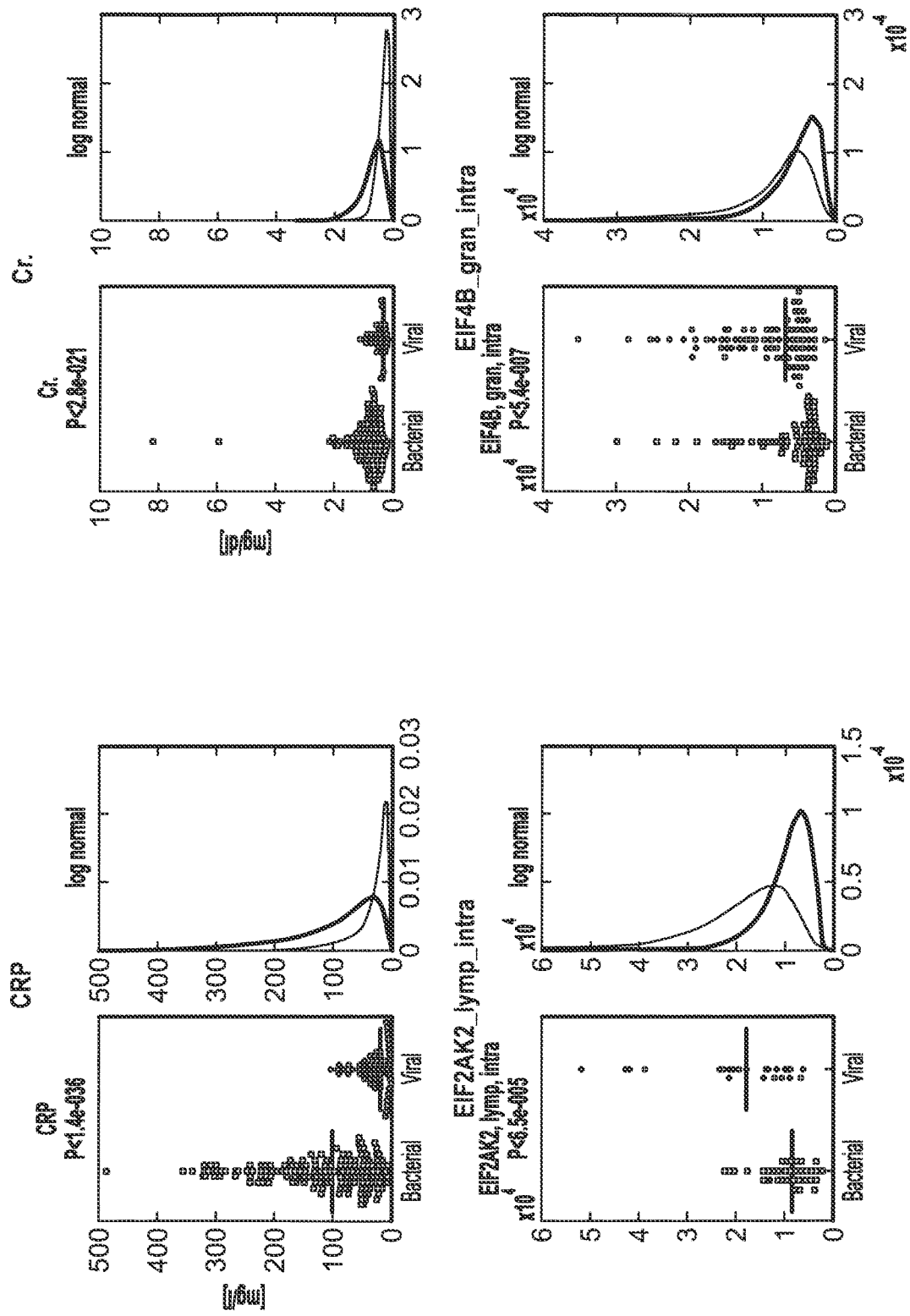
Figure 20F:
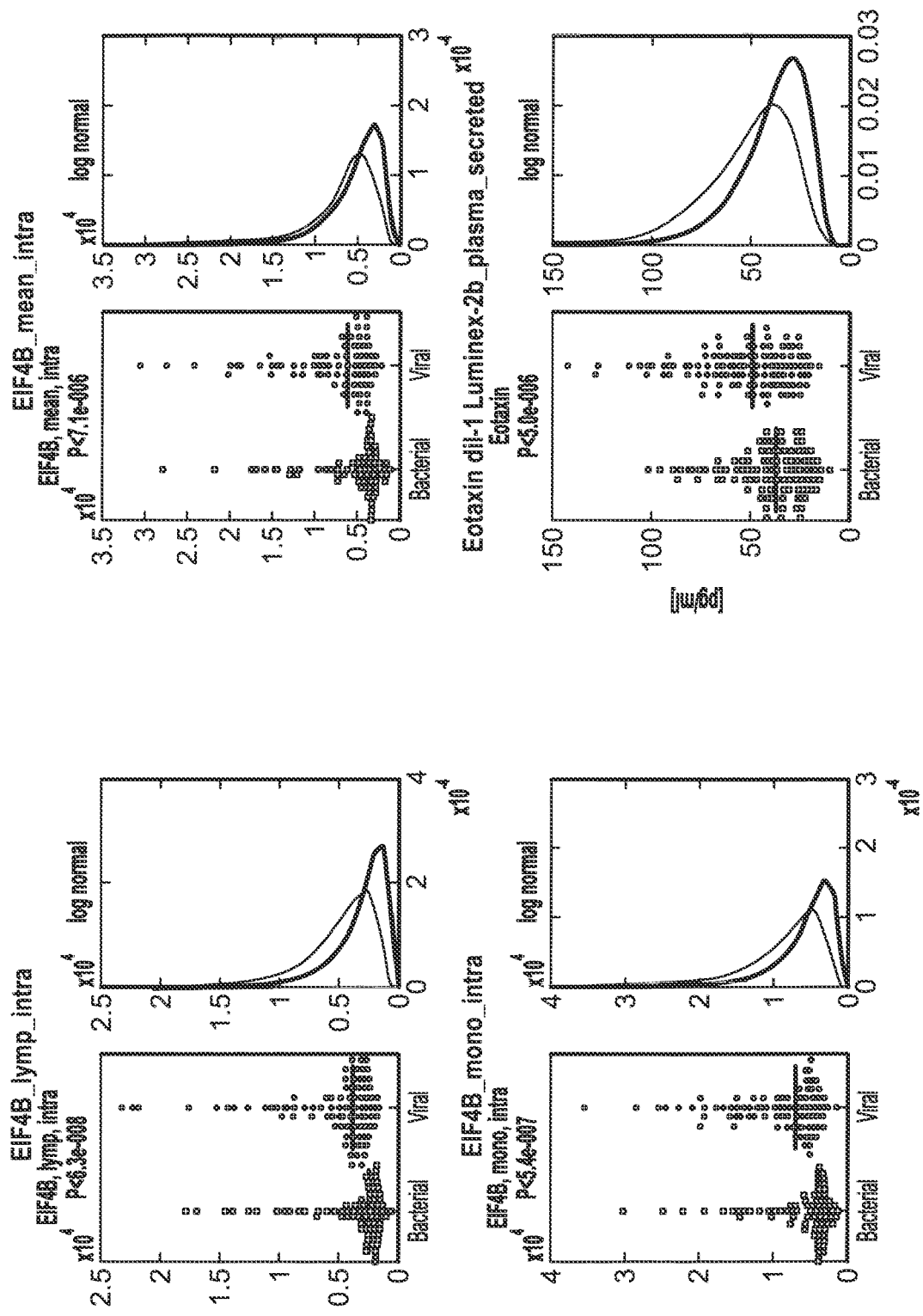
Figure 20G:
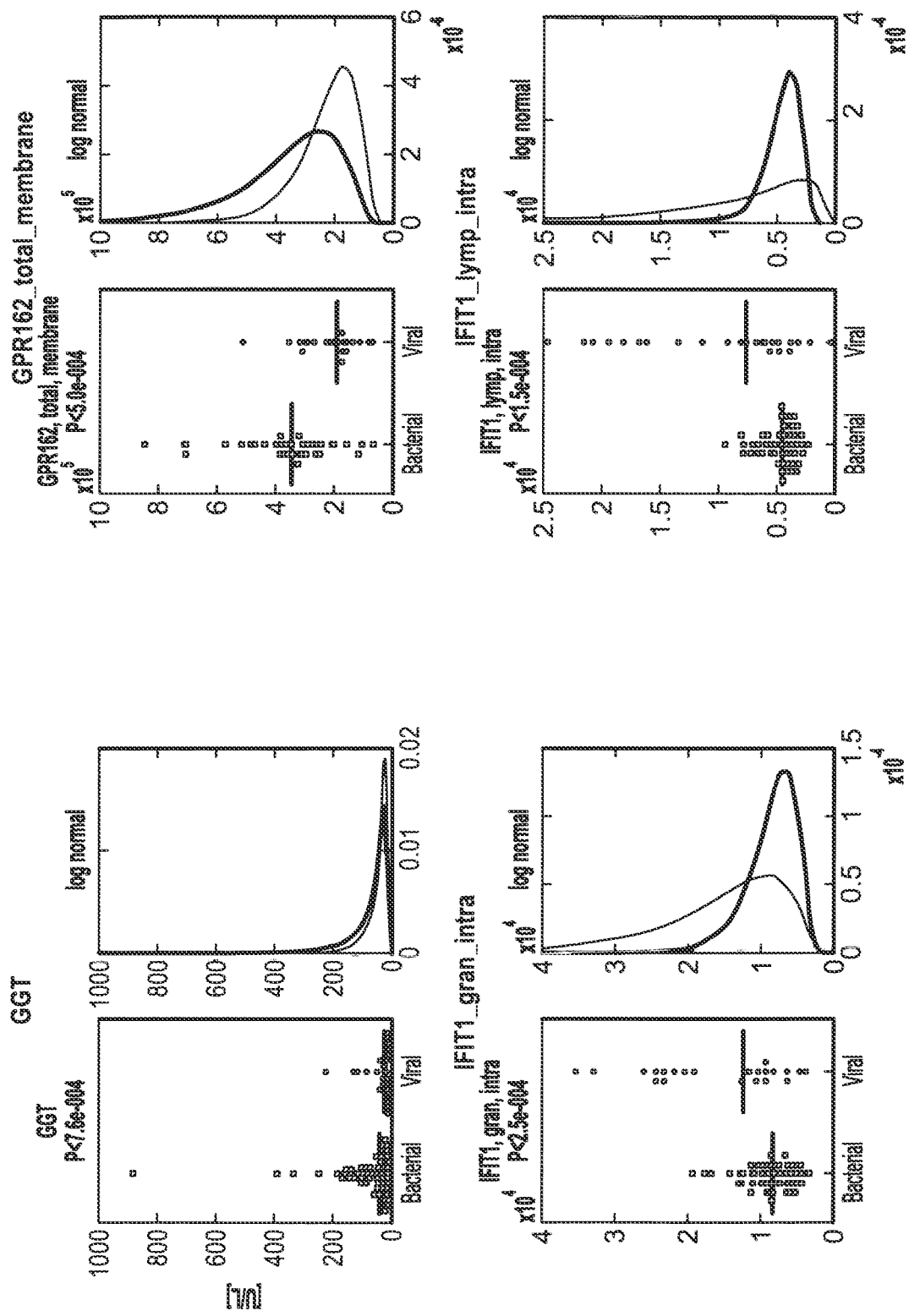
Figure 20H:
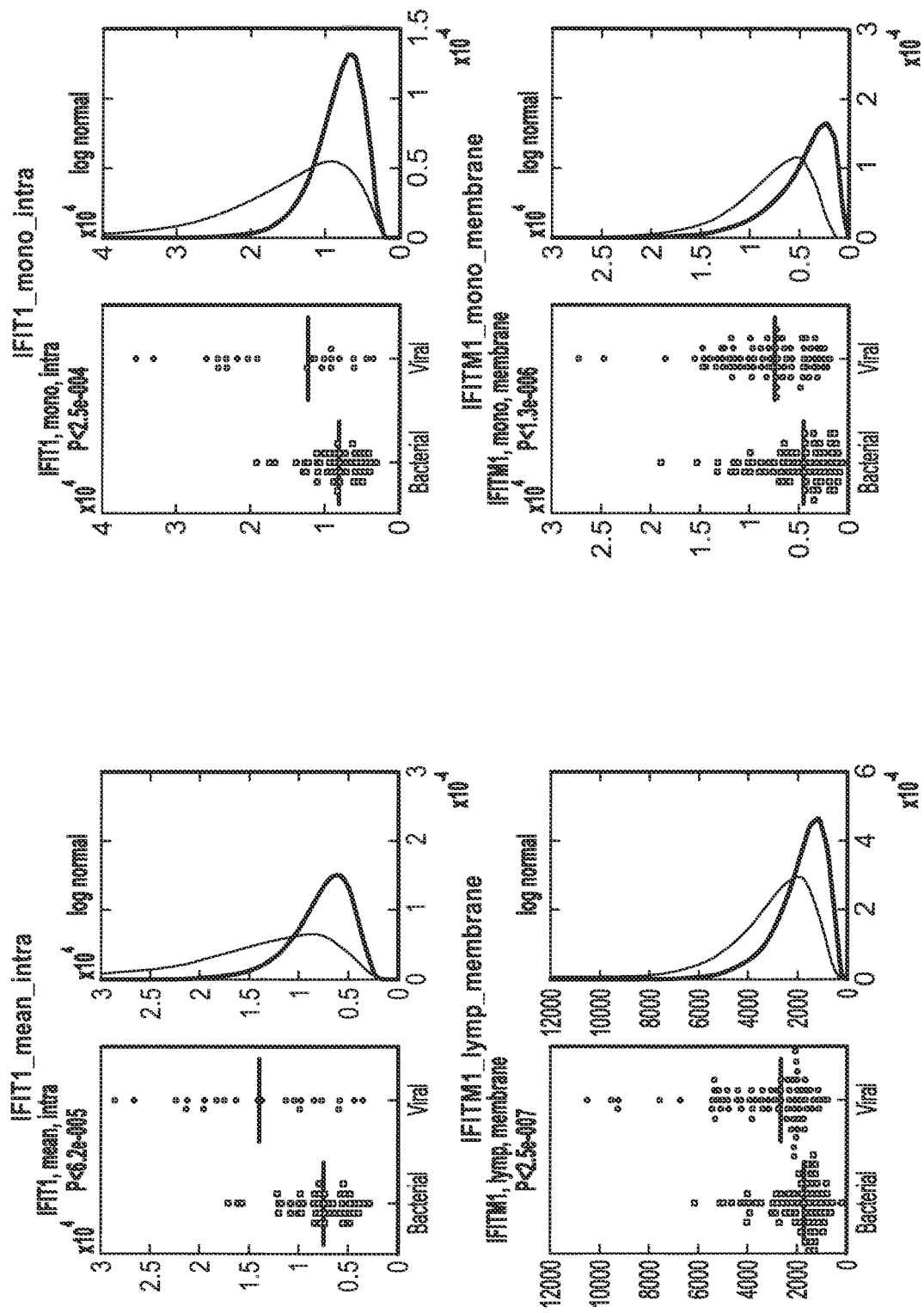
Figure 20I:
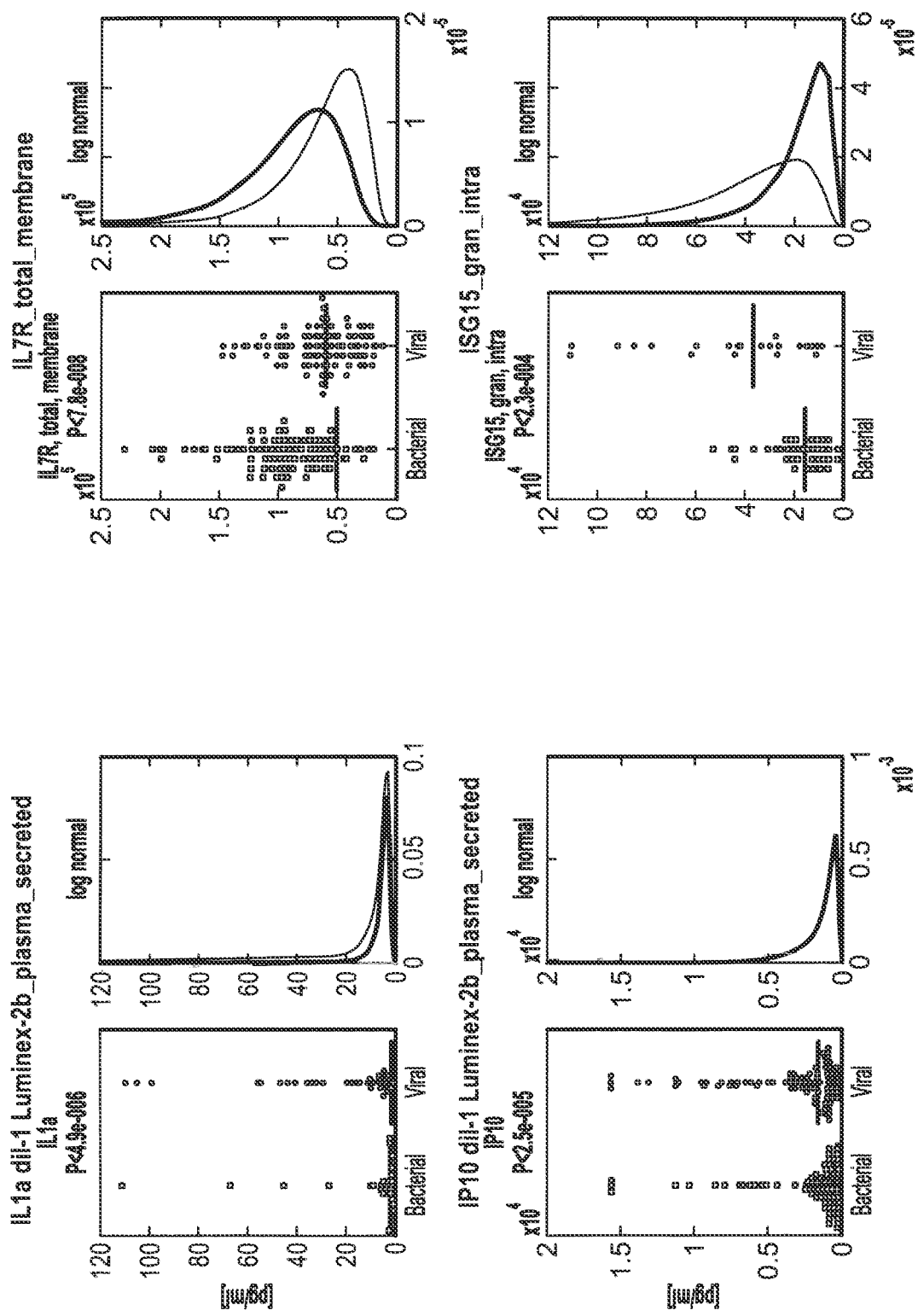
Figure 20J:
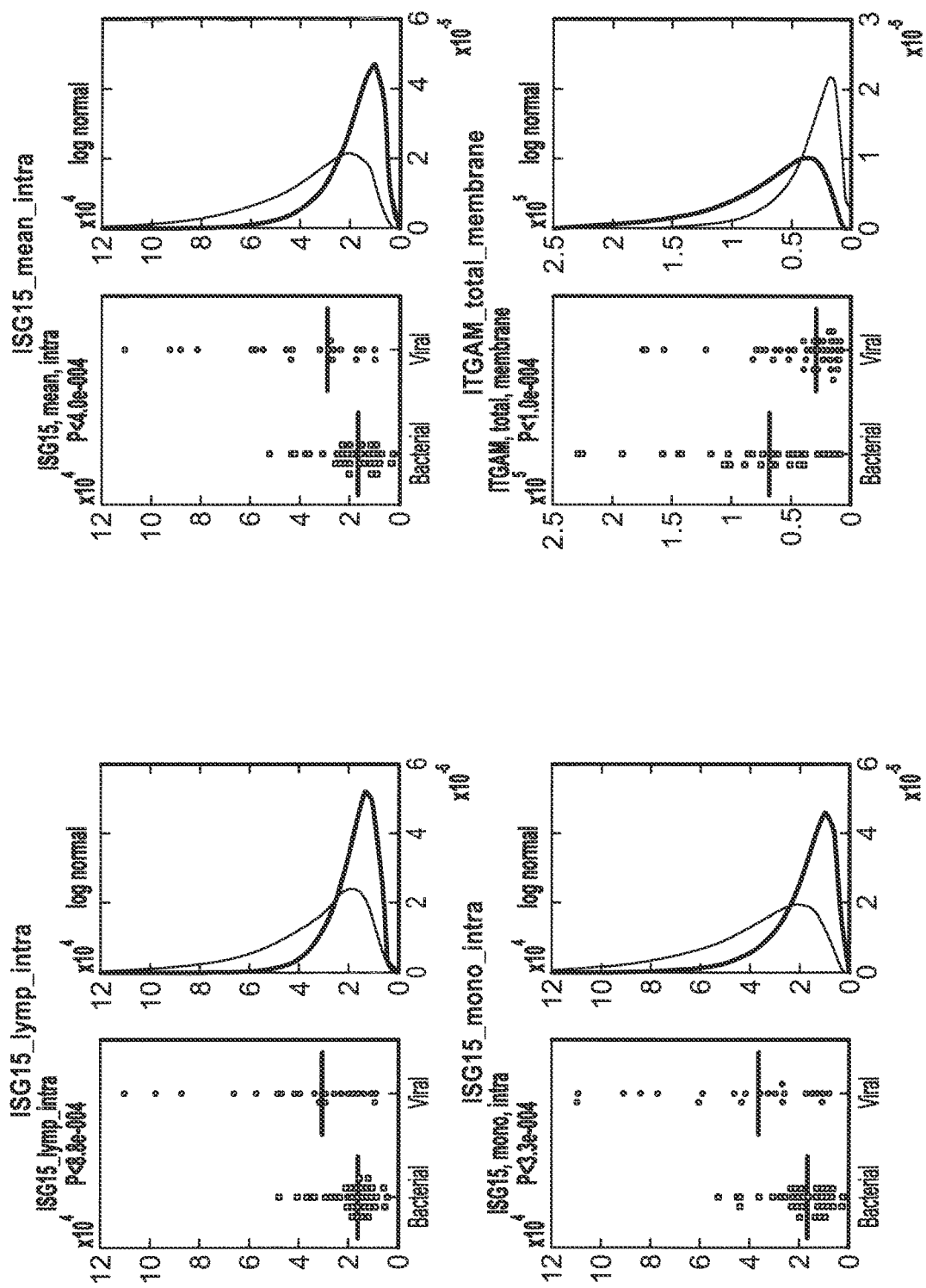
Figure 20K:
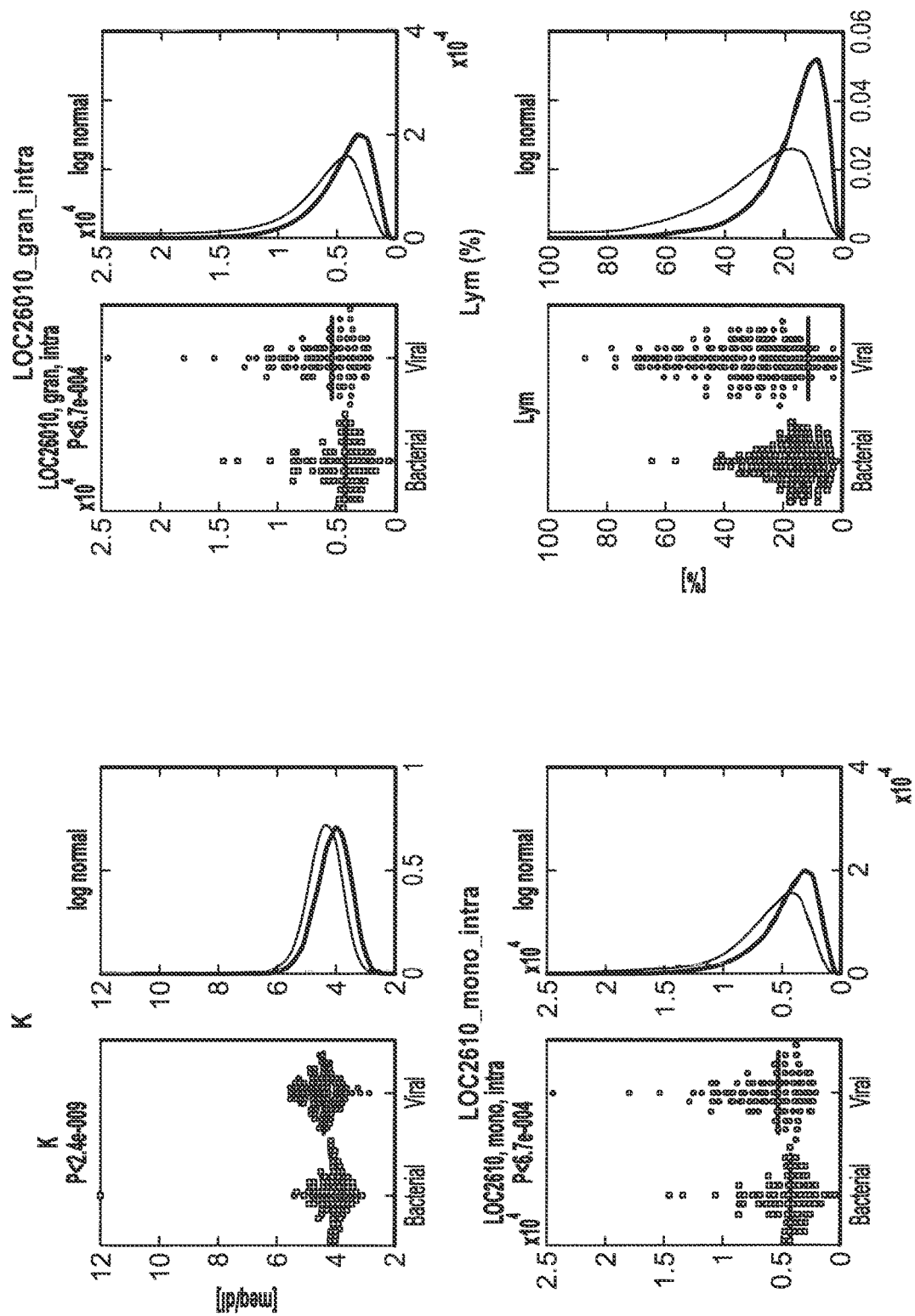
Figure 20L:
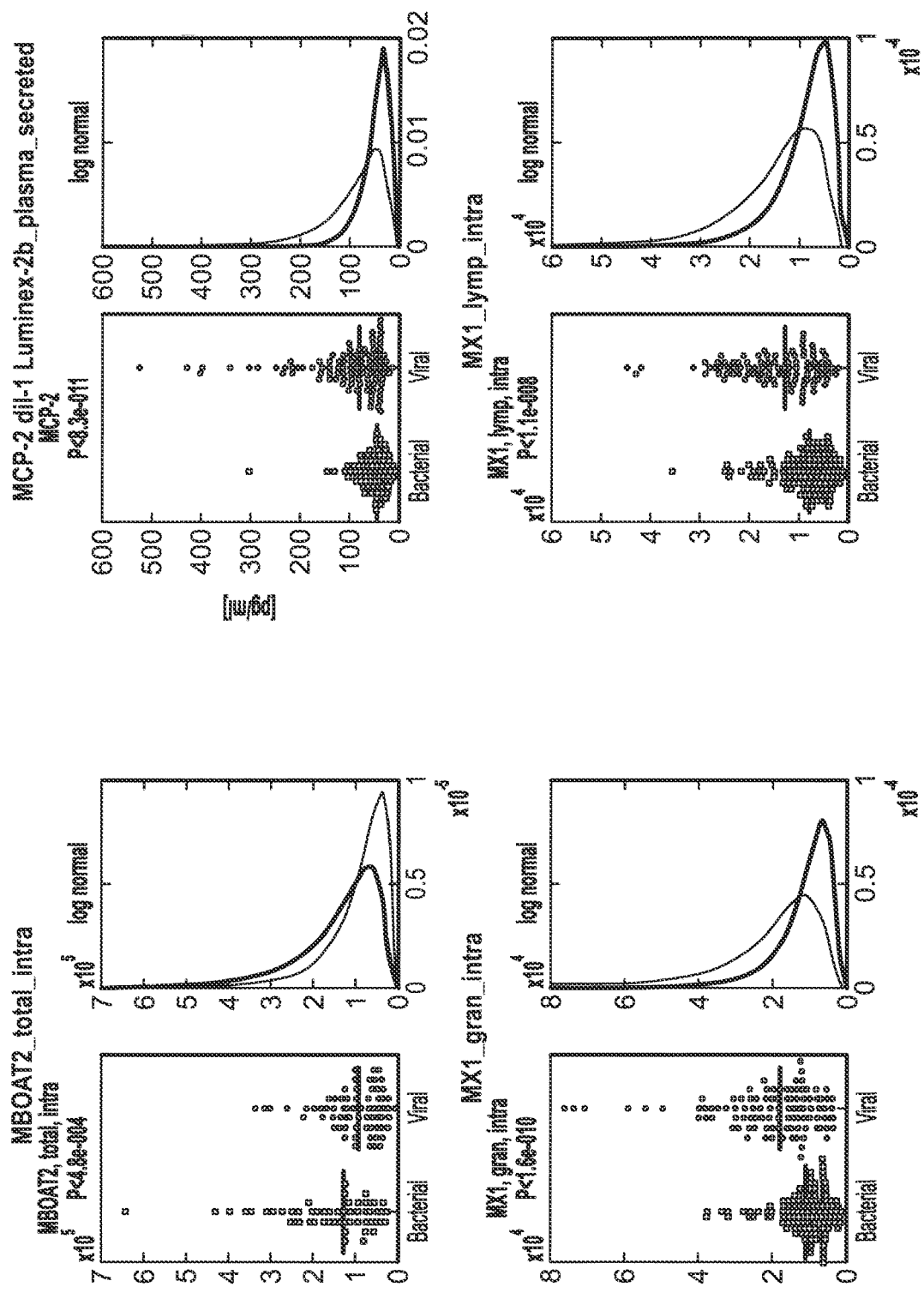
Figure 20M:
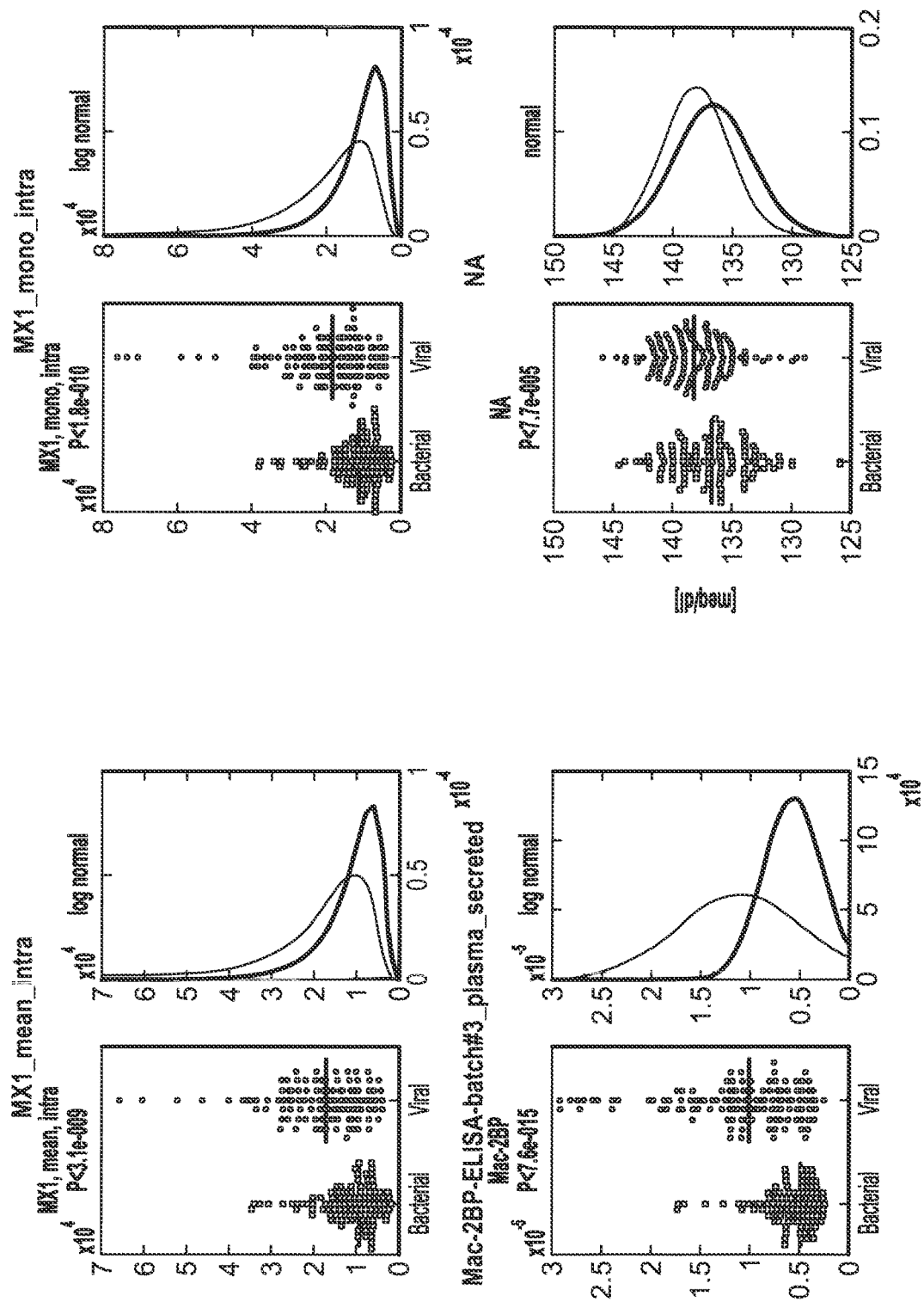
Figure 20N:
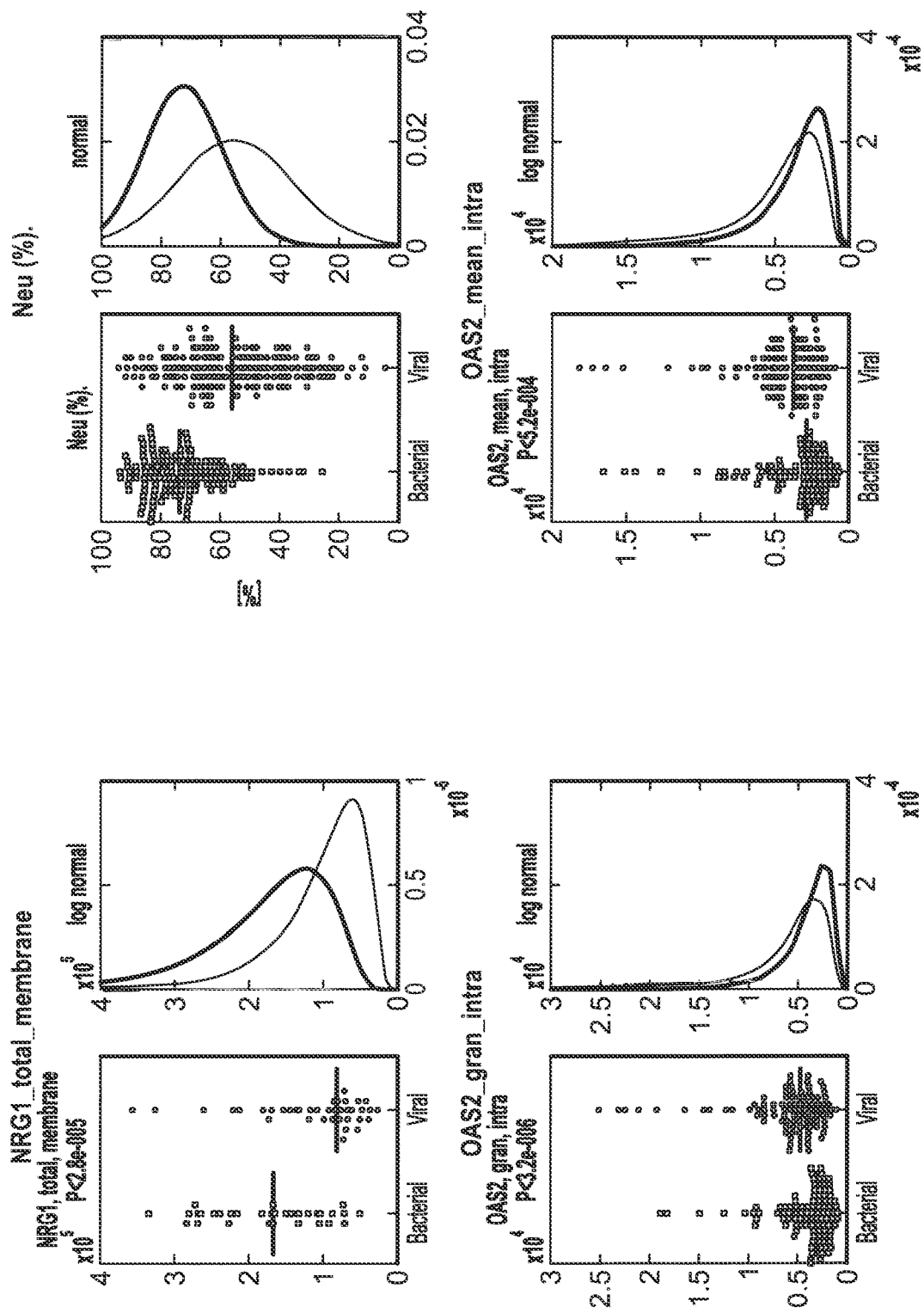
Figure 20O:
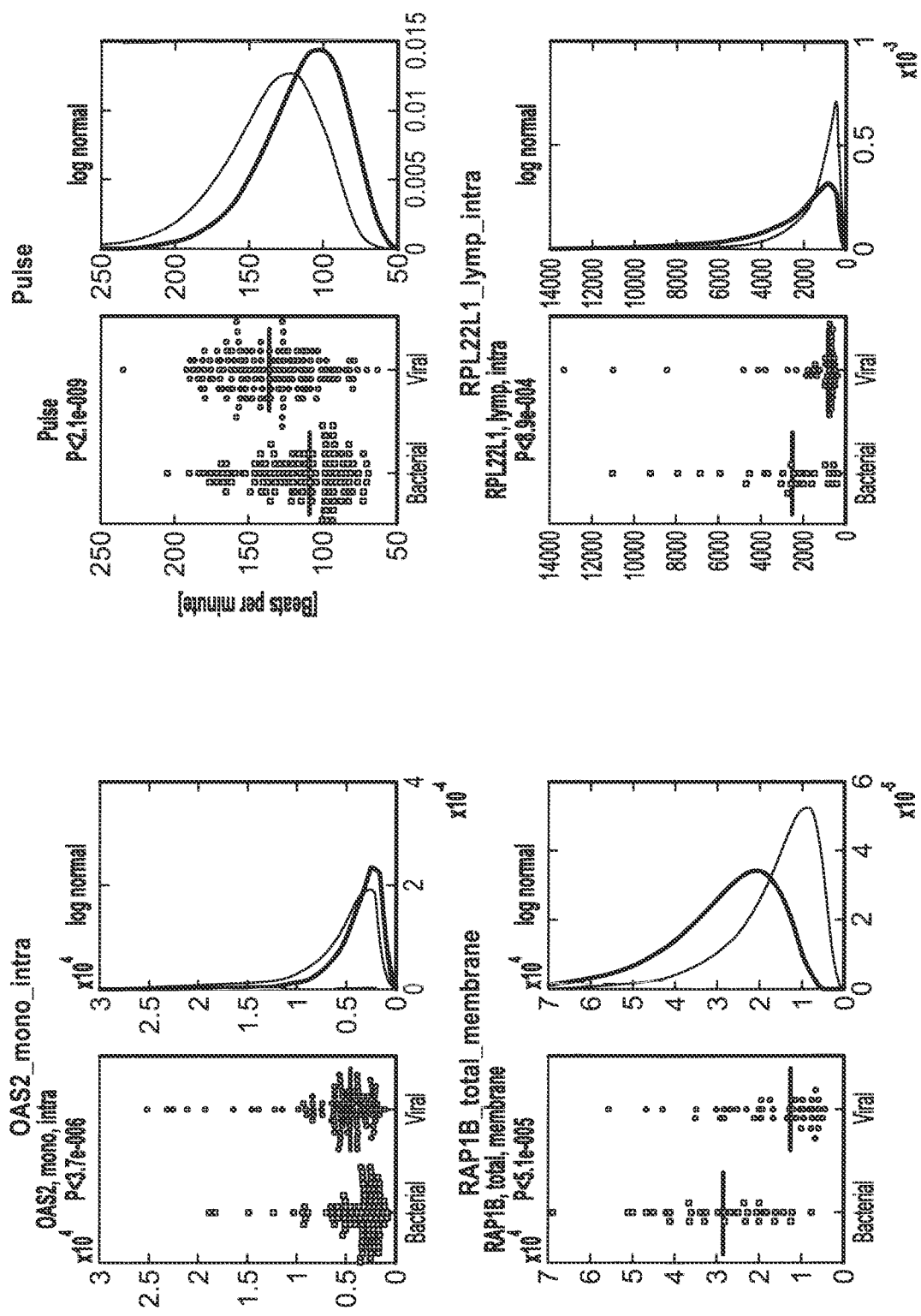
Figure 20P:
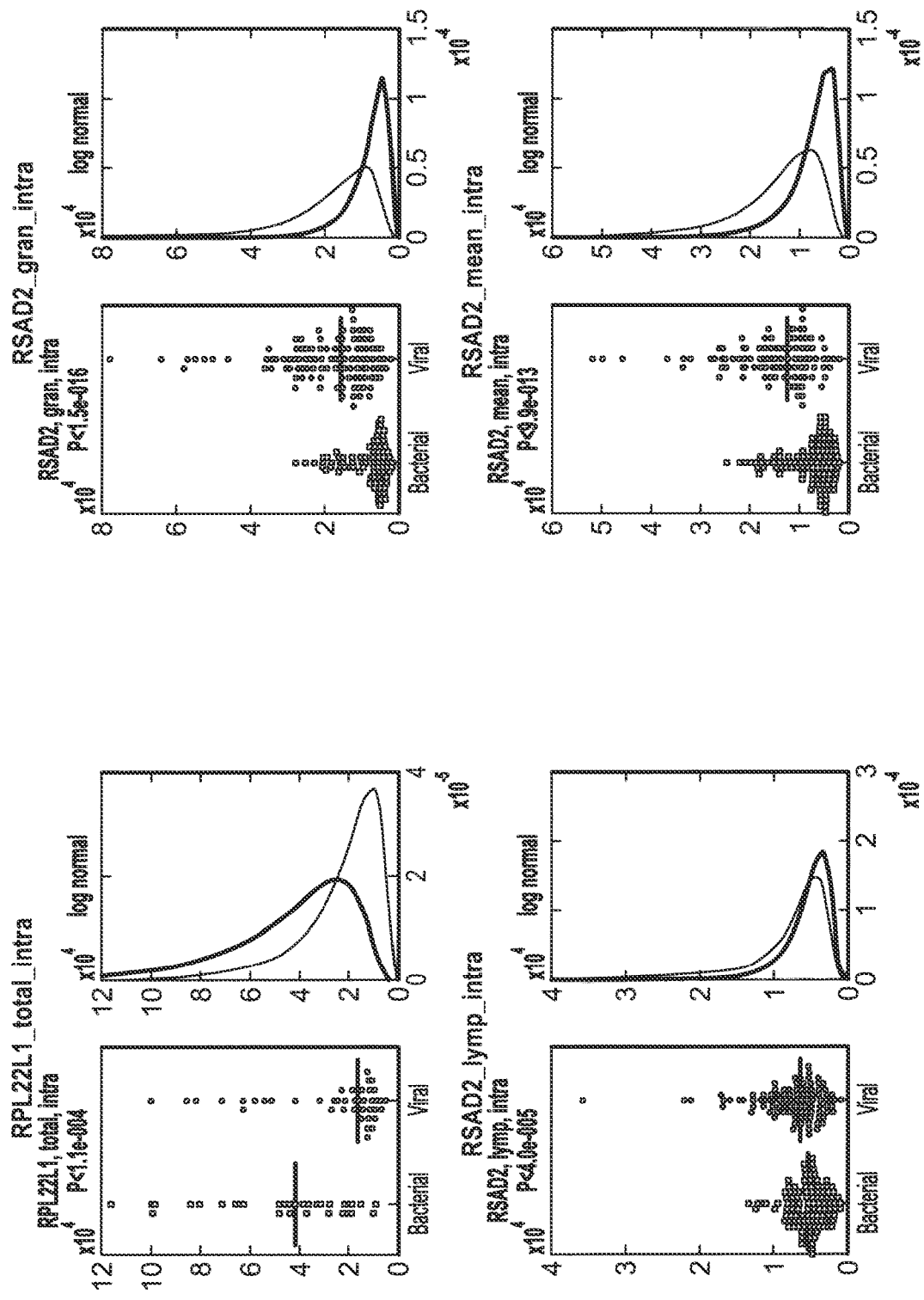
Figure 20Q:
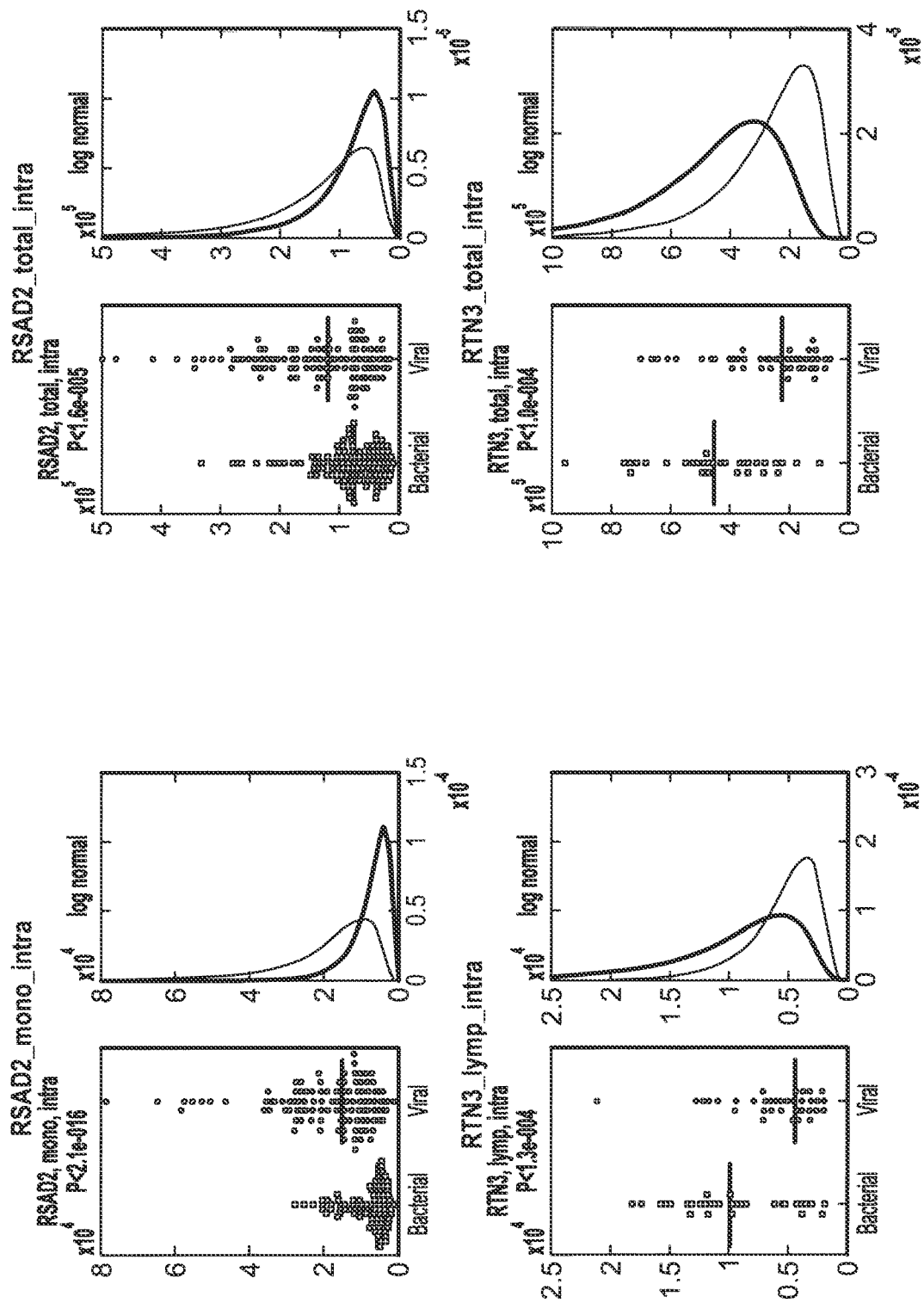
Figure 20R:
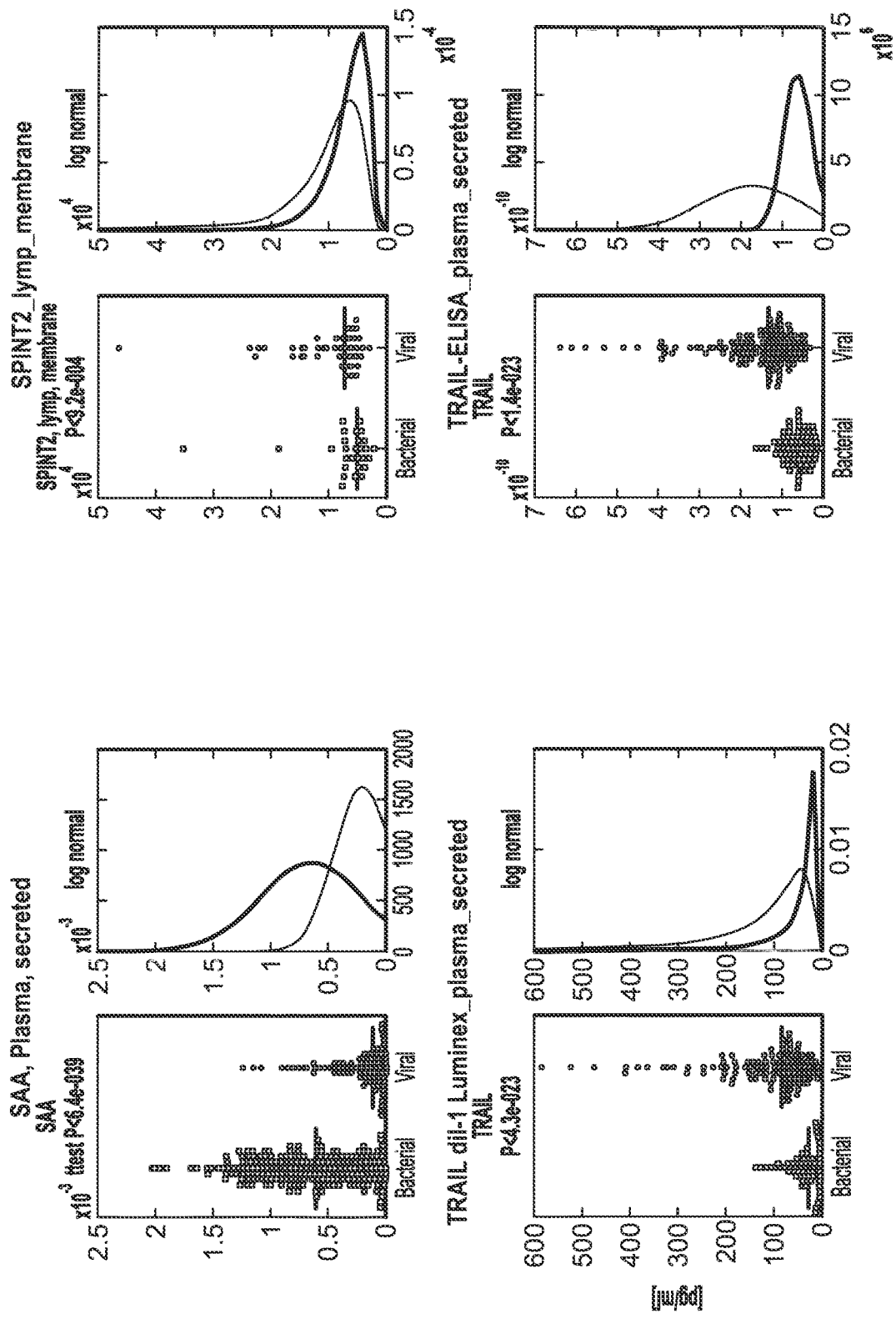
Figure 20S:
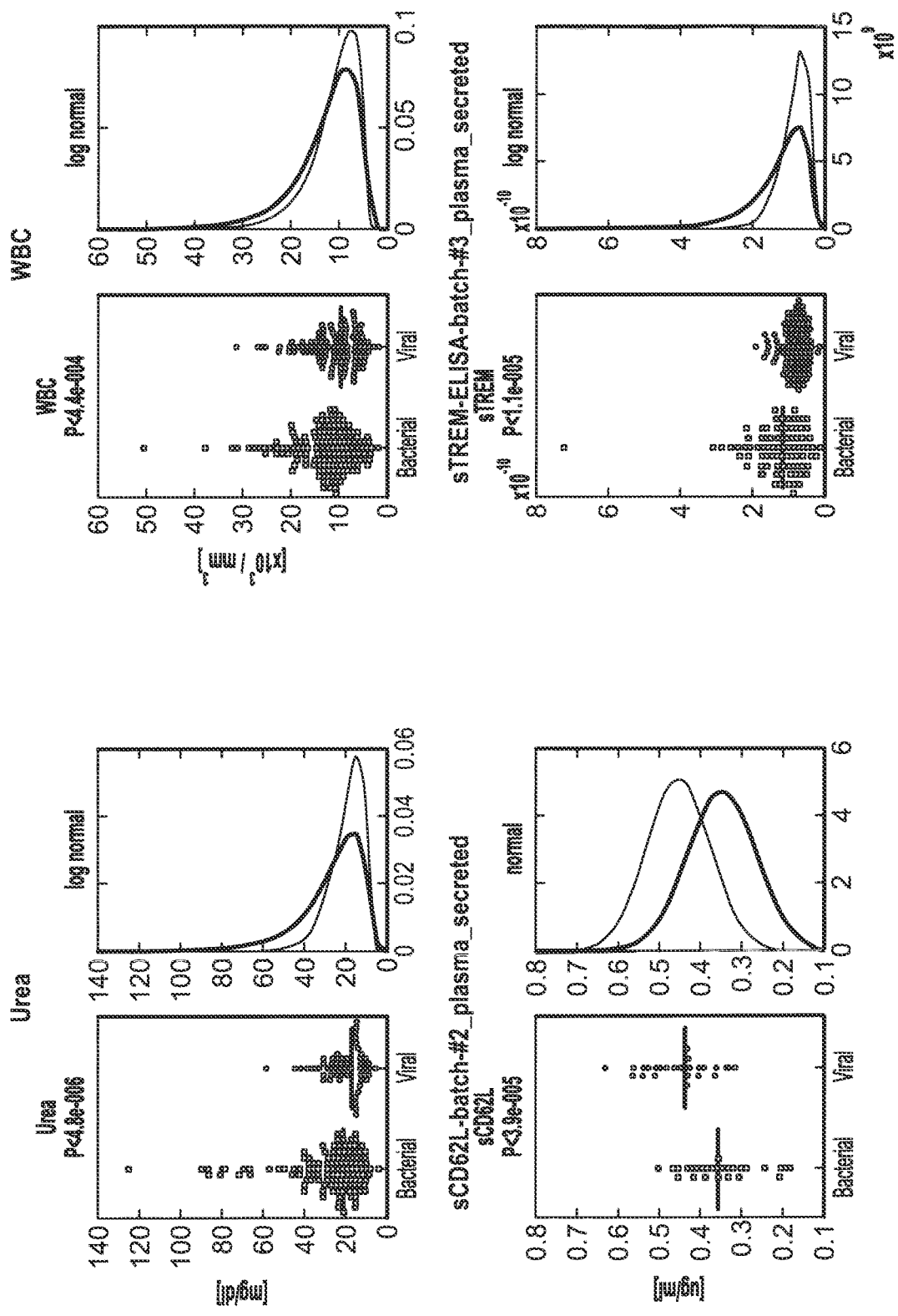
Figure 20T:
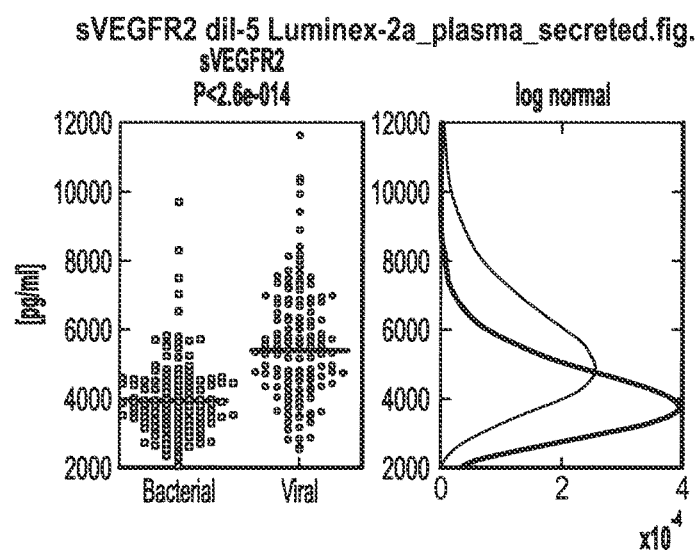

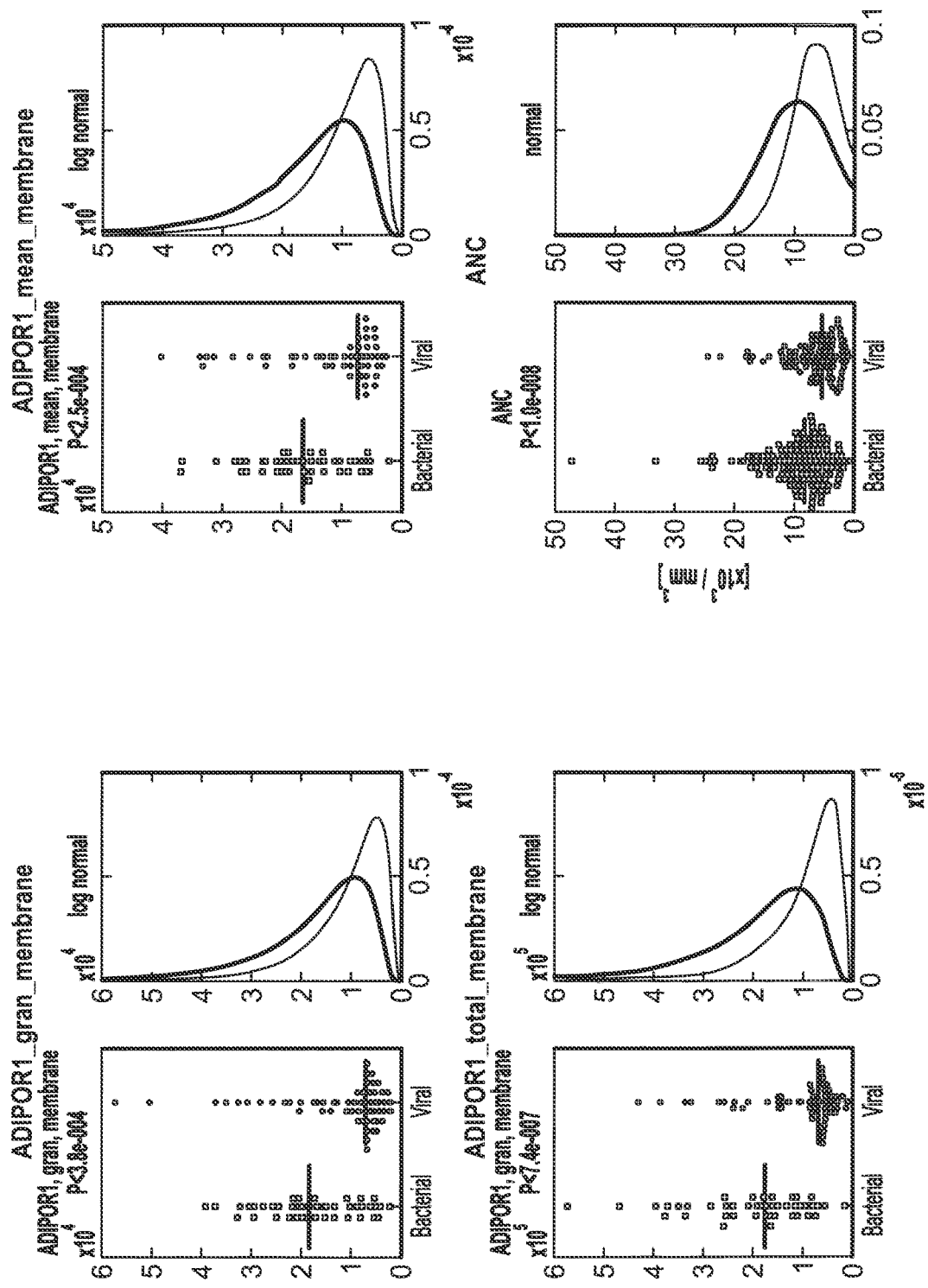
FIG. 20A INDIVIDUAL POLYPEPTIDES: BACTERIAL VERSUS VIRAL

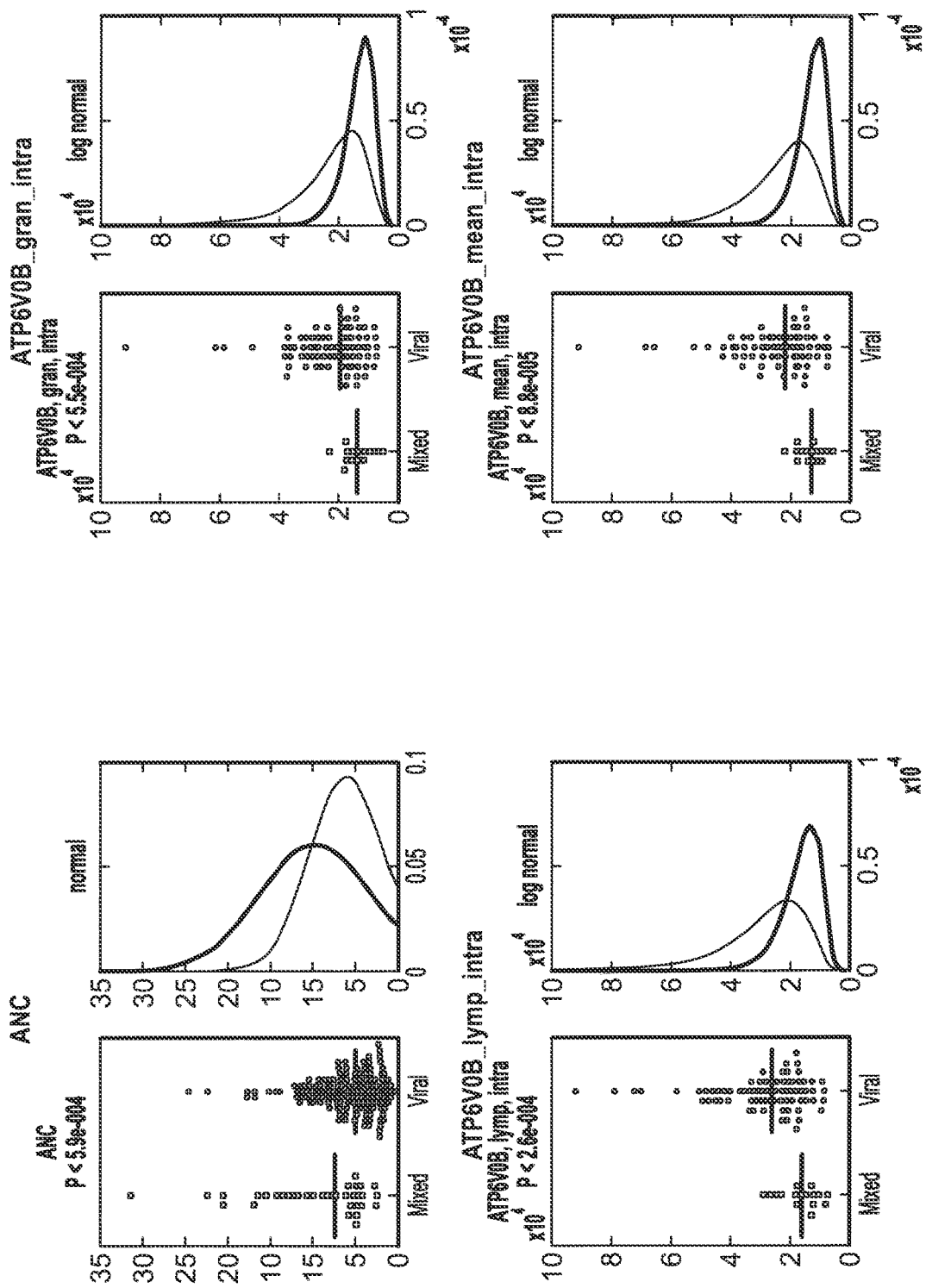
FIG. 21A-1 INDIVIDUAL POLYPEPTIDES: MIXED VERSUS VIRAL

INDIVIDUAL POLYPEPTIDES: INFECTIOUS VERSUS NON-INFECTIOUS

INDIVIDUAL POLYPEPTIDES: INFECTIOUS VERSUS HEALTHY

POLYPEPTIDES COMBINATIONS: BACTERIAL VERSUS VIRAL

POLYPEPTIDE COMBINATIONS: MIXED VERSUS VIRAL

ACCURACY OF THE TCM-SIGNATURE AS A FUNCTION OF TIME FROM SYMPTOM ONSET.

Error Bars Represent 95% CI.

ACCURACY OF THE TCM-SIGNATURE AS A FUNCTION OF MAXIMAL FEVER MEASURED

Error Bars Represent 95% CI.

AGE DEPENDENT DETERMINANT BEHAVIOR

ERROR BARS REPRESENT 95% CI.

ROC CURVE FOR THE ANALYTE TRAIL (ANALYSIS PERFORMED USING THE 'CONSENSUS [BACTERIAL, VIRAL]' COHORT, N = 343).

REMOVING PATIENTS WITH MARGINAL TRAIL LEVELS INCREASES ITS ACCURACY

FIG. 38A-1
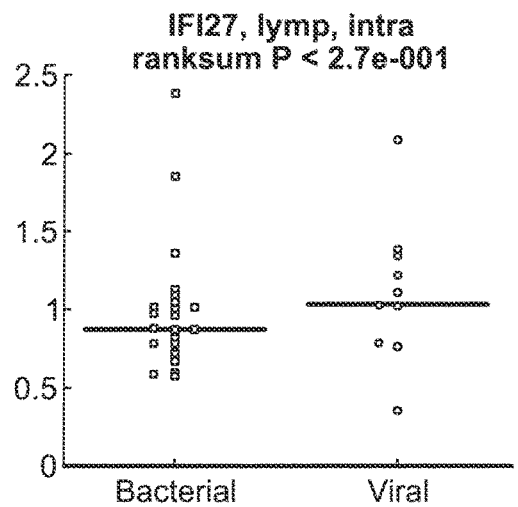
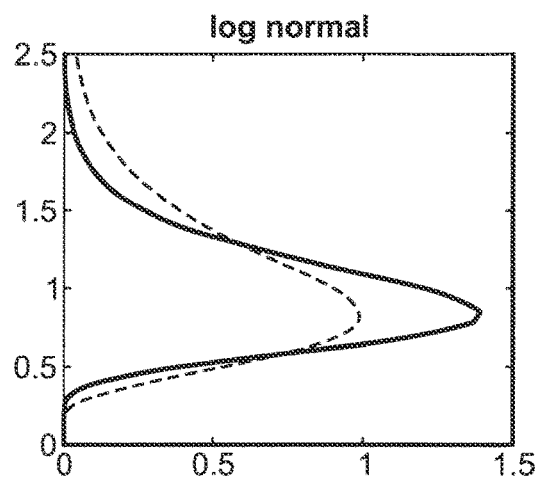
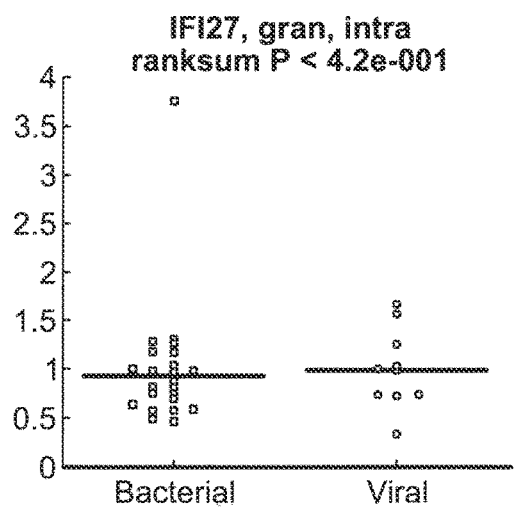
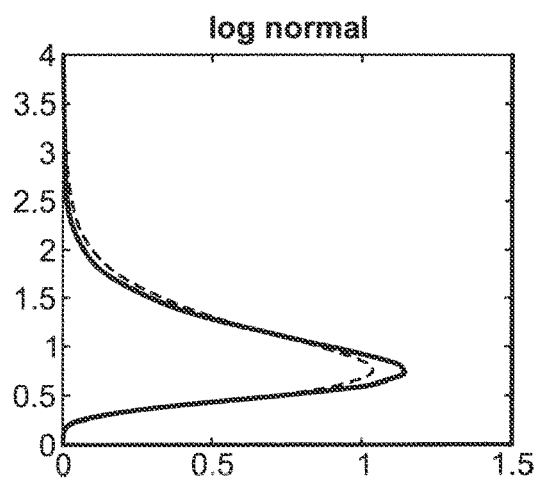
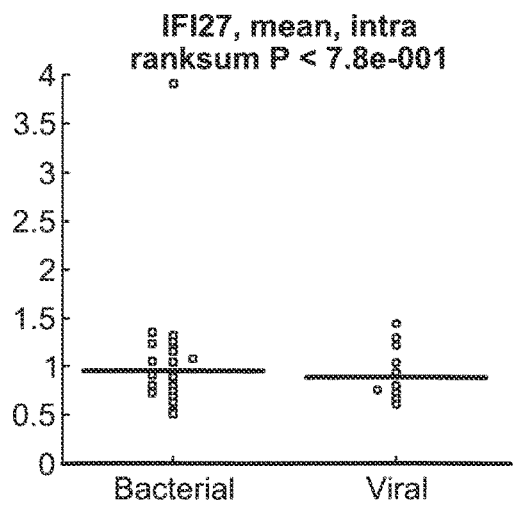
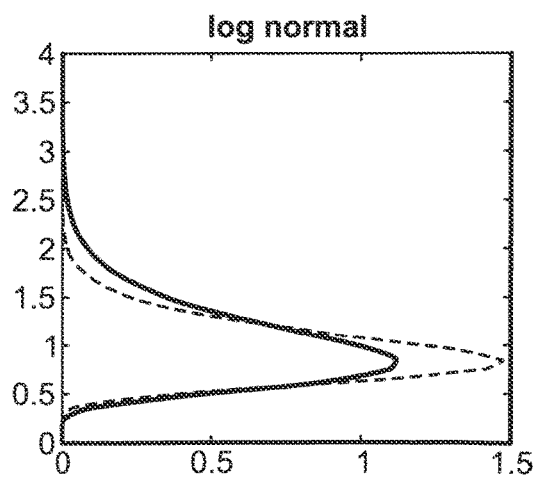

FIG. 38A-2
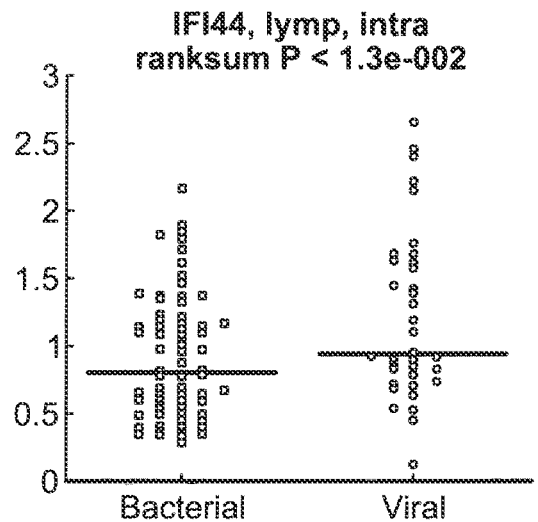
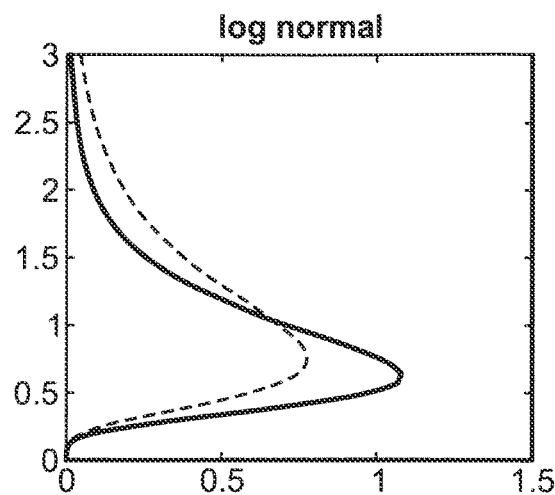
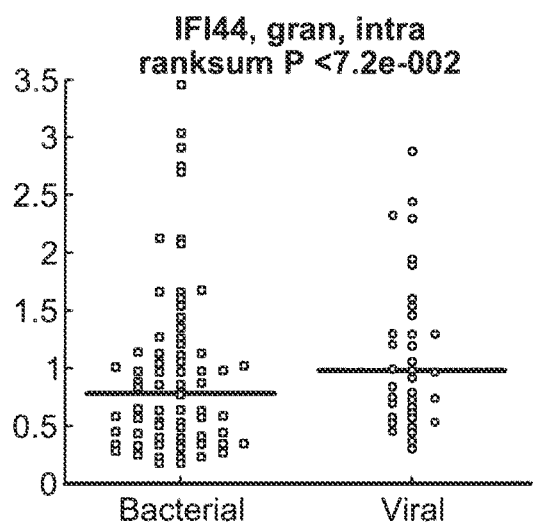
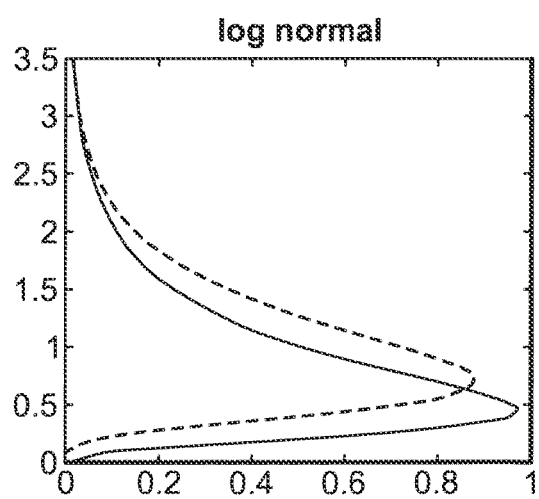
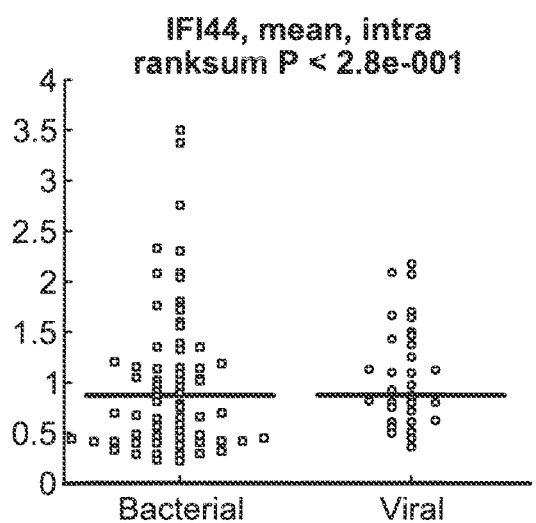
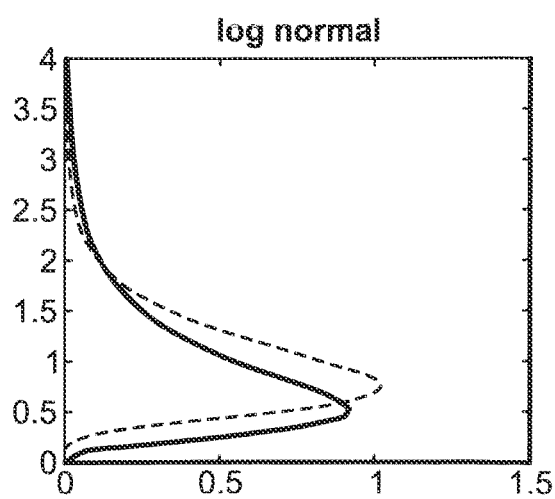

FIG. 38A-3
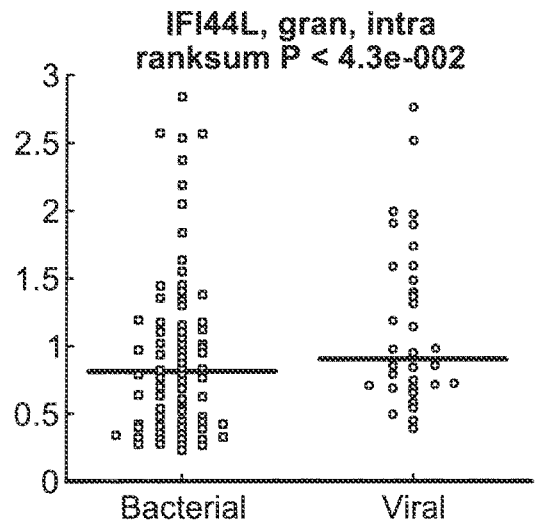
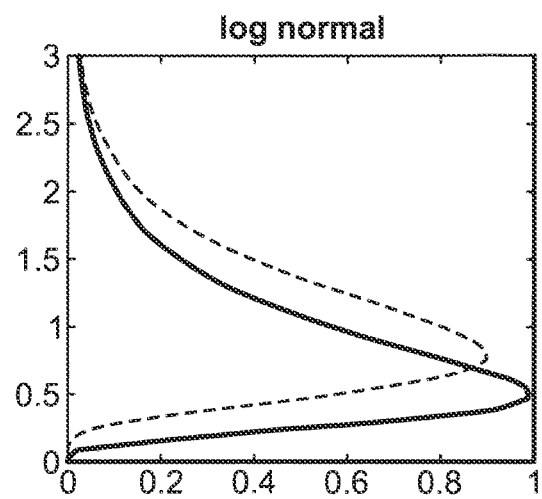
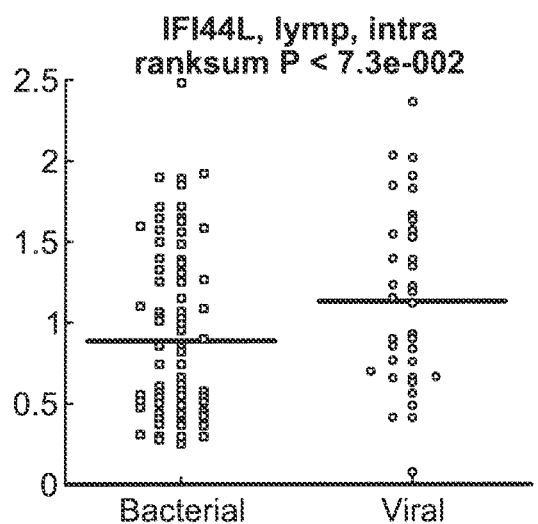
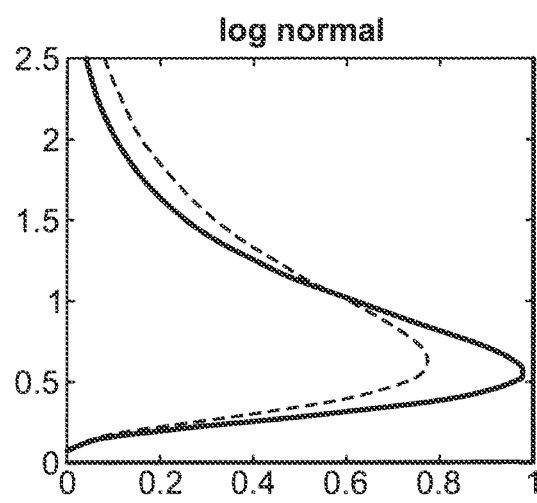
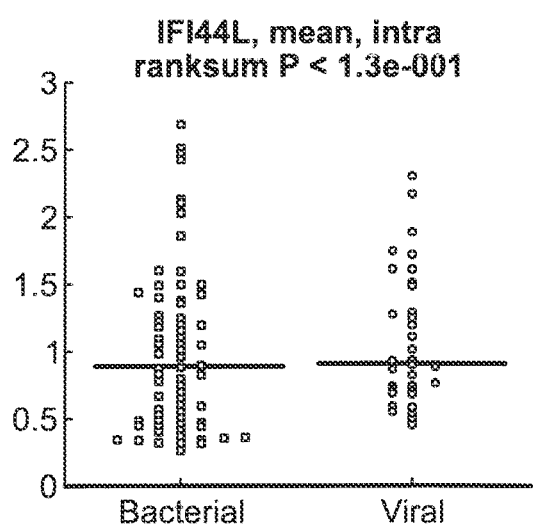
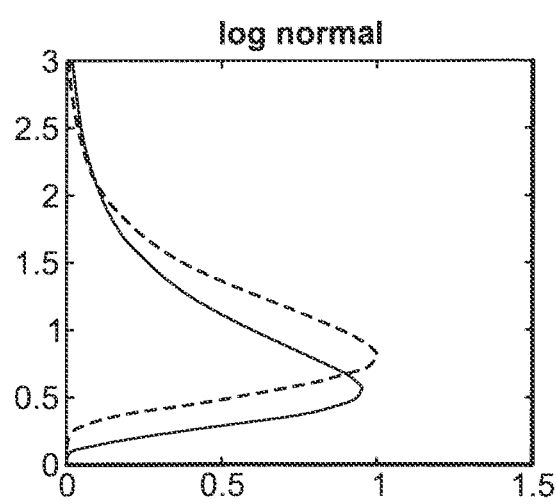

FIG. 38B
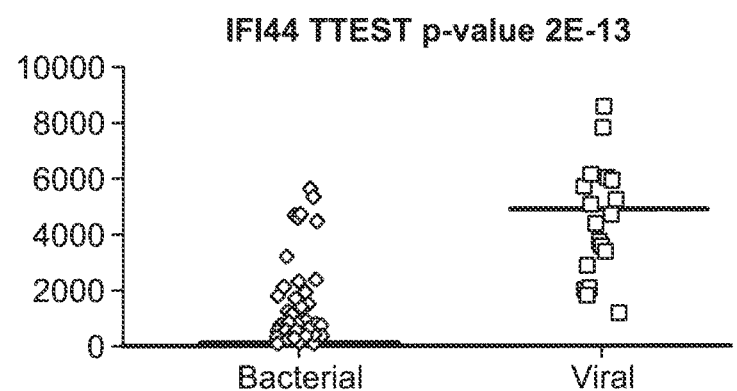
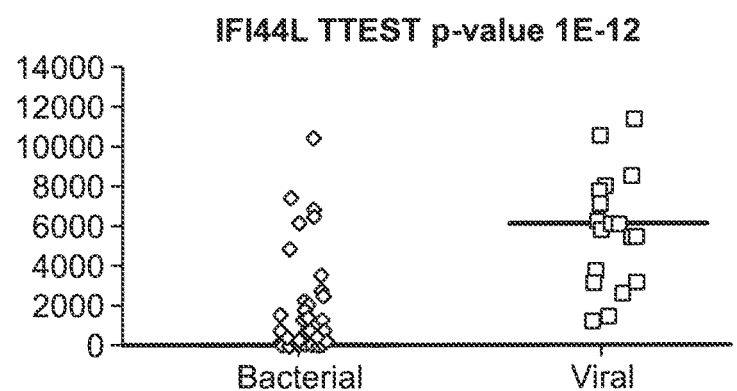
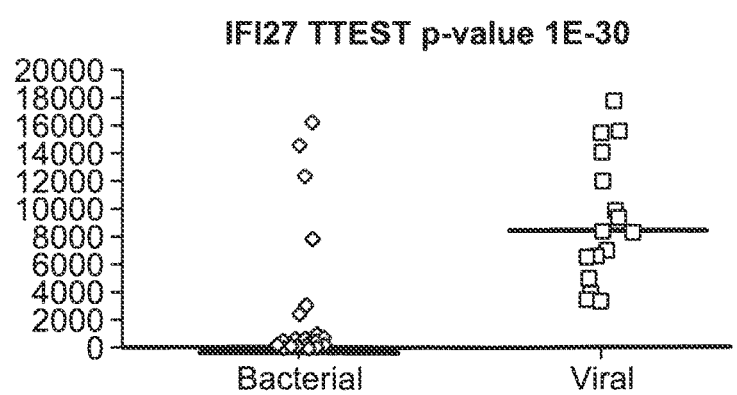

COMPARISON OF THE GENETIC SEQUENCE OF TRAIL ACROSS ORGANISMS.

SIGNATURES AND DETERMINANTS FOR DIAGNOSING INFECTIONS AND METHODS OF USE THEREOF

RELATED APPLICATIONS

This application is a continuation of U.S. patent application Ser. No. 16/687,726 filed on Nov. 19, 2019, which is a division of U.S. patent application Ser. No. 15/237,728 filed on Aug. 16, 2016, now U.S. Pat. No. 10,502,739, which is a division of U.S. patent application Ser. No. 14/377,887 filed on Aug. 11, 2014, now U.S. Pat. No. 9,726,668, which is a National Phase of PCT Patent Application No. PCT/EP2013/052619 having International Filing Date of Feb. 8, 2013, which claims the benefit of priority under USC § 119(e) of U.S. Provisional Patent Application Nos. 61/596,950 filed on Feb. 9, 2012 and 61/652,631 filed on May 29, 2012. The contents of the above applications are all incorporated by reference as if fully set forth herein in their entirety.

FIELD AND BACKGROUND OF THE INVENTION

The present invention, in some embodiments thereof, relates generally to the identification of biological signatures and determinants associated with bacterial and viral infections and methods of using such biological signatures in the screening diagnosis, therapy, and monitoring of infection.

Antibiotics (Abx) are the world's most prescribed class of drugs with a 25-30 billion $US global market. Abx are also the world's most misused drug with a significant fraction of all drugs (40-70%) being wrongly prescribed (Linder, J. A. and R. S. Stafford 2001; Scott, J. G. and D. Cohen, et al. 2001; Davey, P. and E. Brown, et al 2006; Cadieux, G. and R. Tamblyn, et al. 2007; Pulcini, C. and E. Cua, et al. 2007)("CDC—Get Smart: Fast Facts About Antibiotic Resistance" 2011).

One type of Abx misuse is when the drug is administered in case of a non-bacterial disease, such as a viral infection, for which Abx is ineffective. For example, according to the USA center for disease control and prevention CDC, over 60 Million wrong Abx prescriptions are given annually to treat flu in the US. The health-care and economic consequences of the Abx over-prescription include: (i) the cost of antibiotics that are unnecessarily prescribed globally, estimated at >$10 billion annually; (ii) side effects resulting from unnecessary Abx treatment are reducing quality of healthcare, causing complications and prolonged hospitalization (e.g. allergic reactions, Abx associated diarrhea, intestinal yeast etc.) and (iii) the emergence of resistant strains of bacteria as a result of the overuse (the CDC has declared the rise in antibiotic resistance of bacteria as "one of the world's most pressing health problems in the 21$^{st}$ century" (Arias, C. A. and B. E. Murray 2009; "CDC—About Antimicrobial Resistance" 2011)).

Antibiotics under-prescription is not uncommon either. For example up to 15% of adult bacterial pneumonia hospitalized patients in the US receive delayed or no Abx treatment, even though in these instances early treatment can save lives and reduce complications(Houck, P. M. and D. W. Bratzler, et al 2002).

Technologies for infectious disease diagnostics have the potential to reduce the associated health and financial burden associated with Abx misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

Current solutions (such as culture, PCR and immunoassays) do not fulfill all these requirements: (i) Some of the assays yield poor diagnostic accuracy (e.g. low sensitivity or specificity)(Uyeki et al. 2009), and are restricted to a limited set of bacterial or viral strains; (ii) they often require hours to days; (iii) they do not distinguish between pathogenic and non-pathogenic bacteria (Del Mar, C 1992), thus leading to false positives; (iv) they often fail to distinguish between a mixed and a pure viral infections and (v) they require direct sampling of the infection site in which traces of the disease causing agent are searched for, thus prohibiting the diagnosis in cases where the pathogen resides in an inaccessible tissue, which is often the case.

Consequentially, there still a diagnostic gap, which in turn often leads physicians to either over-prescribe Abx (the "Just-in-case-approach"), or under-prescribe Abx (the "Wait-and-see-approach") (Little, P. S. and I. Williamson 1994; Little, P. 2005; Spiro, D. M. and K. Y. Tay, et al 2006), both of which have far reaching health and financial consequences.

Accordingly, a need exists for a rapid method that accurately differentiates between bacterial, viral, mixed and non-infectious disease patients that addresses these challenges.

SUMMARY OF THE INVENTION

The present invention, in some embodiments thereof, is based on the identification of signatures and determinants associated with bacterial, viral and mixed (i.e., bacterial and viral co-infections) infections, patients with a non-infectious disease and healthy subjects. The methods of the invention allow for the identification of type of infection a subject is suffering from, which in turn allows for the selection of an appropriate treatment regimen. Various embodiments of the invention address limitations of current diagnostic solutions by: (i) allowing accurate diagnostics on a broad range of pathogens; (ii) enabling rapid diagnosis (within minutes); (iii) insensitivity to the presence of non-pathogenic bacteria and viruses (thus reducing the problem of false-positive); (iv) providing means for distinguishing between mixed from pure viral infections, and (v) eliminating the need for direct sampling of the pathogen, thus enabling diagnosis of inaccessible infections. Thus, some methods of the invention allow for the selection of subjects for whom antibiotic treatment is desired and prevent unnecessary antibiotic treatment of subjects having only a viral infection or a non-infectious disease. Some methods of the invention also allow for the selection of subjects for whom anti-viral treatment is advantageous.

To develop and validate various aspects of the invention, the inventors conducted a large prospective multi-center clinical trial enrolling 655 hospital patients with different types of infections as well as controls (patients with a non-infectious disease and healthy individuals).

The inventors then performed meticulous molecular and biochemical experimentation and measured the levels of over 570 polypeptides and other physiological determinants in these patients using quantitative assays. They found that most determinants were not indicative of the underlying infection type (e.g. bacterial, viral mixed and non-infectious disease). Moreover, even determinants with a well-established immunological role in the host response to infection failed to robustly distinguish between patients with different underlying infection types. Diverging from this norm were a few unique determinants, which the inventors were able to identify, that were able to differentiate between various types of infections.

In various aspects the invention provides methods of ruling out a bacterial infection in a subject by measuring the polypeptide concentration of TRAIL in a subject derived sample; and ruling out a bacterial infection for the subject if the polypeptide concentration of TRAIL determined is higher than a pre-determined first threshold value. Optionally, the method further includes ruling in a viral infection in the subject if the polypeptide concentration of TRAIL is higher than a pre-determined second threshold value.

In another aspect the invention provides a method of ruling out a viral infection in a subject measuring the polypeptide concentration of TRAIL in a subject derived sample; and ruling out a viral infection for the subject if the polypeptide concentration of TRAIL determined is lower than a pre-determined first threshold value. Optionally, the method further includes ruling in a bacterial infection in the subject if the polypeptide concentration of TRAIL determined in step (a) is lower than a pre-determined second threshold value.

In a further aspect the invention provides a method of ruling in a bacterial infection in a subject by measuring the polypeptide concentration of TRAIL in a subject derived sample ruling in a bacterial infection for the subject if the polypeptide concentration of TRAIL is lower than a pre-determined first threshold value.

In another aspects the invention provides a method of ruling in a viral infection in a subject by measuring the polypeptide concentration of TRAIL in a subject derived sample; and ruling in a viral infection for the subject if the polypeptide concentration of TRAIL is higher than a pre-determined first threshold value.

In various aspects the invention includes a method of distinguishing between a bacterial infection and a viral infection in a subject by measuring the polypeptide concentration of TRAIL and CRP in a subject derived sample, applying a pre-determined mathematical function on the concentrations of TRAIL and CRP to compute a score and comparing the score to a predetermined reference value.

In another aspect, the invention provides a method of distinguishing between a bacterial or mixed infection, and a viral infection in a subject by measuring the polypeptide concentration of TRAIL and CRP in a subject derived sample, applying a pre-determined mathematical function on the concentrations of TRAIL and CRP to compute a score and comparing the score to a predetermined reference value.

In various embodiments any of the above described methods further includes measuring the polypeptide concentration of one or more polypeptide selected from the group consisting of SAA, PCT, B2M Mac-2BP, IL1RA and IP10, applying a pre-determined mathematical function on the concentrations of the polypeptide concentration measure to compute a score, comparing the score to a predetermined reference value. Specifically in some embodiments TRAIL, CRP and SAA are measured; TRAIL, CRP and IP10 are measured; TRAIL, CRP and PCT are measured; TRAIL, CRP and IL1RA are measured; TRAIL, CRP and B2M are measured; TRAIL, CRP and Mac-2BP are measured; TRAIL, CRP, SAA and PCT are measured; TRAIL, CRP, Mac-2BP and SAA are measured; TRAIL, CRP, SAA and IP10 are measured; TRAIL, CRP, SAA and IL1RA are measured; TRAIL, CRP, SAA, PCT and IP10 are measured; TRAIL, CRP, SAA, PCT and IL1RA are measured; or TRAIL, CRP, SAA, IP10 and IL1RA are measured.

In a further aspect the invention includes method of providing a treatment recommendation i.e., selecting a treatment regimen for a subject by measuring the polypeptide concentration of TRAIL in a subject derived sample; and recommending that the subject receives an antibiotic treatment if polypeptide concentration of TRAIL is lower than a pre-determined threshold value; recommending that the patient does not receive an antibiotic treatment if the polypeptide concentration of TRAIL is higher than a pre-determined threshold value; or recommending that the patient receive an anti-viral treatment if the polypeptide concentration of TRAIL determined in step (a) is higher than a pre-determined threshold value.

In another aspect the invention includes a method of providing a treatment recommendation for a subject by identifying the type infection (i.e., bacterial, viral, mixed infection or no infection) in the subject according to the method of any of the disclosed methods and recommending that the subject receive an antibiotic treatment if the subject is identified as having bacterial infection or a mixed infection; or an anti-viral treatment is if the subject is identified as having a viral infection.

In yet another aspect the invention provides a method of providing a diagnostic test recommendation for a subject by measuring the polypeptide concentration of TRAIL in a subject derived sample; and recommending testing the sample for a bacteria if the polypeptide concentration of TRAIL is lower than a pre-determined threshold value; or recommending testing the sample for a virus if the polypeptide concentration of TRAIL is higher than a pre-determined threshold value.

In a further aspect the invention includes method of providing a diagnostic test recommendation for a subject by identifying the infection type (i.e., bacterial, viral, mixed infection or no infection) in the subject according to any of the disclosed methods.

Recommending a test to determine the source of the bacterial infection if the subject is identified as having a bacterial infection or a mixed infection; or a test to determine the source of the viral infection if the subject is identified as having a viral infection.

In various aspects any of the above methods further includes measuring one or more of the following DETERMINANTS IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC; IFITM3, IFIT3, EIF4B, IFIT1, LOC26010, MBOAT2, MX1, OAS2, RSAD2, ADIPOR1, CD15, CD8A, IFITM1, IL7.

CRP, SAA, TREM-1, PCT, IL-8, TREM-1 and IL6; Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea.

In another aspect the invention provide a method of distinguishing between a subject having an infectious disease and one having a non-infectious disease. For example, in one embodiment the an infectious disease is ruled out in a subject measuring the polypeptide concentration of one or more polypeptides including TRAIL, IP10, IL1Ra or Mac-2BP in a subject derived sample, applying a pre-determined mathematical function on the concentrations of the polypeptides measured to compute a score, comparing the score to a predetermined reference value. Optionally, the polypeptide concentration of one or more polypeptides including SAA, CRP, IL6, IL8, and PCT, TREM-1 are measured.

In various aspects the method distinguishes a virally infected subject from either a subject with non-infectious disease or a healthy subject; a bacterially infected subject, from either a subject with non-infectious disease or a healthy subject; a subject with an infectious disease from either a subject with an non-infectious disease or a healthy subject; a bacterially infected subject from a virally infected subject; a mixed infected subject from a virally infected subject; a mixed infected subject from a bacterially infected subject and a bacterially or mixed infected and subject from a virally infected subject.

These methods include measuring the levels of a first DETERMINANT including TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC and TNFR1 in a sample from the subject and measuring the levels of a second DETERMINANT including TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC TNFR1; IFITM3, IFIT3, EIF4B, IFIT1, LOC26010, MBOAT2, MX1, OAS2, RSAD2, ADIPOR1, CD15, CD8A, IFITM1, IL7; CRP, SAA, TREM-1, PCT, IL-8, TREM-1 and IL6; Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea and comparing the levels of the first and second DETERMINANTS to a reference value thereby identifying the type of infection in the subject wherein the measurement of the second DETERMINANT increases the accuracy of the identification of the type of infection over the measurement of the first DETERMINANT.

Optionally, further includes measuring the level of a one or more additional DETERMINANTS including: TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC TNFR1; IFITM3, IFIT3, EIF4B, IFIT1, LOC26010, MBOAT2, MX1, OAS2, RSAD2, ADIPOR1, CD15, CD8A, IFITM1, IL7; CRP, SAA, TREM-1, PCT, IL-8, TREM-1 and IL6; Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea; wherein the measurement of the additional DETERMINANTS increases the accuracy of the identification of the type of infection over the measurement of the first and second DETERMINANTS. In one aspect the method distinguishes a bacterially infected subject from a virally infected subject by measuring one or more DETERMINANTS selected from B2M, BCA-1, CHI3L1, Eotaxin, IL1RA, IP10, MCP, Mac-2BP, TRAIL, CD62L and VEGFR2 are measured and one or more DETERMINANTS selected from the group consisting of CRP, TREM-1, SAA, PCT, IL-8, IL6, ANC, ALC, Neu (%), Lym (%), Mono (%), Maximal temperature, Time from symptoms, Age, Creatinine (Cr), Potassium (K), Pulse and Urea. For example, CRP and TRAIL are measured; CRP and TRAIL and SAA are measured; CRP and TRAIL and Mac-2BP are measured; CRP and TRAIL and PCT and are measured; CRP and TRAIL and SAA and Mac-2BP are measured; PCT and TRAIL are measured; or SAA and TRAIL are measured. In a another aspect the method distinguishes between a mixed infected subject and a virally infected subject by measuring wherein one or more DETERMINANTS selected from TRAIL, IP10, IL1RA, CHI3L1, CMPK2 and MCP-2 are measured and optionally one or more DETERMINANTS selected from the group consisting of CRP, SAA, ANC, ATP6V0B, CES1, CORO1A, HERC5, IFITM1, LIPT1, LOC26010, LRDD, Lym (%), MCP-2, MX1, Neu (%), OAS2, PARP9, RSAD2, SART3, WBC, PCT, IL-8, IL6 and TREM-1.

In another aspect the method distinguishes between a bacterial or mixed infected subject and a virally infected subject by measuring wherein one or more DETERMINANTS selected from TRAIL, IL1RA, IP10, ARG1, CD337, CD73, CD84, CHI3L1, CHP, CMPK2, CORO1C, EIF2AK2, Eotaxin, GPR162, HLA-A/B/C, ISG15, ITGAM, Mac-2BP, NRG1, RAP1B, RPL22L1, SSEA1, RSAD2, RTN3, SELI, VEGFR2, CD62L and VEGFR2 are measured and optionally one or more DETERMINANTS selected from the group consisting of CRP, SAA, PCT, IL6, IL8, ADIPOR1, ANC, Age, B2M, Bili total, CD15, Cr, EIF4B, IFIT1, IFIT3, IFITM1, IL7R, K (potassium), KIAA0082, LOC26010, Lym (%), MBOAT2, MCP-2, MX1, Na, Neu (%), OAS2, PARP9, PTEN, Pulse, Urea, WBC, ZBP1, mIgG1 and TREM-1.

In another aspect the method distinguishes between a subject with an infectious disease and a subject with a non-infectious disease or a healthy subject by measuring one or more DETERMINANTS selected from IP10, IL1RA, TRAIL, BCA-1, CCL19-MIP3b, CES1 and CMPK2. Optionally, one or more DETERMINANTS selected from CRP, SAA, PCT, IL6, IL8, ARPC2, ATP6V0B, Cr, Eos (%), HERC5, IFI6, IFIT3, KIAA0082, LIPT1, LOC26010, LRDD, MBOAT2, MX1, Maximal temperature, OAS2, PARP9, Pulse, QARS, RAB13, RPL34, RSAD2, SART3, RIM22, UBE2N, XAF1, IL11, I-TAC and TNFR1 are measured.

Any of the above described methods can be used to further select a treatment regimen for the subject. For example, if a subject identified as having a viral infection the subject is selected to receive an anti-viral treatment regimen. When a subject is identified as having a non-viral disease the subject is selected not to receive an anti-viral treatment regimen. When a subject is identified as having a bacterial or a mixed infection the subject is selected to receive an antibiotic treatment regimen. When a subject identified as having a viral infection, a non-infectious disease or healthy the subject is not selected to receive an antibiotic treatment regimen.

In a further aspect the invention provides for monitoring the effectiveness of treatment for an infection by detecting the level of one or more polypeptide-DETERMINANTS selected from the group consisting of TRAIL, IL1RA, IP10, B2M, Mac-2BP, BCA-1, CHI3L1, Eotaxin, MCP, Mac-2BP, TRAIL, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IL11, IL1a, T-TAC and TNFR1 in a first sample from the subject at a first period of time; detecting the level of one or more polypeptide-DETERMINANTS selected from the group consisting of TRAIL, IL1RA, IP10, B2M, Mac-2BP, BCA-1, CHI3L1, EotaxinMCP, Mac-2BP, TRAIL, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IL11, IL1a, I-TAC and TNFR1 in a second sample from the subject at a second period of time; and comparing the level of the one or more polypeptide detected in the first sample to the level detected the second sample, or to a reference value, The effectiveness of treatment is monitored by a change in the level of one or more polypeptides. Optionally, the method further includes detecting one or more polypeptide-DETERMINANTS selected from CRP, SAA, TREM-1, PCT, IL-8 and IL6 in the first and second samples.

The subject has previously been treated for the infection. Alternatively the subject has not been previously treated for the infection. In some aspects the first sample is taken from the subject prior to being treated for the infection and the second sample is taken from the subject after being treated for the infection. In some aspects, the second sample is taken from the subject after recurrence of the infection or prior to recurrence of the infection.

The sample is for example, whole blood or a fraction thereof. A blood fraction sample contains cells that include lymphocytes, monocytes and granulocytes. The expression level of the polypeptide is determined by electrophoretically, or immunochemically. The immunochemical detection is for example, by flow cytometry, radioimmunoassay, immunofluorescence assay or by an enzyme-linked immunosorbent assay.

A clinically significant alteration in the level of the one or more polypeptides in the sample indicates an infection in the subject. In some aspects the level of the one or more DETERMINANTS is compared to a reference value, such as an index value. In some aspects the reference value or index value are determined after performing age dependent normalization or stratification. In any of the above methods the DETERMINANTS are preferably selected such that their MCC is >=0.4 or the AUC is >=0.7. In other aspects DETERMINANTS are preferably selected such that their Wilcoxon rank sum p-values are less than $10^{-6}$ or less than $10^{-4}$ or less than $10^{-3}$.

In any of the above methods the concentration of TRAIL is measured within about 24 hours after sample is obtained or is measured in a sample that was stored at 120 C or lower, wherein the storage begins less than 24 hours after the sample is obtained.

The infection further includes an infection reference expression profile, having a pattern of levels of two or more polypeptides selected from the group consisting of TRAIL, IL1RA, IP10, B2M, BCA-1, CHI3L1, Eotaxin, MCP, Mac-2BP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IL11, IL1a, I-TAC and TNFR1, and optionally further having a pattern of levels of one or more polypeptides selected from the group consisting of CRP, SAA, TREM-1, PCT, IL-8 and IL6. Also include in the invention is a machine readable media containing one or more infection reference expression profiles according to the invention.

In another aspect the invention includes a kit having a plurality of polypeptide detection reagents that detect the corresponding polypeptides including TRAIL, IL1RA, IP10, B2M, BCA-1, CHI3L1, Eotaxin, IL1a, MCP, Mac-2BP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, I11, I-TAC and TNFR1, and optionally further plurality of polypeptide detection reagents that detect the corresponding polypeptide including CRP, SAA, TREM-1, PCT, IL-8 and IL6. The detection reagent is comprises one or more antibodies or fragments thereof.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below.

All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE SEVERAL VIEWS OF THE DRAWING(S)

FIG. 1: Clinical study workflow.

FIG. 2: Characterization of the 575 patients enrolled in the clinical study.

FIG. 3: Summary of patient cohorts.

FIGS. 4A and 4B: Age distribution of the entire study population (A) (N=575) and pediatric patients (B) (N=350).

FIGS. 5A and 5B: Distribution of isolated pathogens by pathogenic subgroups (A) and by strains (B) (stains isolated from >1% of patients are presented).

FIG. 6: Distribution of involved physiologic systems in infectious disease patients. (N=484).

FIGS. 7A and 7B: Distribution of major clinical syndromes (A) and specific clinical syndromes (B) of the patients enrolled in the clinical study (all enrolled patients, N=575).

FIG. 8: Distribution of maximal body temperatures (all enrolled patients, N=575).

FIG. 9: Distribution of time from initiation of symptoms (all enrolled patients, N=575).

FIGS. 10A and 10B: Distribution of comorbidities of the patient population (A) and distribution of chronic medications (B) of the patients enrolled in the clinical study (all chronically ill patients, N=170).

FIG. 11: Distribution of recruitment sites (all enrolled patients, N=575).

Figures 12A, 12B, 12C:
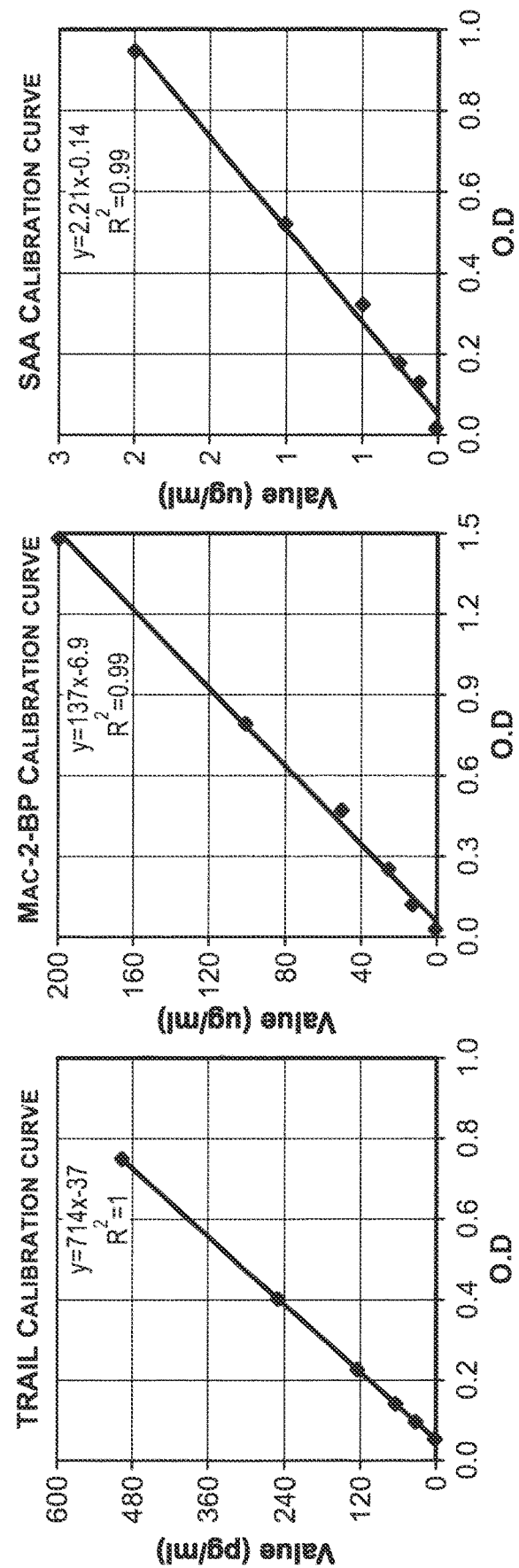

FIGS. 12A, 12B and 12C: Calibration curves for TRAIL (A), Mac-2BP (B) and SAA (C).

Figures 13A, 13B, 13C:
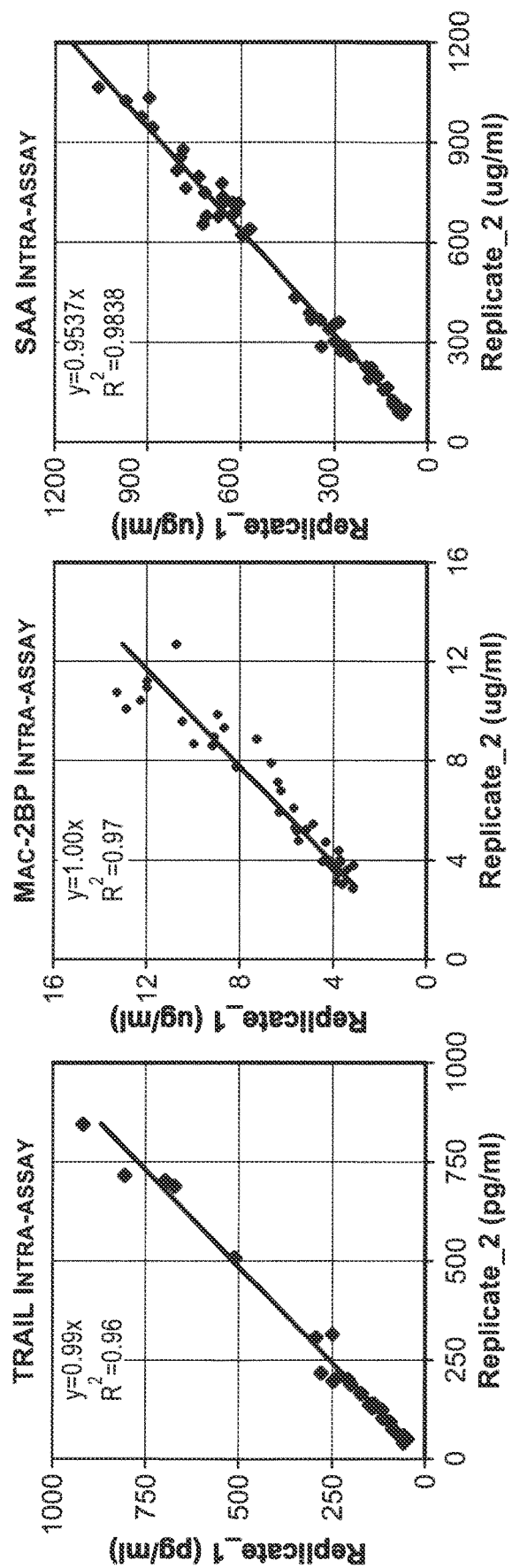

FIGS. 13A, 13B and 13C: Intra-assay variability for TRAIL (A), Mac-2-BP (B) and SAA (C).

FIGS. 14A, 14B and 14C: Inter-assay variability for TRAIL (A), Mac-2-BP (B) and SAA (C).

FIGS. 15A, 15B and 15C: Measurements of plasma vs. serum concentrations of TRAIL (A), Mac-2-BP (B) and SAA (C).

Figure 16C:
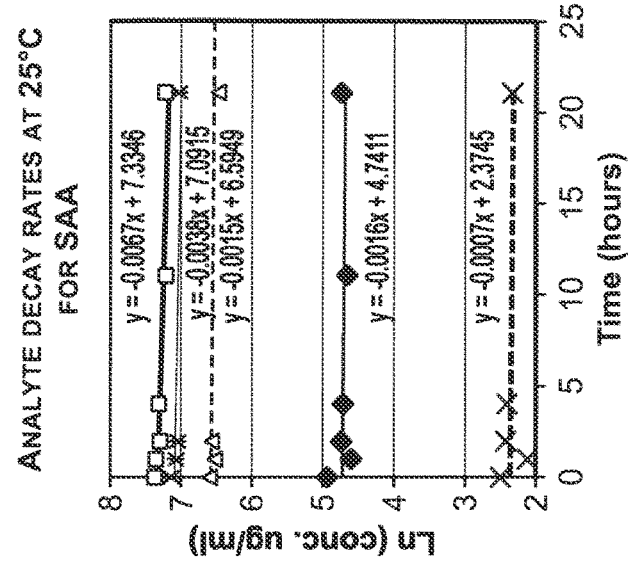
Figure 16B:
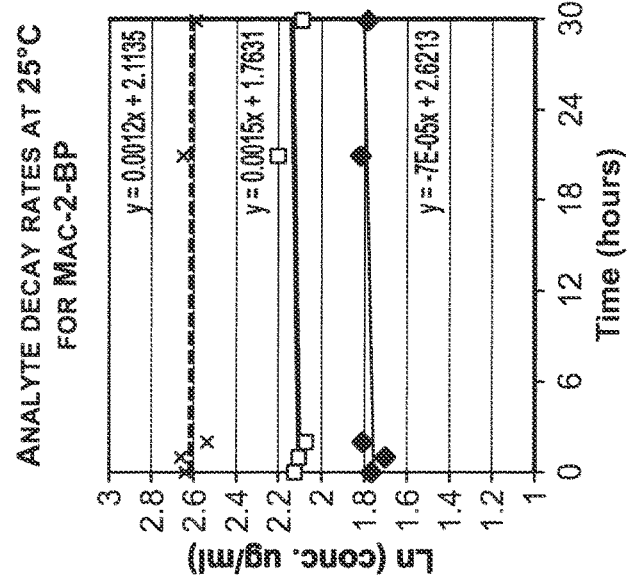
Figure 16A:
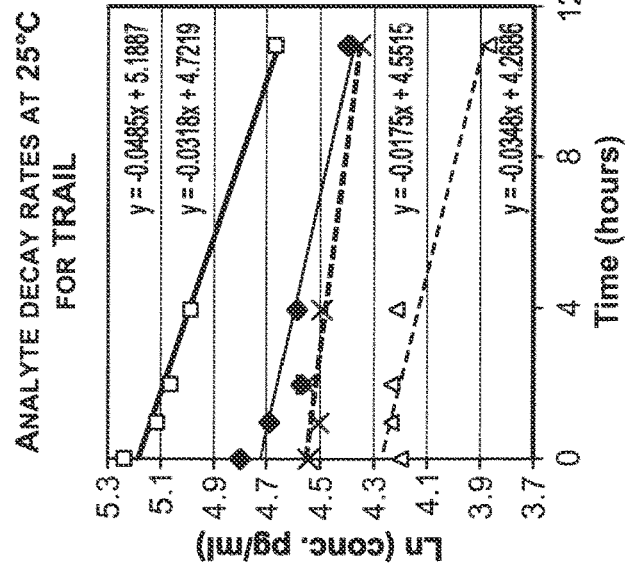

FIGS. 16A, 16B and 16C: The analytes decay rates at 25° C. for TRAIL (A), Mac-2-BP (B) and SAA (C).

FIG. 17: Correlation of TRAIL levels measured using ELISA and Luminex.

FIGS. 18A, 18B, 18C, 18D, 18E, 18F, 18G and 18H: Polypeptides with an immunological role do not necessarily show a differential response.

FIG. 19: In-vitro differentially expressed polypeptides do not necessarily show in-vivo differential expression.

FIGS. 20A, 20B, 20C, 20D, 20E, 20F, 20G, 20H, 20I, 20J, 20K, 20L, 20M, 20N, 20O, 20P, 20Q, 20R, 20S and 20T: Examples of DETERMINANTS that differentiate between bacterial versus viral infected subjects.

FIGS. 21A-1, 21A-2, 21A-3, 21A-4, 21A-5, 21A-6, 21A-7, 21A-8, 21A-9, 21A-10, 21A-11, 21A-12, 21B-1, 21B-2, 21B-3, 21B-4, 21C-1, 21C-2 and 21C-3: Examples of DETERMINANTS that differentiate between mixed versus viral infected subjects (A), infectious versus non-infectious subjects (B) and infectious versus healthy subjects (C).

Figure 22:
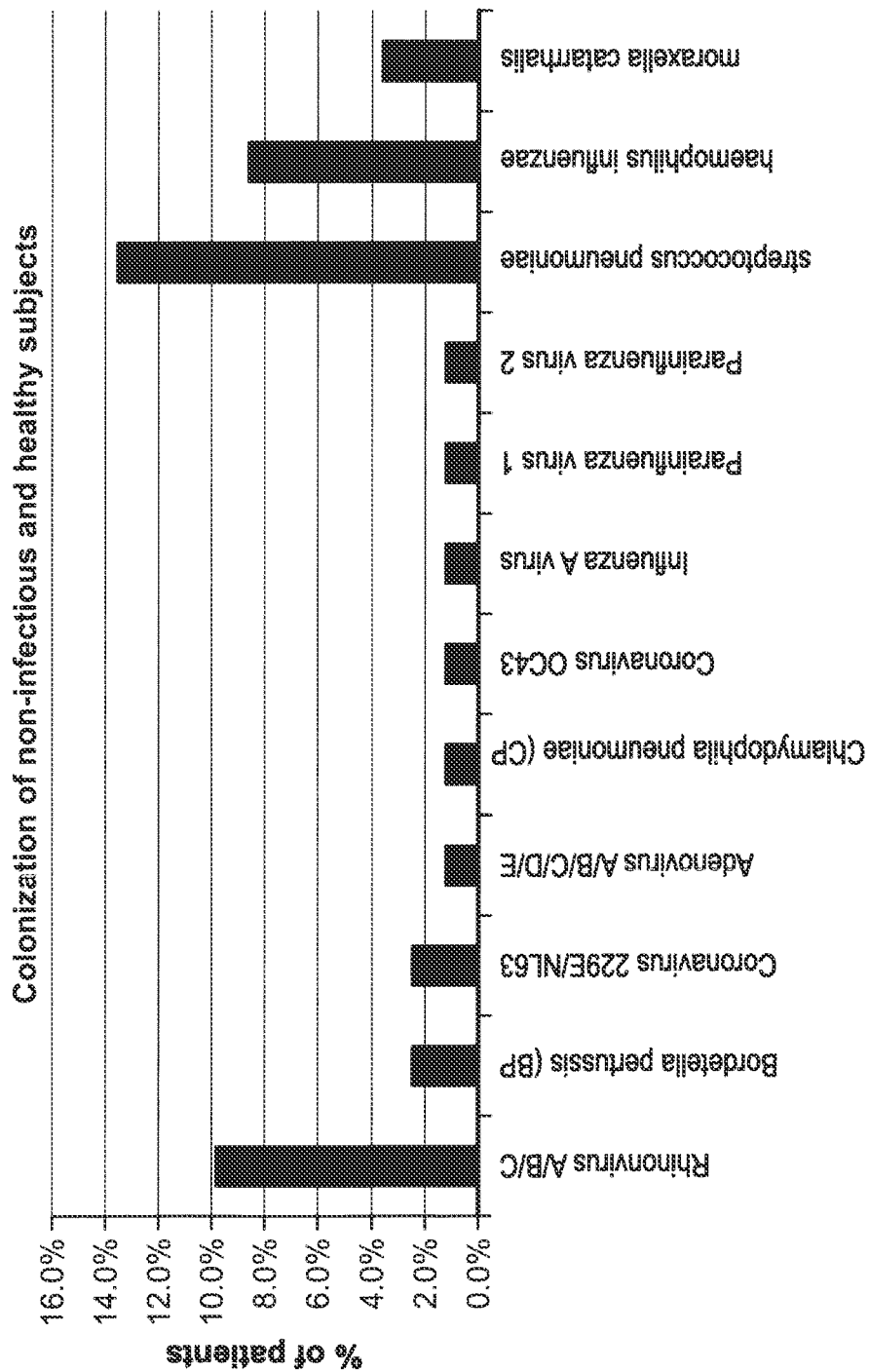

FIG. 22: Colonization of non-infectious and healthy subjects.

Figure 23A:
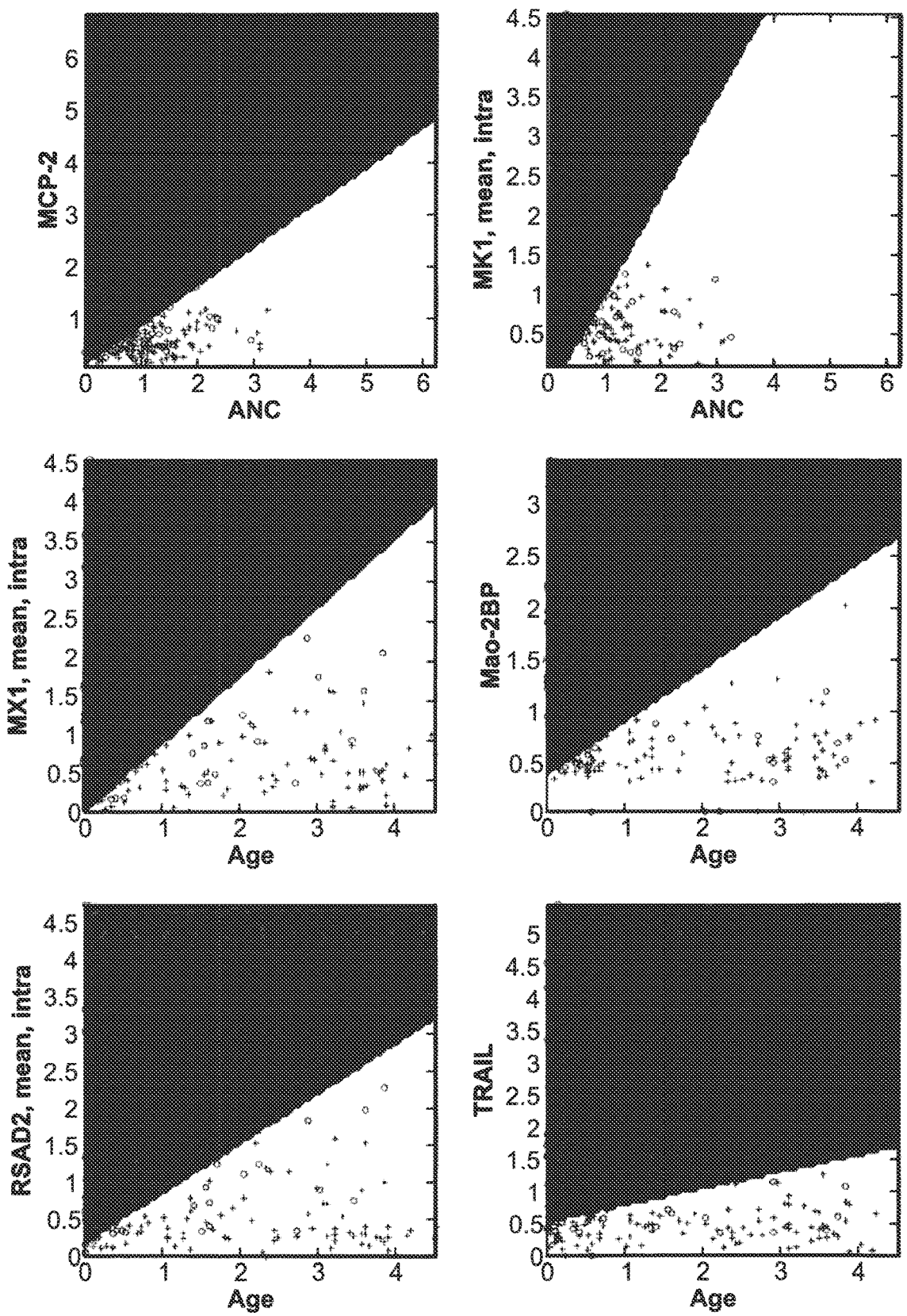
Figure 23B:
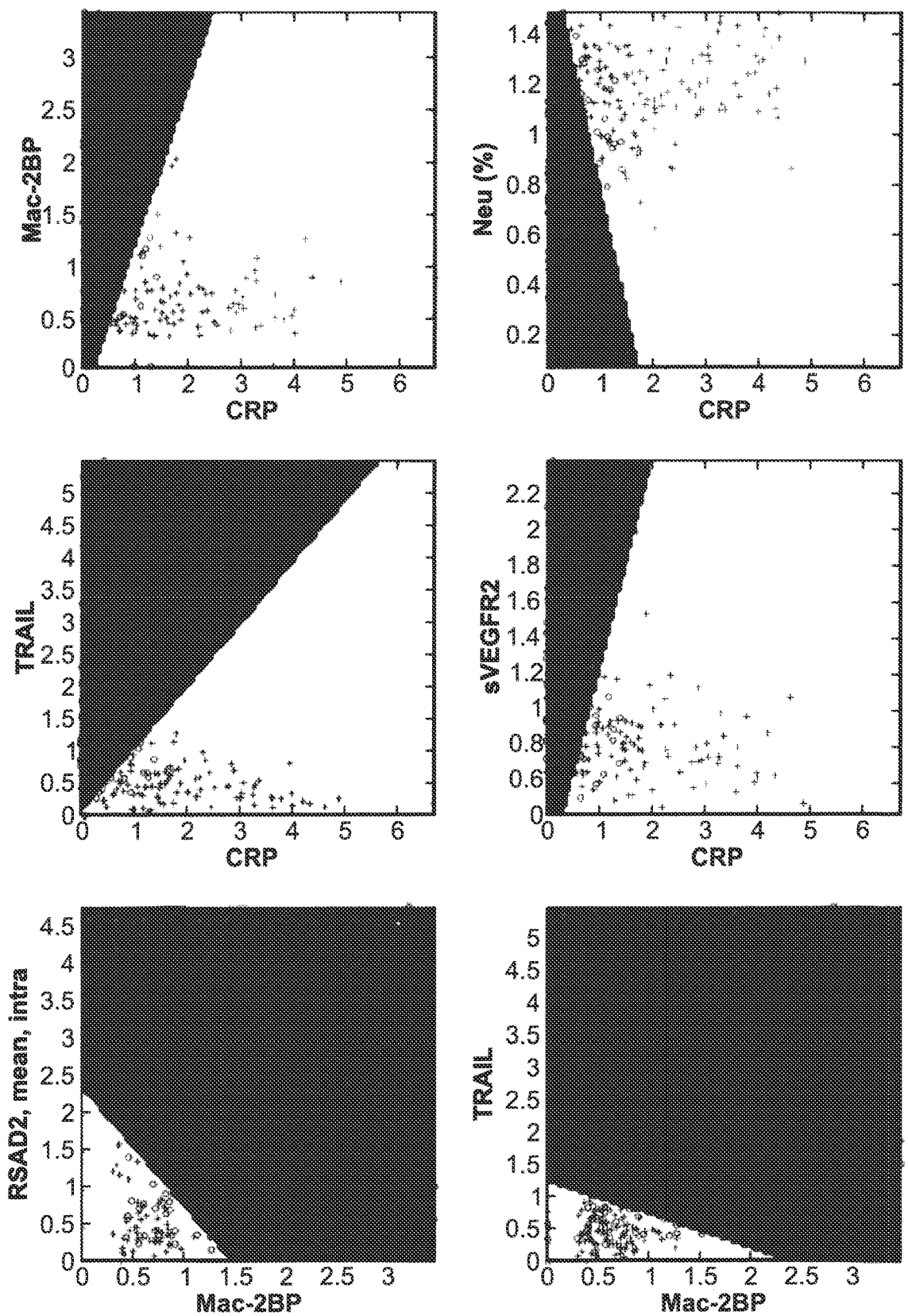

FIGS. 23A and 23B: Examples of scatter graphs showing the diagnosis of bacterial ('+' marks) versus viral ('0' marks) infected patients using a combination of two statistically significant DETERMINANTS. Patient classification was performed using a linear SVM trained on 90% of the data, where white and gray regions indicate the space of DETERMINANT combinations that were classified as viral and bacterial respectively. Each plot corresponds to a different combination of two DETERMINANTS.

Figure 24:
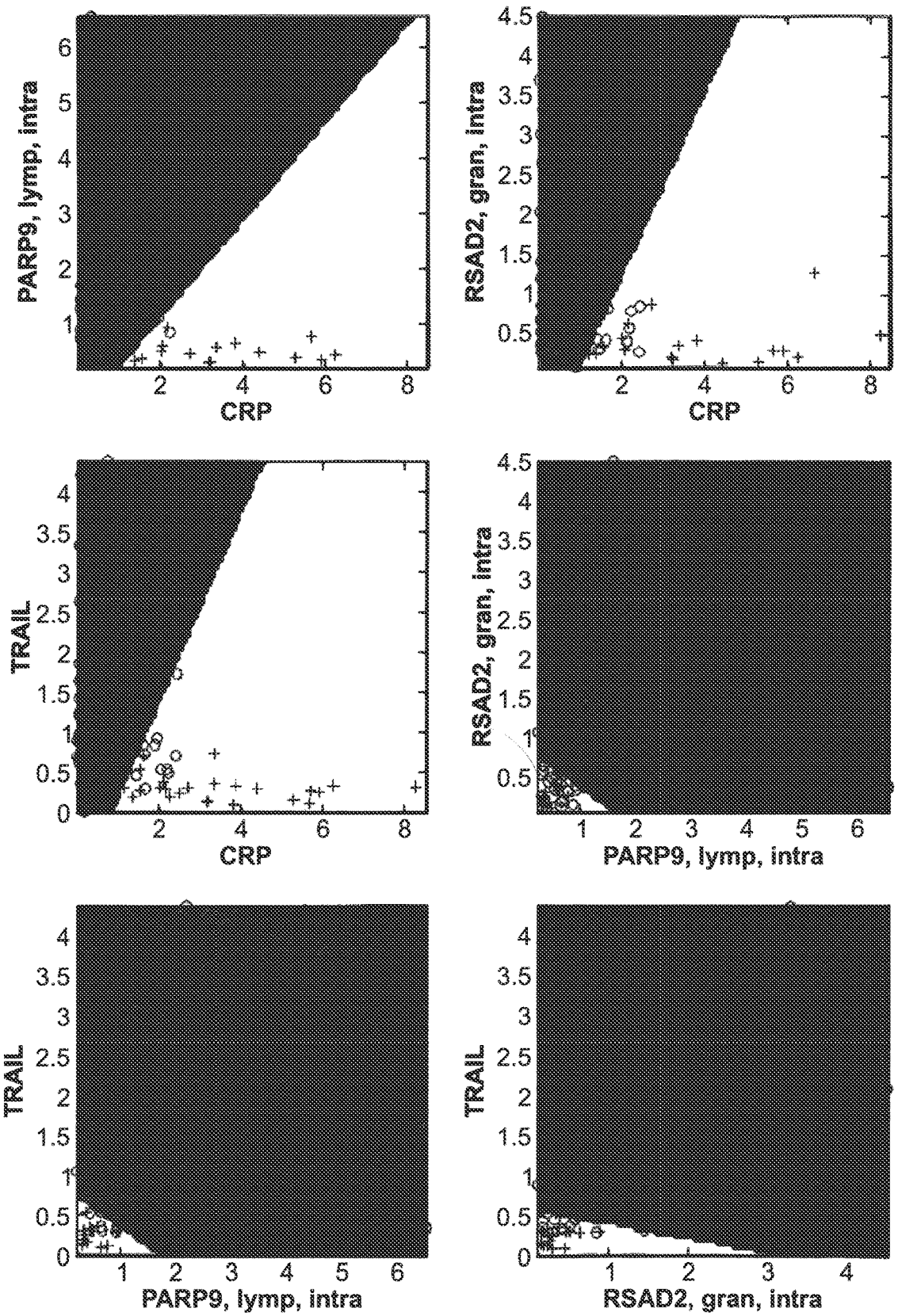

FIG. 24: Examples of scatter graphs showing the diagnosis of Mixed ('+' marks) versus viral ('0' marks) infected patients using a combination of two statistically significant DETERMINANTS.

Figure 25:
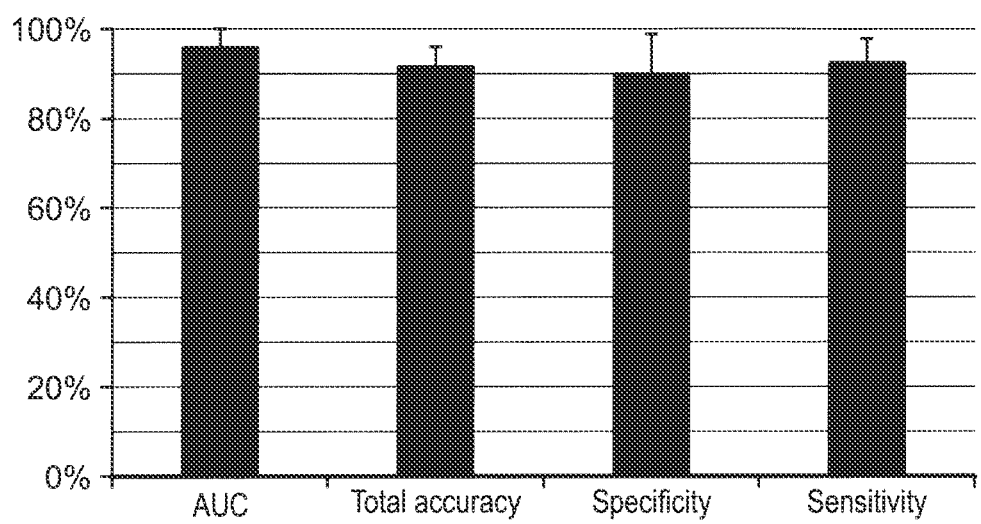

FIG. 25: The TCM-signature accuracy in diagnosing bacterial vs. viral infections in patients whose diagnosis was clear. The analysis was performed using the 'Clear (bacterial, viral)' cohort; N=170.

Figure 26:
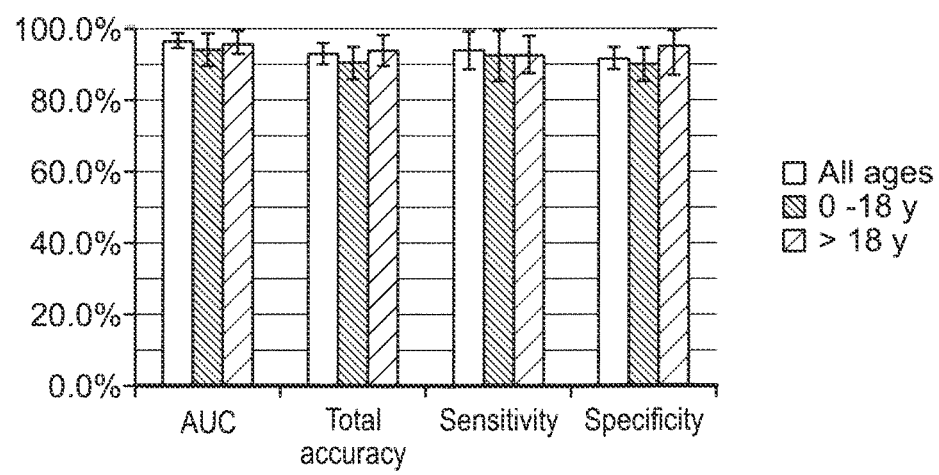

FIG. 26: The TCM-signature accuracy in diagnosing bacterial vs. viral infections in patients whose diagnosis was determined by a consensus of experts. The analysis was performed using the 'Consensus (bacterial, viral)' cohort.

Figure 27:
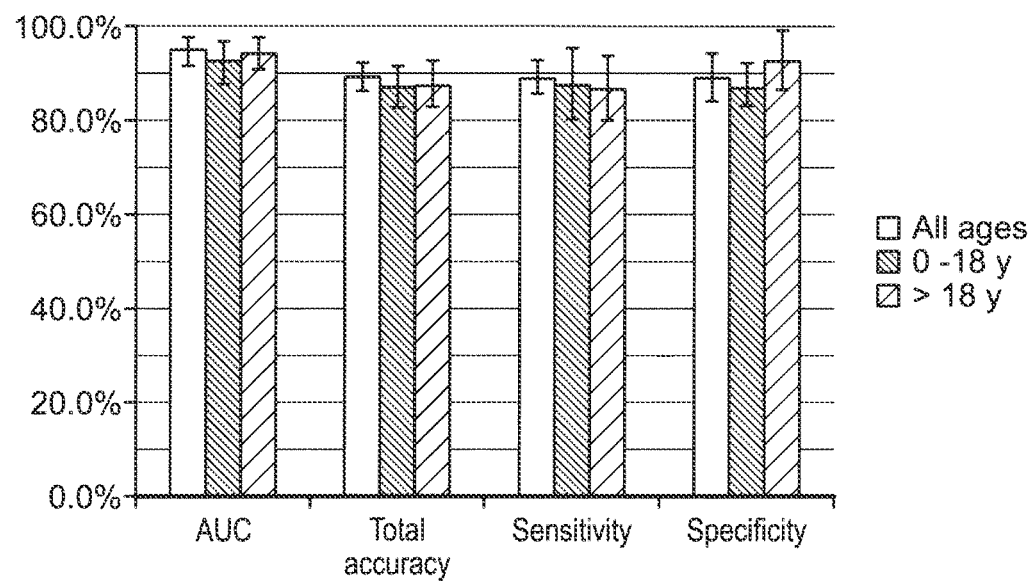

FIG. 27: the TCM-signature accuracy in diagnosing bacterial vs. viral patients in patients whose diagnosis was determined by majority of an expert panel. The analysis was performed using the 'Majority (bacterial, viral)' cohort.

Figure 28:
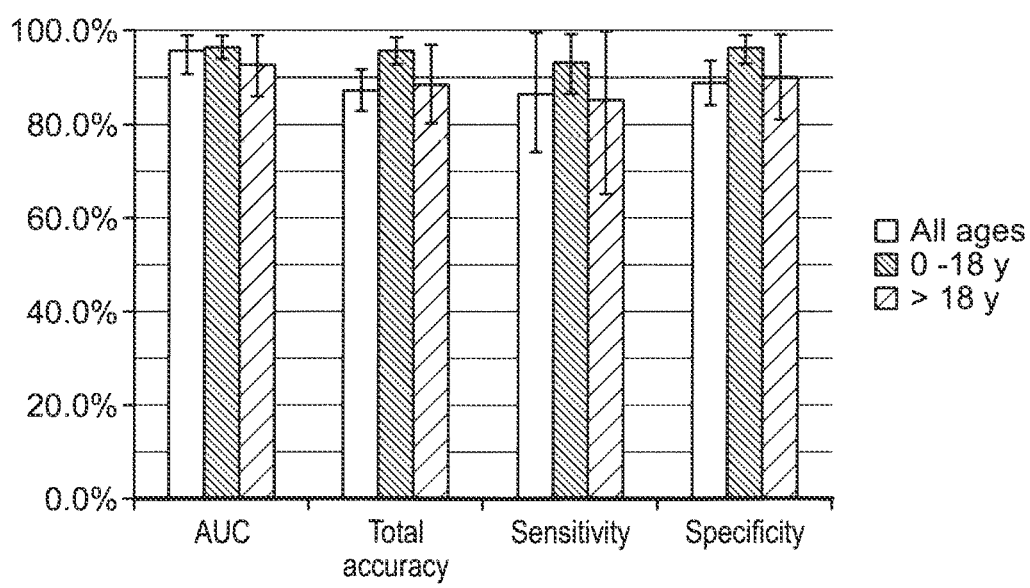

FIG. 28: the TCM-signature accuracy in distinguishing mixed co-infections from pure viral infections in patients whose diagnosis was determined by majority of an expert panel. The analysis was performed using the 'Majority (viral, mixed)' cohort.

Figure 29A:
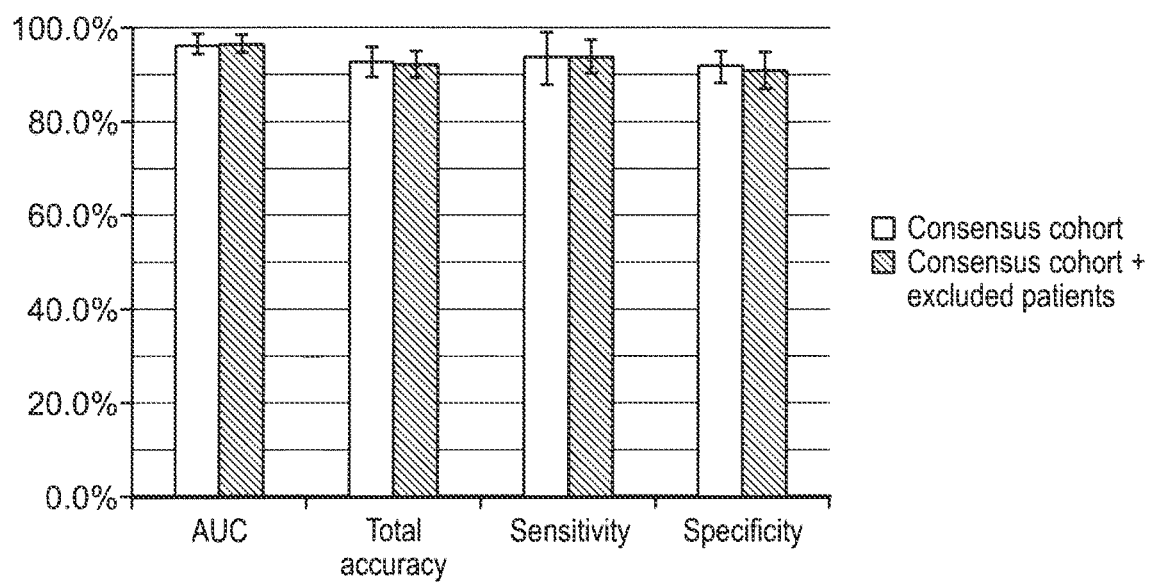
Figure 29B:
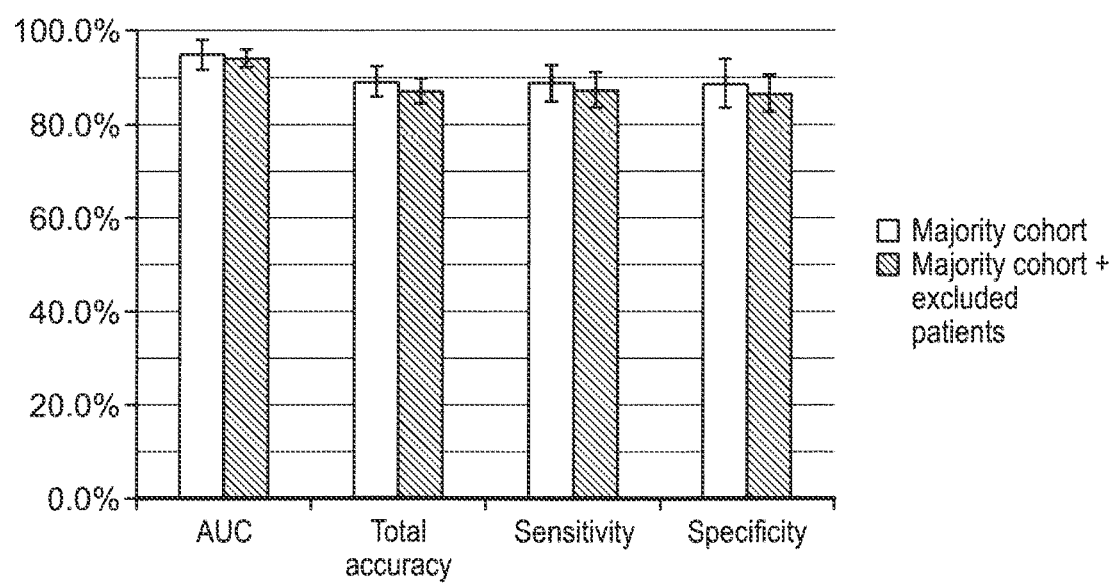

FIGS. 29A and 29B: The TCM-signature accuracy in diagnosing bacterial vs. viral patients in the 'Consensus (bacterial, viral)' cohort and the 'Majority (bacterial, viral)' cohort before and after inclusion of patients who were initially excluded from the study.

Figure 30:
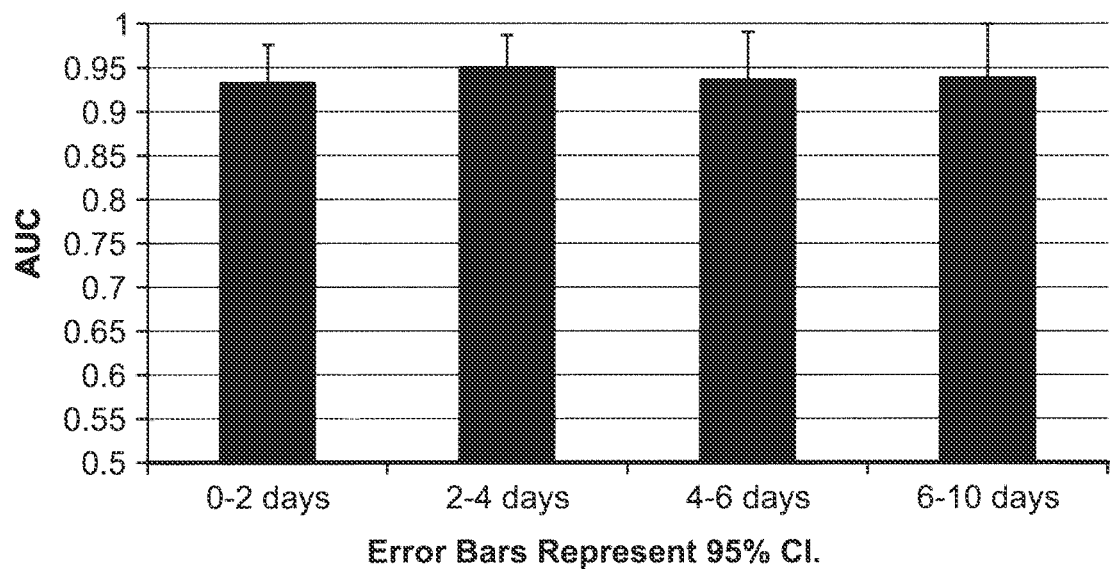

FIG. 30: Accuracy of the TCM-signature as a function of time from symptom onset. Error bars represent 95% CI.

Figure 31:
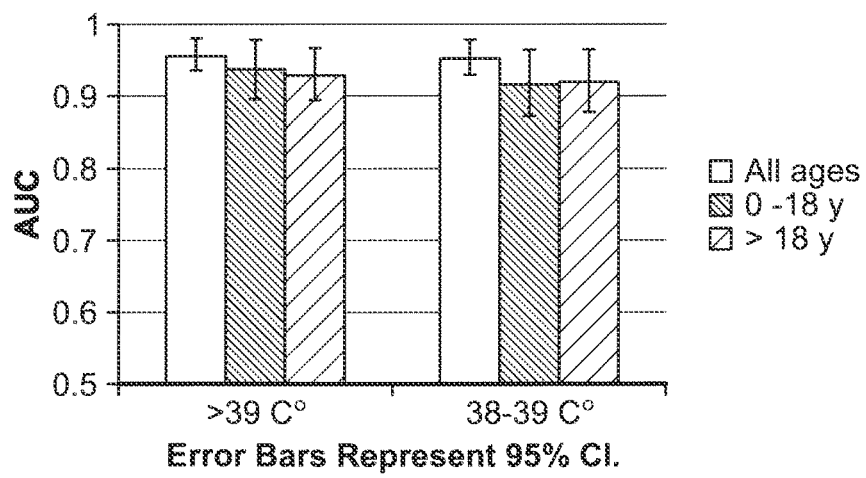

FIG. 31: Accuracy of the TCM-signature as a function of maximal fever measured. Error bars represent 95% CI.

Figure 32:
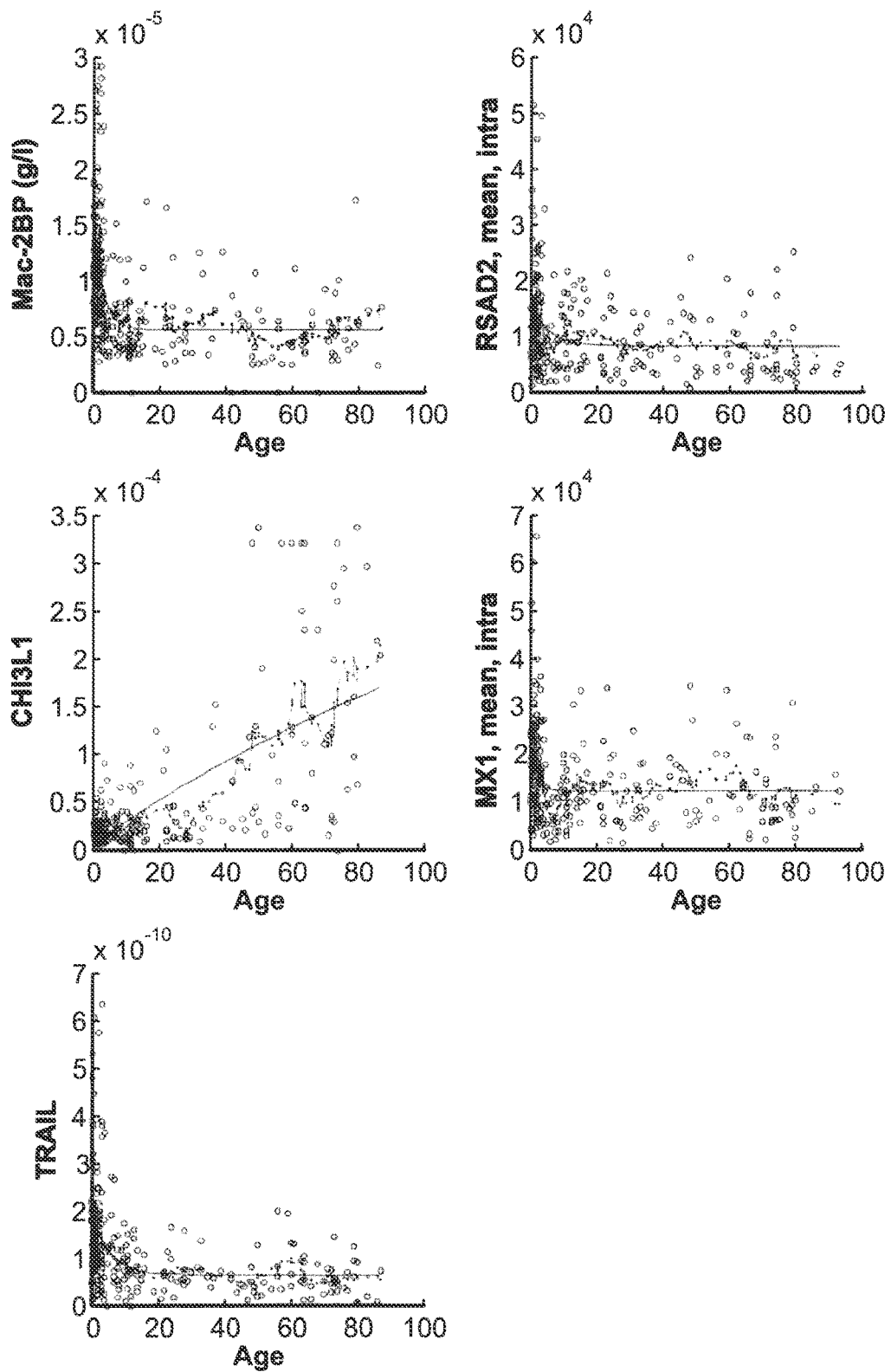

FIG. 32: DETERMINANT levels in different infections as a function of Age.

Figure 33A:
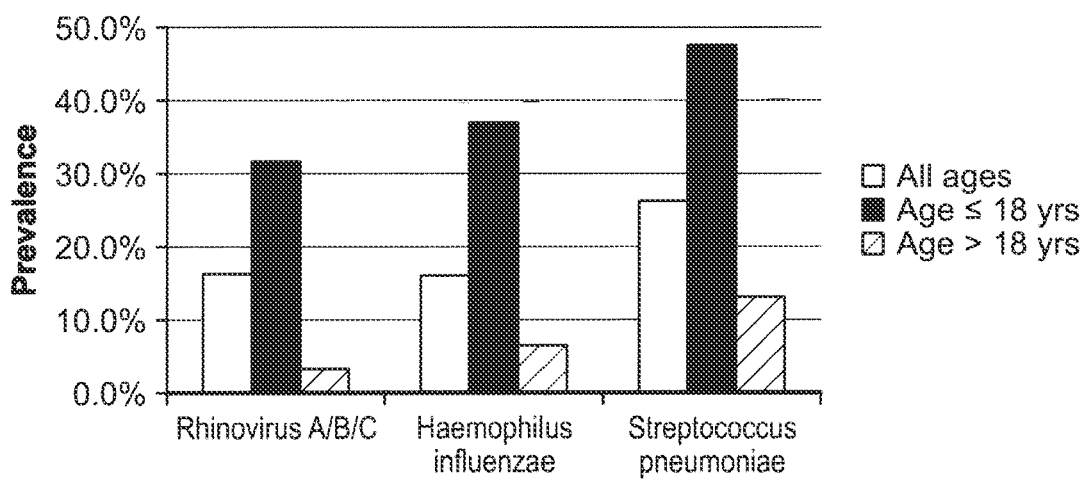
Figure 33B:
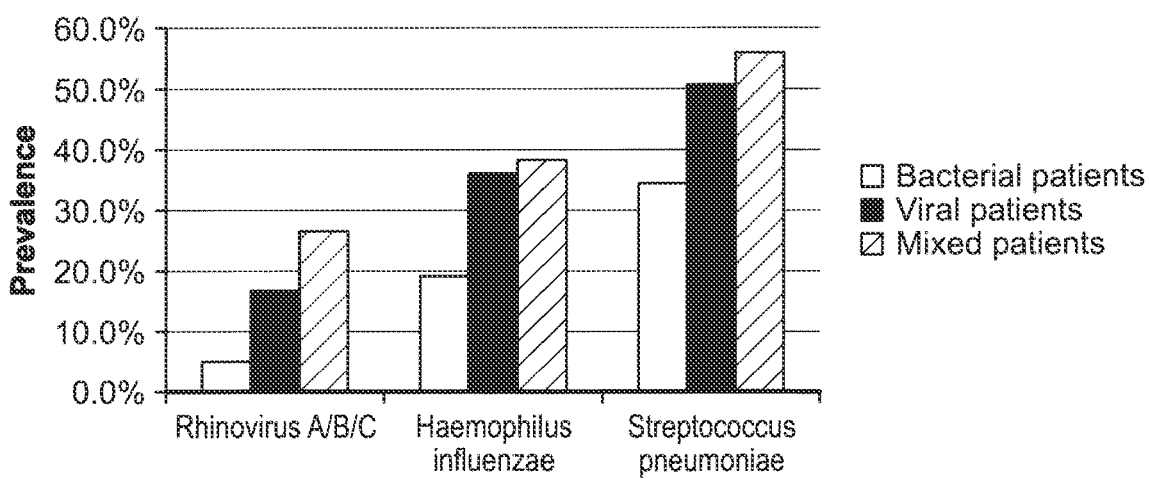

FIGS. 33A and 33B: Prevalence of select bacterial and viral strains in patients with non-infectious (A) and infectious diseases (B) in the 'Majority (bacterial, viral, mixed, non-infectious)' cohort.

Figure 34:
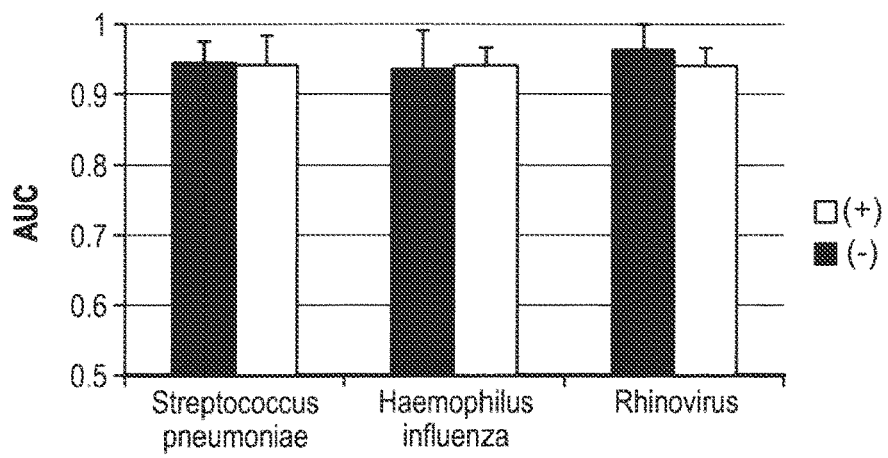

FIG. 34: TCM signature performance in patients with (+) and without (−) colonization by select bacterial and viral strains. Error bars represent 95% CI.

Figure 35:
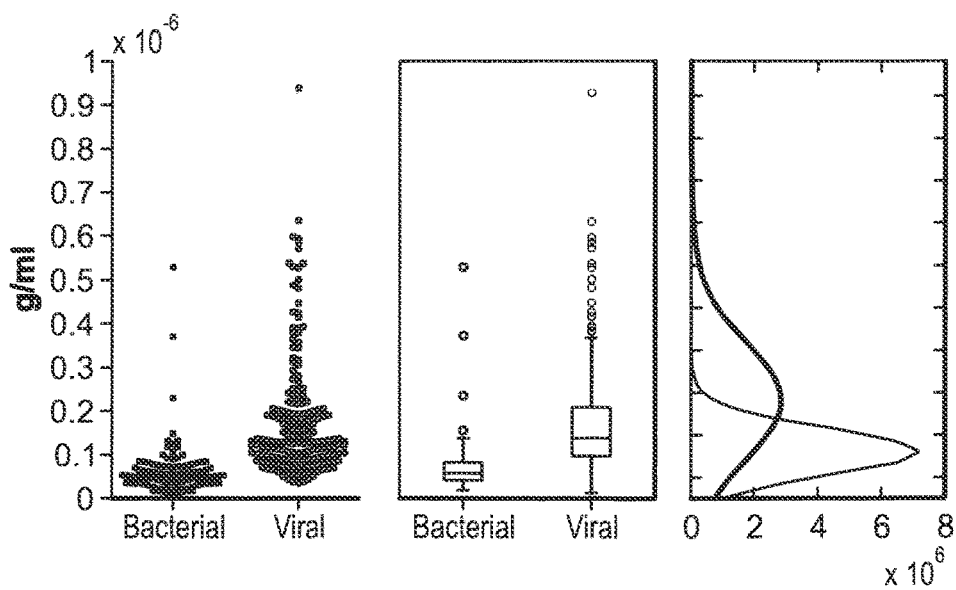

FIG. 35: Scatter plots (left panel), box plots (middle panel) and the approximation of the log normal distributions (right panel) of the levels of TRAIL in bacterial and viral patients. The analysis was performed using the 'Consensus (bacterial, viral)' cohort, N=434.

Figure 36:
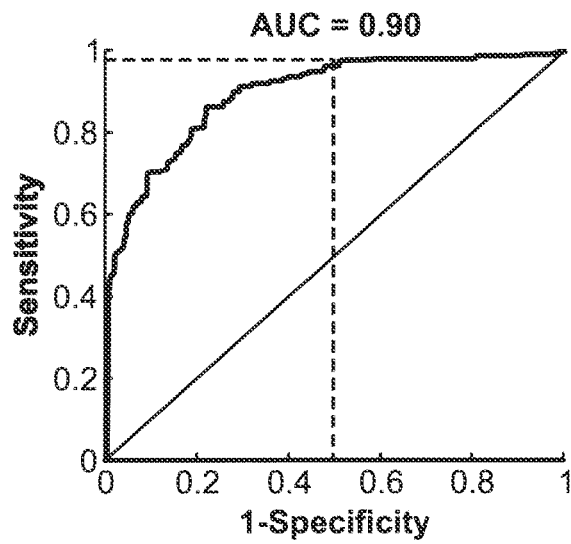

FIG. 36: ROC curve for the analyte TRAIL. The analysis was performed using the 'Consensus [bacterial, viral]' cohort, N=343.

Figure 37:
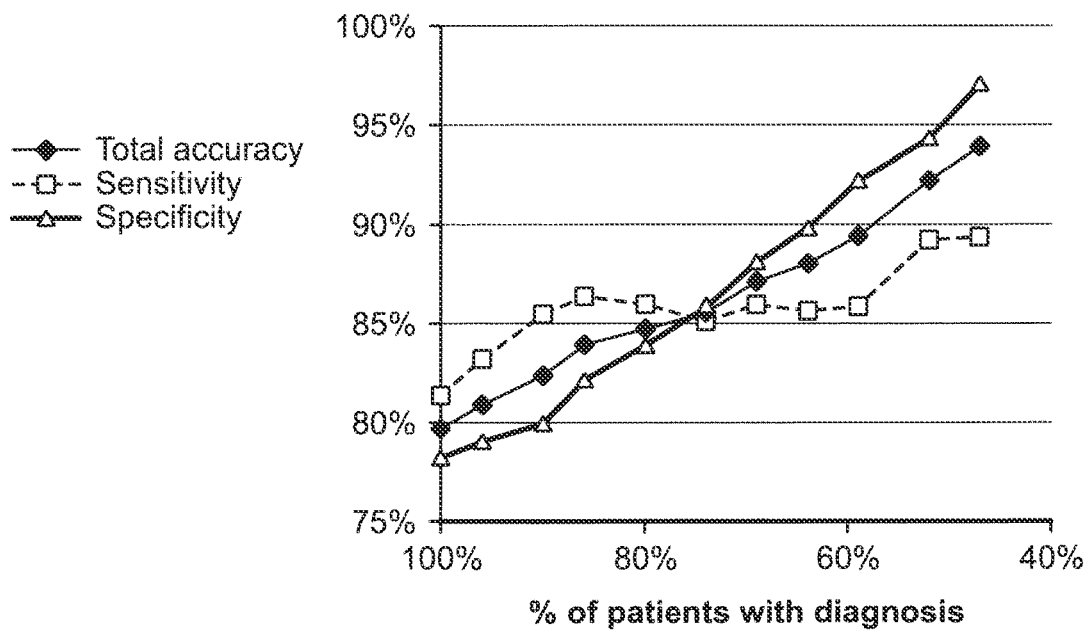

FIG. 37: The balance between the number of patients diagnosed and the accuracy of the TRAIL assay.

FIGS. 38A-1, 38A-2, 38A-3 and 38B: Examples of DETERMINANTS whose mRNA levels have been found to be differentially expressed in viral compared to bacterial infections, but their polypeptide levels in bacterial versus viral infected patients show no significant differential response. (A) The protein levels of IFI44, IFI44L and IFI27 in bacterial (diamonds) and viral (squares) infections. (B) The mRNA expression levels of the IFI44, IFI44L, and IFI27 genes in bacterial (diamonds) and viral (squares) infections. Median value is indicated with a solid line.

Figure 39:
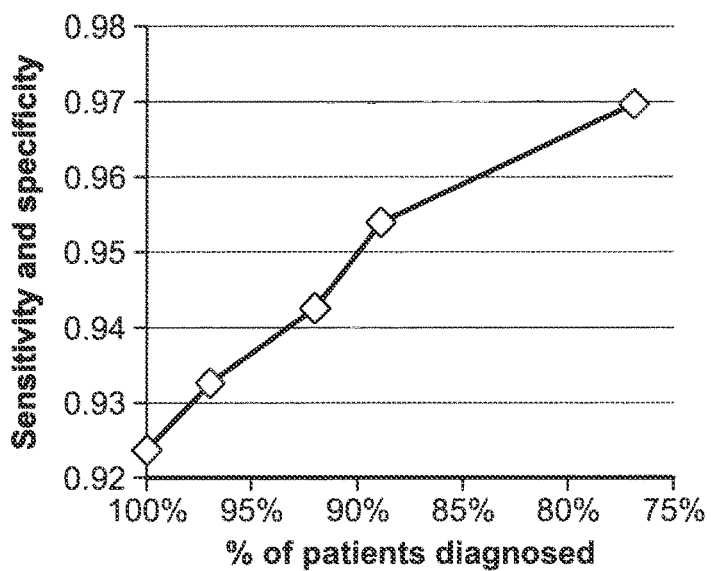

FIG. 39: TCM-signature sensitivity and specificity increase as the cutoffs used for filtering out patients with marginal responses become more stringent. The analysis was performed using the 'Consensus (bacterial, viral)' cohort. Every point corresponds to the sensitivity and specificity attained at the cutoff in which the two measures were kept equal.

Figure 40:
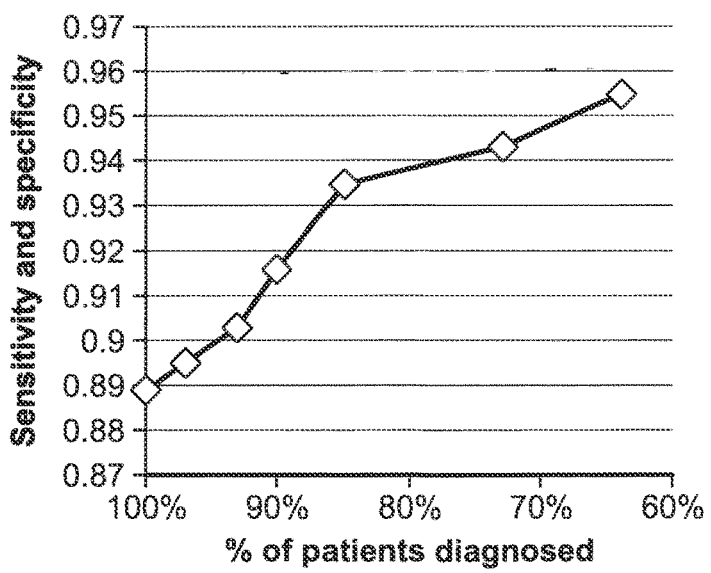

FIG. 40: TCM-signature sensitivity and specificity increase as the cutoffs used for filtering out patients with marginal responses become more stringent. The analysis was performed using the 'Majority (bacterial, viral)' cohort. Every point corresponds to the sensitivity and specificity attained at the cutoff in which the two measures were kept equal.

Figure 41A:
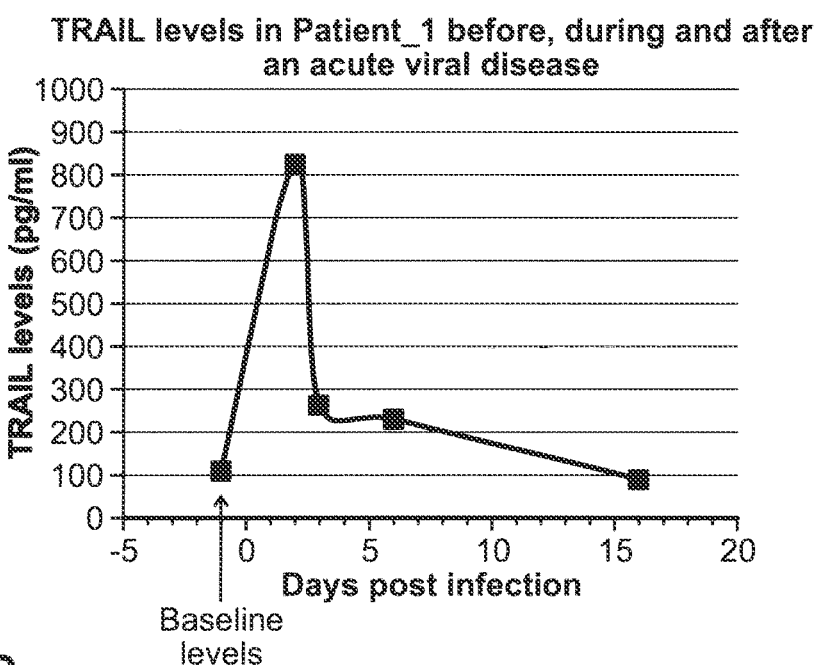
Figure 41B:
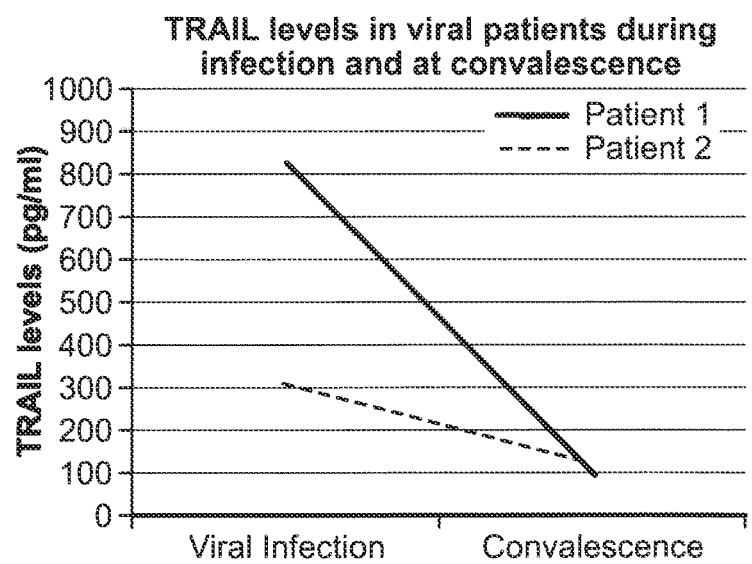
Figure 41C:
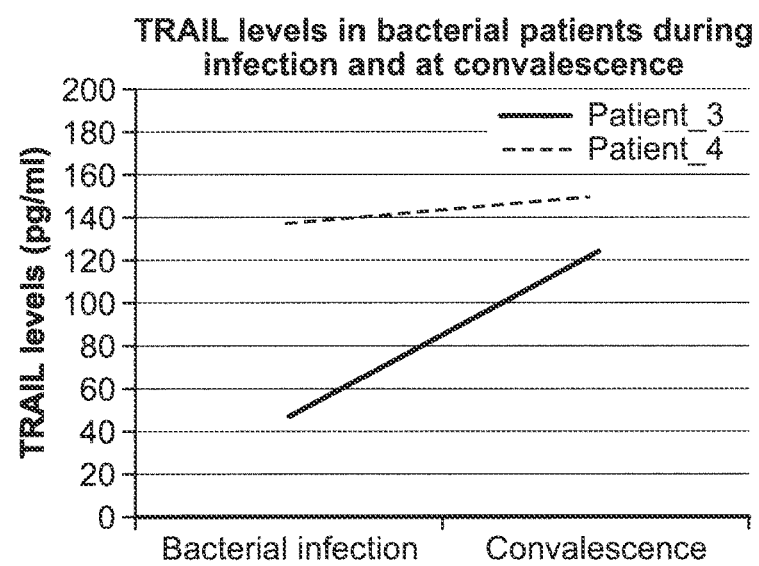

FIGS. 41A, 41B and 41C: The levels of TRAIL increase during the acute phase of a viral infection and then gradually decrease to baseline levels (A, B). In patients with an acute bacterial infection its levels decrease and then increase back to baseline levels during convalescence (C).

Figure 42:
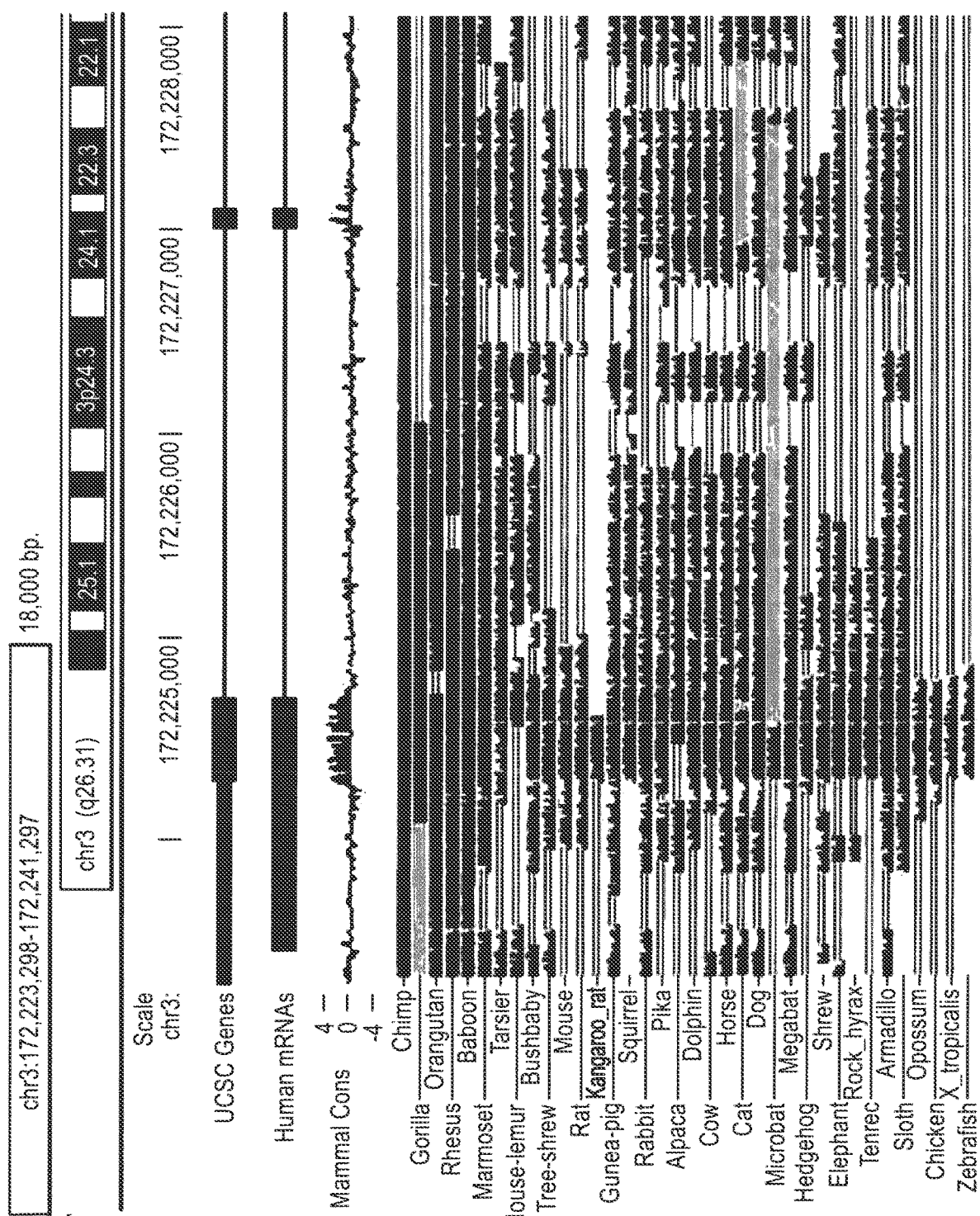
Figure 42:
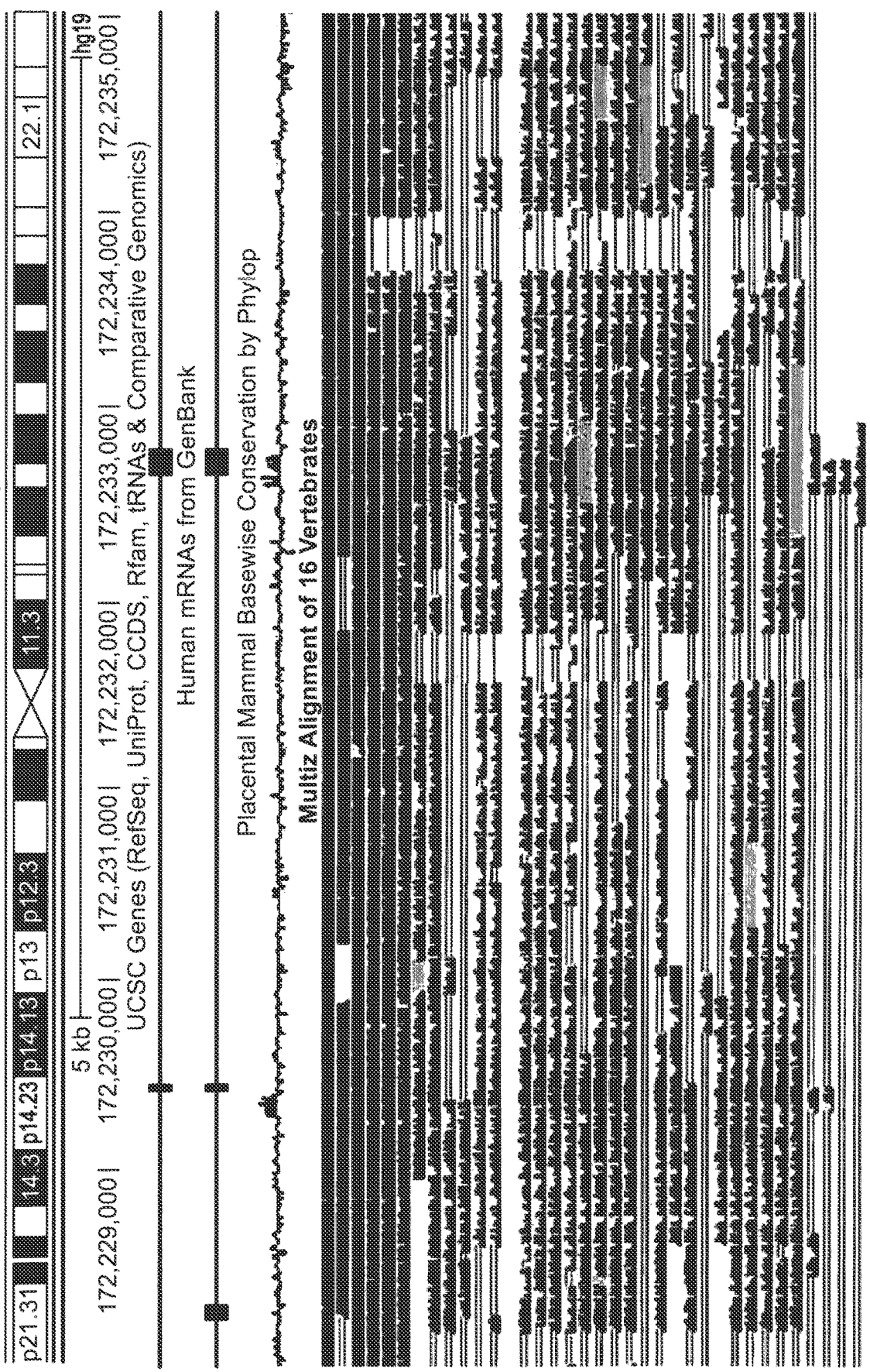
Figure 42:
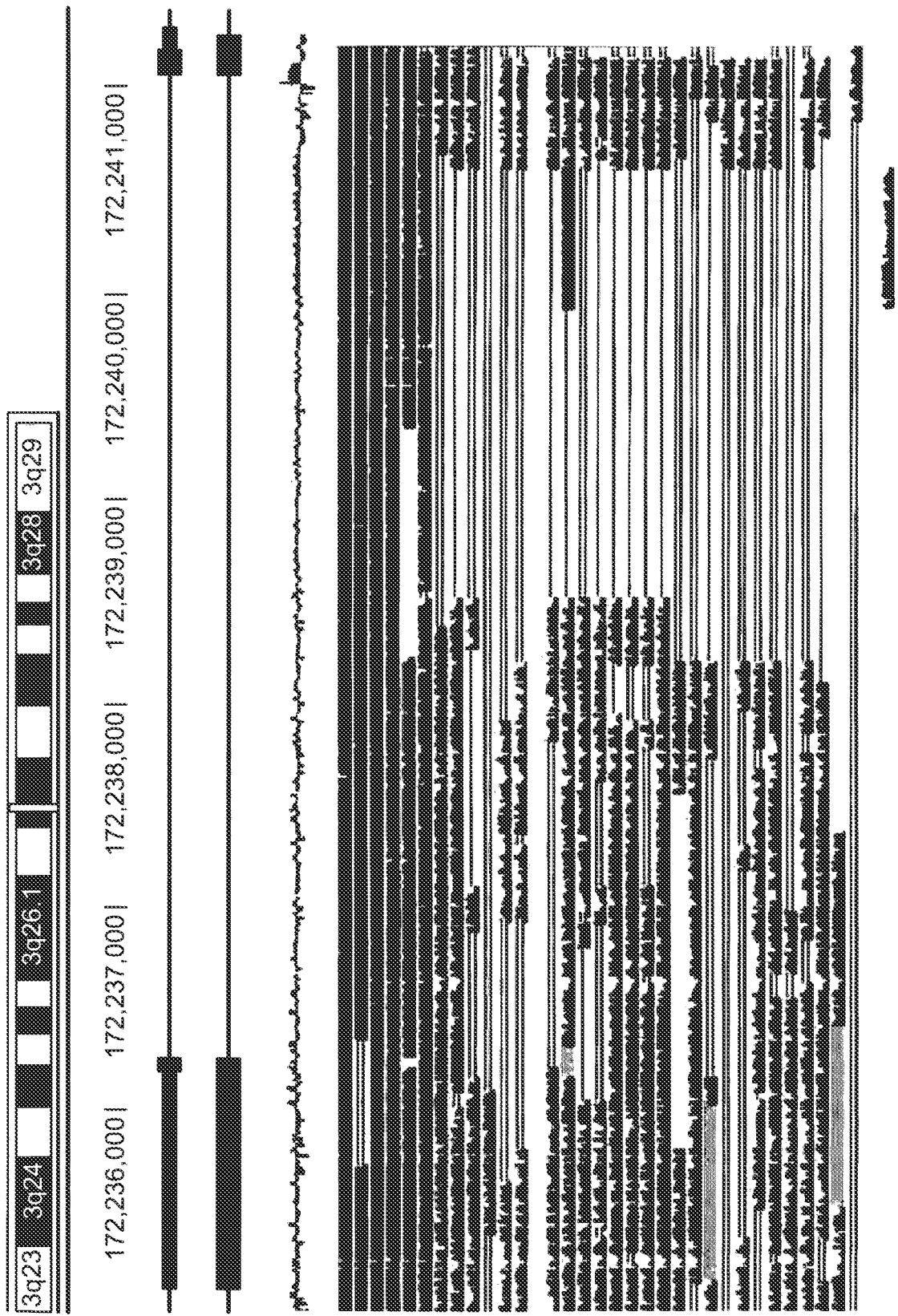

FIG. 42: Comparison of the genetic sequence of TRAIL across organisms.

DESCRIPTION OF SPECIFIC EMBODIMENTS OF THE INVENTION

The present invention, in some embodiments thereof, relates to the identification of signatures and determinants associated with bacterial, viral and mixed (i.e., bacterial and viral co-infections) infections. More specifically we discovered that certain polypeptide-DETERMINANTS are differentially expressed in a statistically significant manner in subjects with bacteria, viral or mixed (i.e., bacterial and viral co-infections) as well as non-infectious disease and healthy subjects. These polypeptide-DETERMINANTS include TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC, TNFR1, IFITM3, IFIT3, EIF4B, IFIT1, LOC26010, MBOAT2, MX1, OAS2, RSAD2, ADIPOR1, CD15, CD8A, IFITM1, IL7, CRP, SAA, TREM-1, PCT, IL-8, TREM-1, IL6, ARG1, ARPC2, ATP6V0B, BCA-1, BRI3BP, CCL19-MIP3b, CES1, CORO1A, HERC5, IFI6, IFIT3, KIAA0082, LIPT1, LRDD, MCP-2, PARP9, PTEN, QARS, RAB13, RPL34, SART3, TRIM22, UBE2N, XAF1 and ZBP1.

In some embodiments the polypeptide-DETERMINANTS are soluble-polypeptides that include B2M, BCA-1, CHI3L1, Eotaxin, IL1a, IP10, MCP, Mac-2BP, TRAIL, CD62L, VEGFR2, IL11, IL1RA, I-TAC and TNFR1.

In other embodiments the polypeptide-DETERMINANTS are intracellular-polypeptides that include CHP, CMPK2, CORO1C, EIF2AK2, ISG15, RPL22L1 and RTN3.

In other embodiments the polypeptide-DETERMINANTS are membrane polypeptides that include CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2 and SSEA1.

In other embodiments the polypeptide-DETERMINANTS further include polypeptides selected from the group consisting of: EIF4B, IFIT1, IFIT3, LOC26010, MBOAT2, MX1, OAS2, RSAD2, ADIPOR1, CD15, CD8A, IFITM1, IFITM3, IL7R, CRP, SAA, sTREM, PCT, IL-8 and IL6.

In other embodiments the DETERMINANTS further include clinical-DETERMINANTS selected from the group consisting of: ANC, ALC, Neu (%), Lym (%), Mono (%), Maximal temperature, Time from symptoms, Age, Creatinine (Cr), Potassium (K), Pulse and Urea.

In some embodiments, the DETERMINANTS further comprise measurements of one or more polypeptides or clinical-DETERMINANTS selected from the group consisting of: ARG1, ARPC2, ATP6V0B, BILI (BILIRUBIN), BRI3BP, CCL19-MIP3B, CES1, CORO1A, EOS (%), HERC5, IFI6, IFIT3, KIAA0082, LIPT1, LRDD, MCP-2, NA (Sodium), PARP9, PTEN, QARS, RAB13, RPL34, SART3, TRIM22, UBE2N, WBC (Whole Blood Count), XAF1 and ZBP1.

Different infectious agents have unique molecular patterns that can be identified and targeted by the immune system. Pathogen-associated molecular patterns (PAMPs) are an example of such molecules that are associated with different groups of pathogens and may be recognized by cells of the innate immune system using Toll-like receptors (TLRs) and other pattern recognition receptors (e.g. NOD proteins) (Akira, S. and S. Uematsu, et al 2006; Murphy, K. and P. Travers, et al 2007). These patterns may vary considerably between different classes of pathogens and thus elicit different immune responses. For example, TLR-4 can recognize lipopolysaccharide, a constituent of gram negative bacteria, as well as lipoteichoic acids, constituent of gram positive bacteria, hence promoting an anti-microbial response of the immune system (Akira, S. and S. Uematsu, et al 2006; Murphy, K. and P. Travers, et al 2007). TLR-3 can recognize single stranded RNA (often indicative of a viral infection) and thus prompt the appropriate anti-viral response (Akira, S. and S. Uematsu, et al 2006; Murphy, K. and P. Travers, et al 2007). By distinguishing between different classes of pathogens (e.g bacterial versus viral) the immune system can mount the appropriate defense.

In the past few decades, several host markers have been identified that can be used for differential diagnosis of infection source in various indications. One example is Procalcitonin (PCT), a precursor of the hormone calcitonin produced by the C-cells of the thyroid gland. PCT levels in the blood stream of healthy individuals is hardly detectable (in the pg/ml range) but it might increase dramatically, as a result of a severe infection with levels rising up to 100 ng/ml.

PCT is heavily used to diagnose patients with systemic infection, sepsis, with sensitivity of 76% and specificity of 70% (Jones, A. E. and J. F. Fiechtl, et al 2007). However, studies that tested the diagnostic value of PCT in other non-systemic infection such as pneumonia or upper respiratory tract infections found it to be limited (Brunkhorst, F. M. and B. Al-Nawas, et al 2002; Tang M. P. and Eslick G D 2007), especially when used in isolation.

Another widely used marker is the acute phase protein, C-reactive protein (CRP). CRP levels in the blood often rise in response to inflammation. Therefore, when used as an adjunct biomarker in the right clinical context, CRP may prove useful for improving detection accuracy of infections (Povoa P. 2002). However, in some indications such as sepsis its specificity and sensitivity were found to be considerably lower than PCT (Hatherill, M. and S. M. Tibby, et al 1999). Additionally, its clinical utility as a stand-alone marker for Abx prescription decision making has been criticized (Brian Clyne and Jonathan S Olshaker 1999).

One reason for CRP's limited accuracy in the context of infectious disease stems from the fact that CRP may rise in indications other than bacterial infection. For example some viral infections including adenoviruses (Appenzeller C et al. 2002; A. Putto, O. Meurman, and O. Ruuskanen 1986) are known to cause a significant increase in the levels of CRP that mimics a bacterial response, thus limiting CRP's accuracy as a single marker for differentiating between viral and bacterial infections. CRP may also rise in non-infectious disease such as trauma. Other proposed markers for detection of different sources of infection and sepsis include CD64 (Rudensky, B. and G. Sirota, et al 2008), and HNL (Fjaertoft, G. and T. Foucard, et al. 2005). The reliability and evidence supporting the usage of these markers for the purpose of diagnostics of viral versus bacterial infections in a broad setting are limited.

The present invention, in some embodiments thereof, seeks to overcome the above mentioned diagnostic challenges by: (i) enabling accurate differentiation between a broad range of bacterial versus viral infections; (ii) enabling rapid diagnostics (within minutes); (iii) avoiding the "false positive" identification of non-pathogenic bacteria that are part of the body's natural flora, (iv) allowing accurate differentiation between mixed and pure viral infections and (v) allowing diagnosis in cases where the pathogen is inaccessible.

To this end the inventors sought to identify and test a novel set of biomarkers whose levels are differentially expressed in viral, bacterial and mixed infected patients, and in patients with a non-infectious disease and to use the combined measurements of these biomarkers coupled with pattern recognition algorithms to accurately identify the source of infection with the aim of assisting physicians to accurately prescribe the correct treatment.

To facilitate a solution that is generally applicable, the inventors performed a large clinical trial in which they enrolled a heterogeneous cohort of 655 patients including different ages, medical backgrounds, ethnicities, pathogen types, clinical syndromes and time from appearance of symptoms, fever, co-morbidities (see FIGS. 4-10). The inventors then measured the levels of over 570 different polypeptides using quantitative assays, and were able to screen a small subset of polypeptides that was robustly differentially expressed in different types of infections. They used the combined signature of these selected polypeptides to develop and test various aspects of the present solution.

To address the challenge of rapid diagnosis, some aspects of the invention focus on biomarkers that can be rapidly measured, such as proteins, rather than biomarkers whose measurement may require hours to days, such as nucleic-acid based biomarkers. Note that high-throughput quantitative measurements of nucleic-acids for the purpose of biomarker discovery have become feasible in recent years using technologies such as microarrays and deep sequencing. However, performing such quantitative high-throughput measurements on the proteome level remains a challenge. Thus, some aspects of the present invention focus on the proteome level.

To address the clinical challenge of mixed infection diagnosis and treatment, some aspects of the present invention include a method for differentiating between mixed infections (which require Abx treatment despite the presence of a virus) and pure viral infections (which do not require Abx treatment).

Some aspects of the present invention also address the challenge of "false-positive" diagnostics due to non-pathogenic strains of bacteria that are part of the body's natural flora. This is achieved by measuring biomarkers derived from the host rather than the pathogen.

Another aspect of the present invention enables the diagnosis of different infections, which is invariant to the presence or absence of colonizers (e.g. bacteria and viruses that are part of the natural flora). This addresses one of the major challenges in infectious disease diagnostics today: "false-positives" due to colonizers.

Importantly, some aspects of the current invention do not require direct access to the pathogen, because the immune system circulates in the entire body, thereby facilitating diagnosis in cases in which the pathogen is inaccessible.

Another aspect of the present invention is the fraction in which the biomarkers are measured, which affects the ease by which the assay can be performed in the clinical settings, and especially the point-of-care. For example, it is easier to measure proteins in the serum or plasma fraction compared to nucleic acids or intra-cellular proteins in the leukocytes fraction (the latter requires an additional experimental step in which leukocytes are isolated from the whole blood sample, washed and lysed). Accordingly, some aspects of the present invention also describe serum and plasma based protein signatures that are easily measurable using various immunoassays available in clinical settings.

Other aspects of the invention provide methods for identifying subjects who have an infection by the detection of DETERMINANTS associated with an infection, including those subjects who are asymptomatic for the infection. These signatures and DETERMINANTS are also useful for monitoring subjects undergoing treatments and therapies for infection, and for selecting or modifying diagnostics, therapies and treatments that would be efficacious in subjects having an infection.

Exemplary Polypeptide-DETERMINANT Measured in the Present Invention

The polypeptide-DETERMINANT names presented herein are given by way of example. Many alternative names, aliases, modifications, isoforms and variations will be apparent to those skilled in the art. Accordingly, it is intended to embrace all the alternative protein names, aliases, modifications isoforms and variations.

B2M: additional alias of B2M include without limitation beta-2-microglobulin and CDABP0092. B2M is a component of MHC class I molecules, which are present on all nucleated cells. The protein encoded by this gene also encodes an isoform present in the serum.

The protein has a predominantly beta-pleated sheet structure that can form amyloid fibrils in some pathological conditions.

BCA1: BCA1 is a B lymphocyte chemoattractant, independently cloned and named Angie, is a CXC chemokine strongly expressed in the follicles of the spleen, lymph nodes, and Peyer's patches. It preferentially promotes the migration of B lymphocytes (compared to T cells and macrophages), apparently by stimulating calcium influx into, and chemotaxis of, cells expressing Burkitt's lymphoma receptor 1 (BLR-1). It may therefore function in the homing of B lymphocytes to follicles (provided by RefSeq).

CHI3L1: chitinase 3-like 1 (cartilage glycoprotein-39); additional aliases of CHI3L1 include without limitation ASRT7, CGP-39, GP-39, GP39, HC-gp39, HCGP-3P, YKL-40, YKL40, YYL-40 and hCGP-39. Chitinases catalyze the hydrolysis of chitin, which is an abundant glycopolymer found in insect exoskeletons and fungal cell walls. The glycoside hydrolase 18 family of chitinases includes eight human family members. This gene encodes a glycoprotein member of the glycosyl hydrolase 18 family that lacks chitinase activity can be secreted by activated macrophages, chondrocytes, neutrophils and synovial cells. CHI3L1 inhibits oxidant-induced lung injury, augments adaptive Th2 immunity, regulates apoptosis, stimulates alternative macrophage activation, and contributes to fibrosis and wound healing.

Eotaxin: This gene is one of several Cys-Cys (CC) cytokine genes clustered on the q-arm of chromosome 17. Cytokines are a family of secreted proteins involved in immunoregulatory and inflammatory processes. The CC cytokines are proteins characterized by two adjacent cysteines. The cytokine encoded by this gene displays chemotactic activity for eosinophils, but not mononuclear cells or neutrophils. This eosinophil specific chemokine assumed to be involved in eosinophilic inflammatory diseases such as atopic dermatitis, allergic rhinitis, asthma and parasitic infections (provided by RefSeq). In response to the presence of allergens, this protein directly promotes the accumulation of eosinophils, a prominent feature of allergic inflammatory reactions.

IL1A: The protein encoded by this gene is a member of the interleukin 1 cytokine family. This cytokine is a pleiotropic cytokine involved in various immune responses, inflammatory processes, and hematopoiesis. This cytokine can be produced by monocytes and macrophages as a proprotein, which is proteolytically processed and released in response to cell injury, and thus induces apoptosis. This gene and eight other interleukin 1 family genes form a cytokine gene cluster on chromosome 2. IL-1 proteins are involved in the inflammatory response, being identified as endogenous pyrogens, and are reported to stimulate the release of prostaglandin and collagenase from synovial cells.

MCP: The protein encoded by this gene is a type I membrane protein and is a regulatory part of the complement system. The encoded protein has cofactor activity for inactivation of complement components C3b and C4b by serum factor I, which protects the host cell from damage by complement.

Edmonston strain of measles virus, human herpesvirus-6, and type IV pili of pathogenic *Neisseria*. The protein encoded by this gene may be involved in the fusion of the spermatozoa with the oocyte during fertilization. Mutations at this locus have been associated with susceptibility to hemolytic uremic syndrome. Alternatively spliced transcript variants encoding different isoforms have been described (provided by RefSeq).

MAC-2-BP: Additional aliases of MAC-2-BP include without limitation LGALS3BP, 90K, serum protein 90K, BTBD17B, M2BP and lectin, galactoside-binding, soluble, 3 binding protein. The galectins are a family of beta-galactoside-binding proteins implicated in modulating cell-cell and cell-matrix interactions. The levels of MAC-2-BP were found to be elevated in the serum of cancer patients. It appears to be implicated in immune response associated with natural killer (NK) and lymphokine-activated killer (LAK) cell cytotoxicity. The native protein can bind specifically to a human macrophage-associated lectin known as Mac-2 as well as galectin 1.

CD62L: This gene encodes a cell surface adhesion molecule that belongs to a family of adhesion/homing receptors. The encoded protein contains a C-type lectin-like domain, a calcium-binding epidermal growth factor-like domain, and two short complement-like repeats. The gene product is required for binding and subsequent rolling of leucocytes on endothelial cells, facilitating their migration into secondary lymphoid organs and inflammation sites. Single-nucleotide polymorphisms in this gene have been associated with various diseases including immunoglobulin A nephropathy. Alternatively spliced transcript variants have been found for this gene (provided by RefSeq). The protein encoded by this gene has a soluble form denoted sCD62L.

VEGFR2: Vascular endothelial growth factor (VEGF) is a major growth factor for endothelial cells. This gene encodes one of the two receptors of the VEGF. This receptor, known as kinase insert domain receptor, is a type III receptor tyrosine kinase. It functions as the main mediator of VEGF-induced endothelial proliferation, survival, migration, tubular morphogenesis and sprouting. The signaling and trafficking of this receptor are regulated by multiple factors, including Rab GTPase, P2Y purine nucleotide receptor, integrin alphaVbeta3, T-cell protein tyrosine phosphatase, etc. Mutations of this gene are implicated in infantile capillary hemangiomas (provided by RefSeq). The protein encoded by this gene has a soluble form denoted sVEGFR2.

TRAIL: The protein encoded by this gene is a cytokine that belongs to the tumor necrosis factor (TNF) ligand family. Additional names of the gene include without limitations APO2L, TNF-related apoptosis-inducing ligand, TNFSF10 and CD253. TRAIL exists in a membrane bound form and a soluble form, both of which can induce apoptosis in different cells, such as transformed tumor cells. This protein binds to several members of the TNF receptor superfamily such as TNFRSF10A/TRAILR1, NFRSF10B/TRAILR2, NFRSF10C/TRAILR3, TNFRSF10D/TRAILR4, and possibly also to NFRSF11B/OPG. The activity of this protein may be modulated by binding to the decoy receptors such as NFRSF10C/TRAILR3, TNFRSF10D/TRAILR4, and NFRSF11B/OPG that cannot induce apoptosis. The binding of this protein to its receptors has been shown to trigger the activation of MAPK8/JNK, caspase 8, and caspase 3. Alternatively spliced transcript variants encoding different isoforms have been found for this gene. TRAIL can be proteolytically cleaved from the cell surface to produce a soluble form that has a homotrimeric structure.

CHP: This gene encodes a phosphoprotein that binds to the Na+/H+ exchanger NHE1. This protein serves as an essential cofactor which supports the physiological activity of NHE family members and may play a role in the mitogenic regulation of NHE1. The protein shares similarity with calcineurin B and calmodulin and it is also known to be an endogenous inhibitor of calcineurin activity (provided by RefSeq).

CMPK2: This gene encodes a protein that may participate in dUTP and dCTP synthesis in mitochondria. Is able to phosphorylate dUMP, dCMP, CMP, UMP and monophosphates of the pyrimidine nucleoside analogs ddC, dFdC, araC, BVDU and FdUrd with ATP as phosphate donor. Efficacy is highest for dUMP followed by dCMP; CMP and UMP are poor substrates. May be involved in mtDNA depletion caused by long term treatment with ddC or other pyrimidine analogs.

CORO1C: This gene encodes a member of the WD repeat protein family. WD repeats are minimally conserved regions of approximately 40 amino acids typically bracketed by gly-his and trp-asp (GH-WD), which may facilitate formation of heterotrimeric or multiprotein complexes. Members of this family are involved in a variety of cellular processes, including cell cycle progression, signal transduction, apoptosis, and gene regulation.

EIF2AK2: EIF2AK2 is a protein serine/threonine kinase that acquires enzymatic activity following autophosphorylation, a process mediated by double-stranded RNA (dsRNA). Additional aliases include without limitation: PKR, PRKR, EIF2AK1, protein kinase, interferon-inducible double stranded RNA dependent, p68 kinase, etc. Activation of EIF2AK2 allows the kinase to phosphorylate its natural substrate, the alpha subunit of eukaryotic protein synthesis initiation factor-2 (EIF2-alpha; MIM 603907), leading to the inhibition of protein synthesis.

ISG15: ISG15 ubiquitin-like modifier; additional aliases of ISG15 include without limitation G1P2, IFI15, IP17, UCRP and hUCRP. This ubiquitin-like protein is conjugated to intracellular target proteins after IFN-alpha or IFN-beta stimulation. Its enzymatic pathway is partially distinct from that of ubiquitin, differing in substrate specificity and interaction with ligating enzymes. ISG15 conjugation pathway uses a dedicated E1 enzyme, but seems to converge with the Ub conjugation pathway at the level of a specific E2 enzyme. Targets include STAT1, SERPINA3G/SPI2A, JAKI, MAPK3/ERK1, PLCG1, EIF2AK2/PKR, MX1/MxA, and RIG-1. Shows specific chemotactic activity towards neutrophils and activates them to induce release of eosinophil chemotactic factors. May serve as a trans-acting binding factor directing the association of ligated target proteins to intermediate filaments. May also be involved in autocrine, paracrine and endocrine mechanisms, as in cell-to-cell signaling, possibly partly by inducing IFN-gamma secretion by monocytes and macrophages.

RTN3: May be involved in membrane trafficking in the early secretory pathway. Inhibits BACE1 activity and amyloid precursor protein processing. May induce caspase-8 cascade and apoptosis. May favor BCL2 translocation to the mitochondria upon endoplasmic reticulum stress. In case of enteroviruses infection, RTN3 may be involved in the viral replication or pathogenesis.

CD112: This gene encodes a single-pass type I membrane glycoprotein with two Ig-like C2-type domains and an Ig-like V-type domain. This protein is one of the plasma membrane components of adherens junctions. It also serves as an entry for certain mutant strains of herpes simplex virus and pseudorabies virus, and it is involved in cell to cell spreading of these viruses.

Variations in this gene have been associated with differences in the severity of multiple sclerosis.

Alternate transcriptional splice variants, encoding different isoforms, have been characterized. (provided by RefSeq).

CD134: The protein encoded by this gene is a member of the TNF-receptor superfamily. This receptor has been shown to activate NF-kappaB through its interaction with adaptor proteins TRAF2 and TRAF5. Knockout studies in mice suggested that this receptor promotes the expression of apoptosis inhibitors BCL2 and BCL21L1/BCL2-XL, and thus suppresses apoptosis. The knockout studies also suggested the roles of this receptor in CD4+ T cell response, as well as in T cell-dependent B cell proliferation and differentiation (provided by RefSeq).

CD182: The protein encoded by this gene is a member of the G-protein-coupled receptor family. This protein is a receptor for interleukin 8 (IL8). It binds to IL8 with high affinity, and transduces the signal through a G-protein activated second messenger system. This receptor also binds to chemokine (C-X-C motif) ligand 1 (CXCL1/MGSA), a protein with melanoma growth stimulating activity, and has been shown to be a major component required for serum-dependent melanoma cell growth. This receptor mediates neutrophil migration to sites of inflammation. The angiogenic effects of IL8 in intestinal microvascular endothelial cells are found to be mediated by this receptor. Knockout studies in mice suggested that this receptor controls the positioning of oligodendrocyte precursors in developing spinal cord by arresting their migration. This gene, IL8RA, a gene encoding another high affinity IL8 receptor, as well as IL8RBP, a pseudogene of IL8RB, form a gene cluster in a region mapped to chromosome 2q33-q36. Alternatively spliced variants, encoding the same protein, have been identified (provided by RefSeq).

CD231: The protein encoded by this gene is a member of the transmembrane 4 superfamily, also known as the tetraspanin family. Most of these members are cell-surface proteins that are characterized by the presence of four hydrophobic domains. The proteins mediate signal transduction events that play a role in the regulation of cell development, activation, growth and motility. This encoded protein is a cell surface glycoprotein and may have a role in the control of neurite outgrowth. It is known to complex with integrins. This gene is associated with X-linked mental retardation and neuropsychiatric diseases such as Huntington's chorea, fragile X syndrome and myotonic dystrophy (provided by RefSeq).

CD235a: CD235a is the major intrinsic membrane protein of the erythrocyte. The N-terminal glycosylated segment, which lies outside the erythrocyte membrane, has MN blood group receptors. Appears to be important for the function of SLC4A1 and is required for high activity of SLC4A1. May be involved in translocation of SLC4A1 to the plasma membrane. Is a receptor for influenza virus. Is a receptor for *Plasmodium falciparum* erythrocyte-binding antigen 175 (EBA-175); binding of EBA-175 is dependent on sialic acid residues of the O-linked glycans. Appears to be a receptor for Hepatitis A virus (HAV).

CD335: Cytotoxicity-activating receptor that may contribute to the increased efficiency of activated natural killer (NK) cells to mediate tumor cell lysis.

CD337: The protein encoded by this gene is a natural cytotoxicity receptor (NCR) that may aid NK cells in the lysis of tumor cells. The encoded protein interacts with CD3-zeta (CD247), a T-cell receptor. A single nucleotide polymorphism in the 5' untranslated region of this gene has been associated with mild malaria susceptibility. Three transcript variants encoding different isoforms have been found for this gene.

CD45: The protein encoded by this gene is a member of the protein tyrosine phosphatase (PTP) family. PTPs are known to be signaling molecules that regulate a variety of cellular processes including cell growth, differentiation, mitotic cycle, and oncogenic transformation. This PTP contains an extracellular domain, a single transmembrane segment and two tandem intracytoplasmic catalytic domains, and thus belongs to receptor type PTP. This gene is specifically expressed in hematopoietic cells. This PTP has been shown to be an essential regulator of T- and B-cell antigen receptor signaling. It functions through either direct interaction with components of the antigen receptor complexes, or by activating various Src family kinases required for the antigen receptor signaling. This PTP also suppresses JAK kinases, and thus functions as a regulator of cytokine receptor signaling. Several alternatively spliced transcripts variants of this gene, which encode distinct isoforms, have been reported.

CD49d: The product of this gene belongs to the integrin alpha chain family of proteins. Integrins are heterodimeric integral membrane proteins composed of an alpha chain and a beta chain. This gene encodes an alpha 4 chain. Unlike other integrin alpha chains, alpha 4 neither contains an I-domain, nor undergoes disulfide-linked cleavage. Alpha 4 chain associates with either beta 1 chain or beta 7 chain (provided by RefSeq).

CD66a: This gene encodes a member of the carcinoembryonic antigen (CEA) gene family, which belongs to the immunoglobulin superfamily. Two subgroups of the CEA family, the CEA cell adhesion molecules and the pregnancy-specific glycoproteins, are located within a 1.2 Mb cluster on the long arm of chromosome 19. Eleven pseudogenes of the CEA cell adhesion molecule subgroup are also found in the cluster. The encoded protein was originally described in bile ducts of liver as biliary glycoprotein. Subsequently, it was found to be a cell-cell adhesion molecule detected on leukocytes, epithelia, and endothelia. The encoded protein mediates cell adhesion via homophilic as well as heterophilic binding to other proteins of the subgroup. Multiple cellular activities have been attributed to the encoded protein, including roles in the differentiation and arrangement of tissue three-dimensional structure, angiogenesis, apoptosis, tumor suppression, metastasis, and the modulation of innate and adaptive immune responses. Multiple transcript variants encoding different isoforms have been reported.

CD66c: Carcinoembryonic antigen (CEA; MIM 114890) is one of the most widely used tumor markers in serum immunoassay determinations of carcinoma. An apparent lack of absolute cancer specificity for CEA probably results in part from the presence in normal and neoplastic tissues of antigens that share antigenic determinants with the 180-kD form of CEA (Barnett et al., 1988 (PubMed 3220478)). For background information on the CEA family of genes, see CEACAM1 (MIM 109770) (supplied by OMIM).

CD66d: This gene encodes a member of the family of carcinoembryonic antigen-related cell adhesion molecules (CEACAMs), which are used by several bacterial pathogens to bind and invade host cells. The encoded transmembrane protein directs phagocytosis of several bacterial species that is dependent on the small GTPase Rac. It is thought to serve an important role in controlling human-specific pathogens by the innate immune system. Alternatively spliced transcript variants have been described, but their biological validity has not been determined (provided by RefSeq).

CD66e: CD66e, a member of the CEACAM subfamily, serves as a surface glycoprotein that plays a role in cell adhesion and in intracellular signaling. CD66e also serves a receptor for E. coli Dr adhesins.

CD84: CD84 plays a role as adhesion receptor functioning by homophilic interactions and by clustering. Recruits SH2 domain-containing proteins SH2D1A/SAP. Increases proliferative responses of activated T-cells and SH2D1A/SAP does not seem to be required for this process. Homophilic interactions enhance interferon gamma/IFNG secretion in lymphocytes and induce platelet stimulation via a SH2D1A/SAP-dependent pathway. CD84 may also serve as a marker for hematopoietic progenitor cells EGFR: The protein encoded by this gene is a transmembrane glycoprotein that is a member of the protein kinase superfamily. This protein is a receptor for members of the epidermal growth factor family. EGFR is a cell surface protein that binds to epidermal growth factor. Binding of the protein to a ligand induces receptor dimerization and tyrosine autophosphorylation and leads to cell proliferation. Mutations in this gene are associated with lung cancer. Multiple alternatively spliced transcript variants that encode different protein isoforms have been found for this gene (provided by RefSeq).

GPR162: This gene was identified upon genomic analysis of a gene-dense region at human chromosome 12p13. It appears to be mainly expressed in the brain; however, its function is not known. Alternatively spliced transcript variants encoding different isoforms have been identified (provided by RefSeq).

HLA-A: HLA-A belongs to the HLA class I heavy chain paralogues. This class I molecule is a heterodimer consisting of a heavy chain and a light chain (beta-2 microglobulin).

The heavy chain is anchored in the membrane. Class I molecules play a central role in the immune system by presenting peptides derived from the endoplasmic reticulum lumen. They are expressed in nearly all cells. The heavy chain is approximately 45 kDa and its gene contains 8 exons. Exon 1 encodes the leader peptide, exons 2 and 3 encode the alpha1 and alpha2 domains, which both bind the peptide, exon 4 encodes the alpha3 domain, exon 5 encodes the transmembrane region, and exons 6 and 7 encode the cytoplasmic tail. Polymorphisms within exon 2 and exon 3 are responsible for the peptide binding specificity of each class one molecule.

Typing for these polymorphisms is routinely done for bone marrow and kidney transplantation. Hundreds of HLA-A alleles have been described (provided by RefSeq).

HLA-B: HLA-B belongs to the HLA class I heavy chain paralogues. This class I molecule is a heterodimer consisting of a heavy chain and a light chain (beta-2 microglobulin).

The heavy chain is anchored in the membrane. Class I molecules play a central role in the immune system by presenting peptides derived from the endoplasmic reticulum lumen. They are expressed in nearly all cells. The heavy chain is approximately 45 kDa and its gene contains 8 exons. Exon 1 encodes the leader peptide, exon 2 and 3 encode the alpha1 and alpha2 domains, which both bind the peptide, exon 4 encodes the alpha3 domain, exon 5 encodes the transmembrane region and exons 6 and 7 encode the cytoplasmic tail. Polymorphisms within exon 2 and exon 3 are responsible for the peptide binding specificity of each class one molecule.

Typing for these polymorphisms is routinely done for bone marrow and kidney transplantation. Hundreds of HLA-B alleles have been described (provided by RefSeq).

HLA-C: HLA-C belongs to the HLA class I heavy chain paralogues. This class I molecule is a heterodimer consisting of a heavy chain and a light chain (beta-2 microglobulin).

The heavy chain is anchored in the membrane. Class I molecules play a central role in the immune system by presenting peptides derived from endoplasmic reticulum lumen. They are expressed in nearly all cells. The heavy chain is approximately 45 kDa and its gene contains 8 exons. Exon one encodes the leader peptide, exons 2 and 3 encode the alpha1 and alpha2 domain, which both bind the peptide, exon 4 encodes the alpha3 domain, exon 5 encodes the transmembrane region, and exons 6 and 7 encode the cytoplasmic tail. Polymorphisms within exon 2 and exon 3 are responsible for the peptide binding specificity of each class one molecule.

Typing for these polymorphisms is routinely done for bone marrow and kidney transplantation. Over one hundred HLA-C alleles have been described (provided by RefSeq).

ITGAM: This gene encodes the integrin alpha M chain. Integrins are heterodimeric integral membrane proteins composed of an alpha chain and a beta chain. This I-domain containing alpha integrin combines with the beta 2 chain (ITGB2) to form a leukocyte-specific integrin referred to as macrophage receptor 1 ('Mac-1'), or inactivated-C3b (iC3b) receptor 3 ('CR3'). The alpha M beta 2 integrin is important in the adherence of neutrophils and monocytes to stimulated endothelium, and also in the phagocytosis of complement coated particles. Multiple transcript variants encoding different isoforms have been found for this gene (provided by RefSeq).

NRG1: The protein encoded by this gene was originally identified as a 44-kD glycoprotein that interacts with the NEU/ERBB2 receptor tyrosine kinase to increase its phosphorylation on tyrosine residues. This protein is a signaling protein that mediates cell-cell interactions and plays critical roles in the growth and development of multiple organ systems. It is known that an extraordinary variety of different isoforms are produced from this gene through alternative promoter usage and splicing. These isoforms are tissue-specifically expressed and differ significantly in their structure, and thereby these isoforms are classified into types I, II, III, IV, V and VI. The gene dysregulation has been linked to diseases such as cancer, schizophrenia and bipolar disorder (BPD)(provided by RefSeq).

RAP1B: GTP-binding protein that possesses intrinsic GTPase activity. Contributes to the polarizing activity of KRIT1 and CDH5 in the establishment and maintenance of correct endothelial cell polarity and vascular lumen. Required for the localization of phosphorylated PRKCZ, PARD3 and TIAM1 to the cell junction.

SELI: This gene encodes a selenoprotein, which contains a selenocysteine (Sec) residue at its active site. The selenocysteine is encoded by the UGA codon that normally signals translation termination. The 3' UTR of selenoprotein genes have a common stem-loop structure, the sec insertion sequence (SECIS), that is necessary for the recognition of UGA as a Sec codon rather than as a stop signal (provided by RefSeq).

SPINT2: This gene encodes a transmembrane protein with two extracellular Kunitz domains that inhibits a variety of serine proteases. The protein inhibits HGF activator which prevents the formation of active hepatocyte growth factor. This gene is a putative tumor suppressor, and mutations in this gene result in congenital sodium diarrhea.

Multiple transcript variants encoding different isoforms have been found for this gene (provided by RefSeq).

EIF4B: Required for the binding of mRNA to ribosomes. Functions in close association with EIF4-F and EIF4-A. It binds near the 5'-terminal cap of mRNA in the presence of EIF-4F and ATP. It promotes the ATPase activity and the ATP-dependent RNA unwinding activity of both EIF4-A and EIF4-F.

IFIT1: Interferon-induced protein with tetratricopeptide repeats.

IFITM3/IFITM2: IFN-induced antiviral protein that mediates cellular innate immunity to at least three major human pathogens, namely influenza A H1N1 virus, West Nile virus (WNV), and dengue virus (WNV), by inhibiting the early step(s) of replication.

RSAD2: Radical S-adenosyl methionine domain containing 2; additional aliases of RSAD2 include without limitation 2510004L01Rik, cig33, cig5 and vig1. RSAD2 can impair virus budding by disrupting lipid rafts at the plasma membrane, a feature which is essential for the budding process of many viruses. Acts through binding with and inactivating FPPS, an enzyme involved in synthesis of cholesterol, farnesylated and geranylated proteins, ubiquinone dolichol and heme.

ADIPOR1: ADIPOR1 is a receptor for globular and full-length adiponectin (APM1), an essential hormone secreted by adipocytes that acts as an antidiabetic. It is probably involved in metabolic pathways that regulate lipid metabolism such as fatty acid oxidation. It mediates increased AMPK, PPARA ligand activity, fatty acid oxidation and glucose uptake by adiponectin. ADIPOR1 has some high-affinity receptors for globular adiponectin and low-affinity receptors for full-length adiponectin.

CD15 (FUT4): The product of this gene transfers fucose to N-acetyllactosamine polysaccharides to generate fucosylated carbohydrate structures. It catalyzes the synthesis of the non-sialylated antigen, Lewis x (CD15).

CD73: The protein encoded by this gene is a plasma membrane protein that catalyzes the conversion of extracellular nucleotides to membrane-permeable nucleosides. The encoded protein is used as a determinant of lymphocyte differentiation. Defects in this gene can lead to the calcification of joints and arteries. Two transcript variants encoding different isoforms have been found for this gene.

CD8A: The CD8 antigen is a cell surface glycoprotein found on most cytotoxic T lymphocytes that mediates efficient cell-cell interactions within the immune system. The CD8 antigen acts as a corepressor with the T-cell receptor on the T lymphocyte to recognize antigens displayed by an antigen presenting cell (APC) in the context of class I MHC molecules. The coreceptor functions as either a homodimer composed of two alpha chains, or as a heterodimer composed of one alpha and one beta chain. Both alpha and beta chains share significant homology to immunoglobulin variable light chains. This gene encodes the CD8 alpha chain isoforms. Multiple transcript variants encoding different isoforms have been found for this gene (provided by RefSeq).

IFITM1: IFN-induced antiviral protein that mediate cellular innate immunity to at least three major human pathogens, namely influenza A H1N1 virus, West Nile virus, and dengue virus by inhibiting the early step(s) of replication. Plays a key role in the antiproliferative action of IFN-gamma either by inhibiting the ERK activation or by arresting cell growth in G1 phase in a p53-dependent manner. Implicated in the control of cell growth. Component of a multimeric complex involved in the transduction of antiproliferative and homotypic adhesion signals.

IFITM3: IFN-induced antiviral protein that mediates cellular innate immunity to at least three major human pathogens, namely influenza A H1N1 virus, West Nile virus (WNV), and dengue virus (WNV), by inhibiting the early step(s) of replication.

IL7R: The protein encoded by this gene is a receptor for interleukine 7 (1L7). The function of this receptor requires the interleukin 2 receptor, gamma chain (IL2RG), which is a common gamma chain shared by the receptors of various cytokines, including interleukin 2, 4, 7, 9, and 15. This protein has been shown to play a critical role in the V(D)J recombination during lymphocyte development. This protein is also found to control the accessibility of the TCR gamma locus by STAT5 and histone acetylation. Knockout studies in mice suggested that blocking apoptosis is an essential function of this protein during differentiation and activation of T lymphocytes. The functional defects in this protein may be associated with the pathogenesis of the severe combined immunodeficiency (SCID).

CRP: C-reactive protein; additional aliases of CRP include without limitation RP11-419N10.4 and PTX1. The protein encoded by this gene belongs to the pentaxin family. It is involved in several host defense related functions based on its ability to recognize foreign pathogens and damaged cells of the host and to initiate their elimination by interacting with humoral and cellular effector systems in the blood. Consequently, the level of this protein in plasma increases greatly during acute phase response to tissue injury, infection, or other inflammatory stimuli. CRP displays several functions associated with host defense: it promotes agglutination, bacterial capsular swelling, phagocytosis and complement fixation through its calcium-dependent binding to phosphorylcholine.

TREM1: Triggering receptor expressed on myeloid cells 1; additional aliases of TREM1 are CD354 and TREM-1. This gene encodes a receptor belonging to the Ig superfamily that is expressed on myeloid cells. This protein amplifies neutrophil and monocyte-mediated inflammatory responses triggered by bacterial and fungal infections by stimulating release of pro-inflammatory chemokines and cytokines, as well as increased surface expression of cell activation markers. Alternatively spliced transcript variants encoding different isoforms have been noted for this gene. The protein encoded by this gene has a soluble form which is denoted by sTREM1.

PCT: Procalcitonin (PCT) is a peptide precursor of the hormone calcitonin, the latter being involved with calcium homeostasis. The levels of procalcitonin rise in a response to a proinflammatory stimulus.

SAA: encodes a member of the serum amyloid A family of apolipoproteins. The encoded protein is a major acute phase protein that is highly expressed in response to inflammation and tissue injury. This protein also plays an important role in HDL metabolism and cholesterol homeostasis. High levels of this protein are associated with chronic inflammatory diseases including atherosclerosis, rheumatoid arthritis, Alzheimer's disease and Crohn s disease.

This protein may also be a potential biomarker for certain tumors. Alternate splicing results in multiple transcript variants that encode the same protein.

IL6: This gene encodes a cytokine that functions in inflammation and the maturation of B cells. In addition, the encoded protein has been shown to be an endogenous pyrogen capable of inducing fever in people with autoimmune diseases or infections. The protein is primarily produced at sites of acute and chronic inflammation, where it is secreted into the serum and induces a transcriptional inflammatory response through interleukin 6 receptor, alpha. The functioning of this gene is implicated in a wide variety of inflammation-associated disease states, including susceptibility to diabetes mellitus and systemic juvenile rheumatoid arthritis (provided by RefSeq).

ARG1: Arginase catalyzes the hydrolysis of arginine to ornithine and urea. At least two isoforms of mammalian arginase exist (types I and II) which differ in their tissue distribution, subcellular localization, immunologic crossreactivity and physiologic function. The type I isoform encoded by this gene, is a cytosolic enzyme and expressed predominantly in the liver as a component of the urea cycle. Inherited deficiency of this enzyme results in argininemia, an autosomal recessive disorder characterized by hyperammonemia (provided by RefSeq).

ARPC2: This gene encodes one of seven subunits of the human Arp2/3 protein complex. The Arp2/3 protein complex has been implicated in the control of actin polymerization in cells and has been conserved through evolution. The exact role of the protein encoded by this gene, the p34 subunit, has yet to be determined. Two alternatively spliced variants have been characterized to date. Additional alternatively spliced variants have been described but their full length nature has not been determined (provided by RefSeq).

ATP6V0B: $H^+$-ATPase (vacuolar ATPase, V-ATPase) is an enzyme transporter that functions to acidify intracellular compartments in eukaryotic cells. It is ubiquitously expressed and is present in endomembrane organelles such as vacuoles, lysosomes, endosomes, the Golgi apparatus, chromaffin granules and coated vesicles, as well as in the plasma membrane. $H^+$-ATPase is a multi-subunit complex composed of two domains. The V1 domain is responsible for ATP hydrolysis and the V0 domain is responsible for protein translocation. There are two main mechanisms of regulating $H^+$-ATPase activity; recycling of $H^+$-ATPase-containing vesicles to and from the plasma membrane and glucose-sensitive assembly/disassembly of the holo-enzyme complex. These transporters play an important role in processes such as receptor-mediated endocytosis, protein degradation and coupled transport. They have a function in bone reabsorption and mutations in the A3 gene cause recessive osteopetrosis. Furthermore, $H^+$-ATPases have been implicated in tumor metastasis and regulation of sperm motility and maturation.

BRI3BP: Involved in tumorigenesis and may function by stabilizing p53/TP53.

CCL19: This gene is one of several CC cytokine genes clustered on the p-arm of chromosome 9. Cytokines are a family of secreted proteins involved in immunoregulatory and inflammatory processes. The CC cytokines are proteins characterized by two adjacent cysteines.

The cytokine encoded by this gene may play a role in normal lymphocyte recirculation and homing. It also plays an important role in trafficking of T cells in thymus, and in T cell and B cell migration to secondary lymphoid organs. It specifically binds to chemokine receptor CCR7 (provided by RefSeq).

CES1: Involved in the detoxification of xenobiotics and in the activation of ester and amide prodrugs. Hydrolyzes aromatic and aliphatic esters, but has no catalytic activity toward amides or a fatty acyl-CoA ester. Hydrolyzes the methyl ester group of cocaine to form benzoylecgonine. Catalyzes the transesterification of cocaine to form cocaethylene. Displays fatty acid ethyl ester synthase activity, catalyzing the ethyl esterification of oleic acid to ethyloleate.

CORO1A: May be a crucial component of the cytoskeleton of highly motile cells, functioning both in the invagination of large pieces of plasma membrane, as well as in forming protrusions of the plasma membrane involved in cell locomotion. In mycobacteria-infected cells, its retention on the phagosomal membrane prevents fusion between phagosomes and lysosomes.

HERC5: Major E3 ligase for ISG15 conjugation. Acts as a positive regulator of innate antiviral response in cells induced by interferon. Makes part of the ISGylation machinery that recognizes target proteins in a broad and relatively non-specific manner. Catalyzes ISGylation of IRF3 which results in sustained activation. It attenuates IRF3-PIN1 interaction, which antagonizes IRF3 ubiquitination and degradation, and boosts the antiviral response.

Catalyzes ISGylation of influenza A viral NS1 which attenuates virulence; ISGylated NS1 fails to form homodimers and thus to interact with its RNA targets. It catalyzes ISGylation of papillomavirus type 16 L1 protein which results in dominant-negative effect on virus infectivity. Physically associated with polyribosomes, broadly modifies newly synthesized proteins in a co-translational manner. In an interferon-stimulated cell, newly translated viral proteins are primary targets of ISG15.

IFI6: This gene was first identified as one of the many genes induced by interferon. The encoded protein may play a critical role in the regulation of apoptosis. A mini satellite that consists of 26 repeats of a 12 nucleotide repeating element resembling the mammalian splice donor consensus sequence begins near the end of the second exon. Alternatively spliced transcript variants that encode different isoforms by using the two downstream repeat units as splice donor sites have been described.

IFIT3: Additional aliases of the protein include without limitation: interferon-induced protein with tetratricopeptide repeats 3, IFI60, ISG60 and Interferon-induced 60 kDa protein.

MBOAT2: Acyltransferase which mediates the conversion of lysophosphatidyl-ethanolamine (1-acyl-sn-glycero-3-phosphoethanolamine or LPE) into phosphatidyl-ethanolamine (1,2-diacyl-sn-glycero-3-phosphoethanolamine or PE) (LPEAT activity). Catalyzes also the acylation of lysophosphatidic acid (LPA) into phosphatidic acid (PA) (LPAAT activity).

Has also a very weak lysophosphatidyl-choline acyltransferase (LPCAT activity). Prefers oleoyl-CoA as the acyl donor. Lysophospholipid acyltransferases (LPLATs) catalyze the reacylation step of the phospholipid remodeling pathway also known as the Lands cycle.

MX1/MXA: myxovirus (influenza virus) resistance 1; additional aliases of MX1 include without limitation IFI-78K, IFI78, MX and MxA. In mouse, the interferon-inducible Mx protein is responsible for a specific antiviral state against influenza virus infection. The protein encoded by this gene is similar to the mouse protein as determined by its antigenic relatedness, induction conditions, physicochemical properties, and amino acid analysis. This cytoplasmic protein is a member of both the dynamin family and the family of large GTPases.

OAS2: This gene encodes a member of the 2-5A synthetase family, essential proteins involved in the innate immune response to viral infection. The encoded protein is induced by interferons and uses adenosine triphosphate in 2'-specific nucleotidyl transfer reactions to synthesize 2', 5'-oligoadenylates (2-5As). These molecules activate latent RNase L, which results in viral RNA degradation and the inhibition of viral replication. The three known members of this gene family are located in a cluster on chromosome 12. Alternatively spliced transcript variants encoding different isoforms have been described.

KIAA0082 (FTSJD2): S-adenosyl-L-methionine-dependent methyltransferase that mediates mRNA cap1 2'-O-ribose methylation to the 5'-cap structure of mRNAs. Methylates the ribose of the first nucleotide of a m(7)GpppG-capped mRNA to produce m(7)GpppNmp (cap1).

Cap1 modification is linked to higher levels of translation. May be involved in the interferon.

LIPT1: The process of transferring lipoic acid to proteins is a two-step process. The first step is the activation of lipoic acid by lipoate-activating enzyme to form lipoyl-AMP. For the second step, the protein encoded by this gene transfers the lipoyl moiety to apoproteins.

Alternative splicing in the 5' UTR of this gene results in five transcript variants that encode the same protein. (provided by RefSeq).

LRDD: The protein encoded by this gene contains a leucine-rich repeat and a death domain. This protein has been shown to interact with other death domain proteins, such as Fas (TNFRSF6)-associated via death domain (FADD) and MAP-kinase activating death domain-containing protein (MADD), and thus may function as an adaptor protein in cell death-related signaling processes. The expression of the mouse counterpart of this gene has been found to be positively regulated by the tumor suppressor p53 and to induce cell apoptosis in response to DNA damage, which suggests a role for this gene as an effector of p53-dependent apoptosis.

Alternative splicing results in multiple transcript variants.

MCP-2: This gene is one of several cytokine genes clustered on the q-arm of chromosome 17. Cytokines are a family of secreted proteins involved in immunoregulatory and inflammatory processes. The protein encoded by this gene is structurally related to the CXC subfamily of cytokines. Members of this subfamily are characterized by two cysteines separated by a single amino acid. This cytokine displays chemotactic activity for monocytes, lymphocytes, basophils and eosinophils. By recruiting leukocytes to sites of inflammation this cytokine may contribute to tumor-associated leukocyte infiltration and to the antiviral state against HIV infection (provided by RefSeq).

PARP9: Poly (ADP-ribose) polymerase (PARP) catalyzes the post-translational modification of proteins by the addition of multiple ADP-ribose moieties. PARP transfers ADP-ribose from nicotinamide dinucleotide (NAD) to glu/asp residues on the substrate protein, and also polymerizes ADP-ribose to form long/branched chain polymers. PARP inhibitors are being developed for use in a number of pathologies including cancer, diabetes, stroke and cardiovascular diseases.

PTEN: Tumor suppressor. Acts as a dual-specificity protein phosphatase, ephosphorylating tyrosine-, serine- and threonine-phosphorylated proteins. Also acts as a lipid phosphatase, removing the phosphate in the D3 position of the inositol ring from phosphatidylinositol (PI) 3,4,5-trisphosphate, PI 3,4-diphosphate, PI 3-phosphate and inositol 1,3,4,5-tetrakisphosphate with order of substrate preference in vitro PtdIns(3,4,5)P3>PtdIns(3,4)P2>PtdIns3P>Ins(1,3,4,5)P4. The lipid phosphatase activity is critical for its tumor suppressor function. Antagonizes the PI3K-AKT/PKB signaling pathway by dephosphorylating phosphoinositides and thereby modulating cell cycle progression and cell survival. The un-phosphorylated form cooperates with AIP1 to suppress AKT1 activation. Dephosphorylates tyrosine-phosphorylated focal adhesion kinase and inhibits cell migration and integrin-mediated cell spreading and focal adhesion formation. Plays a role as a key modulator of the AKT-mTOR signaling pathway controlling the tempo of the process of newborn neurons integration during adult neurogenesis, including correct neuron positioning, dendritic development and synapse formation. May be a negative regulator of insulin signaling and glucose metabolism in adipose tissue. The nuclear monoubiquitinated form possesses greater apoptotic potential, whereas the cytoplasmic nonubiquitinated form induces less tumor suppressive ability.

OARS: Aminoacyl-tRNA synthetases catalyze the aminoacylation of tRNA by their cognate amino acid. Because of their central role in linking amino acids with nucleotide triplets contained in tRNAs, aminoacyl-tRNA synthetases are thought to be among the first proteins that appeared in evolution. In metazoans, 9 aminoacyl-tRNA synthetases specific for glutamine (gln), glutamic acid (glu), and 7 other amino acids are associated within a multienzyme complex.

Although present in eukaryotes, glutaminyl-tRNA synthetase (QARS) is absent from many prokaryotes, mitochondria, and chloroplasts, in which Gln-tRNA(Gln) is formed by transamidation of the misacylated Glu-tRNA(Gln). Glutaminyl-tRNA synthetase belongs to the class-I aminoacyl-tRNA synthetase family.

RAB13: could participate in polarized transport, in the assembly and/or the activity of tight junctions.

RPL34: Ribosomes, the organelles that catalyze protein synthesis, consist of a small 40S subunit and a large 60S subunit. Together these subunits are composed of 4 RNA species and approximately 80 structurally distinct proteins. This gene encodes a ribosomal protein that is a component of the 60S subunit. The protein belongs to the L34E family of ribosomal proteins. It is located in the cytoplasm. This gene originally was thought to be located at 17q21, but it has been mapped to 4q. Transcript variants derived from alternative splicing, alternative transcription initiation sites, and/or alternative polyadenylation exist; these variants encode the same protein.

As is typical for genes encoding ribosomal proteins, there are multiple processed pseudogenes of this gene dispersed through the genome.

SART3: The protein encoded by this gene is an RNA-binding nuclear protein that is a tumor-rejection antigen. This antigen possesses tumor epitopes capable of inducing HLA-A24-restricted and tumor-specific cytotoxic T lymphocytes in cancer patients and may be useful for specific immunotherapy. This gene product is found to be an important cellular factor for HIV-1 gene expression and viral replication. It also associates transiently with U6 and U4/U6 snRNPs during the recycling phase of the spliceosome cycle. This encoded protein is thought to be involved in the regulation of mRNA splicing.

TRIM22: Interferon-induced antiviral protein involved in cell innate immunity. The antiviral activity could in part be mediated by TRIM22-dependent ubiquitination of viral proteins. Plays a role in restricting the replication of HIV-1, encephalomyocarditis virus (EMCV) and hepatitis B virus (HBV). Acts as a transcriptional repressor of HBV core promoter. May have E3 ubiquitin-protein ligase activity.

UBE2N: The UBE2V1-UBE2N and UBE2V2-UBE2N heterodimers catalyze the synthesis of non-canonical 'Lys-63'-linked polyubiquitin chains. This type of polyubiquitination does not lead to protein degradation by the proteasome. It mediates transcriptional activation of target genes. It plays a role in the control of progress through the cell cycle and differentiation.

Plays a role in the error-free DNA repair pathway and contributes to the survival of cells after DNA damage. Acts together with the E3 ligases, HLTF and SHPRH, in the 'Lys-63'-linked poly ubiquitination of PCNA upon genotoxic stress, which is required for DNA repair. It appears to act together with E3 ligase RNF5 in the 'Lys-63'-linked polyubiquitination of JKAMP thereby regulating JKAMP function by decreasing its association with components of the proteasome and ERAD.

XAF1: Seems to function as a negative regulator of members of the IAP (inhibitor of apoptosis protein) family. Inhibits anti-caspase activity of BIRC4. Induces cleavage and inactivation of BIRC4 independent of caspase activation. Mediates TNF-alpha-induced apoptosis and is involved in apoptosis in trophoblast cells. May inhibit BIRC4 indirectly by activating the mitochondrial apoptosis pathway. After translocation to mitochondra, promotes translocation of BAX to mitochondria and cytochrome c release from mitochondria. Seems to promote the redistribution of BIRC4 from the cytoplasm to the nucleus, probably independent of BIRC4 inactivation which seems to occur in the cytoplasm. The BIRC4-XAF1 complex mediates down-regulation of BIRC5/survivin; the process requires the E3 ligase activity of BIRC4. Seems to be involved in cellular sensitivity to the proapoptotic actions of TRAIL. May be a tumor suppressor by mediating apoptosis resistance of cancer cells.

ZBP1: DLM1 encodes a Z-DNA binding protein. Z-DNA formation is a dynamic process, largely controlled by the amount of supercoiling. May play a role in host defense against tumors and pathogens. Binds Z-DNA (By similarity).

IL11: The protein encoded by this gene is a member of the gp130 family of cytokines. These cytokines drive the assembly of multisubunit receptor complexes, all of which contain at least one molecule of the transmembrane signaling receptor IL6ST (gp130). This cytokine is shown to stimulate the T-cell-dependent development of immunoglobulin-producing B cells. It is also found to support the proliferation of hematopoietic stem cells and megakaryocyte progenitor cells.

IL1RA: The protein encoded by this gene is a cytokine receptor that belongs to the interleukin 1 receptor family. This protein is a receptor for interleukin alpha (IL1A), interleukin beta (IL1B), and interleukin 1 receptor, type I (IL1R1/IL1RA). It is an important mediator involved in many cytokine induced immune and inflammatory responses. Additional names of the gene include without limitations: CD121A, IL-1RT1, p80, CD121a antigen, CD121A, IL1R and IL1ra.

IP10: This gene encodes a chemokine of the CXC subfamily and ligand for the receptor CXCR3. Binding of this protein to CXCR3 results in pleiotropic effects, including stimulation of monocytes, natural killer and T-cell migration, and modulation of adhesion molecule expression. Additional names of the gene include without limitations: CXCL10, Gamma-IP10, INP10 and chemokine (C-X-C motif) ligand 10.

I-TAC: Chemotactic for interleukin-activated T-cells but not unstimulated T-cells, neutrophils or monocytes. Induces calcium release in activated T-cells. Binds to CXCR3. May play an important role in CNS diseases which involve T-cell recruitment. Additional names of the gene include without limitations: SCYB11, SCYB9B and CXCL11.

TNFR1: Receptor for TNFSF2/TNF-alpha and homotrimeric TNFSF1/lymphotoxin-alpha. The adapter molecule FADD recruits caspase-8 to the activated receptor. The resulting death-inducing signaling complex (DISC) performs caspase-8 proteolytic activation which initiates the subsequent cascade of caspases (aspartate-specific cysteine proteases) mediating apoptosis. Additional names of the gene include without limitations: TNFRSF1A, TNFAR, p55, p60, CD120a antigen and CD120a antigen.

IL-8: The protein encoded by this gene is a member of the CXC chemokine family. Additional aliases of IL-8 include without limitation: Interleukin 8, K60, CXCL8, SCYB8, GCP-1, TSG-1, MDNCF, b-ENAP, MONAP, alveolar macrophage chemotactic factor I, NAP-1, beta endothelial cell-derived neutrophil activating peptide, GCP1, beta-thromboglobulin-like protein, LECT, chemokine (C-X-C motif) ligand 8, LUCT, emoctakin, LYNAP, interleukin-8, NAF, lung giant cell carcinoma-derived chemotactic protein, NAP1, lymphocyte derived neutrophil activating peptide, IL-8, neutrophil-activating peptide 1, Granulocyte chemotactic protein 1, small inducible cytokine subfamily B, member 8, Monocyte-derived neutrophil chemotactic factor, tumor necrosis factor-induced gene 1, Monocyte-derived neutrophil-activating peptide, Emoctakin, T-cell chemotactic factor, C-X-C motif chemokine 8, 3-10C, Neutrophil-activating protein 1, AMCF-I and Protein 3-10C. This chemokine is one of the major mediators of the inflammatory response. This chemokine is secreted by several cell types. It functions as a chemoattractant, and is also a potent angiogenic factor. This gene is believed to play a role in the pathogenesis of bronchiolitis, a common respiratory tract disease caused by viral infection. This gene and other ten members of the CXC chemokine gene family form a chemokine gene cluster in a region mapped to chromosome 4q. (provided by RefSeq, July 2008).

IL-8 is a chemotactic factor that attracts neutrophils, basophils, and T-cells, but not monocytes. It is also involved in neutrophil activation. IL-8(6-77) has a 5-10-fold higher activity on neutrophil activation, IL-8(5-77) has increased activity on neutrophil activation and IL-8(7-77) has a higher affinity to receptors CXCR1 and CXCR2 as compared to IL-8(1-77), respectively.

Definitions

"DETERMINANTS" in the context of the present invention encompass, without limitation, polypeptides, peptide, proteins, protein isoforms (e.g. decoy receptor isoforms), and metabolites. DETERMINANTS can also include mutated proteins. "DETERMINANT" OR "DETERMINANTS" encompass one or more of all polypeptides or whose levels are changed in subjects who have an infection. Individual DETERMINANTS include TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC, TNFR1, IFITM3, IFIT3, EIF4B, IFIT1, LOC26010, MBOAT2, MX1, OAS2, RSAD2, ADIPOR1, CD15, CD8A, IFITM1, IL7, CRP, SAA, TREM-1, PCT, IL-8, TREM-1, IL6, ARG1, ARPC2, ATP6V0B, BCA-1, BRI3BP, CCL19-MIP3b, CES1, CORO1A, HERC5, IFI6, IFIT3, KIAA0082, LIPT1, LRDD, MCP-2, PARP9, PTEN, QARS, RAB13, RPL34, SART3, TRIM22, UBE2N, XAF1 and ZBP1 and are collectively referred to herein as, inter alia, "infection-associated proteins" or "infection-associated polypeptides", "DETERMINANT-polypeptides", "polypeptide-DETERMINANTS", "DETERMINANT-proteins" or "protein-DETERMINANTS".

DETERMINANTS also encompass non-polypeptide, non-blood borne factors or non-analyte physiological markers of health status referred to herein as, inter alia, "clinical-DETERMINANTS" or "clinical DETERMINANTS".

DETERMINANTS also include any calculated indices created mathematically or combinations of any one or more of the foregoing measurements, including temporal trends and differences. Where available, and unless otherwise described herein, DETERMINANTS, which are gene products are identified based on the official letter abbreviation or gene symbol assigned by the international Human Genome Organization Naming Committee (HGNC) and listed at the date of this filing at the US National Center for Biotechnology Information (NCBI) web site (http://wwwdotncbidotnlmdotnihdotgov/sites/entrez?db=gene), also known as Entrez Gene.

"Clinical-DETERMINANTS" encompass non-polypeptide, non-blood borne factors or non-analyte physiological markers of health status including "clinical parameters" defined herein, as well as "traditional laboratory risk factors", also defined herein.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms") or family history (abbreviated FamHX).

"soluble-DETERMINANTS", "secreted-DETERMINANTS" and "soluble polypeptides" are polypeptide-DETERMINANTS that exist outside the cellular interior in different body fluids such as serum, plasma, urine, CSF, sputum, sweat, stool, seminal fluid, etc.

"intracellular-DETERMINANTS", "intracellular proteins" and "intracellular polypeptides" are polypeptides that are present within a cell.

"membrane-DETERMINANTS", "membrane proteins" and "intracellular determinants" are polypeptides that are present on the cell surface or membrane.

An "Infection Reference Expression Profile," is a set of values associated with two or more DETERMINANTS resulting from evaluation of a biological sample (or population or set of samples).

A "Subject with non-infectious disease" is one whose disease is not caused by an infectious disease agent (e.g. bacteria or virus). In the study presented herein this includes patients with acute myocardial infarction, physical injury, epileptic attack etc.

An "Acute Infection" is characterized by rapid onset of disease, a relatively brief period of symptoms, and resolution within days.

A "chronic infection" is an infection that develops slowly and lasts a long time. Viruses that may cause a chronic infection include Hepatitis C and HIV. One difference between acute and chronic infection is that during acute infection the immune system often produces IgM+ antibodies against the infectious agent, whereas the chronic phase of the infection is usually characteristic of IgM−/IgG+ antibodies. In addition, acute infections cause immune mediated necrotic processes while chronic infections often cause inflammatory mediated fibrotic processes and scaring (e.g. Hepatitis C in the liver). Thus, acute and chronic infections may elicit different underlying immunological mechanisms.

By infection type is meant to include bacterial infections, mixed infections, viral infections, no infection, infectious or non-infectious.

By "ruling in" an infection it is meant that the subject has that type of infection.

By "ruling out" an infection it is meant that the subject does not have that type of infection.

The "natural flora", or "colonizers" refers to microorganisms, such as bacteria or viruses, that may be present in healthy a-symptomatic subjects and in sick subjects.

An "anti-viral treatment" includes the administration of a compound, drug, regimen or an action that when performed by a subject with a viral infection can contribute to the subject's recovery from the infection or to a relief from symptoms. Examples of anti-viral treatments include without limitation the administration of the following drugs: oseltamivir, RNAi antivirals, monoclonal antibody respigams, zanamivir, and neuriminidase blocking agents.

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathwes Correlation coefficient) is calculated as follows: $MCC=(TP*TN-FP*FN)/\{(TP+FN)*(TP+FP)*(TN+FP)*(TN+FN)\}^{0.5}$ where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

Often, for binary disease state classification approaches using a continuous diagnostic test measurement, the sensitivity and specificity is summarized by a Receiver Operating Characteristics (ROC) curve according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), $4^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Matheus correlation coefficient (MCC), or as a likelihood, odds ratio, Receiver Operating Charachteristic (ROC) curve, Area Under the Curve (AUC) among other measures.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-DETERMINANTS, such as gender, age, or ethnicity), rules and guidelines, statistical classification models, and neural networks trained on historical populations. Of particular use in combining DETERMINANTS are linear and non-linear equations and statistical classification analyses to determine the relationship between levels of DETERMINANTS detected in a subject sample and the subject's probability of having an infection or a certain type of infection. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a DETERMINANT selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters or clinical-DETERMINANTS.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

A "sample" in the context of the present invention is a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, or whole blood cells.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention is preferably a human. A subject can be male or female. A subject can be one who has been previously diagnosed or identified as having an infection, and optionally has already undergone, or is undergoing, a therapeutic intervention for the infection. Alternatively, a subject can also be one who has not been previously diagnosed as having an infection. For example, a subject can be one who exhibits one or more risk factors for having an infection.

In the context of the present invention the following abbreviations may be used: Antibiotics (Abx), Adverse Event (AE), Arbitrary Units (A.U.), Complete Blood Count (CBC), Case Report Form (CRF), Chest X-Ray (CXR), Electronic Case Report Form (eCRF), Food and Drug Administration (FDA), Good Clinical Practice (GCP), Gastrointestinal (GI), Gastroenteritis (GE), International Conference on Harmonization (ICH), Infectious Disease (ID), In vitro diagnostics (IVD), Lower Respiratory Tract Infection (LRTI), Myocardial infarction (MI), Polymerase chain reaction (PCR), Per-oss (P.O), Per-rectum (P.R), Standard of Care (SoC), Standard Operating Procedure (SOP), Urinary Tract Infection (UTI), Upper Respiratory Tract Infection (URTI).

Methods and Uses of the Invention

The methods disclosed herein are used to identify subjects with an infection or a specific infection type. By type of infection it is meant to include bacterial infections, viral infections, mixed infections, no infection (i.e., non-infectious) More specifically, some methods of the invention are used to distinguish subjects having a bacterial infection, a viral infection, a mixed infection (i.e., bacterial and viral co-infection), patients with a non-infectious disease and healthy individuals. Some methods of the present invention can also be used to monitor or select a treatment regimen for a subject who has a an infection, and to screen subjects who have not been previously diagnosed as having an infection, such as subjects who exhibit risk factors developing an infection. Some methods of the present invention are used to identify and/or diagnose subjects who are asymptomatic for an infection. "Asymptomatic" means not exhibiting the traditional signs and symptoms.

The term "Gram-positive bacteria" are bacteria that are stained dark blue by Gram staining. Gram-positive organisms are able to retain the crystal violet stain because of the high amount of peptidoglycan in the cell wall.

The term "Gram-negative bacteria" are bacteria that do not retain the crystal violet dye in the Gram staining protocol.

The term "Atypical bacteria" are bacteria that do not fall into one of the classical "Gram" groups. They are usually, though not always, intracellular bacterial pathogens. They include, without limitations, *Mycoplasmas* spp., *Legionella* spp. *Rickettsiae* spp., and *Chlamydiae* spp.

As used herein, infection is meant to include any infectious agent of viral or bacterial origin. The bacterial infection may be the result of gram-positive, gram-negative bacteria or atypical bacteria.

A subject having an infection is identified by measuring the amounts (including the presence or absence) of an effective number (which can be one or more) of DETERMINANTS in a subject-derived sample. A clinically significant alteration in the level of the DETERMINANT is determined. Alternatively, the amounts are compared to a reference value.

Alterations in the amounts and patterns of expression DETERMINANTS in the subject sample compared to the reference value are then identified. In various embodiments, two, three, four, five, six, seven, eight, nine, ten or more DETERMINANTS are measured. For example, the combination of DETERMINANTS may be selected according to any of the models enumerated in Tables 2-3.

In some embodiments the combination of DETERMINANTS comprise measurements of one or more polypeptides selected from the group consisting of TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC and TNFR1.

In some embodiments the combination of DETERMINANTS comprise measurements of one or more soluble-polypeptides selected from the group consisting of B2M, BCA-1, CHI3L1, Eotaxin, IL1a, IL1RA, IP10, MCP, Mac-2BP, TRAIL, CD62L and VEGFR2.

In some embodiments the combination of DETERMINANTS comprise measurements of one or more intracellular-polypeptides selected from the group consisting of CHP, CMPK2, CORO1C, EIF2AK2, ISG15, RPL22L1 and RTN3.

In some embodiments the combination of DETERMINANTS comprise measurements of one or more membrane-polypeptides selected from the group consisting of TRAIL, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2 and SSEA1.

In some embodiments, the polypeptides measurements further comprise measurements of one or more polypeptides selected from the group consisting of EIF4B, IFIT1, IFIT3, LOC26010, MBOAT2, MX1, OAS2, RSAD2, ADIPOR1, CD15, CD8A, IFITM1, IFITM3, IL7R, CRP, SAA, sTREM, PCT, IL-8 and IL6.

In some embodiments, the polypeptides measurements further comprise measurements of one or more clinical-DETERMINANTS selected from the group consisting of ANC, ALC, Neu (%), Lym (%), Mono (%), Maximal temperature, Time from symptoms, Age, Creatinine (Cr), Potassium (K), Pulse and Urea.

In some embodiments, the polypeptides or clinical-DETERMINANTS measurements further comprise measurements of one or more polypeptide or clinical-DETERMINANTS selected from the group consisting of ARG1, ARPC2, ATP6V0B, BILI (Bilirubin), BRI3BP, CCL19-MIP3B, CES1, CORO1A, EOS (%), HERC5, IFI6, IFIT3, KIAA0082, LIPT1, LRDD, MCP-2, NA (Sodium), PARP9, PTEN, QARS, RAB13, RPL34, SART3, TRIM22, UBE2N, WBC (Whole Blood Count), XAF1 and ZBP1.

In various aspects the method distinguishes a virally infected subject from either a subject with non-infectious disease or a healthy subject; a bacterially infected subject, from either a subject with non-infectious disease or a healthy subject; a subject with an infectious disease from either a subject with an non-infectious disease or a healthy subject; a bacterially infected subject from a virally infected subject; a mixed infected subject from a virally infected subject; a mixed infected subject from a bacterially infected subject and a bacterially or mixed infected and subject from a virally infected subject.

For example, the invention provides a method of identifying the type of infection in a subject by measuring the levels of a first DETERMINANT selected from the group consisting of TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC and TNFR1 in a sample from the subject; and measuring the levels of a second DETERMINANT. The second DETERMINANT is selected from TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC and TNFR1; IFITM3, IFIT3, EIF4B, IFIT1, LOC26010, MBOAT2, MX1, OAS2, RSAD2, ADIPOR1, CD15, CD8A, IFITM1, and IL7; CRP, SAA, TREM-1, PCT, IL-8, TREM-1 and IL6; Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea. The levels of the first and second DETERMINANTS is compared to a reference value thereby identifying the type of infection in the subject wherein the measurement of the second DETERMINANT increases the accuracy of the identification of the type of infection over the measurement of the first DETERMINANT alone. Optionally, one or more additional DETERMINANTS selected from TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC and TNFR1; IFITM3, IFIT3, EIF4B, IFIT1, LOC26010, MBOAT2, MX1, OAS2, RSAD2, ADIPOR1, CD15, CD8A, IFITM1, and IL7; CRP, SAA, TREM-1, PCT, IL-8, TREM-1 and IL6; Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea are measured. The measurement of the additional DETERMINANTS increases the accuracy of the identification of the type of infection over the measurement of the first and second DETERMINANTS.

In preferred embodiments the following DETERMINANTS are measured:

B2M is measured and a second DETERMINANT selected from the group consisting of BCA-1, CHI3L1, Eotaxin, IL1a, IP10, MCP, Mac-2BP, TRAIL, sCD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

BCA-1 is measured and a second DETERMINANT selected from the group consisting of, CHI3L1, Eotaxin, IL1a, IP10, MCP, Mac-2BP, TRAIL, CD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

CHI3L1 is measured and a second DETERMINANT selected from the group consisting of Eotaxin, IL1a, IP10, MCP, Mac-2BP, TRAIL, CD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

Eotaxin is measured and a second DETERMINANT selected from the group consisting of IL1a, IP10, MCP, Mac-2BP, TRAIL, CD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

IL1a is measured and a second DETERMINANT selected from the group consisting of IP10, MCP, Mac-2BP, TRAIL, CD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

IP10 is measured and a second DETERMINANT selected from the group consisting of MCP, Mac-2BP, TRAIL, CD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

MCP is measured and a second DETERMINANT selected from the group consisting of Mac-2BP, TRAIL, CD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

Mac-2BP is measured and a second DETERMINANT selected from the group consisting of TRAIL, CD62L, VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

TRAIL is measured and a second DETERMINANT selected from the group consisting of CD62L, VEGFR2, CRP, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

CD62L is measured and a second DETERMINANT selected from the group consisting of VEGFR2, CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured;

VEGFR2 is measured and a second DETERMINANT selected from the group consisting of CRP, SAA, TREM-1, PCT, IL-8, IL6, ANC, ALC, Neu (%), Lym (%), Mono (%), Maximal temperature, Time from symptoms, Age, Creatinine (Cr), Potassium (K), Pulse and Urea is measured; or TREM-1 is measured and a second DETERMINANT selected from the group consisting of CRP, PCT, IL-8, IL6, ANC, ALC, Neu (%), Lym (%), Mono (%), Maximal temperature, Time from symptoms, Age, Creatinine (Cr), Potassium (K), Pulse and Urea is measured.

In one aspect the method distinguishes a bacterially infected subject from a virally infected subject by measuring one or more DETERMINANTS selected from B2M, BCA-1, CHI3L1, Eotaxin, IL1RA, IP10, MCP, Mac-2BP, TRAIL, CD62L and VEGFR2 are measured and one or more DETERMINANTS selected from the group consisting of CRP, TREM-1, SAA, PCT, IL-8, IL6, ANC, ALC, Neu (%), Lym (%), Mono (%), Maximal temperature, Time from symptoms, Age, Creatinine (Cr), Potassium (K), Pulse and Urea. For example, CRP and TRAIL are measured; CRP and TRAIL and SAA are measured; CRP and TRAIL and Mac-2BP are measured; CRP and TRAIL and PCT and are measured; CRP and TRAIL and SAA and Mac-2BP are measured; PCT and TRAIL are measured; or SAA and TRAIL are measured. In a another aspect the method distinguishes between a mixed infected subject and a virally infected subject by measuring wherein one or more DETERMINANTS selected from TRAIL, IP10, IL1RA, CHI3L1, CMPK2 and MCP-2 are measured and optionally one or more DETERMINANTS selected from the group consisting of CRP, SAA, ANC, ATP6V0B, CES1, CORO1A, HERC5, IFITM1, LIPT1, LOC26010, LRDD, Lym (%), MCP-2, MX1, Neu (%), OAS2, PARP9, RSAD2, SART3, WBC, PCT, IL-8, 1L6 and TREM-1.

In another aspect the method distinguishes between a bacterial or mixed infected subject and a virally infected subject by measuring wherein one or more DETERMINANTS selected from TRAIL, IL1RA, IP10, ARG1, CD337, CD73, CD84, CHI3L1, CHP, CMPK2, CORO1C, EIF2AK2, Eotaxin, GPR162, HLA-A/B/C, ISG15, ITGAM, Mac-2BP, NRG1, RAP1B, RPL22L1, SSEA1, RSAD2, RTN3, SELI, VEGFR2, CD62L and VEGFR2 are measured and optionally one or more DETERMINANTS selected from the group consisting of CRP, SAA, PCT, IL6, IL8, ADIPOR1, ANC, Age, B2M, Bili total, CD15, Cr, EIF4B, IFIT1, IFIT3, IFITM1, IL7R, K (potassium), KIAA0082, LOC26010, Lym (%), MBOAT2, MCP-2, MX1, Na, Neu (%), OAS2, PARP9, PTEN, Pulse, Urea, WBC, ZBP1, mIgG1 and TREM-1.

In another aspect the method distinguishes between a subject with an infectious disease and a subject with a non-infectious disease or a healthy subject by measuring one or more DETERMINANTS selected from IP10, IL1RA, TRAIL, BCA-1, CCL19-MIP3b, CES1 and CMPK2. Optionally, one or more DETERMINANTS selected from CRP, SAA, PCT, IL6, IL8, ARPC2, ATP6V0B, Cr, Eos (%), HERC5, IFI6, IFIT3, KIAA0082, LIPT1, LOC26010, LRDD, MBOAT2, MX1, Maximal temperature, OAS2, PARP9, Pulse, QARS, RAB13, RPL34, RSAD2, SART3, RIM22, UBE2N, XAF1, IL11, I-TAC and TNFR1 are measured.

In specific embodiments the invention includes determining if a subject does not have a bacterial infection (i.e. ruling out a bacterial infection). A bacterial infection is ruled out if the polypeptide concentration of TRAIL determined is higher than a pre-determined first threshold value. Optionally, the method further includes determining if a subject has a viral infection (i.e., ruling in a viral infection). A viral infection is rule in if the polypeptide concentration of TRAIL is higher than a pre-determined second threshold value.

In another specific embodiment the invention includes determining if a subject does not have a viral infection (i.e. ruling out a viral infection). A viral infection is ruled out if the polypeptide concentration of TRAIL determined is lower than a pre-determined first threshold value. Optionally, the method further includes determining if a subject has a bacterial infection (i.e., ruling in a bacterial infection). A bacterial infection is rule in if the polypeptide concentration of TRAIL is lower than a pre-determined second threshold value.

In other embodiments the invention includes a method of distinguishing between a bacterial infection and a viral infection in a subject by measuring the polypeptide concentration of TRAIL and CRP in a subject derived sample, applying a pre-determined mathematical function on the concentrations of TRAIL and CRP to compute a score and comparing the score to a predetermined reference value. Optionally, one or more of SAA, PCT, B2M Mac-2BP, IL1RA or IP10 is measured.

In another embodiment, the invention provides a method of distinguishing between a bacterial or mixed infection, and a viral infection in a subject by measuring the polypeptide concentration of TRAIL and CRP in a subject derived sample, applying a pre-determined mathematical function on the concentrations of TRAIL and CRP to compute a score and comparing the score to a predetermined reference value. Optionally, one or more of SAA, PCT, B2M Mac-2BP, IL1RA or IP10 is measured.

For example to distinguish between a bacterial infection and a viral infection or bacterial or mixed infection, and a viral infection TRAIL, CRP and SAA are measured; TRAIL, CRP and IP10 are measured; TRAIL, CRP and PCT are measured; TRAIL, CRP and IL1RA are measured; TRAIL, CRP and B2M are measured; TRAIL, CRP and Mac-2BP are measured; TRAIL, CRP, SAA and PCT are measured; TRAIL, CRP, Mac-2BP and SAA are measured; TRAIL, CRP, SAA and IP10 are measured; TRAIL, CRP, SAA and IL1RA are measured; TRAIL, CRP, SAA, PCT and IP10 are measured; TRAIL, CRP, SAA, PCT and IL1RA are measured; or TRAIL, CRP, SAA, IP10 and IL1RA are measured.

A reference value can be relative to a number or value derived from population studies, including without limitation, such subjects having the same infection, subject having the same or similar age range, subjects in the same or similar ethnic group, or relative to the starting sample of a subject undergoing treatment for an infection. Such reference values can be derived from statistical analyses and/or risk prediction data of populations obtained from mathematical algorithms and computed indices of infection. Reference DETERMINANT indices can also be constructed and used using algorithms and other methods of statistical and structural classification.

In one embodiment of the present invention, the reference value is the amount (i.e. level) of DETERMINANTS in a control sample derived from one or more subjects who do not have an infection (i.e., healthy, and or non-infectious individuals). In a further embodiment, such subjects are monitored and/or periodically retested for a diagnostically relevant period of time ("longitudinal studies") following such test to verify continued absence of infection. Such period of time may be one day, two days, two to five days, five days, five to ten days, ten days, or ten or more days from the initial testing date for determination of the reference value. Furthermore, retrospective measurement of DETERMINANTS in properly banked historical subject samples may be used in establishing these reference values, thus shortening the study time required.

A reference value can also comprise the amounts of DETERMINANTS derived from subjects who show an improvement as a result of treatments and/or therapies for the infection. A reference value can also comprise the amounts of DETERMINANTS derived from subjects who have confirmed infection by known techniques.

In another embodiment, the reference value is an index value or a baseline value. An index value or baseline value is a composite sample of an effective amount of DETERMINANTS from one or more subjects who do not have an infection. A baseline value can also comprise the amounts of DETERMINANTS in a sample derived from a subject who has shown an improvement in treatments or therapies for the infection. In this embodiment, to make comparisons to the subject-derived sample, the amounts of DETERMINANTS are similarly calculated and compared to the index value. Optionally, subjects identified as having an infection, are chosen to receive a therapeutic regimen to slow the progression or eliminate the infection.

Additionally, the amount of the DETERMINANT can be measured in a test sample and compared to the "normal control level," utilizing techniques such as reference limits, discrimination limits, or risk defining thresholds to define cutoff points and abnormal values. The "normal control level" means the level of one or more DETERMINANTS or combined DETERMINANT indices typically found in a subject not suffering from an infection. Such normal control level and cutoff points may vary based on whether a DETERMINANT is used alone or in a formula combining with other DETERMINANTS into an index. Alternatively, the normal control level can be a database of DETERMINANT patterns from previously tested subjects.

The effectiveness of a treatment regimen can be monitored by detecting a DETERMINANT in an effective amount (which may be one or more) of samples obtained from a subject over time and comparing the amount of DETERMINANTS detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections.) This will allow patients to be stratified and treated accordingly.

In a specific embodiment of the invention a treatment recommendation (i.e., selecting a treatment regimen) for a subject is provided by measuring the polypeptide concentration of TRAIL in a subject derived sample; and recommending that the subject receives an antibiotic treatment if polypeptide concentration of TRAIL is lower than a pre-determined threshold value; recommending that the patient does not receive an antibiotic treatment if the polypeptide concentration of TRAIL is higher than a pre-determined threshold value; or recommending that the patient receive an anti-viral treatment if the polypeptide concentration of TRAIL determined in step (a) is higher than a pre-determined threshold value.

In another specific embodiment of the invention a treatment recommendation (i.e., selecting a treatment regimen) for a subject is provided by identifying the type infection (i.e., bacterial, viral, mixed infection or no infection) in the subject according to the method of any of the disclosed methods and recommending that the subject receive an antibiotic treatment if the subject is identified as having bacterial infection or a mixed infection; or an anti-viral treatment is if the subject is identified as having a viral infection.

In another embodiment, the methods of the invention can be used to prompt additional targeted diagnosis such as pathogen specific PCRs, chest-X-ray, cultures etc. For example, a reference value that indicates a viral infection, may prompt the usage of additional viral specific multiplex-PCRs, whereas a reference value that indicates a bacterial infection may prompt the usage of a bacterial specific multiplex-PCR. Thus, one can reduce the costs of unwarranted expensive diagnostics.

In a specific embodiment, a diagnostic test recommendation for a subject is provided by measuring the polypeptide concentration of TRAIL in a subject derived sample; and recommending testing the sample for a bacteria if the polypeptide concentration of TRAIL is lower than a pre-determined threshold value; or recommending testing the sample for a virus if the polypeptide concentration of TRAIL is higher than a pre-determined threshold value.

In another specific embodiment, a diagnostic test recommendation for a subject is provided by identifying the infection type (i.e., bacterial, viral, mixed infection or no infection) in the subject according to any of the disclosed methods.

Recommending a test to determine the source of the bacterial infection if the subject is identified as having a bacterial infection or a mixed infection; or a test to determine the source of the viral infection if the subject is identified as having a viral infection.

Some aspects of the present invention also comprise a kit with a detection reagent that binds to one or more DETERMINANT. Also provided by the invention is an array of detection reagents, e.g., antibodies that can bind to one or more DETERMINANT-polypeptides. In one embodiment, the DETERMINANTS are polypeptides and the array contains antibodies that bind one or more DETERMINANTS selected from TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC, TNFR1, IFITM3, IFIT3, EIF4B, IFIT1, LOC26010, MBOAT2, MX1, OAS2, RSAD2, ADIPOR1, CD15, CD8A, IFITM1, IL7, CRP, SAA, TREM-1, PCT, IL-8, TREM-1, IL6, ARG1, ARPC2, ATP6V0B, BCA-1, BRI3BP, CCL19-MIP3b, CES1, CORO1A, HERC5, IFI6, IFIT3, KIAA0082, LIPT1, LRDD, MCP-2, PARP9, PTEN, QARS, RAB13, RPL34, SART3, TRIM22, UBE2N, XAF1 and ZBP1 sufficient to measure a statistically significant alteration in DETERMINANT expression.

Preferably, the concentration of the polypeptide-DETERMINANTS is measured within about 24 hours after sample is obtained. Alternatively, the concentration of the polypeptide-DETERMINANTS measured in a sample that was stored at 12° C. or lower, when storage begins less than 24 hours after the sample is obtained.

In another embodiment the DETERMINANT is TRAIL and the array contains antibodies that bind TRAIL. In another embodiment the DETERMINANTS are TRAIL and CRP and the array contains antibodies that bind TRAIL and CRP. In another embodiment the DETERMINANTS are TRAIL, CRP and VEGFR2 and the array contains antibodies that bind TRAIL, CRP and VEGFR2. In another embodiment the DETERMINANTS are TRAIL, CRP and Mac2-BP and the array contains antibodies that bind TRAIL, CRP and Mac2-BP. In another embodiment the DETERMINANTS are TRAIL, CRP, VEGFR2 and Mac2-BP and the array contains antibodies that bind TRAIL, CRP, VEGFR2 and Mac2-BP. In another embodiment the DETERMINANTS are TRAIL, CRP and SAA and the array contains antibodies that bind TRAIL, CRP and SAA. In another embodiment the DETERMINANTS are TRAIL, CRP, SAA and Mac2-BP and the array contains antibodies that bind TRAIL, CRP, SAA and Mac2-BP. In another embodiment the DETERMINANTS are TRAIL, CRP, SAA and IL1RA and the array contains antibodies that bind TRAIL, CRP, SAA and IL1RA. The levels of DETERMIANT in different types of infections are depicted in FIGS. 21-22. Our findings that TRAIL concentrations in viral infected patients are higher than bacterial infected patients (median of 121±132 pg/ml versus 52±65 pg/ml), support the embodiments wherein TRAIL concentrations are measured. Furthermore, when we monitored TRAIL concentrations over time in patients infected with a virus, we found a substantial increase in concentrations shortly after the infection, followed by a gradual decrease and returning to basal levels (for example see FIG. 41). More examples of TRAIL concentrations in different infections are presented in FIGS. 35-39. Interestingly, we find that combining TRAIL levels, which are higher in viral compared to bacterial infections, and CRP levels, which are higher in bacterial compared to viral infections, enables a diagnostic accuracy that is superior to any of the individual biomarkers. For example, we found that combining the levels of CRP and TRAIL by computing a pre-determined mathematical formula produces a score that diagnoses the source of infection more accurately then each of the biomarkers individually (TRAIL AUC=0.89, CRP AUC=0.89, TRAIL and CRP combined AUC=0.94). For example see FIGS. 23-24 visualizes a linear formula that is used to incorporate the levels of TRAIL and CRP into a single score. Other formulas exist, which are known to someone skilled in the art. The TRAIL and CRP diagnostic synergism, may be attributed to the low correlation between these two biomarkers. We observe similar results when combining the concentrations of SAA and TRAIL (for example see FIGS. 23-24).

We compared the genomic sequence of TRAIL across different organisms using the UCSC genome browser (Human February 2009 (GRCh37/hg19) assembly, and found that it is evolutionary conserved (especially in the exon regions) (see FIG. 42). For example, we find sequence conservation in large and small mammals such as cow, horse, dog and cat. This suggests that TRAIL may have a similar protein behavior across different organisms similar to what we found in human (including up regulation in viral infections).

Of note, TRAIL is highly expressed in other tissues and samples including without limitation CSF, saliva and epithelial cells, bone marrow aspiration, urine, stool, alveolar lavage, sputum, saliva (Secchiero, Lamberti et al. 2009). Thus, some embodiments of the present invention can be used to measure TRAIL in such tissues and samples, wherein an increase of TRAIL concentrations indicate increased likelihood of a viral infection.

Some aspects of the present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes. Measurements of effective amounts of the biomarkers of the invention and/or the resulting evaluation of risk from those biomarkers can be implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system used in some aspects of the invention may also be considered to be implemented as a computer-readable storage medium, configured with a computer program, where the storage medium so configured causes a computer to operate in a specific and predefined manner to perform various functions described herein.

The DETERMINANTS of the present invention, in some embodiments thereof, can be used to generate a "reference DETERMINANT profile" of those subjects who do not have an infection. The DETERMINANTS disclosed herein can also be used to generate a "subject DETERMINANT profile" taken from subjects who have an infection. The subject DETERMINANT profiles can be compared to a reference DETERMINANT profile to diagnose or identify subjects with an infection. The subject DETERMINANT profile of different infection types can be compared to diagnose or identify the type of infection. The reference and subject DETERMINANT profiles of the present invention, in some embodiments thereof, can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

Performance and Accuracy Measures of the Invention

The performance and thus absolute and relative clinical usefulness of the invention may be assessed in multiple ways as noted above. Amongst the various assessments of performance, some aspects of the invention are intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant and diagnostically significant) in the levels of a DETERMINANT. By "effective amount" it is meant that the measurement of an appropriate number of DETERMINANTS (which may be one or more) to produce a "significant alteration" (e.g. level of expression or activity of a DETERMINANT) that is different than the predetermined cut-off point (or threshold value) for that DETERMINANT(S) and therefore indicates that the subject has an infection for which the DETERMINANT(S) is a determinant. The difference in the level of DETERMINANT is preferably statistically significant. As noted below, and without any limitation of the invention, achieving statistical significance, and thus the preferred analytical, diagnostic, and clinical accuracy, may require that combinations of several DETERMINANTS be used together in panels and combined with mathematical algorithms in order to achieve a statistically significant DETERMINANT index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. One way to achieve this is by using the MCC metric, which depends upon both sensitivity and specificity. Use of statistics such as AUC, encompassing all potential cut point values, is preferred for most categorical risk measures when using some aspects of the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test used in some aspects of the invention for determining the clinically significant presence of DETERMINANTS, which thereby indicates the presence an infection type) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an infection or response to therapy with at least 75% total accuracy, more preferably 80%, 85%, 90%, 95%, 97%, 98%, 99% or greater total accuracy.

Alternatively, the methods predict the presence or absence of an infection or response to therapy with an MCC larger than 0.2, 0.3, 0.4, 0.5, 0.6, 0.7, 0.8, 0.9 or 1.0.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon).

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, California).

In general, by defining the degree of diagnostic accuracy, i.e., cut points on a ROC curve, defining an acceptable AUC value, and determining the acceptable ranges in relative concentration of what constitutes an effective amount of the DETERMINANTS of the invention allows for one of skill in the art to use the DETERMINANTS to identify, diagnose, or prognose subjects with a pre-determined level of predictability and performance.

Furthermore, other unlisted biomarkers will be very highly correlated with the DETRMINANTS (for the purpose of this application, any two variables will be considered to be "very highly correlated" when they have a Coefficient of Determination (R2) of 0.5 or greater).

Some aspects of the present invention encompass such functional and statistical equivalents to the aforementioned DETERMINANTS. Furthermore, the statistical utility of such additional DETERMINANTS is substantially dependent on the cross-correlation between multiple biomarkers and any new biomarkers will often be required to operate within a panel in order to elaborate the meaning of the underlying biology.

One or more of the listed DETERMINANTS can be detected in the practice of the present invention, in some embodiments thereof. For example, two (2), three (3), four (4), five (5), ten (10), fifteen (15), twenty (20), forty (40), or more DETERMINANTS can be detected.

In some aspects, all DETERMINANTS listed herein can be detected. Preferred ranges from which the number of DETERMINANTS can be detected include ranges bounded by any minimum selected from between one and, particularly two, three, four, five, six, seven, eight, nine ten, twenty, or forty. Particularly preferred ranges include two to five (2-5), two to ten (2-10), two to twenty (2-20), or two to forty (2-40).

Construction of DETERMINANT Panels

Groupings of DETERMINANTS can be included in "panels", also called "DETERMINANT-signatures", "DETER-MINANT signatures", or "multi-DETERMINANT signatures." A "panel" within the context of the present invention means a group of biomarkers (whether they are DETERMINANTS, clinical parameters, or traditional laboratory risk factors) that includes one or more DETERMINANTS. A panel can also comprise additional biomarkers, e.g., clinical parameters, traditional laboratory risk factors, known to be present or associated with infection, in combination with a selected group of the DETERMINANTS listed herein.

As noted above, many of the individual DETERMINANTS, clinical parameters, and traditional laboratory risk factors listed, when used alone and not as a member of a multi-biomarker panel of DETERMINANTS, have little or no clinical use in reliably distinguishing individual normal subjects, subjects at risk for having an infection (e.g., bacterial, viral or co-infection), and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual DETERMINANT performance, and the general performance of formulas combining only the traditional clinical parameters and few traditional laboratory risk factors, the present inventors have noted that certain specific combinations of two or more DETERMINANTS can also be used as multi-biomarker panels comprising combinations of DETERMINANTS that are known to be involved in one or more physiological or biological pathways, and that such information can be combined and made clinically useful through the use of various formulae, including statistical classification algorithms and others, combining and in many cases extending the performance characteristics of the combination beyond that of the individual DETERMINANTS. These specific combinations show an acceptable level of diagnostic accuracy, and, when sufficient information from multiple DETERMINANTS is combined in a trained formula, they often reliably achieve a high level of diagnostic accuracy transportable from one population to another.

The general concept of how two less specific or lower performing DETERMINANTS are combined into novel and more useful combinations for the intended indications, is a key aspect of some embodiments of the invention. Multiple biomarkers can yield better performance than the individual components when proper mathematical and clinical algorithms are used; this is often evident in both sensitivity and specificity, and results in a greater AUC or MCC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in DETERMINANT selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the DETERMINANTS can be advantageously used. Pathway informed seeding of such statistical classification techniques also may be employed, as may rational approaches based on the selection of individual DETERMINANTS based on their participation across in particular pathways or physiological functions.

Ultimately, formula such as statistical classification algorithms can be directly used to both select DETERMINANTS and to generate and train the optimal formula necessary to combine the results from multiple DETERMINANTS into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of DETERMINANTS used. The position of the individual DETERMINANT on a forward or backwards selected panel can be closely related to its provision of incremental information content for the algorithm, so the order of contribution is highly dependent on the other constituent DETERMINANTS in the panel.

Construction of Clinical Algorithms

Any formula may be used to combine DETERMINANT results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from DETERMINANT results in the relevant training population. Amongst other uses, such formula may be intended to map the feature space derived from one or more DETERMINANT inputs to a set of subject classes (e.g. useful in predicting class membership of subjects as normal, having an infection), to derive an estimation of a probability function of risk using a Bayesian approach, or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual DETERMINANT measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-DETERMINANTS such as age, time from symptoms, gender, race, or sex, where specific formula are used solely on subjects within a class or continuously combining a clinical-DETERMINANTS as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

Some DETERMINANTS may exhibit trends that depends on the patient age (e.g. the population baseline may rise or fall as a function of age). One can use a 'Age dependent normalization or stratification' scheme to adjust for age related differences. Performing age dependent normalization or stratification can be used to improve the accuracy of DETERMINANTS for differentiating between different types of infections. For example, one skilled in the art can generate a function that fits the population mean levels of each DETERMINANT as function of age and use it to normalize the DETERMINANT of individual subjects levels across different ages. Another example is to stratify subjects according to their age and determine age specific thresholds or index values for each age group independently.

Measurement of DETERMINANTS

The actual measurement of levels or amounts of the DETERMINANTS can be determined at the protein or polypeptide level using any method known in the art.

For example, by measuring the levels of polypeptide encoded by the gene products described herein, or subcellular localization or activities thereof. Such methods are well known in the art and include, e.g., immunoassays based on antibodies to proteins, aptamers or molecular imprints. Any biological material can be used for the detection/quantification of the protein or its activity. Alternatively, a suitable method can be selected to determine the activity of proteins encoded by the marker genes according to the activity of each protein analyzed.

The DETERMINANT proteins, polypeptides, mutations, and polymorphisms thereof can be detected in any suitable manner, but is typically detected by contacting a sample from the subject with an antibody, which binds the DETERMINANT protein, polypeptide, mutation, polymorphism, or post translational modification additions (e.g. carbohydrates) and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological sample as described above, and may be the same sample of biological sample used to conduct the method described above.

Immunoassays carried out in accordance with some embodiments of the present invention may be homogeneous assays or heterogeneous assays. In a homogeneous assay the immunological reaction usually involves the specific antibody (e.g., anti-DETERMINANT protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." The DETERMINANT can also be detected with antibodies using flow cytometry. Those skilled in the art will be familiar with flow cytometric techniques which may be useful in carrying out the methods disclosed herein(Shapiro 2005). These include, without limitation, Cytokine Bead Array (Becton Dickinson) and Luminex technology.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of DETERMINANT proteins, polypeptides, mutations, and polymorphisms, such as tyrosine phosphorylation, threonine phosphorylation, serine phosphorylation, glycosylation (e.g., 0-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth U. and Muller D. 2002).

For DETERMINANT-proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. In this regard, other DETERMINANT analytes can be measured using the above-mentioned detection methods, or other methods known to the skilled artisan. For example, circulating calcium ions (Ca 2+) can be detected in a sample using fluorescent dyes such as the poly-amino carboxylic acid, Fluo series, Fura-2A, Rhod-2, the ratiometric calcium indicator Indo-1, among others.

Other DETERMINANT metabolites can be similarly detected using reagents that are specifically designed or tailored to detect such metabolites.

Kits

Some aspects of the invention also include a DETERMINANT-detection reagent, or antibodies packaged together in the form of a kit. The kit may contain in separate containers an antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a sandwich ELISA as known in the art.

For example, DETERMINANT detection reagents can be immobilized on a solid matrix such as a porous strip to form at least one DETERMINANT detection site. The measurement or detection region of the porous strip may include a plurality of sites. A test strip may also contain sites for negative and/or positive controls. Alternatively, control sites can be located on a separate strip from the test strip. Optionally, the different detection sites may contain different amounts of immobilized detection reagents, e.g., a higher amount in the first detection site and lesser amounts in subsequent sites. Upon the addition of test sample, the number of sites displaying a detectable signal provides a quantitative indication of the amount of DETERMINANTS present in the sample. The detection sites may be configured in any suitably detectable shape and are typically in the shape of a bar or dot spanning the width of a test strip.

Suitable sources for antibodies for the detection of DETERMINANTS include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptide DETERMINANTS described herein.

We note that the fraction in which the polypeptide DETERMINANTS reside affects the ease by which the assay can be performed at the clinical setting. For example, in the clinical setting, especially the point-of-care, it is often easier to measure polypeptides that are present in the serum or plasma fraction compared to intra-cellular polypeptides within the leukocytes fraction. This is because the latter requires an additional experimental step in which leukocytes are isolated from the whole blood sample, washed and lysed.

We note that in some clinical settings it is more convenient to apply assays that measure polypeptides, rather than RNA. In particular we found that RNA levels that are differentially induced in different types of infections do not necessarily show the same behavior on the polypeptide level. For example, the mRNAs of IFI44, IFI44L and IFI27 have been found to be differentially expressed in viral compared to bacterial infections. However, when we measured and compared their polypeptide levels in bacterial versus viral infected patients we did not observe a significant differential response (FIG. 38).

Examples of "Monoclonal antibodies for measuring TRAIL", include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1.

Examples of "Monoclonal antibodies for measuring CRP", include without limitation: Mouse, Monoclonal (108-

2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG.

Examples of "Monoclonal antibodies for measuring SAA", include without limitation: Mouse, Monoclonal (SAA15), IgG1; Mouse, Monoclonal (504), IgG2b; Mouse, Monoclonal (SAA6), IgG1; Mouse, Monoclonal (585), IgG2b; Mouse, Monoclonal (426), IgG2b; Mouse, Monoclonal (38), IgG2b; Mouse, Monoclonal (132), IgG3; Mouse, Monoclonal (S3-F11), IgM; Mouse, Monoclonal (513), IgG1; Mouse, Monoclonal (291), IgG2b; Mouse, Monoclonal (607), IgG1; Mouse, Monoclonal (115), IgG1; Mouse, Monoclonal (B332A), IgG1; Mouse, Monoclonal (B336A), IgG1; Mouse, Monoclonal (B333A), IgG1; Rabbit, Monoclonal (EPR2927); Rabbit, Monoclonal (EPR4134); Mouse, Monoclonal (Reu86-1), IgG1; Mouse, Monoclonal (Reu86-5), IgG1; Mouse, Monoclonal (291), IgG2b kappa; Mouse, Monoclonal (504), IgG2b kappa; Mouse, Monoclonal (585), IgG2b kappa; Mouse, Monoclonal (S3), IgM kappa; Mouse, Monoclonal (mcl), IgG2a kappa; Mouse, Monoclonal (Reu 86-2), IgG2a; Mouse, Monoclonal (3C11-2C1), IgG2b kappa and Rabbit, Monoclonal (EPR2926), IgG.

Polyclonal antibodies for measuring DETERMINANTS include without limitation antibodies that were produced from sera by active immunization of one or more of the following: Rabbit, Goat, Sheep, Chicken, Duck, Guinea Pig, Mouse, Donkey, Camel, Rat and Horse.

Examples of Detection agents, include without limitation: scFv, dsFv, Fab, sVH, F(ab')2, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

EXAMPLES

Example 1: General Methods

Clinical Study Overview

We performed a multi-center, observational, prospective clinical study whose goal was to develop and test a DETERMINANT-signature for the purpose of rapid and accurate diagnosis of patients with viral and bacterial diseases. We recruited a total of 655 patients of whom 609 had a suspected infectious disease and 46 had a non-infectious disease (control group). The study was approved by the institutional review boards (IRB) of Bnai Zion and Hillel Yaffe Medical Centers in Israel, where patients were recruited from 2010 to 2012.

An overview of study workflow is depicted in FIG. 1. Briefly, a data-minable electronic case report form (eCRF) was used to record the clinical investigations, medical history, microbiological, radiological, and laboratory data of each patient (eCRF records were designed to preserve patient anonymity). Based on the clinical syndrome, one or more of the following samples were sent to thorough microbiological and molecular investigations: blood, urine, stool, sputum, cerebrospinal fluid (CSF), and nasal swabs. A total of 44 different pathogen strains were identified in the cohort of patients with suspected infectious diseases through the composite application of cultures, serology, antigen assays, and multiplex-PCRs methodologies.

Diagnosis (bacterial, viral, mixed, non-infectious, and undetermined) was determined by a panel of at least three experts (the attending physician at the hospital, two independent senior infectious disease experts [IDEs], and a senior pediatrician if the patient was ≤18 years of age), based on a consensus or majority decision of the expert panel, and was recorded on the eCRF. In addition, we quantified the levels of 570 different analyte biomarkers (e.g., proteins and metabolites) in blood drawn from these patients (some of the proteins were only measured in a subset of the patients due to sample volume constraints). We constructed a database that included all the eCRF-contained data for each patient (i.e., hundreds of numerical and categorical features as well as the biomarker biochemical measurements). This database was then used to develop and test the DETERMINANT-signatures.

Inclusion Criteria

Patients who were at least one month old and were willing (either the subject or legal guardian) to sign an informed consent were eligible for inclusion. For the infectious and non-infectious disease groups, additional inclusion criteria had to be met. These included:

Infectious disease group:
  Peak fever >37.5° C.
  Clinical suspicion of an acute infectious disease
  Symptoms duration ≤10 days
Non-infectious disease control group:
  Clinical suspicion of a non-infectious disease Exclusion Criteria Patients who met the following criteria were excluded from the study:
  Evidence of another episode of acute infectious disease in the last two weeks
  Diagnosed congenital immune deficiency (CID)
  Current treatment with immunosuppressive therapy such as:
    Active chemotherapy
    Post-transplant drugs
    High dose steroids (>40 mg/day prednisone or equivalent)
    Active radiotherapy
    Immune-modulating/suppressive drugs including monoclonal antibodies, intravenous immunoglobulin (IVIG), cyclosporine, and anti-tumor necrosis factor (TNF) agents
  Current treatment with immunostimulants such as:
    Interleukin (IL)-2
    Granulocyte colony-stimulating factor (G-CSF) or granulocyte-macrophage colony-stimulating factor (GM-CSF)
    Interferon (all kinds)
  An active hematological malignancy (e.g., chronic lymphocytic leukemia [CLL])

A diagnosis of myelodysplastic syndrome (MDS) or myeloproliferative disease (MPD)

A proven or suspected human immunodeficiency virus (HIV)-1, hepatitis B virus (HBV), or hepatitis C virus (HCV) infection The Enrollment Process After signing an informed consent, each patient underwent the following procedures:

Physical examination and recording of baseline variables including:
        Demographics: gender, age, date of birth, date of recruitment, site of recruitment, etc.
        Medical history: main complaints, background diseases, chronically-administrated drugs, time of symptom onset, maximal fever, etc.
        Physical examination: directed physical examination, pulse, auscultation, throat exam, skin rash, lymphadenopathy screening, etc.
        Disease-specific variables (e.g., chest X-ray for suspected lower respiratory tract infections [LRTI], flank tenderness for suspected urinary tract infection [UTI])
        Complete blood count (CBC) investigation including: whole blood count, absolute neutrophil count (ANC), % neutrophils, % lymphocytes, etc.
    Chemistry lab: Creatinine, urea, liver enzymes, etc.
    Sampling of the upper respiratory tract with a nasal swab for further microbiological investigation
    Sample collection based on clinical symptoms (e.g., urine culture in a patient with a suspected UTI, stool sampling in a patient with a suspected gastroenteritis)
    Blood sampling for analyte biomarker measurements in MeMed labs: 2-6 ml of peripheral venous blood was collected in EDTA containing CBC tubes. The blood was then stored in 4P degrees for 1-4 hours.

Thirty days after enrollment, disease course and response to treatment were recorded on the eCRF as well as details such as clinical, radiological, laboratory, and microbiological results that were unavailable at the day of enrollment.

Microbiological and Molecular Tests

To enable the expert panel to establish a final diagnosis with high confidence level, we performed a thorough microbiological and molecular investigation by testing for most of the disease-causing agents in the Western world. In this section, we present an overview of the microbiological and molecular investigations.

For each patient, we applied two state-of-the-art CE-in vitro diagnostics (IVD)-marked multiplex PCR assays on the specimens obtained from the nasopharyngeal swab:

The Seeplex® RV15 ACE (SeeGene Ltd, Seoul, Korea). This assay is designed to detect the majority of known respiratory viruses (15 virus subgroups including, parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus)
    Seeplex® PneumoBacter ACE (SeeGene Ltd, Seoul, Korea). This assay is designed to detect six pneumonia-causing bacteria simultaneously (*Streptococcus pneumoniae* [SP], *Haemophilus* influenza [HI], *Chlamydophila* pneumonia[CP], *Legionella pneumophila*[LP], *Bordetella pertussis*[BP], and *Mycoplasma* pneumonia [MP])

Patients were tested for additional pathogens according to their suspected clinical syndrome (for details see Clinical Study Protocol). For example:

Stool samples from patients with gastroenteritis were analyzed using a multiplex PCR assay designed to detect 10 pathogens (Rotavirus, Astrovirus, Enteric adenovirus, Norovirus GI, Norovirus GII, *Vibrio* spp., *Shigella* spp., *Campylobacter* spp., *Clostridium Difficile* Toxin B, and *Salmonella* spp.)
    Serological testing for cytomegalovirus (CMV), Epstein bar virus (EBV), MP, and *Coxiella Burnetii* (Q-Fever) was performed in all the clinically relevant subgroups
    Blood, urine, and stool cultures were performed in clinically relevant subgroups Overall, our process detected a pathogen in >50% of the patients with an infectious disease. We also used these results to examine the yield and accuracy of different diagnostic methods and to evaluate the rates of false discovery among patients with a non-infectious disease.

Creating the Reference Standard

Currently, no single reference standard exists for determining bacterial and viral infections in a wide range of clinical syndromes. Therefore, we followed the Standards for Reporting of Diagnostic Accuracy (STARD) recommendation (Bossuyt et al. 2003) and created a highly rigorous composite reference standard for testing the DETERMINANT signatures. The composite reference standard was created in two steps. First, for each patient we performed a thorough investigation. This included the collection of traditional types of diagnostic information such as recording of medical history, clinical symptoms, disease course, and lab measurements, as well as more advanced diagnostic information including microbiological, serological, and molecular investigations (as described above). Then, we gave all the accumulated raw information to a panel of at least three experts (for adult patients [>18 years of age], the experts included the attending physician at the hospital and two independent senior IDEs; for children [≤18 years of age], the panel included a senior pediatrician as a fourth member of the expert panel). Based on the information, each member of the expert panel assigned one of the following diagnostic labels to each of the patients: (i) bacterial; (ii) viral; (iii) mixed (i.e., bacterial and viral co-infection); (iv) non-infectious; or (v) undetermined. Importantly, the experts were blinded to the diagnostic labels of their peers on the expert panel. The diagnosis was then determined by majority of the expert panel. In our study, after applying the aforementioned process to the enrolled patients (n=575), the cohort included 242 patients (42%) with a viral infection, 208 patients (36%) with a bacterial infection, 34 patients (6%) with a mixed infection, 46 patients (8%) with a non-infectious disease, and 45 patients (8%) with an undetermined diagnosis (either because no majority was reached by the expert panel [6% of all patients] or because the panel assigned the patient an 'undetermined' diagnosis [2% of all patients]) (FIG. 2).

The diagnostic labels assigned by our expert panel were then used to create cohorts with an increasing level of confidence.

The majority cohort: Patients were included in this cohort if they were assigned a diagnosis of a bacterial ('bacterial patient'), viral ('viral patient'), mixed infection ('mixed patient'), or non-infectious disease, by a majority (>50%) of the expert panel.
    The consensus cohort: This subset of the majority cohort included the patients for whom the expert panel assigned a diagnosis (bacterial, viral, mixed, or non-infectious) unanimously.
    The clear diagnosis cohort: This subset of the consensus cohort included patients with a bacterial or viral infection that were assigned these diagnoses unanimously by the expert panel and who also met the following additional criteria. To be included as a bacterial patients, patients had to have bacteremia (with positive blood culture), bacterial meningitis (with positive CSF culture or >1,000 neutrophils/µL), pyelonephritis (with positive urine culture and an ultrasound information of renal involvement), UTI (with positive urine culture), septic shock (with positive blood culture), cellulitis, or peri-tonsillar abscess (proven by surgical exploration) (Thorn et al. 1977). To be included as a viral patient, patients had to have a positive microbiological isolate of an obligatory virus.

Of note, in the following examples tables and figures, unless explicitly mentioned otherwise, patient reference standards were determined based on the majority cohort. The above-mentioned composite reference standard strategy adheres to the recommended best practice guidelines in studies of diagnostics of infectious disease. The DETERMINAT and DETERMINANT-signature performances reported herein were analyzed against this reference standard.

Measurements of membrane bound or intra-cellular polypeptide DETERMINANTS Whole blood was fractionated to cellular and plasma fractions and subsequantially treated with red blood cell lysing buffer (BD Bioscience). White blood cells were subsequently washed three times with phosphate buffered saline pH 7.3. In order to measure the levels of membrane associated DETERMINANT polypeptides, the cells were incubated with primary antibodies for 40 minutes, washed twice and incubated with PE conjugated secondary antibody (Jackson Laboratories, emission 575 nm) for additional 20 minutes. In case of intracellular DETERMINANT polypeptides, cells were first fixed and permeabilized with fixation and permeabilization buffer kit (eBioscience). Following fixation and permeabilization cells were incubated with primary antibodies for 40 minutes, washed twice and incubated with PE conjugated secondary antibody for additional 20 minutes. IgG Isotype controls were used for each mode of staining as negative control background. Following the staining procedure, cells were analyzed by using an LSRII flow cytometer. Granulocytes, monocytes, platelets and lymphocytes were distinguished from each other by using an SSC/FSC dot plot. Background and specific staining were determined for lymphocytes, monocytes and granulocytes for each specific antigen. Total leukocytes mean levels was computed by summing the DETERMINANT polypeptides levels of all the cell types and dividing by the white blood count.

Polypeptide-DETERMINANTS that were measured using this protocol include:

CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, EIF4B, IFIT1, IFIT3, LOC26010, MBOAT2, MX1, OAS2, RSAD2, ADIPOR1, CD15, CD8A, IFITM1, IFITM3, IL7R, ARG1, ARPC2, ATP6V0B, BCA-1, BRI3BP, CCL19-MIP3b, CES1, CORO1A, HERC5, IFI6, IFIT3, KIAA0082, LIPT1, LRDD, MCP-2, PARP9, PTEN, QARS, RAB13, RPL34, SART3, TRIM22, UBE2N, XAF1 and ZBP1.

Measurements of Soluble-DETERMINANTS Using ELISA

To determine the concentrations of soluble-DETERMINANTS in human plasma samples we used a standard Sandwich ELISA (Enzyme-linked immunosorbent assay). Briefly, the wells of 96-well plate were coated with capture-antibody specific to the soluble DETERMINANT of interest and diluted in coating buffer (e.g. 1×PBS) followed by overnight incubation at 4° C. The wells were washed twice with washing buffer (e.g. 1×PBS with 0.2% Tween-20) and subsequently blocked with blocking buffer containing proteins (e.g. 1×PBS with 0.2% Tween-20 and 5% non-fat milk) for at least 2 hours at room temperature or overnight at 4° C. This that step increases assay signal-to-noise-ratio. Wells were then washed twice with washing buffer. Protein standard and plasma samples were diluted using a dilution buffer (e.g. 1×PBS with 0.2% Tween-20 and 5% non-fat milk) at the adequate concentration and dilution factors, respectively, followed by a two hour incubation at room temperature. Then, the wells were washed three times with the washing buffer and subsequently incubated with biotinylated detection-antibody specific to the soluble DETERMINANT of interest, diluted in blocking buffer for at least two hours at room temperature.

The wells were washed four times with a washing buffer and then incubated with streptavidin-HRP (i.e. horseradish peroxidase) diluted in blocking buffer for one hour at room temperature. The wells were washed four times with the washing buffer and then incubated with a reaction solution that contained a chromogenic HRP substrate (e.g. TMB; 3, 3', 5,5'-Tetramethylbenzidine). After adequate color development, a stop solution was added to each well. The absorbance of the HRP reaction product was determined with an ELISA plate reader. Soluble polypeptides that we measured using the above mentioned protocol comprise of: B2M, CHI3L1, Mac-2BP, SAA, TRAIL, sCD62L, sTREM, IL11, IL1RA, IP10, T-TAC and TNFR1.

Measurements of Soluble DETERMINANTS Using Luminex

To determine the concentrations of soluble DETERMINANTS in human plasma samples we also used the xMAP immunoassay (Luminex Corporation, Austin, Tex.) (protocol details are available from the supplier). Briefly, the assay uses five-micron polystyrene beads that have been impregnated with a precise ratio of two fluorescent dyes, creating up to 100 spectrally identifiable beads. The surface of these beads is coated with carboxyl terminals (an estimated one million per bead), which serve as the attachment point for the analyte specific antibody. Using standard immunoassay principles, a sandwich format or competition assay was performed for each target biomarker. This included preparation of standards with predetermined analyte concentrations, six hour incubation of the sample followed by a flow cytometer readout.

Two lasers query the beads: one for its specific ID number; the second for the intensity of the phycoerythrin (PE) signal resulting from the immunoassay. This assay enables the simultaneous measurement of a few dozen analyte specific beads to be measured simultaneously thus enabling biomarker screening.

More specifically, prepare standards and antibody conjugated beads and samples within one hour of performing the assay. Reconstitute the protein standard in 0.5 mL of Assay Diluent when working with serum/plasma samples, or 50% Assay Diluent+50% of serum matrix for other types of samples. Avoid mixing. Determine the number of wells required for the assay. Standard curves and samples may be run singly or in replicates, as desired. Pre-wet the 96 micro-titer plate. Pipette 0.2 mL of Working wash solution into designated wells. Wait 15 to 30 seconds and aspirate the wash solution from the wells using the vacuum manifold. Immediately before dispensing, vortex the beads for 30 seconds followed by sonication in a sonicating water bath for 30 seconds. Pipette 25 uL of the desired beads into each well. Once dispensed the beads should be kept protected from light using an aluminum foil-wrapped plate cover. Aspirate the liquid by gentle vacuum using the vacuum manifold. Prepare a 1× capture bead solution from the additional 10× capture bead concentrate(s) to be multiplexed. Pipette 25 uL of the additional 1× bead solution into each well. Add 0.2 mL Working wash solution into the wells. Allow the beads to soak for 15 to 30 seconds, then remove the Working wash solution from the wells by aspiration with the vacuum manifold. Repeat this washing step. Blot the bottom of the filter plate on clean paper towels to remove residual liquid. Pipette 50 uL incubation buffer into each well.

To the wells designated for the standard curve, pipette 100 uL of appropriate standard dilution.

To the wells designated for the sample measurement, pipette 50 uL assay diluent followed by 50 uL sample. Incubate the plate for 2 hours at room temperature on an orbital shaker. Shaking should be sufficient to keep beads suspended during the incubation (500-600 rpm). Ten to fifteen minutes prior to the end of this incubation, prepare the biotinylated detector antibody. After the 2 hour capture bead incubation, remove the liquid from the wells by aspiration with the vacuum manifold. Add 0.2 mL Working wash solution to the wells. Allow the beads to soak for 15 to 20 seconds, then aspirate with the vacuum manifold. Repeat this washing step. Blot the bottom of the filter plate on clean paper towels to remove residual liquid. Add 100 uL of prepared 1× Biotinylated Detector Antibody to each well and incubate the plate for 1 hour at room temperature on an orbital shaker. Shaking should be sufficient to keep beads suspended during incubation (500-600 rpm). Ten to fifteen minutes prior to the end of the detector incubation step, prepare the Streptavidin-RPE. Remove the liquid from the wells by aspiration with the vacuum manifold. Add 0.2 mL Working wash solution to the wells. Allow the beads to soak for 15 to 30 seconds, then aspirate with the vacuum manifold. Repeat this washing step. Blot the bottom of the filter plate with clean paper towels to remove residual liquid. Add 100 uL of the prepared 1× Streptavidin-RPE to each well and incubate the plate for 30 minutes at room temperature on an orbital shaker. Shaking should be sufficient to keep beads suspended during incubation (500-600 rpm). Prepare the Luminex instrument during this incubation step. Remove the liquid from the wells by aspiration with the vacuum manifold. Note that a minimal pressure of 5 inches Hg is required. Wash the beads by adding 0.2 mL working wash solution to the wells, allow the beads to soak for 10 seconds, then aspirate with the vacuum manifold. Repeat this washing step two additional times for a total of 3 washes. Add 100 uL working wash solution to each well. Shake the plate on an orbital shaker (500-600 rpm) for 2-3 minutes to re-suspend the beads. Uncover the plate; insert plate into the XY platform of the Luminex instrument and analyze the samples.

Determine the concentration of the samples from the standard curve using curve fitting software. The four parameter algorithm usually provides the best fit. If the plates cannot be read on the day of the assay, they may be covered and stored in a dark location overnight at 2-8° C. for reading the following day without significant loss of fluorescent intensity. Aspirate working wash solution from stored plated and add 100 uL fresh working wash solution. Place the plates on an orbital shaker for 2-3 minutes prior to analysis. Soluble polypeptides that we measured using the above mentioned protocol comprise of: BCA-1, TRAIL, Eotaxin, IL1a, IP10, MCP and VEGFR2.

Measurements of CRP Soluble DETERMINANT

CRP concentrations were measured using automated immunoassay machines in the chemical laboratories of the hospitals in which the patients were enrolled.

DETERMINANT Normalization

To avoid numerical biases, some multi parametric models (such as SVMs) require that the numerical DETERMINANTS used in the model be similarly scaled. Thus, when performing multi-parametric analysis, we used the following linear normalization: the DETERMINANT levels of each patient were divided by the DETERMINANT mean levels computed over all the population in the study. To avoid numerical errors due to outliers (>mean±3×std), such measurements were truncated and assigned the value mean±3×std.

Handling of Missing Values/Censoring/Discontinuations

Missing DETERMINANT values might arise due to technical issues in the measurement process (e.g. deterioration of an antibody used to measure a specific DETERMINANT). Furthermore, some of the DETERMINANTS, especially the polypeptide DETERMINANTS, could only be measured on a subset of the patients, because the amount clinical sample drawn from any given patient was insufficient in order to measure the entire panel of DETERMINANTS. Consequentially, some subjects may have missing values for some of their DETERMINANT measurements. To address this, the accuracy of each DETERMINANT or multi-DETERMINANT signature is computed only on the patients that do not have any missing value in the respective signature.

DETERMINANT Diagnosis Statistical Analysis

The classification accuracy and statistical significant of individual DETERMINANTS was measured in terms of sensitivity, specificity, PPV, NPV, MCC, AUC and Wilcoxon rank sum P-value or t-test P-value. The diagnostic accuracy of the multi-DETERMINANT signatures was determined using a leave-10%-out cross-validation scheme for training and testing a support vector machine (SVM) with a linear (CJC Burges, 1998). Classification accuracy was measured using the same criteria as in the single DETERMINANT. We also tested the classification accuracy using other multi-parametric models including: (i) an RBF kernel SVM, (ii) an artificial neural network (one hidden layer with three nodes, one output node and tansig transfer functions), (iii) a naïve bayes network and (iv) a k-nearest-neighbor classification algorithm. For most of the tested DETERMINANT combinations the linear SVM yielded roughly the same classification results in terms of AUC and MCC compared the other models. We therefore report herein only the results of the linear SVM.

Example 2: To Facilitate a Diagnostic Solution that is Broadly Applicable we Performed a Clinical Study on a Highly Heterogeneous Cohort of Patients Summary of the Patient Cohorts Used in this Study A total of 655 patients were recruited for this study and 575 patients were eligible for enrollment. Based on the reference standard process described above, patients were assigned to five different diagnosis groups: viral infection (42% of patients), bacterial infection (36% of patients), mixed infection (6% of patients), non-infectious disease (8% of patients), and undetermined (8% of patients) (FIG. 2). In total, 92% of all enrolled patients were assigned a diagnosis, a rate which approaches the literature-documented limit (Clements et al. 2000; Johnstone et al. 2008; Hatipoglu et al. 2011).

The development and testing of the DETERMINANT signature technology was performed in a series of patient cohorts with increased confidence levels, as described above (Creating the reference standard). Of the 575 enrolled patients, 530 had a diagnosis (bacterial, viral, mixed, or non-infectious) assigned by the majority of the expert panel. Of these 530 patients, 376 had these diagnoses assigned unanimously (i.e., a 'consensus' diagnosis). Of the 376 patients, 170 patients had a clear diagnosis determined as described above.

The various cohorts and the number of bacterial, viral, mixed, and non-infectious patients within each cohort are depicted in FIG. 3.

Age and Gender Distribution

Patients of all ages were recruited to the study. The study population (n=575) included more pediatric (≤18 years) than adult (>18 years) patients (60% vs 40%). The age distribution was relatively uniform for patients aged 20-80 years and peaked at ≤4 years of age for pediatric patients (FIG. 4). The observed age distribution for pediatric patients is consistent with that expected and represents the background distribution in the inpatient setting (Craig et al. 2010) (e.g., the emergency department [ED], pediatrics departments, and internal departments).

Patients of both genders were recruited to the study. The patient population was balanced in respect to gender distribution (49% females, 51% males).

Isolated Pathogens

We used a wide panel of microbiological tools in order to maximize pathogen isolation rate. At least one pathogen was isolated in 53% of patients with an acute infectious disease (49% of all 575 enrolled patients). A total of 33 different pathogens were actively detected using multiplex PCR, antigen detection, and serological investigation. Additional 11 pathogens were isolated using standard culture techniques or in-house PCR. Altogether, 44 different pathogens from all major pathogenic subgroups were isolated (FIG. 5A). This rate of pathogen identification is similar to that reported in previously published studies (Cillóniz et al. 2011; Restrepo et al. 2008; Song et al. 2008; Johansson et al. 2010; Shibli et al. 2010) and included pathogens from all major pathogenic subgroups (Gram-negative bacteria, Gram-positive bacteria, atypical bacteria, RNA viruses, and DNA viruses). In nearly 20% of the patients, pathogens from >1 of the aforementioned pathogenic subgroups were detected (FIG. 5A).

The pathogenic strains found in this study are responsible for the vast majority of acute infectious diseases in the Western world and included key pathogens such as Influenza A/B, respiratory syncytial virus (RSV), Parainfluenza, *E. Coli*, Group A *Streptococcus*, etc.

Notably, analysis of the isolated pathogens revealed that none of the pathogens is dominant (FIG. 5B). The absence of influenza A or RSV dominance is attributed to two reasons: year-round sampling (i.e., sampling was not limited to the winter season) and the non-occurrence of influenza and RSV epidemics in Israel during the study timeframe (2010-2012).

Involved Physiologic Systems and Clinical Syndromes

The infectious disease patients (all patients with a final diagnosis excluding those with non-infectious diseases, n=484) presented with infections in a variety of physiologic systems (FIG. 6). The most frequently involved physiologic system was the respiratory system (45%), followed by systemic infections (18%). All infections that did not involve the aforementioned systems and were not gastrointestinal, urinary, cardiovascular, or central nervous system (CNS) infections were categorized as 'Other' (e.g., cellulitis, abscess). The observed distribution of physiologic system involvement represents the natural distribution and is consistent with that reported for large cohorts of patients sampled year-round (CDC.gov 2012).

The patients in our study (all enrolled patients, n=575) presented with a variety of clinical syndromes (FIG. 7) that reflects the expected clinical heterogeneity in a cohort of pediatric and adult patients collected year-round. The most frequent clinical syndrome was LRTI (25%) including mainly pneumonia, bronchitis, bronchiolitis, chronic obstructive pulmonary disease (COPD) exacerbation, and non-specific LRTI. The second most frequent clinical syndrome was URTI (20%) including mainly acute tonsillitis, acute pharyngitis, non-specific URTI, acute sinusitis, and acute otitis media. The third most frequent syndrome was systemic infection (17%) including mainly fever without a source and occult bacteremia cases. Systemic infections were primarily detected in children <3 years of age but were also detected in a few adult patients.

Systemic infections constitute a real clinical challenge as balancing between patient risk and the costs of testing/treatment is unclear. The next most frequent syndromes were gastroenteritis (11%), UTI (8%), and cellulitis (4%). CNS infections (2%) included septic and aseptic meningitis. All other clinical syndromes (3%) were classified as 'Other' and included less common infections (e.g., peritonsillar abscess, otitis externa, epididymitis, etc.). The observed pattern of clinical syndrome distribution represents most of the frequent and clinically relevant syndromes and is consistent with previously published large studies (Craig et al. 2010).

Core Body Temperature

Core body temperature is an important parameter in evaluating infectious disease severity. We examined the distribution of maximal body temperatures in all enrolled patients (n=575) using the highest measured body temperature (per-os or per-rectum). The distribution of the maximal body temperatures was relatively uniform between 38° C. and 40° C. with a peak of at 39° C. (FIG. 8). Body temperature ≤37.5° C. was reported for 8% of patients (the subgroup of patients with non-infectious diseases). Body temperature ≥40.5° C. was rare (<3% of patients).

Altogether, the observed distribution represents the normal range of temperatures in the clinical setting (Craig et al. 2010).

Time from Symptoms Onset

'Time from symptoms' was defined as the duration (days) from the appearance of the first presenting symptom (the first presenting symptom could be fever but could also be another symptom such as nausea or headache preceding the fever). The distribution of 'time from symptoms' in our cohort (all enrolled patients, n=575) peaked at 2-4 days after the initiation of symptoms (40% of patients) with substantial proportions of patients turning to medical assistance either sooner or later (FIG. 9). The observed distribution of time from initiation of symptoms represents a typical pattern in the clinical setting.

Comorbidities and Chronic Drug Regimens

Comorbidities and chronic drug regimens may, theoretically, affect a diagnostic test. Our patient population (all enrolled patients, n=575) included patients (70%) that had no comorbidities and were not treated with chronic medications and patients (30%) that had ≥1 chronic disease and were treated with chronic medications. The most frequent chronic diseases in our patient population were hypertension, lipid abnormalities, lung diseases (e.g., COPD, asthma, etc.) diabetes mellitus (mostly type 2), and ischemic heart disease, mirroring the most common chronic diseases in the Western world (FIG. 10A). All patients with chronic diseases were chronically treated with medications. The distribution of chronic drugs used by our patient population strongly correlated with the range of reported chronic diseases (e.g., 42% of the patients with comorbidities had lipid abnormalities and lipid lowering agents were the most frequently used drugs). Other frequently used drugs included aspirin, blood glucose control drugs, and beta blockers (FIG. 10B).

Patient Recruitment Sites

The recruitment sites in our study included ED (pediatric, adults) and other hospital departments (pediatric, adults). The pediatric ED was the most common recruitment site (43%) and the other sites were comparable (17-22%) reflecting a relatively balanced recruitment process. The ratio between ED patients and hospitalized patients was ~1:1 for adults and ~2:1 for children (FIG. 11).

Comparing Baseline Characteristics of the Bacterial and Viral Groups

We compared baseline characteristics of the bacterial and viral groups by age (children vs adults; Table 4). In both children and adults, lab parameters such as WBC levels, neutrophils (%), lymphocytes (%) and ANC, differed significantly (P<0.001) between bacterial and viral patients, in accordance with the well-established differences between these two infection types (Christensen, Bradley, and Rothstein 1981; Peltola, Mertsola, and Ruuskanen 2006). In children, significant differences were also observed for age (P<0.001) and maximal body temperature (P<0.007). These findings are consistent with the increased prevalence of viral infections in younger children and with the higher temperature often present in bacterial vs. viral infections (Pickering and DuPont 1986). The other variables (e.g., respiratory rate, urea, and heart rate) did not demonstrate a statistically significant difference between the bacterial and viral groups indicating a similar clinical appearance in both groups.

Characteristics of Excluded Patients

Of the 655 patients recruited for the study, 80 patients (12%) were excluded. The most frequent reason for exclusion was having a fever below the study threshold of 37.5° C. (n=40; 50% of all excluded patients), followed by time from symptom initiation of >10 days (n=15, 19% of all excluded patients) and having a recent (in the preceding 14 days) infectious disease (n=13, 16% of all excluded patients). Other reasons for exclusion included having a malignancy (hematological [9% of all excluded patients], solid [5% of all excluded patients]) and being immunocompromised (e.g., due to treatment with an immunosuppressive drug; 1% of all excluded patients).

Example 3: Measurements of DETERMINANT Levels were Highly Reproducible Across Day-to-Day Technical Repeats and Different Measurement Platforms Assay Performance and QA Calibration curves were linear within the physiological concentration range Standard preparations provided by the assay manufacturer served as a reference standard for the calibration curves. Representative samples of calibration curves for TRAIL, Mac-2BP and SAA are presented in FIG. 12. We found that all the optimal cutoff values between bacterial and viral infections were in the linear range of the scale and that all standard curves exhibited a dynamic range of ~2-2.5 log scale.

Intra-Assay Variability

We tested the intra-assay variability on eight independent serum samples of patients within the same ELISA plate (FIG. 13). We found intra-assay CV % of 4.4%, 7.5% and 4.4% for TRAIL, Mac-2-BP, and SAA respectively. These values are within the range of normal intra-assay variation compared with other manual ELISA assays. Using automated devices or improving assay format may lower the intra-assay variability and increase biomarker accuracy.

Inter-Assay Variability

We tested the inter-assay variability for TRAIL, Mac-2BP, and SAA in 20, 8 and 8 independent samples, respectively. We observed variations of 6.6%, 8.1%, and 12.3%, respectively (FIG. 14).

Analyte Levels were Similar in Serum and Plasma

We tested the levels of TRAIL, Mac-2-BP, and SAA in a cohort of paired serum and plasma samples of 32, 35 and 46 individuals, respectively. For all three analytes we observed a strong correlation ($r2$ between 0.88 and 0.98) and comparable concentrations (slopes between 0.92 and 1.05) between plasma and serum concentrations (FIG. 15).

Analytes are Stable Under Conditions Typical for the Clinical Setting

The utility of a biomarker depends on its stability in real-life clinical settings (e.g., its decay rate when the sample is stored at room temperature prior to analyte measurement). To address this, we examined the stability of TRAIL, Mac-2-BP, and SAA in serum samples from four, three, and five independent individuals during 21 hours at 4° C. (refrigeration) and 25° C. (room temperature). Aliquots of 100 µL from each plasma sample were pipetted into 0.2 mL tubes and kept at 4° C. or 25° C. from 0 to 21 hours. Subsequently, we measured the levels of the analytes (different time-points of the same analytes were measured using the same plate and reagents). The mean levels of all three analytes were roughly stable over the first 21 hours at 4° C. The analyte half-lives at 25° C. were 24±5, >48, and >48 hours for TRAIL, Mac-2-BP, and SAA, respectively (FIG. 16). These half-lives are comparable to those observed for other biomarkers used in the clinical emergency setting (Rehak and Chiang 1988; Boyanton and Blick 2002; Guder et al. 2007). Of note, in the real clinical setting, if the samples are stored at room temperature, the concentrations of TRAIL should be measured within about 24 after the sample is obtained. Alternatively, the sample should be stored at lower than 12° C., and then TRAIL can be measured more than 24 after obtaining the sample.

Measurements are Reproducible Across Different Platforms

The levels of TRAIL in 80 independent samples were tested using two different platforms (ELISA and Luminex) and the results were correlated and comparable ($r2=0.89$, $P<10-5$; FIG. 17). Importantly, the ELISA and Luminex assays differ in some basic aspects. For example, the Luminex assay is based on direct fluorescence detection, whereas ELISA is based on colorimetric detection. Furthermore, the set of capture and detection antibodies were different between the assays. Despite these and other differences, the results were comparable demonstrating adoptability of the DETERMINANT-signature approach to other platforms.

Example 4: Most Polypeptide-DETERMINANTS, Even Those with an Immunological Role, were not Differentially Expressed in Patients with Different Types of Infections To screen for potential DETERMINANTS that might be differentially expressed in different types of infections we performed biochemical measurements of over 500 polypeptides, in samples taken from the patients enrolled in the clinical study. We found that most DETERMINANTS were not differentially expressed in subjects with different types of infections. Moreover, we found that even polypeptide-DETERMINATS that have a well-established mechanistic role in the immune defense against infections or participate in inflammatory processes often showed poor diagnostic accuracy for identifying the source of infection. This point is illustrated in FIG. 18 and Table 1, which show examples of polypeptide-DETERMINANTS with an established immunological or inflammatory role that were not differentially expressed between patients with viral or bacterial infections. For example, different types of INF-alpha (INF-a) have a well-established role in antiviral cellular processes. They are mainly produced by leukocytes and may be potentiated by febrile temperatures. We measured the plasma levels of INF-a in 22 bacterial and 27 viral patients and found no differential response (Wilcoxon rank sum P=0.8) (FIG. 18). The protein INF-gamma (ING-g) is another cytokine that is critical to the innate and adaptive immunity against viral and bacterial infections, which showed no differential response (Wilcoxon rank sum P=0.9). TNF-alpha (TNF-α) is a cytokine produced mainly by activated macrophages. It is a major extrinsic mediator of apoptosis and was found to play a role in viral infections (Gong et al. 1991). Following these observations hypothesize that TNF-α may be used to diagnose the source of infection. We measured TNF-α levels in patients with bacterial and viral infected patients and found poor differential response (Wilcoxon rank sum P=0.9). Yet, another example is CD95, a Fas ligand receptor that participates in the process of death-inducing-signaling-complex, during apoptosis. This receptor was found to be involved in the host response to different infections (Grassmé et al. 2000). We find that the levels of CD95 on lymphocytes and monocytes were not differentially expressed between bacterial and viral patients in a statistically significant manner (P=0.1, and P=0.9, respectively). We also measured the levels of many other interleukins, cytokines and their receptors, chemokines and their receptors, HLAs and other determinants that participate in the immune response to infection and found that in most cases the levels of the determinants was not differentially expressed between viral and bacterial infections (for more examples see FIG. 18). Thus, an immunological or inflammatory role of a polypeptide-DETERMINAT does not necessarily imply diagnostic utility.

Example 5: In-Vitro Differential Response to Different Types of Infections does not Necessarily Indicate a Corresponding In-Vivo Differential Response We examined whether biomarkers that are differentially expressed during in-vitro infections are also likely to be accurate diagnostic markers in-vivo. We found that in many cases, an in-vitro differential expression did not necessarily translate into the corresponding in-vivo differential expression. The following section presents examples of this comparison.

Previous in-vitro studies indicated that the mRNA and protein levels of arginase 1 (ARG1) are up regulated in viral infections and remain low in bacterial infections. Briefly, the in-vitro transfection of human hepatoblastoma HepG2 cells and human hepatoma Huh-7 cells with an infectious cDNA clone of Hepatitis C virus (HCV) resulted in about threefold elevation of ARG1 mRNA and protein levels (P<0.01)(Cao et al. 2009). In contrast, ARG1 mRNA expression levels of mouse macrophages, cocultured with *H. pylori* SS1, were not elevated (Gobert et al. 2002).

Taken together, these two in-vitro studies prompted us to examine whether ARG1 may serve as a reliable in-vivo diagnostic marker that is up-regulated in viral infections while maintaining basal levels in bacterial infections. We measured the ARG1 protein levels of 41 patients with bacterial infections and compared it to the levels in 46 patients with viral infections. Measurements were performed on the granulocytes, lymphocytes and total leukocytes. In all cases, we did not observe an increase of ARG1 levels in viral compared to bacterial infected patients (FIG. 19). Specifically, ARG1 levels on granulocytes were not differentially expressed (Wilcoxon rank sum P=0.3), whereas lymphocytes and total leukocytes showed a slight increase in bacterial compared to viral infected patients (Wilcoxon rank sum P=0.09, and 0.003 respectively), an opposite behavior to the one reported in the in-vitro studies.

Another example is interleukin-8 (IL-8), whose levels increased in cell culture medium of human gastric SGC-7901 adenocarcinoma cells after treatment with *Helicobacter pylori*Sydney strain 1 lipopolysaccharide (Zhou et al. 2008). In contrast, in-vivo IL-8 serum levels of *H. pylori*-infected patients were found similar to IL-8 serum levels of *H. pylori*-negative control group (Bayraktaroğlu et al. 2004).

Thus, differential expression in different in-vitro infections does not necessarily imply differential expression in-vivo.

Example 6: DETERMINANTS that Differentiate Between Different Types of Infections We measured over 570 polypeptides and found that most (over 95%) did not differentiate between different types of infections. Diverging from this norm were unique subsets of polypeptides that showed consistent and robust differential response across a wide range of patient characteristics and pathogens (for details see patient characteristics section). The following sections describe polypeptides and their combinations, which were useful for diagnosing different sources of infection.

DETERMINANTS that Differentiate Between Bacterial Versus Viral Infected Subjects We identified a subset of DETERMINANTS that were differentially expressed in subjects with bacterial versus viral infections in a statistically significant manner (Wilcoxon ranksum P<0.001). DETERMINANT names and classification accuracies are listed in Table 2A. The distributions and individual subject measurements for each of the DETERMINANTS are depicted in FIG. 20 (dots corresponds to DETERMINANTS measurement in individual subjects and bars indicate group medians). Each subplot corresponds to a different DETERMINANT. The abbreviations mono, lymp, gran, mean and total are used to denote polypeptide-DETERMINANT measurements on monocytes, lymphocytes, granulocytes as well as mean and total leukocytes measurements respectively. The abbreviations intra and membrane are used to denote proteins that were measured in the intra cellular and membrane fraction respectively.

Additionally, we found that using non-specific mouse IgG1 and IgG3 isotype controls as a primary antibody (coupled with the appropriate fluorescent marker) consistently showed an increased signal in the lymphocytes and monocytes of viral patients compared to bacterial patients (Table 2A). A similar differential response was observed when measuring the signal of PE conjugated goat IgG (Table 2A). Although the differential signal was weak in terms of absolute levels, compared to the signal obtained from specific bindings, it was statistically significant (Wilcoxon ranksum P<0.001). This phenomenon may be due to non-specific binding of IgG to Fc gamma receptors, or other receptors that bind Ig like domains, whose levels may be elevated on host cells that respond to a viral infection.

DETERMINANTS that Differentiate Between Mixed Versus Viral Infected Subjects

Differentiating between a mixed infection (i.e. bacterial and viral co-infection) and a pure viral infection is important for deciding the appropriate treatment. To address this we identified a set of DETERMINANTS that were differentially expressed in subjects with mixed infections versus viral infections in a statistically significant manner (Wilcoxon ranksum P<0.001). DETERMINANT names and classification accuracies are listed in Table 2B. The distributions and individual subject measurements for each of the DETERMINANTS are depicted in FIG. 21.

DETERMINANTS that Differentiate Between Mixed Versus Bacterial Infected Subjects.

We identified a set of DETERMINANTS that were differentially expressed in subjects with mixed infections versus bacterial infections in a statistically significant manner (Wilcoxon ranksum P<0.001). DETERMINANT names and classification accuracies are listed in Table 2C.

DETERMINANTS that Differentiate Between Bacterial or Mixed Versus Viral Infected Subjects.

We identified a set of DETERMINANTS that were differentially expressed in subjects with bacterial or mixed infections versus viral infections in a statistically significant manner (Wilcoxon ranksum P<0.001). DETERMINANT names and classification accuracies are listed in Tables 2D, 2E and 2F.

Figures 1, 21B:
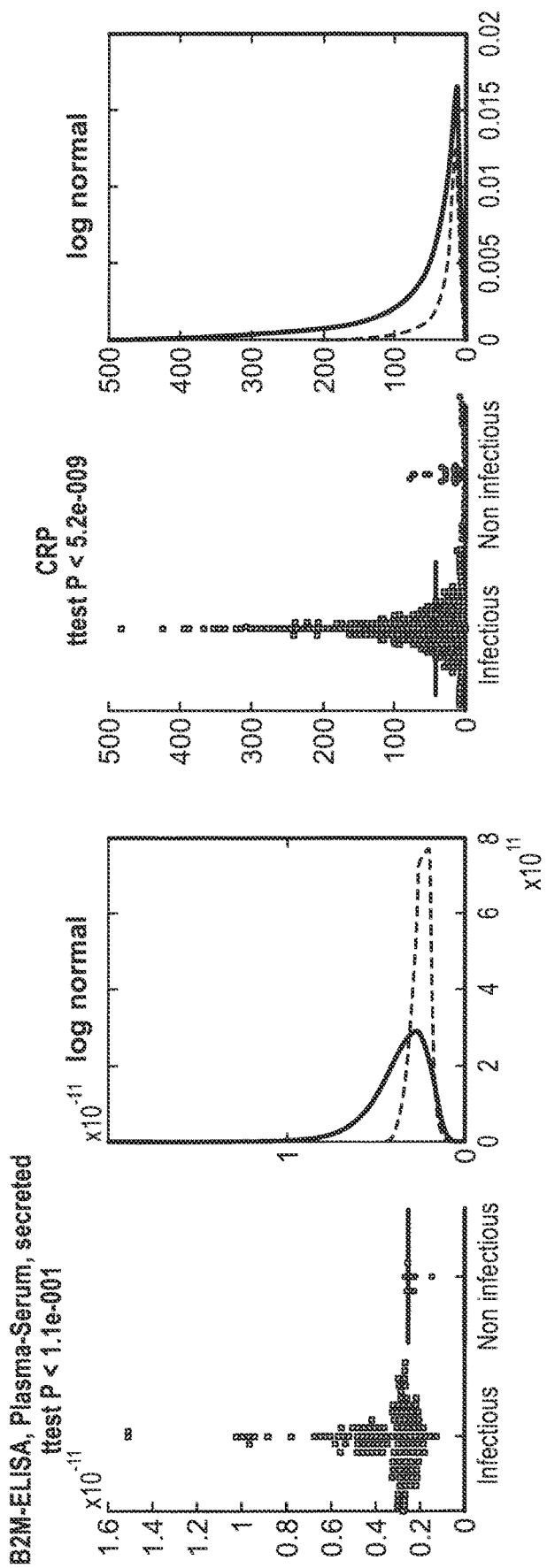
Figures 2, 21B:
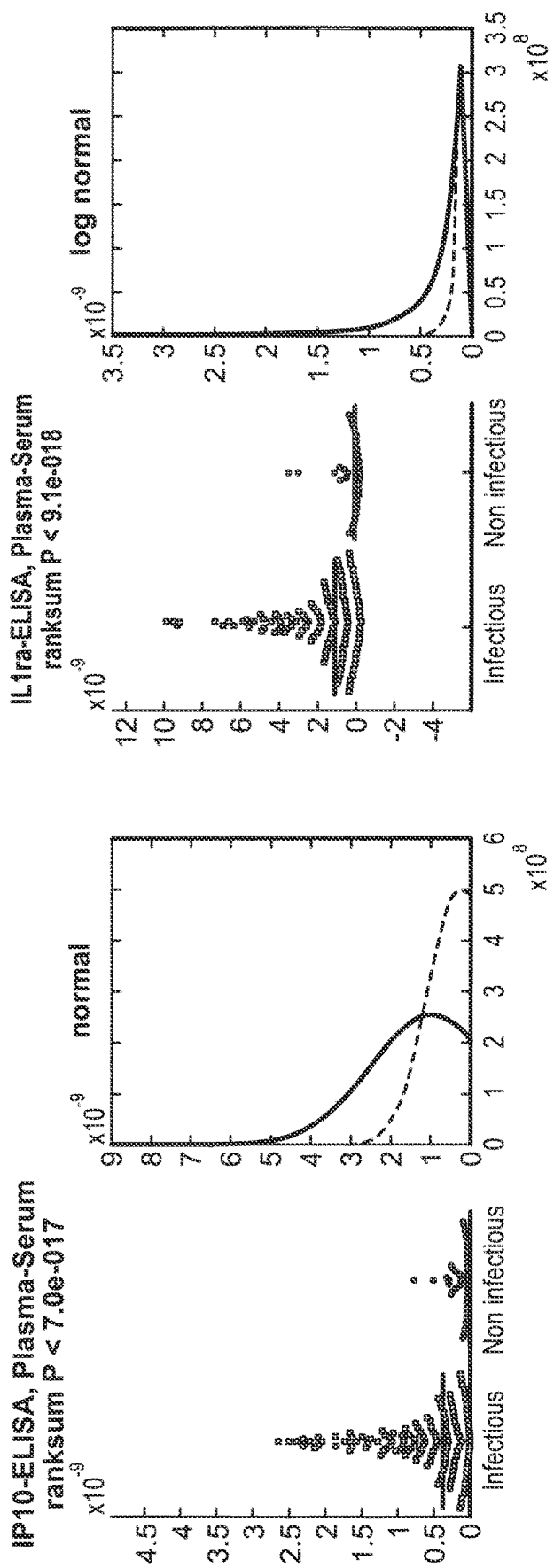
Figures 3, 21B:
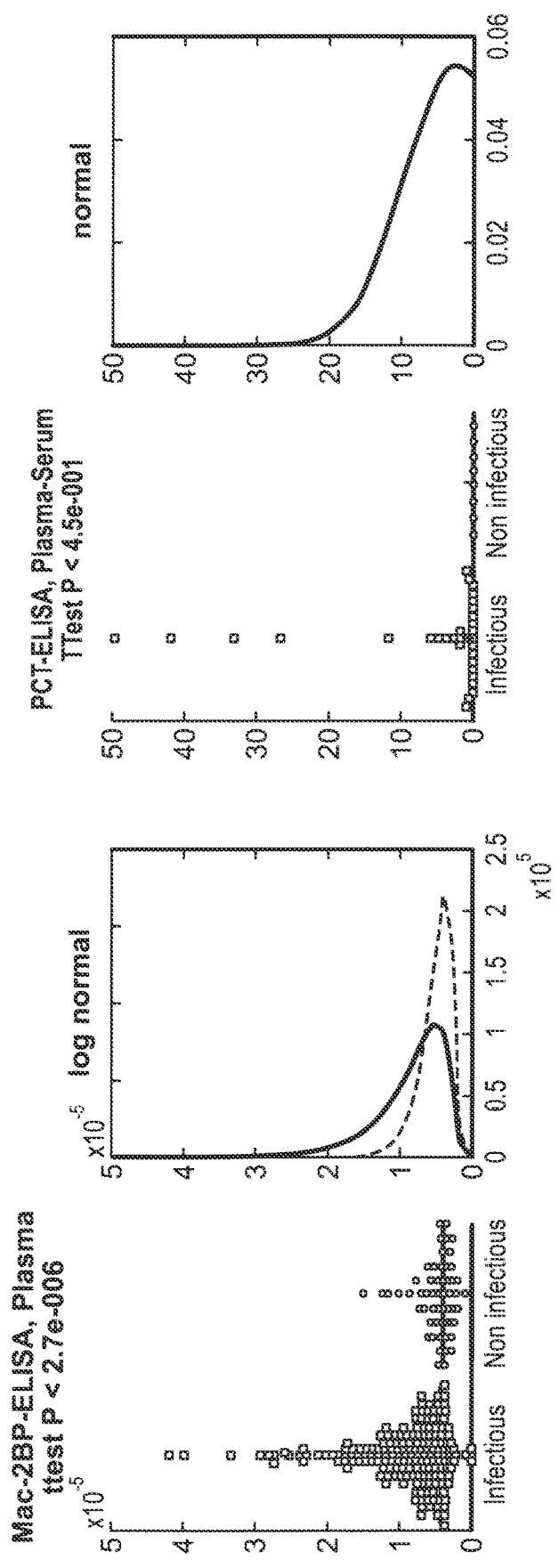
Figures 4, 21B:
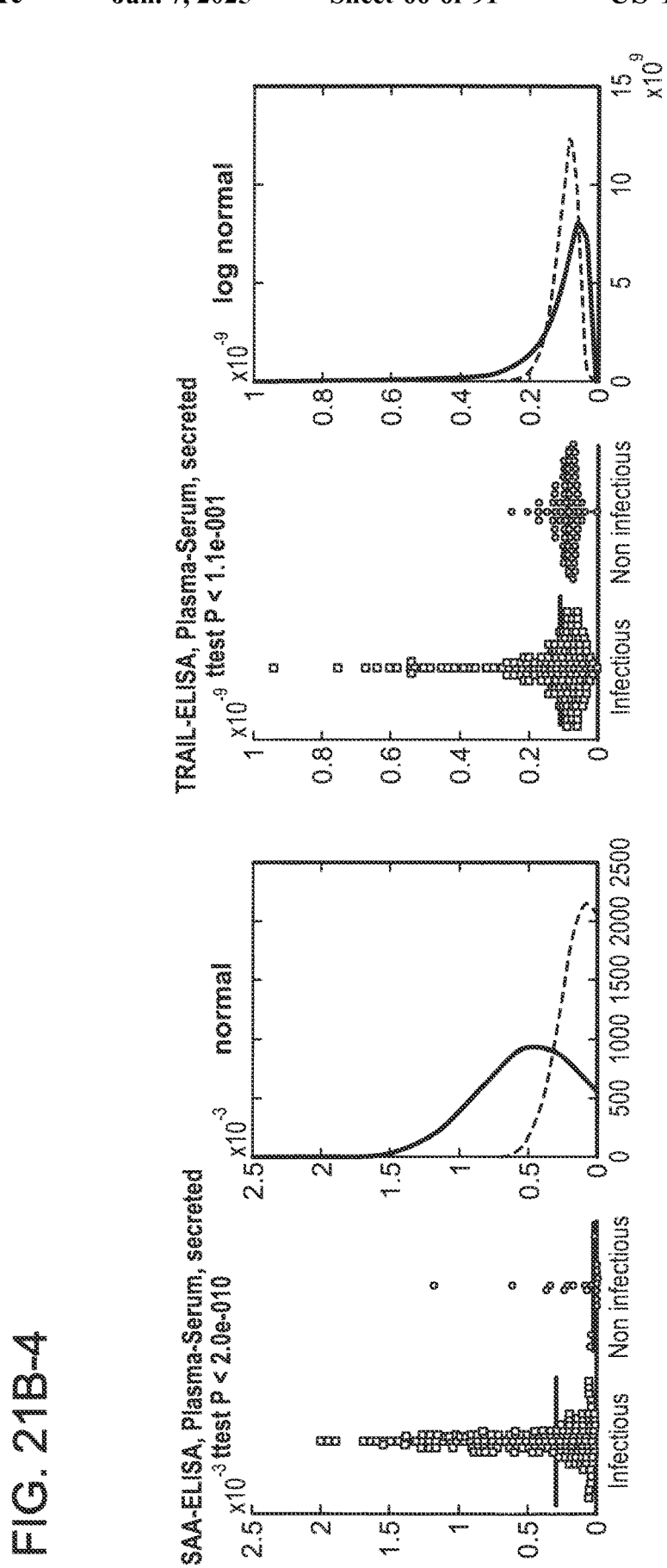

DETERMINANTS that Differentiate Between Subjects with an Infectious Versus a Non-Infectious Disease We identified a set of DETERMINANTS that were differentially expressed in subjects with an infectious disease versus subjects with a non-infections disease in a statistically significant manner (Wilcoxon ranksum P<0.001). DETERMINANT names and classification accuracy are listed in Table 2G. The distributions and individual subject measurements for some of the DETERMINANTS are depicted in FIG. 21B. Note that the diagnostic accuracy reported in Table 2G was obtained despite the presence of non-pathogenic micro-organisms in the group of patients with a non-infectious disease (for details see FIG. 22). The presence of such non-pathogenic micro-organisms poses a major challenge to diagnostic methods that seek to identify the pathogen directly, often leading to "false positives". This challenge is overcome by some methods of the present invention. To further establish the results some DETERMINANTS were measured on additional non-infectious patients (up to 83 patients) as depicted in Table 2G.

Figures 1, 21C:
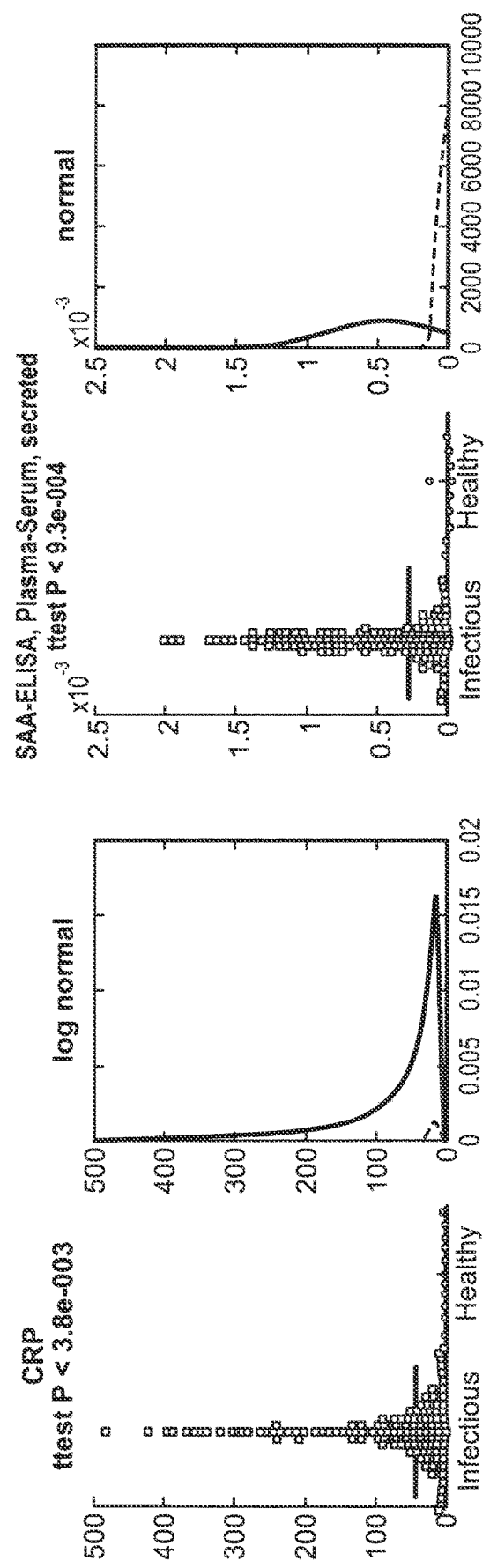
Figures 2, 21C:
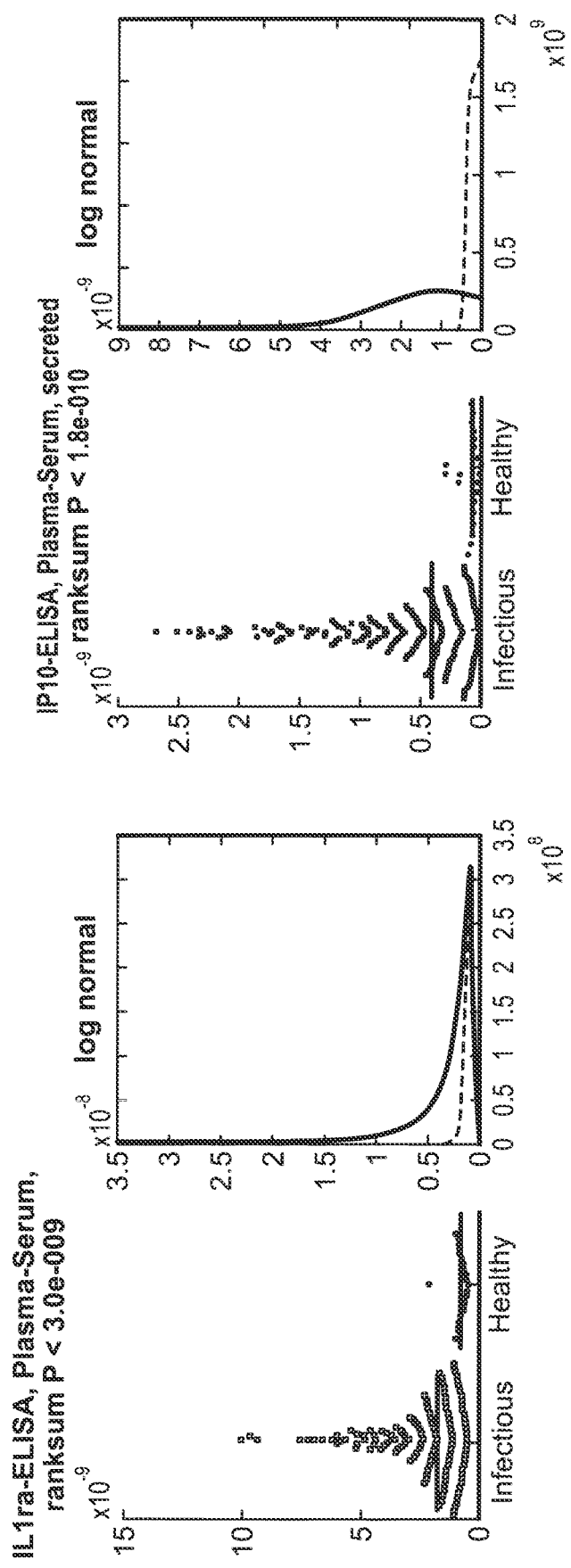
Figures 3, 21C:
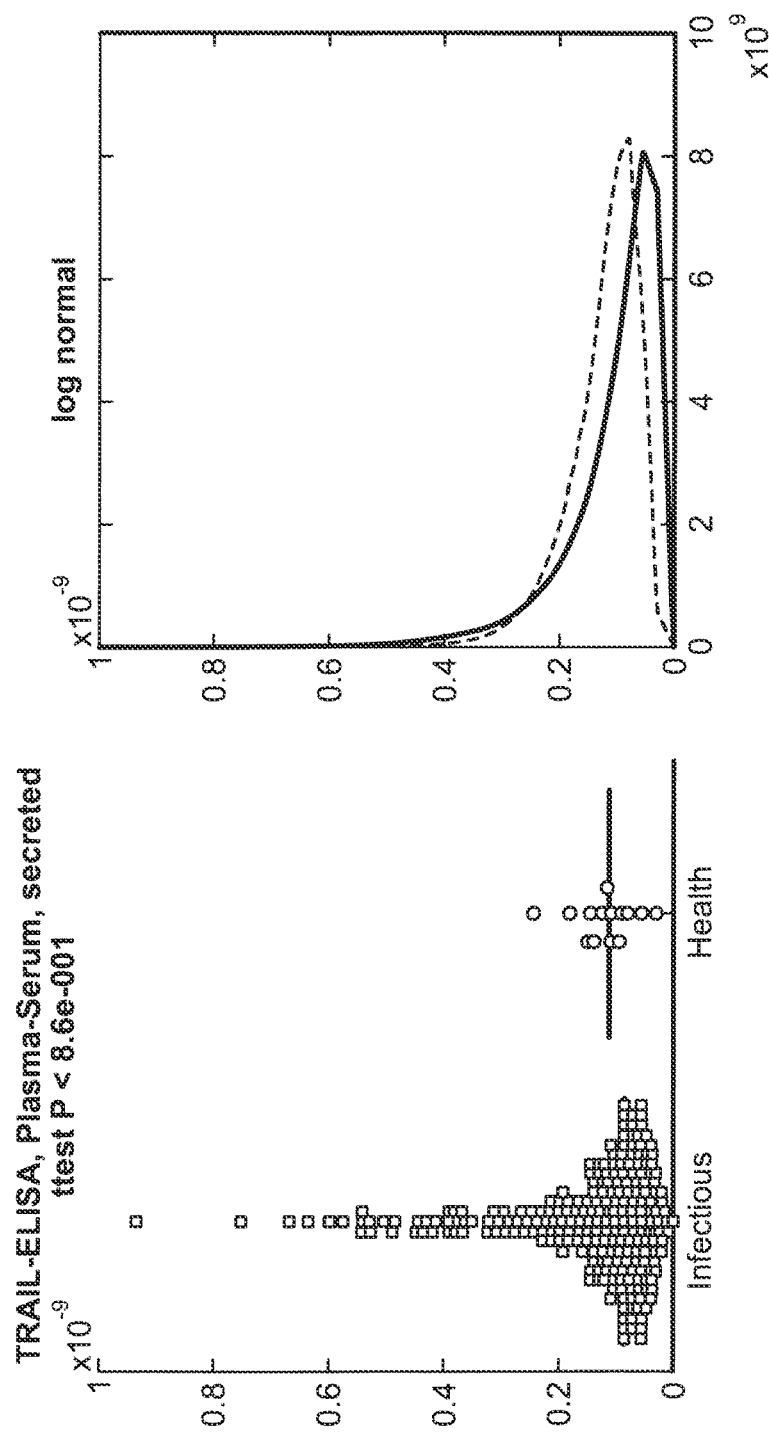

DETERMINANTS that Differentiate Between Subjects with an Infectious Disease Versus Healthy Subjects We identified a set of DETERMINANTS that were differentially expressed in subjects with an infectious disease versus healthy subjects in a statistically significant manner (Wilcoxon ranksum P<0.001). DETERMINANT names and classification accuracies are listed in Table 2H. The distributions and individual subject measurements for some of the DETERMINANTS are depicted in FIG. 21C. Note that the diagnostic accuracy reported in Table 2H was obtained despite the presence of non-pathogenic micro-organisms in the healthy subjects (see FIG. 22). The presence of such non-pathogenic micro-organisms in healthy subjects poses a major challenge to diagnostic methods that seek to identify the pathogen directly, often leading to "false positives". This challenge is overcome by methods of the present invention.

Example 7: DETERMINANT Signatures can Improve the Diagnostic Accuracy of Different Infections Types DETERMINANT Signatures for Differentiating Between Bacterial Versus Viral Infected Subjects We scanned the space of DETERMINANT combinations and identified pairs and triplets of DETERMINANTS whose combined signature (using multi-parametric models) differentiated between subjects with bacterial versus viral infections in a way that significantly improved over the classification accuracy of the corresponding individual DETERMINANTS.

For example the diagnostic accuracy of TRAIL, Mac-2BP and CRP are 0.86, 0.78 and 0.85 AUC respectively. The combination (TRAIL, CRP), (Mac-2B, CRP) and (TRAIL, Mac-2BP, CRP) show increased diagnostic accuracy of 0.945, 0.939 and 0.954 AUC, respectively. Further examples of the combined classification accuracies of DETERMINANT pairs, triplets and quadruplets are depicted in Table 3A, B, G and FIG. 23.

DETERMINANT Signatures for Differentiating Between Mixed Versus Viral Infected Subjects We identified pairs of DETERMINANTS whose combined signature differentiated between subjects with mixed versus viral infections. The combined classification accuracies of DETERMINANT pairs, triplets and quadruplets are depicted in Table 3C, D, G and FIG. 24.

DETERMINANT Signatures for Differentiating Between Subjects with an Infectious Disease Versus Subjects with a Non-Infectious Disease We identified pairs of DETERMINANTS whose combined signature differentiated between subjects with an infectious verses a non-infectious disease. The combined classification accuracies of DETERMINANT pairs and triplets are depicted in Table 3E,F.

Example 8: Performance Analysis: Multi-DETERMINAT Signatures Accurately Diagnoses Different Sources of Infection DETERMINANT Signatures that Include Measurements of CRP and TRAIL are Highly Accurate for Differentiating Between Patients with Different Types of Infections We find that DETERMINANT signatures that include TRAIL and CRP generate particularly high levels of accuracy. By way of example and not limitation, some the following sections present results we obtained for the multi-DETERMNINANT signature that combines the measurements of serum or plasma levels of TRAIL, CRP and Mac-2BP, termed "TCM-signature". Examples of other multi-DETERMNINANT signatures that produce accurate diagnosis include without limitation (TRAIL and CRP), (TRAIL, CRP and Age), (TRAIL, CRP and SAA), (TRAIL, CRP, SAA and IL1RA) and (TRAIL, CRP, SAA and IP10). By way of example, we assessed the diagnostic accuracy of TCM-signature in a series of analyses using the aforementioned patient cohorts, starting with the cohort for which the confidence of the reference standard was the greatest. The cohort used in the first analysis included patients whose diagnosis (bacterial, viral) was clear (i.e., the 'Clear [bacterial, viral]' cohort). This cohort included 170 patients. The cohorts used in the second and third analyses included patients who were diagnosed as either bacterial or viral patients unanimously (the 'Consensus [bacterial, viral]' cohort; n=343), or by majority (the 'Majority [bacterial, viral]' cohort; n=450) of the expert panel. The fourth analysis evaluated the ability of TCM-signature to differentiate viral from mixed infections in a cohort of patients whose diagnosis (either viral or mixed) was assigned by the majority of our expert panel (the 'Majority [viral, mixed]' cohort; n=276). The last analyses in this series evaluated whether the TCM-signature technology could perform an accurate diagnosis even after adding back the patients who were initially excluded from the study but for whom a viral or bacterial diagnosis was made by the expert panel (either unanimously or by majority).

The cohorts used for these analyses included 368 patients (unanimously diagnosed by the expert panel) and 504 patients (majority diagnosis).

Accuracy of Distinguishing Between Bacterial Vs Viral Infections in Patients Whose Diagnosis was Clear We began by examining the accuracy of TCM-signature in bacterial and viral patients with a clear diagnosis (the 'Clear [bacterial, viral]' cohort; for details see previous sections). Briefly, patients were assigned a bacterial diagnosis if they were diagnosed unanimously by our expert panel and had bacteremia (with positive blood culture), bacterial meningitis, pyelonephritis, UTI, septic shock, cellulitis, or peritonsillar abscess. Patients were assigned a viral diagnosis if they were diagnosed unanimously by our expert panel and had a positive microbiological test for an obligatory virus. The cohort for this analysis included 170 patients (57 bacterial and 113 viral).

We tested the accuracy of the TCM-signature using a leave-10%-out cross-validation scheme and found a high diagnostic accuracy (AUC of 0.96). Details of different diagnostic measures of accuracy and their 95% CIs are depicted in FIG. 25 and Table 5.

The accuracy of the TCM-signature was also evaluated using a train set consisting of ⅔ of the patients and an independent test set consisting of the remaining ⅓ of the patients. This evaluation yielded similar results to those obtained using the cross validation scheme.

Accuracy of Distinguishing Between Bacterial Vs Viral Infections in Patients Whose Diagnosis was Determined by a Consensus of Experts Next, we examined the accuracy of the TCM-signature in a cohort of 343 patients who were unanimously diagnosed as bacterial (153 patients) or viral (190 patients) by our expert panel (the 'Consensus [bacterial, viral]' cohort). A leave-10%-out cross-validation scheme yielded a very accurate diagnosis with an AUC of 0.97. Additional measures of diagnostic accuracy and their 95% CIs are depicted in FIG. 26 and Table 6. Assessment of the performance of the TCM-signature using a train set (⅔ of the patients) and an independent test set (⅓ of the patients), yielded similar results.

Since the pathogen repertoire found in children and adults often differs, we stratified the patients by age and repeated the analysis. We found that the TCM-signature performance remained stable across different age groups (FIG. 26).

Accuracy of Distinguishing Between Bacterial Vs Viral Infections in Patients Whose Diagnosis was Determined by Majority of the Expert Panel Next, we examined the accuracy of the TCM-signature in a cohort of patients who were diagnosed as bacterial or viral by the majority of our expert panel (the 'Majority [bacterial, viral]' cohort). The cohort consisted of 450 patients (208 bacterial, 242 viral). A leave-10%-out cross-validation scheme yielded a diagnosis with an AUC of 0.95. Additional measures of diagnostic accuracy and their 95% CIs are depicted in FIG. 27 and Table 7. Assessment of the performance of the TCM-signature using a train set (⅔ of patients) and an independent test set (⅓ of patients), yielded similar results. Age-based stratification analysis also produced comparable results (FIG. 27 and Table 7).

The slight decrease in performance in this cohort compared with the 'Consensus (bacterial, viral)' cohort (AUC of 0.95 vs 0.97) may be partially attributed to the higher confidence in the diagnosis of patients in the latter cohort. Thus, the accuracy measures reported for the 'Majority (bacterial, viral)' cohort probably represents a lower bound on the true accuracy of the TCM-signature. Consequently, to generate a conservative estimate of the TCM-signature performance, we report on the 'Majority' cohorts from here onward, unless otherwise mentioned.

Accuracy of Distinguishing Between Mixed Co-Infections Vs Pure Viral Infections

A total of 34 patients (~6% of all patients with an infectious disease) were diagnosed by the majority of experts in our panel as having a mixed co-infection (i.e., a bacterial infection with a viral co-infection in the background). Clinically, it is important to distinguish between mixed co-infections and pure viral infections, as only the former should be treated with antibiotics. Correct diagnosis of mixed co-infection is challenging, because the dual response of the host to the bacterial and viral infections may alter the immune-signature.

We tested the ability of the TCM-signature to distinguish between mixed co-infections and pure viral infections using a leave-10%-out cross-validation scheme in a cohort of patients whose diagnosis was determined as viral or mixed by the majority of experts in our panel (the 'Majority [viral, mixed]' cohort). The diagnostic accuracy in terms of AUC was 0.97, 0.93, and 0.95 in children, adults, and all ages, respectively, demonstrating the ability of the TCM-signature to successfully distinguish between these two infection types (FIG. 28, Table 8).

Diagnostic Accuracy Remains Robust when Testing Cohorts that Include Patients that were Initially Excluded from the Study The TCM-signature was originally designed to diagnose patients with acute bacterial/viral infections that adhere to a pre-defined list of inclusion/exclusion criteria.

We tested the ability of the TCM-signature to diagnose the excluded patients (e.g., patients with fever below 37.5° C.) by adding the excluded patients (for whom a diagnosis was determined unanimously or by majority of our expert panel) to the 'Consensus (bacterial, viral)' cohort and the 'Majority (bacterial, viral)' cohort, respectively and comparing the diagnostic accuracy before and after the addition, using the leave-10%-out cross-validation scheme (Table 9 and FIG. 29). The accuracy in the 'Consensus (bacterial, viral)' cohort with (n=368) and without (n=343) the excluded patients remained the same (AUC of 0.97 in both cases). The accuracy in the 'Majority (bacterial, viral)' cohort was also similar with (n=450) and without (n=504) the excluded patients (AUC of 0.95 vs 0.94). Thus, the TCM-signature performance remained robust even after adding the excluded patients to the analysis.

By Excluding Patients with Marginal DETERMINANT-Signatures the Level of Diagnostic Accuracy can be Increased By excluding patients with marginal DETERMINANT-signatures (i.e. DETERMINANT-signatures that yield intermediate scores, such as scores that are neither characteristic of viral nor bacterial behavior), one can further improve the levels of diagnostic accuracy (for example see Table 14-15 and FIGS. 39-40).

Example 9. The Diagnostics Accuracy of DETERMINANT Signatures Remains Robust Across Different Patient Subgroups We asked whether the diagnostic accuracy of the DETERMINANT signatures remains robust across different patient subgroups and clinical settings. To this end, we stratified the patients according to a wide range of patient characteristics including time from symptom onset, the specific clinical syndrome, maximal temperature, pathogen subfamily, comorbidities, and treatment with drugs for chronic diseases, and found that the diagnostic accuracy remained robust. By way of example and not limitation, the following section that the TCM-signature diagnostic accuracy is robust across different patient subgroups. We observed robust levels of accuracy in other DETERMINANT signatures including without limitation: (TRAIL and CRP), (TRAIL and CRP and SAA), (TRAIL and CRP and Age), (TRAIL and CRP and SAA and Age) (TRAIL, CRP, SAA, Mac-2BP), (TRAIL and CRP and SAA and IL1RA) as well as (TRAIL and CRP and SAA and IP-10). These results further demonstrate the diagnostics utility of some embodiments of the present invention in the context of the real clinical setting and its inherent complexity that stems from patient heterogeneity.

Stratification Based on Time from Onset of Symptoms

The levels of molecules that participate in the immune response to an infection usually exhibit a temporal behavior (e.g., different antibody isotypes such as IgM and IgG show distinct temporal responses to infection onset). Not surprisingly, we found that many of the analytes tested in the present study exhibited various temporal dynamics after initial appearance of symptoms. The DETERMINANT signatures aims to maintain accuracy levels that are invariant to time from symptoms onset (up to 10 days), by considering the levels of multiple analytes with different temporal dynamics, which are used to compensate one another.

To examine the performance of the DETERMINANT signatures as a function of time from onset of symptoms, we stratified all patients in the 'Majority (bacterial, viral)' cohort according to the time from the initial appearance of symptoms (0-2, 2-4, 4-6, and 6-10 days) and tested the DETERMINANT signatures performance in each subgroup. The accuracy remained roughly the same across the evaluated subgroups (for example, the performance of the TCM-signature is depicted in FIG. 30 and Table 10A), indicating that the performance is generally robust in the first 10 days after symptom onset.

We examined the accuracy of the DETERMINANT signatures in infections occurring in different physiological systems and clinical syndromes (Table 10B). The TCM-signature demonstrated very high accuracy in respiratory and systemic infections (AUC of 0.95 and 0.96, respectively) and slightly lower accuracy in gastrointestinal infections (AUC of 0.89). The TCM-signature performance was also robust in different clinical syndromes including fever without source, community acquired pneumonia, and acute tonsillitis (AUCs of 0.96, 0.94, and 0.94, respectively). Other panels, including panels that measured CRP and TRAIL, showed similar robust results.

Maximal Temperature Stratification

The accuracy of diagnostic assays may depend on disease severity. The severity of an infectious disease could be assessed using the maximal core body temperature measured during the infection. We examined whether the DETERMINANT signatures performance depends on patients' fever, by stratifying the patients in the 'Majority (bacterial, viral)' cohort based on their maximal temperature and testing the performance in each group. We found that the diagnostic accuracy in patients with high fever (>39° C.) was similar to that observed in patients with low-to-medium fever (38-39° C.), (for example AUC of the TCM-signature was 0.956 and 0.952, respectively) (FIG. 31).

Since children tend to have higher fevers than adults, we divided the cohort to children (≤18 years) and adults (>18 years) and repeated the analysis. Again, no significant difference in the DETERMINANT signatures performance was observed for patients with high vs low-to-medium fever (FIG. 30).

Pathogen Subfamily Stratification

A total of 44 different pathogens strains were isolated from the patients enrolled in the current study. We assessed the DETERMINANT signatures performance on different strains.

To this end, patients from the 'Majority (bacterial, viral, mixed)' cohort with a positive isolation were stratified according to the isolated pathogen. Each bacterial strain was tested against all viral patients and each viral strain was tested against all bacterial patients (for example see Table 10C). We observe robust results across a wide range of pathogens with a mean AUC of 0.94.

Accurately Diagnosing Adenoviruses—a Viral Subgroup that is Particularly Challenging to Diagnose Adenoviruses are a subgroup of viruses that are particularly challenging to diagnose because they induce clinical symptoms and lab results that often mimic those induced by a bacterial infection. Consequently, adenovirus infections are often treated as a bacterial infection (Kunze, Beier, and Groeger 2010). Furthermore, this subgroup is particularly important because of their wide prevalence in children (5-15% of the respiratory and gastrointestinal infections in children) (Kunze, Beier, and Groeger 2010). We tested DETERMINANT signatures accuracy in children (age ≤18 years) with any bacterial infection vs children with viral infections and a positive isolation of an adenovirus (79 and 27 children, respectively). The DETERMINANT signatures achieved significantly higher accuracy levels compared with standard clinical and laboratory parameters (for example see Table 10D).

Accurately Diagnosing Atypical Bacteria

Atypical bacterial infections often cause clinical symptoms resembling those of a viral infection, thus posing a clinical diagnostic challenge (Principi and Esposito 2001). Patients infected with atypical bacteria could benefit from macrolides antibiotics; yet, they are often left untreated (Marc et al. 2000). Additionally, patients with viral infections are often suspected of having atypical bacteria leading to erroneous administration of antibiotics (Hersh et al. 2011). We tested the DETERMINANT signatures accuracy in 23 patients that were infected with atypical bacterial (16 Mycoplasma pneumonia, 4 Chlamydia pneumonia, 2 *Legionella pneumophila*, and 1 Rickettsia coroni) vs 242 viral patients. The same test was performed using standard clinical and laboratory parameters. Results are summarized in Table 10E. For example, the performance of the TCM-signature was significantly better than that of any of the clinical and lab parameters (P<0.001 when comparing any of the clinical or lab parameter AUCs to that the TCM-signature).

Comorbidity-Based Stratification

In real-world clinical practice, patients often have background comorbidities, which could, potentially, affect the level of analytes measured by the DETERMINANT signatures. We therefore examined whether particular comorbidities impact the performance of the DETERMINANT signatures. To this end, we analyzed the most prevalent comorbidities in our patient cohort: hypertension, hyperlipidemia, obesity, asthma, atherosclerosis-related diseases (e.g., ischemic heart disease, myocardial infarction and cerebrovascular accident), diabetes mellitus 2, and inflammatory diseases (e.g., rheumatoid arthritis, ulcerative colitis, Behcet's disease, Crohn's disease, diabetes mellitus 1, fibromyalgia, and familial Mediterranean fever [FMF]). For each of these comorbidities, we examined the concentrations of the analytes building some of the DETERMINANT signatures and searched for differences in analyte levels between patients with and without the comorbidity. Specifically, patients were first divided by disease type (bacterial or mixed, viral, and non-infectious disease). For each of the comorbidities, patients were further divided according to whether they had it (target group) or not (background group). Since some comorbidities are age dependent, we controlled for age differences in the target and background groups by computing a characteristic age interval in the target group (mean±2×SD) and excluded any patients that fell outside this interval in both the target and background groups. Next, we tested whether the concentrations of the analytes building some of the DETERMINANT signatures were different in the target vs the background groups using WS P-values (Table 10F). None of the evaluated comorbidities were associated with significant alterations in the levels of signature analytes (target vs background groups), indicating that the analytes building the DETERMINANT signatures are by and large insensitive to the evaluated comorbidities.

Stratification by Chronic Drug Regimens

In real-world clinical practice, patients are often under various chronic drug regimens, which could, potentially, affect the level of analytes included in the DETERMINANT signatures. We therefore examined whether specific drugs impact the performance of the DETERMINANT signatures by performing the same analysis as for the comorbidities (see above). We examined the following drugs: statins (Simvastatin, Pravastatin, Lipitor, and Crestor), diabetes-related drugs (insulin, Metformin, Glyburide, Repaglinide, Sitagliptin, and Acarbose), beta blockers (Atenolol, Carvedilol, Metoprolol, Normalol, Propranolol, and Bisprolol), Aspirin, antacids (Omeprazole, Ranitidine, and Famotidine), inhaled corticosteroids (Budesonide, Salmeterol, Budesonide in combination with formoterol, and Hydrocortisone), bronchodilators (Ipratropium, Salbutamol, and Montelukast) and diuretics (Furosemide, Disothiazide, and Spironolactone). Table 10G depicts the WS P-values for comparing analyte concentrations measured in patients who were under a specific drug regimen vs those who were not. None of the evaluated drug groups were associated with significant alterations in the levels of the DETERMINANT signatures analytes.

Sepsis Based Stratification

Sepsis is a potentially fatal medical condition characterized by a whole-body inflammatory state (called systemic inflammatory response syndrome [SIRS]) and the presence of a known or suspected infection (Levy et al. 2003). Patients with a bacterial sepsis benefit from early antibiotic therapy; delayed or misdiagnosis can have serious or even fatal consequences (Bone et al. 1992; Rivers et al. 2001). We focused on adult patients for whom the definition of SIRS is clear and examined the ability of the DETERMINANT signatures to distinguish between adult patients with bacterial sepsis and those with viral infections as well as between adult patients with bacterial sepsis and those with viral sepsis.

Adult patients with bacterial sepsis were defined according to the American College of Chest Physicians and the Society of Critical Care Medicine (Bone et al. 1992). SIRS was defined by the presence of at least two of the following findings: (i) body temperature <36° C. or >38° C., (ii) heart rate >90 beats per minute, (iii) respiratory rate >20 breaths per minute or, on blood gas, a PaCO2<32 mm Hg (4.3 kPa), and (iv) WBC<4,000 cells/mm3 or >12,000 cells/mm3 or >10% band forms. We found that the DETERMINANT signatures achieved very high levels of accuracy in distinguishing between adult patients with bacterial sepsis and those with viral infections (for example the TCM-signature showed an AUC of 0.98 and 0.96 for the 'Consensus [adult bacterial sepsis, adult viral]' and the 'Majority [adult bacterial sepsis, adult viral]' cohorts, respectively, Table 10H). We observed similar results for distinguishing between patients with bacterial sepsis and those with viral sepsis (AUC of 0.97 and 0.95 for the 'Consensus [adult bacterial sepsis, adult viral sepsis]' and the 'Majority [adult bacterial sepsis, adult viral sepsis]' cohorts, respectively). These results demonstrate the utility of the DETERMINANT signatures in differentiating adult patients with bacterial sepsis from adult patients with viral infections.

Example 10: The DETERMINANT Signatures Performance Remains Robust Across Different Clinical Sites and Settings Clinical-Setting Based Stratification We compared the DETERMINANT signatures performance in the following clinical settings: Emergency setting (i.e., pediatric ED [PED] and ED) and non-emergency setting (i.e., pediatrics and internal departments) (Table 11). Performances in the emergency and non-emergency settings were similar (for example TCM-signature had an AUC of 0.95 vs 0.96 in the 'Consensus [bacterial, viral]' cohort, and 0.92 vs 0.91 in the 'Majority [bacterial, vital, mixed]' cohort, respectively).

In addition, we compared the DETERMINANT signatures performance in patients enrolled in two different hospitals and found that the performance was similar across sites (Table 12).

Example 11: Determinant Levels Change as a Function of Age

We examined the DETERMINAT levels of viral and bacterial patients as a function of age. We found that the levels of many DETERMINANTS are age dependent. For example, the levels of viral induced DETERMINANTS RSAD2, MX1, TRAIL and Mac-2BP show relatively high levels in young children, followed by a gradual decrease with age. In contrast the DETERMINANT levels of CHI3L1 increases with age. FIG. 32 shows examples of DETERMI- NANT levels in different infections as a function of Age. This finding can be used to improve the accuracy of DETERMINANTS for differentiating between different types of infections by performing age dependent normalization or stratification (i.e. age dependent normalization or stratification). For example, one skilled in the art can generate a function that fits the population mean levels of each DETERMINANT as function of age and uses it to normalize the DETERMINANT of individual subjects levels across different ages. Another way to improve diagnostic accuracy is to stratify subjects according to their age and determine thresholds or index values for each age group independently. For example, when testing the DETERMINANT accuracy only on young children (age 0-5 years) the following DETERMINANTS improved their accuracy: TRAIL (0.9 to 0.93 AUC), RSAD2 (0.81 to 0.83 AUC) and Mac-2BP (0.78 to 0.85 AUC).

Example 12: Performance is Robust to the Presence of Bacteria and Viruses that are Part of the Natural Flora Many disease-causing pathogens are also part of the natural flora, and are frequently found in healthy individuals and in patients with non-infectious diseases (Vaneechoutte et al. 1990; Regev-Yochay et al. 2004; Shaikh, Leonard, and Martin 2010). These non-pathogenic bacteria and viruses, termed colonizers, pose a considerable diagnostic challenge because their presence does not necessarily imply pathogenicity. In other words, merely isolating these bacterial/viral strains from a patient does not necessarily indicate that they are the disease-causing agents; therefore, the appropriate treatment may remain unclear.

We investigated whether the DETERMINANT signatures performance is influenced by colonization, focusing on the most prevalent bacterial strains in our patient cohort, *Streptococcus pneumoniae* (SP) and *Haemophilus influenzae* (HI), and the viral strain Rhinovirus A/B/C. To detect these strains, we applied multiplex-PCR to the nasopharyngeal wash of the 'Majority (bacterial, viral, mixed, non-infectious)' cohort. First, we examined the prevalence of these strains in patients with non-infectious diseases (n=46) (FIG. 33A). Isolation rate was higher (about 5-fold) in children (≤18 years) then in adults (>18 years), in accordance with previous studies (Regev-Yochay et al. 2012). Next, we examined the prevalence of these strains in patients with bacterial (n=208), viral (n=242), and mixed (n=34) infections as determined by the majority of our expert panel (FIG. 33B and Table 13). The bacterial strains SP and HI were highly prevalent in viral patients (51% and 36%, respectively) and rhinovirus A/B/C was detected in 4% of the bacterial patients. Thus, bacterial or viral etiologies cannot be inferred merely based on isolation of a specific strain.

To test whether the DETERMINANT signatures performance is influenced by SP colonization, we stratified the patients based on SP colonization and examined the accuracy of the DETERMINANT signatures (viral vs bacterial) in each group separately. For example, we found that the TCM-signature performed similarly in both groups (AUC of 0.95±0.03 vs 0.94±0.04 in the groups with and without SP colonization, respectively). We used the same approach to evaluate the impact of HI and rhinovirus A/B/C colonization and the findings were comparable (FIG. 34). Thus, our findings indicate that the DETERMINANT signatures performance is robust to the colonization of patients by SP, HI, or rhinovirus A/B/C.

Example 13: Trail is an Effective Polypeptide for Diagnosing Viral Infections

In a setting where resources are limited (e.g., a family physician's office), it may be advantageous to have a rapid, easy-to-perform assay, even at the cost of a reduced diagnostic accuracy. In this section, we explore the accuracy of TRAIL as a single polypeptide, to detect viral infections. Although the accuracy of TRAIL is lower than that of some DETERMINANT signatures, it requires the measurement of a single polypeptide and is thus readily measurable on a wide range of machines including lateral flow immunoassay analyzers that are widely spread at the point-of-care setting.

We examined the diagnostic utility of TRAIL using the 'Consensus (bacterial, viral)' cohort (n=343, 153 bacterial and 190 viral) and found that TRAIL concentrations were substantially higher in viral vs bacterial patients (t-test $P<10^{-23}$) (FIG. 35) and that the AUC was 0.9 (FIG. 36).

One application of the TRAIL-based assay is to rule out bacterial infections (e.g., using a cutoff that produces a sensitivity of 97% and specificity of 55%; FIG. 36). In an outpatient setting where the ratio between bacterial and viral infections is ~1:4, this would translate to an NPV of 99% and PPV of 35%. Thus, antibiotics can be withheld in case of a negative test result, whereas a positive test result would require an additional workup to facilitate an informed treatment decision.

Excluding patients with marginal TRAIL calls (i.e., patients that fall near the cutoff), can further increase the level of accuracy. The balance between the number of patients diagnosed and the accuracy of the assay is depicted in FIG. 37.

Interestingly, when comparing TRAIL levels across different patient subgroups we found that its concentrations were highest in viral patients (median of 121±132 pg/ml), lower in healthy and non-infectious patients (median of 88±41 pg/ml), and lowest in bacterial patients (52±65 pg/ml). These results suggest that not only does viral infections up-regulate TRAIL levels, but also that bacterial infections down-regulate them. The finding that bacterial infections down regulate TRAIL is further supported by our observation that in viral and bacterial co-infections (i.e. mixed infections) TRAIL levels are low (which may be due to bacterial response dominance). Altogether, in addition to TRAIL's up-regulation in viral infections, its down regulation in bacterial infections, contribute to its ability to accurately distinguish between viral and bacterial infections. This point is further illustrated in FIG. 41.

Of note, TRAIL dynamics is correlated with the disease stage (FIG. 41). Thus TRAIL can be used not only for diagnosis of infection, but also for identifying disease stage and prognosis.

Tables

In the following tables the abbreviations mono, lymp, gran, mean and total are used to denote polypeptide-DETERMINANT measurements on monocytes, lymphocytes, granulocytes as well as mean and total leukocytes measurements respectively. The abbreviations intra and membrane are used to denote proteins that were measured in the intra cellular and membrane fraction respectively.

TABLE 1

Examples of polypeptide-DETERMINANTS with an immunological role that do not differentiate between bacterial versus viral infected subjects.
Positives and negatives correspond to bacterial and viral infected patients respectively. Positives (P) and Negatives (N) correspond to bacterial and viral infected patients respectively. TA, Sen, Spe and log2(R) correspond total accuracy sensitivity, specificity and log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| sIL-2Ra, soluble | 0.53 | 2.2E−01 | 0.19 | 57 | 76 | 42 | 52 | 69 | 21 | 26 | −0.27 |
| IL-9, soluble | 0.52 | 1.1E−01 | 0.13 | 55 | 67 | 46 | 50 | 63 | 21 | 26 | −0.31 |
| IL-8, soluble | 0.66 | 9.2E−01 | −0.23 | 38 | 43 | 35 | 35 | 43 | 21 | 26 | −0.48 |
| IL-4, soluble | 0.64 | 1.9E−01 | 0.07 | 49 | 86 | 19 | 46 | 63 | 21 | 26 | 0.00 |
| IL-33, soluble | 0.55 | 7.6E−01 | 0.08 | 55 | 38 | 69 | 50 | 58 | 21 | 26 | 0.61 |
| IL-3, soluble | 0.54 | 1.9E−01 | 0.01 | 49 | 67 | 35 | 45 | 56 | 21 | 26 | −0.11 |
| IL-28A, soluble | 0.50 | 5.3E−01 | 0.03 | 51 | 57 | 46 | 46 | 57 | 21 | 26 | 0.00 |
| IL-23, soluble | 0.58 | 5.9E−01 | −0.05 | 50 | 24 | 72 | 42 | 53 | 21 | 25 | 0.41 |
| IL-21, soluble | 0.55 | 4.2E−01 | 0.11 | 57 | 33 | 77 | 54 | 59 | 21 | 26 | −0.06 |
| IL-20, soluble | 0.57 | 3.2E−01 | 0.03 | 51 | 57 | 46 | 46 | 57 | 21 | 26 | −0.16 |
| IL-2, soluble | 0.51 | 1.3E−01 | −0.04 | 47 | 62 | 35 | 43 | 53 | 21 | 26 | 0.22 |
| IL-1ra, soluble | 0.56 | 5.8E−01 | −0.08 | 45 | 62 | 31 | 42 | 50 | 21 | 26 | −0.27 |
| IL, soluble | 0.76 | 4.2E−01 | −0.35 | 32 | 43 | 23 | 31 | 33 | 21 | 26 | 0.08 |
| IL17A, soluble | 0.76 | 8.3E−01 | −0.31 | 34 | 57 | 15 | 35 | 31 | 21 | 26 | 0.42 |
| IL-16, soluble | 0.65 | 7.1E−01 | −0.16 | 40 | 62 | 23 | 39 | 43 | 21 | 26 | −0.06 |
| IL-15, soluble | 0.56 | 2.8E−01 | 0 | 49 | 62 | 38 | 45 | 56 | 21 | 26 | 0.00 |
| IL-13, soluble | 0.47 | 2.5E−01 | 0.12 | 53 | 76 | 35 | 48 | 64 | 21 | 26 | −0.33 |
| IL12(p70), soluble | 0.76 | 9.2E−01 | −0.43 | 30 | 14 | 44 | 18 | 38 | 21 | 25 | 0.28 |
| CDH23, mono, membrane | 0.53 | 4.5E−01 | 0.04 | 51 | 47 | 57 | 64 | 39 | 38 | 23 | 0.20 |
| CDH23, mean, membrane | 0.56 | 2.8E−01 | 0.14 | SS | 49 | 65 | 69 | 44 | 37 | 23 | 0.14 |
| CDH23, lymp, membrane | 0.54 | 1.7E−01 | 0.09 | 53 | 49 | 61 | 67 | 42 | 37 | 23 | 0.08 |
| CDH23, gran, membrane | 0.56 | 2.5E−01 | 0.18 | 61 | 66 | 52 | 69 | 48 | 38 | 23 | −0.15 |
| CD99R, mono, membrane | 0.47 | 4.6E−01 | 0.11 | 59 | 76 | 34 | 64 | 48 | 45 | 29 | −0.34 |
| CD99R, mean, membrane | 0.53 | 4.9E−01 | 0.12 | 58 | 64 | 48 | 65 | 47 | 44 | 29 | −0.14 |
| CD99R, gran, membrane | 0.57 | 6.2E−01 | −0.03 | 50 | 56 | 41 | 60 | 38 | 45 | 29 | −0.08 |
| CD69, gran, membrane | 0.55 | 6.0E−01 | 0.13 | 56 | 63 | 50 | 56 | 57 | 8 | 8 | 0.23 |
| CD66F, gran, membrane | 0.77 | 8.8E−01 | −0.25 | 38 | 38 | 38 | 38 | 38 | 8 | 8 | 0.01 |
| CD64, lymp, membrane | 0.69 | 6.4E−01 | −0.13 | 44 | 63 | 25 | 45 | 40 | 8 | 8 | −0.07 |
| CD62P, lymp, membrane | 0.75 | 8.9E−01 | −0.52 | 25 | 38 | 13 | 30 | 17 | 8 | 8 | −1.74 |
| CD62P, gran, membrane | 0.77 | 7.4E−01 | −0.26 | 38 | 25 | 50 | 33 | 40 | 8 | 8 | −1.60 |
| CD62L, lymp, membrane | 0.75 | 8.0E−01 | −0.26 | 38 | 50 | 25 | 40 | 33 | 8 | 8 | 0.21 |
| CD62L, gran, membrane | 0.88 | 8.8E−01 | −0.63 | 19 | 25 | 13 | 22 | 14 | 8 | 8 | −0.04 |
| CD62E, lymp, membrane | 0.69 | 3.6E−01 | −0.26 | 38 | 50 | 25 | 40 | 33 | 8 | 8 | −0.06 |
| CD62E, gran, membrane | 0.92 | 7.4E−01 | −0.63 | 19 | 25 | 13 | 22 | 14 | 8 | 8 | 0.50 |
| CD61, gran, membrane | 0.50 | 1.5E−01 | 0.13 | 56 | 38 | 75 | 60 | 55 | 8 | 8 | −0.06 |
| CD57, lymp, membrane | 0.70 | 7.2E−01 | −0.25 | 38 | 38 | 38 | 38 | 38 | 8 | 8 | 0.22 |
| CD57, gran, membrane | 0.91 | 8.7E−01 | −0.52 | 25 | 13 | 38 | 17 | 30 | 8 | 8 | −0.25 |
| CD56, gran, membrane | 0.63 | 5.7E−01 | 0 | 50 | 63 | 38 | 50 | 50 | 8 | 8 | −0.06 |
| CD55, lymp, membrane | 0.58 | 7.7E−01 | 0.13 | 56 | 63 | 50 | 56 | 57 | 8 | 8 | 0.12 |
| CD55, gran, membrane | 0.77 | 7.3E−01 | −0.29 | 38 | 13 | 63 | 25 | 42 | 8 | 8 | 0.00 |
| CD54, mono, membrane | 0.58 | 7.0E−01 | −0.07 | 47 | 51 | 41 | 57 | 35 | 45 | 29 | −0.15 |
| CD54, mean, membrane | 0.63 | 8.4E−01 | −0.16 | 42 | 45 | 38 | 53 | 31 | 44 | 29 | 0.18 |
| CD54, lymp, membrane | 0.55 | 5.3E−01 | −0.11 | 45 | 45 | 43 | 54 | 35 | 44 | 30 | 0.21 |
| CD54, gran, membrane | 0.66 | 9.7E−01 | −0.14 | 44 | 49 | 37 | 54 | 32 | 45 | 30 | 0.17 |
| CD53, lymp, membrane | 0.81 | 8.9E−01 | −0.25 | 38 | 38 | 38 | 38 | 38 | 8 | 8 | −0.12 |
| CD51/CD61, gran, membrane | 0.48 | 3.1E−01 | 0.13 | 56 | 63 | 50 | 56 | 57 | 8 | 8 | −0.30 |
| CD50, lymp, membrane | 0.80 | 7.8E−01 | −0.26 | 38 | 50 | 25 | 40 | 33 | 8 | 8 | −0.01 |
| CD50, gran, membrane | 0.53 | 4.7E−01 | 0.13 | 56 | 63 | 50 | 56 | 57 | 8 | 8 | 0.07 |
| CD5, lymp, membrane | 0.77 | 9.1E−01 | −0.26 | 38 | 25 | 50 | 33 | 40 | 8 | 8 | −0.09 |
| CD49E, gran, membrane | 0.83 | 4.9E−01 | −0.25 | 38 | 38 | 38 | 38 | 38 | 8 | 8 | −0.30 |
| CD49D, lymp, membrane | 0.75 | 5.5E−01 | −0.29 | 38 | 13 | 63 | 25 | 42 | 8 | 8 | −0.06 |
| CD49D, gran, membrane | 0.84 | 7.1E−01 | −0.52 | 25 | 13 | 38 | 17 | 30 | 8 | 8 | 0.17 |
| CD49C, lymp, membrane | 0.77 | 5.9E−01 | −0.25 | 38 | 38 | 38 | 38 | 38 | 8 | 8 | −0.13 |
| CD49C, gran, membrane | 0.84 | 9.9E−01 | −0.38 | 31 | 25 | 38 | 29 | 33 | 8 | 8 | −0.22 |
| CD49A, gran, membrane | 0.73 | 3.5E−01 | 0.16 | 56 | 88 | 25 | 54 | 67 | 8 | 8 | 0.25 |
| CD49I, mono, membrane | 0.48 | 4.7E−01 | 0.13 | 56 | 63 | 50 | 56 | 57 | 8 | 8 | −0.41 |
| CD49I, mean, membrane | 0.77 | 6.7E−01 | −0.26 | 38 | 25 | 50 | 33 | 40 | 8 | 8 | 0.08 |
| CD49I, gran, membrane | 0.77 | 7.1E−01 | −0.38 | 31 | 25 | 38 | 29 | 33 | 8 | 8 | −0.21 |
| CD48, gran, membrane | 0.84 | 9.8E−01 | −0.63 | 19 | 13 | 25 | 14 | 22 | 8 | 8 | −0.08 |
| CD47, lymp, membrane | 0.70 | 7.8E−01 | −0.13 | 44 | 50 | 38 | 44 | 43 | 8 | 8 | 0.12 |
| CD47, gran, membrane | 0.55 | 6.8E−01 | −0.29 | 38 | 63 | 13 | 42 | 25 | 8 | 8 | 0.09 |
| CD46, gran, membrane | 0.52 | 2.1E−01 | 0.16 | 56 | 88 | 25 | 54 | 67 | 8 | 8 | −0.05 |
| CD45RO, lymp, membrane | 0.92 | 8.0E−01 | −0.63 | 19 | 13 | 25 | 14 | 22 | 8 | 8 | −0.19 |
| CD45RB, lymp, membrane | 0.58 | 6.3E−01 | 0.13 | 56 | 75 | 38 | 55 | 60 | 8 | 8 | 0.07 |
| CD45RA, lymp, membrane | 0.66 | 7.7E−01 | −0.13 | 44 | 50 | 38 | 44 | 43 | 8 | 8 | −0.02 |
| CD45RA, gran, membrane | 1.00 | 1.0E+00 | −0.88 | 6 | 13 | 0 | 11 | 0 | 8 | 8 | 0.22 |
| CD45, mono, membrane | 0.52 | 7.1E−01 | −0.07 | 46 | 52 | 41 | 41 | 52 | 54 | 68 | −0.09 |
| CD45, mean, membrane | 0.52 | 4.5E−01 | 0.03 | 49 | 70 | 32 | 45 | 58 | 54 | 68 | 0.14 |
| CD45, gran, membrane | 0.57 | 6.6E−01 | −0.05 | 46 | 63 | 32 | 42 | 52 | 54 | 69 | 0.34 |
| CD44, lymp, membrane | 0.83 | 5.6E−01 | −0.63 | 19 | 13 | 25 | 14 | 22 | 8 | 8 | −0.07 |
| CD43, lymp, membrane | 0.73 | 5.9E−01 | −0.13 | 44 | 38 | 50 | 43 | 44 | 8 | 8 | −0.35 |

TABLE 1-continued

Examples of polypeptide-DETERMINANTS with an immunological role that do not differentiate between bacterial versus viral infected subjects.
Positives and negatives correspond to bacterial and viral infected patients respectively. Positives (P) and Negatives (N) correspond to bacterial and viral infected patients respectively. TA, Sen, Spe and log2(R) correspond total accuracy sensitivity, specificity and log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| CD41b, gran, membrane | 0.70 | 4.5E−01 | −0.13 | 44 | 25 | 63 | 40 | 45 | 8 | 8 | −0.08 |
| CD41a, lymp, membrane | 0.56 | 2.8E−01 | 0.16 | 56 | 88 | 25 | 54 | 67 | 8 | 8 | −0.31 |
| CD40, gran, membrane | 0.80 | 9.7E−01 | −0.38 | 31 | 25 | 38 | 29 | 33 | 8 | 8 | −0.09 |
| CD4, lymp, membrane | 0.61 | 8.9E−01 | 0 | 50 | 38 | 63 | 50 | 50 | 8 | 8 | −0.25 |
| CD4, gran, membrane | 0.88 | 8.4E−01 | −0.52 | 25 | 13 | 38 | 17 | 30 | 8 | 8 | 0.06 |
| CD39, gran, membrane | 0.77 | 8.7E−01 | −0.38 | 31 | 38 | 25 | 33 | 29 | 8 | 8 | 0.17 |
| CD38, mono, membrane | 0.73 | 9.8E−01 | −0.36 | 32 | 36 | 28 | 43 | 22 | 45 | 29 | −0.25 |
| CD38, gran, membrane | 0.52 | 3.6E−01 | 0.01 | 52 | 58 | 43 | 60 | 41 | 45 | 30 | 0.09 |
| CD37, lymp, membrane | 0.45 | 4.6E−01 | 0.15 | 56 | 68 | 46 | 49 | 66 | 41 | 54 | −0.18 |
| CD36, lymp, membrane | 0.58 | 4.7E−01 | 0.16 | 56 | 25 | 88 | 67 | 54 | 8 | 8 | −0.30 |
| CD337-PE, lymp, membrane | 0.52 | 4.4E−01 | −0.06 | 47 | 46 | 48 | 59 | 35 | 37 | 23 | −0.31 |
| CD33, gran, membrane | 0.63 | 3.7E−01 | 0.16 | 56 | 25 | 88 | 67 | 54 | 8 | 8 | −0.08 |
| CD326, mean, membrane | 0.55 | 3.4E−01 | 0 | 50 | 25 | 75 | 50 | 50 | 8 | 8 | 0.05 |
| CD326, gran, membrane | 0.52 | 3.2E−01 | 0.16 | 56 | 25 | 88 | 67 | 54 | 8 | 8 | −0.07 |
| CD32, lymp, membrane | 0.81 | 9.6E−01 | −0.63 | 19 | 13 | 25 | 14 | 22 | 8 | 8 | −0.11 |
| CD31, lymp, membrane | 0.64 | 2.2E−01 | −0.16 | 44 | 13 | 75 | 33 | 46 | 8 | 8 | −0.05 |
| CD30, lymp, membrane | 0.83 | 8.0E−01 | −0.52 | 25 | 38 | 13 | 30 | 17 | 8 | 8 | 0.13 |
| CD3, lymp, membrane | 0.61 | 4.7E−01 | −0.13 | 44 | 38 | 50 | 43 | 44 | 8 | 8 | −0.05 |
| CD294, mean, membrane | 0.72 | 7.9E−01 | −0.29 | 38 | 13 | 63 | 25 | 42 | 8 | 8 | 0.13 |
| CD294, gran, membrane | 0.81 | 9.1E−01 | −0.38 | 31 | 25 | 38 | 29 | 33 | 8 | 8 | −0.12 |
| CD28, gran, membrane | 0.58 | 5.0E−01 | 0.16 | 56 | 88 | 25 | 54 | 67 | 8 | 8 | 0.03 |
| CD275, mean, membrane | 0.64 | 7.3E−01 | −0.13 | 44 | 38 | 50 | 43 | 44 | 8 | 8 | −0.06 |
| CD275, gran, membrane | 0.56 | 5.9E−01 | −0.13 | 44 | 38 | 50 | 43 | 44 | 8 | 8 | 0.09 |
| CD274, gran, membrane | 0.64 | 3.9E−01 | −0.38 | 38 | 75 | 0 | 43 | 0 | 8 | 8 | −0.18 |
| CD27, gran, membrane | 0.86 | 7.0E−01 | −0.52 | 25 | 38 | 13 | 30 | 17 | 8 | 8 | −0.14 |
| CD267, mean, membrane | 0.92 | 7.7E−01 | −0.29 | 38 | 13 | 63 | 25 | 42 | 8 | 8 | −0.09 |
| CD267, gran, membrane | 0.75 | 7.5E−01 | −0.26 | 38 | 25 | 50 | 33 | 40 | 8 | 8 | −0.12 |
| CD26, gran, membrane | 0.59 | 6.7E−01 | 0 | 50 | 63 | 38 | 50 | 50 | 8 | 8 | −0.05 |
| CD25, lymp, membrane | 0.95 | 9.1E−01 | −0.77 | 13 | 25 | 0 | 20 | 0 | 8 | 8 | −0.15 |
| CD25, gran, membrane | 0.75 | 7.5E−01 | −0.26 | 38 | 50 | 25 | 40 | 33 | 8 | 8 | 0.07 |
| CD244, mono, membrane | 0.72 | 7.0E−01 | −0.26 | 38 | 25 | 50 | 33 | 40 | 8 | 8 | 0.15 |
| CD244, mean, membrane | 0.86 | 7.7E−01 | −0.26 | 38 | 50 | 25 | 40 | 33 | 8 | 8 | 0.34 |
| CD244, gran, membrane | 0.88 | 7.9E−01 | −0.48 | 31 | 63 | 0 | 38 | 0 | 8 | 8 | 0.49 |
| CD243, mono, membrane | 0.78 | 8.8E−01 | −0.38 | 31 | 38 | 25 | 33 | 29 | 8 | 8 | −0.11 |
| CD243, mean, membrane | 0.86 | 7.1E−01 | −0.63 | 19 | 25 | 13 | 22 | 14 | 8 | 8 | −0.09 |
| CD243, gran, membrane | 0.88 | 7.8E−01 | −0.63 | 19 | 25 | 13 | 22 | 14 | 8 | 8 | 0.00 |
| CD235A, mono, membrane | 0.86 | 8.2E−01 | −0.58 | 25 | 0 | 50 | 0 | 33 | 8 | 8 | 0.02 |
| CD235A, lymp, membrane | 0.88 | 8.0E−01 | −0.5 | 25 | 25 | 25 | 25 | 25 | 8 | 8 | −0.48 |
| CD226, gran, membrane | 0.70 | 3.8E−01 | −0.26 | 44 | 88 | 0 | 47 | 0 | 8 | 8 | −0.12 |
| CD22, gran, membrane | 0.53 | 2.9E−01 | 0.13 | 56 | 38 | 75 | 60 | 55 | 8 | 8 | 0.27 |
| CD212, mono, membrane | 0.81 | 7.6E−01 | −0.52 | 25 | 38 | 13 | 30 | 17 | 8 | 8 | −0.31 |
| CD212, mean, membrane | 0.73 | 7.1E−01 | −0.26 | 38 | 25 | 50 | 33 | 40 | 8 | 8 | 0.00 |
| CD212, gran, membrane | 0.81 | 8.0E−01 | −0.38 | 31 | 25 | 38 | 29 | 33 | 8 | 8 | −0.14 |
| CD210, mono, membrane | 0.80 | 8.2E−01 | −0.25 | 38 | 38 | 38 | 38 | 38 | 8 | 8 | 0.04 |
| CD210, mean, membrane | 0.80 | 7.6E−01 | −0.13 | 44 | 25 | 63 | 40 | 45 | 8 | 8 | 0.11 |
| CD210, gran, membrane | 0.86 | 9.6E−01 | −0.52 | 25 | 13 | 38 | 17 | 30 | 8 | 8 | −0.15 |
| CD21, gran, membrane | 0.47 | 6.1E−01 | 0.13 | 56 | 38 | 75 | 60 | 55 | 8 | 8 | −0.06 |
| CD205, mono, membrane | 0.52 | 6.8E−01 | 0.02 | 53 | 62 | 40 | 61 | 41 | 45 | 30 | −0.30 |
| CD205, mean, membrane | 0.57 | 2.5E−01 | 0.1 | 57 | 64 | 47 | 64 | 47 | 44 | 30 | −0.44 |
| CD205, lymp, membrane | 0.59 | 8.5E−01 | −0.09 | 49 | 61 | 30 | 56 | 35 | 44 | 30 | −0.06 |
| CD201, mono, membrane | 0.89 | 6.2E−01 | −0.4 | 31 | 13 | 50 | 20 | 36 | 8 | 8 | 0.47 |
| CD201, mean, membrane | 0.80 | 6.4E−01 | −0.48 | 31 | 0 | 63 | 0 | 38 | 8 | 8 | 0.12 |
| CD201, lymp, membrane | 0.80 | 8.7E−01 | −0.67 | 19 | 38 | 0 | 27 | 0 | 8 | 8 | −0.14 |
| CD201, gran, membrane | 0.80 | 7.7E−01 | −0.38 | 31 | 25 | 38 | 29 | 33 | 8 | 8 | −0.17 |
| CD200, lymp, membrane | 0.64 | 5.4E−01 | −0.13 | 44 | 63 | 25 | 45 | 40 | 8 | 8 | 0.07 |
| CD20, lymp, membrane | 0.83 | 7.0E−01 | −0.38 | 31 | 25 | 38 | 29 | 33 | 8 | 8 | −0.34 |
| CD20, gran, membrane | 0.64 | 5.1E−01 | 0.13 | 56 | 75 | 38 | SS | 60 | 8 | 8 | −0.03 |
| CD2, gran, membrane | 0.64 | 6.4E−01 | −0.26 | 38 | 25 | 50 | 33 | 40 | 8 | 8 | −0.10 |
| CD1D, gran, membrane | 0.59 | 6.2E−01 | −0.13 | 44 | 38 | 50 | 43 | 44 | 8 | 8 | −0.28 |
| CD1B, gran, membrane | 0.69 | 9.8E−01 | −0.38 | 31 | 38 | 25 | 33 | 29 | 8 | 8 | −0.15 |
| CD195, mean, membrane | 0.73 | 6.0E−01 | −0.26 | 38 | 50 | 25 | 40 | 33 | 8 | 8 | −0.06 |
| CD195, gran, membrane | 0.95 | 9.2E−01 | −0.77 | 13 | 25 | 0 | 20 | 0 | 8 | 8 | 0.13 |
| CD19, gran, membrane | 0.66 | 8.3E−01 | −0.25 | 38 | 38 | 38 | 38 | 38 | 8 | 8 | 0.00 |
| CD184, mono, membrane | 0.80 | 9.9E−01 | −0.52 | 25 | 13 | 38 | 17 | 30 | 8 | 8 | −0.32 |
| CD184, mean, membrane | 0.66 | 7.5E−01 | 0 | 50 | 25 | 75 | 50 | 50 | 8 | 8 | −0.14 |
| CD184, lymp, membrane | 0.73 | 8.7E−01 | −0.13 | 44 | 38 | 50 | 43 | 44 | 8 | 8 | −0.49 |
| CD184, gran, membrane | 0.55 | 6.2E−01 | 0 | 50 | 38 | 63 | 50 | 50 | 8 | 8 | 0.08 |
| CD183, mono, membrane | 0.92 | 8.7E−01 | −0.52 | 25 | 38 | 13 | 30 | 17 | 8 | 8 | 0.21 |
| CD183, mean, membrane | 0.73 | 4.7E−01 | −0.29 | 38 | 63 | 13 | 42 | 25 | 8 | 8 | 0.09 |
| CD182, mean, membrane | 0.57 | 5.0E−01 | −0.22 | 43 | 56 | 23 | 54 | 24 | 36 | 22 | 0.02 |
| CD182, gran, membrane | 0.54 | 2.3E−01 | −0.06 | 51 | 62 | 32 | 61 | 33 | 37 | 22 | 0.01 |

TABLE 1-continued

Examples of polypeptide-DETERMINANTS with an immunological role that do not differentiate between bacterial versus viral infected subjects.
Positives and negatives correspond to bacterial and viral infected patients respectively. Positives (P) and Negatives (N) correspond to bacterial and viral infected patients respectively. TA, Sen, Spe and log2(R) correspond total accuracy sensitivity, specificity and log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| CD181, mono, membrane | 0.58 | 8.4E−01 | −0.03 | 48 | 47 | 50 | 58 | 38 | 45 | 30 | −0.16 |
| CD181, mean, membrane | 0.53 | 5.4E−01 | 0.05 | 51 | 45 | 60 | 63 | 43 | 44 | 30 | 0.08 |
| CD181, gran, membrane | 0.59 | 7.7E−01 | −0.1 | 45 | 47 | 43 | 55 | 35 | 45 | 30 | −0.06 |
| CD180, mono, membrane | 0.57 | 2.9E−01 | 0.09 | 55 | 56 | 53 | 64 | 44 | 45 | 30 | −0.58 |
| CD180, mean, membrane | 0.55 | 2.8E−01 | 0.09 | 57 | 66 | 43 | 63 | 46 | 44 | 30 | −0.21 |
| CD180, lymp, membrane | 0.55 | 4.8E−01 | −0.06 | 46 | 41 | 53 | 56 | 38 | 44 | 30 | 0.16 |
| CD180, gran, membrane | 0.56 | 1.9E−01 | 0.11 | 59 | 73 | 37 | 63 | 48 | 45 | 30 | −0.27 |
| CD177, mono, membrane | 0.67 | 7.7E−01 | −0.38 | 31 | 25 | 38 | 29 | 33 | 8 | 8 | −0.78 |
| CD172B, mono, membrane | 0.98 | 6.5E−01 | −0.88 | 6 | 0 | 13 | 0 | 11 | 8 | 8 | 0.10 |
| CD171, mono, membrane | 0.50 | 6.3E−01 | 0.13 | 56 | 50 | 63 | 57 | 56 | 8 | 8 | −0.73 |
| CD171, mean, membrane | 0.86 | 7.3E−01 | −0.4 | 31 | 50 | 13 | 36 | 20 | 8 | 8 | 0.24 |
| CD171, gran, membrane | 0.88 | 7.1E−01 | −0.48 | 31 | 63 | 0 | 38 | 0 | 8 | 8 | 0.36 |
| CD166, mono, membrane | 0.78 | 7.5E−01 | −0.13 | 44 | 25 | 63 | 40 | 45 | 8 | 8 | −0.17 |
| CD166, mean, membrane | 0.81 | 8.3E−01 | −0.5 | 25 | 25 | 25 | 25 | 25 | 8 | 8 | 0.32 |
| CD166, gran, membrane | 0.88 | 9.3E−01 | −0.52 | 25 | 38 | 13 | 30 | 17 | 8 | 8 | 0.37 |
| CD165, mono, membrane | 0.52 | 4.0E−01 | −0.13 | 44 | 50 | 38 | 44 | 43 | 8 | 8 | −0.06 |
| CD165, mean, membrane | 0.47 | 3.7E−01 | 0.13 | 56 | 75 | 38 | 55 | 60 | 8 | 8 | 0.03 |
| CD165, gran, membrane | 0.72 | 4.2E−01 | 0 | 50 | 88 | 13 | 50 | 50 | 8 | 8 | 0.16 |
| CD164, mean, membrane | 0.80 | 5.9E−01 | −0.26 | 38 | 50 | 25 | 40 | 33 | 8 | 8 | 0.02 |
| CD164, gran, membrane | 0.75 | 6.8E−01 | −0.29 | 38 | 63 | 13 | 42 | 25 | 8 | 8 | −0.14 |
| CD163, mono, membrane | 0.72 | 8.2E−01 | −0.25 | 38 | 38 | 38 | 38 | 38 | 8 | 8 | −0.27 |
| CD163, mean, membrane | 0.55 | 3.4E−01 | 0 | 50 | 63 | 38 | 50 | 50 | 8 | 8 | −0.43 |
| CD162, lymp, membrane | 0.53 | 2.9E−01 | −0.13 | 44 | 50 | 38 | 44 | 43 | 8 | 8 | −0.06 |
| CD162, gran, membrane | 0.56 | 4.5E−01 | 0 | 50 | 50 | 50 | 50 | 50 | 8 | 8 | 0.13 |
| CD161, mean, membrane | 0.64 | 3.9E−01 | −0.16 | 44 | 75 | 13 | 46 | 33 | 8 | 8 | −0.16 |
| CD161, gran, membrane | 0.69 | 3.6E−01 | 0 | 50 | 88 | 13 | 50 | 50 | 8 | 8 | 0.05 |
| CD16, gran, membrane | 0.86 | 6.7E−01 | −0.5 | 25 | 25 | 25 | 25 | 25 | 8 | 8 | −0.16 |
| CD15s, gran, membrane | 0.84 | 5.5E−01 | −0.63 | 19 | 25 | 13 | 22 | 14 | 8 | 8 | −0.02 |
| CD158B, gran, membrane | 0.52 | 3.7E−01 | 0.13 | 56 | 75 | 38 | 55 | 60 | 8 | 8 | −0.05 |
| CD153, gran, membrane | 0.59 | 3.6E−01 | 0 | 50 | 88 | 13 | 50 | 50 | 8 | 8 | −0.11 |
| CD152, mono, membrane | 0.89 | 9.3E−01 | −0.63 | 19 | 13 | 25 | 14 | 22 | 8 | 8 | −0.13 |
| CD152, mean, membrane | 0.95 | 8.3E−01 | −0.67 | 19 | 38 | 0 | 27 | 0 | 8 | 8 | 0.38 |
| CD152, gran, membrane | 0.95 | 9.6E−01 | −0.63 | 19 | 25 | 13 | 22 | 14 | 8 | 8 | 0.05 |
| CD151, gran, membrane | 0.59 | 3.5E−01 | 0 | 50 | 88 | 13 | 50 | 50 | 8 | 8 | −0.13 |
| CD15, mono, membrane | 0.55 | 6.3E−01 | −0.08 | 45 | 59 | 33 | 42 | 50 | 56 | 69 | 0.09 |
| CD15, lymp, membrane | 0.44 | 4.5E−01 | 0.01 | 48 | 68 | 33 | 45 | 56 | 56 | 70 | −0.27 |
| CD15, gran, membrane | 0.64 | 9.1E−01 | −0.2 | 40 | 38 | 43 | 34 | 46 | 56 | 70 | 0.18 |
| CD147, gran, membrane | 0.95 | 9.5E−01 | −0.67 | 19 | 38 | 0 | 27 | 0 | 8 | 8 | 0.57 |
| CD146, gran, membrane | 0.52 | 4.0E−01 | −0.13 | 44 | 63 | 25 | 45 | 40 | 8 | 8 | −0.24 |
| CD144, gran, membrane | 0.84 | 7.6E−01 | −0.52 | 25 | 13 | 38 | 17 | 30 | 8 | 8 | −0.48 |
| CD141, mean, membrane | 0.92 | 7.8E−01 | −0.4 | 31 | 50 | 13 | 36 | 20 | 8 | 8 | 0.54 |
| CD141, gran, membrane | 0.94 | 6.2E−01 | −0.26 | 44 | 88 | 0 | 47 | 0 | 8 | 8 | 0.62 |
| CD140B, mono, membrane | 0.64 | 5.8E−01 | −0.13 | 44 | 50 | 38 | 44 | 43 | 8 | 8 | −0.43 |
| CD140B, lymp, membrane | 0.52 | 3.1E−01 | 0 | 50 | 63 | 38 | 50 | 50 | 8 | 8 | −0.37 |
| CD140A, mono, membrane | 0.70 | 7.4E−01 | 0 | 50 | 38 | 63 | 50 | 50 | 8 | 8 | −0.29 |
| CD140A, mean, membrane | 0.91 | 9.2E−01 | −0.77 | 13 | 25 | 0 | 20 | 0 | 8 | 8 | 0.05 |
| CD140A, gran, membrane | 0.95 | 9.6E−01 | −0.63 | 19 | 25 | 13 | 22 | 14 | 8 | 8 | 0.06 |
| CD14, gran, membrane | 0.84 | 6.7E−01 | −0.4 | 31 | 13 | 50 | 20 | 36 | 8 | 8 | 0.45 |
| CD137L, mono, membrane | 0.72 | 9.3E−01 | −0.38 | 31 | 25 | 38 | 29 | 33 | 8 | 8 | 0.02 |
| CD137L, mean, membrane | 0.61 | 6.0E−01 | −0.26 | 38 | 50 | 25 | 40 | 33 | 8 | 8 | 0.11 |
| CD137L, gran, membrane | 0.75 | 5.6E−01 | −0.16 | 44 | 75 | 13 | 46 | 33 | 8 | 8 | 0.06 |
| CD137, mono, membrane | 0.53 | 7.5E−01 | −0.13 | 44 | 63 | 25 | 45 | 40 | 8 | 8 | −0.63 |
| CD137, gran, membrane | 0.47 | 4.3E−01 | 0 | 50 | 50 | 50 | 50 | 50 | 8 | 8 | −0.19 |
| CD135, mono, membrane | 0.84 | 9.1E−01 | −0.5 | 25 | 25 | 25 | 25 | 25 | 8 | 8 | 0.10 |
| CD127, mono, membrane | 0.44 | 2.2E−01 | 0.13 | 56 | 75 | 38 | 55 | 60 | 8 | 8 | −0.28 |
| CD127, gran, membrane | 0.50 | 4.6E−01 | 0 | 50 | 50 | 50 | 50 | 50 | 8 | 8 | −0.12 |
| CD126, mean, membrane | 0.56 | 4.7E−01 | 0.13 | 56 | 63 | 50 | 56 | 57 | 8 | 8 | −0.17 |
| CD126, gran, membrane | 0.64 | 5.9E−01 | −0.26 | 38 | 50 | 25 | 40 | 33 | 8 | 8 | 0.00 |
| CD124, mono, membrane | 0.53 | 2.2E−01 | 0.13 | 56 | 75 | 38 | 55 | 60 | 8 | 8 | −0.07 |
| CD124, mean, membrane | 0.56 | 3.6E−01 | 0 | 50 | 88 | 13 | 50 | 50 | 8 | 8 | −0.27 |
| CD124, gran, membrane | 0.66 | 3.8E−01 | −0.26 | 44 | 88 | 0 | 47 | 0 | 8 | 8 | 0.00 |
| CD123, gran, membrane | 0.47 | 2.7E−01 | 0 | 50 | 75 | 25 | 50 | 50 | 8 | 8 | −0.02 |
| CD120B, mono, membrane | 0.69 | 9.4E−01 | −0.25 | 38 | 38 | 38 | 38 | 38 | 8 | 8 | 0.27 |
| CD120B, mean, membrane | 0.70 | 5.5E−01 | −0.13 | 44 | 25 | 63 | 40 | 45 | 8 | 8 | 0.20 |
| CD120B, gran, membrane | 0.75 | 6.1E−01 | −0.38 | 31 | 25 | 38 | 29 | 33 | 8 | 8 | −0.11 |
| CD11C, mean, membrane | 0.55 | 4.2E−01 | −0.03 | 52 | 66 | 31 | 59 | 38 | 44 | 29 | 0.14 |
| CD11C, lymp, membrane | 0.54 | 5.7E−01 | −0.12 | 51 | 77 | 13 | 57 | 29 | 44 | 30 | −0.21 |
| CD11C, gran, membrane | 0.52 | 3.2E−01 | −0.05 | 51 | 62 | 33 | 58 | 37 | 45 | 30 | −0.12 |
| CD11a, lymp, membrane | 0.57 | 2.2E−01 | 0.13 | 57 | 47 | 66 | 51 | 62 | 47 | 61 | 0.11 |
| CD11a, gran, membrane | 0.47 | 4.6E−01 | 0.12 | 56 | 51 | 61 | 50 | 62 | 47 | 61 | 0.11 |
| CD119, mono, membrane | 0.55 | 2.9E−01 | 0.13 | 56 | 50 | 63 | 57 | 56 | 8 | 8 | −0.05 |

TABLE 1-continued

Examples of polypeptide-DETERMINANTS with an immunological role that do not differentiate between bacterial versus viral infected subjects.
Positives and negatives correspond to bacterial and viral infected patients respectively. Positives (P) and Negatives (N) correspond to bacterial and viral infected patients respectively. TA, Sen, Spe and log2(R) correspond total accuracy sensitivity, specificity and log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| CD119, mean, membrane | 0.72 | 5.5E−01 | 0.16 | 56 | 88 | 25 | 54 | 67 | 8 | 8 | 0.17 |
| CD119, lymp, membrane | 0.44 | 2.6E−01 | 0.13 | 56 | 75 | 38 | 55 | 60 | 8 | 8 | −0.26 |
| CD119, gran, membrane | 0.83 | 5.3E−01 | −0.38 | 38 | 75 | 0 | 43 | 0 | 8 | 8 | 0.25 |
| CD116, mono, membrane | 0.47 | 4.2E−01 | 0.13 | 56 | 63 | 50 | 56 | 57 | 8 | 8 | −0.64 |
| CD114, mean, membrane | 0.89 | 8.9E−01 | −0.63 | 19 | 13 | 25 | 14 | 22 | 8 | 8 | −0.18 |
| CD107A, mono, membrane | 0.55 | 6.5E−01 | 0.08 | 54 | 53 | 55 | 65 | 43 | 45 | 29 | −0.19 |
| CD107A, mean, membrane | 0.53 | 2.9E−01 | −0.01 | 51 | 55 | 45 | 60 | 39 | 44 | 29 | −0.06 |
| CD107A, gran, membrane | 0.43 | 2.4E−01 | −0.12 | 49 | 64 | 24 | 57 | 30 | 45 | 29 | 0.26 |
| CD104, gran, membrane | 0.69 | 5.8E−01 | −0.25 | 38 | 38 | 38 | 38 | 38 | 8 | 8 | −0.06 |
| CD10, lymp, membrane | 0.58 | 4.6E−01 | 0 | 50 | 25 | 75 | 50 | 50 | 8 | 8 | 0.54 |

TABLE 2A

DETERMINANTS that differentiate between bacterial versus viral infected subjects.
Positives (P) and Negatives (N) correspond to bacterial and viral infected patients respectively. TA, Sen, Spe and log2(R) correspond total accuracy sensitivity, specificity and log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| B2M, soluble | 0.45 | 9.41E−02 | 0.126 | 45 | 62 | 60 | 70 | 51 | 68 | 45 | 0.45 |
| BCA-1, soluble | 0.65 | 3.1E−03 | 0.21 | 60 | 72 | 49 | 55 | 66 | 116 | 131 | −0.50 |
| CHI3L1, soluble | 0.77 | 7.6E−11 | 0.43 | 70 | 44 | 93 | 85 | 65 | 114 | 129 | 1.19 |
| Eotaxin, soluble | 0.67 | 4.4E−06 | 0.28 | 63 | 74 | 54 | 59 | 70 | 118 | 131 | −0.41 |
| IL1a, soluble | 0.62 | 2.2E−02 | 0.27 | 58 | 95 | 24 | 53 | 84 | 118 | 131 | −0.06 |
| IP10, soluble | 0.63 | 1.8E−02 | 0.21 | 58 | 85 | 34 | 53 | 71 | 118 | 131 | −0.85 |
| MCP, soluble | 0.74 | 5.3E−09 | 0.35 | 66 | 81 | 53 | 61 | 75 | 118 | 130 | −0.92 |
| Mac-2BP*, soluble | 0.77 | 1.6E−17 | 0.43 | 71 | 77 | 66 | 66 | 77 | 176 | 208 | |
| Mac-2BP, soluble | 0.73 | 7.0E−19 | 0.35 | 68 | 71 | 65 | 65 | 71 | 243 | 268 | |
| TRAIL, soluble (measured with Luminex) | 0.86 | 0.0E+00 | 0.56 | 78 | 85 | 71 | 72 | 84 | 118 | 131 | −1.76 |
| TRAIL*, soluble (measured with ELISA) | 0.89 | 2.6E−22 | 0.6 | 81 | 84 | 79 | 77 | 85 | 177 | 213 | −1.21 |
| TRAIL, soluble (measured with ELISA) | 0.85 | 3.8E−25 | 0.52 | 77 | 78 | 76 | 74 | 80 | 245 | 273 | −1.18 |
| sCD62L, soluble | 0.81 | 8.0E−06 | 0.44 | 72 | 72 | 71 | 72 | 71 | 29 | 28 | −0.29 |
| sVEGFR2, soluble | 0.77 | 7.1E−14 | 0.46 | 72 | 82 | 63 | 67 | 80 | 118 | 131 | −0.45 |
| CHP, total, intra | 0.73 | 2.0E−03 | 0.23 | 63 | 45 | 76 | 58 | 66 | 33 | 46 | 1.07 |
| CMPK2, lymp, intra | 0.71 | 2.2E−03 | 0.34 | 65 | 80 | 54 | 55 | 80 | 50 | 72 | −0.55 |
| CORO1C, total, intra | 0.71 | 5.0E−04 | 0.26 | 65 | 52 | 74 | 59 | 68 | 33 | 46 | 0.82 |
| EIF2AK2, lymp, intra | 0.79 | 2.6E−05 | 0.47 | 75 | 82 | 65 | 79 | 68 | 38 | 23 | −1.12 |
| ISG15, gran, intra | 0.76 | 2.5E−05 | 0.47 | 75 | 84 | 61 | 78 | 70 | 38 | 23 | −1.22 |
| ISG15, lymp, intra | 0.73 | 1.3E−04 | 0.47 | 75 | 82 | 65 | 79 | 68 | 38 | 23 | −0.96 |
| ISG15, mean, intra | 0.75 | 7.1E−05 | 0.42 | 73 | 84 | 57 | 76 | 68 | 37 | 23 | −0.86 |
| ISG15, mono, intra | 0.75 | 3.7E−05 | 0.46 | 75 | 84 | 61 | 78 | 70 | 37 | 23 | −1.16 |
| RPL22L1, lymp, intra | 0.69 | 3.2E−02 | 0.36 | 69 | 48 | 84 | 70 | 69 | 33 | 45 | 1.91 |
| RPL22L1, total, intra | 0.74 | 9.1E−04 | 0.33 | 68 | 55 | 78 | 64 | 70 | 33 | 45 | 1.42 |
| RTN3, lymp, intra | 0.75 | 3.2E−05 | 0.53 | 77 | 70 | 83 | 74 | 79 | 33 | 46 | 1.21 |
| RTN3, total, intra | 0.74 | 9.3E−05 | 0.32 | 67 | 61 | 72 | 61 | 72 | 33 | 46 | 1.03 |
| EIF4B, gran, intra | 0.70 | 6.8E−04 | 0.24 | 60 | 78 | 45 | 56 | 69 | 86 | 96 | −0.84 |
| EIF4B, lymp, intra | 0.73 | 5.0E−03 | 0.18 | 57 | 81 | 34 | 53 | 67 | 86 | 96 | −0.71 |
| EIF4B, mean, intra | 0.68 | 6.4E−03 | 0.14 | 55 | 75 | 38 | 52 | 63 | 84 | 93 | −0.73 |
| EIF4B, mono, intra | 0.70 | 6.8E−04 | 0.24 | 60 | 78 | 45 | 56 | 69 | 86 | 96 | −0.84 |
| IFIT1, gran, intra | 0.74 | 1.6E−06 | 0.4 | 75 | 84 | 54 | 80 | 62 | 51 | 24 | −0.59 |
| IFIT1, lymp, intra | 0.76 | 4.2E−07 | 0.47 | 78 | 90 | 52 | 79 | 72 | 51 | 25 | −0.85 |
| IFIT1, mean, intra | 0.77 | 3.9E−07 | 0.44 | 76 | 84 | 58 | 81 | 64 | 51 | 24 | −0.91 |
| IFIT1, mono, intra | 0.74 | 1.6E−06 | 0.4 | 75 | 84 | 54 | 80 | 62 | 51 | 24 | −0.59 |
| IFIT3, gran, intra | 0.76 | 2.1E−04 | 0.32 | 69 | 79 | 52 | 73 | 60 | 38 | 23 | −0.77 |
| IFIT3, lymp, intra | 0.73 | 1.4E−03 | 0.43 | 74 | 84 | 57 | 76 | 68 | 38 | 23 | −1.09 |
| IFIT3, mono, intra | 0.75 | 2.9E−04 | 0.32 | 68 | 78 | 52 | 73 | 60 | 37 | 23 | −0.63 |
| LOC26010, gran, intra | 0.64 | 3.9E−04 | 0.2 | 59 | 72 | 47 | 55 | 65 | 86 | 96 | −0.34 |
| LOC26010, mono, intra | 0.64 | 3.9E−04 | 0.2 | 59 | 72 | 47 | 55 | 65 | 86 | 96 | −0.34 |
| MBOAT2, total, intra | 0.67 | 1.5E−04 | 0.22 | 63 | 49 | 72 | 56 | 67 | 59 | 83 | 0.49 |
| MX1, gran, intra | 0.74 | 6.7E−10 | 0.36 | 68 | 78 | 57 | 66 | 72 | 124 | 119 | −0.90 |
| MX1, lymp, intra | 0.71 | 1.9E−08 | 0.29 | 65 | 74 | 55 | 63 | 67 | 124 | 119 | −0.66 |
| MX1, mean, intra | 0.72 | 9.7E−09 | 0.37 | 68 | 77 | 59 | 66 | 71 | 121 | 116 | −0.92 |
| MX1, mono, intra | 0.73 | 7.9E−10 | 0.36 | 68 | 78 | 57 | 65 | 72 | 123 | 119 | −0.91 |

TABLE 2A-continued

DETERMINANTS that differentiate between bacterial versus viral infected subjects.
Positives (P) and Negatives (N) correspond to bacterial and viral infected patients respectively. TA, Sen,
Spe and log2(R) correspond total accuracy sensitivity, specificity and log2 ratio between medians of the
positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| OAS2, gran, intra | 0.66 | 6.4E−04 | 0.22 | 61 | 73 | 48 | 59 | 63 | 124 | 120 | −0.63 |
| OAS2, mean, intra | 0.61 | 2.8E−02 | 0.15 | 58 | 70 | 44 | 57 | 59 | 121 | 117 | −0.46 |
| OAS2, mono, intra | 0.66 | 7.1E−04 | 0.21 | 60 | 73 | 48 | 59 | 63 | 123 | 120 | −0.61 |
| PCT, soluble | 0.65 | 0.008626 | 0.22 | 59 | 49 | 68 | 56 | 62 | 47 | 57 | −0.067 |
| RSAD2, gran, intra | 0.81 | 2.2E−14 | 0.41 | 70 | 79 | 61 | 68 | 74 | 119 | 115 | −1.50 |
| RSAD2, lymp, intra | 0.65 | 6.1E−06 | 0.19 | 59 | 68 | 50 | 59 | 60 | 119 | 115 | −0.38 |
| RSAD2, mean, intra | 0.77 | 1.6E−11 | 0.34 | 67 | 76 | 58 | 65 | 70 | 116 | 112 | −1.15 |
| RSAD2, mono, intra | 0.81 | 3.1E−14 | 0.4 | 70 | 79 | 61 | 67 | 74 | 118 | 115 | −1.50 |
| RSAD2, total, intra | 0.66 | 4.0E−06 | 0.3 | 64 | 78 | 51 | 62 | 69 | 116 | 112 | −0.67 |
| CD112, lymp, membrane | 0.89 | 6.5E−03 | 0.6 | 80 | 88 | 71 | 78 | 83 | 8 | 7 | −1.10 |
| CD134, lymp, membrane | 0.89 | 5.4E−03 | 0.4 | 69 | 88 | 50 | 64 | 80 | 8 | 8 | −1.21 |
| CD182, lymp, membrane | 0.70 | 3.5E−02 | 0.44 | 74 | 83 | 59 | 77 | 68 | 36 | 22 | −0.70 |
| CD231, mono, membrane | 0.81 | 2.1E−02 | 0.67 | 81 | 100 | 63 | 73 | 100 | 8 | 8 | −0.70 |
| CD235A, total, membrane | 0.94 | 1.7E−03 | 0.63 | 81 | 75 | 88 | 86 | 78 | 8 | 8 | 1.06 |
| CD335, lymp, membrane | 0.96 | 5.5E−02 | 0.73 | 87 | 88 | 86 | 88 | 86 | 8 | 7 | −0.57 |
| CD337, lymp, membrane | 0.96 | 4.3E−03 | 0.64 | 80 | 100 | 57 | 73 | 100 | 8 | 7 | −0.55 |
| CD45, lymp, membrane | 0.64 | 6.1E−03 | 0.25 | 63 | 54 | 71 | 59 | 66 | 54 | 69 | 0.47 |
| CD49D, total, membrane | 0.88 | 1.0E−02 | 0.61 | 80 | 75 | 86 | 86 | 75 | 8 | 7 | 1.03 |
| CD66A/C/D/E, lymp, membrane | 0.92 | 7.0E−02 | 0.52 | 75 | 88 | 63 | 70 | 83 | 8 | 8 | −0.50 |
| CD73, total, membrane | 0.98 | 1.2E−02 | 0.75 | 86 | 75 | 100 | 100 | 75 | 8 | 6 | 1.05 |
| CD84, total, membrane | 0.95 | 5.6E−02 | 0.73 | 85 | 75 | 100 | 100 | 71 | 8 | 5 | 0.51 |
| EGFR, lymp, membrane | 0.95 | 1.3E−02 | 0.76 | 87 | 100 | 71 | 80 | 100 | 8 | 7 | −1.01 |
| GPR162, total, membrane | 0.77 | 1.0E−03 | 0.39 | 70 | 70 | 70 | 79 | 59 | 37 | 23 | 0.84 |
| HLA-A/B/C, lymp, membrane | 0.84 | 4.3E−03 | 0.47 | 73 | 88 | 57 | 70 | 80 | 8 | 7 | −0.58 |
| HLA-A/B/C, mono, membrane | 0.86 | 1.1E−03 | 0.76 | 87 | 75 | 100 | 100 | 78 | 8 | 7 | −0.75 |
| ITGAM, gran, membrane | 0.68 | 8.6E−03 | 0.26 | 65 | 52 | 74 | 59 | 68 | 33 | 46 | 1.43 |
| ITGAM, mean, membrane | 0.67 | 1.1E−02 | 0.15 | 59 | 45 | 70 | 52 | 64 | 33 | 46 | 1.31 |
| ITGAM, total, membrane | 0.74 | 4.8E−04 | 0.37 | 70 | 58 | 78 | 66 | 72 | 33 | 46 | 1.29 |
| NRG1, mean, membrane | 0.68 | 3.1E−02 | 0.45 | 73 | 67 | 78 | 69 | 77 | 33 | 46 | 0.97 |
| NRG1, total, membrane | 0.76 | 1.0E−04 | 0.39 | 71 | 61 | 78 | 67 | 73 | 33 | 46 | 1.06 |
| RAP1B, gran, membrane | 0.66 | 5.4E−02 | 0.38 | 70 | 64 | 74 | 64 | 74 | 33 | 46 | 1.07 |
| RAP1B, mean, membrane | 0.68 | 2.2E−02 | 0.21 | 62 | 52 | 70 | 55 | 67 | 33 | 46 | 0.87 |
| RAP1B, total, membrane | 0.76 | 9.0E−05 | 0.32 | 67 | 58 | 74 | 61 | 71 | 33 | 46 | 1.17 |
| SELI, total, membrane | 0.67 | 7.2E−03 | 0.31 | 66 | 64 | 67 | 58 | 72 | 33 | 46 | 0.68 |
| SPINT2, lymp, membrane | 0.65 | 5.6E−02 | 0.28 | 59 | 85 | 41 | 51 | 79 | 33 | 46 | −0.53 |
| SSEA1, gran, membrane | 0.95 | 1.6E−03 | 0.6 | 80 | 88 | 71 | 78 | 83 | 8 | 7 | −0.68 |
| SSEA1, lymp, membrane | 0.84 | 3.1E−02 | 0.66 | 80 | 63 | 100 | 100 | 70 | 8 | 7 | −1.60 |
| ADIPOR1, gran, membrane | 0.68 | 8.3E−03 | 0.34 | 68 | 60 | 74 | 64 | 70 | 47 | 61 | 1.37 |
| ADIPOR1, mean, membrane | 0.69 | 2.2E−03 | 0.37 | 69 | 62 | 75 | 66 | 72 | 47 | 61 | 1.21 |
| ADIPOR1, total, membrane | 0.77 | 1.5E−05 | 0.41 | 71 | 60 | 80 | 70 | 72 | 47 | 61 | 1.41 |
| CD15, mean, membrane | 0.67 | 4.2E−02 | 0.29 | 65 | 59 | 70 | 61 | 68 | 56 | 69 | 0.78 |
| CD15, total, membrane | 0.74 | 3.0E−04 | 0.36 | 69 | 55 | 80 | 69 | 69 | 56 | 69 | 0.86 |
| CD8A, total, membrane | 0.97 | 3.0E−03 | 0.84 | 92 | 88 | 100 | 100 | 80 | 8 | 4 | 1.85 |
| IFITM1, lymp, membrane | 0.73 | 2.2E−06 | 0.29 | 63 | 76 | 52 | 58 | 71 | 79 | 90 | −0.64 |
| IFITM1, mono, membrane | 0.72 | 6.6E−06 | 0.32 | 66 | 72 | 60 | 61 | 71 | 79 | 90 | −0.75 |
| IFITM3, mono, membrane | 0.56 | 3.1E−01 | 0.02 | 52 | 64 | 39 | 54 | 49 | 99 | 88 | −0.70 |
| IL7R, mean, membrane | 0.60 | 1.3E−01 | 0.17 | 59 | 52 | 65 | 58 | 59 | 100 | 106 | 0.52 |
| IL7R, total, membrane | 0.71 | 5.5E−08 | 0.33 | 67 | 58 | 75 | 68 | 65 | 100 | 106 | 0.57 |
| CRP*, soluble | 0.89 | 1.2E−47 | 0.68 | 84 | 82 | 85 | 83 | 85 | 180 | 216 | 2.64 |
| CRP, soluble | 0.87 | 7.9E−50 | 0.61 | 81 | 78 | 83 | 81 | 81 | 249 | 277 | 2.4 |
| sTREM, soluble | 0.67 | 1.2E−05 | 0.33 | 66 | 56 | 77 | 70 | 64 | 96 | 98 | 0.55 |
| SAA*, soluble | 0.83 | 5.3E−33 | 0.53 | 78 | 77 | 79 | 75 | 80 | 177 | 213 | 1.56 |
| SAA, soluble | 0.80 | 9.5E−39 | 0.50 | 75 | 71 | 78 | 74 | 75 | 244 | 274 | 1.50 |
| ANC | 0.68 | 1.6E−07 | 0.26 | 63 | 53 | 72 | 65 | 62 | 151 | 159 | 0.68 |
| Age | 0.81 | 0.0E+00 | 0.48 | 73 | 55 | 90 | 84 | 67 | 179 | 181 | 3.52 |
| Cr | 0.81 | 6.4E−10 | 0.51 | 76 | 68 | 83 | 79 | 73 | 148 | 160 | 1.01 |
| K | 0.70 | 1.1E−04 | 0.34 | 67 | 72 | 62 | 65 | 69 | 149 | 151 | −0.10 |
| Lym (%) | 0.78 | 0.0E+00 | 0.43 | 71 | 79 | 63 | 68 | 75 | 178 | 179 | −1.00 |
| Neu (%) | 0.76 | 0.0E+00 | 0.41 | 70 | 77 | 63 | 68 | 74 | 179 | 180 | 0.39 |
| Pulse | 0.70 | 2.7E−09 | 0.34 | 67 | 68 | 66 | 63 | 70 | 141 | 163 | −0.32 |
| Urea | 0.64 | 1.7E−07 | 0.19 | 59 | 48 | 70 | 60 | 59 | 149 | 162 | 0.46 |
| goat IgG, lymp, membrane | 0.63 | 1.7E−01 | 0.27 | 63 | 78 | 47 | 60 | 68 | 83 | 83 | −0.54 |
| mouse IgG1, lymp, membrane | 0.91 | 1.0E−02 | 0.87 | 93 | 100 | 86 | 89 | 100 | 8 | 7 | −1.58 |
| mouse IgG1, mono, membrane | 1.00 | 1.9E−02 | 0.76 | 87 | 100 | 71 | 80 | 100 | 8 | 7 | −1.48 |
| mouse IgG3, lymp, membrane | 0.93 | 1.3E−02 | 0.87 | 93 | 100 | 86 | 89 | 100 | 8 | 7 | −1.43 |

*Results obtained on patients whose reference standard was determined by an expert consensus

TABLE 2B

DETERMINANTS that differentiate between mixed versus viral infected subjects
Positives (P) and Negatives (N) correspond to mixed (i.e. bacterial and viral co-infections) and
viral infected patients respectively. TA, Sen, Spe and log2(R) correspond total accuracy
sensitivity, specificity and log2 ratio between medians of the positive and negative classes
respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| ANC | 0.68 | 4.95E−05 | 0.18 | 69 | 47 | 74 | 29 | 86 | 36 | 159 | 0.5751 |
| ATP6V0B, gran, intra | 0.77 | 4.97E−03 | 0.3 | 64 | 81 | 60 | 28 | 95 | 16 | 86 | −0.55 |
| ATP6V0B, lymp, intra | 0.78 | 2.09E−03 | 0.26 | 63 | 75 | 60 | 26 | 93 | 16 | 86 | −0.71912 |
| ATP6V0B, mean, intra | 0.81 | 1.86E−03 | 0.39 | 69 | 88 | 65 | 33 | 96 | 16 | 83 | −0.74317 |
| ATP6V0B, mono, intra | 0.77 | 4.97E−03 | 0.3 | 64 | 81 | 60 | 28 | 95 | 16 | 86 | −0.55 |
| B2M, Plasma | 0.8 | 0.0008 | 0.44 | 74 | 63 | 81 | 67 | 78 | 16 | 26 | −0.33734 |
| CES1, gran, intra | 0.80 | 7.13E−03 | 0.24 | 61 | 75 | 58 | 25 | 93 | 16 | 86 | −0.87267 |
| CES1, lymp, intra | 0.78 | 1.07E−02 | 0.37 | 67 | 88 | 63 | 30 | 96 | 16 | 86 | −0.75882 |
| CES1, mean, intra | 0.81 | 6.88E−03 | 0.29 | 66 | 75 | 64 | 29 | 93 | 16 | 83 | −0.84451 |
| CES1, mono, intra | 0.80 | 7.13E−03 | 0.24 | 61 | 75 | 58 | 25 | 93 | 16 | 86 | −0.87267 |
| CHI3L1, plasma, secreted | 0.70 | 3.05E−05 | 0.43 | 84 | 50 | 91 | 56 | 89 | 28 | 129 | 1.167 |
| CMPK2, lymp, intra | 0.79 | 3.33E−03 | 0.36 | 72 | 77 | 71 | 32 | 94 | 13 | 72 | −0.80191 |
| CORO1A, mean, intra | 0.75 | 7.62E−04 | 0.27 | 59 | 81 | 54 | 27 | 93 | 21 | 101 | −0.86925 |
| CRP | 0.92 | 0.00E+00 | 0.62 | 88 | 79 | 89 | 61 | 95 | 38 | 179 | 2.7501 |
| HERC5, lymp, intra | 0.75 | 6.80E−02 | 0.28 | 61 | 81 | 57 | 27 | 94 | 16 | 84 | −0.78318 |
| IFITM1, lymp, membrane | 0.78 | 1.40E−02 | 0.22 | SS | 81 | 50 | 22 | 94 | 16 | 90 | −1.1503 |
| LIPT1, gran, intra | 0.76 | 7.28E−03 | 0.23 | 60 | 75 | 57 | 24 | 92 | 16 | 86 | −0.44913 |
| LIPT1, lymp, intra | 0.80 | 6.47E−03 | 0.35 | 65 | 88 | 60 | 29 | 96 | 16 | 86 | −0.95089 |
| LIPT1, mean, intra | 0.75 | 8.21E−03 | 0.22 | 59 | 75 | 55 | 24 | 92 | 16 | 83 | −0.45201 |
| LIPT1, mono, intra | 0.76 | 7.28E−03 | 0.23 | 60 | 75 | 57 | 24 | 92 | 16 | 86 | −0.44913 |
| LIPT1, mono, intra | 0.84 | 7.77E−04 | 0.37 | 68 | 88 | 65 | 29 | 97 | 16 | 96 | −0.83291 |
| LOC26010, lymp, intra | 0.83 | 9.65E−04 | 0.39 | 71 | 88 | 68 | 31 | 97 | 16 | 96 | −0.90319 |
| LOC26010, mean, intra | 0.83 | 7.68E−04 | 0.37 | 68 | 88 | 65 | 30 | 97 | 16 | 93 | −0.84355 |
| LOC26010, mono, intra | 0.84 | 7.77E−04 | 0.37 | 68 | 88 | 65 | 29 | 97 | 16 | 96 | −0.83291 |
| LRDD, lymp, intra | 0.84 | 3.82E−03 | 0.48 | 78 | 88 | 76 | 39 | 97 | 8 | 46 | −1.042 |
| Lym (%) | 0.68 | 3.41E−04 | 0.14 | 57 | 62 | 56 | 24 | 87 | 39 | 179 | −0.94237 |
| MCP-2, serum, secreted | 0.71 | 3.26E−03 | 0.22 | 56 | 77 | 52 | 27 | 91 | 30 | 130 | −0.79708 |
| MX1, gran, intra | 0.79 | 2.16E−03 | 0.31 | 61 | 86 | 57 | 26 | 96 | 21 | 119 | −1.2255 |
| MX1, lymp, intra | 0.76 | 1.55E−03 | 0.27 | 61 | 81 | 57 | 25 | 94 | 21 | 119 | −1.1924 |
| MX1, mean, intra | 0.77 | 1.89E−03 | 0.31 | 64 | 81 | 61 | 27 | 95 | 21 | 116 | −1.1255 |
| MX1, mono, intra | 0.79 | 2.16E−03 | 0.31 | 61 | 86 | 57 | 26 | 96 | 21 | 119 | −1.2255 |
| Neu (%) | 0.67 | 4.46E−04 | 0.14 | 58 | 62 | 57 | 24 | 87 | 39 | 180 | 0.36 |
| OAS2, gran, intra | 0.75 | 4.54E−02 | 0.23 | 55 | 81 | 51 | 22 | 94 | 21 | 120 | −0.77111 |
| OAS2, mono, intra | 0.75 | 4.54E−02 | 0.23 | 55 | 81 | 51 | 22 | 94 | 21 | 120 | −0.77111 |
| PARP9, gran, intra | 0.77 | 2.40E−03 | 0.33 | 66 | 81 | 63 | 30 | 94 | 16 | 81 | −0.77811 |
| PARP9, lymp, intra | 0.87 | 2.42E−03 | 0.48 | 76 | 88 | 74 | 40 | 97 | 16 | 81 | −1.0077 |
| PARP9, mono, intra | 0.77 | 2.40E−03 | 0.33 | 66 | 81 | 63 | 30 | 94 | 16 | 81 | −0.77811 |
| RSAD2, gran, intra | 0.83 | 2.11E−04 | 0.34 | 65 | 86 | 62 | 29 | 96 | 21 | 115 | −1.5097 |
| RSAD2, lymp, intra | 0.75 | 3.01E−03 | 0.28 | 61 | 81 | 57 | 26 | 94 | 21 | 115 | −0.80053 |
| RSAD2, mean, intra | 0.79 | 4.35E−04 | 0.35 | 65 | 86 | 62 | 30 | 96 | 21 | 112 | −1.2099 |
| RSAD2, mono, intra | 0.83 | 2.11E−04 | 0.34 | 65 | 86 | 62 | 29 | 96 | 21 | 115 | −1.5097 |
| SART3, lymp, intra | 0.82 | 5.82E−03 | 0.36 | 68 | 82 | 65 | 32 | 95 | 11 | 55 | −1.0403 |
| SAA, Plasma, secreted | 0.90 | 0.00353 | 0.63 | 82 | 100 | 78 | 50 | 100 | 5 | 23 | 0.61466 |
| TRAIL, Plasma, secreted | 0.88 | 1.46E−06 | 0.49 | 77 | 83 | 76 | 45 | 95 | 30 | 129 | −1.5522 |
| WBC | 0.68 | 8.15E−06 | 0.18 | 67 | 51 | 71 | 27 | 87 | 39 | 180 | 0.44066 |
| Mac-2BP, Plasma | 0.61 | 0.007982 | 0.16 | 55 | 68 | 53 | 24 | 89 | 47 | 220 | −0.5046 |
| sVEGFR2, Plasma | 0.73 | 0.003814 | 0.32 | 69 | 71 | 69 | 36 | 90 | 34 | 134 | −0.42652 |

TABLE 2C

DETERMINANTS that differentiate between mixed versus bacterial infected subjects
Positives (P) and Negatives (N) correspond to mixed (i.e. bacterial and viral co-infections) and bacterial
infected patients respectively. TA, Sen, Spe and log2(R) correspond total accuracy sensitivity,
specificity and log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| BRI3BP, gran, intra | 0.91 | 2.96E−04 | 0.37 | 75 | 71 | 76 | 36 | 93 | 7 | 37 | −1.9632 |
| BRI3BP, mean, intra | 0.91 | 2.73E−04 | 0.4 | 77 | 71 | 78 | 38 | 94 | 7 | 37 | −1.9369 |
| BRI3BP, mono, intra | 0.91 | 2.96E−04 | 0.37 | 75 | 71 | 76 | 36 | 93 | 7 | 37 | −1.9632 |
| CES1, gran, intra | 0.78 | 1.03E−03 | 0.29 | 64 | 75 | 61 | 33 | 90 | 16 | 61 | −1.0125 |
| CES1, lymp, intra | 0.78 | 2.40E−03 | 0.38 | 65 | 88 | 59 | 36 | 95 | 16 | 61 | −0.77096 |
| CES1, mean, intra | 0.79 | 6.48E−04 | 0.35 | 65 | 81 | 61 | 36 | 92 | 16 | 59 | −1.1055 |
| CES1, mono, intra | 0.78 | 1.03E−03 | 0.29 | 64 | 75 | 61 | 33 | 90 | 16 | 61 | −1.0125 |
| Cr | 0.69 | 6.56E−02 | 0.19 | 53 | 76 | 48 | 25 | 90 | 34 | 148 | −0.87447 |
| LOC26010, lymp, intra | 0.77 | 1.01E−03 | 0.34 | 68 | 81 | 65 | 30 | 95 | 16 | 86 | −0.78619 |
| PARP9, lymp, intra | 0.76 | 1.91E−03 | 0.38 | 68 | 81 | 64 | 39 | 92 | 16 | 56 | −0.60984 |

TABLE 2C-continued

DETERMINANTS that differentiate between mixed versus bacterial infected subjects
Positives (P) and Negatives (N) correspond to mixed (i.e. bacterial and viral co-infections) and bacterial
infected patients respectively. TA, Sen, Spe and log2(R) correspond total accuracy sensitivity,
specificity and log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| TRIM22, gran, intra | 0.80 | 8.44E−04 | 0.36 | 70 | 82 | 68 | 31 | 96 | 11 | 63 | −0.96135 |
| TRIM22, mean, intra | 0.81 | 7.76E−04 | 0.36 | 70 | 82 | 68 | 31 | 96 | 11 | 63 | −0.91131 |
| TRIM22, mono, intra | 0.80 | 8.44E−04 | 0.36 | 70 | 82 | 68 | 31 | 96 | 11 | 63 | −0.96135 |

TABLE 2D

DETERMINANTS that differentiate between bacterial or mixed versus viral infected subjects
Positives (P) and Negatives (N) correspond to bacterial or mixed and viral infected patients
respectively. TA, Sen, Spe and log2(R) correspond total accuracy sensitivity, specificity and
log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| ADIPOR1, total, membrane | 0.74 | 3.63E−05 | 0.42 | 71 | 61 | 80 | 75 | 68 | 59 | 61 | 1.38 |
| ANC | 0.69 | 3.39E−08 | 0.24 | 61 | 51 | 72 | 69 | 56 | 187 | 159 | 0.62 |
| ARG1, total, intra | 0.73 | 1.82E−04 | 0.31 | 66 | 56 | 74 | 66 | 65 | 41 | 46 | 0.75 |
| AST (GOT) | 0.37 | 5.98E−01 | 0.13 | 62 | 77 | 35 | 69 | 45 | 131 | 71 | −0.54 |
| Age | 0.78 | 0.00E+00 | 0.43 | 68 | SO | 90 | 86 | 60 | 218 | 181 | 3.36 |
| B2M, plasma, secreted | 0.78 | 6.25E−05 | 0.49 | 75 | 74 | 75 | 82 | 66 | 43 | 28 | −0.28 |
| Bili total | 0.72 | 7.24E−03 | 0.28 | 60 | 54 | 79 | 90 | 34 | 96 | 29 | 0.82 |
| CD15, total, membrane | 0.73 | 4.01E−04 | 0.35 | 67 | 56 | 78 | 73 | 64 | 71 | 69 | 0.84 |
| CD337, lymp, membrane | 0.96 | 1.58E−03 | 0.67 | 83 | 100 | 57 | 79 | 100 | 11 | 7 | −0.52 |
| CD73, total, membrane | 0.99 | 7.22E−03 | 0.78 | 88 | 82 | 100 | 100 | 75 | 11 | 6 | 1.06 |
| CD84, total, membrane | 0.95 | 4.24E−02 | 0.59 | 81 | 82 | 80 | 90 | 67 | 11 | 5 | 0.53 |
| CHI3L1, plasma, secreted | 0.76 | 1.67E−10 | 0.44 | 68 | 45 | 94 | 89 | 61 | 142 | 129 | 1.19 |
| CHP, total, intra | 0.73 | 4.15E−03 | 0.28 | 64 | 51 | 76 | 66 | 64 | 41 | 46 | 0.98 |
| CMPK2, lymp, intra | 0.73 | 1.63E−04 | 0.37 | 67 | 79 | 57 | 62 | 76 | 63 | 72 | −0.59 |
| CORO1C, total, intra | 0.71 | 4.22E−04 | 0.26 | 63 | 54 | 72 | 63 | 63 | 41 | 46 | 0.83 |
| CRP, soluble | 0.87 | 7.9E−50 | 0.61 | 81 | 78 | 83 | 81 | 81 | 249 | 277 | 2.68 |
| Cr | 0.76 | 5.27E−09 | 0.45 | 72 | 64 | 81 | 79 | 66 | 182 | 160 | 1.00 |
| EIF2AK2, lymp, intra | 0.78 | 2.06E−05 | 0.43 | 74 | 81 | 61 | 80 | 64 | 43 | 23 | −0.99 |
| EIF4B, gran, intra | 0.69 | 1.33E−03 | 0.17 | 59 | 75 | 41 | 57 | 61 | 102 | 96 | −0.75 |
| EIF4B, lymp, intra | 0.70 | 1.04E−02 | 0.13 | 57 | 78 | 33 | 56 | 59 | 102 | 96 | −0.67 |
| EIF4B, mean, intra | 0.67 | 1.85E−02 | 0.08 | 54 | 72 | 35 | SS | 54 | 100 | 93 | −0.70 |
| EIF4B, mono, intra | 0.69 | 1.33E−03 | 0.17 | 59 | 75 | 41 | 57 | 61 | 102 | 96 | −0.75 |
| Eotaxin, plasma, secreted | 0.64 | 5.27E−06 | 0.23 | 62 | 69 | 53 | 63 | 60 | 148 | 131 | −0.39 |
| GPR162, total, membrane | 0.74 | 1.20E−03 | 0.41 | 71 | 69 | 74 | 83 | 57 | 42 | 23 | 0.79 |
| HLA-A/B/C, mono, membrane | 0.94 | 1.66E−04 | 0.8 | 89 | 82 | 100 | 100 | 78 | 11 | 7 | −0.80 |
| IFIT1, gran, intra | 0.76 | 5.38E−07 | 0.41 | 76 | 85 | 54 | 81 | 62 | 54 | 24 | −0.63 |
| IFIT1, lymp, intra | 0.75 | 1.77E−07 | 0.44 | 77 | 89 | 52 | 80 | 68 | 54 | 25 | −0.84 |
| IFIT1, mean, intra | 0.79 | 1.28E−07 | 0.45 | 77 | 85 | 58 | 82 | 64 | 54 | 24 | −0.92 |
| IFIT1, mono, intra | 0.76 | 5.38E−07 | 0.41 | 76 | 85 | 54 | 81 | 62 | 54 | 24 | −0.63 |
| IFIT3, gran, intra | 0.75 | 1.81E−04 | 0.35 | 71 | 81 | 52 | 76 | 60 | 43 | 23 | −0.63 |
| IFIT3, mono, intra | 0.74 | 2.48E−04 | 0.34 | 71 | 81 | 52 | 76 | 60 | 42 | 23 | −0.60 |
| IFITM1, lymp, membrane | 0.74 | 1.01E−06 | 0.29 | 64 | 77 | 51 | 62 | 68 | 95 | 90 | −0.73 |
| IFITM1, mono, membrane | 0.70 | 4.13E−06 | 0.31 | 65 | 72 | 59 | 65 | 66 | 95 | 90 | −0.62 |
| IL1a, plasma, secreted | 0.64 | 1.73E−02 | 0.24 | 61 | 93 | 24 | 58 | 76 | 148 | 131 | −0.06 |
| IL7R, total, membrane | 0.71 | 1.56E−08 | 0.37 | 68 | 59 | 77 | 75 | 62 | 122 | 106 | 0.56 |
| IP10, plasma, secreted | 0.61 | 7.41E−02 | 0.19 | 59 | 83 | 33 | 58 | 63 | 148 | 131 | −0.78 |
| ISG15, gran, intra | 0.75 | 1.70E−05 | 0.45 | 76 | 86 | 57 | 79 | 68 | 43 | 23 | −1.16 |
| ISG15, mean, intra | 0.74 | 4.72E−05 | 0.41 | 74 | 83 | 57 | 78 | 65 | 42 | 23 | −0.80 |
| ISG15, mono, intra | 0.75 | 2.48E−05 | 0.44 | 75 | 86 | 57 | 78 | 68 | 42 | 23 | −1.07 |
| ITGAM, total, membrane | 0.73 | 3.29E−04 | 0.36 | 68 | 51 | 83 | 72 | 66 | 41 | 46 | 1.26 |
| K | 0.68 | 1.30E−04 | 0.3 | 66 | 69 | 61 | 68 | 62 | 183 | 151 | −0.10 |
| KIAA0082, gran, intra | 0.65 | 2.33E−04 | 0.2 | 60 | 68 | 52 | 57 | 64 | 77 | 84 | −0.26 |
| KIAA0082, mono, intra | 0.65 | 2.33E−04 | 0.2 | 60 | 68 | 52 | 57 | 64 | 77 | 84 | −0.26 |
| LOC26010, gran, intra | 0.67 | 1.67E−05 | 0.24 | 62 | 75 | 49 | 61 | 64 | 102 | 96 | −0.45 |
| LOC26010, mean, intra | 0.65 | 1.32E−04 | 0.22 | 61 | 73 | 48 | 60 | 63 | 100 | 93 | −0.39 |
| LOC26010, mono, intra | 0.67 | 1.67E−05 | 0.24 | 62 | 75 | 49 | 61 | 64 | 102 | 96 | −0.45 |
| Lym (%) | 0.76 | 0.00E+00 | 0.41 | 71 | 77 | 63 | 72 | 70 | 217 | 179 | −0.97 |
| MBOAT2, total, intra | 0.66 | 8.46E−05 | 0.24 | 62 | 51 | 72 | 62 | 62 | 75 | 83 | 0.57 |
| MCP-2, plasma, secreted | 0.73 | 2.17E−10 | 0.34 | 67 | 80 | 53 | 66 | 70 | 148 | 130 | −0.90 |
| MX1, gran, intra | 0.74 | 7.00E−11 | 0.38 | 69 | 79 | 57 | 69 | 69 | 145 | 119 | −1.00 |
| MX1, lymp, intra | 0.72 | 1.40E−09 | 0.32 | 67 | 77 | SS | 67 | 66 | 145 | 119 | −0.70 |
| MX1, mean, intra | 0.73 | 1.10E−09 | 0.36 | 69 | 77 | 59 | 69 | 67 | 142 | 116 | −0.93 |
| MX1, mono, intra | 0.74 | 8.16E−11 | 0.37 | 69 | 79 | 57 | 69 | 69 | 144 | 119 | −1.00 |
| Mac-2BP, plasma, secreted | 0.76 | 9.56E−12 | 0.46 | 73 | 86 | 58 | 69 | 79 | 142 | 129 | −0.87 |

TABLE 2D-continued

DETERMINANTS that differentiate between bacterial or mixed versus viral infected subjects
Positives (P) and Negatives (N) correspond to bacterial or mixed and viral infected patients
respectively. TA, Sen, Spe and log2(R) correspond total accuracy sensitivity, specificity and
log2 ratio between medians of the positive and negative classes respectively.

| DETERMINANT | AUC | t-test P-value | MCC | TA % | Sen % | Spe % | PPV % | NPV % | P | N | log2(R) |
|---|---|---|---|---|---|---|---|---|---|---|---|
| Mac-2BP, soluble | 0.73 | 7.0E−19 | 0.35 | 68 | 71 | 65 | 65 | 71 | 243 | 268 | −0.84 |
| NA | 0.62 | 3.88E−05 | 0.18 | 59 | 58 | 60 | 63 | SS | 190 | 164 | −0.01 |
| NRG1, total, membrane | 0.77 | 3.91E−05 | 0.42 | 71 | 63 | 78 | 72 | 71 | 41 | 46 | 1.06 |
| Neu (%) | 0.74 | 0.00E+00 | 0.36 | 68 | 74 | 62 | 70 | 66 | 218 | 180 | 0.39 |
| OAS2, gran, intra | 0.67 | 2.55E−04 | 0.24 | 63 | 76 | 48 | 64 | 62 | 145 | 120 | −0.68 |
| OAS2, mean, intra | 0.63 | 1.34E−02 | 0.18 | 60 | 73 | 44 | 61 | 57 | 142 | 117 | −0.49 |
| OAS2, mono, intra | 0.67 | 2.82E−04 | 0.24 | 63 | 76 | 48 | 63 | 62 | 144 | 120 | −0.67 |
| PARP9, gran, intra | 0.65 | 5.17E−04 | 0.21 | 59 | 72 | 48 | SS | 66 | 72 | 81 | −0.43 |
| PARP9, lymp, intra | 0.70 | 2.63E−04 | 0.29 | 64 | 72 | 57 | 60 | 70 | 72 | 81 | −0.53 |
| PARP9, mono, intra | 0.65 | 5.17E−04 | 0.21 | 59 | 72 | 48 | SS | 66 | 72 | 81 | −0.43 |
| PBS_Mem_2, lymp, membrane | 0.61 | 6.40E−01 | −0.1 | 43 | 20 | 70 | 44 | 42 | 100 | 83 | −0.54 |
| PTEN, gran, intra | 0.62 | 5.00E−02 | 0.16 | 59 | 70 | 46 | 60 | 56 | 92 | 78 | −0.68 |
| Pulse | 0.66 | 1.91E−07 | 0.24 | 62 | 64 | 60 | 64 | 60 | 178 | 163 | −0.25 |
| RAP1B, total, membrane | 0.77 | 2.25E−05 | 0.33 | 67 | 59 | 74 | 67 | 67 | 41 | 46 | 1.17 |
| RPL22L1, total, intra | 0.74 | 1.11E−03 | 0.37 | 69 | 59 | 78 | 71 | 67 | 41 | 45 | 1.29 |
| RSAD2, gran, intra | 0.81 | 2.22E−16 | 0.41 | 71 | 80 | 60 | 71 | 71 | 140 | 115 | −1.50 |
| RSAD2, lymp, intra | 0.67 | 3.27E−07 | 0.22 | 62 | 69 | 52 | 64 | 58 | 140 | 115 | −0.46 |
| RSAD2, mean, intra | 0.78 | 4.19E−13 | 0.39 | 70 | 77 | 61 | 71 | 69 | 137 | 112 | −1.17 |
| RSAD2, mono, intra | 0.81 | 3.33E−16 | 0.41 | 71 | 80 | 60 | 71 | 71 | 139 | 115 | −1.50 |
| RSAD2, total, intra | 0.65 | 3.12E−06 | 0.29 | 65 | 77 | 51 | 66 | 64 | 137 | 112 | −0.67 |
| RTN3, total, intra | 0.74 | 5.53E−05 | 0.31 | 66 | 56 | 74 | 66 | 65 | 41 | 46 | 1.03 |
| SELI, total, membrane | 0.71 | 9.85E−04 | 0.4 | 70 | 66 | 74 | 69 | 71 | 41 | 46 | 0.73 |
| SSEA1, gran, membrane | 0.94 | 8.39E−04 | 0.53 | 78 | 82 | 71 | 82 | 71 | 11 | 7 | −0.67 |
| SAA, soluble | 0.80 | 9.50E−39 | 0.5 | 75 | 71 | 78 | 74 | 75 | 244 | 274 | 1.61 |
| TRAIL, soluble | 0.85 | 3.8E−25 | 0.52 | 77 | 78 | 76 | 74 | 80 | 245 | 273 | −1.30 |
| Urea | 0.62 | 1.51E−06 | 0.18 | 58 | 48 | 69 | 64 | 54 | 187 | 162 | 0.39 |
| VEGFR2, plasma, secreted | 0.74 | 2.46E−03 | 0.31 | 66 | 81 | 48 | 64 | 68 | 36 | 31 | −0.25 |
| WBC | 0.62 | 2.22E−05 | 0.17 | 57 | 48 | 68 | 65 | 52 | 218 | 180 | 0.29 |
| ZBP1, total, intra | 0.74 | 8.14E−05 | 0.29 | 65 | SS | 74 | 65 | 65 | 40 | 46 | 0.83 |
| mIgG1, mono, membrane | 0.94 | 1.12E−02 | 0.64 | 83 | 91 | 71 | 83 | 83 | 11 | 7 | −1.36 |
| sCD62L, plasma, secreted | 0.77 | 1.90E−05 | 0.38 | 69 | 67 | 71 | 78 | 59 | 43 | 28 | −0.27 |
| sTREM, plasma, secreted | 0.69 | 1.90E−06 | 0.33 | 66 | 56 | 77 | 73 | 60 | 111 | 98 | 0.56 |
| sTREM1, plasma, secreted | 0.75 | 2.94E−04 | 0.4 | 68 | 58 | 82 | 83 | 56 | 43 | 28 | 0.38 |
| sVEGFR2, plasma, secreted | 0.74 | 7.05E−10 | 0.4 | 70 | 79 | 60 | 69 | 72 | 148 | 131 | −0.41 |

TABLE 2E

DETERMINANTS pairs that differentiate between bacterial or mixed versus viral infected subjects
Positives (P) and Negatives (N) correspond to bacterial or mixed and viral infected patients
respectively. TA, Sen, Spe and log2(R) correspond total accuracy sensitivity, specificity and
log2 ratio between medians of the positive and negative classes respectively.

| DETERMINANT #1 | DETERMINANT #2 | AUC | MCC | Sen % | Spe % | PPV % | NPV % | P | N |
|---|---|---|---|---|---|---|---|---|---|
| CRP, soluble | Mac-2BP, soluble | 0.91 | 0.66 | 83 | 85 | 83 | 84 | 243 | 268 |
| CRP, soluble | SAA, soluble | 0.87 | 0.64 | 78 | 83 | 80 | 81 | 244 | 274 |
| CRP, soluble | TRAIL (measured with ELISA), soluble | 0.91 | 0.66 | 84 | 82 | 81 | 85 | 245 | 273 |
| Mac-2BP, soluble | SAA, soluble | 0.85 | 0.54 | 76 | 80 | 77 | 78 | 243 | 268 |
| Mac-2BP, soluble | TRAIL (measured with ELISA), soluble | 0.87 | 0.54 | 78 | 80 | 78 | 80 | 243 | 267 |
| SAA, soluble | TRAIL (measured with ELISA), soluble | 0.88 | 0.61 | 82 | 80 | 78 | 83 | 244 | 273 |

TABLE 2F

DETERMINANTS triplets that differentiate between bacterial or mixed versus viral infected subjects
Positives (P) and Negatives (N) correspond to bacterial or mixed and viral infected patients respectively.
TA, Sen, Spe and log2(R) correspond total accuracy sensitivity, specificity and log2 ratio between
medians of the positive and negative classes respectively.

| DETERMINANT #1 | DETERMINANT #2 | DETERMINANT #3 | AUC | MCC | Sen % | Spe % | PPV % | NPV % | P | N |
|---|---|---|---|---|---|---|---|---|---|---|
| CRP, soluble | Mac-2BP, soluble | SAA, soluble | 0.91 | 0.66 | 83 | 84 | 83 | 85 | 243 | 268 |
| CRP, soluble | Mac-2BP, soluble | TRAIL (measured with ELISA), soluble | 0.93 | 0.71 | 84 | 88 | 86 | 86 | 243 | 267 |
| CRP, soluble | SAA, soluble | TRAIL (measured with ELISA), soluble | 0.91 | 0.65 | 83 | 83 | 81 | 85 | 244 | 273 |
| Mac-2BP, soluble | SAA, soluble | TRAIL (measured with ELISA), soluble | 0.90 | 0.64 | 83 | 82 | 81 | 84 | 243 | 267 |

TABLE 2G

DETERMINANTS that differentiate between subjects with an infectious versus non-infectious diseases
Positives (P) and Negatives (N) correspond to patients with an infectious and non-infectious disease
respectively. TA, Sen, Spe and log2(R) correspond total accuracy sensitivity, specificity and log2 ratio
between medians of the positive and negative classes respectively.

| Gene Symbol | AUC | t-test P-value | MCC | TA % | Sen % | Spe % | PPV % | NPV % | P | N | log2(R) |
|---|---|---|---|---|---|---|---|---|---|---|---|
| ARPC2, total, intra | 0.73 | 4.57E−03 | 0.27 | 57 | 53 | 88 | 97 | 21 | 170 | 24 | 1.01 |
| ATP6V0B, total, intra | 0.76 | 4.50E−05 | 0.3 | 61 | 56 | 84 | 95 | 28 | 158 | 32 | 0.69 |
| BCA-1, serum, secreted | 0.83 | 3.23E−03 | 0.22 | 69 | 69 | 79 | 98 | 11 | 277 | 14 | 1.27 |
| CCL19-MIP3b, serum, secreted | 0.84 | 2.40E−03 | 0.26 | 72 | 71 | 86 | 99 | 13 | 280 | 14 | 1.30 |
| CES1, total, intra | 0.73 | 5.71E−04 | 0.16 | 54 | 50 | 72 | 90 | 23 | 158 | 32 | 0.84 |
| CMPK2, total, intra | 0.87 | 3.35E−04 | 0.39 | 68 | 64 | 95 | 99 | 28 | 130 | 19 | 1.06 |
| Cr | 0.68 | 1.22E−01 | 0.13 | 69 | 72 | 46 | 90 | 19 | 342 | 48 | −0.55 |
| Eos (%) | 0.73 | 3.56E−06 | 0.22 | 77 | 81 | 47 | 92 | 25 | 334 | 45 | −2.15 |
| HERC5, total, intra | 0.73 | 2.50E−04 | 0.28 | 61 | 57 | 81 | 94 | 27 | 157 | 31 | 0.72 |
| IFI6, total, intra | 0.80 | 3.10E−04 | 0.41 | 70 | 67 | 89 | 97 | 33 | 105 | 19 | 0.90 |
| IFIT3, gran, intra | 0.74 | 1.65E−03 | 0.24 | 58 | 54 | 80 | 94 | 23 | 206 | 35 | 1.59 |
| IFIT3, mean, intra | 0.76 | 1.27E−03 | 0.23 | 56 | 53 | 81 | 95 | 21 | 203 | 31 | 1.57 |
| IFIT3, mono, intra | 0.75 | 1.61E−03 | 0.26 | 58 | 54 | 82 | 95 | 23 | 205 | 34 | 1.62 |
| IFIT3, total, intra | 0.81 | 1.03E−04 | 0.29 | 64 | 62 | 81 | 95 | 24 | 203 | 31 | 1.90 |
| KIAA0082, total, intra | 0.75 | 6.81E−05 | 0.3 | 63 | 59 | 81 | 94 | 29 | 156 | 32 | 0.54 |
| LIPT1, total, intra | 0.73 | 1.50E−04 | 0.25 | 59 | 56 | 78 | 93 | 26 | 158 | 32 | 0.75 |
| LOC26010, total, intra | 0.76 | 4.30E−05 | 0.33 | 63 | 59 | 88 | 97 | 26 | 193 | 32 | 0.64 |
| LRDD, total, intra | 0.86 | 4.02E−02 | 0.41 | 73 | 71 | 91 | 98 | 29 | 87 | 11 | 0.83 |
| Maximal temperature | 0.92 | 0.00E+00 | 0.55 | 86 | 86 | 86 | 98 | 44 | 397 | 51 | 0.08 |
| MBOAT2, total, intra | 0.72 | 2.99E−04 | 0.26 | 62 | 59 | 75 | 92 | 27 | 158 | 32 | 1.27 |
| Mouse IgG_Intra, total, intra | 0.74 | 2.00E−02 | 0.33 | 63 | 59 | 84 | 95 | 30 | 157 | 32 | 0.72 |
| MX1, gran, intra | 0.76 | 1.62E−05 | 0.26 | 61 | 58 | 80 | 95 | 23 | 264 | 41 | 1.15 |
| MX1, lymp, intra | 0.71 | 2.42E−04 | 0.22 | 56 | 52 | 80 | 95 | 21 | 264 | 41 | 0.65 |
| MX1, mean, intra | 0.76 | 1.99E−05 | 0.25 | 60 | 57 | 81 | 95 | 21 | 258 | 37 | 1.09 |
| MX1, mono, intra | 0.77 | 1.12E−05 | 0.28 | 62 | 59 | 83 | 96 | 23 | 263 | 40 | 1.16 |
| MX1, total, intra | 0.81 | 5.34E−07 | 0.31 | 65 | 62 | 84 | 96 | 24 | 258 | 37 | 1.47 |
| OAS2, gran, intra | 0.74 | 1.56E−04 | 0.24 | 61 | 59 | 76 | 94 | 22 | 265 | 41 | 0.69 |
| OAS2, mean, intra | 0.74 | 1.44E−04 | 0.23 | 61 | 59 | 76 | 94 | 21 | 259 | 37 | 0.75 |
| OAS2, mono, intra | 0.74 | 1.54E−04 | 0.25 | 62 | 59 | 78 | 95 | 22 | 264 | 40 | 0.70 |
| OAS2, total, intra | 0.80 | 5.45E−06 | 0.31 | 66 | 63 | 84 | 96 | 24 | 259 | 37 | 1.24 |
| PARP9, total, intra | 0.77 | 2.76E−04 | 0.33 | 64 | 60 | 85 | 96 | 28 | 148 | 27 | 0.90 |
| PBS_Intra_2, total, intra | 0.76 | 6.27E−03 | 0.34 | 62 | 57 | 88 | 96 | 30 | 114 | 24 | 0.59 |
| Pulse | 0.79 | 6.81E−11 | 0.36 | 68 | 66 | 88 | 97 | 26 | 341 | 48 | 0.49 |
| QARS, total, intra | 0.88 | 3.15E−01 | 0.47 | 74 | 71 | 100 | 100 | 31 | 87 | 11 | 1.03 |
| RAB13, gran, intra | 0.81 | 2.00E−03 | 0.38 | 67 | 63 | 89 | 97 | 30 | 105 | 19 | 0.67 |
| RAB13, mean, intra | 0.80 | 1.01E−03 | 0.36 | 65 | 60 | 89 | 97 | 29 | 105 | 19 | 0.55 |
| RAB13, mono, intra | 0.81 | 2.00E−03 | 0.38 | 67 | 63 | 89 | 97 | 30 | 105 | 19 | 0.67 |
| RAB13, total, intra | 0.88 | 2.65E−04 | 0.52 | 75 | 70 | 100 | 100 | 38 | 105 | 19 | 1.10 |
| RPL34, total, intra | 0.92 | 3.33E−04 | 0.49 | 81 | 79 | 91 | 99 | 36 | 87 | 11 | 1.47 |
| RSAD2, gran, intra | 0.75 | 1.07E−04 | 0.31 | 59 | 55 | 92 | 98 | 22 | 255 | 36 | 1.21 |
| RSAD2, mean, intra | 0.72 | 3.90E−04 | 0.26 | 58 | 54 | 88 | 97 | 20 | 249 | 32 | 0.93 |
| RSAD2, mono, intra | 0.75 | 1.21E−04 | 0.31 | 60 | 56 | 91 | 98 | 22 | 254 | 35 | 1.24 |
| RSAD2, total, intra | 0.78 | 1.65E−05 | 0.34 | 67 | 65 | 88 | 98 | 24 | 249 | 32 | 1.19 |
| SART3, total, intra | 0.83 | 2.72E−04 | 0.38 | 70 | 68 | 84 | 96 | 32 | 105 | 19 | 0.87 |
| TRIM22, total, intra | 0.80 | 1.19E−04 | 0.3 | 67 | 65 | 79 | 96 | 24 | 139 | 19 | 1.34 |
| UBE2N, gran, intra | 0.80 | 1.05E−03 | 0.35 | 67 | 63 | 84 | 96 | 30 | 104 | 19 | 0.84 |
| UBE2N, mean, intra | 0.77 | 9.48E−03 | 0.29 | 64 | 62 | 79 | 94 | 27 | 104 | 19 | 0.93 |
| UBE2N, mono, intra | 0.80 | 1.05E−03 | 0.35 | 67 | 63 | 84 | 96 | 30 | 104 | 19 | 0.84 |
| UBE2N, total, intra | 0.86 | 3.21E−05 | 0.52 | 77 | 74 | 95 | 99 | 40 | 104 | 19 | 1.44 |
| UBE2N, total, intra | 0.76 | 1.08E−03 | 0.31 | 62 | 57 | 88 | 97 | 25 | 148 | 24 | 0.74 |
| IP10 (Luminex measurements) | 0.83 | 6.13E−05 | 0.17 | 0.8 | 0.79 | 0.79 | 99 | 17 | 266 | 14 | 1.87 |

TABLE 2G-continued

DETERMINANTS that differentiate between subjects with an infectious versus non-infectious diseases
Positives (P) and Negatives (N) correspond to patients with an infectious and non-infectious disease
respectively. TA, Sen, Spe and log2(R) correspond total accuracy sensitivity, specificity and log2 ratio
between medians of the positive and negative classes respectively.

| Gene Symbol | AUC | t-test P-value | MCC | TA % | Sen % | Spe % | PPV % | NPV % | P | N | log2(R) |
|---|---|---|---|---|---|---|---|---|---|---|---|
| I-TAC | 0.78 | 1.66E−04 | 0.33 | 0.7 | 0.72 | 0.65 | 68 | 69 | 36 | 34 | 2.25 |
| Mac-2BP | 0.71 | 2.40E−09 | 0.20 | 0.6 | 0.62 | 0.76 | 95 | 21 | 560 | 74 | 0.70 |
| CRP | 0.873 | 0 | 0.43 | 71 | 79 | 83 | 95 | 51 | 265 | 70 | 1.69 |
| IL1ra | 0.823 | 3.43E−13 | 0.44 | 70 | 74 | 84 | 95 | 46 | 265 | 70 | 0.68 |
| IP10 (ELISA measurements) | 0.816 | 1.38E−14 | 0.44 | 69 | 75 | 80 | 93 | 46 | 265 | 70 | 0.92 |
| Lym (%) | 0.668 | 9.41E−07 | 0.17 | 0.6 | 63 | 68 | 93 | 22 | 555 | 82 | |
| Neu (%) | 0.628 | 0.000185 | 0.14 | 0.5 | 49 | 74 | 92 | 17 | 557 | 82 | |
| Pulse | 0.783 | 5.49E−16 | 0.33 | 0.7 | 66 | 80 | 95 | 26 | 522 | 79 | |
| SAA | 0.845 | 0 | 0.46 | 72 | 86 | 76 | 93 | 58 | 265 | 70 | 2.22 |
| TNFR1 | 0.78 | 5.70E−05 | 0.49 | 0.8 | 72 | 79 | 788 | 73 | 36 | 34 | |
| TRAIL | 0.655 | 1.49E−05 | 0.17 | 0.6 | 53 | 73 | 94 | 17 | 572 | 73 | |
| WBC | 0.645 | 2.08E−05 | 0.16 | 0.6 | 56 | 73 | 93 | 19 | 558 | 82 | |

TABLE 2H

A. DETERMINANTS that differentiate between subjects with an infectious disease
versus healthy subjects; B. DETERMINANTS pairs that differentiate between subjects with an
infectious disease versus healthy subjects; C. DETERMINANTS triplets that differentiate
between subjects with an infectious disease versus healthy subjects
Positives (P) and Negatives (N) correspond to patients with an infectious disease and healthy
subjects respectively. TA, Sen, Spe and log2(R) correspond total accuracy sensitivity, specificity
and log2 ratio between medians of the positive and negative classes respectively.

A.

| DETERMINANT | AUC | t-test P-value | MCC | TA % | Sen % | Spe % | PPV % | NPV % | P | N | log2(R) |
|---|---|---|---|---|---|---|---|---|---|---|---|
| ANC | 0.79 | 2.03E−03 | 0.18 | 67 | 66 | 79 | 99 | 9 | 346 | 14 | 0.59066 |
| LOC26010, total, intra | 0.86 | 8.58E−03 | 0.26 | 73 | 73 | 88 | 99 | 12 | 193 | 8 | 0.92663 |
| MX1, gran, intra | 0.79 | 6.38E−03 | 0.18 | 66 | 65 | 77 | 98 | 10 | 264 | 13 | 1.0446 |
| MX1, mean, intra | 0.84 | 1.38E−02 | 0.2 | 69 | 68 | 88 | 99 | 8 | 258 | 8 | 1.1112 |
| MX1, mono, intra | 0.79 | 6.37E−03 | 0.18 | 66 | 65 | 77 | 98 | 10 | 263 | 13 | 1.0513 |
| MX1, total, intra | 0.89 | 5.96E−03 | 0.27 | 74 | 73 | 100 | 100 | 10 | 258 | 8 | 1.3168 |
| Maximal temperature | 1.00 | 0.00E+00 | 0.63 | 95 | 95 | 100 | 100 | 41 | 397 | 14 | 0.09163 |
| CRP | 0.759 | 0.00050258 | 0.24 | 53 | 54 | 91 | 97 | 14 | 265 | 22 | −0.95832 |
| IL1ra | 0.832 | 2.15E−05 | 0.321 | 66 | 77 | 86 | 97 | 24 | 265 | 22 | −0.54337 |
| IP10 | 0.844 | 1.94E−06 | 0.317 | 67 | 80 | 82 | 98 | 26 | 265 | 22 | −0.78014 |
| SAA | 0.929 | 1.41E−11 | 0.416 | 75 | 86 | 100 | 100 | 37 | 265 | 22 | −1.7295 |
| Pulse | 0.93 | 3.09E−04 | 0.25 | 80 | 80 | 100 | 100 | 8 | 341 | 6 | 0.66879 |

B.

| DETERMINANT #1 | DETERMINANT #2 | AUC | MCC | Sen % | Spe % | PPV % | NPV % | P | N |
|---|---|---|---|---|---|---|---|---|---|
| CRP | IL1ra | 0.863 | 0.339 | 80 | 86 | 99 | 27 | 265 | 22 |
| CRP | IP10 | 0.911 | 0.391 | 82 | 86 | 99 | 29 | 265 | 22 |
| CRP | SAA | 0.946 | 0.43 | 86 | 95 | 100 | 37 | 265 | 22 |
| IL1ra | IP10 | 0.879 | 0.348 | 83 | 86 | 99 | 29 | 265 | 22 |
| IL1ra | SAA | 0.93 | 0.484 | 92 | 95 | 100 | 49 | 265 | 22 |
| IP10 | SAA | 0.943 | 0.517 | 89 | 95 | 100 | 43 | 265 | 22 |

C.

| DETERMINANT #1 | DETERMINANT #2 | DETERMINANT #3 | AUC | MCC | Sen % | Spe % | PPV % | NPV % | P | N |
|---|---|---|---|---|---|---|---|---|---|---|
| CRP | IL1ra | IP10 | 0.912 | 0.401 | 84 | 86 | 99 | 31 | 265 | 22 |
| CRP | IL1ra | SAA | 0.944 | 0.498 | 91 | 95 | 100 | 47 | 265 | 22 |
| CRP | IP10 | SAA | 0.953 | 0.527 | 91 | 95 | 100 | 46 | 265 | 22 |
| IL1ra | IP10 | SAA | 0.942 | 0.517 | 92 | 91 | 99 | 49 | 265 | 22 |

TABLE 3A

DETERMINANTS pairs that differentiate between bacterial versus viral infected subjects
Positives and negatives correspond to bacterial and viral infected patients respectively

| DETERMINANT | Gene Symbol #2 | AUC | MCC | Sen % | Spe % | PPV % | NPV % | P | N |
|---|---|---|---|---|---|---|---|---|---|
| CRP | VEGFR2, plasma | 0.96 | 0.8 | 81 | 97 | 94 | 88 | 21 | 31 |
| PCT, soluble | SAA, soluble | 0.77 | 0.53 | 68 | 86 | 80 | 80 | 47 | 57 |
| CRP | PCT soluble | 0.86 | 0.64 | 77 | 95 | 92 | 83 | 47 | 57 |
| PCT soluble | TRAIL soluble | 0.88 | 0.52 | 79 | 75 | 72 | 81 | 47 | 57 |
| B2M, soluble | PCT soluble | 0.80 | 0.21 | 45 | 72 | 75 | 42 | 33 | 18 |
| B2M, soluble | SAA, soluble | 0.82 | 0.43 | 72 | 78 | 83 | 65 | 68 | 45 |
| CRP*, soluble | TRAIL* (measured with ELISA), soluble | 0.94 | 0.74 | 84 | 91 | 88 | 87 | 177 | 213 |
| CRP, soluble | TRAIL (measured with ELISA), soluble | 0.91 | 0.66 | 84 | 82 | 81 | 85 | 245 | 273 |
| TRAIL, plasma | VEGFR2, plasma | 0.94 | 0.67 | 90 | 77 | 73 | 92 | 21 | 31 |
| CRP*, soluble | Mac-2BP*, soluble | 0.93 | 0.72 | 87 | 87 | 85 | 89 | 176 | 208 |
| CRP, soluble | Mac-2BP, soluble | 0.90 | 0.66 | 83 | 85 | 83 | 84 | 243 | 268 |
| B2M, Plasma | CRP | 0.94 | 0.71 | 80 | 92 | 94 | 75 | 41 | 26 |
| CRP | RSAD2, mean, intra | 0.93 | 0.73 | 83 | 89 | 86 | 88 | 72 | 95 |
| CRP | RSAD2, gran, intra | 0.93 | 0.72 | 83 | 89 | 89 | 83 | 117 | 113 |
| CRP | IFIT1, mean, intra | 0.92 | 0.6 | 80 | 83 | 91 | 66 | 51 | 23 |
| CRP | Eotaxin, plasma | 0.92 | 0.66 | 76 | 89 | 86 | 80 | 116 | 129 |
| CRP | MCP-2, plasma | 0.92 | 0.65 | 75 | 89 | 86 | 80 | 116 | 128 |
| BCA-1, plasma | CRP | 0.92 | 0.7 | 78 | 91 | 88 | 82 | 114 | 129 |
| CRP | Cr | 0.92 | 0.68 | 80 | 88 | 86 | 82 | 147 | 159 |
| CRP | RSAD2, mean, intra | 0.92 | 0.69 | 79 | 90 | 89 | 80 | 114 | 110 |
| CRP | sVEGFR2, plasma | 0.92 | 0.68 | 79 | 88 | 86 | 83 | 116 | 129 |
| MX1, gran, intra | VEGFR2, plasma | 0.92 | 0.71 | 100 | 71 | 71 | 100 | 12 | 17 |
| MX1, mono, intra | VEGFR2, plasma | 0.92 | 0.71 | 100 | 71 | 71 | 100 | 12 | 17 |
| RSAD2, mean, intra | VEGFR2, plasma | 0.92 | 0.51 | 86 | 67 | 60 | 89 | 7 | 12 |
| TRAIL, plasma | sCD62L, plasma | 0.92 | 0.71 | 90 | 80 | 83 | 89 | 21 | 20 |
| CMPK2, lymp, intra | CRP | 0.92 | 0.69 | 73 | 93 | 88 | 83 | 49 | 70 |
| Cr | TRAIL, plasma | 0.91 | 0.7 | 89 | 81 | 81 | 89 | 113 | 121 |
| CRP | IP10,plasma | 0.91 | 0.66 | 76 | 89 | 86 | 80 | 116 | 129 |
| CRP | MX1, gran, intra | 0.91 | 0.69 | 80 | 89 | 88 | 81 | 122 | 117 |
| B2M, Plasma | TRAIL, Plasma | 0.91 | 0.74 | 93 | 80 | 88 | 87 | 40 | 25 |
| CHI3L1, plasma | EIF2AK2, lymp, intra | 0.91 | 0.75 | 78 | 100 | 100 | 71 | 9 | 5 |
| CRP | MX1, mono, intra | 0.91 | 0.69 | 80 | 89 | 88 | 81 | 121 | 117 |
| EIF2AK2, lymp, intra | sVEGFR2, plasma | 0.91 | 0.52 | 85 | 67 | 79 | 75 | 26 | 18 |
| Age | CRP | 0.91 | 0.65 | 77 | 88 | 86 | 80 | 177 | 179 |
| EIF4B, lymp, intra | IFIT1, mean, intra | 0.91 | 0.65 | 84 | 83 | 91 | 71 | 51 | 24 |
| CHI3L1, plasma | CRP | 0.91 | 0.65 | 73 | 91 | 87 | 79 | 112 | 127 |
| CRP | Pulse | 0.91 | 0.65 | 73 | 91 | 87 | 80 | 139 | 161 |
| CRP | MX1, mean, intra | 0.91 | 0.66 | 78 | 88 | 87 | 79 | 119 | 114 |
| CRP | IFITM1, mono, membrane | 0.90 | 0.63 | 74 | 88 | 84 | 79 | 78 | 88 |
| CRP | IL1a, plasma | 0.90 | 0.64 | 73 | 89 | 86 | 79 | 116 | 129 |
| CRP | sTREM, plasma | 0.90 | 0.66 | 78 | 88 | 86 | 80 | 94 | 96 |
| CRP | Lym (%) | 0.90 | 0.66 | 74 | 90 | 89 | 78 | 176 | 177 |
| CRP | MX1, lymp, intra | 0.90 | 0.65 | 77 | 88 | 87 | 79 | 122 | 117 |
| CRP | Neu (%) | 0.90 | 0.64 | 73 | 89 | 87 | 77 | 177 | 178 |
| Age | TRAIL, plasma | 0.90 | 0.68 | 86 | 82 | 81 | 87 | 117 | 129 |
| CRP | OAS2, gran, intra | 0.90 | 0.62 | 73 | 88 | 86 | 76 | 122 | 118 |
| CRP | Urea | 0.90 | 0.64 | 72 | 91 | 88 | 78 | 148 | 161 |
| CHI3L1, plasma | OAS2, gran, intra | 0.90 | 0.41 | 57 | 83 | 80 | 63 | 14 | 12 |
| CHI3L1, plasma | OAS2, mono, intra | 0.90 | 0.41 | 57 | 83 | 80 | 63 | 14 | 12 |
| CRP | K | 0.90 | 0.61 | 72 | 89 | 86 | 76 | 148 | 150 |
| CRP | OAS2, mono, intra | 0.90 | 0.62 | 73 | 88 | 86 | 76 | 121 | 118 |
| CRP | RSAD2, lymp, intra | 0.90 | 0.61 | 74 | 86 | 84 | 76 | 117 | 113 |
| CRP | sCD62L, plasma | 0.90 | 0.68 | 82 | 86 | 85 | 83 | 28 | 28 |
| MX1, mean, intra | VEGFR2, plasma | 0.90 | 0.56 | 92 | 65 | 65 | 92 | 12 | 17 |
| Neu (%) | VEGFR2, plasma | 0.90 | 0.51 | 81 | 71 | 65 | 85 | 21 | 31 |
| ANC | CRP | 0.90 | 0.63 | 72 | 89 | 86 | 77 | 149 | 157 |
| Cr | IFIT1, mean, intra | 0.90 | 0.65 | 88 | 77 | 88 | 77 | 26 | 13 |
| CRP | IFITM1, lymp, membrane | 0.90 | 0.64 | 76 | 88 | 84 | 80 | 78 | 88 |
| CRP | EIF2AK2, lymp, intra | 0.89 | 0.53 | 76 | 78 | 85 | 67 | 37 | 23 |
| CHI3L1, plasma | IFIT1, mean, intra | 0.89 | 0.53 | 73 | 83 | 90 | 59 | 26 | 12 |
| CRP | NA | 0.89 | 0.62 | 70 | 90 | 87 | 77 | 151 | 163 |
| EIF4B, gran, intra | TRAIL, plasma | 0.89 | 0.61 | 80 | 81 | 76 | 85 | 51 | 69 |
| EIF4B, mono, intra | TRAIL, plasma | 0.89 | 0.61 | 80 | 81 | 76 | 85 | 51 | 69 |
| CRP | EIF4B, mean, intra | 0.89 | 0.63 | 71 | 90 | 87 | 77 | 83 | 91 |
| EIF2AK2, lymp, intra | TRAIL, plasma | 0.89 | 0.62 | 85 | 78 | 85 | 78 | 26 | 18 |
| EIF4B, mean, intra | TRAIL, plasma | 0.89 | 0.58 | 80 | 79 | 74 | 84 | 50 | 66 |
| TRAIL, plasma | sVEGFR2, plasma | 0.89 | 0.63 | 88 | 74 | 76 | 87 | 117 | 128 |
| TRAIL, plasma | Urea | 0.89 | 0.61 | 85 | 76 | 76 | 85 | 113 | 123 |
| EIF4B, lymp, intra | TRAIL, plasma | 0.89 | 0.59 | 78 | 81 | 75 | 84 | 51 | 69 |
| Cr | RSAD2, gran, intra | 0.89 | 0.58 | 78 | 80 | 79 | 80 | 91 | 97 |
| EIF2AK2, lymp, intra | Mac-2BP, plasma | 0.89 | 0.58 | 81 | 78 | 84 | 74 | 26 | 18 |

TABLE 3A-continued

DETERMINANTS pairs that differentiate between bacterial versus viral infected subjects
Positives and negatives correspond to bacterial and viral infected patients respectively

| DETERMINANT | Gene Symbol #2 | AUC | MCC | Sen % | Spe % | PPV % | NPV % | P | N |
|---|---|---|---|---|---|---|---|---|---|
| IFIT1, mean, intra | RSAD2, mean, intra | 0.89 | 0.56 | 82 | 75 | 88 | 67 | 51 | 24 |
| Lym (%) | VEGFR2, plasma | 0.89 | 0.64 | 90 | 74 | 70 | 92 | 21 | 31 |
| Cr | RSAD2, mono, intra | 0.88 | 0.58 | 78 | 80 | 79 | 80 | 90 | 97 |
| CRP | EIF4B, gran, intra | 0.88 | 0.63 | 71 | 90 | 87 | 77 | 85 | 94 |
| CRP | EIF4B, mono, intra | 0.88 | 0.63 | 71 | 90 | 87 | 77 | 85 | 94 |
| CRP | EIF4B, lymp, intra | 0.88 | 0.61 | 68 | 90 | 87 | 76 | 85 | 94 |
| MX1, gran, intra | TRAIL, plasma | 0.88 | 0.58 | 84 | 74 | 74 | 84 | 77 | 87 |
| IFIT1, mean, intra | RSAD2, gran, intra | 0.88 | 0.58 | 84 | 75 | 88 | 69 | 51 | 24 |
| IFIT1, mean, intra | RSAD2, mono, intra | 0.88 | 0.58 | 84 | 75 | 88 | 69 | 51 | 24 |
| Mac-2BP*, soluble | TRAIL* (measured with ELISA), soluble | 0.91 | 0.63 | 85 | 84 | 81 | 87 | 176 | 208 |
| Mac-2BP, soluble | TRAIL (measured with ELISA), soluble | 0.87 | 0.54 | 78 | 81 | 78 | 80 | 243 | 267 |
| CHI3L1, plasma | MX1, gran, intra | 0.88 | 0.62 | 79 | 83 | 85 | 77 | 14 | 12 |
| CHI3L1, plasma | MX1, mono, intra | 0.88 | 0.62 | 79 | 83 | 85 | 77 | 14 | 12 |
| Lym (%) | TRAIL, plasma | 0.88 | 0.6 | 85 | 74 | 75 | 85 | 116 | 128 |
| MX1, mono, intra | TRAIL, plasma | 0.88 | 0.57 | 84 | 72 | 73 | 84 | 76 | 87 |
| Eotaxin, plasma | TRAIL, plasma | 0.88 | 0.56 | 83 | 73 | 74 | 82 | 117 | 128 |
| Cr | RSAD2, mean, intra | 0.88 | 0.56 | 74 | 82 | 79 | 77 | 88 | 96 |
| K | TRAIL, plasma | 0.88 | 0.67 | 88 | 79 | 80 | 86 | 113 | 113 |
| Neu (%) | TRAIL, plasma | 0.88 | 0.61 | 85 | 75 | 76 | 85 | 117 | 128 |
| Pulse | TRAIL, plasma | 0.88 | 0.6 | 84 | 76 | 75 | 85 | 109 | 125 |
| MX1, lymp, intra | TRAIL, plasma | 0.88 | 0.6 | 86 | 75 | 75 | 86 | 77 | 87 |
| MX1, mean, intra | TRAIL, plasma | 0.88 | 0.62 | 87 | 75 | 76 | 86 | 75 | 84 |
| MX1, lymp, intra | VEGFR2, plasma | 0.88 | 0.56 | 92 | 65 | 65 | 92 | 12 | 17 |
| RSAD2, gran, intra | TRAIL, plasma | 0.88 | 0.56 | 82 | 74 | 74 | 82 | 72 | 82 |
| CHI3L1, plasma | CRP | 0.88 | 0.65 | 75 | 89 | 88 | 78 | 28 | 28 |
| RSAD2, mono, intra | TRAIL, plasma | 0.88 | 0.56 | 82 | 74 | 73 | 82 | 71 | 82 |
| Cr | Eotaxin, plasma | 0.87 | 0.6 | 80 | 80 | 79 | 81 | 114 | 123 |
| IFITM1, lymp, membrane | TRAIL, plasma | 0.87 | 0.5 | 79 | 71 | 67 | 82 | 47 | 63 |
| MCP-2, plasma | TRAIL, plasma | 0.87 | 0.61 | 86 | 75 | 76 | 86 | 117 | 127 |
| IP10, plasma | TRAIL, plasma | 0.87 | 0.61 | 85 | 75 | 76 | 85 | 117 | 128 |
| BCA-1, plasma | TRAIL, plasma | 0.87 | 0.59 | 84 | 74 | 75 | 84 | 115 | 128 |
| Cr | MX1, lymp, intra | 0.87 | 0.58 | 77 | 81 | 80 | 79 | 96 | 101 |
| NA | TRAIL, plasma | 0.87 | 0.61 | 85 | 75 | 76 | 85 | 116 | 124 |
| OAS2, gran, intra | TRAIL, plasma | 0.87 | 0.6 | 86 | 75 | 75 | 86 | 77 | 87 |
| CHI3L1, plasma | TRAIL, plasma | 0.87 | 0.61 | 85 | 76 | 76 | 85 | 113 | 127 |
| Cr | MX1, gran, intra | 0.87 | 0.54 | 74 | 80 | 78 | 76 | 96 | 101 |
| Cr | Mac-2BP, plasma | 0.87 | 0.54 | 76 | 78 | 76 | 78 | 110 | 121 |
| OAS2, mono, intra | TRAIL, plasma | 0.87 | 0.6 | 86 | 75 | 75 | 86 | 76 | 87 |
| RSAD2, lymp, intra | VEGFR2, plasma | 0.87 | 0.43 | 86 | 58 | 55 | 88 | 7 | 12 |
| RSAD2, mean, intra | TRAIL, plasma | 0.87 | 0.58 | 86 | 72 | 73 | 85 | 70 | 79 |
| Cr | MCP-2, plasma | 0.87 | 0.61 | 79 | 82 | 80 | 81 | 114 | 122 |
| Cr | MX1, mono, intra | 0.87 | 0.54 | 74 | 80 | 78 | 76 | 95 | 101 |
| Cr | VEGFR2, plasma | 0.87 | 0.6 | 81 | 80 | 74 | 86 | 21 | 30 |
| IL1a, plasma | TRAIL, plasma | 0.87 | 0.6 | 85 | 74 | 75 | 85 | 117 | 128 |
| Lym (%) | RSAD2, gran, intra | 0.87 | 0.6 | 83 | 76 | 79 | 81 | 119 | 114 |
| Lym (%) | RSAD2, mono, intra | 0.87 | 0.59 | 83 | 75 | 78 | 81 | 118 | 114 |
| ANC | TRAIL, plasma | 0.87 | 0.63 | 86 | 76 | 77 | 85 | 115 | 123 |
| Cr | MX1, mean, intra | 0.87 | 0.54 | 74 | 80 | 78 | 77 | 93 | 100 |
| CHI3L1, plasma | MX1, mean, intra | 0.86 | 0.53 | 71 | 82 | 83 | 69 | 14 | 11 |
| Cr | RSAD2, lymp, intra | 0.86 | 0.56 | 73 | 84 | 80 | 76 | 91 | 97 |
| Lym (%) | RSAD2, mean, intra | 0.86 | 0.59 | 83 | 76 | 78 | 81 | 116 | 112 |
| CHI3L1, plasma | MX1, lymp, intra | 0.86 | 0.55 | 71 | 83 | 83 | 71 | 14 | 12 |
| RSAD2, lymp, intra | TRAIL, plasma | 0.86 | 0.58 | 85 | 73 | 73 | 85 | 72 | 82 |
| ANC | VEGFR2, plasma | 0.86 | 0.53 | 86 | 68 | 64 | 88 | 21 | 31 |
| CHI3L1, plasma | VEGFR2, plasma | 0.86 | 0.62 | 71 | 90 | 80 | 84 | 17 | 29 |
| Cr | EIF2AK2, lymp, intra | 0.86 | 0.45 | 73 | 73 | 82 | 62 | 37 | 22 |
| Cr | sTREM, plasma | 0.86 | 0.59 | 74 | 85 | 83 | 76 | 92 | 91 |
| Neu (%) | sCD62L, plasma | 0.86 | 0.54 | 76 | 79 | 79 | 76 | 29 | 28 |
| Neu (%) | RSAD2, gran, intra | 0.86 | 0.57 | 82 | 75 | 77 | 80 | 119 | 114 |
| IFIT1, mean, intra | TRAIL, plasma | 0.86 | 0.51 | 85 | 67 | 85 | 67 | 26 | 12 |
| Neu (%) | RSAD2, mono, intra | 0.86 | 0.57 | 82 | 75 | 77 | 80 | 118 | 114 |
| Age | Eotaxin, plasma | 0.86 | 0.6 | 77 | 82 | 80 | 80 | 118 | 131 |
| Age | RSAD2, gran, intra | 0.86 | 0.57 | 77 | 80 | 80 | 77 | 119 | 115 |
| Lym (%) | sCD62L, plasma | 0.86 | 0.5 | 79 | 71 | 73 | 77 | 28 | 28 |
| Age | RSAD2, mono, intra | 0.86 | 0.58 | 78 | 80 | 80 | 78 | 118 | 115 |
| BCA-1, plasma | EIF2AK2, lymp, intra | 0.86 | 0.44 | 77 | 67 | 77 | 67 | 26 | 18 |
| CHI3L1, plasma | IFITM1, mono, membrane | 0.86 | −0.1 | 17 | 71 | 33 | 50 | 6 | 7 |
| Cr | sVEGFR2, plasma | 0.86 | 0.59 | 79 | 80 | 78 | 80 | 114 | 123 |
| MX1, gran, intra | sCD62L, plasma | 0.86 | 0.61 | 86 | 75 | 80 | 82 | 14 | 12 |
| MX1, mono, intra | sCD62L, plasma | 0.86 | 0.61 | 86 | 75 | 80 | 82 | 14 | 12 |
| RSAD2, gran, intra | sCD62L, plasma | 0.86 | 0.54 | 79 | 75 | 79 | 75 | 14 | 12 |
| RSAD2, gran, intra | sVEGFR2, plasma | 0.86 | 0.56 | 79 | 76 | 74 | 81 | 73 | 84 |

TABLE 3A-continued

DETERMINANTS pairs that differentiate between bacterial versus viral infected subjects
Positives and negatives correspond to bacterial and viral infected patients respectively

| DETERMINANT | Gene Symbol #2 | AUC | MCC | Sen % | Spe % | PPV % | NPV % | P | N |
|---|---|---|---|---|---|---|---|---|---|
| RSAD2, mono, intra | sCD62L, plasma | 0.86 | 0.54 | 79 | 75 | 79 | 75 | 14 | 12 |
| Age | Mac-2BP, plasma | 0.86 | 0.55 | 77 | 78 | 75 | 79 | 114 | 129 |
| Age | VEGFR2, plasma | 0.86 | 0.49 | 71 | 77 | 68 | 80 | 21 | 31 |
| RSAD2, mono, intra | sVEGFR2, plasma | 0.86 | 0.55 | 79 | 76 | 74 | 81 | 72 | 84 |
| CHI3L1, plasma | Cr | 0.86 | 0.58 | 70 | 87 | 83 | 76 | 110 | 121 |
| Neu (%) | RSAD2, mean, intra | 0.86 | 0.58 | 81 | 77 | 78 | 80 | 116 | 112 |
| EIF2AK2, lymp, intra | Neu (%) | 0.85 | 0.54 | 84 | 70 | 82 | 73 | 38 | 23 |
| Mac-2BP, plasma | RSAD2, gran, intra | 0.85 | 0.57 | 86 | 71 | 72 | 85 | 72 | 82 |
| Cr | IFITM1, lymp, membrane | 0.85 | 0.6 | 76 | 84 | 78 | 83 | SS | 74 |
| Cr | IFITM1, mono, membrane | 0.85 | 0.56 | 75 | 81 | 75 | 81 | SS | 74 |
| IFIT1, mean, intra | Pulse | 0.85 | 0.62 | 88 | 73 | 85 | 79 | 25 | 15 |
| Lym (%) | MCP-2, plasma | 0.85 | 0.59 | 85 | 74 | 75 | 85 | 117 | 129 |
| TRAIL, plasma | sTREM, plasma | 0.85 | 0.53 | 80 | 72 | 74 | 79 | 96 | 98 |
| CHI3L1, plasma | Mac-2BP, plasma | 0.85 | 0.56 | 81 | 75 | 74 | 82 | 114 | 129 |
| EIF4B, lymp, intra | RSAD2, gran, intra | 0.85 | 0.49 | 80 | 68 | 69 | 79 | 81 | 91 |
| EIF4B, lymp, intra | RSAD2, mono, intra | 0.85 | 0.49 | 80 | 68 | 69 | 79 | 81 | 91 |
| IFITM1, mono, membrane | TRAIL, plasma | 0.85 | 0.54 | 83 | 71 | 68 | 85 | 47 | 63 |
| Mac-2BP, plasma | RSAD2, mono, intra | 0.85 | 0.57 | 86 | 71 | 72 | 85 | 71 | 82 |
| Age | CHI3L1, plasma | 0.85 | 0.49 | 56 | 90 | 83 | 70 | 114 | 129 |
| MCP-2, plasma | VEGFR2, plasma | 0.85 | 0.5 | 81 | 70 | 65 | 84 | 21 | 30 |
| NA | VEGFR2, plasma | 0.85 | 0.57 | 90 | 67 | 66 | 91 | 21 | 30 |
| Urea | VEGFR2, plasma | 0.85 | 0.38 | 62 | 76 | 65 | 73 | 21 | 29 |
| CHI3L1, plasma | sVEGFR2, plasma | 0.85 | 0.56 | 81 | 75 | 77 | 79 | 21 | 20 |
| Cr | OAS2, gran, intra | 0.85 | 0.55 | 73 | 82 | 80 | 76 | 96 | 101 |
| MCP-2, plasma | Neu (%) | 0.85 | 0.59 | 86 | 72 | 74 | 85 | 118 | 129 |
| sCD62L, plasma | sVEGFR2, plasma | 0.85 | 0.66 | 86 | 80 | 82 | 84 | 21 | 20 |
| Cr | OAS2, mono, intra | 0.85 | 0.55 | 73 | 82 | 79 | 76 | 95 | 101 |
| EIF4B, mean, intra | RSAD2, gran, intra | 0.85 | 0.49 | 81 | 68 | 70 | 80 | 79 | 88 |
| EIF4B, mean, intra | RSAD2, mono, intra | 0.85 | 0.49 | 81 | 68 | 70 | 80 | 79 | 88 |
| Age | Lym (%) | 0.85 | 0.52 | 75 | 78 | 77 | 76 | 178 | 179 |
| CHI3L1, plasma | TRAIL, plasma | 0.85 | 0.62 | 90 | 70 | 76 | 88 | 21 | 20 |
| CHI3L1, plasma | RSAD2, gran, intra | 0.85 | 0.6 | 76 | 83 | 80 | 80 | 72 | 82 |
| EIF4B, gran, intra | RSAD2, gran, intra | 0.85 | 0.49 | 80 | 68 | 69 | 79 | 81 | 91 |
| EIF4B, gran, intra | RSAD2, mono, intra | 0.85 | 0.49 | 80 | 68 | 69 | 79 | 81 | 91 |
| EIF4B, mono, intra | RSAD2, gran, intra | 0.85 | 0.49 | 80 | 68 | 69 | 79 | 81 | 91 |
| EIF4B, mono, intra | RSAD2, mono, intra | 0.85 | 0.49 | 80 | 68 | 69 | 79 | 81 | 91 |
| Mac-2BP, plasma | sCD62L, plasma | 0.85 | 0.52 | 86 | 65 | 72 | 81 | 21 | 20 |
| OAS2, gran, intra | VEGFR2, plasma | 0.85 | 0.48 | 83 | 65 | 63 | 85 | 12 | 17 |
| OAS2, mono, intra | VEGFR2, plasma | 0.85 | 0.48 | 83 | 65 | 63 | 85 | 12 | 17 |
| Cr | IP10, plasma | 0.85 | 0.54 | 75 | 80 | 77 | 77 | 114 | 123 |
| K | sCD62L, plasma | 0.85 | 0.54 | 78 | 76 | 78 | 76 | 27 | 25 |
| Age | MCP-2, plasma | 0.85 | 0.54 | 67 | 86 | 81 | 74 | 118 | 130 |
| CHI3L1, plasma | RSAD2, mono, intra | 0.85 | 0.58 | 76 | 82 | 78 | 80 | 71 | 82 |
| CMPK2, lymp, intra | Cr | 0.85 | 0.66 | 75 | 89 | 84 | 83 | 48 | 66 |
| CHI3L1, plasma | RSAD2, gran, intra | 0.85 | 0.46 | 71 | 75 | 77 | 69 | 14 | 12 |
| CHI3L1, plasma | RSAD2, mono, intra | 0.85 | 0.46 | 71 | 75 | 77 | 69 | 14 | 12 |
| EIF4B, gran, intra | Mac-2BP, plasma | 0.85 | 0.57 | 90 | 68 | 67 | 90 | 49 | 69 |
| EIF4B, mono, intra | Mac-2BP, plasma | 0.85 | 0.57 | 90 | 68 | 67 | 90 | 49 | 69 |
| IFITM1, mono, membrane | RSAD2, gran, intra | 0.85 | 0.5 | 81 | 69 | 69 | 81 | 78 | 90 |
| IFITM1, mono, membrane | RSAD2, mono, intra | 0.85 | 0.5 | 81 | 69 | 69 | 81 | 78 | 90 |
| MCP-2, plasma | sCD62L, plasma | 0.85 | 0.66 | 81 | 85 | 85 | 81 | 21 | 20 |
| ANC | sCD62L, plasma | 0.84 | 0.44 | 70 | 74 | 73 | 71 | 27 | 27 |
| EIF4B, lymp, intra | Mac-2BP, plasma | 0.84 | 0.57 | 88 | 70 | 67 | 89 | 49 | 69 |
| IFITM1, lymp, membrane | RSAD2, gran, intra | 0.84 | 0.44 | 79 | 64 | 66 | 78 | 78 | 90 |
| IFITM1, lymp, membrane | RSAD2, mono, intra | 0.84 | 0.44 | 79 | 64 | 66 | 78 | 78 | 90 |
| RSAD2, mean, intra | sCD62L, plasma | 0.84 | 0.37 | 64 | 73 | 75 | 62 | 14 | 11 |
| ANC | Age | 0.84 | 0.53 | 69 | 84 | 80 | 74 | 151 | 159 |
| CHI3L1, plasma | IFITM1, mono, membrane | 0.84 | 0.49 | 62 | 86 | 76 | 75 | 47 | 63 |
| CMPK2, lymp, intra | TRAIL, plasma | 0.84 | 0.54 | 83 | 72 | 68 | 85 | 41 | 57 |
| ANC | Cr | 0.84 | 0.53 | 71 | 81 | 79 | 74 | 146 | 150 |
| CHI3L1, plasma | MX1, gran, intra | 0.84 | 0.58 | 73 | 84 | 80 | 78 | 75 | 87 |
| Cr | IL1a, plasma | 0.84 | 0.57 | 75 | 82 | 79 | 78 | 114 | 123 |
| Age | MX1, lymp, intra | 0.84 | 0.48 | 67 | 81 | 78 | 70 | 124 | 119 |
| Age | Neu (%) | 0.84 | 0.52 | 74 | 78 | 77 | 75 | 179 | 180 |
| EIF2AK2, lymp, intra | Lym (%) | 0.84 | 0.47 | 82 | 65 | 79 | 68 | 38 | 23 |
| RSAD2, mean, intra | sVEGFR2, plasma | 0.84 | 0.56 | 82 | 74 | 73 | 82 | 71 | 81 |
| CHI3L1, plasma | MCP-2, plasma | 0.84 | 0.51 | 75 | 76 | 74 | 77 | 114 | 127 |
| CHI3L1, plasma | MX1, mono, intra | 0.84 | 0.57 | 73 | 84 | 79 | 78 | 74 | 87 |
| EIF4B, mean, intra | Mac-2BP, plasma | 0.84 | 0.6 | 90 | 71 | 69 | 90 | 48 | 66 |
| Age | sVEGFR2, plasma | 0.84 | 0.51 | 69 | 82 | 77 | 74 | 118 | 131 |
| CHI3L1, plasma | CMPK2, lymp, intra | 0.84 | 0.58 | 69 | 88 | 81 | 79 | 42 | 57 |
| CHI3L1, plasma | IFITM1, lymp, | 0.84 | 0.53 | 64 | 87 | 79 | 76 | 47 | 63 |

TABLE 3A-continued

DETERMINANTS pairs that differentiate between bacterial versus viral infected subjects
Positives and negatives correspond to bacterial and viral infected patients respectively

| DETERMINANT | Gene Symbol #2 | AUC | MCC | Sen % | Spe % | PPV % | NPV % | P | N |
|---|---|---|---|---|---|---|---|---|---|
| Eotaxin, plasma | VEGFR2, plasma | 0.84 | 0.52 | 90 | 61 | 61 | 90 | 21 | 31 |
| OAS2, gran, intra | sCD62L, plasma | 0.84 | 0.35 | 50 | 83 | 78 | 59 | 14 | 12 |
| OAS2, mono, intra | sCD62L, plasma | 0.84 | 0.35 | 50 | 83 | 78 | 59 | 14 | 12 |
| Cr | Lym (%) | 0.84 | 0.54 | 77 | 77 | 76 | 78 | 147 | 159 |
| Mac-2BP, plasma | RSAD2, mean, intra | 0.84 | 0.53 | 86 | 67 | 70 | 84 | 70 | 79 |
| MX1, gran, intra | Mac-2BP, plasma | 0.84 | 0.55 | 88 | 67 | 69 | 87 | 75 | 87 |
| Age | MX1, gran, intra | 0.84 | 0.53 | 73 | 80 | 79 | 74 | 124 | 119 |
| Age | RSAD2, mean, intra | 0.84 | 0.49 | 71 | 79 | 77 | 72 | 116 | 112 |
| MX1, mono, intra | Mac-2BP, plasma | 0.84 | 0.55 | 88 | 67 | 69 | 87 | 74 | 87 |
| Age | MX1, mono, intra | 0.84 | 0.54 | 74 | 80 | 79 | 75 | 123 | 119 |
| BCA-1, plasma | Cr | 0.84 | 0.56 | 73 | 82 | 79 | 77 | 112 | 123 |
| CHI3L1, plasma | EIF4B, gran, intra | 0.84 | 0.62 | 65 | 93 | 86 | 79 | 49 | 69 |
| CHI3L1, plasma | EIF4B, mean, intra | 0.84 | 0.61 | 63 | 94 | 88 | 78 | 48 | 66 |
| CHI3L1, plasma | EIF4B, mono, intra | 0.84 | 0.62 | 65 | 93 | 86 | 79 | 49 | 69 |
| CHI3L1, plasma | Eotaxin, plasma | 0.84 | 0.54 | 72 | 82 | 78 | 77 | 114 | 128 |
| Cr | EIF4B, gran, intra | 0.84 | 0.64 | 75 | 89 | 83 | 82 | 59 | 79 |
| Cr | EIF4B, lymp, intra | 0.84 | 0.64 | 75 | 89 | 83 | 82 | 59 | 79 |
| Cr | EIF4B, mono, intra | 0.84 | 0.64 | 75 | 89 | 83 | 82 | 59 | 79 |
| Age | IL1a, plasma | 0.84 | 0.51 | 58 | 89 | 83 | 70 | 118 | 131 |
| EIF2AK2, lymp, intra | sTREM, plasma | 0.84 | 0.53 | 81 | 72 | 81 | 72 | 26 | 18 |
| CHI3L1, plasma | MX1, lymp, intra | 0.83 | 0.49 | 65 | 83 | 77 | 73 | 75 | 87 |
| Cr | EIF4B, mean, intra | 0.83 | 0.66 | 75 | 90 | 84 | 83 | 57 | 78 |
| MX1, mean, intra | Mac-2BP, plasma | 0.83 | 0.55 | 84 | 71 | 72 | 83 | 73 | 84 |
| Age | IP10, plasma | 0.83 | 0.48 | 56 | 89 | 83 | 69 | 118 | 131 |
| CHI3L1, plasma | EIF2AK2, lymp, intra | 0.83 | 0.44 | 77 | 67 | 77 | 67 | 26 | 18 |
| IFIT1, mean, intra | MCP-2, plasma | 0.83 | 0.55 | 96 | 50 | 81 | 86 | 26 | 12 |
| ANC | EIF2AK2, lymp, intra | 0.83 | 0.58 | 84 | 74 | 84 | 74 | 38 | 23 |
| CHI3L1, plasma | MX1, mean, intra | 0.83 | 0.55 | 73 | 82 | 78 | 78 | 73 | 84 |
| EIF2AK2, lymp, intra | Pulse | 0.83 | 0.46 | 80 | 65 | 78 | 68 | 35 | 23 |
| Lym (%) | RSAD2, lymp, intra | 0.83 | 0.51 | 79 | 72 | 75 | 77 | 119 | 114 |
| Age | IFITM1, lymp, membrane | 0.83 | 0.5 | 63 | 86 | 79 | 73 | 79 | 90 |
| Age | MX1, mean, intra | 0.83 | 0.52 | 71 | 81 | 80 | 73 | 121 | 116 |
| Age | sTREM, plasma | 0.83 | 0.51 | 58 | 90 | 85 | 69 | 96 | 98 |
| B2M, Plasma | Mac-2BP, Plasma | 0.82 | 0.59 | 79 | 80 | 86 | 71 | 39 | 25 |
| SAA*, soluble | CRP*, soluble | 0.91 | 0.68 | 84 | 84 | 81 | 86 | 177 | 213 |
| SAA, soluble | CRP, soluble | 0.87 | 0.64 | 78 | 83 | 80 | 81 | 244 | 274 |
| SAA*, soluble | TRAIL* (measured with ELISA), soluble | 0.91 | 0.66 | 83 | 84 | 81 | 85 | 177 | 213 |
| SAA, soluble | TRAIL (measured with ELISA), soluble | 0.88 | 0.61 | 82 | 78 | 78 | 83 | 244 | 273 |
| SAA, Plasma | sVEGFR2 | 0.796 | 0.46 | 76 | 73 | 86 | 57 | 25 | 11 |
| SAA*, soluble | Mac-2BP*, soluble | 0.88 | 0.62 | 77 | 85 | 81 | 81 | 176 | 208 |
| SAA, soluble | Mac-2BP, soluble | 0.85 | 0.54 | 76 | 79 | 77 | 78 | 243 | 268 |

*Results obtained on patients whose reference standard was determined by an expert consensus

TABLE 3B

DETERMINANTS triplets that differentiate between bacterial versus viral infected subjects

| DETERMINANT #1 | DETERMINANT #2 | DETERMINANT #3 | AUC | MCC | Sen % | Spe % | PPV % | NPV % | P | N |
|---|---|---|---|---|---|---|---|---|---|---|
| CRP*, soluble | Mac-2BP*, soluble | SAA*, soluble | 0.94 | 0.71 | 89 | 86 | 84 | 90 | 176 | 208 |
| CRP, soluble | Mac-2BP, soluble | SAA, soluble | 0.91 | 0.66 | 83 | 84 | 83 | 85 | 243 | 268 |
| CRP*, soluble | SAA*, soluble | TRAIL* (ELISA), soluble | 0.95 | 0.73 | 87 | 87 | 85 | 89 | 177 | 213 |
| CRP, soluble | SAA, soluble | TRAIL (ELISA), soluble | 0.91 | 0.65 | 83 | 83 | 81 | 85 | 244 | 273 |
| Mac-2BP*, soluble | SAA*, soluble | TRAIL* (ELISA), soluble | 0.92 | 0.73 | 89 | 86 | 84 | 90 | 176 | 208 |
| Mac-2BP, soluble | SAA, soluble | TRAIL (ELISA), soluble | 0.90 | 0.64 | 83 | 82 | 81 | 84 | 243 | 267 |
| CRP | MX1, mean, intra | Mac-2BP, plasma | 0.96 | 0.76 | 87 | 89 | 87 | 89 | 71 | 82 |
| CRP*, soluble | Mac-2BP*, soluble | TRAIL* (ELISA), soluble | 0.96 | 0.80 | 90 | 91 | 89 | 92 | 176 | 208 |
| CRP, soluble | Mac-BP, soluble | TRAIL(ELISA), soluble | 0.93 | 0.71 | 84 | 88 | 86 | 86 | 243 | 267 |
| CRP | Mac-2BP, plasma | RSAD2, mean, intra | 0.96 | 0.76 | 85 | 91 | 89 | 88 | 68 | 77 |
| CRP | Cr | TRAIL, plasma | 0.96 | 0.73 | 84 | 89 | 88 | 86 | 112 | 120 |

TABLE 3B-continued

DETERMINANTS triplets that differentiate between bacterial versus viral infected subjects

| DETERMINANT #1 | DETERMINANT #2 | DETERMINANT #3 | AUC | MCC | Sen % | Spe % | PPV % | NPV % | P | N |
|---|---|---|---|---|---|---|---|---|---|---|
| CRP | MX1, mean, intra | TRAIL, plasma | 0.96 | 0.74 | 88 | 87 | 85 | 89 | 73 | 82 |
| CRP | MX1, mean, intra | sVEGFR2, plasma | 0.95 | 0.75 | 85 | 89 | 88 | 87 | 74 | 84 |
| Age | CRP | TRAIL, plasma | 0.95 | 0.72 | 83 | 89 | 87 | 85 | 115 | 127 |
| CRP | K | TRAIL, plasma | 0.95 | 0.73 | 81 | 91 | 90 | 83 | 112 | 112 |
| CRP | RSAD2, mean, intra | TRAIL, plasma | 0.95 | 0.78 | 88 | 90 | 88 | 90 | 68 | 77 |
| CRP | RSAD2, mean, intra | sVEGFR2, plasma | 0.95 | 0.71 | 83 | 89 | 86 | 85 | 69 | 79 |
| CRP | TRAIL, plasma | sVEGFR2, plasma | 0.95 | 0.73 | 85 | 88 | 87 | 87 | 115 | 126 |
| CRP | MCP-2, plasma | TRAIL, plasma | 0.95 | 0.68 | 80 | 88 | 86 | 83 | 115 | 125 |
| CRP | Lym (%) | TRAIL, plasma | 0.95 | 0.76 | 86 | 90 | 88 | 88 | 114 | 126 |
| CRP | Pulse | TRAIL, plasma | 0.95 | 0.74 | 83 | 90 | 88 | 86 | 107 | 123 |
| CRP | MCP-2, plasma | Mac-2BP, plasma | 0.95 | 0.77 | 85 | 92 | 90 | 87 | 112 | 125 |
| CRP | Neu (%) | TRAIL, plasma | 0.95 | 0.75 | 85 | 90 | 88 | 87 | 115 | 126 |
| ANC | CRP | TRAIL, plasma | 0.94 | 0.7 | 82 | 88 | 86 | 84 | 113 | 121 |
| CRP | Cr | Mac-2BP, plasma | 0.94 | 0.78 | 87 | 91 | 90 | 89 | 109 | 120 |
| B2M, Plasma | CRP | Mac-2BP, Plasma | 0.94 | 0.75 | 84 | 92 | 94 | 79 | 38 | 25 |
| B2M, Plasma | CRP | TRAIL, Plasma | 0.94 | 0.68 | 85 | 84 | 89 | 78 | 39 | 25 |
| CHI3L1, plasma | CRP | TRAIL, plasma | 0.94 | 0.7 | 82 | 88 | 86 | 85 | 111 | 125 |
| CRP | Cr | RSAD2, mean, intra | 0.94 | 0.74 | 83 | 91 | 89 | 85 | 87 | 95 |
| ANC | CRP | Mac-2BP, plasma | 0.94 | 0.75 | 84 | 91 | 89 | 86 | 110 | 121 |
| CRP | Cr | MCP-2, plasma | 0.94 | 0.74 | 82 | 91 | 89 | 85 | 113 | 121 |
| CRP | K | Mac-2BP, plasma | 0.94 | 0.75 | 83 | 92 | 91 | 85 | 109 | 113 |
| CRP | Lym (%) | Mac-2BP, plasma | 0.94 | 0.76 | 85 | 91 | 90 | 87 | 111 | 126 |
| CRP | Mac-2BP, plasma | Neu (%) | 0.94 | 0.76 | 85 | 91 | 90 | 87 | 112 | 126 |
| Age | CRP | Mac-2BP, plasma | 0.94 | 0.78 | 87 | 91 | 90 | 89 | 112 | 127 |
| CRP | Cr | MX1, mean, intra | 0.94 | 0.71 | 80 | 90 | 88 | 83 | 92 | 99 |
| CRP | MCP-2, plasma | MX1, mean, intra | 0.94 | 0.69 | 81 | 88 | 86 | 84 | 74 | 83 |
| CHI3L1, plasma | CRP | MX1, mean, intra | 0.94 | 0.71 | 82 | 89 | 87 | 85 | 71 | 82 |
| CRP | Mac-2BP, plasma | sVEGFR2, plasma | 0.94 | 0.76 | 85 | 91 | 90 | 87 | 112 | 126 |
| CRP | MCP-2, plasma | RSAD2, mean, intra | 0.94 | 0.7 | 81 | 88 | 86 | 84 | 69 | 78 |
| CHI3L1, plasma | CRP | Mac-2BP, plasma | 0.94 | 0.77 | 84 | 92 | 90 | 87 | 112 | 127 |
| CRP | Mac-2BP, plasma | Pulse | 0.94 | 0.76 | 85 | 91 | 89 | 88 | 105 | 123 |
| CHI3L1, plasma | CRP | RSAD2, mean, intra | 0.94 | 0.72 | 84 | 88 | 86 | 86 | 68 | 77 |
| CRP | Lym (%) | RSAD2, mean, intra | 0.93 | 0.72 | 85 | 87 | 87 | 85 | 114 | 110 |
| CRP | MCP-2, plasma | Neu (%) | 0.93 | 0.68 | 78 | 89 | 87 | 82 | 116 | 127 |
| CRP | Neu (%) | RSAD2, mean, intra | 0.93 | 0.7 | 82 | 87 | 87 | 83 | 114 | 110 |
| CRP | Cr | sVEGFR2, plasma | 0.93 | 0.71 | 82 | 89 | 87 | 84 | 113 | 122 |
| CRP | Lym (%) | MCP-2, plasma | 0.93 | 0.7 | 79 | 91 | 88 | 83 | 115 | 127 |
| CRP | K | MCP-2, plasma | 0.93 | 0.67 | 76 | 90 | 89 | 79 | 113 | 113 |
| Age | CRP | MCP-2, plasma | 0.93 | 0.7 | 80 | 89 | 87 | 83 | 116 | 128 |
| CRP | Cr | K | 0.93 | 0.7 | 80 | 90 | 88 | 82 | 143 | 146 |
| CRP | MCP-2, plasma | sVEGFR2, plasma | 0.93 | 0.68 | 81 | 87 | 85 | 83 | 116 | 128 |
| Cr | MX1, mean, intra | TRAIL, plasma | 0.93 | 0.74 | 90 | 84 | 83 | 90 | 72 | 79 |
| Cr | RSAD2, mean, intra | TRAIL, plasma | 0.93 | 0.68 | 87 | 81 | 81 | 87 | 67 | 75 |
| Age | CRP | sVEGFR2, plasma | 0.93 | 0.7 | 83 | 87 | 85 | 85 | 116 | 129 |
| CRP | Cr | Lym (%) | 0.93 | 0.71 | 81 | 90 | 88 | 84 | 146 | 158 |
| ANC | CRP | MCP-2, plasma | 0.93 | 0.65 | 77 | 88 | 85 | 80 | 114 | 122 |
| Age | CRP | RSAD2, mean, intra | 0.93 | 0.67 | 79 | 88 | 87 | 80 | 114 | 110 |
| CRP | K | sVEGFR2, plasma | 0.93 | 0.69 | 79 | 89 | 88 | 81 | 113 | 114 |
| CHI3L1, plasma | CRP | Cr | 0.92 | 0.65 | 77 | 88 | 85 | 81 | 109 | 120 |
| CRP | Lym (%) | MX1, mean, intra | 0.92 | 0.69 | 82 | 88 | 87 | 82 | 119 | 114 |
| ANC | Age | CRP | 0.92 | 0.69 | 81 | 89 | 87 | 83 | 149 | 157 |
| ANC | CRP | Cr | 0.92 | 0.69 | 79 | 89 | 88 | 82 | 145 | 149 |
| CHI3L1, plasma | CRP | MCP-2, plasma | 0.92 | 0.68 | 79 | 89 | 86 | 82 | 112 | 125 |
| CRP | Neu (%) | sVEGFR2, plasma | 0.92 | 0.7 | 81 | 89 | 87 | 84 | 116 | 128 |
| Age | CRP | Lym (%) | 0.92 | 0.73 | 82 | 91 | 90 | 83 | 176 | 177 |
| CRP | Cr | Neu (%) | 0.92 | 0.71 | 81 | 89 | 88 | 84 | 147 | 159 |
| CRP | Lym (%) | sVEGFR2, plasma | 0.92 | 0.72 | 81 | 91 | 89 | 84 | 115 | 128 |
| CRP | MCP-2, plasma | Pulse | 0.92 | 0.69 | 78 | 90 | 88 | 82 | 108 | 124 |
| CRP | MX1, mean, intra | Neu (%) | 0.92 | 0.65 | 78 | 87 | 86 | 79 | 119 | 114 |
| Age | CRP | Neu (%) | 0.92 | 0.69 | 79 | 89 | 88 | 81 | 177 | 178 |

*Results obtained on patients whose reference standard was determined by an expert consensus

TABLE 3C

DETERMINANTS pairs that differentiate between mixed versus viral infected subjects
*Positives and negatives correspond to mixed and viral infected patients

| DETERMINANT #1 | DETERMINANT #2 | AUC | MCC | Sen % | Spe % | PPV % | NPV % | P | N |
|---|---|---|---|---|---|---|---|---|---|
| ATP6V0B, mean, intra | CRP | 0.995 | 0.77 | 93 | 93 | 70 | 99 | 15 | 81 |
| CRP | LIPT1, lymp, intra | 0.995 | 0.87 | 100 | 95 | 79 | 100 | 15 | 84 |
| CES1, gran, intra | CRP | 0.993 | 0.85 | 93 | 96 | 82 | 99 | 15 | 84 |

TABLE 3C-continued

DETERMINANTS pairs that differentiate between mixed versus viral infected subjects
*Positives and negatives correspond to mixed and viral infected patients

| DETERMINANT #1 | DETERMINANT #2 | AUC | MCC | Sen % | Spe % | PPV % | NPV % | P | N |
|---|---|---|---|---|---|---|---|---|---|
| CES1, mean, intra | CRP | 0.992 | 0.82 | 93 | 95 | 78 | 99 | 15 | 81 |
| CRP | PARP9, lymp, intra | 0.992 | 0.84 | 100 | 94 | 75 | 100 | 15 | 79 |
| PARP9, lymp, intra | TRAIL, plasma | 0.991 | 0.76 | 100 | 88 | 65 | 100 | 15 | 64 |
| CES1, gran, intra | TRAIL, plasma | 0.986 | 0.83 | 100 | 93 | 75 | 100 | 15 | 69 |
| CES1, mean, intra | TRAIL, plasma | 0.986 | 0.78 | 100 | 89 | 68 | 100 | 15 | 66 |
| ATP6V0B, mean, intra | TRAIL, plasma | 0.985 | 0.81 | 100 | 91 | 71 | 100 | 15 | 66 |
| LOC26010, lymp, intra | TRAIL, plasma | 0.978 | 0.71 | 93 | 88 | 64 | 98 | 15 | 69 |
| CRP | LOC26010, lymp, intra | 0.977 | 0.75 | 87 | 95 | 72 | 98 | 15 | 94 |
| MX1, gran, intra | TRAIL, plasma | 0.972 | 0.72 | 94 | 89 | 63 | 99 | 18 | 87 |
| MX1, mean, intra | TRAIL, plasma | 0.97 | 0.69 | 94 | 87 | 61 | 99 | 18 | 84 |
| LOC26010, gran, intra | TRAIL, plasma | 0.969 | 0.71 | 93 | 88 | 64 | 98 | 15 | 69 |
| CRP | LOC26010, gran, intra | 0.968 | 0.66 | 87 | 90 | 59 | 98 | 15 | 94 |
| CRP | LOC26010, mean, intra | 0.968 | 0.66 | 87 | 90 | 59 | 98 | 15 | 91 |
| LOC26010, mean, intra | TRAIL, plasma | 0.965 | 0.71 | 93 | 88 | 64 | 98 | 15 | 66 |
| RSAD2, gran, intra | TRAIL, plasma | 0.964 | 0.71 | 94 | 88 | 63 | 99 | 18 | 82 |
| LIPT1, lymp, intra | TRAIL, plasma | 0.962 | 0.69 | 87 | 90 | 65 | 97 | 15 | 69 |
| RSAD2, mean, intra | TRAIL, plasma | 0.956 | 0.63 | 89 | 85 | 57 | 97 | 18 | 79 |
| CRP | MX1, gran, intra | 0.953 | 0.7 | 85 | 92 | 65 | 97 | 20 | 117 |
| CRP | MX1, mean, intra | 0.949 | 0.69 | 85 | 92 | 65 | 97 | 20 | 114 |
| CRP | TRAIL, plasma | 0.933 | 0.61 | 83 | 87 | 59 | 96 | 29 | 127 |
| CRP | RSAD2, mean, intra | 0.924 | 0.76 | 95 | 92 | 68 | 99 | 20 | 110 |
| CRP | RSAD2, gran, intra | 0.923 | 0.75 | 95 | 91 | 66 | 99 | 20 | 113 |
| PARP9, lymp, intra | RSAD2, gran, intra | 0.918 | 0.5 | 88 | 77 | 42 | 97 | 16 | 81 |
| B2M, Plasma | CRP | 0.916 | 0.8 | 88 | 92 | 88 | 92 | 16 | 26 |
| LOC26010, lymp, intra | RSAD2, gran, intra | 0.906 | 0.49 | 88 | 77 | 40 | 97 | 16 | 91 |
| PARP9, lymp, intra | RSAD2, mean, intra | 0.903 | 0.48 | 88 | 74 | 41 | 97 | 16 | 78 |
| CES1, mean, intra | RSAD2, gran, intra | 0.898 | 0.51 | 88 | 77 | 44 | 97 | 16 | 78 |
| ATP6V0B, mean, intra | RSAD2, gran, intra | 0.897 | 0.51 | 88 | 77 | 44 | 97 | 16 | 78 |
| CES1, gran, intra | RSAD2, gran, intra | 0.896 | 0.5 | 88 | 77 | 42 | 97 | 16 | 81 |
| CHI3L1, plasma | CRP | 0.894 | 0.54 | 78 | 85 | 53 | 95 | 27 | 127 |
| LOC26010, gran, intra | RSAD2, gran, intra | 0.894 | 0.47 | 88 | 75 | 38 | 97 | 16 | 91 |
| LOC26010, mean, intra | RSAD2, gran, intra | 0.893 | 0.47 | 88 | 75 | 39 | 97 | 16 | 88 |
| CHI3L1, plasma | PARP9, lymp, intra | 0.888 | 0.56 | 71 | 89 | 59 | 93 | 14 | 64 |
| LOC26010, lymp, intra | RSAD2, mean, intra | 0.881 | 0.47 | 81 | 78 | 41 | 96 | 16 | 88 |
| LIPT1, lymp, intra | RSAD2, gran, intra | 0.878 | 0.44 | 81 | 75 | 39 | 95 | 16 | 81 |
| CES1, mean, intra | CHI3L1, plasma | 0.876 | 0.62 | 71 | 92 | 67 | 94 | 14 | 66 |
| ATP6V0B, mean, intra | RSAD2, mean, intra | 0.874 | 0.48 | 88 | 74 | 41 | 97 | 16 | 78 |
| LOC26010, lymp, intra | PARP9, lymp, intra | 0.873 | 0.41 | 81 | 72 | 36 | 95 | 16 | 81 |
| CHI3L1, plasma | RSAD2, gran, intra | 0.873 | 0.46 | 71 | 83 | 46 | 93 | 17 | 82 |
| CES1, gran, intra | RSAD2, mean, intra | 0.873 | 0.39 | 75 | 74 | 38 | 94 | 16 | 78 |
| MX1, gran, intra | PARP9, lymp, intra | 0.87 | 0.59 | 94 | 80 | 48 | 98 | 16 | 81 |
| B2M, Plasma | TRAIL, Plasma | 0.87 | 0.58 | 88 | 72 | 67 | 90 | 16 | 25 |
| CES1, mean, intra | RSAD2, mean, intra | 0.869 | 0.4 | 75 | 76 | 39 | 94 | 16 | 78 |
| CHI3L1, plasma | LIPT1, lymp, intra | 0.867 | 0.6 | 71 | 91 | 63 | 94 | 14 | 69 |
| LOC26010, gran, intra | RSAD2, mean, intra | 0.866 | 0.52 | 88 | 80 | 44 | 97 | 16 | 88 |
| LOC26010, gran, intra | PARP9, lymp, intra | 0.865 | 0.46 | 88 | 73 | 39 | 97 | 16 | 81 |
| MX1, mean, intra | PARP9, lymp, intra | 0.865 | 0.59 | 94 | 79 | 48 | 98 | 16 | 78 |
| ATP6V0B, mean, intra | CHI3L1, plasma | 0.863 | 0.54 | 64 | 91 | 60 | 92 | 14 | 66 |
| LOC26010, lymp, intra | MX1, mean, intra | 0.863 | 0.46 | 88 | 74 | 37 | 97 | 16 | 93 |
| ATP6V0B, mean, intra | PARP9, lymp, intra | 0.863 | 0.47 | 88 | 73 | 40 | 97 | 16 | 78 |
| CES1, gran, intra | PARP9, lymp, intra | 0.863 | 0.39 | 81 | 70 | 35 | 95 | 16 | 81 |
| CES1, mean, intra | PARP9, lymp, intra | 0.863 | 0.41 | 81 | 72 | 37 | 95 | 16 | 78 |
| LOC26010, mean, intra | RSAD2, mean, intra | 0.862 | 0.51 | 88 | 78 | 42 | 97 | 16 | 88 |
| LOC26010, lymp, intra | MX1, gran, intra | 0.861 | 0.45 | 88 | 74 | 36 | 97 | 16 | 96 |
| LOC26010, mean, intra | PARP9, lymp, intra | 0.861 | 0.47 | 88 | 73 | 40 | 97 | 16 | 78 |
| B2M, Plasma | Mac-2BP, Plasma | 0.749 | 0.51 | 67 | 84 | 71 | 81 | 15 | 25 |
| SAA, Plasma | CRP | 0.882 | 0.51 | 71 | 81 | 83 | 68 | 42 | 31 |
| Mac-2BP, Plasma | SAA, Plasma | 0.831 | 0.61 | 85 | 76 | 83 | 79 | 40 | 29 |
| SAA, Plasma | TRAIL, Plasma | 0.873 | 0.6 | 78 | 83 | 86 | 73 | 40 | 29 |
| SAA Plasma | sVEGFR2, secreted | 0.796 | 0.46 | 76 | 73 | 86 | 57 | 25 | 11 |

TABLE 3D

DETERMINANTS triplets that differentiate between mixed versus viral infected subjects
Positives and negatives correspond to mixed and viral infected patients respectively

| DETERMINANT #1 | DETERMINANT #2 | DETERMINANT #3 | AUC | MCC | Sen % | Spe % | PPV % | NPV % | P | N |
|---|---|---|---|---|---|---|---|---|---|---|
| CES1, gran, intra | CRP | TRAIL, plasma | 1 | 0.96 | 100 | 99 | 93 | 100 | 14 | 67 |
| CES1, mean, intra | CRP | TRAIL, plasma | 1 | 0.96 | 100 | 98 | 93 | 100 | 14 | 64 |
| ATP6V0B, mean, intra | CRP | TRAIL, plasma | 0.999 | 0.92 | 100 | 97 | 88 | 100 | 14 | 64 |
| CRP | LIPT1, lymp, intra | PARP9, lymp, intra | 0.999 | 0.84 | 100 | 94 | 75 | 100 | 15 | 79 |

TABLE 3D-continued

DETERMINANTS triplets that differentiate between mixed versus viral infected subjects
Positives and negatives correspond to mixed and viral infected patients respectively

| DETERMINANT #1 | DETERMINANT #2 | DETERMINANT #3 | AUC | MCC | Sen % | Spe % | PPV % | NPV % | P | N |
|---|---|---|---|---|---|---|---|---|---|---|
| CRP | LIPT1, lymp, intra | TRAIL, plasma | 0.998 | 0.92 | 100 | 97 | 88 | 100 | 14 | 67 |
| CRP | PARP9, lymp, intra | RSAD2, gran, intra | 0.998 | 0.87 | 100 | 95 | 79 | 100 | 15 | 79 |
| CES1, gran, intra | CRP | PARP9, lymp, intra | 0.997 | 0.85 | 93 | 96 | 82 | 99 | 15 | 79 |
| CES1, gran, intra | CRP | RSAD2, gran, intra | 0.997 | 0.88 | 93 | 97 | 88 | 99 | 15 | 79 |
| CRP | LIPT1, lymp, intra | RSAD2, gran, intra | 0.997 | 0.9 | 100 | 96 | 83 | 100 | 15 | 79 |
| CRP | PARP9, lymp, intra | TRAIL, plasma | 0.997 | 0.92 | 100 | 97 | 88 | 100 | 14 | 62 |
| ATP6V0B, mean, intra | CRP | PARP9, lymp, intra | 0.996 | 0.86 | 100 | 95 | 79 | 100 | 15 | 76 |
| ATP6V0B, mean, intra | CRP | RSAD2, gran, intra | 0.996 | 0.86 | 100 | 95 | 79 | 100 | 15 | 76 |
| ATP6V0B, mean, intra | CRP | RSAD2, mean, intra | 0.996 | 0.84 | 100 | 93 | 75 | 100 | 15 | 76 |
| CES1, gran, intra | CRP | RSAD2, mean, intra | 0.996 | 0.88 | 93 | 97 | 88 | 99 | 15 | 76 |
| CES1, mean, intra | CRP | PARP9, lymp, intra | 0.996 | 0.82 | 93 | 95 | 78 | 99 | 15 | 76 |
| CES1, mean, intra | CRP | RSAD2, gran, intra | 0.996 | 0.88 | 93 | 97 | 88 | 99 | 15 | 76 |
| CES1, mean, intra | CRP | RSAD2, mean, intra | 0.996 | 0.85 | 93 | 96 | 82 | 99 | 15 | 76 |
| CRP | LIPT1, lymp, intra | MX1, gran, intra | 0.996 | 0.87 | 100 | 95 | 79 | 100 | 15 | 84 |
| CRP | LIPT1, lymp, intra | MX1, mean, intra | 0.996 | 0.87 | 100 | 95 | 79 | 100 | 15 | 81 |
| CRP | LIPT1, lymp, intra | RSAD2, mean, intra | 0.996 | 0.86 | 100 | 95 | 79 | 100 | 15 | 76 |
| CRP | PARP9, lymp, intra | RSAD2, mean, intra | 0.996 | 0.84 | 100 | 93 | 75 | 100 | 15 | 76 |
| ATP6V0B, mean, intra | CRP | MX1, gran, intra | 0.995 | 0.82 | 93 | 95 | 78 | 99 | 15 | 81 |
| CES1, gran, intra | CRP | MX1, gran, intra | 0.995 | 0.85 | 93 | 96 | 82 | 99 | 15 | 84 |
| CES1, gran, intra | CRP | MX1, mean, intra | 0.995 | 0.85 | 93 | 96 | 82 | 99 | 15 | 81 |
| CES1, mean, intra | CRP | MX1, gran, intra | 0.995 | 0.85 | 93 | 96 | 82 | 99 | 15 | 81 |
| CES1, mean, intra | CRP | MX1, mean, intra | 0.995 | 0.82 | 93 | 95 | 78 | 99 | 15 | 81 |
| CRP | MX1, gran, intra | PARP9, lymp, intra | 0.995 | 0.84 | 100 | 94 | 75 | 100 | 15 | 79 |
| ATP6V0B, mean, intra | CRP | LIPT1, lymp, intra | 0.994 | 0.79 | 93 | 94 | 74 | 99 | 15 | 81 |
| CES1, gran, intra | CRP | LIPT1, lymp, intra | 0.994 | 0.82 | 93 | 95 | 78 | 99 | 15 | 84 |
| CRP | LOC26010, gran, intra | TRAIL, plasma | 0.994 | 0.89 | 100 | 96 | 82 | 100 | 14 | 67 |
| CRP | LOC26010, lymp, intra | TRAIL, plasma | 0.994 | 0.92 | 100 | 97 | 88 | 100 | 14 | 67 |
| ATP6V0B, mean, intra | CES1, gran, intra | CRP | 0.993 | 0.79 | 93 | 94 | 74 | 99 | 15 | 81 |
| ATP6V0B, mean, intra | CRP | MX1, mean, intra | 0.993 | 0.77 | 93 | 93 | 70 | 99 | 15 | 81 |
| CES1, mean, intra | CRP | LIPT1, lymp, intra | 0.993 | 0.82 | 93 | 95 | 78 | 99 | 15 | 81 |
| CRP | LIPT1, lymp, intra | LOC26010, lymp, intra | 0.993 | 0.87 | 100 | 95 | 79 | 100 | 15 | 84 |
| CRP | MX1, mean, intra | PARP9, lymp, intra | 0.993 | 0.79 | 93 | 93 | 74 | 99 | 15 | 76 |
| ATP6V0B, mean, intra | CES1, mean, intra | CRP | 0.992 | 0.79 | 93 | 94 | 74 | 99 | 15 | 81 |
| CES1, mean, intra | CRP | LOC26010, lymp, intra | 0.992 | 0.82 | 93 | 95 | 78 | 99 | 15 | 81 |
| CRP | LOC26010, mean, intra | TRAIL, plasma | 0.992 | 0.89 | 100 | 95 | 82 | 100 | 14 | 64 |
| CES1, gran, intra | CES1, mean, intra | CRP | 0.991 | 0.85 | 93 | 96 | 82 | 99 | 15 | 81 |
| CES1, gran, intra | CRP | LOC26010, lymp, intra | 0.991 | 0.82 | 93 | 95 | 78 | 99 | 15 | 84 |
| CRP | LIPT1, lymp, intra | LOC26010, gran, intra | 0.991 | 0.82 | 93 | 95 | 78 | 99 | 15 | 84 |
| CRP | LOC26010, lymp, intra | MX1, gran, intra | 0.991 | 0.8 | 93 | 95 | 74 | 99 | 15 | 94 |
| CRP | LOC26010, lymp, intra | PARP9, lymp, intra | 0.991 | 0.82 | 93 | 95 | 78 | 99 | 15 | 79 |
| CRP | LOC26010, lymp, intra | RSAD2, gran, intra | 0.991 | 0.8 | 93 | 94 | 74 | 99 | 15 | 89 |
| CES1, gran, intra | CRP | LOC26010, gran, intra | 0.99 | 0.85 | 93 | 96 | 82 | 99 | 15 | 84 |
| CES1, mean, intra | CRP | LOC26010, mean, intra | 0.99 | 0.82 | 93 | 95 | 78 | 99 | 15 | 81 |
| CRP | LIPT1, lymp, intra | LOC26010, mean, intra | 0.99 | 0.82 | 93 | 95 | 78 | 99 | 15 | 81 |
| CRP | LOC26010, lymp, intra | MX1, mean, intra | 0.99 | 0.8 | 93 | 95 | 74 | 99 | 15 | 91 |
| ATP6V0B, mean, intra | CRP | LOC26010, lymp, intra | 0.989 | 0.77 | 93 | 93 | 70 | 99 | 15 | 81 |
| ATP6V0B, mean, intra | CRP | LOC26010, mean, intra | 0.989 | 0.74 | 93 | 91 | 67 | 99 | 15 | 81 |
| CES1, gran, intra | CRP | LOC26010, mean, intra | 0.989 | 0.82 | 93 | 95 | 78 | 99 | 15 | 81 |
| CES1, gran, intra | PARP9, lymp, intra | TRAIL, plasma | 0.989 | 0.78 | 93 | 92 | 74 | 98 | 15 | 64 |
| CES1, mean, intra | CRP | LOC26010, gran, intra | 0.989 | 0.82 | 93 | 95 | 78 | 99 | 15 | 81 |
| CRP | LOC26010, gran, intra | PARP9, lymp, intra | 0.989 | 0.79 | 93 | 94 | 74 | 99 | 15 | 79 |
| CRP | LOC26010, mean, intra | PARP9, lymp, intra | 0.989 | 0.79 | 93 | 93 | 74 | 99 | 15 | 76 |
| PARP9, lymp, intra | RSAD2, gran, intra | TRAIL, plasma | 0.989 | 0.8 | 100 | 91 | 71 | 100 | 15 | 64 |
| ATP6V0B, mean, intra | CRP | LOC26010, gran, intra | 0.988 | 0.77 | 93 | 93 | 70 | 99 | 15 | 81 |
| ATP6V0B, mean, intra | PARP9, lymp, intra | TRAIL, plasma | 0.988 | 0.75 | 93 | 90 | 70 | 98 | 15 | 61 |
| CRP | LOC26010, gran, intra | MX1, gran, intra | 0.988 | 0.73 | 87 | 94 | 68 | 98 | 15 | 94 |
| CRP | LOC26010, gran, intra | MX1, mean, intra | 0.988 | 0.73 | 87 | 93 | 68 | 98 | 15 | 91 |
| CRP | LOC26010, mean, intra | MX1, gran, intra | 0.988 | 0.73 | 87 | 93 | 68 | 98 | 15 | 91 |
| CRP | LOC26010, mean, intra | MX1, mean, intra | 0.988 | 0.73 | 87 | 93 | 68 | 98 | 15 | 91 |
| MX1, gran, intra | PARP9, lymp, intra | TRAIL, plasma | 0.988 | 0.76 | 93 | 91 | 70 | 98 | 15 | 64 |
| MX1, mean, intra | PARP9, lymp, intra | TRAIL, plasma | 0.987 | 0.75 | 93 | 90 | 70 | 98 | 15 | 61 |
| PARP9, lymp, intra | RSAD2, mean, intra | TRAIL, plasma | 0.987 | 0.8 | 100 | 90 | 71 | 100 | 15 | 61 |
| CES1, gran, intra | CES1, mean, intra | TRAIL, plasma | 0.986 | 0.81 | 100 | 91 | 71 | 100 | 15 | 66 |
| CRP | LOC26010, lymp, intra | RSAD2, mean, intra | 0.986 | 0.8 | 93 | 94 | 74 | 99 | 15 | 86 |
| ATP6V0B, mean, intra | CES1, mean, intra | TRAIL, plasma | 0.985 | 0.81 | 100 | 91 | 71 | 100 | 15 | 66 |
| CES1, mean, intra | PARP9, lymp, intra | TRAIL, plasma | 0.985 | 0.83 | 100 | 92 | 75 | 100 | 15 | 61 |
| ATP6V0B, mean, intra | CES1, gran, intra | TRAIL, plasma | 0.984 | 0.83 | 100 | 92 | 75 | 100 | 15 | 66 |
| CES1, gran, intra | LOC26010, lymp, intra | TRAIL, plasma | 0.984 | 0.79 | 93 | 93 | 74 | 98 | 15 | 69 |
| CES1, gran, intra | MX1, gran, intra | TRAIL, plasma | 0.984 | 0.79 | 93 | 93 | 74 | 98 | 15 | 69 |
| CRP | LOC26010, gran, intra | RSAD2, mean, intra | 0.984 | 0.73 | 87 | 93 | 68 | 98 | 15 | 86 |
| CES1, gran, intra | LOC26010, mean, intra | TRAIL, plasma | 0.983 | 0.79 | 93 | 92 | 74 | 98 | 15 | 66 |
| CES1, gran, intra | MX1, mean, intra | TRAIL, plasma | 0.983 | 0.83 | 100 | 92 | 75 | 100 | 15 | 66 |
| CES1, gran, intra | RSAD2, gran, intra | TRAIL, plasma | 0.983 | 0.83 | 100 | 92 | 75 | 100 | 15 | 64 |
| CES1, mean, intra | LOC26010, gran, intra | TRAIL, plasma | 0.983 | 0.79 | 93 | 92 | 74 | 98 | 15 | 66 |
| CES1, mean, intra | LOC26010, lymp, intra | TRAIL, plasma | 0.983 | 0.76 | 93 | 91 | 70 | 98 | 15 | 66 |

TABLE 3D-continued

DETERMINANTS triplets that differentiate between mixed versus viral infected subjects
Positives and negatives correspond to mixed and viral infected patients respectively

| DETERMINANT #1 | DETERMINANT #2 | DETERMINANT #3 | AUC | MCC | Sen % | Spe % | PPV % | NPV % | P | N |
| --- | --- | --- | --- | --- | --- | --- | --- | --- | --- | --- |
| CES1, mean, intra | LOC26010, mean, intra | TRAIL, plasma | 0.983 | 0.79 | 93 | 92 | 74 | 98 | 15 | 66 |
| CES1, mean, intra | MX1, gran, intra | TRAIL, plasma | 0.983 | 0.83 | 100 | 92 | 75 | 100 | 15 | 66 |
| CES1, mean, intra | MX1, mean, intra | TRAIL, plasma | 0.983 | 0.83 | 100 | 92 | 75 | 100 | 15 | 66 |
| LOC26010, lymp, intra | PARP9, lymp, intra | TRAIL, plasma | 0.983 | 0.76 | 93 | 91 | 70 | 98 | 15 | 64 |
| ATP6V0B, mean, intra | MX1, mean, intra | TRAIL, plasma | 0.982 | 0.76 | 93 | 91 | 70 | 98 | 15 | 66 |
| CES1, gran, intra | LOC26010, gran, intra | TRAIL, plasma | 0.982 | 0.79 | 93 | 93 | 74 | 98 | 15 | 69 |
| CRP | LOC26010, mean, intra | RSAD2, mean, intra | 0.982 | 0.73 | 87 | 93 | 68 | 98 | 15 | 86 |
| ATP6V0B, mean, intra | LOC26010, lymp, intra | TRAIL, plasma | 0.981 | 0.79 | 93 | 92 | 74 | 98 | 15 | 66 |
| ATP6V0B, mean, intra | MX1, gran, intra | TRAIL, plasma | 0.981 | 0.76 | 93 | 91 | 70 | 98 | 15 | 66 |
| CES1, mean, intra | RSAD2, gran, intra | TRAIL, plasma | 0.981 | 0.83 | 100 | 92 | 75 | 100 | 15 | 61 |
| ATP6V0B, mean, intra | RSAD2, gran, intra | TRAIL, plasma | 0.98 | 0.78 | 100 | 89 | 68 | 100 | 15 | 61 |
| ATP6V0B, mean, intra | RSAD2, mean, intra | TRAIL, plasma | 0.98 | 0.8 | 100 | 90 | 71 | 100 | 15 | 61 |
| CES1, gran, intra | RSAD2, mean, intra | TRAIL, plasma | 0.98 | 0.83 | 100 | 92 | 75 | 100 | 15 | 61 |
| CES1, mean, intra | RSAD2, mean, intra | TRAIL, plasma | 0.98 | 0.83 | 100 | 92 | 75 | 100 | 15 | 61 |
| LOC26010, gran, intra | PARP9, lymp, intra | TRAIL, plasma | 0.98 | 0.73 | 93 | 89 | 67 | 98 | 15 | 64 |
| CRP | LOC26010, mean, intra | RSAD2, gran, intra | 0.979 | 0.75 | 87 | 94 | 72 | 98 | 15 | 86 |
| LOC26010, mean, intra | PARP9, lymp, intra | TRAIL, plasma | 0.979 | 0.73 | 93 | 89 | 67 | 98 | 15 | 61 |
| ATP6V0B, mean, intra | LOC26010, gran, intra | TRAIL, plasma | 0.978 | 0.76 | 93 | 91 | 70 | 98 | 15 | 66 |
| CES1, mean, intra | LIPT1, lymp, intra | TRAIL, plasma | 0.978 | 0.73 | 93 | 89 | 67 | 98 | 15 | 66 |
| CRP | LOC26010, gran, intra | RSAD2, gran, intra | 0.978 | 0.75 | 87 | 94 | 72 | 98 | 15 | 89 |
| LIPT1, lymp, intra | PARP9, lymp, intra | TRAIL, plasma | 0.978 | 0.78 | 93 | 92 | 74 | 98 | 15 | 64 |
| ATP6V0B, mean, intra | LOC26010, mean, intra | TRAIL, plasma | 0.977 | 0.76 | 93 | 91 | 70 | 98 | 15 | 66 |
| CES1, gran, intra | LIPT1, lymp, intra | TRAIL, plasma | 0.977 | 0.79 | 93 | 93 | 74 | 98 | 15 | 69 |
| CES1, mean, intra | CHI3L1, plasma | TRAIL, plasma | 0.977 | 0.7 | 86 | 91 | 67 | 97 | 14 | 65 |
| LOC26010, lymp, intra | RSAD2, gran, intra | TRAIL, plasma | 0.976 | 0.76 | 93 | 91 | 70 | 98 | 15 | 64 |
| CES1, gran, intra | CHI3L1, plasma | TRAIL, plasma | 0.975 | 0.73 | 86 | 93 | 71 | 97 | 14 | 68 |
| ATP6V0B, mean, intra | LIPT1, lymp, intra | TRAIL, plasma | 0.974 | 0.76 | 93 | 91 | 70 | 98 | 15 | 66 |
| ATP6V0B, mean, intra | CHI3L1, plasma | CRP | 0.972 | 0.76 | 92 | 92 | 71 | 98 | 13 | 64 |
| CRP | MX1, mean, intra | TRAIL, plasma | 0.972 | 0.75 | 88 | 93 | 71 | 97 | 17 | 82 |
| LOC26010, lymp, intra | MX1, mean, intra | TRAIL, plasma | 0.972 | 0.79 | 93 | 92 | 74 | 98 | 15 | 66 |
| LOC26010, lymp, intra | RSAD2, mean, intra | TRAIL, plasma | 0.972 | 0.75 | 93 | 90 | 70 | 98 | 15 | 61 |
| ATP6V0B, mean, intra | CHI3L1, plasma | TRAIL, plasma | 0.971 | 0.7 | 86 | 91 | 67 | 97 | 14 | 65 |
| CHI3L1, plasma | LIPT1, lymp, intra | TRAIL, plasma | 0.971 | 0.73 | 86 | 93 | 71 | 97 | 14 | 68 |
| CRP | LOC26010, gran, intra | LOC26010, lymp, intra | 0.971 | 0.68 | 87 | 91 | 62 | 98 | 15 | 94 |
| CRP | MX1, gran, intra | TRAIL, plasma | 0.971 | 0.8 | 88 | 95 | 79 | 98 | 17 | 85 |
| CES1, gran, intra | CHI3L1, plasma | CRP | 0.97 | 0.74 | 92 | 91 | 67 | 98 | 13 | 67 |
| CRP | LOC26010, lymp, intra | LOC26010, mean, intra | 0.97 | 0.68 | 87 | 91 | 62 | 98 | 15 | 91 |
| LOC26010, gran, intra | RSAD2, gran, intra | TRAIL, plasma | 0.97 | 0.76 | 93 | 91 | 70 | 98 | 15 | 64 |
| LOC26010, lymp, intra | MX1, gran, intra | TRAIL, plasma | 0.97 | 0.79 | 93 | 93 | 74 | 98 | 15 | 69 |
| B2M, Plasma | CRP | TRAIL, Plasma | 0.93 | 0.64 | 75 | 88 | 80 | 85 | 16 | 25 |
| B2M, Plasma | CRP | Mac-2BP, Plasma | 0.928 | 0.73 | 80 | 92 | 86 | 88 | 15 | 25 |
| B2M, Plasma | Mac-2BP, Plasma | TRAIL, Plasma | 0.853 | 0.54 | 80 | 76 | 67 | 86 | 15 | 25 |

TABLE 3E

DETERMINANTS pairs that differentiate between infectious
versus non-infectious disease patients
Positives (P) and Negatives (N) correspond to patients with
an infectious and non-infectious disease respectively.

| DETERMINANT #1 | DETERMINANT #2 | AUC | TA | Sen | Spe | PPV | NPV | P | N |
| --- | --- | --- | --- | --- | --- | --- | --- | --- | --- |
| CRP | IL1ra | 0.908 | 0.791 | 0.84 | 0.84 | 0.95 | 0.58 | 265 | 70 |
| CRP | IP10 | 0.93 | 0.797 | 0.87 | 0.81 | 0.95 | 0.63 | 265 | 70 |
| CRP | Lym (%) | 0.847 | 0.814 | 0.824 | 0.74 | 0.958 | 0.37 | 552 | 77 |
| CRP | Neu (%) | 0.837 | 0.791 | 0.792 | 0.779 | 0.963 | 0.343 | 554 | 77 |
| CRP | Pulse | 0.879 | 0.852 | 0.857 | 0.811 | 0.969 | 0.448 | 519 | 74 |
| CRP | SAA | 0.896 | 0.743 | 0.84 | 0.80 | 0.94 | 0.58 | 265 | 70 |
| CRP | TNFR1 | 0.862 | 0.821 | 0.806 | 0.839 | 0.853 | 0.788 | 36 | 31 |
| CRP | TRAIL | 0.843 | 0.777 | 0.78 | 0.75 | 0.963 | 0.29 | 569 | 68 |
| CRP | WBC | 0.828 | 0.775 | 0.777 | 0.766 | 0.96 | 0.322 | 555 | 77 |
| IL1ra | IP10 | 0.858 | 0.728 | 0.79 | 0.81 | 0.94 | 0.50 | 265 | 70 |
| IL1ra | Lym (%) | 0.849 | 0.8 | 0.833 | 0.765 | 0.789 | 0.813 | 36 | 34 |
| IL1ra | Neu (%) | 0.827 | 0.786 | 0.806 | 0.765 | 0.784 | 0.788 | 36 | 34 |
| IL1ra | Pulse | 0.829 | 0.825 | 0.742 | 0.906 | 0.885 | 0.784 | 31 | 32 |
| IL1ra | SAA | 0.879 | 0.776 | 0.80 | 0.86 | 0.95 | 0.54 | 265 | 70 |
| IL1ra | TNFR1 | 0.821 | 0.786 | 0.778 | 0.794 | 0.8 | 0.771 | 36 | 34 |
| IL1ra | TRAIL | 0.835 | 0.785 | 0.758 | 0.813 | 0.806 | 0.765 | 33 | 32 |
| IL1ra | WBC | 0.79 | 0.771 | 0.806 | 0.735 | 0.763 | 0.781 | 36 | 34 |
| IP10 | Lym (%) | 0.868 | 0.814 | 0.889 | 0.735 | 0.78 | 0.862 | 36 | 34 |
| IP10 | Neu (%) | 0.85 | 0.8 | 0.917 | 0.676 | 0.75 | 0.885 | 36 | 34 |
| IP10 | Pulse | 0.86 | 0.857 | 0.806 | 0.906 | 0.893 | 0.829 | 31 | 32 |

TABLE 3E-continued

DETERMINANTS pairs that differentiate between infectious versus non-infectious disease patients
Positives (P) and Negatives (N) correspond to patients with an infectious and non-infectious disease respectively.

| DETERMINANT #1 | DETERMINANT #2 | AUC | TA | Sen | Spe | PPV | NPV | P | N |
|---|---|---|---|---|---|---|---|---|---|
| IP10 | SAA | 0.896 | 0.785 | 0.80 | 0.84 | 0.95 | 0.53 | 265 | 70 |
| IP10 | TNFR1 | 0.847 | 0.8 | 0.833 | 0.765 | 0.789 | 0.813 | 36 | 34 |
| IP10 | TRAIL | 0.861 | 0.831 | 0.818 | 0.844 | 0.844 | 0.818 | 33 | 32 |
| IP10 | WBC | 0.821 | 0.8 | 0.806 | 0.794 | 0.806 | 0.794 | 36 | 34 |
| Lym (%) | Neu (%) | 0.698 | 0.669 | 0.67 | 0.659 | 0.93 | 0.228 | 555 | 82 |
| Lym (%) | Pulse | 0.821 | 0.753 | 0.752 | 0.759 | 0.953 | 0.319 | 516 | 79 |
| Lym (%) | SAA | 0.871 | 0.794 | 0.788 | 0.838 | 0.972 | 0.354 | 534 | 74 |
| Lym (%) | TNFR1 | 0.827 | 0.771 | 0.833 | 0.706 | 0.75 | 0.8 | 36 | 34 |
| Lym (%) | TRAIL | 0.711 | 0.643 | 0.636 | 0.699 | 0.94 | 0.206 | 538 | 73 |
| Lym (%) | WBC | 0.72 | 0.673 | 0.674 | 0.671 | 0.933 | 0.233 | 555 | 82 |
| Neu (%) | Pulse | 0.799 | 0.698 | 0.678 | 0.835 | 0.964 | 0.283 | 518 | 79 |
| Neu (%) | SAA | 0.865 | 0.796 | 0.793 | 0.824 | 0.97 | 0.355 | 535 | 74 |
| Neu (%) | TNFR1 | 0.801 | 0.786 | 0.75 | 0.824 | 0.818 | 0.757 | 36 | 34 |
| Neu (%) | TRAIL | 0.684 | 0.61 | 0.598 | 0.699 | 0.936 | 0.19 | 540 | 73 |
| Neu (%) | WBC | 0.682 | 0.643 | 0.646 | 0.622 | 0.921 | 0.206 | 557 | 82 |
| Pulse | SAA | 0.871 | 0.886 | 0.898 | 0.803 | 0.97 | 0.528 | 501 | 71 |
| Pulse | TNFR1 | 0.799 | 0.825 | 0.871 | 0.781 | 0.794 | 0.862 | 31 | 32 |
| Pulse | TRAIL | 0.786 | 0.735 | 0.738 | 0.714 | 0.949 | 0.273 | 507 | 70 |
| Pulse | WBC | 0.793 | 0.727 | 0.717 | 0.797 | 0.959 | 0.3 | 519 | 79 |
| SAA | TNFR1 | 0.854 | 0.826 | 0.861 | 0.788 | 0.816 | 0.839 | 36 | 33 |
| SAA | TRAIL | 0.867 | 0.797 | 0.792 | 0.843 | 0.976 | 0.335 | 562 | 70 |
| SAA | WBC | 0.861 | 0.8 | 0.797 | 0.824 | 0.97 | 0.359 | 536 | 74 |
| TNFR1 | TRAIL | 0.799 | 0.785 | 0.758 | 0.813 | 0.806 | 0.765 | 33 | 32 |
| TNFR1 | WBC | 0.801 | 0.757 | 0.778 | 0.735 | 0.757 | 0.758 | 36 | 34 |
| TRAIL | WBC | 0.708 | 0.718 | 0.726 | 0.658 | 0.94 | 0.245 | 541 | 73 |

TABLE 3F

DETERMINANTS triplets that differentiate between infectious versus non-infectious disease patients
Positives (P) and Negatives (N) correspond to patients with an infectious and non-infectious disease respectively.

| DETERMINANT #1 | DETERMINANT #2 | DETERMINANT #3 | AUC | TA | Sen | Spe | P | N |
|---|---|---|---|---|---|---|---|---|
| CRP | IL1ra | IP10 | 0.931 | 0.788 | 0.85 | 0.84 | 265 | 70 |
| CRP | IL1ra | Lym (%) | 0.864 | 0.821 | 0.778 | 0.871 | 36 | 31 |
| CRP | IL1ra | Neu (%) | 0.872 | 0.821 | 0.806 | 0.839 | 36 | 31 |
| CRP | IL1ra | Pulse | 0.859 | 0.9 | 0.871 | 0.931 | 31 | 29 |
| CRP | IL1ra | SAA | 0.92 | 0.797 | 0.87 | 0.81 | 265 | 70 |
| CRP | IL1ra | TNFR1 | 0.866 | 0.836 | 0.861 | 0.806 | 36 | 31 |
| CRP | IL1ra | TRAIL | 0.888 | 0.855 | 0.939 | 0.759 | 33 | 29 |
| CRP | IL1ra | WBC | 0.905 | 0.851 | 0.889 | 0.806 | 36 | 31 |
| CRP | IP10 | Lym (%) | 0.9 | 0.821 | 0.806 | 0.839 | 36 | 31 |
| CRP | IP10 | Neu (%) | 0.9 | 0.836 | 0.833 | 0.839 | 36 | 31 |
| CRP | IP10 | Pulse | 0.889 | 0.9 | 0.903 | 0.897 | 31 | 29 |
| CRP | IP10 | SAA | 0.935 | 0.8 | 0.83 | 0.86 | 265 | 70 |
| CRP | IP10 | TNFR1 | 0.882 | 0.821 | 0.806 | 0.839 | 36 | 31 |
| CRP | IP10 | TRAIL | 0.903 | 0.887 | 0.879 | 0.897 | 33 | 29 |
| CRP | IP10 | WBC | 0.894 | 0.836 | 0.833 | 0.839 | 36 | 31 |
| CRP | Lym (%) | Neu (%) | 0.843 | 0.8 | 0.803 | 0.779 | 552 | 77 |
| CRP | Lym (%) | Pulse | 0.882 | 0.838 | 0.842 | 0.811 | 513 | 74 |
| CRP | Lym (%) | SAA | 0.871 | 0.827 | 0.831 | 0.797 | 531 | 69 |
| CRP | Lym (%) | TNFR1 | 0.818 | 0.791 | 0.778 | 0.806 | 36 | 31 |
| CRP | Lym (%) | TRAIL | 0.86 | 0.746 | 0.731 | 0.868 | 535 | 68 |
| CRP | Lym (%) | WBC | 0.846 | 0.738 | 0.728 | 0.805 | 552 | 77 |
| CRP | Neu (%) | Pulse | 0.886 | 0.846 | 0.85 | 0.811 | 515 | 74 |
| CRP | Neu (%) | SAA | 0.867 | 0.819 | 0.823 | 0.783 | 532 | 69 |
| CRP | Neu (%) | TNFR1 | 0.821 | 0.791 | 0.778 | 0.806 | 36 | 31 |
| CRP | Neu (%) | TRAIL | 0.857 | 0.757 | 0.747 | 0.838 | 537 | 68 |
| CRP | Neu (%) | WBC | 0.84 | 0.721 | 0.709 | 0.805 | 554 | 77 |
| CRP | Pulse | SAA | 0.864 | 0.837 | 0.835 | 0.848 | 498 | 66 |
| CRP | Pulse | TNFR1 | 0.84 | 0.85 | 0.903 | 0.793 | 31 | 29 |
| CRP | Pulse | TRAIL | 0.869 | 0.831 | 0.827 | 0.862 | 504 | 65 |
| CRP | Pulse | WBC | 0.886 | 0.829 | 0.826 | 0.851 | 516 | 74 |
| CRP | SAA | TNFR1 | 0.857 | 0.833 | 0.833 | 0.833 | 36 | 30 |
| CRP | SAA | TRAIL | 0.869 | 0.817 | 0.819 | 0.8 | 559 | 65 |
| CRP | SAA | WBC | 0.859 | 0.827 | 0.833 | 0.783 | 533 | 69 |
| CRP | TNFR1 | TRAIL | 0.853 | 0.806 | 0.758 | 0.862 | 33 | 29 |
| CRP | TNFR1 | WBC | 0.872 | 0.806 | 0.833 | 0.774 | 36 | 31 |
| CRP | TRAIL | WBC | 0.852 | 0.762 | 0.76 | 0.779 | 538 | 68 |
| IL1ra | IP10 | Lym (%) | 0.863 | 0.829 | 0.861 | 0.794 | 36 | 34 |

TABLE 3F-continued

DETERMINANTS triplets that differentiate between infectious versus non-infectious disease patients
Positives (P) and Negatives (N) correspond to patients with an infectious and non-infectious disease respectively.

| DETERMINANT #1 | DETERMINANT #2 | DETERMINANT #3 | AUC | TA | Sen | Spe | P | N |
|---|---|---|---|---|---|---|---|---|
| IL1ra | IP10 | Neu (%) | 0.863 | 0.814 | 0.861 | 0.765 | 36 | 34 |
| IL1ra | IP10 | Pulse | 0.88 | 0.905 | 0.871 | 0.938 | 31 | 32 |
| IL1ra | IP10 | SAA | 0.899 | 0.8 | 0.79 | 0.89 | 265 | 70 |
| IL1ra | IP10 | TNFR1 | 0.837 | 0.8 | 0.833 | 0.765 | 36 | 34 |
| IL1ra | IP10 | TRAIL | 0.879 | 0.862 | 0.848 | 0.875 | 33 | 32 |
| IL1ra | IP10 | WBC | 0.835 | 0.829 | 0.861 | 0.794 | 36 | 34 |
| IL1ra | Lym (%) | Neu (%) | 0.837 | 0.786 | 0.722 | 0.853 | 36 | 34 |
| IL1ra | Lym (%) | Pulse | 0.869 | 0.841 | 0.774 | 0.906 | 31 | 32 |
| IL1ra | Lym (%) | SAA | 0.887 | 0.841 | 0.833 | 0.848 | 36 | 33 |
| IL1ra | Lym (%) | TNFR1 | 0.826 | 0.771 | 0.778 | 0.765 | 36 | 34 |
| IL1ra | Lym (%) | TRAIL | 0.836 | 0.785 | 0.697 | 0.875 | 33 | 32 |
| IL1ra | Lym (%) | WBC | 0.85 | 0.814 | 0.778 | 0.853 | 36 | 34 |
| IL1ra | Neu (%) | Pulse | 0.849 | 0.825 | 0.774 | 0.875 | 31 | 32 |
| IL1ra | Neu (%) | SAA | 0.893 | 0.855 | 0.889 | 0.818 | 36 | 33 |
| IL1ra | Neu (%) | TNFR1 | 0.811 | 0.757 | 0.778 | 0.735 | 36 | 34 |
| IL1ra | Neu (%) | TRAIL | 0.813 | 0.754 | 0.758 | 0.75 | 33 | 32 |
| IL1ra | Neu (%) | WBC | 0.842 | 0.8 | 0.806 | 0.794 | 36 | 34 |
| IL1ra | Pulse | SAA | 0.864 | 0.903 | 0.903 | 0.903 | 31 | 31 |
| IL1ra | Pulse | TNFR1 | 0.833 | 0.825 | 0.871 | 0.781 | 31 | 32 |
| IL1ra | Pulse | TRAIL | 0.837 | 0.847 | 0.828 | 0.867 | 29 | 30 |
| IL1ra | Pulse | WBC | 0.826 | 0.841 | 0.742 | 0.938 | 31 | 32 |
| IL1ra | SAA | TNFR1 | 0.875 | 0.841 | 0.889 | 0.788 | 36 | 33 |
| IL1ra | SAA | TRAIL | 0.899 | 0.877 | 0.939 | 0.813 | 33 | 32 |
| IL1ra | SAA | WBC | 0.936 | 0.884 | 0.889 | 0.879 | 36 | 33 |
| IL1ra | TNFR1 | TRAIL | 0.789 | 0.769 | 0.758 | 0.781 | 33 | 32 |
| IL1ra | TNFR1 | WBC | 0.828 | 0.771 | 0.806 | 0.735 | 36 | 34 |
| IL1ra | TRAIL | WBC | 0.775 | 0.723 | 0.727 | 0.719 | 33 | 32 |
| IP10 | Lym (%) | Neu (%) | 0.855 | 0.786 | 0.833 | 0.735 | 36 | 34 |
| IP10 | Lym (%) | Pulse | 0.889 | 0.841 | 0.774 | 0.906 | 31 | 32 |
| IP10 | Lym (%) | SAA | 0.911 | 0.87 | 0.917 | 0.818 | 36 | 33 |
| IP10 | Lym (%) | TNFR1 | 0.841 | 0.757 | 0.806 | 0.706 | 36 | 34 |
| IP10 | Lym (%) | TRAIL | 0.856 | 0.8 | 0.879 | 0.719 | 33 | 32 |
| IP10 | Lym (%) | WBC | 0.855 | 0.786 | 0.833 | 0.735 | 36 | 34 |
| IP10 | Neu (%) | Pulse | 0.873 | 0.841 | 0.774 | 0.906 | 31 | 32 |
| IP10 | Neu (%) | SAA | 0.911 | 0.87 | 0.889 | 0.848 | 36 | 33 |
| IP10 | Neu (%) | TNFR1 | 0.834 | 0.771 | 0.861 | 0.676 | 36 | 34 |
| IP10 | Neu (%) | TRAIL | 0.83 | 0.769 | 0.758 | 0.781 | 33 | 32 |
| IP10 | Neu (%) | WBC | 0.837 | 0.786 | 0.861 | 0.706 | 36 | 34 |
| IP10 | Pulse | SAA | 0.884 | 0.903 | 0.903 | 0.903 | 31 | 31 |
| IP10 | Pulse | TNFR1 | 0.855 | 0.841 | 0.871 | 0.813 | 31 | 32 |
| IP10 | Pulse | TRAIL | 0.872 | 0.864 | 0.828 | 0.9 | 29 | 30 |
| IP10 | Pulse | WBC | 0.845 | 0.841 | 0.806 | 0.875 | 31 | 32 |
| IP10 | SAA | TNFR1 | 0.885 | 0.826 | 0.778 | 0.879 | 36 | 33 |
| IP10 | SAA | TRAIL | 0.916 | 0.892 | 0.909 | 0.875 | 33 | 32 |
| IP10 | SAA | WBC | 0.923 | 0.884 | 0.917 | 0.848 | 36 | 33 |
| IP10 | TNFR1 | TRAIL | 0.832 | 0.8 | 0.848 | 0.75 | 33 | 32 |
| IP10 | TNFR1 | WBC | 0.86 | 0.786 | 0.694 | 0.882 | 36 | 34 |
| IP10 | TRAIL | WBC | 0.803 | 0.769 | 0.848 | 0.688 | 33 | 32 |
| Lym (%) | Neu (%) | Pulse | 0.83 | 0.773 | 0.771 | 0.785 | 516 | 79 |
| Lym (%) | Neu (%) | SAA | 0.863 | 0.796 | 0.792 | 0.824 | 534 | 74 |
| Lym (%) | Neu (%) | TNFR1 | 0.827 | 0.771 | 0.75 | 0.794 | 36 | 34 |
| Lym (%) | Neu (%) | TRAIL | 0.733 | 0.722 | 0.73 | 0.658 | 538 | 73 |
| Lym (%) | Neu (%) | WBC | 0.723 | 0.661 | 0.652 | 0.72 | 555 | 82 |
| Lym (%) | Pulse | SAA | 0.878 | 0.843 | 0.845 | 0.831 | 496 | 71 |
| Lym (%) | Pulse | TNFR1 | 0.834 | 0.825 | 0.935 | 0.719 | 31 | 32 |
| Lym (%) | Pulse | TRAIL | 0.805 | 0.757 | 0.754 | 0.771 | 501 | 70 |
| Lym (%) | Pulse | WBC | 0.826 | 0.79 | 0.802 | 0.709 | 516 | 79 |
| Lym (%) | SAA | TNFR1 | 0.843 | 0.768 | 0.75 | 0.788 | 36 | 33 |
| Lym (%) | SAA | TRAIL | 0.887 | 0.836 | 0.841 | 0.8 | 529 | 70 |
| Lym (%) | SAA | WBC | 0.865 | 0.778 | 0.772 | 0.824 | 534 | 74 |
| Lym (%) | TNFR1 | TRAIL | 0.822 | 0.769 | 0.788 | 0.75 | 33 | 32 |
| Lym (%) | TNFR1 | WBC | 0.824 | 0.786 | 0.861 | 0.706 | 36 | 34 |
| Lym (%) | TRAIL | WBC | 0.746 | 0.722 | 0.727 | 0.685 | 538 | 73 |
| Neu (%) | Pulse | SAA | 0.886 | 0.856 | 0.861 | 0.817 | 497 | 71 |
| Neu (%) | Pulse | TNFR1 | 0.833 | 0.841 | 0.935 | 0.75 | 31 | 32 |
| Neu (%) | Pulse | TRAIL | 0.78 | 0.712 | 0.7 | 0.8 | 503 | 70 |
| Neu (%) | Pulse | WBC | 0.796 | 0.737 | 0.734 | 0.759 | 518 | 79 |
| Neu (%) | SAA | TNFR1 | 0.848 | 0.812 | 0.861 | 0.758 | 36 | 33 |
| Neu (%) | SAA | TRAIL | 0.885 | 0.803 | 0.798 | 0.843 | 530 | 70 |
| Neu (%) | SAA | WBC | 0.862 | 0.783 | 0.781 | 0.797 | 535 | 74 |
| Neu (%) | TNFR1 | TRAIL | 0.802 | 0.785 | 0.818 | 0.75 | 33 | 32 |
| Neu (%) | TNFR1 | WBC | 0.822 | 0.771 | 0.778 | 0.765 | 36 | 34 |
| Neu (%) | TRAIL | WBC | 0.714 | 0.672 | 0.676 | 0.644 | 540 | 73 |
| Pulse | SAA | TNFR1 | 0.811 | 0.823 | 0.903 | 0.742 | 31 | 31 |
| Pulse | SAA | TRAIL | 0.865 | 0.878 | 0.885 | 0.821 | 497 | 67 |

TABLE 3F-continued

DETERMINANTS triplets that differentiate between infectious versus non-infectious disease patients
Positives (P) and Negatives (N) correspond to patients with an infectious and non-infectious disease respectively.

| DETERMINANT #1 | DETERMINANT #2 | DETERMINANT #3 | AUC | TA | Sen | Spe | P | N |
|---|---|---|---|---|---|---|---|---|
| Pulse | SAA | WBC | 0.878 | 0.889 | 0.902 | 0.803 | 498 | 71 |
| Pulse | TNFR1 | TRAIL | 0.803 | 0.814 | 0.862 | 0.767 | 29 | 30 |
| Pulse | TNFR1 | WBC | 0.833 | 0.825 | 0.871 | 0.781 | 31 | 32 |
| Pulse | TRAIL | WBC | 0.784 | 0.749 | 0.748 | 0.757 | 504 | 70 |
| SAA | TNFR1 | TRAIL | 0.859 | 0.785 | 0.788 | 0.781 | 33 | 32 |
| SAA | TNFR1 | WBC | 0.891 | 0.812 | 0.833 | 0.788 | 36 | 33 |
| SAA | TRAIL | WBC | 0.879 | 0.832 | 0.836 | 0.8 | 531 | 70 |
| TNFR1 | TRAIL | WBC | 0.79 | 0.754 | 0.758 | 0.75 | 33 | 32 |

TABLE 3G

DETERMINANTS quadruplets diagnostic accuracy

| DETERMINANT #1 | DETERMINANT #2 | DETERMINANT #3 | DETERMINANT #4 | AUC | Sen % | Spe % |
|---|---|---|---|---|---|---|
| Mixed versus viral infected patients (DETERMINANT quadruplets) | | | | | | |
| CRP | Mac-2BP, Plasma | TRAIL, Plasma | sVEGFR2, Plasma | 0.949 | 94 | 89 |
| CRP | Mac-2BP, Plasma | SAA, Plasma | sVEGFR2, Plasma | 0.909 | 100 | 82 |
| Mac-2BP, Plasma | SAA, Plasma | TRAIL, Plasma | sVEGFR2, Plasma | 0.864 | 100 | 73 |
| CRP | SAA, Plasma | TRAIL, Plasma | sVEGFR2, Plasma | 0.727 | 100 | 55 |
| CRP | Mac-2BP, Plasma | SAA, Plasma | TRAIL, Plasma | 0.63 | 67 | 89 |
| Bacterial or Mixed versus viral infected patients (DETERMINANT quadruplets) | | | | | | |
| CRP | Mac-2BP, Plasma | TRAIL, Plasma | sVEGFR2, Plasma | 0.956 | 93 | 90 |
| CRP | SAA, Plasma | TRAIL, Plasma | sVEGFR2, Plasma | 0.941 | 87 | 91 |
| Mac-2BP, Plasma | SAA, Plasma | TRAIL, Plasma | sVEGFR2, Plasma | 0.941 | 91 | 82 |
| CRP, soluble | Mac-2BP, soluble | SAA, soluble | TRAIL (ELISA), soluble | 0.932 | 85 | 88 |
| CRP | Mac-2BP, Plasma | SAA, Plasma | sVEGFR2, Plasma | 0.893 | 83 | 82 |
| Bacterial versus viral infected patients (DETERMINANT quadruplets) | | | | | | |
| CRP | Mac-2BP, Plasma | TRAIL, Plasma | sVEGFR2, Plasma | 0.947 | 93 | 89 |
| CRP | SAA, Plasma | TRAIL, Plasma | sVEGFR2, Plasma | 0.922 | 90 | 82 |
| CRP*, soluble | Mac-2BP*, soluble | SAA*, soluble | TRAIL* (ELISA), soluble | 0.958 | 91 | 90 |
| CRP, soluble | Mac-2BP, soluble | SAA, soluble | TRAIL (ELISA), soluble | 0.932 | 85 | 88 |
| Mac-2BP, Plasma | SAA, Plasma | TRAIL, Plasma | sVEGFR2, Plasma | 0.905 | 86 | 82 |
| CRP | Mac-2BP, Plasma | SAA, Plasma | sVEGFR2, Plasma | 0.87 | 90 | 82 |

*Results obtained on patients whose reference standard was determined by an expert consensus

TABLE 4

Baseline characteristics of bacterial and viral patients by age group.
A, Pediatric patients; B. Adult patients.

A. Pediatric patients.

|  | Bacterial patients (n = 79) | Viral patients (n = 201) | P-value* |
|---|---|---|---|
| Age, y | 6.18 (4.5) | 3.64 (3.9) | <0.001 |
| Gender, % | | | |
| Female | 52 | 47 | 0.39 |
| Male | 48 | 53 | 0.4 |
| Ethnicity, % | | | |
| Muslim | 34 | 35 | 0.8 |
| Jewish Sephardi | 31 | 33 | 0.64 |
| Jewish Ashkenazy | 27 | 24 | 0.67 |
| Christian | 1.2 | 1.4 | 0.9 |
| CBC | | | |
| WBC, ×1000/μL | 16.4 (8.5) | 11.1 (5.58) | <0.001 |
| Lymphocytes, % | 17.9 (13.3) | 33.2 (18.3) | <0.001 |
| Neutrophils, % | 72.7 (16) | 56.2 (19.7) | <0.001 |
| ANC, ×1000/μL | 12.5 (8.2) | 6.5 (4.48) | <0.001 |
| Clinical/Laboratory | | | |
| Maximal temp, °C. | 39.4 (0.74) | 39.1 (0.72) | 0.007 |
| Respiratory rate, breath/minute | 31 (13) | 32 (11.9) | 0.66 |
| Pulse, beats/minute | 141 (25) | 137 (27.5) | 0.32 |
| Auscultatory findings, % | 12 | 14 | 0.67 |
| Urea, mg/dL | 19.9 (8.9) | 18.8 (7.73) | 0.29 |

B. Adult patients.

|  | Bacterial patients (n = 129) | Viral patients (n = 41) | P-value* |
|---|---|---|---|
| Age, y | 50.4 (19.1) | 43.4 (17.5) | 0.04 |
| Gender, % | | | |
| Female | 48 | 57 | 0.28 |
| Male | 52 | 43 | 0.18 |
| Ethnicity, % | | | |
| Muslim | 15.8 | 18 | 0.71 |
| Jewish Sephardi | 25 | 16 | 0.22 |
| Jewish Ashkenazy | 52 | 47 | 0.63 |
| Christian | 0.8 | 4 | 0.09 |
| Comorbidities, % | | | |
| Asthma | 6.8 | 5 | 0.6 |
| Chronic obstructive pulmonary disease (COPD) | 4.5 | 5 | 0.99 |
| Congestive heart failure (CHF) | 2.2 | 5 | 0.43 |
| Hypertension | 36.1 | 18 | 0.03 |
| Hypercholesterolemia | 2.3 | 5 | 0.43 |
| CBC | | | |
| WBC, ×1000/μL | 10.57 (4.42) | 6.92 (3.17) | <0.001 |
| Lymphocytes, % | 16.23 (8.42) | 23.54 (13.79) | <0.001 |
| Neutrophils, % | 74.14 (11.36) | 64.93 (15.42) | <0.001 |
| ANC, ×1000/μL | 8.12 (4.12) | 4.27 (2.79) | <0.001 |
| Clinical/Laboratory | | | |
| Maximal temp, °C. | 38.8   0.62 | 38.6   0.68 | 0.1 |
| Respiratory rate, breath/minute | 17.8   5.9 | 17.8   8.2 | 0.98 |
| Pulse, beats/minute | 94.5   15.9 | 93   16.4 | 0.61 |
| Auscultatory findings, % | 33.5 | 26.9 | 0.06 |
| Urea, mg/dL | 0.2   0.4 | 0.1   0.3 | 0.13 |

TABLE 5

TCM-signature accuracy in diagnosing bacterial vs viral infections in patients whose diagnosis was clear (the 'Clear [bacterial, viral]' cohort). Accuracy measure (95% CI)

| | | |
|---|---|---|
| LR+ | 12.9 | [8.0, 20.5] |
| LR− | 0.108 | [0.071, 0.16] |
| DOR | 119.6 | [60.2, 237.5] |

TABLE 6

A. Age distribution of the 'Consensus [bacterial, viral]' cohort; B. TCM-signature accuracy in diagnosing bacterial vs viral infections in this cohort by age group.

A.

| | Total patients, n | Bacterial patients, n (%)* | Viral patients, n (%)* |
|---|---|---|---|
| All ages | 343 | 153 (45%) | 190 (55%) |
| ≤18 y | 219 | 53 (24%) | 166 (76%) |
| >18 y | 124 | 100 (81%) | 24 (19%) |

B.

| | LR+ [95% CI] | LR− [95% CI] | DOR [95% CI] |
|---|---|---|---|
| All ages | 11.8 [7.2, 19.1] | 0.065 [0.035, 0.122] | 180.2 [76.6, 423.8] |
| ≤18 y | 9.7 [6.0, 15.5] | 0.077 [0.029, 0.207] | 125.1 [39.9, 392.0] |
| >18 y | 23.3 [3.3, 165.2] | 0.073 [0.036, 0.150] | 318.9 [37.3, 2722.1] |

*Of the patients in the same age group.

TABLE 7

A. Age distribution of the 'Majority [bacterial, viral]' cohort; B. TCM-signature accuracy in diagnosing bacterial vs viral infections in this cohort by age group.

A.

| | Total patients, n | Bacterial patients, n (%)* | Viral patients, n (%)* |
|---|---|---|---|
| All ages | 450 | 208 (46%) | 242 (54%) |
| ≤18 y | 280 | 79 (28%) | 201 (72%) |
| >18 y | 170 | 129 (24%) | 41 (76%) |

B.

| | LR+ [95% CI] | LR− [95% CI] | DOR [95% CI] |
|---|---|---|---|
| All ages | 8.1 [5.6, 11.6] | 0.124 [0.084, 0.182] | 65.5 [36.3, 118.1] |

TABLE 7-continued

A. Age distribution of the 'Majority [bacterial, viral]' cohort; B. TCM-signature accuracy in diagnosing bacterial vs viral infections in this cohort by age group.

| | | | |
|---|---|---|---|
| ≤18 y | 7.4 [5.0, 10.8] | 0.138 [0.076, 0.251] | 53.3 [24.2, 117.2] |
| >18 y | 11.8 [3.9, 35.1] | 0.151 [0.098, 0.234] | 78.0 [21.8, 279.6] |

*Of the patients in the same age group.

TABLE 8

Age distribution of the 'Majority [viral, mixed]' cohort.

| | Total patients, n | Mixed co-infected patients, n (%)* | Viral patients, n (%)* |
|---|---|---|---|
| All ages | 276 | 34 (12.3%) | 242 (87.7%) |
| ≤18 y | 221 | 20 (9.1%) | 201 (91.0%) |
| >18 y | 55 | 14 (25.4%) | 41 (74.5%) |

*Of the patients in the same age group.

TABLE 9

Patient cohorts used to investigate the performance of the TCM-signature in patients that were initially excluded.

| | Total patients, n | Bacterial patients, n | Viral patient, n |
|---|---|---|---|
| 'Consensus (bacterial, viral)' cohort | 343 | 153 | 190 |
| 'Consensus (bacterial, viral)' cohort + excluded patients with unanimous diagnosis | 368 | 167 | 201 |
| 'Majority (bacterial, viral)' cohort | 450 | 208 | 242 |
| 'Majority (bacterial, viral)' cohort + excluded patients with majority diagnosis | 504 | 238 | 266 |

TABLE 10A

Distribution of time from symptom onset in the 'Majority (bacterial, viral)' cohort.

| Time from symptom onset | Total patients, n | Bacterial patients, n (%)* | Viral patients, n (%)* |
|---|---|---|---|
| 0-2 days | 185 | 71 (38.4%) | 114 (61.6%) |
| 2-4 days | 133 | 67 (50.4%) | 66 (49.6%) |
| 4-6 days | 85 | 45 (52.9%) | 40 (47.1%) |
| 6-10 days | 47 | 25 (53.2%) | 22 (46.8%) |

*Of the patients in the same subgroup.

TABLE 10B

Accuracy of TCM-signature across physiological systems and clinical syndromes (analysis was performed using the 'Majority [bacterial, viral]' cohort and therefore the reported levels of accuracy are conservative estimates of the actual accuracy).

| | AUC [95% CI] | Total accuracy [95% CI] | Sensitivity [95% CI] | Specificity [95% CI] | Total patients, n | Bacterial patients, n | Viral patients, n |
|---|---|---|---|---|---|---|---|
| Physiological System | | | | | | | |
| Respiratory | 0.95 [0.92, 0.98] | 0.90 [0.85, 0.95] | 0.90 [0.84, 0.96] | 0.89 [0.83, 0.95] | 241 | 129 | 112 |
| Systemic | 0.96 [0.89, 1.00] | 0.96 [0.91, 1.00] | 0.91 [0.79, 1.00] | 0.97 [0.93, 1.00] | 92 | 23 | 69 |
| Gastrointestinal | 0.89 [0.70, 0.99] | 0.83 [0.72, 0.92] | 0.87 [0.72, 1.00] | 0.80 [0.67, 0.93] | 63 | 23 | 40 |
| Clinical Syndromes | | | | | | | |
| Fever without a source | 0.96 [0.89, 1.00] | 0.95 [0.91, 1.00] | 0.92 [0.73, 1.00] | 0.96 [0.91, 1.00] | 84 | 12 | 72 |

TABLE 10B-continued

Accuracy of TCM-signature across physiological systems and clinical syndromes (analysis was performed using the 'Majority [bacterial, viral]' cohort and therefore the reported levels of accuracy are conservative estimates of the actual accuracy).

|  | AUC [95% CI] | Total accuracy [95% CI] | Sensitivity [95% CI] | Specificity [95% CI] | Total patients, n | Bacterial patients, n | Viral patients, n |
|---|---|---|---|---|---|---|---|
| Pneumonia | 0.94 [0.88, 0.99] | 0.87 [0.79, 0.94] | 0.85 [0.76, 0.94] | 0.94 [0.81, 1.00] | 79 | 63 | 16 |
| Acute tonsillitis | 0.94 [0.87, 1.00] | 0.91 [0.82, 1.00] | 0.96 [0.89, 1.00] | 0.81 [0.61, 1.00] | 44 | 28 | 16 |

TABLE 10C

Accuracy of TCM-signature on different pathogens (analysis was performed using the 'Majority [bacterial, viral, mixed]' cohort).

| Pathogen | AUC [95% CI | Total accuracy [95% CI] | Sensitivity [95% CI] | Specificity [95% CI] | Total patients, n | Bacterial patients, n | Viral patients, n |
|---|---|---|---|---|---|---|---|
| Viruses | | | | | | | |
| Influenza A/B | 0.97 [0.95, 0.99] | 0.96 [0.93, 0.98] | 0.95 [0.93, 0.98] | 0.96 [0.89, 1.00] | 269 | 242 | 27 |
| Adenovirus | 0.91 [0.87, 0.95] | 0.85 [0.81, 0.90] | 0.85 [0.81, 0.90] | 0.85 [0.71, 1.00] | 269 | 242 | 27 |
| Parainfluenza 1/2/3/4 | 0.96 [0.93, 0.98] | 0.92 [0.88, 0.95] | 0.92 [0.88, 0.95] | 0.90 [0.76, 1.00] | 262 | 242 | 20 |
| Respiratory syncytial A/B | 0.97 [0.95, 0.99] | 0.91 [0.87 0.94] | 0.90 [0.86, 0.94] | 1.00 [1.00, 1.00] | 259 | 242 | 17 |
| Enterovirus | 0.95 [0.92, 0.98] | 0.88 [0.84, 0.92] | 0.88 [0.84, 0.92] | 0.92 [0.76, 1.00] | 255 | 242 | 13 |
| Bocavirus 1/2/3/4 | 0.97 [0.95, 1.00] | 0.94 [0.91, 0.97] | 0.94 [0.91, 0.97] | 1.00 [1.00, 1.00] | 252 | 242 | 10 |
| Metapneumovirus | 0.91 [0.85, 0.97] | 0.84 [0.80, 0.89] | 0.84 [0.79, 0.89] | 0.89 [0.63, 1.00] | 251 | 242 | 9 |
| CMV | 0.92 [0.86, 0.97] | 0.84 [0.79, 0.88] | 0.83 [0.79, 0.88] | 0.89 [0.63, 1.00] | 251 | 242 | 9 |
| Bacteria | | | | | | | |
| *E. Coli* | 0.90 [0.82, 0.98] | 0.81 [0.76, 0.86] | 0.89 [0.76, 1.00] | 0.80 [0.75, 0.85] | 269 | 27 | 242 |
| Group A Strep | 0.96 [0.87, 1.00] | 0.91 [0.87, 0.95] | 1.00 [1.00, 1.00] | 0.90 [0.87, 0.90] | 253 | 11 | 242 |
| Atypical bacteria | | | | | | | |
| *Mycoplasma pneu.* | 0.88 [0.78, 1.00] | 0.75 [0.70, 0.80] | 0.86 [0.65, 1.00] | 0.74 [0.69, 0.8] | 256 | 14 | 242 |
| *Chlamydophila pneu.* | 0.96 [0.82, 1.00] | 0.92 [0.89, 0.96] | 1.00 [1.00, 1.00] | 0.92 [0.89, 0.96] | 246 | 4 | 242 |

TABLE 10D

Comparing the TCM-signature and standard laboratory parameters for the identification of bacterial vs adenoviral infections.

|  | AUC [95% CI] | Total accuracy [95% CI] | Sensitivity [95% CI] | Specificity [95% CI] |
|---|---|---|---|---|
| TCM signature | 0.91 [0.85, 0.96] | 0.85 [0.78, 0.92] | 0.85 [0.78, 0.93] | 0.85 [0.71, 1.00] |
| ANC | 0.68 [0.58, 0.79] | 0.63 [0.53, 0.71] | 0.57 [0.46, 0.68] | 0.76 [0.60, 0.92] |
| Lym (%) | 0.78 [0.70, 0.86] | 0.74 [0.67, 0.82] | 0.74 [0.65, 0.84] | 0.76 [0.60, 0.92] |
| Maximal temperature | 0.52 [0.41, 0.64] | 0.54 [0.45, 0.63] | 0.5 [0.38, 0.61] | 0.66 [0.48, 0.84] |
| WBC | 0.53 [0.41, 0.65] | 0.54 [0.45, 0.63] | 0.5 [0.40, 0.62] | 0.63 [0.45, 0.81] |

TABLE 10E

Comparing TCM-signature and standard laboratory parameters for the identification of atypical bacteria.

|  | AUC [95% CI] | Total accuracy [95% CI] | Sensitivity [95% CI] | Specificity [95% CI] |
|---|---|---|---|---|
| TCM-signature | 0.91 [0.83, 1.00] | 0.89 [0.87, 0.94] | 0.76 [0.55, 0.96] | 0.90 [0.86, 0.93] |
| ANC | 0.70 [0.57, 0.83] | 0.76 [0.56, 0.96] | 0.63 [0.57, 0.69] | 0.64 [0.59, 0.70] |
| Lym (%) | 0.73 [0.61, 0.86] | 0.71 [0.50, 0.92] | 0.74 [0.69, 0.80] | 0.74 [0.69, 0.79] |
| Neu (%) | 0.73 [0.60, 0.85] | 0.67 [0.45, 0.89] | 0.75 [0.69, 0.80] | 0.74 [0.69, 0.79] |
| Maximal temperature | 0.52 [0.39, 0.65] | 0.61 [0.55, 0.67] | 0.43 [0.20, 0.66] | 0.63 [0.57, 0.69] |
| WBC | 0.62 [0.48, 0.75] | 0.71 [0.5, 0.92] | 0.52 [0.46, 0.58] | 0.54 [0.48, 0.60] |

TABLE 10F

Evaluation of the sensitivity of DETERMINANTS to various comorbidities

| | WS P-value (target vs background groups) | | | Target group | Background group | |
|---|---|---|---|---|---|---|
| | TRAIL | Mac-2BP | CRP | (patients with a comorbidity), n | patients without a comorbidity), n | Age interval, y |
| Bacterial/Mixed | | | | | | |
| Hypertension | 0.27 | 0.34 | 0.57 | 57 | 49 | [38, 94] |
| Hyperlipidemia | 0.26 | 0.18 | 0.81 | 39 | 55 | [36, 90] |
| Obesity | 0.29 | 0.77 | 0.18 | 21 | 114 | [23, 87] |
| Asthma | 0.73 | 0.46 | 0.63 | 17 | 225 | All ages |
| Atherosclerosis | 0.44 | 0.42 | 0.95 | 22 | 91 | [34, 94] |
| Diabetes mellitus 2 | 0.37 | 0.77 | 0.14 | 17 | 66 | [44, 80] |
| Inflammatory | 0.24 | 0.61 | 0.13 | 9 | 233 | All ages |
| Viral | | | | | | |
| Hypertension | 0.23 | 0.19 | 0.55 | 8 | 27 | [38, 94] |
| Hyperlipidemia | 0.512 | 0.16 | 0.91 | 4 | 21 | [36, 90] |
| Asthma | 0.46 | 0.51 | 0.05 | 8 | 234 | All ages |
| Diabetes mellitus 2 | 0.34 | 0.49 | 0.08 | 4 | 14 | [44, 80] |
| Non-infectious | | | | | | |
| Inflammatory | 0.442 | 0.692 | 0.498 | 7 | 39 | All |

TABLE 10G

Evaluation of the sensitivity of the DETERMINANTS to various types of chronic drug regimens.

| | WS P-value (patients treated with a specific drug vs untreated patients) | | | Patients treated with the drug, n | Patients not treated with the drug, n | Age interval, y |
|---|---|---|---|---|---|---|
| | TRAIL | Mac-2BP | CRP | | | |
| Bacterial or mixed | | | | | | |
| Statins | 0.30 | 0.70 | 0.76 | 40 | 86 | [26, 90] |
| Diabetes related | 0.11 | 0.17 | 0.53 | 28 | 75 | [39, 87] |
| Beta blockers | 0.61 | 0.13 | 0.76 | 22 | 108 | [24, 106] |
| Aspirin | 0.44 | 0.65 | 0.09 | 32 | 79 | [36, 96] |
| Antacid | 0.27 | 0.05 | 0.78 | 27 | 119 | [21, 101] |
| Inhaled corticosteroids | 0.17 | 0.96 | 0.97 | 16 | 226 | All ages |
| Bronchodilators | 0.84 | 0.77 | 0.76 | 11 | 231 | All ages |
| Diuretics | 0.27 | 0.64 | 0.15 | 14 | 42 | [55, 82] |
| Viral | | | | | | |
| Statins | 0.26 | 0.12 | 0.35 | 6 | 35 | [26, 90] |
| Aspirin | 0.36 | 0.77 | 0.71 | 4 | 22 | [36, 96] |
| Antacid | 0.82 | 0.23 | 0.16 | 5 | 39 | [21, 101] |
| Inhaled corticosteroids | 0.68 | 0.78 | 0.21 | 7 | 235 | All ages |
| Bronchodilators | 0.09 | 0.11 | 0.10 | 7 | 235 | All ages |

TABLE 10H

TCM-signature accuracy in diagnosing bacterial sepsis vs viral infections in adult patients.

| | AUC [95% CI] | Total accuracy [95% CI] | Sensitivity [95% CI] | Specificity [95% CI] | Total patients (adults), n | Patients with bacterial sepsis (adults), n | Viral patients (adults), n |
|---|---|---|---|---|---|---|---|
| 'Consensus (adult bacterial sepsis, adult viral)' cohort | 0.98 [0.95, 1.00] | 0.96 [0.91, 1.00] | 0.96 [0.90, 1.00] | 0.96 [0.87, 1] | 89 | 65 | 24 |
| 'Majority (adult bacterial sepsis, adult viral)' cohort | 0.96 [0.93, 0.99] | 0.91 [0.86, 0.96] | 0.90 [0.83, 0.97] | 0.93 [0.85, 1] | 128 | 87 | 41 |

TABLE 11

Evaluation of the sensitivity of TCM- signature to various types of clinical settings.

| | Department | AUC [95% CI] | Patients, n | Bacterial patients, n | Viral patients, n |
|---|---|---|---|---|---|
| 'Consensus (bacterial, viral, mixed)' cohort* | PED & ED | 0.95 [0.90, 0.99] | 201 | 56 | 145 |
| | PED | 0.91 [0.84, 0.98] | 157 | 30 | 127 |
| | ED | 0.98 [0.94, 1.00] | 44 | 26 | 18 |
| | Pediatrics & Internal | 0.96 [0.93, 0.99] | 147 | 102 | 45 |
| | Pediatrics | 0.95 [0.90, 1.00] | 66 | 27 | 39 |
| | Internal | NA NA | NA | NA | NA |
| 'Majority (bacterial, viral, mixed)' cohort | PED & ED | 0.92 [0.88, 0.95] | 286 | 110 | 176 |
| | PED | 0.89 [0.83, 0.95] | 210 | 59 | 151 |
| | ED | 0.95 [0.91, 1.00] | 76 | 51 | 25 |
| | Pediatrics & Internal | 0.91 [0.87, 0.95] | 198 | 132 | 66 |
| | Pediatrics | 0.92 [0.86, 0.98] | 91 | 41 | 50 |
| | Internal | 0.9 [0.83, 0.96] | 107 | 91 | 16 |

*The internal department 'Consensus (bacterial, viral)' had only a small number of viral patients (n = 6) and was therefore excluded from this analysis.

TABLE 12

Evaluation of the sensitivity of TCM-signature to clinical sites

| | Hospital | AUC [95% CI] | Total patients, n | Bacterial patients, n | Viral patients, n |
|---|---|---|---|---|---|
| 'Consensus (bacterial, viral, mixed)' cohort | Hillel Yaffe Medical Center | 0.94 [0.89, 0.99] | 190 | 44 | 146 |
| | Bnai Zion Medical Center | 0.94 [0.91, 0.98] | 158 | 114 | 44 |
| 'Majority (bacterial, viral, mixed)' cohort | Hillel Yaffe Medical Center | 0.93 [0.89, 0.97] | 255 | 79 | 176 |
| | Bnai Zion Medical Center | 0.92 [0.89, 0.96] | 229 | 163 | 66 |

TABLE 13

Prevalence of select bacterial and viral strains in patients with infectious diseases by age groups ('Majority [bacterial, viral, mixed]' cohort).

| | All ages (n = 484) | | | Age ≤18 y (n = 300) | | | Age >18 y (n = 184) | | |
|---|---|---|---|---|---|---|---|---|---|
| | Bacterial n = 208 | Viral n = 242 | Mixed n = 34 | Bacterial n = 79 | Viral n = 201 | Mixed n = 20 | Bacterial n = 129 | Viral n = 41 | Mixed n = 14 |
| Streptococcus pneumoniae | 34.4% | 50.6% | 55.9% | 56.1% | 54.5% | 75.0% | 21.1% | 31.8% | 28.6% |
| Haemophilus influenzae | 19.1% | 36.2% | 38.2% | 37.8% | 40.4% | 60.0% | 7.5% | 15.9% | 28.6% |
| Rhinovirus A/B/C | 4.2% | 16.7% | 26.5% | 9.8% | 18.8% | 30.0% | 0.8% | 6.8% | 21.4% |

TABLE 14

TCM-signature diagnostic utility increases as the cutoffs used for filtering out patients with marginal responses become more stringent. Results were computed using the 'Consensus (bacterial, viral)' cohort.

| % of diagnosed patients | DOR | LR+ | LR− |
|---|---|---|---|
| 100% | 145.7 | 12.1 | 0.083 |
| 97% | 190.8 | 13.8 | 0.072 |
| 92% | 268.7 | 16.4 | 0.061 |
| 89% | 430.1 | 20.7 | 0.048 |
| 77% | 1045.4 | 32.3 | 0.031 |

TABLE 15

TCM-signature diagnostic utility increases as the cutoffs used for filtering out patients with marginal responses become more stringent. Results were computed using the 'Majority (bacterial, viral)' cohort.

| % of diagnosed patients | DOR | LR+ | LR− |
| --- | --- | --- | --- |
| 100% | 64.1 | 8.0 | 0.125 |
| 97% | 72.7 | 8.5 | 0.117 |
| 93% | 88.7 | 9.4 | 0.106 |
| 90% | 102.2 | 10.1 | 0.099 |
| 85% | 193.9 | 13.9 | 0.072 |
| 73% | 273.7 | 16.5 | 0.060 |
| 64% | 495.3 | 22.3 | 0.045 |

REFERENCES

A. Putto, O. Meurman, and O. Ruuskanen. 1986. "C-reactive Protein in the Differentiation of Adenoviral, Epstein-Barr Viral and Streptococcal Tonsillitis in Children." European Journal of Pediatrics 145 (3). http://www(dot)springerlink(dot)com/content/n1526441457905p1/.

Akira, S., and S. Uematsu, et al. 2006. "Pathogen Recognition and Innate Immunity." Cell 124 (4): 783-801.

Appenzeller C, Ammann R A, Duppenthaler A, Gorgievski-Hrisoho M, and Aebi C. 2002. "Serum C-reactive Protein in Children with Adenovirus Infection." Swiss Med Wkly 132.

Arias, C. A., and B. E. Murray. 2009. "Antibiotic-resistant Bugs in the 21st Century—a Clinical Super-challenge." The New England Journal of Medicine 360 (5): 439-443.

Bayraktaroğlu, Taner, Ahmet Sükrü Aras, Selim Aydemir, Can Davutoğlu, Yucel Ustündağ, Hulusi Atmaca, and Ali Borazan. 2004. "Serum Levels of Tumor Necrosis Factor-alpha, Interleukin-6 and Interleukin-8 Are Not Increased in Dyspeptic Patients with Helicobacter Pylori-associated Gastritis." Mediators of Inflammation 13 (1) (February): 25-28. doi:10.1080/09629350410001664789.

Bone, R C, R A Balk, F B Cerra, R P Dellinger, A M Fein, W A Knaus, R M Schein, and W J Sibbald. 1992. "Definitions for Sepsis and Organ Failure and Guidelines for the Use of Innovative Therapies in Sepsis. The ACCP/SCCM Consensus Conference Committee. American College of Chest Physicians/Society of Critical Care Medicine." Chest 101 (6) (June): 1644-1655.

Bossuyt, Patrick M, Johannes B Reitsma, David E Bruns, Constantine A Gatsonis, Paul P Glasziou, Les M Irwig, David Moher, Drummond Rennie, Henrica C. W De Vet, and Jeroen G Lijmer. 2003. "The STARD Statement for Reporting Studies of Diagnostic Accuracy: Explanation and Elaboration." Annals of Internal Medicine 138 (1) (January 7): W1-W12.

Brian Clyne, and Jonathan S Olshaker. 1999. "The C-reactive Protein." The Journal of Emergency Medicine 17 (6): 1019-1025. doi:10.1016/S0736-4679(99)00135-3.

Brunkhorst, F. M., and B. Al-Nawas, et al. 2002. "Procalcitonin, C-reactive Protein and APACHE II Score for Risk Evaluation in Patients with Severe Pneumonia." Clinical Microbiology and Infection: The Official Publication of the European Society of Clinical Microbiology and Infectious Diseases 8 (2): 93-100.

Cadieux, G., and R. Tamblyn, et al. 2007. "Predictors of Inappropriate Antibiotic Prescribing Among Primary Care Physicians." CMAJ: Canadian Medical Association Journal=Journal De l'Association Medicale Canadienne 177 (8): 877-883.

Cao, Wenjun, Bill Sun, Mark A Feitelson, Tong Wu, Ran Tur-Kaspa, and Qishi Fan. 2009. "Hepatitis C Virus Targets Over-expression of Arginase I in Hepatocarcinogenesis." International Journal of Cancer. Journal International Du Cancer 124 (12) (June 15): 2886-2892. doi:10.1002/ijc.24265.

"CDC—About Antimicrobial Resistance." 2011. http://www(dot)cdc(dot)gov/drugresistance/about(dot)html.

"CDC—Get Smart: Fast Facts About Antibiotic Resistance." 2011. http://www(dot)cdc(dot)gov/getsmart/antibiotic-use/fast-facts(dot)html.

CDC.gov. 2012. "NAMCS/NHAMCS—NCHS Reports Using Ambulatory Health Care Data." Accessed June 6. http://www(dot)cdc(dot)gov/nchs/ahcd/ahcd_reports(dot)htm.

Christensen, R D, P P Bradley, and G Rothstein. 1981. "The Leukocyte Left Shift in Clinical and Experimental Neonatal Sepsis." The Journal of Pediatrics 98 (1) (January): 101-105.

Cillóniz, Catia, Santiago Ewig, Eva Polverino, Maria Angeles Marcos, Cristina Esquinas, Albert Gabarrús, Josep Mensa, and Antoni Torres. 2011. "Microbial Aetiology of Community-Acquired Pneumonia and Its Relation to Severity." Thorax 66 (4) (April 1): 340-346. doi:10.1136/thx.2010.143982.

Clements, Helena, Terence Stephenson, Vanessa Gabriel, Timothy Harrison, Michael Millar, Alan Smyth, William Tong, and Chris J Linton. 2000. "Rationalised Prescribing for Community Acquired Pneumonia: A Closed Loop Audit." Archives of Disease in Childhood 83 (4) (October 1): 320-324. doi:10.1136/adc.83.4.320.

Craig, Jonathan C, Gabrielle J Williams, Mike Jones, Miriam Codarini, Petra Macaskill, Andrew Hayen, Les Irwig, Dominic A Fitzgerald, David Isaacs, and Mary McCaskill. 2010. "The Accuracy of Clinical Symptoms and Signs for the Diagnosis of Serious Bacterial Infection in Young Febrile Children: Prospective Cohort Study of 15 781 Febrile Illnesses." BMJ: British Medical Journal 340. doi:10.1136/bmj.c1594.

Davey, P., and E. Brown, et al. 2006. "Systematic Review of Antimicrobial Drug Prescribing in Hospitals." Emerging Infectious Diseases 12 (2): 211-216.

Fjaertoft, G., and T. Foucard, et al. 2005. "Human Neutrophil Lipocalin (HNL) as a Diagnostic Tool in Children with Acute Infections: a Study of the Kinetics." Acta Paediatrica (Oslo, Norway: 1992) 94 (6): 661-666.

Gobert, Alain P, Yulan Cheng, Jian-Ying Wang, Jean-Luc Boucher, Ramaswamy K Iyer, Stephen D Cederbaum, Robert A Casero Jr, Jamie C Newton, and Keith T Wilson. 2002. "Helicobacter Pylori Induces Macrophage Apoptosis by Activation of Arginase II." Journal of Immunology (Baltimore, Md.: 1950) 168 (9) (May 1): 4692-4700.

Gong, Jh, H Sprenger, F Hinder, A Bender, A Schmidt, S Horch, M Nain, and D Gemsa. 1991. "Influenza A Virus Infection of Macrophages. Enhanced Tumor Necrosis Factor-alpha (TNF-alpha) Gene Expression and Lipopolysaccharide-Triggered TNF-alpha Release." The Journal of Immunology 147 (10) (November 15): 3507-3513.

Grassmé, Heike, Susanne Kirschnek, Joachim Riethmueller, Andrea Riehle, Gabriele von Kürthy, Florian Lang, Michael Weller, and Erich Gulbins. 2000. "CD95/CD95 Ligand Interactions on Epithelial Cells in Host Defense to

*Pseudomonas Aeruginosa."* Science 290 (5491) (October 20): 527-530. doi: 10.1126/science.290.5491.527.

Hatherill, M., and S. M. Tibby, et al. 1999. "Diagnostic Markers of Infection: Comparison of Procalcitonin with C Reactive Protein and Leucocyte Count." *Archives of Disease in Childhood* 81 (5): 417-421.

Hatipoğlu, Nevin, Ayper Somer, Selim Badur, Emin Unüvar, Meral Akgay-Ciblak, Ensar Yekeler, Nuran Salman, Melike Keser, Hüsem Hatipoglu, and Rengin Siraneci. 2011. "Viral Etiology in Hospitalized Children with Acute Lower Respiratory Tract Infection." *The Turkish Journal of Pediatrics* 53 (5) (October): 508-516.

Hersh, Adam L, Daniel J Shapiro, Andrew T *Pavia*, and Samir S Shah. 2011. "Antibiotic Prescribing in Ambulatory Pediatrics in the United States." *Pediatrics* 128 (6) (December): 1053-1061. doi:10.1542/peds.2011-1337.

Houck, P. M., and D. W. Bratzler, et al. 2002. "Pneumonia Treatment Process and Quality." *Archives of Internal Medicine* 162 (7): 843-844.

Johansson, Niclas, Mats Kalin, Annika Tiveljung-Lindell, Christian G Giske, and Jonas Hedlund. 2010. "Etiology of Community-acquired Pneumonia: Increased Microbiological Yield with New Diagnostic Methods." *Clinical Infectious Diseases: An Official Publication of the Infectious Diseases Society of America* 50 (2) (January 15): 202-209. doi: 10.1086/648678.

Johnstone, Jennie, Sumit R Majumdar, Julie D Fox, and Thomas J Marrie. 2008. "Viral Infection in Adults Hospitalized With Community-Acquired Pneumonia Prevalence, Pathogens, and Presentation." *Chest* 134 (6) (December 1): 1141-1148. doi:10.1378/chest.08-0888.

Jones, A. E., and J. F. Fiechtl, et al. 2007. "Procalcitonin Test in the Diagnosis of Bacteremia: a Meta-analysis." *Annals of Emergency Medicine* 50 (1): 34-41.

Kunze, Wolfgang, Dietmar Beier, and Katrin Groeger. 2010. "Adenovirus Respiratory Infections In Children. Do They Mimic Bacterial Infections?" (October 31). http://www(dot)webmedcentral(dot)com/article_view/1098.

Levy, Mitchell M, Mitchell P Fink, John C Marshall, Edward Abraham, Derek Angus, Deborah Cook, Jonathan Cohen, Steven M Opal, Jean-Louis Vincent, and Graham Ramsay. 2003. "2001 SCCM/ESICM/ACCP/ATS/SIS International Sepsis Definitions Conference." *Critical Care Medicine* 31 (4) (April): 1250-1256. doi:10.1097/01.CCM.0000050454.01978.3B.

Linder, J. A., and R. S. Stafford. 2001. "Antibiotic Treatment of Adults with Sore Throat by Community Primary Care Physicians: a National Survey, 1989-1999." *JAMA: The Journal of the American Medical Association* 286 (10): 1181-1186.

Little, P. 2005. "Delayed Prescribing of Antibiotics for Upper Respiratory Tract Infection." *BMJ (Clinical Research Ed.)* 331 (7512): 301-302.

Little, P. S., and I. Williamson. 1994. "Are Antibiotics Appropriate for Sore Throats? Costs Outweigh the Benefits." *BMJ (Clinical Research Ed.)* 309 (6960): 1010-1011.

Del Mar, C. 1992. "Managing Sore Throat: a Literature Review. I. Making the Diagnosis." *The Medical Journal of Australia* 156 (8): 572-575.

Marc, E, M Chaussain, F Moulin, J L Iniguez, G Kalifa, J Raymond, and D Gendrel. 2000. "Reduced Lung Diffusion Capacity After *Mycoplasma Pneumoniae* Pneumonia." *The Pediatric Infectious Disease Journal* 19 (8) (August): 706-710.

Murphy, K., and P. Travers, et al. 2007. "Janeway's Immunobiology, Seventh Edition I Mendeley." http://www(dot) mendeley(dot)com/research/janeways-immunobiology-seventh-edition-immunobiology-immune-system-janeway/.

Peltola, Ville, Jussi Mertsola, and Olli Ruuskanen. 2006. "Comparison of Total White Blood Cell Count and Serum C-reactive Protein Levels in Confirmed Bacterial and Viral Infections." *The Journal of Pediatrics* 149 (5) (November): 721-724. doi:10.1016/j.jpeds.2006.08.051.

Pickering, Larry K., and Herbert L. DuPont. 1986. *Infectious Diseases of Children and Adults: a Step-by-step Approach to Diagnosis and Treatment*. Addison-Wesley, Health Sciences Division.

Povoa P. 2002. "C-reactive Protein: a Valuable Marker of Sepsis." *Intensive Care Medicine* 28 (3): 235-243.

Principi, N, and S Esposito. 2001. "Emerging Role of *Mycoplasma Pneumoniae* and *Chlamydia Pneumoniae* in Paediatric Respiratory-tract Infections." *The Lancet Infectious Diseases* 1 (5) (December): 334-344. doi: 10.1016/S1473-3099(01)00147-5.

Pulcini, C., and E. Cua, et al. 2007. "Antibiotic Misuse: a Prospective Clinical Audit in a French University Hospital." *European Journal of Clinical Microbiology & Infectious Diseases: Official Publication of the European Society of Clinical Microbiology* 26 (4): 277-280.

Regev-Yochay, Gili, Izzeldin Abullaish, Richard Malley, Bracha Shainberg, Miriam Varon, Yulia Roytman, Arnona Ziv, et al. 2012. *"Streptococcus Pneumoniae* Carriage in the Gaza Strip." *PloS One* 7 (4): e35061. doi:10.1371/journal.pone.0035061.

Regev-Yochay, Gili, Meir Raz, Ron Dagan, Nurith Porat, Bracha Shainberg, Erica Pinco, Nathan Keller, and Ethan Rubinstein. 2004. "Nasopharyngeal Carriage of *Streptococcus Pneumoniae* by Adults and Children in Community and Family Settings." *Clinical Infectious Diseases* 38 (5) (March 1): 632-639. doi: 10.1086/381547.

Restrepo, Marcos I, Eric M Mortensen, Jose A Velez, Christopher Frei, and Antonio Anzueto. 2008. "A Comparative Study of Community-Acquired Pneumonia Patients Admitted to the Ward and the ICU*." *Chest* 133 (3) (March 1): 610-617. doi:10.1378/chest.07-1456.

Rivers, E, B Nguyen, S Havstad, J Ressler, A Muzzin, B Knoblich, E Peterson, and M Tomlanovich. 2001. "Early Goal-directed Therapy in the Treatment of Severe Sepsis and Septic Shock." *The New England Journal of Medicine* 345 (19) (November 8): 1368-1377. doi:10.1056/NEJMoa010307.

Rudensky, B., and G. Sirota, et al. 2008. "Neutrophil CD64 Expression as a Diagnostic Marker of Bacterial Infection in Febrile Children Presenting to a Hospital Emergency Department." *Pediatric Emergency Care* 24 (11): 745-748.

Scott, J. G., and D. Cohen, et al. 2001. "Antibiotic Use in Acute Respiratory Infections and the Ways Patients Pressure Physicians for a Prescription." *The Journal of Family Practice* 50 (10): 853-858.

Shaikh, Nader, Erica Leonard, and Judith M Martin. 2010. "Prevalence of Streptococcal Pharyngitis and Streptococcal Carriage in Children: a Meta-analysis." *Pediatrics* 126 (3) (September): e557-564. doi: 10.1542/peds.2009-2648.

Shapiro, Howard. 2005. *Practical Flow Cytometry*. http://onlinelibrary(dot)wiley(dot)com/doi/10(dot)1002/0471722731(dot)fmatter/summar y.

Shibli, Fahmi, Bibiana Chazan, Orna Nitzan, Edit Flatau, Hana Edelstein, Orna Blondheim, Raul Raz, and Raul Colodner. 2010. "Etiology of Community-acquired Pneumonia in Hospitalized Patients in Northern Israel." *The Israel Medical Association Journal: IMAJ* 12 (8) (August): 477-482.
Song, Jae-Hoon, Won Sup Oh, Cheol-In Kang, Doo Ryeon Chung, Kyong Ran Peck, Kwan Soo Ko, Joon Sup Yeom, et al. 2008. "Epidemiology and Clinical Outcomes of Community-acquired Pneumonia in Adult Patients in Asian Countries: a Prospective Study by the Asian Network for Surveillance of Resistant Pathogens." *International Journal of Antimicrobial Agents* 31 (2) (February): 107-114. doi:10.1016/j.ijantimicag.2007.09.014.
Spiro, D. M., and K. Y. Tay, et al. 2006. "Wait-and-see Prescription for the Treatment of Acute Otitis Media: a Randomized Controlled Trial." *JAMA: The Journal of the American Medical Association* 296 (10): 1235-1241.
Tang M. P., and Eslick G D. 2007. "Accuracy of Procalcitonin for Sepsis Diagnosis in Critically Ill Patients: Systematic Review and Meta-analysis." *The Lancet Infectious Diseases* 7 (3): 210-217.
Thorn, George W., Adams, Braunwald, Isselbacher, and Petersdorf. 1977. *Harrison's Principles of Internal Medicine.* 8th Edition.
Uyeki, Timothy M, Ramakrishna Prasad, Charles Vukotich, Samuel Stebbins, Charles R Rinaldo, Yu-Hui Ferng, Stephen S Morse, et al. 2009. "Low Sensitivity of Rapid Diagnostic Test for Influenza." *Clinical Infectious Diseases: An Official Publication of the Infectious Diseases Society of America* 48 (9) (May 1): e89-92. doi: 10.1086/597828.
Vaneechoutte, M, G Verschraegen, G Claeys, B Weise, and A M Van den Abeele. 1990. "Respiratory Tract Carrier Rates of *Moraxella* (Branhamella) *Catarrhalis* in Adults and Children and Interpretation of the Isolation of M. Catarrhalis from Sputum." *Journal of Clinical Microbiology* 28 (12) (December): 2674-2680.
Wirth U., and Muller D. 2002. "Post-translational Modification Detection Using Metastable Ions in Reflector Matrix-assisted Laser Desorption/ionization-time of Flight Mass Spectrometry." *Proteomics* 2 (10): 1445-1451.
Zhou, Chao, Feng-Zhen Ma, Xue-Jie Deng, Hong Yuan, and Hong-Sheng Ma. 2008. "Lactobacilli Inhibit Interleukin-8 Production Induced by *Helicobacter Pylori* Lipopolysaccharide-activated Toll-like Receptor 4." *World Journal of Gastroenterology*: WJG 14 (32) (August 28): 5090-5095. doi:10.3748/wjg.14.5090.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A kit comprising antibodies, at least one of said antibodies is a monoclonal antibody, wherein a first antibody of said antibodies specifically binds to TNF-related apoptosis-inducing ligand (TRAIL) protein, a second antibody of said antibodies specifically binds to Procalcitonin (PCT) protein, and a third antibody of said antibodies specifically binds to C-Reactive protein (CRP), wherein the kit does not comprise more than three additional antibodies which specifically bind to additional determinants, each of said three additional antibodies targeting a different soluble determinant of said additional determinants, wherein said determinant is a protein whose level is differentially expressed in a viral and bacterial infection.

2. A kit comprising antibodies immobilized on a solid support, wherein said antibodies consist of a first antibody that specifically binds to TRAIL protein, a second antibody that specifically binds to PCT protein and a third antibody that specifically binds to C-Reactive protein (CRP).

3. The kit of claim 1, further comprising: (i) an antibody that specifically binds to said TRAIL protein at an additional site as to the site to which said first antibody binds; and (ii) an antibody that specifically binds to said PCT protein at an additional site as to the site to which said second antibody binds, wherein each of said antibodies of (i) and (ii) comprise a detectable label selected from the group consisting of a radioactive label, a fluorescent label, a chemiluminescent label, a colorimetric label and an enzyme.

4. The kit of claim 1, wherein said first antibody and said second antibody are immobilized to a solid support.

5. The kit of claim 1, wherein said first antibody and said second antibody are immobilized to a single solid support.

6. The kit of claim 2, wherein each of said first antibody, said second antibody and said third antibody are immobilized to a single solid support.

7. The kit of claim 3, wherein said enzyme is horseradish peroxidase or alkaline phosphatase.

8. The kit of claim 2, being used in a lateral flow immunoassay.

* * * * *